United States Patent
Kuehnert et al.

(10) Patent No.: US 10,807,988 B2
(45) Date of Patent: Oct. 20, 2020

(54) 3-((HETERO-)ARYL)-8-AMINO-2-OXO-1,3-DIAZA-SPIRO-[4.5]-DECANE DERIVATIVES

(71) Applicant: Grünenthal GmbH, Aachen (DE)

(72) Inventors: Sven Kuehnert, Dueren (DE); Rene Koenigs, Erkelenz (DE); Achim Kless, Aachen (DE); Anita Wegert, Aldenhoven (DE); Ingo Konetzki, Aachen (DE); Paul Ratcliffe, Aachen (DE); Ruth Jostock, Stolberg (DE); Thomas Koch, Stolberg (DE); Klaus Linz, Rheinbach (DE); Wolfgang Schroeder, Aachen (DE)

(73) Assignee: Grünenthal GmbH, Aachen (DE)

( * ) Notice: Subject to any disclaimer, the term of this patent is extended or adjusted under 35 U.S.C. 154(b) by 0 days.

(21) Appl. No.: 16/450,331

(22) Filed: Jun. 24, 2019

(65) Prior Publication Data
US 2019/0375754 A1    Dec. 12, 2019

Related U.S. Application Data

(63) Continuation of application No. 16/207,854, filed on Dec. 3, 2018, now abandoned, which is a continuation of application No. 15/923,948, filed on Mar. 16, 2018, now abandoned, which is a continuation of application No. 15/405,485, filed on Jan. 13, 2017, now abandoned.

(30) Foreign Application Priority Data

Jan. 13, 2016 (EP) ..................................... 16151012

(51) Int. Cl.
| | |
|---|---|
| C07D 487/04 | (2006.01) |
| C07D 409/04 | (2006.01) |
| C07D 413/02 | (2006.01) |
| C07D 401/02 | (2006.01) |
| C07D 405/02 | (2006.01) |
| C07D 471/04 | (2006.01) |
| C07D 401/14 | (2006.01) |
| C07D 405/14 | (2006.01) |
| C07D 417/04 | (2006.01) |
| C07D 413/14 | (2006.01) |
| C07D 403/14 | (2006.01) |
| C07D 405/06 | (2006.01) |
| C07D 409/14 | (2006.01) |
| C07D 401/04 | (2006.01) |
| C07D 235/02 | (2006.01) |
| C07D 403/04 | (2006.01) |

(52) U.S. Cl.
CPC ......... *C07D 487/04* (2013.01); *C07D 235/02* (2013.01); *C07D 401/02* (2013.01); *C07D 401/04* (2013.01); *C07D 401/14* (2013.01); *C07D 403/04* (2013.01); *C07D 403/14* (2013.01); *C07D 405/02* (2013.01); *C07D 405/06* (2013.01); *C07D 405/14* (2013.01); *C07D 409/04* (2013.01); *C07D 409/14* (2013.01); *C07D 413/02* (2013.01); *C07D 413/14* (2013.01); *C07D 417/04* (2013.01); *C07D 471/04* (2013.01)

(58) Field of Classification Search
None
See application file for complete search history.

(56) References Cited

U.S. PATENT DOCUMENTS

| | | |
|---|---|---|
| 5,698,567 A | 12/1997 | Guillonneau et al. |
| 7,282,515 B2 | 10/2007 | Meese et al. |
| 2004/0067930 A1 | 4/2004 | Bhatti et al. |
| 2004/0192916 A1 | 9/2004 | Buschmann et al. |
| 2006/0004034 A1 | 1/2006 | Hinze et al. |
| 2007/0254904 A1 | 11/2007 | Janssens et al. |
| 2008/0103183 A1 | 5/2008 | Ackermann et al. |
| 2008/0249122 A1 | 10/2008 | Bignan et al. |
| 2008/0287478 A1 | 11/2008 | Hansen et al. |
| 2009/0247530 A1 | 10/2009 | Nolte et al. |
| 2009/0253727 A1 | 10/2009 | Goehring et al. |
| 2010/0331353 A1 | 12/2010 | Schrimpf et al. |
| 2012/0029006 A1 | 2/2012 | Linz et al. |
| 2017/0197919 A1 | 7/2017 | Kuenert et al. |
| 2017/0197947 A1 | 7/2017 | Kuehnert et al. |
| 2017/0197949 A1 | 7/2017 | Kuehnert et al. |
| 2017/0197970 A1 | 7/2017 | Kuehnert et al. |
| 2017/0197971 A1 | 7/2017 | Kuehnert et al. |
| 2018/0201616 A1 | 7/2018 | Kuehnert et al. |
| 2018/0282341 A1 | 10/2018 | Kuehnert et al. |
| 2019/0016735 A1 | 1/2019 | Smith, II et al. |
| 2019/0016768 A1 | 1/2019 | Chien et al. |
| 2019/0100497 A1 | 4/2019 | Kuehnert et al. |
| 2019/0100515 A1 | 4/2019 | Kuehnert et al. |
| 2019/0106429 A1 | 4/2019 | Kuehnert et al. |
| 2019/0106430 A1 | 4/2019 | Kuehnert et al. |
| 2020/0002319 A1 | 1/2020 | Kuehnert et al. |

FOREIGN PATENT DOCUMENTS

| | | |
|---|---|---|
| CL | 2003-02246 | 5/2004 |
| CL | 2009-00734 | 5/2009 |

(Continued)

OTHER PUBLICATIONS

Schroeder et al., "Functional plasticity of the N/OFQ-NOP receptor system determines analgesic properties of NOP receptor agonists", British Journal of Pharmacology, Apr. 15, 2014, pp. 3777-3800.

(Continued)

*Primary Examiner* — Po-Chih Chen

(74) *Attorney, Agent, or Firm* — Norris McLaughlin, P.A.

(57) ABSTRACT

The invention relates to 3-((hetero-)aryl)-8-amino-2-oxo-1,3-diaza-spiro-[4.5]-decane derivatives, their preparation and their use in medicine, particularly in the treatment of pain.

29 Claims, No Drawings

(56) References Cited

FOREIGN PATENT DOCUMENTS

| | | |
|---|---|---|
| CL | 2013-00266 | 5/2013 |
| CL | 2018-01899 | 11/2013 |
| CL | 2018-01868 | 8/2018 |
| CL | 2018-01909 | 10/2018 |
| CL | 2018-01910 | 10/2018 |
| CL | 2018-01911 | 10/2018 |
| CL | 2018-01912 | 10/2018 |
| CL | 2018-01913 | 10/2018 |
| EP | 1401841 B1 | 8/2005 |
| EP | 1888596 B1 | 11/2006 |
| EP | 1893620 B1 | 11/2006 |
| EP | 2078718 A1 | 7/2009 |
| EP | 2411381 | 9/2010 |
| EP | 2598503 B1 | 2/2012 |
| EP | 2010531 B1 | 11/2017 |
| WO | WO 2004/043967 A1 | 5/2004 |
| WO | WO 2006/122769 A2 | 11/2006 |
| WO | WO 2006/122770 A1 | 11/2006 |
| WO | WO 2007/000325 A2 | 1/2007 |
| WO | WO 2007/124903 A1 | 11/2007 |
| WO | WO 2008/046758 A2 | 4/2008 |
| WO | WO 2009/118168 A1 | 10/2009 |
| WO | WO 2010/108651 A1 | 9/2010 |
| WO | WO 2012/013343 A1 | 2/2012 |
| WO | WO 2015/192039 A1 | 12/2015 |

OTHER PUBLICATIONS

Witkin et al., "The biology of Nociceptin/Orphanin FQ (N/OFQ) related to obesity, stress, anxiety, mood, and drug dependence", Pharmacology & Therapeutics 141, 2014, pp. 283-299, Elsevier.

Jenck et al., "Orphanin FQ acts as an anxiolytic to attenuate behavioral responses to stress", The National Academy of Sciences, Dec. 1997, pp. 14854-14858, vol. 94.

Mabrouk et al., "Stimulation of δ Opioid Receptor and Blockade of Nociceptin/Orphanin FQ Receptor Synergistically Attenuate Parkinsonism", The Journal of Neuroscience, Sep. 24, 2014, vol. 34, No. 19, pp. 12953-12962.

Pradhan et al., "The delta opioid receptor: an evolving target for the treatment of brain disorders", Trends in Pharmacological Sciences, CE Press, Oct. 2011, pp. 581-590, vol. 32, No. 10.

Gupta et al., "A Systematic Review of the Peripheral Analgesic Effects of Intraarticular Morphine", International Anesthesia Research Society, 2001, pp. 761-770, vol. 93.

Kalso et al., "No pain, No gain: clinical excellence and scientific rigour—lessons learned from IA morphine", International Association for the Study of Pain, 2002, pp. 269-275, vol. 98, Elsevier Science B.V.

Stein et al., "Attacking pain at its source: new perspectives on opioids", Nature Medicine, Aug. 2003, pp. 1003-1008, vol. 9, No. 8, Nature Publishing Group.

Zoellner et al., "Topical Fentanyl in a Randomized, Double-blind Study in Patients With Corneal Damage", Clin J Pain, Oct. 2008, pp. 690-696, vol. 24, No. 8, Lippincott Williams & Wilkins.

Bignan et al., "Recent advances towards the discovery of ORL-1 receptor agonists and antagonists", 2005, pp. 357-388, vol. 15, No. 4, Ashley Publications.

U.S. Appl. No. 15/405,482, filed Jan. 13, 2017.
U.S. Appl. No. 15/405,896, filed Jan. 13, 2017.
U.S. Appl. No. 15/405,919, filed Jan. 13, 2017.
U.S. Appl. No. 15/405,627, filed Jan. 13, 2017.

Chu et al., "Synthesis and DNA binding studies of bis-intercalators with a novel spiro-cyclic linke", Tetrahedron, 2006, 62, pp. 5536-5548.

Almutairy, B. et. al., "Development and Characterization of a Floating Drug Delivery System prepared via Hot-Melt Extrusion Technology Coupled with Pressurized CO2 for a Thermo-Labile API," University of Mississippi, 2016, AAPS, Nov. 2016.

3-((HETERO-)ARYL)-8-AMINO-2-OXO-1,3-DIAZA-SPIRO-[4.5]-DECANE DERIVATIVES

This application is a continuation of U.S. patent application Ser. No. 16/207,854, filed Dec. 3, 2018, which is a continuation of U.S. patent application Ser. No. 15/923,948, filed Mar. 16, 2018, abandoned; which is a continuation of U.S. patent application Ser. No. 15/405,485, filed Jan. 13, 2017, abandoned; which claims foreign priority benefit under 35 U.S.C. § 119 of European Patent Application No. 16 151 012.8, filed Jan. 13, 2016, the disclosures of which are incorporated herein by reference.

The invention relates to 3-((hetero-)aryl)-8-amino-2-oxo-1,3-diaza-spiro-[4.5]-decane derivatives, their preparation and use in medicine, particularly in various neurological disorders, including but not limited to pain, neurodegenerative disorders, neuroinflammatory disorders, neuropsychiatric disorders, substance abuse/dependence.

Opioid receptors are a group of Gi/o protein-coupled receptors which are widely distributed in the human body. The opioid receptors are currently subdivided into four major classes, i.e. the three classical opioid receptors mu-opioid (MOP) receptor, kappa-opioid (KOP) receptor, and delta-opioid (DOP) receptor as well as the opioid receptor-like (ORL-1) receptor, which was more recently discovered based on its high homology with said classical opioid receptors. After identification of the endogenous ligand of the ORL-1 receptor, known as nociceptin/orphanin FQ, a highly basic 17 amino acid peptide isolated from tissue extracts in 1995, the ORL-1 receptor was renamed "nociceptin opioid peptide receptor" and abbreviated as "NOP-receptor".

The classical opioid receptors (MOP, KOP and DOP) as well as the NOP receptor are widely distributed/expressed in the human body, including in the brain, the spinal cord, on peripheral sensory neurons and the intestinal tract, wherein the distribution pattern differs between the different receptor classes.

Nociceptin acts at the molecular and cellular level in very much the same way as opioids. However, its pharmacological effects sometimes differ from, and even oppose those of opioids. NOP-receptor activation translates into a complex pharmacology of pain modulation, which, depending on route of administration, pain model and species involved, leads to either pronociceptive or antinociceptive activity. Furthermore, the NOP receptor system is upregulated under conditions of chronic pain. Systemic administration of selective NOP receptor agonists was found to exert a potent and efficacious analgesia in non-human primate models of acute and inflammatory pain in the absence of side effects. The activation of NOP receptors has been demonstrated to be devoid of reinforcing effects but to inhibit opioid-mediated reward in rodents and non-human primates (Review: Schroeder et al, Br J Pharmacol 2014; 171 (16): 3777-3800, and references therein).

Besides the involvement of the NOP receptor in nociception, results from preclinical experiments suggest that NOP receptor agonists might be useful inter alia in the treatment of neuropsychiatric disorders (Witkin et al, Pharmacology & Therapeutics, 141 (2014) 283-299; Jenck et al., Proc. Natl. Acad. Sci. USA 94, 1997, 14854-14858). Remarkably, the DOP receptor is also implicated to modulate not only pain but also neuropsychiatric disorders (Mabrouk et al, 2014; Pradhan et al., 2011).

Strong opioids acting at the MOP receptor site are widely used to treat moderate to severe acute and chronic pain. However, the therapeutic window of strong opioids is limited by severe side effects such as nausea and vomiting, constipation, dizziness, somnolence, respiratory depression, physical dependence and abuse. Furthermore, it is known that MOP receptor agonists show only reduced effectiveness under conditions of chronic and neuropathic pain.

It is known that some of the above mentioned side-effects of strong opioids are mediated by activation of classic opioid-receptors within the central nervous system. Furthermore, peripheral opioid receptors, when activated, can inhibit transmission of nociceptive signals shown in both, clinical and animal studies (Gupta et al., 2001; Kalso et al., 2002; Stein et al., 2003; Zollner et al., 2008).

Thus, to avoid CNS-mediated adverse effects after systemic administration, one approach has been to provide peripherally restricted opioid receptor ligands that do not easily cross the blood-brain barrier and therefore distribute poorly to the central nervous system (see for instance WO 2015/192039). Such peripherally acting compounds might combine effective analgesia with limited side-effects.

Another approach has been to provide compounds which interact with both the NOP receptor and the MOP receptor. Such compounds have for instance been described in WO 2004/043967, WO 2012/013343 and WO 2009/118168.

A further approach has been to provide multi-opioid receptor analgesics that modulate more than one of the opioid receptor subtypes to provide additive or synergistic analgesia and/or reduced side effects like abuse liability or tolerance.

On the one hand, it would be desirable to provide analgesics that selectively act on the NOP receptor system but less pronounced on the classic opioid receptor system, especially MOP receptor system, whereas it would be desirable to distinguish between central nervous activity and peripheral nervous activity. On the other hand, it would be desirable to provide analgesics that act on the NOP receptor system and also to a balanced degree on the MOP receptor system, whereas it would be desirable to distinguish between central nervous activity and peripheral nervous activity.

There is a need for medicaments which are effective in the treatment of pain and which have advantages compared to the compounds of the prior art. Where possible, such medicaments should contain such a small dose of active ingredient that satisfactory pain therapy can be ensured without the occurrence of intolerable treatment-emergent adverse events.

It is an object of the invention to provide pharmacologically active compounds, preferably analgesics that have advantages compared to the prior art.

This object has been achieved by the subject-matter of the patent claims.

A first aspect of the invention relates to 3-((hetero-)aryl)-8-amino-2-oxo-1,3-diaza-spiro-[4.5]-decane derivatives according to general formula (I)

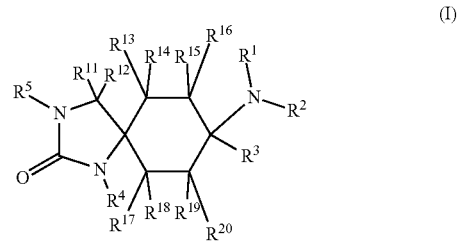

wherein
$R^1$ and $R^2$ independently of one another mean
—H;
—$C_1$-$C_6$-alkyl, linear or branched, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$;
a 3-12-membered cycloalkyl moiety, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$; wherein said 3-12-membered cycloalkyl moiety is optionally connected through —$C_1$-$C_6$-alkylene-, linear or branched, saturated or unsaturated, unsubstituted; or
a 3-12-membered heterocycloalkyl moiety, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$; wherein said 3-12-membered heterocycloalkyl moiety is optionally connected through —$C_1$-$C_6$-alkylene-, linear or branched, saturated or unsaturated, unsubstituted;
or
$R^1$ and $R^2$ together with the nitrogen atom to which they are attached form a ring and mean —(CH$_2$)$_{3-6}$—; —(CH$_2$)$_2$—O—(CH$_2$)$_2$—; or —(CH$_2$)$_2$—NR$^A$—(CH$_2$)$_2$—, wherein R$^A$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;
preferably with the proviso that $R^1$ and $R^2$ do not simultaneously mean —H;
$R^3$ means
—$C_1$-$C_6$-alkyl, linear or branched, saturated or unsaturated, unsubstituted, mono- or polysubstituted;
a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;
a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted;
a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or
a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted;
$R^4$ means
—H;
—$C_1$-$C_6$-alkyl, linear or branched, saturated or unsaturated, unsubstituted, mono- or polysubstituted; wherein said —$C_1$-$C_6$-alkyl is optionally connected through —C(=O)—, —C(=O)O—, or —S(=O)$_2$—;
a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted; or wherein said 3-12-membered cycloalkyl moiety is optionally connected through —C(=O)—, —C(=O)O—, —C(=O)O—CH$_2$—, or —S(=O)$_2$—;
a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted; or wherein said 3-12-membered heterocycloalkyl moiety is optionally connected through —C(=O)—, —C(=O)O—, —C(=O)O—CH$_2$—, or —S(=O)$_2$—;
a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or wherein said 6-14-membered aryl moiety is optionally connected through —C(=O)—, —C(=O)O—, —C(=O)O—CH$_2$—, or —S(=O)$_2$—; or
a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted; or wherein said 5-14-membered heteroaryl moiety is optionally connected through —C(=O)—, —C(=O)O—, —C(=O)O—CH$_2$—, or —S(=O)$_2$—;
$R^5$ means
a 6-14-membered aryl moiety, unsubstituted, mono- or polysubstituted; or
a 5-14-membered heteroaryl moiety, unsubstituted, mono- or polysubstituted;
$R^{11}$, $R^{12}$, $R^{13}$, $R^{14}$, $R^{15}$, $R^{16}$, $R^{17}$, $R^{18}$, $R^{19}$, and $R^{20}$ independently of one another mean —H, —F, —Cl, —Br, —I, —OH, or —$C_1$-$C_6$-alkyl, linear or branched, saturated or unsaturated, unsubstituted, mono- or polysubstituted;
wherein "mono- or polysubstituted" means that one or more hydrogen atoms are replaced by a substituent independently of one another selected from the group consisting of —F, —Cl, —Br, —I, —CN, —R$^{21}$, —C(=O)R$^{21}$, —C(=O)OR$^{21}$, —C(=O)NR$^{21}$R$^{22}$, —C(=O)NH—(CH$_2$CH$_2$—O)$_{1-30}$—CH$_3$, —O—(CH$_2$CH$_2$—O)$_{1-30}$—H, —O—(CH$_2$CH$_2$—O)$_{1-30}$—CH$_3$, =O, —OR$^{21}$, —OC(=O)R$^{21}$, —OC(=O)OR$^{21}$, —OC(=O)NR$^{21}$R$^{22}$, —NO$_2$, —NR$^{21}$R$^{22}$, —NR$^{21}$—(CH$_2$)$_{1-6}$—C(=O)R$^{22}$, —NR$^{21}$—(CH$_2$)$_{1-6}$—C(=O)OR$^{22}$, —NR$^{23}$—(CH$_2$)$_{1-6}$—C(=O)NR$^{21}$R$^{22}$, —NR$^{21}$C(=O)R$^{22}$, —NR$^{21}$C(=O)—OR$^{22}$, —NR$^{23}$C(=O)NR$^{21}$R$^{22}$, —NR$^{21}$S(=O)$_2$R$^{22}$, —SR$^{21}$, —S(=O)R$^{21}$, —S(=O)$_2$R$^{21}$, —S(=O)$_2$OR$^{21}$, and —S(=O)$_2$NR$^{21}$R$^{22}$;
wherein
$R^{21}$, $R^{22}$ and $R^{23}$ independently of one another mean
—H;
—$C_1$-$C_6$-alkyl, linear or branched, saturated or unsaturated, unsubstituted or substituted with one, two, three or four substituents independently of one another selected from the group consisting of —F, —Cl, —Br, —I, —CN, —OH, —NH$_2$, —CO$_2$H, —C(=O)O—$C_1$-$C_6$-alkyl, —C(=O)NH$_2$, —C(=O)NHC$_1$-$C_6$-alkyl, —C(=O)N(C$_1$-$C_6$-alkyl)$_2$, —O—$C_1$-$C_6$-alkyl and —S(=O)$_2$—$C_1$-$C_6$-alkyl;
a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;

a 3-12-membered heterocycloalkyl moiety, saturated or unsaturated, unsubstituted, mono- or polysubstituted; wherein said 3-12-membered heterocycloalkyl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;

a 6-14-membered aryl moiety, unsubstituted, mono- or polysubstituted; wherein said 6-14-membered aryl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;

a 5-14-membered heteroaryl moiety, unsubstituted, mono- or polysubstituted; wherein said 5-14-membered heteroaryl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;

or $R^{21}$ and $R^{22}$ within —C(=O)NR$^{21}$R$^{22}$, —OC(=O)NR$^{21}$R$^{22}$, —NR$^{21}$R$^{22}$, —NR$^{23}$—(CH$_2$)$_{1-6}$—C(=O)NR$^{21}$R$^{22}$, —NR$^{23}$C(=O)NR$^{21}$R$^{22}$, or —S(=O)$_2$NR$^{21}$R$^{22}$ together with the nitrogen atom to which they are attached form a ring and mean —(CH$_2$)$_{3-6}$—; —(CH$_2$)$_2$—O—(CH$_2$)$_2$—; —(CH$_2$)$_2$—S(=O)$_2$—(CH$_2$)$_2$— or —(CH$_2$)$_2$—NR$^B$—(CH$_2$)$_2$—, wherein R$^B$ means —H, —C$_1$-C$_6$-alkyl, —C(=O)—C$_1$-C$_6$-alkyl, or —S(=O)$_2$—C$_1$-C$_6$-alkyl, wherein said —C$_1$-C$_6$-alkyl is linear or branched, saturated or unsaturated, unsubstituted or substituted with one, two, three or four substituents independently of one another selected from the group consisting of —F, —Cl, —Br —I, —OH, —CO$_2$H, —C(=O)O—C$_1$-C$_6$-alkyl and —C(=O)NH$_2$; and wherein said ring is unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;

or a physiologically acceptable salt thereof.

"(Hetero-)aryl" means "heteroaryl or aryl". Preferably, aryl includes but is not limited to phenyl and naphthyl. Preferably, heteroaryl includes but is not limited to -1,2-benzodioxole, -pyrazinyl, -pyridazinyl, -pyridinyl, -pyrimidinyl, -thienyl, -imidazolyl, -benzimidazolyl, -thiazolyl, -1,3,4-thiadiazolyl, -benzothiazolyl, -oxazolyl, -benzoxazolyl, -pyrazolyl, -quinolinyl, -isoquinolinyl, -quinazolinyl, -indolyl, -indolinyl, -benzo[c][1,2,5]oxadiazolyl, -imidazo[1,2-a]pyrazinyl, or -1H-pyrrolo[2,3-b]pyridinyl. Preferably, cycloalkyl includes but is not limited to -cyclopropyl, -cyclobutyl, -cyclopentyl and -cyclohexyl. Preferably, heterocycloalkyl includes but is not limited to -aziridinyl, -azetidinyl, -pyrrolidinyl, -piperidinyl, -piperazinyl, -morpholinyl, -sulfamorpholinyl, -oxiridinyl, -oxetanyl, -tetrahydropyranyl, and -pyranyl.

When a moiety is connected through an asymmetric group such as —C(=O)O— or —C(=O)O—CH$_2$—, said asymmetric group may be arranged in either direction. For example, when R$^4$ is connected to the core structure through —C(=O)O—, the arrangement may be either R$^4$—C(=O)O-core or core-C(=O)O—R$^4$.

In preferred embodiments of the compound according to the invention, $R^{11}$, $R^{12}$, $R^{13}$, $R^{14}$, $R^{15}$, $R^{16}$, $R^{17}$, $R^{18}$, $R^{19}$, and $R^{20}$ independently of one another mean —H, —F, —OH, or —C$_1$-C$_6$-alkyl; preferably —H.

In a preferred embodiment of the compound according to the invention, $R^1$ means —H; and $R^2$ means —C$_1$-C$_6$-alkyl, linear or branched, saturated or unsaturated, unsubstituted, mono- or polysubstituted. Preferably, $R^1$ means —H and $R^2$ means —CH$_3$.

In another preferred embodiment of the compound according to the invention, $R^1$ means —CH$_3$; and $R^2$ means —C$_1$-C$_6$-alkyl, linear or branched, saturated or unsaturated, unsubstituted, mono- or polysubstituted. Preferably, $R^1$ means —CH$_3$ and $R^2$ means —CH$_3$.

In still another preferred embodiment of the compound according to the invention, $R^1$ and $R^2$ together with the nitrogen atom to which they are attached form a ring and mean —(CH$_2$)$_{3-6}$—. Preferably, $R^1$ and $R^2$ together with the nitrogen atom to which they are attached form a ring and mean —(CH$_2$)$_3$—.

In yet another preferred embodiment,
$R^1$ means —H or —CH$_3$; and
$R^2$ means a 3-12-membered cycloalkyl moiety, saturated or unsaturated, unsubstituted; wherein said 3-12-membered cycloalkyl moiety is connected through —CH$_2$—, unsubstituted; preferably —CH$_2$-cycloalkyl, —CH$_2$-cyclobutyl or —CH$_2$-cyclopentyl; or $R^2$ means a 3-12-membered heterocycloalkyl moiety, saturated or unsaturated, unsubstituted; wherein said 3-12-membered heterocycloalkyl moiety is connected through —CH$_2$—, unsubstituted; preferably —CH$_2$-oxetanyl or —CH$_2$-tetrahydrofuranyl.

In a preferred embodiment of the compound according to the invention, $R^3$ means —C$_1$-C$_6$-alkyl, linear or branched, saturated or unsaturated, unsubstituted, mono- or polysubstituted. Preferably, $R^3$ means —C$_1$-C$_6$-alkyl, linear or branched, saturated or unsaturated, unsubstituted or monosubstituted with —OCH$_3$.

In another preferred embodiment of the compound according to the invention, $R^3$ means a 6-14-membered aryl moiety, unsubstituted, mono- or polysubstituted, optionally connected through —C$_1$-C$_6$-alkylene-, linear or branched, saturated or unsaturated, unsubstituted. In a preferred embodiment, $R^3$ means -phenyl unsubstituted, mono- or polysubstituted. More preferably, $R^3$ means -phenyl unsubstituted, mono- or disubstituted with —F, —Cl, —CH$_3$, —CF$_3$, —OH, —OCH$_3$, —OCF$_3$ or —OCH$_2$OCH$_3$, preferably —F. In another preferred embodiment, $R^3$ means -benzyl unsubstituted, mono- or polysubstituted. More preferably, $R^3$ means -benzyl unsubstituted, mono- or disubstituted with —F, —Cl, —CH$_3$, —CF$_3$, —OH, —OCH$_3$, —OCF$_3$ or —OCH$_2$OCH$_3$, preferably —F.

In still another preferred embodiment of the compound according to the invention, $R^3$ means a 5-14-membered heteroaryl moiety, unsubstituted, mono- or polysubstituted. Preferably, $R^3$ means -thienyl or -pyridinyl, in each case unsubstituted, mono- or polysubstituted. More preferably, $R^3$ means -thienyl, -pyridinyl, -imidazolyl or benzimidazolyl, in each case unsubstituted or monosubstituted with —F, —Cl or —CH$_3$.

In a preferred embodiment of the compound according to the invention, $R^4$ means —H.

In another preferred embodiment of the compound according to the invention, $R^4$ means —C$_1$-C$_6$-alkyl, linear or branched, saturated or unsaturated, unsubstituted, monoor polysubstituted. Preferably, $R^4$ means —$C_1$-$C_6$-alkyl, linear or branched, saturated or unsaturated, unsubstituted or monosubstituted with a substituent selected from the group consisting of —F, —Cl, —Br, —I, —CN, —$CF_3$, —OH, —O—$C_1$-$C_4$-alkyl, —$OCF_3$, —O—$(CH_2CH_2—O)_{1-30}$—H, —O—$(CH_2CH_2—O)_{1-30}$—$CH_3$, —OC(=O)$C_1$-$C_4$-alkyl, —C(=O)$C_1$-$C_4$-alkyl, —C(=O)OH, —C(=O)O$C_1$-$C_4$-alkyl, —C(=O)$NH_2$, —C(=O)NH$C_1$-$C_4$-alkyl, —C(=O)NH$C_1$-$C_4$-alkylene-CN, —C(=O)NH$C_1$-$C_4$-alkylene-O—$C_1$-$C_4$-alkyl, —C(=O)N($C_1$-$C_4$-alkyl)$_2$; —S(=O)$C_1$-$C_4$-alkyl, and —S(=O)$_2$$C_1$-$C_4$-alkyl; or with —C(=O)$NR^{21}R^{22}$ wherein $R^{21}$ and $R^{22}$ together with the nitrogen atom to which they are attached form a ring and mean —$(CH_2)_{3-6}$—, —$(CH_2)_2$—O—$(CH_2)_2$—, or —$(CH_2)_2$—$NR^B$—$(CH_2)_2$—, wherein $R^B$ means —H or —$C_1$-$C_6$-alkyl; or with —C(=O)NH-3-12-membered cycloalkyl, saturated or unsaturated, unsubstituted or monosubstituted with —F, —Cl, —Br, —I, —CN, or —OH; or with —C(=O)NH-3-12-membered heterocycloalkyl, saturated or unsaturated, unsubstituted or monosubstituted with —F, —Cl, —Br, —I, —CN, or —OH. More preferably, $R^4$ means —$C_1$-$C_6$-alkyl, linear or branched, saturated or unsaturated, unsubstituted or monosubstituted with —O—$C_1$-$C_4$-alkyl or —C(=O)N($C_1$-$C_4$-alkyl)$_2$.

In still another preferred embodiment of the compound according to the invention, $R^4$ means a 3-12-membered cycloalkyl moiety, saturated or unsaturated, unsubstituted, mono- or polysubstituted; wherein the 3-12-membered cycloalkyl moiety is connected through —$C_1$-$C_6$-alkylene-, linear or branched, saturated or unsaturated, unsubstituted, mono- or polysubstituted. Preferably, $R^4$ means a 3-12-membered cycloalkyl moiety, saturated or unsaturated, unsubstituted, mono- or polysubstituted; wherein said 3-12-membered cycloalkyl moiety is connected through —$CH_2$— or —$CH_2CH_2$—. More preferably, $R^4$ means a 3-12-membered cycloalkyl moiety, saturated or unsaturated, unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2$$C_1$-$C_4$-alkyl; wherein said 3-12-membered cycloalkyl moiety is connected through —$CH_2$— or —$CH_2CH_2$—.

In a preferred embodiment of the compound according to the invention, $R^4$ means a 3-12-membered heterocycloalkyl moiety, saturated or unsaturated, unsubstituted, mono- or polysubstituted; wherein said 3-12-membered heterocycloalkyl moiety is connected through —$C_1$-$C_6$-alkylene-, linear or branched, saturated or unsaturated, unsubstituted, mono- or polysubstituted. Preferably, $R^4$ means a 3-12-membered heterocycloalkyl moiety, saturated or unsaturated, unsubstituted, mono- or polysubstituted; wherein said 3-12-membered heterocycloalkyl moiety is connected through —$CH_2$— or —$CH_2CH_2$—. More preferably, $R^4$ means -oxetanyl, -tetrahydrofuranyl or -tetrahydropyranyl, in each case unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2$$C_1$-$C_4$-alkyl; wherein said -oxetanyl, -tetrahydrofuranyl or -tetrahydropyranyl is connected through —$CH_2$— or —$CH_2CH_2$—.

In yet another preferred embodiment of the compound according to the invention, $R^4$ means a 6-14-membered aryl moiety, unsubstituted, mono- or polysubstituted; wherein said 6-14-membered aryl moiety is connected through —$C_1$-$C_6$-alkylene-, linear or branched, saturated or unsaturated, unsubstituted, mono- or polysubstituted. Preferably, $R^4$ means -phenyl, unsubstituted, mono- or polysubstituted; wherein said -phenyl is connected through —$CH_2$— or —$CH_2CH_2$—. More preferably, $R^4$ means -phenyl, unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2$$C_1$-$C_4$-alkyl; wherein said -phenyl is connected through —$CH_2$— or —$CH_2CH_2$—.

In a further preferred embodiment of the compound according to the invention, $R^4$ means a 5-14-membered heteroaryl moiety, unsubstituted, mono- or polysubstituted; wherein said 5-14-membered heteroaryl moiety is connected through —$C_1$-$C_6$-alkylene-, linear or branched, saturated or unsaturated, unsubstituted, mono- or polysubstituted. Preferably, $R^4$ means a 5-14-membered heteroaryl moiety, unsubstituted, mono- or polysubstituted; wherein said -phenyl is connected through —$CH_2$— or —$CH_2CH_2$—. More preferably, $R^4$ means -pyridinyl, -pyrimidinyl, -pyrazinyl, or -pyrazolinyl, in each case unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2$$C_1$-$C_4$-alkyl; wherein said -pyridinyl, -pyrimidinyl, -pyrazinyl, or -pyrazolinyl is connected through —$CH_2$— or —$CH_2CH_2$—.

In a preferred embodiment of the compound according to the invention, $R^5$ means -phenyl, unsubstituted, mono- or polysubstituted. Preferably, $R^5$ means -phenyl unsubstituted or substituted with one, two, three or four substituents independently of one another selected from the group consisting of —F; —Cl; —Br; —I; —CN; —OH; —$C_1$-$C_4$-alkyl; —$CF_3$; -3-12-membered cycloalkyl, saturated or unsaturated, unsubstituted, mono- or polysubstituted; preferably -cyclopropyl, saturated, unsubstituted; -3-12-membered heterocycloalkyl, saturated or unsaturated, unsubstituted, mono- or polysubstituted; preferably -pyrrolidinyl, -piperidinyl, -morpholinyl, -piperazinyl, -thiomorpholinyl, or -thiomorpholinyl dioxide, in each case saturated, unsubstituted or monosubstituted with —$C_1$-$C_4$-alkyl; -6-14-membered aryl, unsubstituted, mono- or polysubstituted; preferably -phenyl, unsubstituted; —O—$C_1$-$C_4$-alkyl; —S—$C_1$-$C_4$-alkyl; —C(=O)OH; —C(=O)O—$C_1$-$C_4$-alkyl; —C(=O)$NH_2$; —C(=O)NH$C_1$-$C_4$-alkyl; —C(=O)N($C_1$-$C_4$-alkyl)$_2$; —C(=O)N($C_1$-$C_4$-alkyl)($C_1$-$C_4$-alkyl-OH); —C(=O)NH—$(CH_2)_{1-3}$-3-12-membered cycloalkyl, saturated or unsaturated, unsubstituted or monosubstituted with —OH; preferably —C(=O)NH—$(CH_2)_{1-3}$-cyclobutyl, saturated or unsaturated, unsubstituted or monosubstituted with —OH; —C(=O)-3-12-membered heterocycloalkyl, saturated or unsaturated, unsubstituted, mono- or polysubstituted; preferably —C(=O)-morpholinyl, saturated, unsubstituted; —S(=O)$C_1$-$C_4$-alkyl; —S(=O)$_2$$C_1$-$C_4$-alkyl; and —S(=O)$_2$N($C_1$-$C_4$-alkyl)$_2$.

In another preferred embodiment of the compound according to the invention, $R^5$ means -1,2-benzodioxole, -pyrazinyl, -pyridazinyl, -pyridinyl, -pyrimidinyl, -thienyl, -imidazolyl, -benzimidazolyl, -thiazolyl, -1,3,4-thiadiazolyl, -benzothiazolyl, -oxazolyl, -benzoxazolyl, -pyrazolyl, -quinolinyl, -isoquinolinyl, -quinazolinyl, -indolyl, -indolinyl, benzo[c][1,2,5]oxadiazolyl, -imidazo[1,2-a]pyrazinyl, or -1H-pyrrolo[2,3-b]pyridinyl, in each case unsubstituted, mono- or polysubstituted; preferably -pyrazinyl, -pyridazinyl, -pyridinyl, -pyrimidinyl, or -thienyl, in each case unsubstituted, mono- or polysubstituted. Preferably, $R^5$ means -pyrazinyl, -pyridazinyl, -pyridinyl, -pyrimidinyl, or -thienyl, in each case unsubstituted or substituted with one, two, three or four substituents independently of one another selected from the group consisting of —F; —Cl; —Br; —I; —CN; —OH; —$C_1$-$C_4$-alkyl; —$CF_3$; -3-12-membered cycloalkyl, saturated or unsaturated, unsubstituted, mono- or polysubstituted; preferably -cyclopropyl, saturated, unsubstituted; -3-12-membered heterocycloalkyl, saturated or unsaturated, unsubstituted, mono- or polysubstituted; preferably -pyrrolidinyl, -piperidinyl, -morpholinyl, -piperazinyl, -thiomorpholinyl, or -thiomorpholinyl dioxide, in each case saturated, unsubstituted or monosubstituted with —$C_1$-$C_4$-alkyl; -6-14-membered aryl, unsubstituted, mono- or polysubstituted; preferably -phenyl, unsubstituted; —O—$C_1$-$C_4$-alkyl; —S—$C_1$-$C_4$-alkyl; —C(=O)OH; —C(=O)O—$C_1$-$C_4$-alkyl; —C(=O)$NH_2$; —C(=O)$NHC_1$-$C_4$-alkyl; —C(=O)N($C_1$-$C_4$-alkyl)$_2$; —C(=O)N($C_1$-$C_4$-alkyl)($C_1$-$C_4$-alkyl-OH); —C(=O)NH—($CH_2$)$_{1-3}$-3-12-membered cycloalkyl, saturated or unsaturated, unsubstituted or monosubstituted with —OH; preferably —C(=O)NH—($CH_2$)$_{1-3}$-cyclobutyl, saturated or unsaturated, unsubstituted or monosubstituted with —OH; —C(=O)-3-12-membered heterocycloalkyl, saturated or unsaturated, unsubstituted, mono- or polysubstituted; preferably —C(=O)-morpholinyl, saturated, unsubstituted; —S(=O)$C_1$-$C_4$-alkyl; —S(=O)$_2$$C_1$-$C_4$-alkyl; and —S(=O)$_2$N($C_1$-$C_4$-alkyl)$_2$.

In still another preferred embodiment of the compound according to the invention, $R^5$ means a bicyclic 9-10-membered heteroaryl moiety, unsubstituted, mono- or polysubstituted. Preferably, $R^5$ means imidazo[1,2-a]pyrazine, unsubstituted or monosubstituted with —$C_1$-$C_4$-alkyl.

Preferably, $R^5$ means -phenyl, -1,2-benzodioxole, -pyrazinyl, -pyridazinyl, -pyridinyl, -pyrimidinyl, -thienyl, -imidazolyl, -benzimidazolyl, -thiazolyl, -1,3,4-thiadiazolyl, -benzothiazolyl, -oxazolyl, -benzoxazolyl, -pyrazolyl, -quinolinyl, -isoquinolinyl, -quinazolinyl, -indolyl, -indolinyl, -benzo[c][1,2,5]oxadiazolyl, -imidazo[1,2-a]pyrazinyl, or -1H-pyrrolo[2,3-b]pyridinyl, in each case unsubstituted or substituted with one, two, three or four substituents independently of one another selected from the group consisting of
—F; —Cl; —Br; —I;
—CN; —$C_1$-$C_4$-alkyl; —$CF_3$; —$C_1$-$C_4$-alkyl-C(=O)$NH_2$; —$C_1$-$C_4$-alkyl-S(=O)$_2$—$C_1$-$C_4$-alkyl;
—C(=O)—$C_1$-$C_4$-alkyl; —C(=O)OH; —C(=O)O—$C_1$-$C_4$-alkyl; —C(=O)$NH_2$; —C(=O)$NHC_1$-$C_4$-alkyl; —C(=O)N($C_1$-$C_4$-alkyl)$_2$; —C(=O)NH($C_1$-$C_4$-alkyl-OH); —C(=O)N($C_1$-$C_4$-alkyl)($C_1$-$C_4$-alkyl-OH); —C(=O)NH—($CH_2CH_2O$)$_{1-30}$—$CH_3$;
—$NH_2$; —$NHC_1$-$C_4$-alkyl; —N($C_1$-$C_4$-alkyl)$_2$; —$NHC_1$-$C_4$-alkyl-OH; —$NCH_3$$C_1$-$C_4$-alkyl-OH; —NH—$C_1$-$C_4$-alkyl-C(=O)$NH_2$; —$NCH_3$—$C_1$-$C_4$-alkyl-C(=O)$NH_2$; —NHC(=O)—$C_1$-$C_4$-alkyl; —$NCH_3$C(=O)—$C_1$-$C_4$-alkyl;
—OH; —O—$C_1$-$C_4$-alkyl; —$OCF_3$; —O—$C_1$-$C_4$-alkyl-$CO_2H$; —O—$C_1$-$C_4$-alkyl-C(=O)O—$C_1$-$C_4$-alkyl; —O—$C_1$-$C_4$-alkyl-$CONH_2$;
—S—$C_1$-$C_4$-alkyl; —S(=O)$C_1$-$C_4$-alkyl; —S(=O)$_2$$C_1$-$C_4$-alkyl; and —S(=O)$_2$N($C_1$-$C_4$-alkyl)$_2$;

-3-12-membered cycloalkyl, saturated or unsaturated, unsubstituted, mono- or polysubstituted; wherein said 3-12-membered cycloalkyl is optionally connected through —$CH_2$—, —NH—, —$NCH_3$—, —NH—($CH_2$)$_{1-3}$—, —$NCH_3$($CH_2$)$_{1-3}$—, —(C=O)—, —NHC(=O)—, —$NCH_3$C(=O)—, —C(=O)NH—($CH_2$)$_{1-3}$—, —C(=O)$NCH_3$—($CH_2$)$_{1-3}$—;
-3-12-membered heterocycloalkyl, saturated or unsaturated, unsubstituted, mono- or polysubstituted; wherein said 3-12-membered heterocycloalkyl is optionally connected through —$CH_2$—, —NH—, —$NCH_3$—, —NH—($CH_2$)$_{1-3}$—, —$NCH_3$($CH_2$)$_{1-3}$—, —(C=O)—, —NHC(=O)—, —$NCH_3$C(=O)—, —C(=O)NH—($CH_2$)$_{1-3}$—, —C(=O)$NCH_3$—($CH_2$)$_{1-3}$—;
-6-14-membered aryl, unsubstituted, mono- or polysubstituted; wherein said 6-14-membered aryl is optionally connected through —$CH_2$—, —NH—, —$NCH_3$—, —NH—($CH_2$)$_{1-3}$—, —$NCH_3$($CH_2$)$_{1-3}$—, —(C=O)—, —NHC(=O)—, —$NCH_3$C(=O)—, —C(=O)NH—($CH_2$)$_{1-3}$—, —C(=O)$NCH_3$—($CH_2$)$_{1-3}$—; or
-5-14-membered heteroaryl, unsubstituted, mono- or polysubstituted; wherein said 5-14-membered heteroaryl is optionally connected through —$CH_2$—, —NH—, —$NCH_3$—, —NH—($CH_2$)$_{1-3}$—, —$NCH_3$($CH_2$)$_{1-3}$—, —(C=O)—, —NHC(=O)—, —$NCH_3$C(=O)—, —C(=O)NH—($CH_2$)$_{1-3}$—, —C(=O)$NCH_3$—($CH_2$)$_{1-3}$—.

In preferred embodiments, the compound according to the invention has a structure according to any of general formulas (II-A) to (VIII-C):

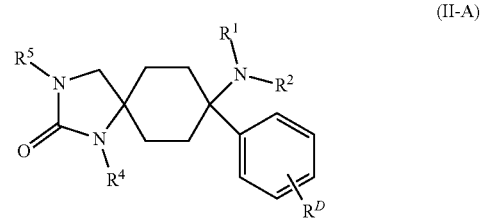

(II-A)

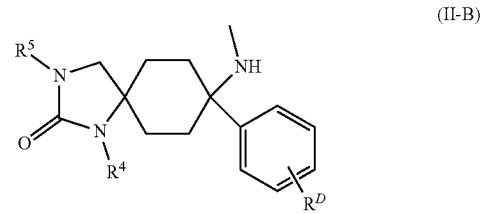

(II-B)

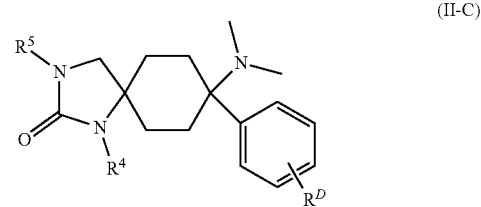

(II-C)

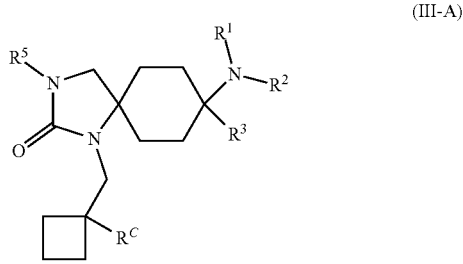

(III-A)

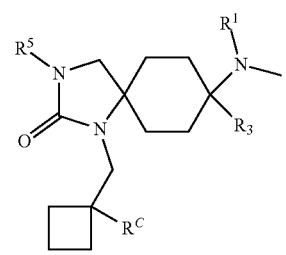
(III-B)
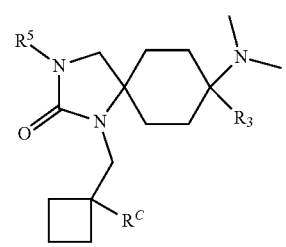
(III-C)
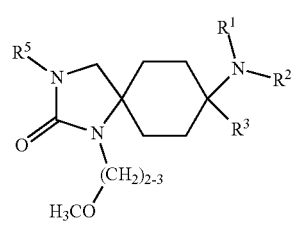
(IV-A)
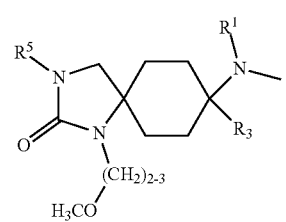
(IV-B)
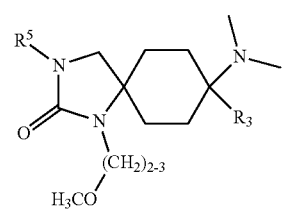
(IV-C)
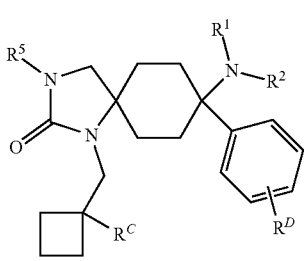
(V-A)
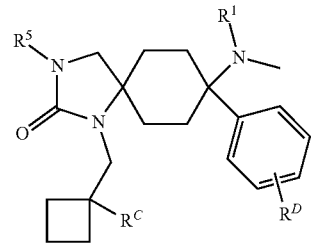
(V-B)
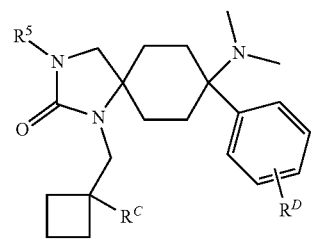
(V-C)
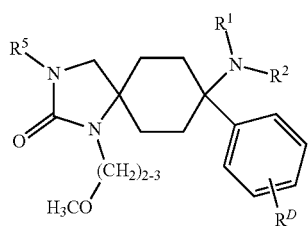
(VI-A)
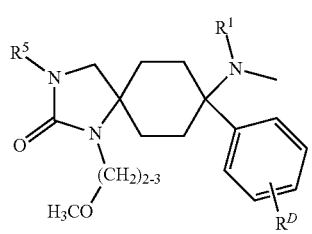
(VI-B)
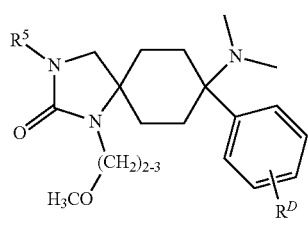
(VI-C)
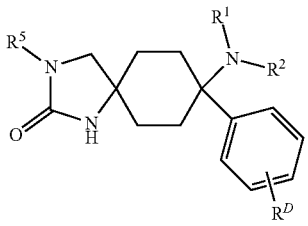
(VII-A)
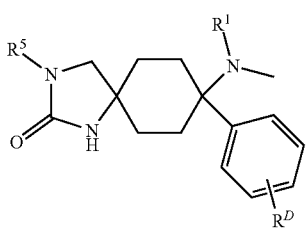
(VII-B)

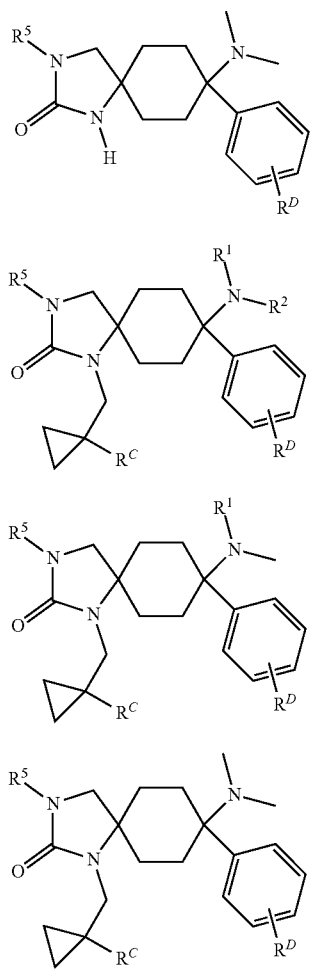
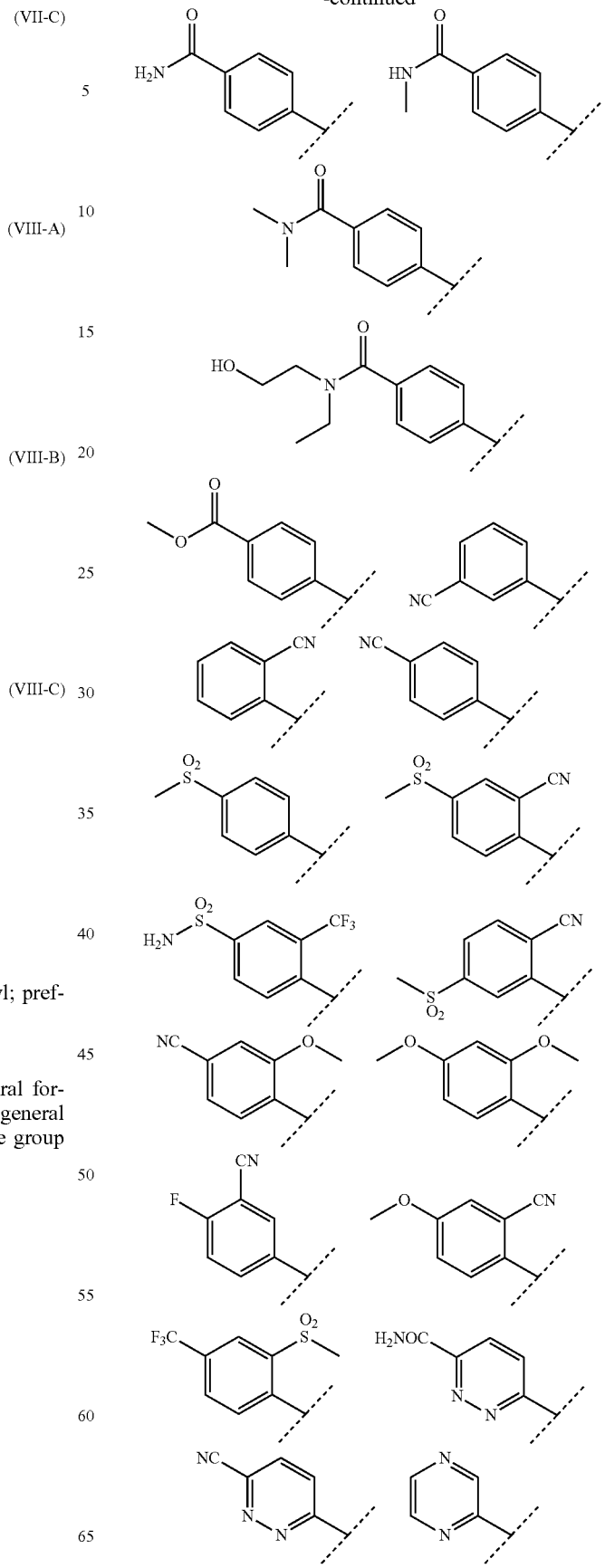
wherein in each case
R¹, R², R³, R⁴, and R⁵ are defined as above,
$R^C$ means —H, —OH, —F, —CN or —C₁-C₄-alkyl; preferably —H or —OH;
$R^D$ means —H or —F;
or a physiologically acceptable salt thereof.
Preferably, in the compounds according to general formula (I) or any of the compounds according to general formulas (II-A) to (VIII-C), R⁵ is selected from the group consisting of:
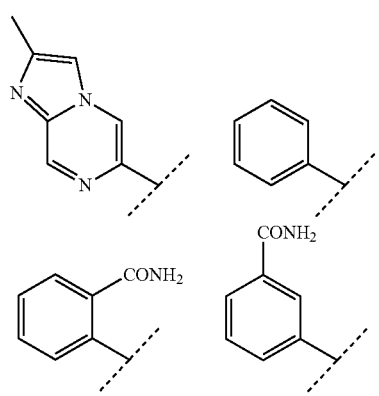

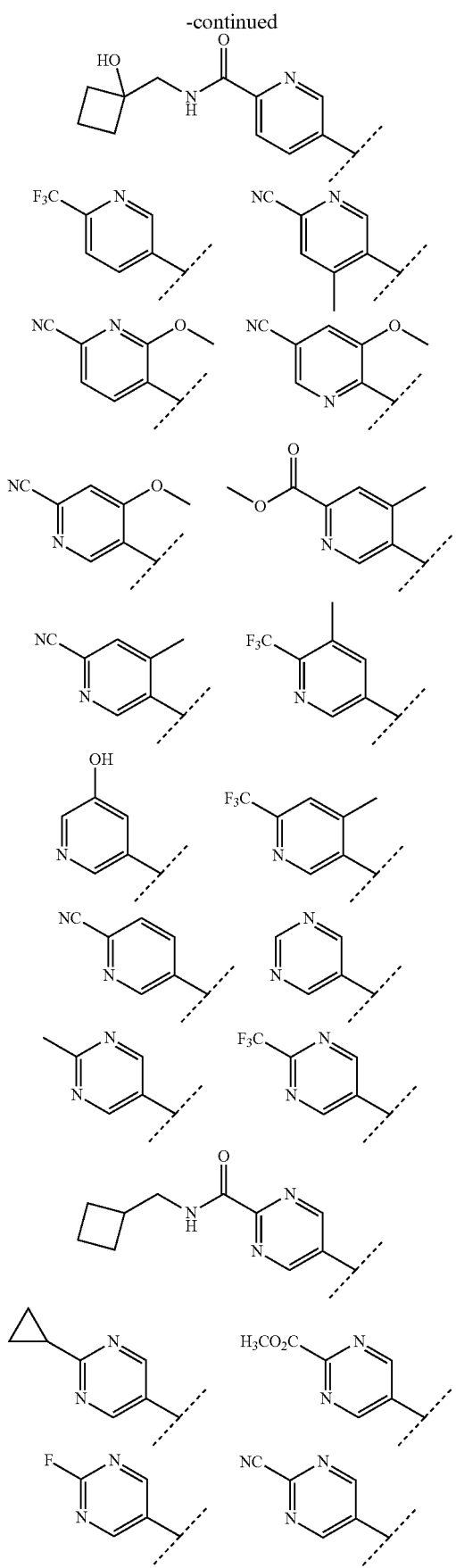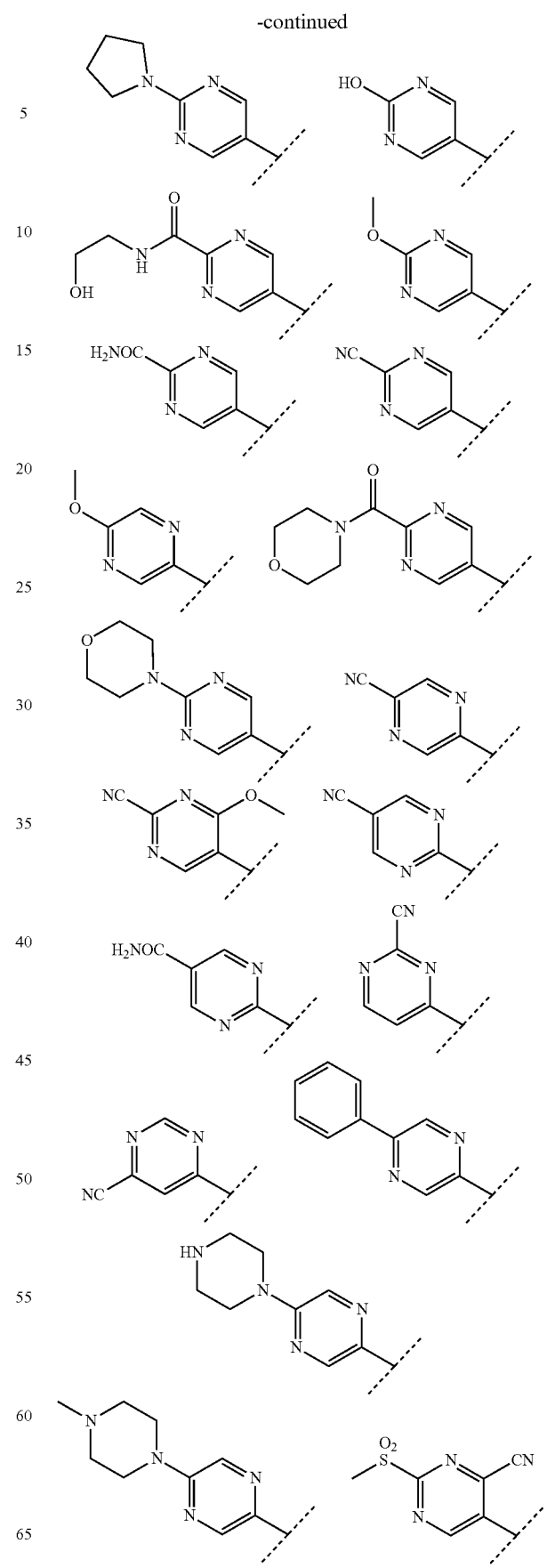

-continued
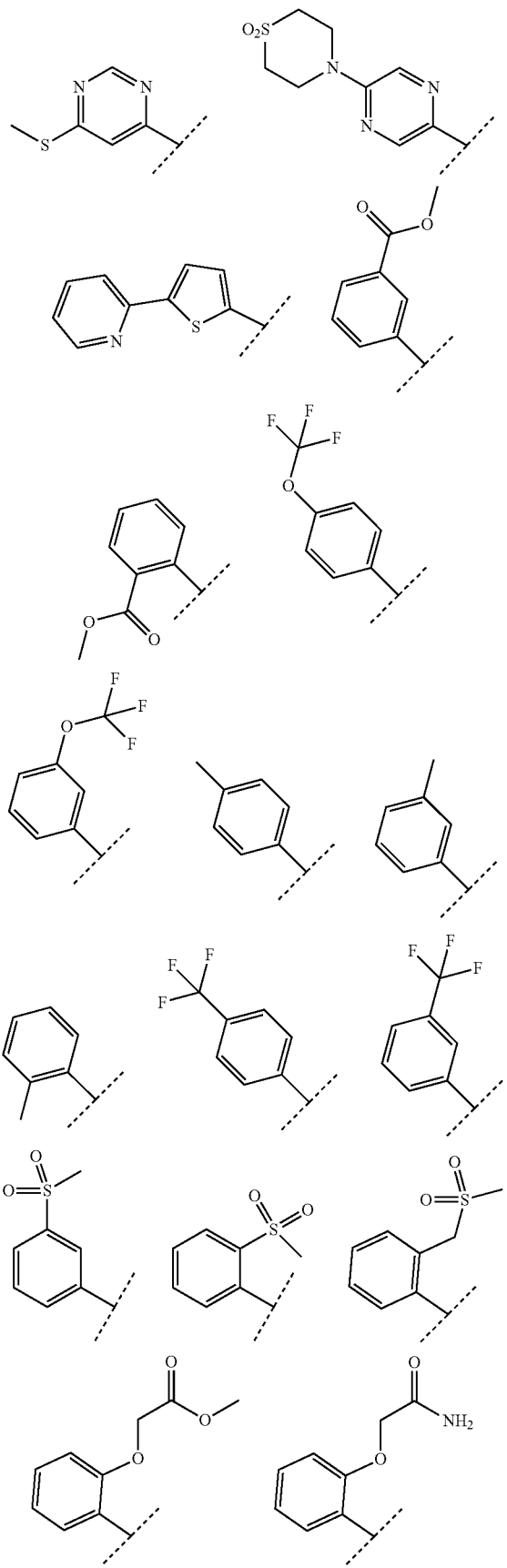
-continued
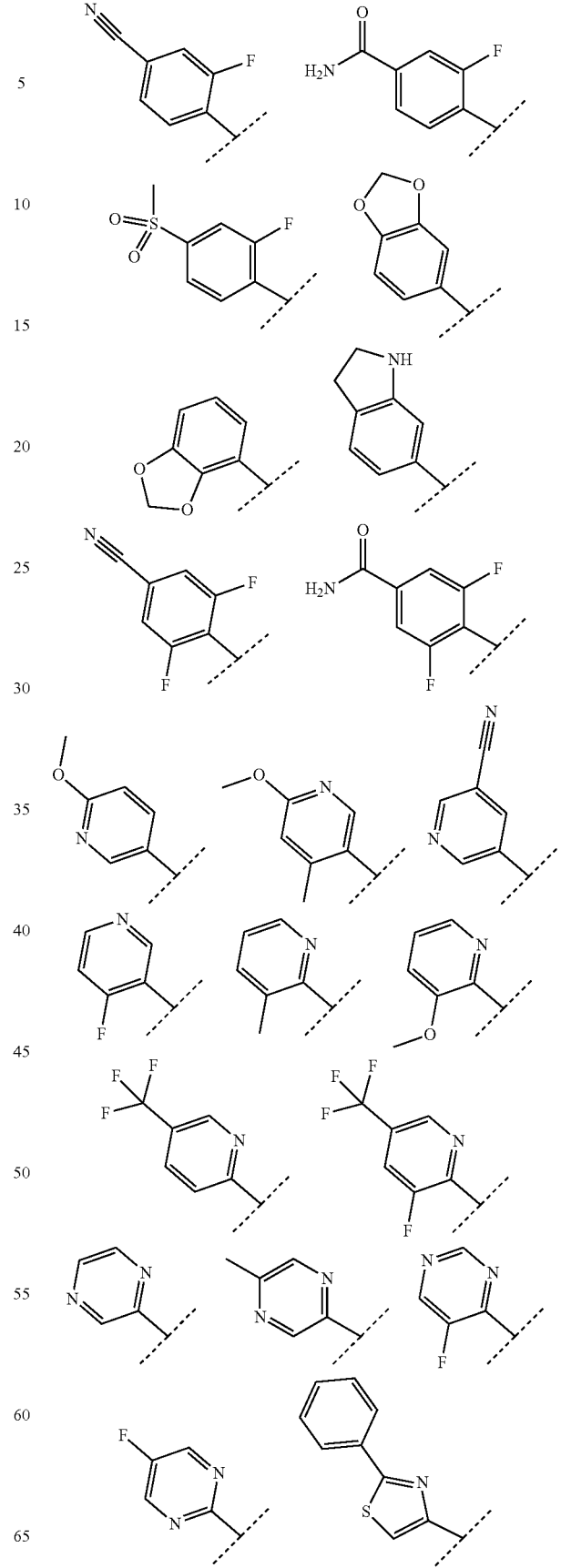

-continued
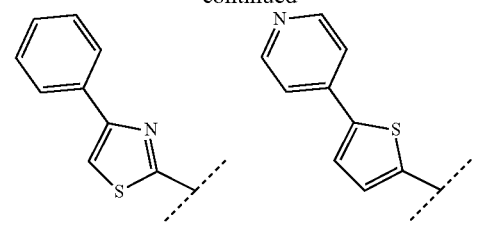
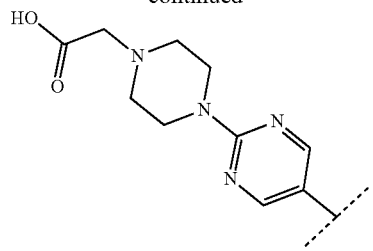
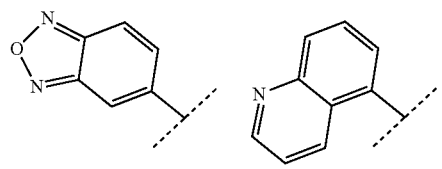
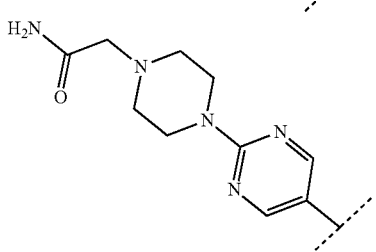
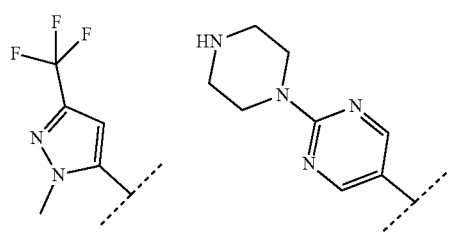
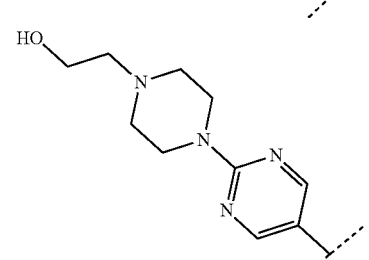
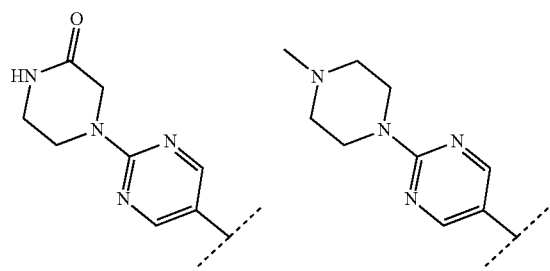
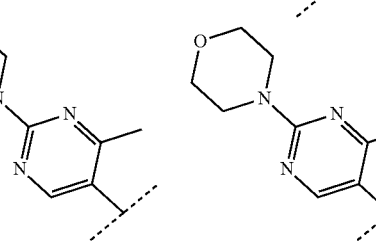
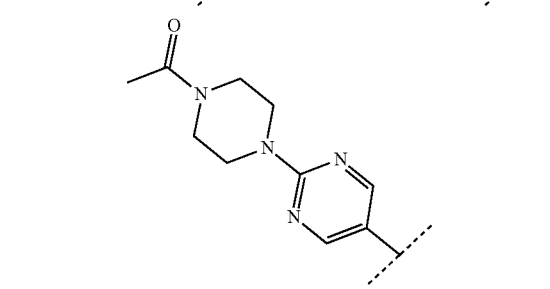
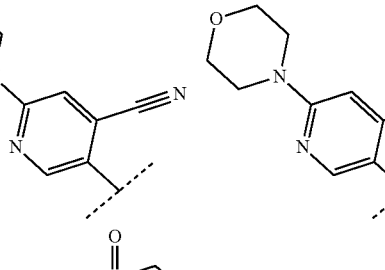
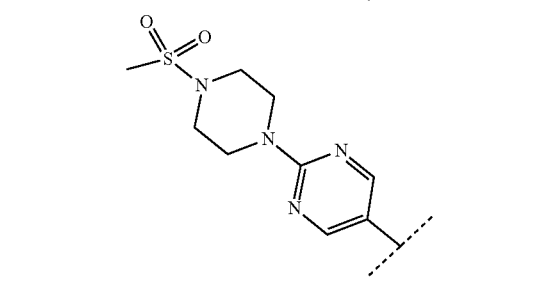
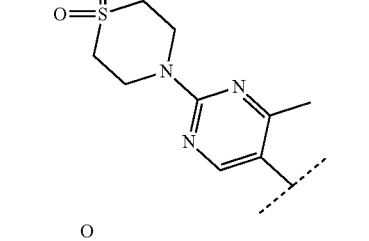
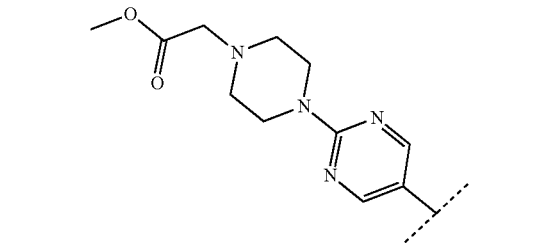
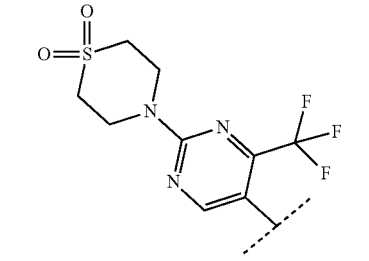

-continued
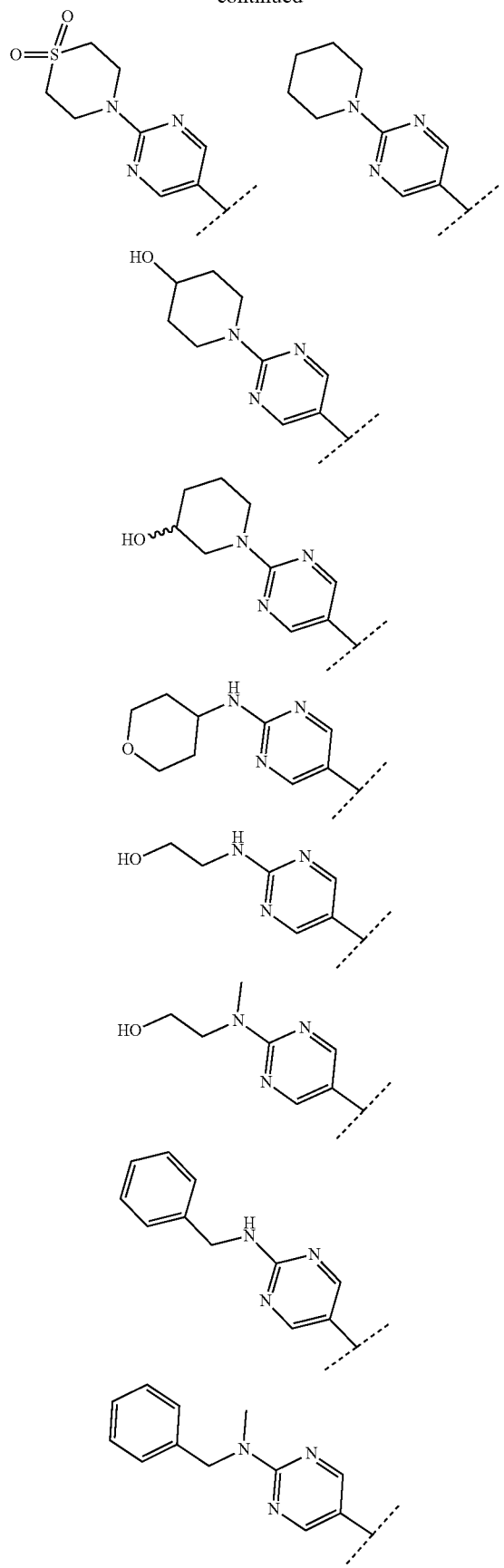
-continued
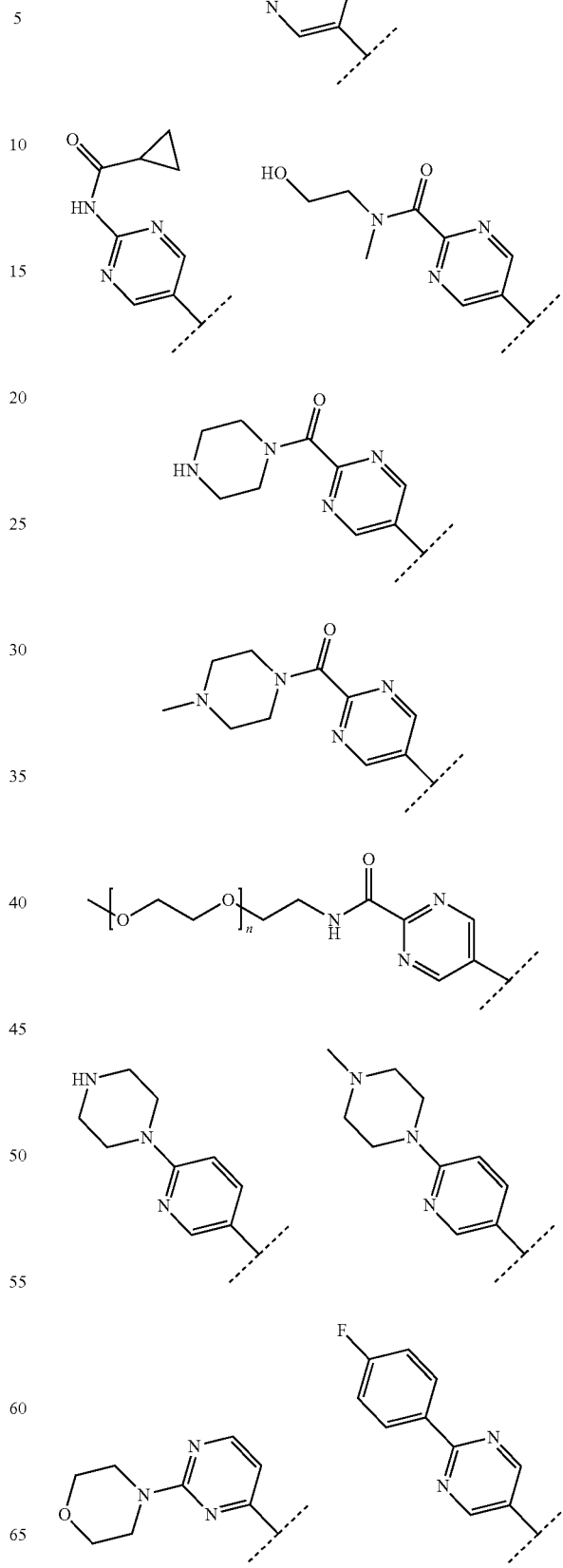

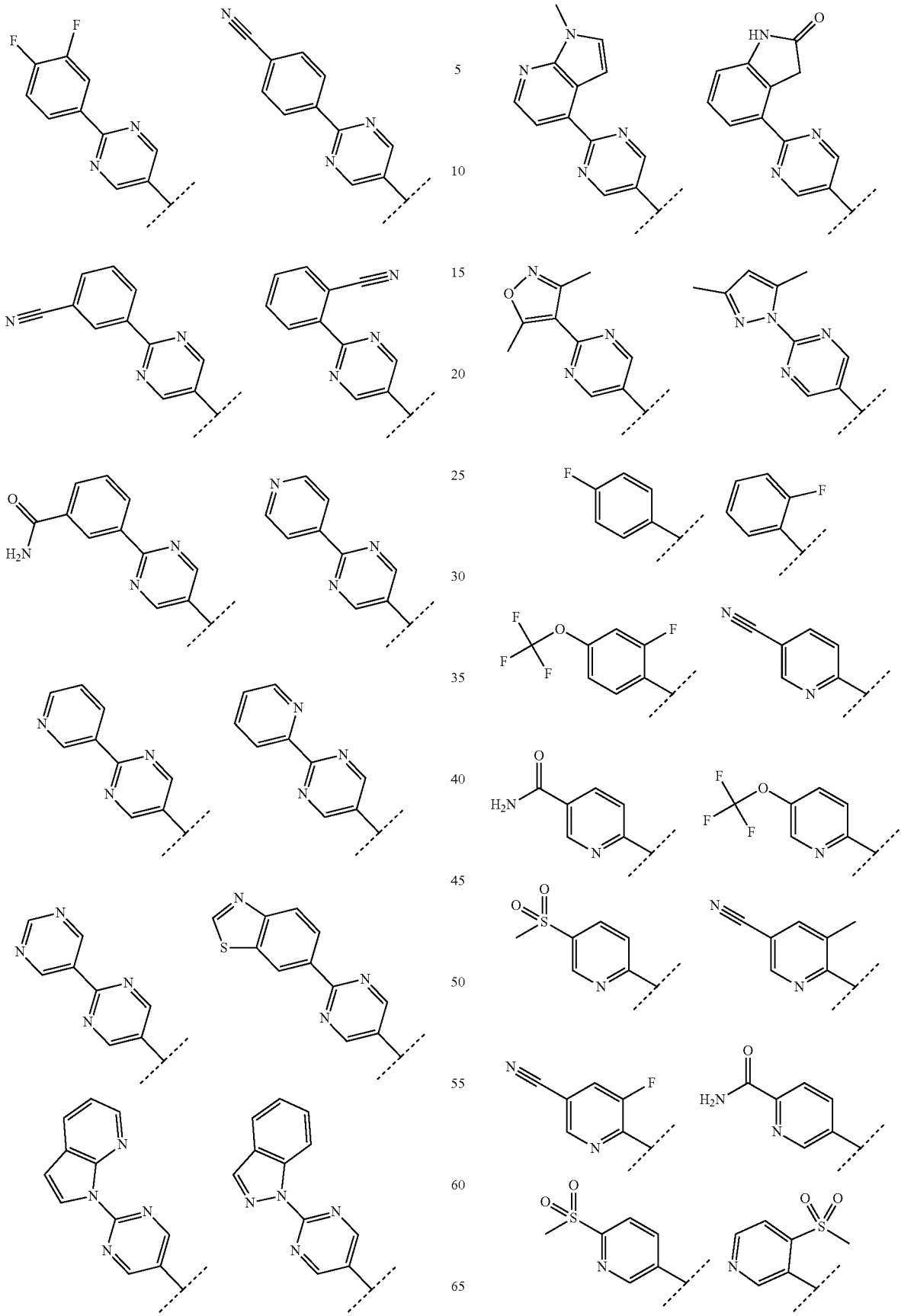

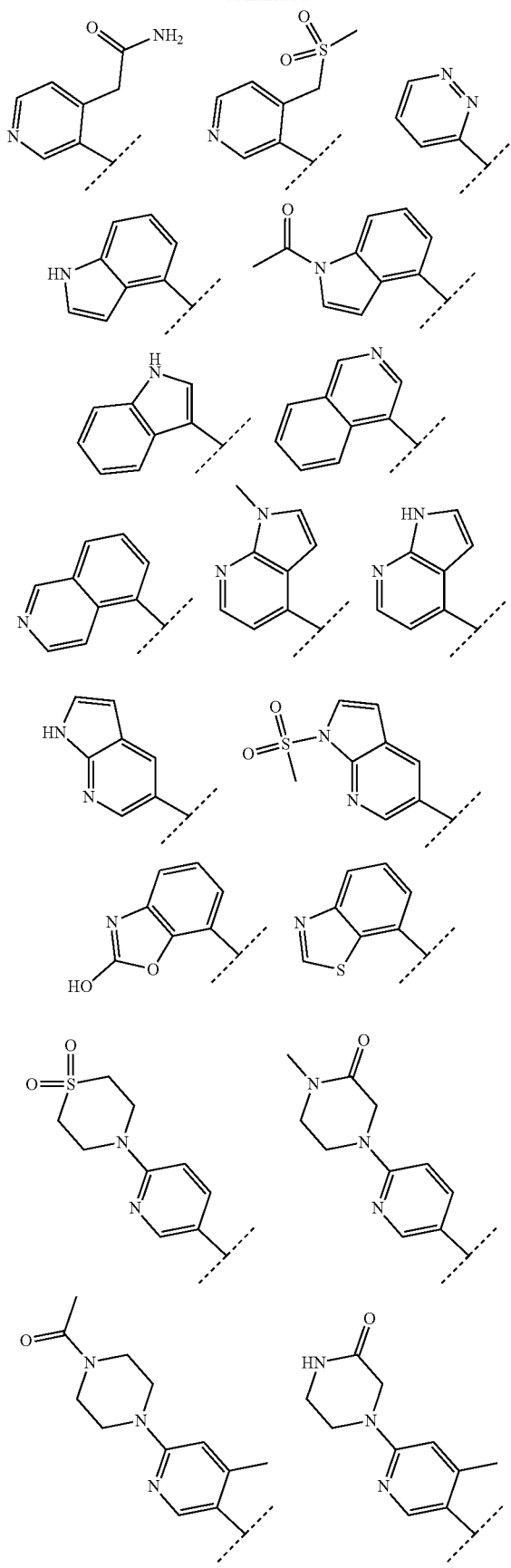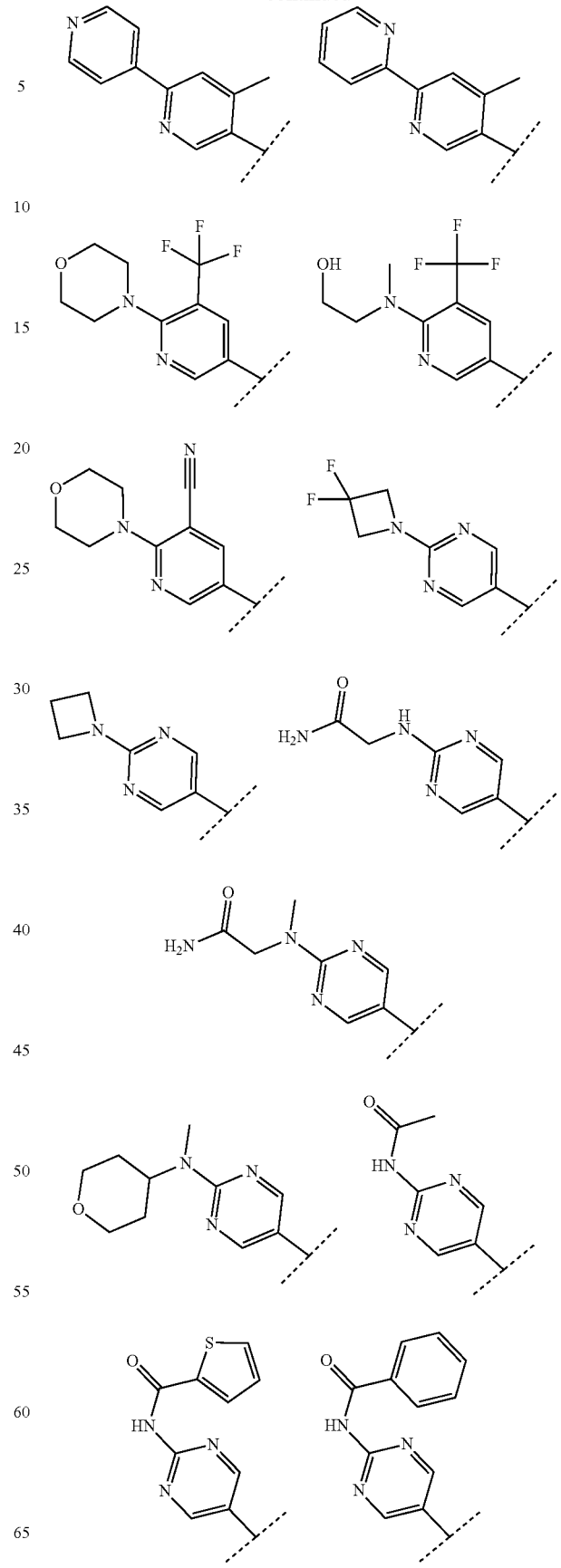

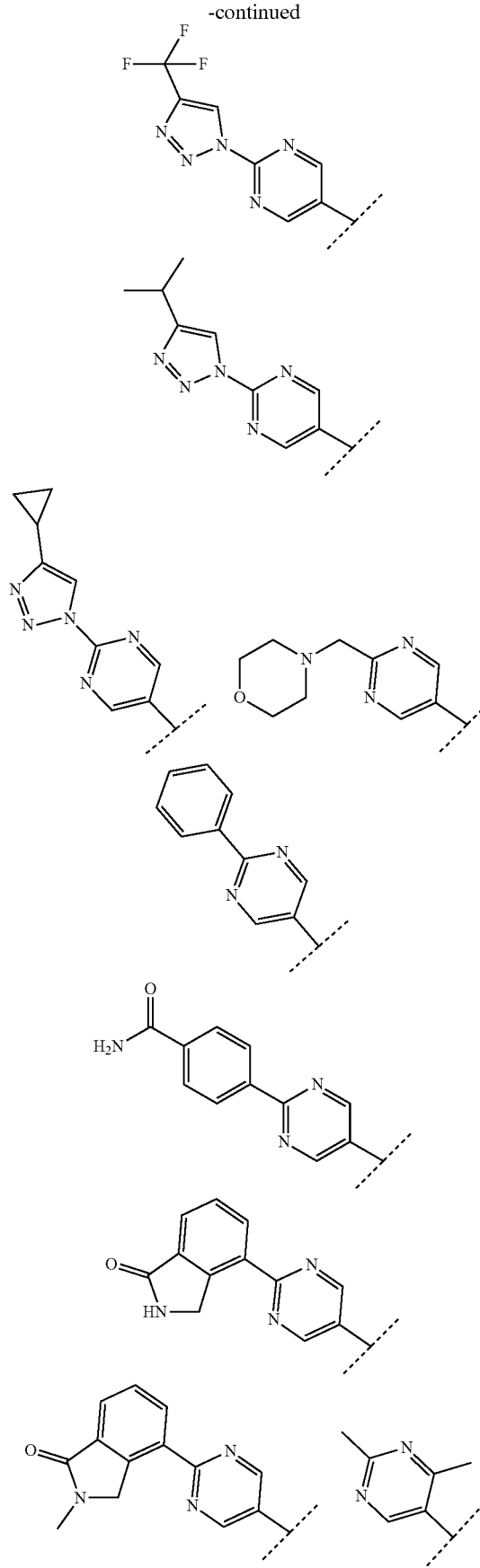
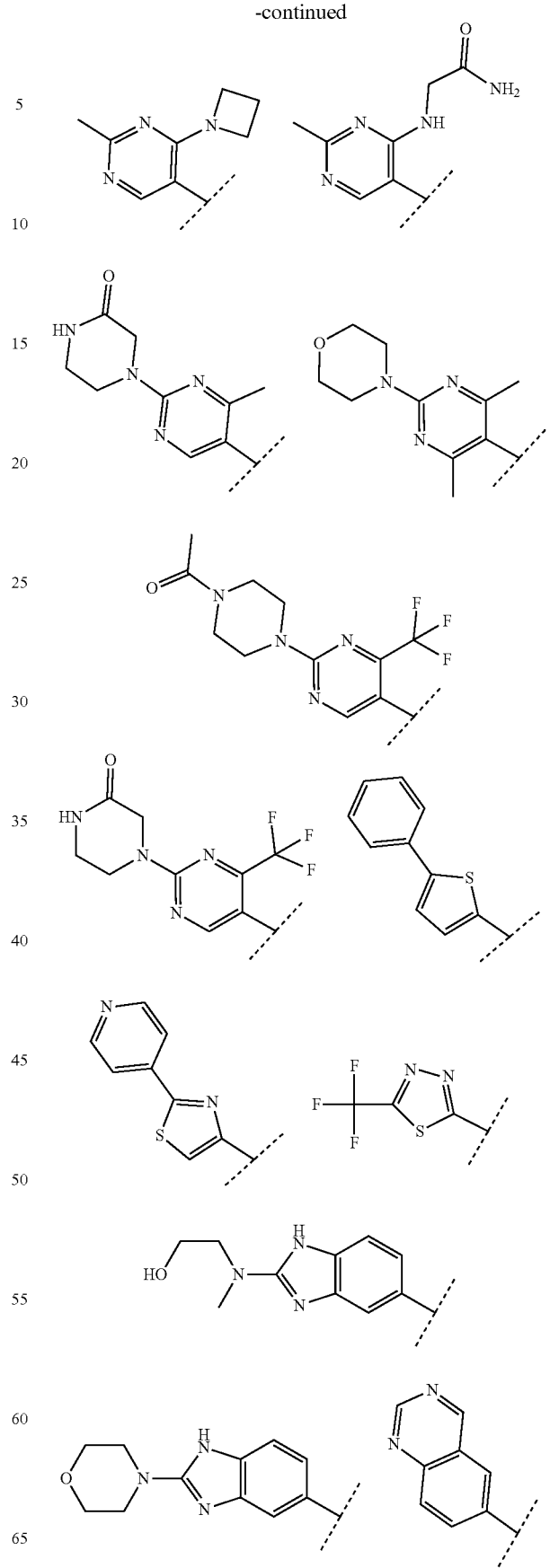

-continued
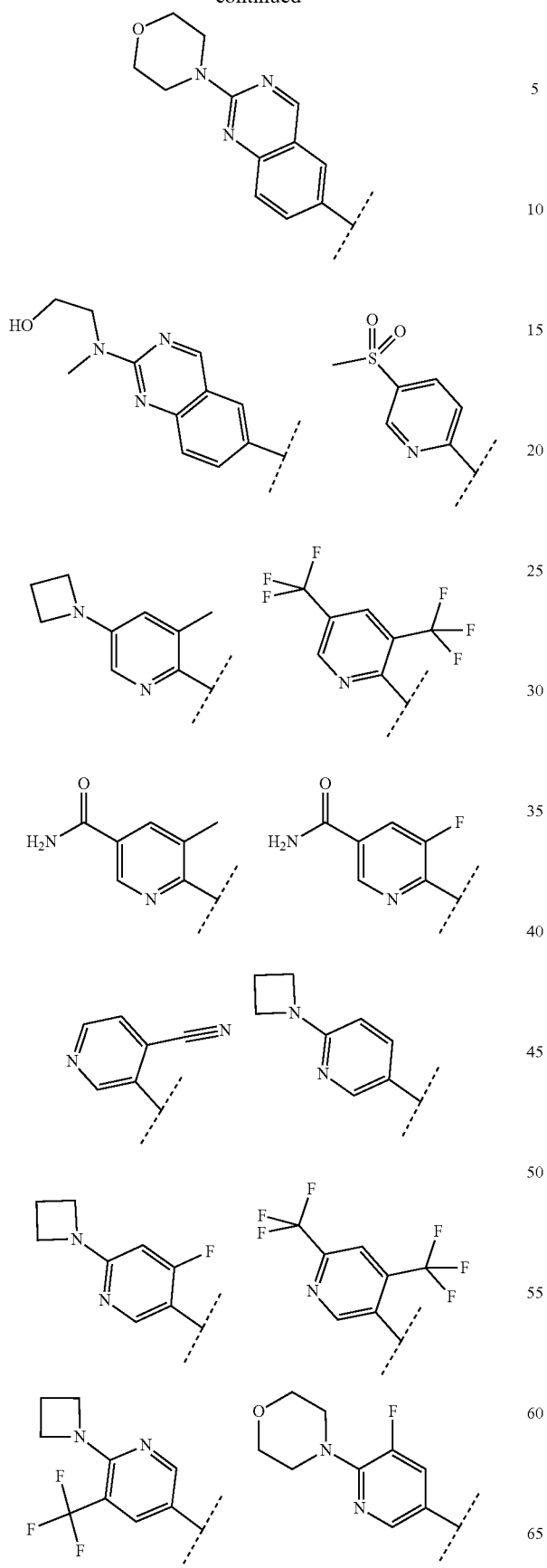
-continued
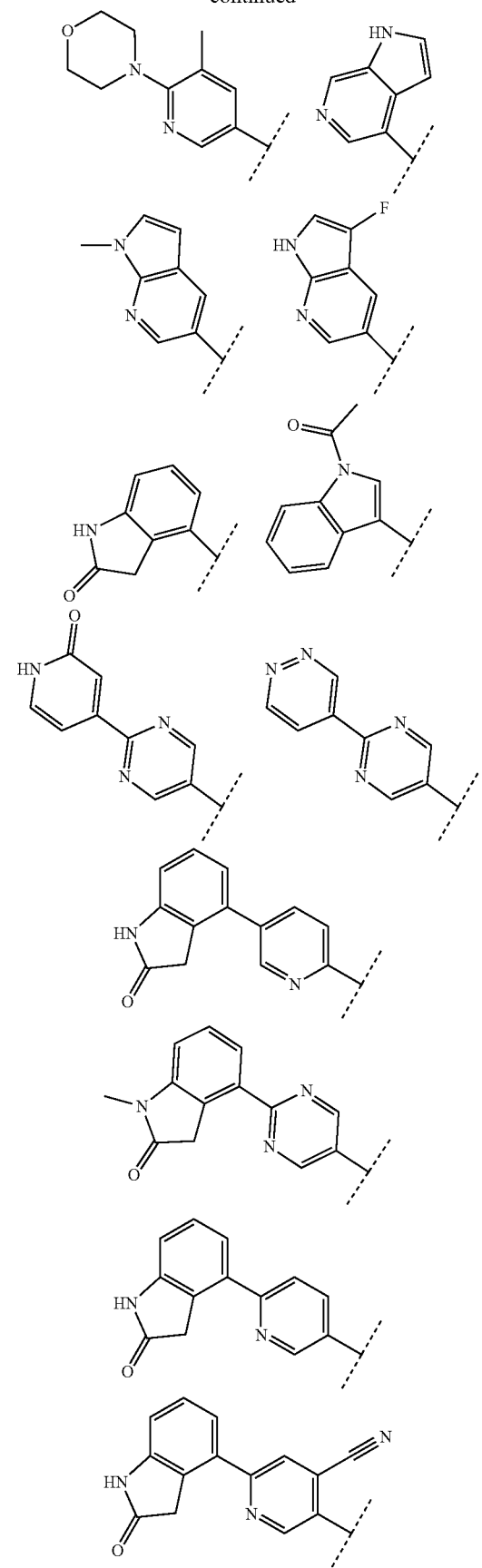

-continued
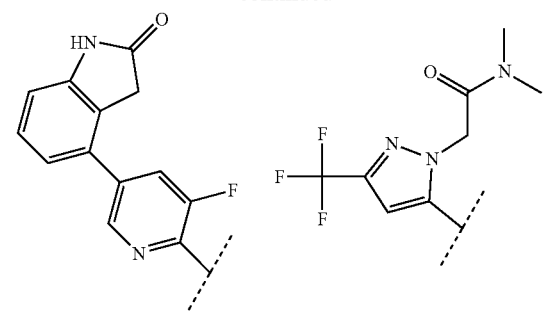
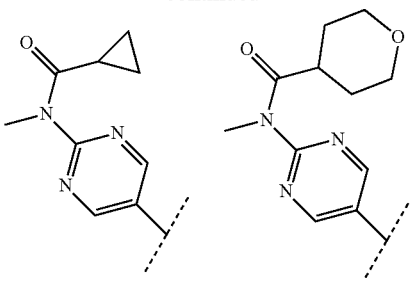
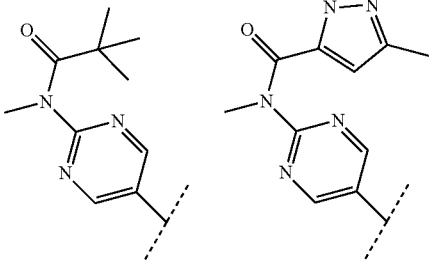
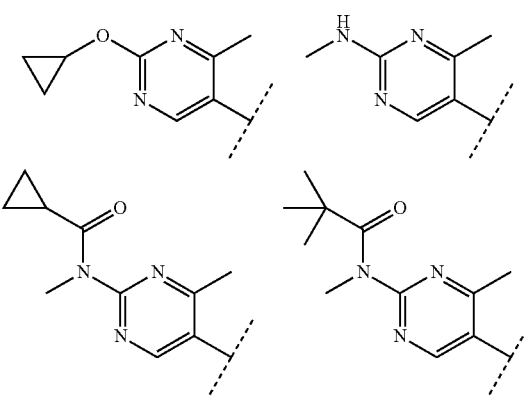
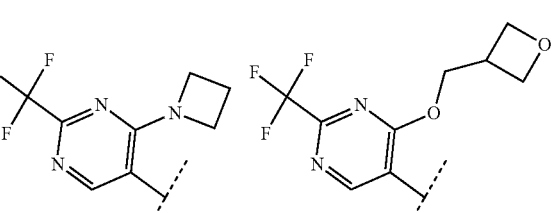
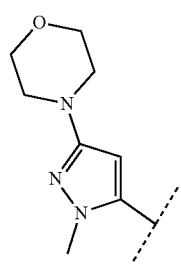 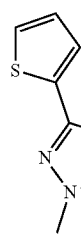 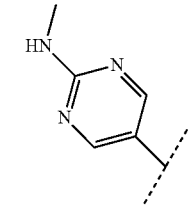
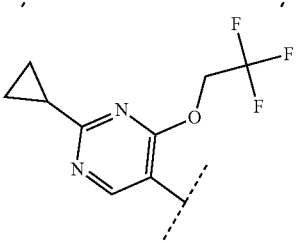
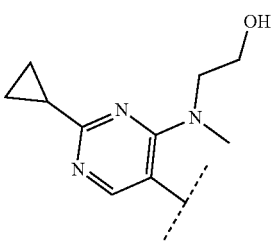 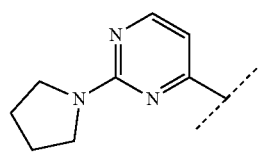

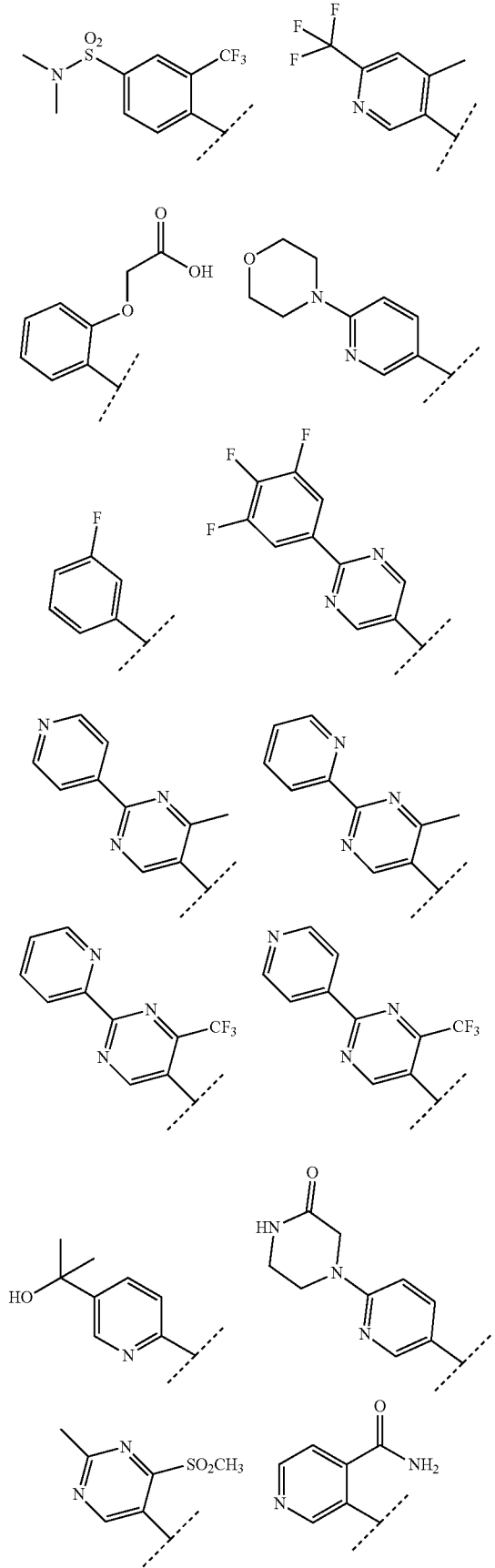
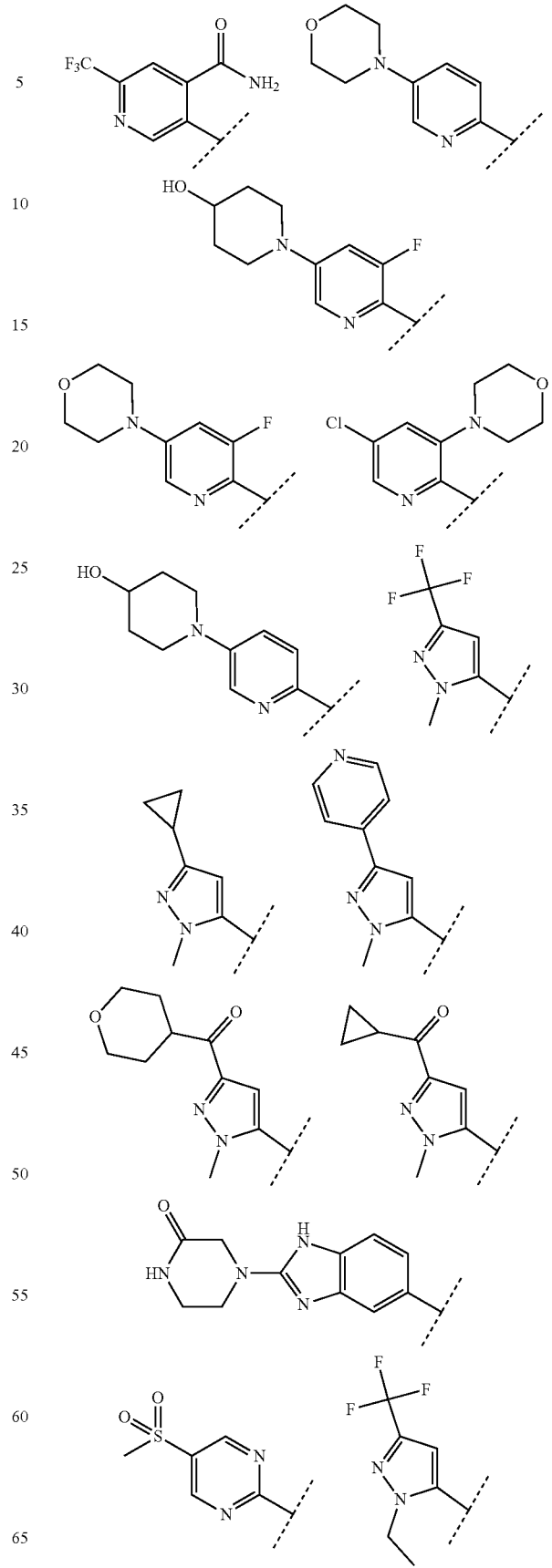

-continued

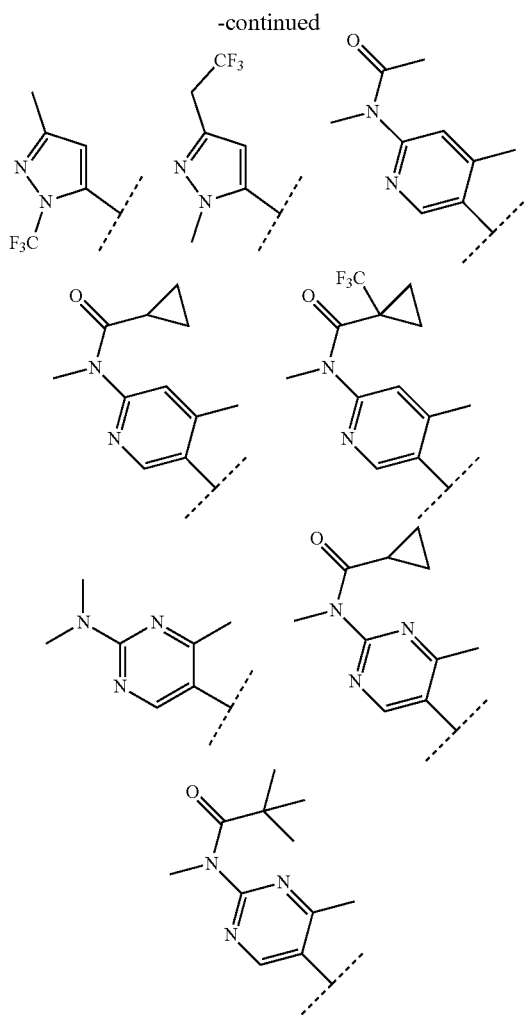

In a particularly preferred embodiment of the compound according to the invention
$R^1$ means —H or —$CH_3$;
$R^2$ means —$C_1$-$C_6$-alkyl, linear or branched, saturated, unsubstituted; cyclopropyl connected through —$CH_2$—; or tetrahydropyranyl connected through —$CH_2$—;
$R^3$ means -phenyl, benzyl, -thienyl or -pyridinyl, in each case unsubstituted or substituted with one, two, three or four substituents independently of one another selected from the group consisting of —F, —Cl, —CN, —$CH_3$, —$CH_2CH_3$, —$CH_2F$, —$CHF_2$, —$CF_3$, —$OCF_3$, —OH, —$OCH_3$, —C(═O)$NH_2$, C(═O)$NHCH_3$, —C(═O)N($CH_3$)$_2$, —$NH_2$, —$NHCH_3$, —N($CH_3$)$_2$, —NHC(═O)$CH_3$, —$CH_2$OH, $SOCH_3$ and $SO_2CH_3$; or
$R^4$ means
—H;
—$C_1$-$C_6$-alkyl, linear or branched, saturated, unsubstituted or substituted with one, two, three or four substituents independently of one another selected from the group consisting of —F, —Cl, —Br, —I, —CN, —OH, —O—$C_1$-$C_4$-alkyl, —C(═O)NH—$C_1$-$C_6$-alkyl, —C(═O)N($C_1$-$C_6$-alkyl)$_2$ or —C(═O)NRR' wherein R and R' together with the nitrogen atom to which they are attached form a ring and mean —($CH_2$)$_{3-5}$—;
3-6-membered cycloalkyl, unsubstituted or substituted with one, two, three or four substituents independently of one another selected from the group consisting of —F, —Cl, —Br, —I, —CN, —OH, and —O—$C_1$-$C_4$-alkyl, wherein said 3-6-membered cycloalkyl is connected through —$C_1$-$C_6$-alkylene;
3-6-membered heterocycloalkyl, unsubstituted or substituted with one, two, three or four substituents independently of one another selected from the group consisting of —F, —Cl, —Br, —I, —CN, —OH, and —O—$C_1$-$C_4$-alkyl, wherein said 3-6-membered heterocycloalkyl is connected through —$C_1$-$C_6$-alkylene;
-phenyl, unsubstituted or monosubstituted with —$OCH_3$; wherein said -phenyl isconnected through —$C_1$-$C_6$-alkylene-; or
-pyridyl, unsubstituted, mono- or polysubstituted; wherein said -pyridyl is connected through —$C_1$-$C_6$-alkylene-;
$R^5$ means
-phenyl, -1,2-benzodioxole, -pyrazinyl, -pyridazinyl, -pyridinyl, -pyrimidinyl, -thienyl, -imidazolyl, -benzimidazolyl, -thiazolyl, -1,3,4-thiadiazolyl, -benzothiazolyl, -oxazolyl, -benzoxazolyl, -pyrazolyl, -quinolinyl, -isoquinolinyl, -quinazolinyl, -indolyl, -indolinyl, -benzo[c][1,2,5]oxadiazolyl, -imidazo[1,2-a]pyrazinyl, or -1H-pyrrolo[2,3-b]pyridinyl, in each case unsubstituted or substituted with one, two, three or four substituents independently of one another selected from the group consisting of
—F; —Cl; —Br; —I;
—CN; —$C_1$-$C_4$-alkyl; —$C_1$-$C_4$-alkyl-OH; —$CF_3$; —$C_1$-$C_4$-alkyl-$CF_3$; —$C_1$-$C_4$-alkyl-C(═O)$NH_2$; —$C_1$-$C_4$-alkyl-C(═O)NH$C_1$-$C_6$-alkyl; —$C_1$-$C_4$-alkyl-C(═O)N($C_1$-$C_6$-alkyl)$_2$; —$C_1$-$C_4$-alkyl-S(═O)$_2$—$C_1$-$C_4$-alkyl;
—C(═O)—$C_1$-$C_4$-alkyl; —C(═O)OH; —C(═O)O—$C_1$-$C_4$-alkyl; —C(═O)$NH_2$; —C(═O)NH$C_1$-$C_4$-alkyl; —C(═O)N($C_1$-$C_4$-alkyl)$_2$; —C(═O)NH($C_1$-$C_4$-alkyl-OH); —C(═O)N($C_1$-$C_4$-alkyl)($C_1$-$C_4$-alkyl-OH);
—C(═O)NH—($CH_2CH_2$O)$_{1-30}$—$CH_3$;
—$NH_2$; —NH$C_1$-$C_4$-alkyl; —N($C_1$-$C_4$-alkyl)$_2$; —NH$C_1$-$C_4$-alkyl-OH; —$NCH_3C_1$-$C_4$-alkyl-OH; —NH—$C_1$-$C_4$-alkyl-C(═O)$NH_2$; —$NCH_3$—$C_1$-$C_4$-alkyl-C(═O)$NH_2$; —NHC(═O)—$C_1$-$C_4$-alkyl; —$NCH_3$C(═O)—$C_1$-$C_4$-alkyl;
—OH; —O—$C_1$-$C_4$-alkyl; —$OCF_3$; —O—$C_1$-$C_4$-alkyl-$CO_2$H; —O—$C_1$-$C_4$-alkyl-C(═O)O—$C_1$-$C_4$-alkyl; —O—$C_1$-$C_4$-alkyl-$CONH_2$;
—S—$C_1$-$C_4$-alkyl; —S(═O)$C_1$-$C_4$-alkyl; —S(═O)$_2$$C_1$-$C_4$-alkyl; and —S(═O)$_2$N($C_1$-$C_4$-alkyl)$_2$;
-3-12-membered cycloalkyl, saturated or unsaturated, unsubstituted, mono- or polysubstituted; wherein said 3-12-membered cycloalkyl is optionally connected through —$CH_2$—, —O—, —NH—, —$NCH_3$—, —NH—($CH_2$)$_{1-3}$—, —$NCH_3$($CH_2$)$_{1-3}$—, —(C═O)—, —NHC(═O)—, —$NCH_3$C(═O)—, —C(═O)NH—($CH_2$)$_{1-3}$—, —C(═O)$NCH_3$—($CH_2$)$_{1-3}$—;
-3-12-membered heterocycloalkyl, saturated or unsaturated, unsubstituted, mono- or polysubstituted; wherein said 3-12-membered heterocycloalkyl is optionally connected through —$CH_2$—, —O—, —NH—, —$NCH_3$—, —NH—($CH_2$)$_{1-3}$—, —$NCH_3$($CH_2$)$_{1-3}$—, —(C═O)—, —NHC(═O)—, —$NCH_3$C(═O)—, —C(═O)NH—($CH_2$)$_{1-3}$—, —C(═O)$NCH_3$—($CH_2$)$_{1-3}$—;
-6-14-membered aryl, unsubstituted, mono- or polysubstituted; wherein said 6-14-membered aryl is optionally connected through —$CH_2$—, —O—, —NH—, —$NCH_3$—, —NH—($CH_2$)$_{1-3}$—, —$NCH_3$($CH_2$)$_{1-3}$—, —(C=O)—, —NHC(=O)—, —NCH$_3$C(=O)—, —C(=O)NH—(CH$_2$)$_{1-3}$—, —C(=O)NCH$_3$—(CH$_2$)$_{1-3}$—; or

- -5-14-membered heteroaryl, unsubstituted, mono- or polysubstituted; wherein said 5-14-membered heteroaryl is optionally connected through —CH$_2$—, —O—, —NH—, —NCH$_3$—, —NH—(CH$_2$)$_{1-3}$—, —NCH$_3$(CH$_2$)$_{1-3}$—, —(C=O)—, —NHC(=O)—, —NCH$_3$C(=O)—, —C(=O)NH—(CH$_2$)$_{1-3}$—, —C(=O)NCH$_3$—(CH$_2$)$_{1-3}$—; and $R^{11}$, $R^{12}$, $R^{13}$, $R^{14}$, $R^{15}$, $R^{16}$, $R^{17}$, $R^{18}$, $R^{19}$, and $R^{20}$ mean —H.

In a particularly preferred embodiment of the compound according to the invention
$R^1$ means —H or —CH$_3$; and/or
$R^2$ means —C$_1$-C$_6$-alkyl, linear or branched, saturated, unsubstituted; preferably, $R^2$ means —CH$_3$ or —CH$_2$CH$_3$; more preferably, $R^1$ and $R^2$ both mean —CH$_3$; and/or
$R^3$ means -phenyl, -thienyl or -pyridinyl, in each case unsubstituted or substituted with one, two, three or four substituents independently of one another selected from the group consisting of —F, —C$_1$, —CN, —CH$_3$, —CH$_2$CH$_3$, —CH$_2$F, —CHF$_2$, —CF$_3$, —OCF$_3$, —OH, —OCH$_3$, —C(=O)NH$_2$, C(=O)NHCH$_3$, —C(=O)N(CH$_3$)$_2$, —NH$_2$, —NHCH$_3$, —N(CH$_3$)$_2$, —NHC(=O)CH$_3$, —CH$_2$OH, SOCH$_3$ and SO$_2$CH$_3$;
preferably, $R^3$ means -phenyl, -thienyl or -pyridinyl, in each case unsubstituted or substituted with —F; more preferably, $R^3$ means phenyl, unsubstituted; and/or
$R^4$ means
—H;
—C$_1$-C$_6$-alkyl, linear or branched, saturated, unsubstituted or substituted with one, two, three or four substituents independently of one another selected from the group consisting of —F, —Cl, —Br, —I, —CN, —OH, and —O—C$_1$-C$_4$-alkyl; or
3-6-membered cycloalkyl, unsubstituted or substituted with one, two, three or four substituents independently of one another selected from the group consisting of —F, —Cl, —Br, —I, —CN, —OH, and —O—C$_1$-C$_4$-alkyl, wherein said 3-6-membered cycloalkyl is connected through —C$_1$-C$_6$-alkylene;

preferably, $R^4$ means 3-6-membered cycloalkyl, unsubstituted or substituted with one, two, three or four substituents independently of one another selected from the group consisting of —F, —Cl, —Br, —I, —CN, —OH, and —O—C$_1$-C$_4$-alkyl, wherein said 3-6-membered cycloalkyl is connected through —CH$_2$— or —CH$_2$CH$_2$—; more preferably, $R^4$ means -cyclobutyl, unsubstituted or monosubstituted with —OH, wherein said -cyclobutyl is connected through —CH$_2$—; and/or $R^5$ means -phenyl, -pyrazinyl, -pyridazinyl, -pyridinyl, -pyrimidinyl, -thienyl, or imidazo[1,2-a]pyrazine, in each case unsubstituted or substituted with one, two, three or four substituents independently of one another selected from the group consisting of —F; —Cl; —Br; —I; —CN; —OH; —C$_1$-C$_4$-alkyl; —CF$_3$; -3-12-membered cycloalkyl, saturated or unsaturated, unsubstituted, mono- or polysubstituted; preferably cyclopropyl, saturated, unsubstituted; -3-12-membered heterocycloalkyl, saturated or unsaturated, unsubstituted, mono- or polysubstituted; preferably -pyrrolidinyl, -morpholinyl, -piperazinyl, -thiomorpholinyl, or -thiomorpholinyl dioxide, in each case saturated, unsubstituted or monosubstituted with —C$_1$-C$_4$-alkyl; -6-14-membered aryl, unsubstituted, mono- or polysubstituted; preferably -phenyl, unsubstituted; —O—C$_1$-C$_4$-alkyl; —S—C$_1$-C$_4$-alkyl; —C(=O)OH; —C(=O)O—C$_1$-C$_4$-alkyl; —C(=O)NH$_2$; —C(=O)NHC$_1$-C$_4$-alkyl; —C(=O)N(C$_1$-C$_4$-alkyl)$_2$; —C(=O)N(C$_1$-C$_4$-alkyl)(C$_1$-C$_4$-alkyl-OH); —C(=O)NH—(CH$_2$)$_{1-3}$-3-12-membered cycloalkyl, saturated or unsaturated, unsubstituted or monosubstituted with —OH; preferably —C(=O)NH—(CH$_2$)$_{1-3}$-cyclobutyl, saturated or unsaturated, unsubstituted or monosubstituted with —OH; —C(=O)-3-12-membered heterocycloalkyl, saturated or unsaturated, unsubstituted, mono- or polysubstituted; preferably —C(=O)-morpholinyl, saturated, unsubstituted; —S(=O)C$_1$-C$_4$-alkyl; —S(=O)$_2$C$_1$-C$_4$-alkyl; and —S(=O)$_2$N(C$_1$-C$_4$-alkyl)$_2$; and/or $R^{11}$, $R^{12}$, $R^{13}$, $R^{14}$, $R^{15}$, $R^{16}$, $R^{17}$, $R^{18}$, $R^{19}$, and $R^{20}$ mean —H.

Preferably, the compound according to the invention is selected from the group consisting of

| | |
|---|---|
| SC_3001 | cis-5-[1-(Cyclobutyl-methyl)-8-dimethylamino-2-oxo-8-phenyl-1,3-diazaspiro[4.5]decan-3-yl]-pyrimidine-2-carbonitrile |
| SC_3002 | cis-5-[1-(Cyclobutyl-methyl)-8-dimethylamino-2-oxo-8-phenyl-1,3-diazaspiro[4.5]decan-3-yl]-pyrazine-2-carbonitrile |
| SC_3003 | cis-5-[1-(Cyclobutyl-methyl)-8-dimethylamino-2-oxo-8-phenyl-1,3-diazaspiro[4.5]decan-3-yl]-4-methoxy-pyrimidine-2-carbonitrile |
| SC_3004 | cis-5-[8-Dimethylamino-1-(2-methoxy-ethyl)-2-oxo-8-phenyl-1,3-diazaspiro[4.5]decan-3-yl]-pyrimidine-2-carbonitrile |
| SC_3005 | cis-5-[1-(Cyclobutyl-methyl)-8-dimethylamino-2-oxo-8-phenyl-1,3-diazaspiro[4.5]decan-3-yl]-pyrimidine-2-carboxylic acid amide |
| SC_3006 | cis-5-[1-(Cyclobutyl-methyl)-8-dimethylamino-2-oxo-8-phenyl-1,3-diazaspiro[4.5]decan-3-yl]-2-methylsulfonyl-pyrimidine-4-carbonitrile |
| SC_3007 | cis-5-[1-(2-Methoxy-ethyl)-8-methylamino-2-oxo-8-phenyl-1,3-diazaspiro[4.5]decan-3-yl]-pyrimidine-2-carbonitrile |
| SC_3008 | cis-2-[1-(Cyclobutyl-methyl)-8-dimethylamino-2-oxo-8-phenyl-1,3-diazaspiro[4.5]decan-3-yl]-5-methylsulfonyl-benzonitrile |
| SC_3009 | cis-2-[1-(Cyclobutyl-methyl)-8-dimethylamino-2-oxo-8-phenyl-1,3-diazaspiro[4.5]decan-3-yl]-benzamide |
| SC_3010 | cis-3-[1-(Cyclobutyl-methyl)-8-dimethylamino-2-oxo-8-phenyl-1,3-diazaspiro[4.5]decan-3-yl]-benzamide |
| SC_3011 | cis-5-[8-Dimethylamino-1-[(1-hydroxy-cyclobutyl)-methyl]-2-oxo-8-phenyl-1,3-diazaspiro[4.5]decan-3-yl]-pyrimidine-2-carboxylic acid amide |
| SC_3012 | cis-5-[1-(Cyclobutyl-methyl)-8-methylamino-2-oxo-8-phenyl-1,3-diazaspiro[4.5]decan-3-yl]-4-methoxy-pyrimidine-2-carbonitrile |
| SC_3013 | cis-5-[8-Dimethylamino-1-[(1-hydroxy-cyclobutyl)-methyl]-2-oxo-8-phenyl-1,3-diazaspiro[4.5]decan-3-yl]-pyrimidine-2-carbonitrile |
| SC_3014 | cis-2-[1-(Cyclobutyl-methyl)-8-dimethylamino-2-oxo-8-phenyl-1,3-diazaspiro[4.5]decan-3-yl]-pyrimidine-5-carbonitrile |

-continued

| | |
|---|---|
| SC_3015 | cis-5-[8-Dimethylamino-1-[(1-hydroxy-cyclobutyl)-methyl]-3-(2-methoxy-pyrimidin-5-yl)-8-phenyl-1,3-diazaspiro[4.5]decan-2-one |
| SC_3016 | cis-2-[1-(Cyclobutyl-methyl)-8-dimethylamino-2-oxo-8-phenyl-1,3-diazaspiro[4.5]decan-3-yl]-pyrimidine-5-carboxylic acid amide |
| SC_3017 | cis-4-[1-(Cyclobutyl-methyl)-8-dimethylamino-2-oxo-8-phenyl-1,3-diazaspiro[4.5]decan-3-yl]-N-methyl-benzamide |
| SC_3018 | cis-5-(8-Dimethylamino-2-oxo-8-phenyl-1-propyl-1,3-diazaspiro[4.5]decan-3-yl)-pyrimidine-2-carbonitrile |
| SC_3019 | cis-5-[8-Dimethylamino-1-(3-methoxy-propyl)-2-oxo-8-phenyl-1,3-diazaspiro[4.5]decan-3-yl]-pyrimidine-2-carbonitrile |
| SC_3020 | cis-5-[1-(Cyclopropyl-methyl)-8-dimethylamino-2-oxo-8-phenyl-1,3-diazaspiro[4.5]decan-3-yl]-pyrimidine-2-carbonitrile |
| SC_3021 | cis-4-[1-(Cyclobutyl-methyl)-8-dimethylamino-2-oxo-8-phenyl-1,3-diazaspiro[4.5]decan-3-yl]-benzamide |
| SC_3022 | cis-1-(Cyclobutyl-methyl)-8-dimethylamino-8-phenyl-3-[2-(trifluoromethyl)-pyrimidin-5-yl]-1,3-diazaspiro[4.51decan-2-one |
| SC_3023 | cis-8-Dimethylamino-1-[(1-hydroxy-cyclobutyl)-methyl]-3-(2-hydroxy-pyrimidin-5-yl)-8-phenyl-1,3-diazaspiro[4.5]decan-2-one |
| SC_3024 | cis-5-[8-Dimethylamino-1-(2-methyl-propy1)-2-oxo-8-phenyl-1,3-diazaspiro[4.5]decan-3-yl]-pyrimidine-2-carbonitrile |
| SC_3025 | cis-5-[8-Dimethylamino-1-(2-hydroxy-ethyl)-2-oxo-8-phenyl-1,3-diazaspiro[4.5]decan-3-yl]-pyrimidine-2-carbonitrile |
| SC_3026 | cis-5-[1-(Cyclobutyl-methyl)-8-methylamino-2-oxo-8-phenyl-1,3-diazaspiro[4.5]decan-3-yl]-4-methyl-pyridine-2-carbonitrile |
| SC_3027 | cis-1-(Cyclobutyl-methyl)-3-(5-methoxy-pyrazin-2-yl)-8-methylamino-8-phenyl-1,3-diazaspiro[4.5]decan-2-one |
| SC_3028 | cis-4-[1-(Cyclobutyl-methyl)-8-dimethylamino-2-oxo-8-phenyl-1,3-diazaspiro[4.5]decan-3-yl]-N,N-dimethyl-benzamide |
| SC_3029 | cis-4-[1-(Cyclobutyl-methyl)-8-dimethylamino-2-oxo-8-phenyl-1,3-diazaspiro[4.5]decan-3-yl]-N-ethyl-N-(2-hydroxy-ethyl)-benzamide |
| SC_3030 | cis-2-[1-(Cyclobutyl-methyl)-8-methylamino-2-oxo-8-phenyl-1,3-diazaspiro[4.5]decan-3-yl]-5-methylsulfonyl-benzonitrile |
| SC_3031 | cis-1-(Cyclobutyl-methyl)-8-methylamino-3-[2-methylsulfony1-4-(trifluoromethyl)-phenyl]-8-phenyl-1,3-diazaspiro[4.5]decan-2-one |
| SC_3032 | cis-4-[1-(Cyclobutyl-methyl)-8-methylamino-2-oxo-8-phenyl-1,3-diazaspiro[4.5]decan-3-yl]-N,N-dimethyl-3-(trifluoromethyl)-benzenesulfonic acid amide |
| SC_3033 | cis-4-[1-(Cyclobutyl-methyl)-8-(ethyl-methyl-amino)-2-oxo-8-phenyl-1,3-diazaspiro[4.5]decan-3-yl]-benzonitrile |
| SC_3034 | cis-1-(Cyclobutyl-methyl)-8-(ethyl-methyl-amino)-8-phenyl-3-[2-(trifluoromethyl)-pyrimidin-5-yl]-1,3-diazaspiro[4.5]decan-2-one |
| SC_3035 | cis-5-[1-(Cyclobutyl-methyl)-8-(ethyl-methyl-amino)-2-oxo-8-phenyl-1,3-diazaspiro[4.5]decan-3-yl]-pyrimidine-2-carbonitrile |
| SC_3036 | cis-5-[8-Dimethylamino-1-](1-methyl-cyclobutyl)-methyl]-2-oxo-8-phenyl-1,3-diazaspiro[4.5]decan-3-yl]-pyrimidine-2-carbonitrile |
| SC_3037 | cis-2-[3-(2-Cyano-pyrimidin-5-yl)-8-dimethylamino-2-oxo-8-phenyl-1,3-diazaspiro[4.5]decan-1-yl]-N,N-dimethyl-acetamide |
| SC_3038 | cis-1-(Cyclobutyl-methyl)-8-methylamino-8-phenyl-3-[2-(trifluoromethyl)-pyrimidin-5-yl]-1,3-diazaspiro[4.5]decan-2-one |
| SC_3039 | cis-5-[8-Dimethy1amino-8-(3-fluorophenyl)-1-(4-methoxy-butyl)-2-oxo-1,3-diazaspiro[4.5]decan-3-yl]-pyrimidine-2-carbonitrile |
| SC_3040 | cis-5-[8-Dimethylamino-1-(3-methoxy-propyl)-2-oxo-8-phenyl-1,3-diazaspiro[4.5]decan-3-yl]-4-methoxy-pyrimidine-2-carbonitrile |
| SC_3041 | cis-5-[1-[(1-Cyano-cyclobutyl)-methyl]-8-dimethylamino-2-oxo-8-phenyl-1,3-diazaspiro[4.5]decan-3-yl]-pyrimidine-2-carbonitrile |
| SC_3042 | cis-N-(Cyclobutyl-methyl)-5-[1-(cyclobutyl-methyl)-8-dimethylamino-8-(3-fluorophenyl)-2-oxo-1,3-diazaspiro[4.5]decan-3-yl]-pyrimidine-2-carboxylic acid amide |
| SC_3043 | cis-5-[1-(3-Methoxy-propyl)-8-methylamino-2-oxo-8-phenyl-1,3-diazaspiro[4.5]decan-3-yl]-pyrimidine-2-carbonitrile |
| SC_3044 | cis-5-[8-Dimethylamino-8-(3-fluorophenyl)-1-methyl-2-oxo-1,3-diazaspiro[4.5]decan-3-yl]-pyrimidine-2-carbonitrile |
| SC_3045 | cis-4-Methoxy-5-[1-(3-methoxy-propyl)-8-methylamino-2-oxo-8-phenyl-1,3-diazaspiro[4.5]decan-3-yl]-pyrimidine-2-carbonitrile |
| SC_3046 | cis-4-[8-Dimethylamino-1-(2-methoxy-ethyl)-2-oxo-8-phenyl-1,3-diazaspiro[4.5]decan-3-yl]-pyrimidine-2-carbonitrile |
| SC_3047 | cis-5-[8-Dimethylamino-1-(2-methoxy-ethyl)-2-oxo-8-phenyl-1,3-diazaspiro[4.5]decan-3-yl]-4-methoxy-pyrimidine-2-carbonitrile |
| SC_3048 | cis-4-[1-(Cyclobuty1-methyl)-8-dimethylamino-2-oxo-8-phenyl-1,3-diazaspiro[4.5]decan-3-yl]-pyrimidine-2-carbonitrile |
| SC_3049 | cis-1-(Cyclobutyl-methyl)-8-dimethylamino-3-(6-methylsulfanyl-pyrimidin-4-yl)-8-phenyl-1,3-diazaspiro[4.5]decan-2-one |
| SC_3050 | cis-2-[3-(2-Cyano-pyrimidin-4-yl)-8-dimethylamino-2-oxo-8-phenyl-1,3-diazaspiro[4.5]decan-1-yl]-N,N-dimethyl-acetamide |
| SC_3051 | cis-6-[1-(Cyclobutyl-methyl)-8-dimethylamino-2-oxo-8-phenyl-1,3-diazaspiro[4.5]decan-3-yl]-pyrimidine-4-carbonitrile |
| SC_3052 | cis-2-(8-Dimethylamino-2-oxo-3,8-diphenyl-1,3-diazaspiro[4.5]decan-1-yl)-N,N-dimethyl-acetamide |

-continued

| | |
|---|---|
| SC_3053 | cis-1-(Cyclobutyl-methyl)-8-dimethylamino-3,8-diphenyl-1,3-diazaspiro[4.5]decan-2-one |
| SC_3054 | cis-2-[8-Dimethylamino-1-(2-methoxy-ethyl)-2-oxo-8-phenyl-1,3-diazaspiro[4.5]decan-3-yl]-pyrimidine-5-carbonitrile |
| SC_3055 | cis-8-Dimethylamino-1-(2-methoxy-ethyl)-3,8-diphenyl-1,3-diazaspiro[4.5]decan-2-one |
| SC_3056 | cis-5-[8-Dimethylamino-1-(2-methoxy-ethyl)-2-oxo-8-phenyl-1,3-diazaspiro[4.5]decan-3-yl]-4-methyl-pyridine-2-carbonitrile |
| SC_3057 | cis-N,N-Dimethyl-2-(8-methylamino-2-oxo-3,8-diphenyl-1,3-diazaspiro[4.5]decan-1-yl)-acetamide |
| SC_3058 | cis-5-[1-[(1-Cyano-cyclobutyl)-methyl]-8-methylamino-2-oxo-8-phenyl-1,3-diazaspiro[4.5]decan-3-yl]-pyrimidine-2-carbonitrile |
| SC_3059 | cis-5-[1-[(1-Cyano-cyclobutyl)-methyl]-8-(ethyl-methyl-amino)-2-oxo-8-phenyl-1,3-diazaspiro[4.5]decan-3-yl]-pyrimidine-2-carbonitrile |
| SC_3060 | cis-4-[8-Dimethylamino-1-[(1-hydroxy-cyclobutyl)-methyl]-2-oxo-8-phenyl-1,3-diazaspiro[4.5]decan-3-yl]-benzonitrile |
| SC_3061 | cis-3-[8-Dimethylamino-1-[(1-hydroxy-cyclobutyl)-methyl]-2-oxo-8-phenyl-1,3-diazaspiro[4.5]decan-3-yl]-benzonitrile |
| SC_3063 | cis-5-[1-[(1-Cyano-cyclobutyl)-methyl]-8-dimethylamino-2-oxo-8-phenyl-1,3-diazaspiro[4.5]decan-3-yl]-pyridine-2-carbonitrile |
| SC_3064 | cis-2-[3-(2-Cyano-pyrimidin-5-yl)-8-dimethylamino-2-oxo-8-phenyl-1,3-diazaspiro[4.5]decan-1-yl]-N-propyl-acetamide |
| SC_3065 | cis-5-[1-(Cyclobutyl-methyl)-8-(ethyl-methyl-amino)-2-oxo-8-phenyl-1,3-diazaspiro[4.5]decan-3-yl]-4-methoxy-pyrimidine-2-carbonitrile |
| SC_3066 | cis-4-[1-(Cyclobutyl-methyl)-8-methylamino-2-oxo-8-phenyl-1,3-diazaspiro[4.5]decan-3-yl]-3-methoxy-benzonitrile |
| SC_3067 | cis-5-[8-Dimethylamino-1-(3-methoxy-propyl)-2-oxo-8-phenyl-1,3-diazaspiro[4.5]decan-3-yl]-6-methoxy-pyridine-2-carbonitrile |
| SC_3068 | cis-4-[8-Dimethylamino-1-[(1-hydroxy-cyclobutyl)-methyl]-2-oxo-8-phenyl-1,3-diazaspiro[4.5]decan-3-yl]-benzamide |
| SC_3069 | cis-5-[8-Dimethylamino-1-[(1-hydroxy-cyclobutyl)-methyl]-2-oxo-8-phenyl-1,3-diazaspiro[4.5]decan-3-yl]-pyridine-2-carbonitrile |
| SC_3070 | cis-5-[8-Dimethylamino-1-[(1-hydroxy-cyclobutyl)-methyl]-2-oxo-8-phenyl-1,3-diazaspiro[4.5]decan-3-yl]-N-[(1-hydroxy-cyclobutyl)-methyl]-pyridine-2-carboxylic acid amide |
| SC_3071 | cis-2-[8-Dimethylamino-1-[(1-hydroxy-cyclobutyl)-methyl]-2-oxo-8-phenyl-1,3-diazaspiro[4.5]decan-3-yl]-benzonitrile |
| SC_3072 | cis-3-[1-(Cyclobutyl-methyl)-8-dimethylamino-2-oxo-8-phenyl-1,3-diazaspiro[4.5]decan-3-yl]-benzonitrile |
| SC_3073 | cis-1-(Cyclobutyl-methyl)-8-dimethylamino-8-phenyl-3-[2-(trifluoromethyl)-pyrimidin-5-yl]-1,3-diazaspiro[4.5]decan-2-one |
| SC_3074 | cis-5-[1-(Cyclobutyl-methyl)-8-dimethylamino-2-oxo-8-phenyl-1,3-diazaspiro[4.5]decan-3-yl]-4-methyl-pyridine-2-carboxylic acid methyl ester |
| SC_3075 | cis-1-(Cyclobutyl-methyl)-8-dimethylamino-3-(5-methoxy-pyrazin-2-yl)-8-phenyl-1,3-diazaspiro[4.5]decan-2-one |
| SC_3076 | cis-1-(Cyclobutyl-methyl)-8-dimethylamino-3-(2-methoxy-pyrimidin-5-yl)-8-phenyl-1,3-diazaspiro[4.5]decan-2-one |
| SC_3077 | cis-4-[1-(Cyclobutyl-methyl)-8-dimethylamino-2-oxo-8-phenyl-1,3-diazaspiro[4.5]decan-3-yl]-benzonitrile |
| SC_3078 | cis-5-[1-(Cyclobutyl-methyl)-8-dimethylamino-2-oxo-8-phenyl-1,3-diazaspiro[4.5]decan-3-yl]-4-methyl-pyridine-2-carbonitrile |
| SC_3079 | cis-1-(Cyclobutyl-methyl)-8-dimethylamino-3-(5-fluoro-pyrimidin-2-yl)-8-phenyl-1,3-diazaspiro[4.5]decan-2-one |
| SC_3080 | cis-4-[1-(Cyclobutyl-methyl)-8-dimethylamino-2-oxo-8-phenyl-1,3-diazaspiro[4.5]decan-3-yl]-3-methoxy-benzonitrile |
| SC_3081 | cis-4-[1-(Cyclobutyl-methyl)-8-dimethylamino-2-oxo-8-phenyl-1,3-diazaspiro[4.5]decan-3-yl]-benzoic acid methyl ester |
| SC_3082 | cis-1-(Cyclobutyl-methyl)-8-dimethylamino-8-phenyl-3-(2-pyrrolidin-1-yl-pyrimidin-4-yl)-1,3-diazaspiro[4.5]decan-2-one |
| SC_3083 | cis-1-(Cyclobutyl-methyl)-8-dimethylamino-8-phenyl-3-(5-pyridin-2-yl-thiophen-2-yl)-1,3-diazaspiro[4.5]decan-2-one |
| SC_3084 | cis-1-(Cyclobutyl-methyl)-8-dimethylamino-3-[2-methylsulfonyl-4-(trifluoromethyl)-phenyl]-8-phenyl-1,3-diazaspiro[4.5]decan-2-one |
| SC_3085 | cis-1-(Cyclobutyl-methyl)-8-dimethylamino-8-phenyl-3-[6-(trifluoromethyl)-pyridin-3-yl]-1,3-diazaspiro[4.5]decan-2-one |
| SC_3086 | cis-1-(Cyclobutyl-methyl)-3-(2,4-dimethoxy-phenyl)-8-dimethylamino-8-phenyl-1,3-diazaspiro[4.5]decan-2-one |
| SC_3087 | cis-2-[1-(Cyclobutyl-methyl)-8-dimethylamino-2-oxo-8-phenyl-1,3-diazaspiro[4.5]decan-3-yl]-4-methylsulfonyl-benzonitrile |
| SC_3088 | cis-5-[1-(Cyclobutyl-methyl)-8-dimethylamino-2-oxo-8-phenyl-1,3-diazaspiro[4.5]decan-3-yl]-2-fluoro-benzonitrile |
| SC_3089 | cis-4-[1-(Cyclobutyl-methyl)-8-dimethylamino-2-oxo-8-phenyl-1,3-diazaspiro[4.5]decan-3-yl]-N,N-dimethyl-3-(trifluoromethyl)-benzenesulfonic acid amide |
| SC_3090 | cis-2-[1-(Cyclobutyl-methyl)-8-dimethylamino-2-oxo-8-phenyl-1,3-diazaspiro[4.5]decan-3-yl]-benzonitrile |
| SC_3091 | cis-1-(Cyclobutyl-methyl)-8-dimethylamino-3-(2-methyl-imidazo[1,2-a]pyrazin-6-yl)-8-phenyl-1,3-diazaspiro[4.5]decan-2-one |

-continued

| | |
|---|---|
| SC_3092 | cis-1-(Cyclobutyl-methyl)-8-dimethylamino-3-(4-methylsulfonyl-phenyl)-8-phenyl-1,3-diazaspiro[4.5]decan-2-one |
| SC_3093 | cis-2-[1-(Cyclobutyl-methyl)-8-dimethylamino-2-oxo-8-phenyl-1,3-diazaspiro[4.5]decan-3-yl]-5-methoxy-benzonitrile |
| SC_3094 | cis-1-(Cyclobutyl-methyl)-8-dimethylamino-3,8-diphenyl-1,3-diazaspiro[4.5]decan-2-one |
| SC_3096 | cis-1-(Cyclobutyl-methyl)-8-dimethylamino-8-phenyl-3-pyrazin-2-yl-1,3-diazaspiro[4.5]decan-2-one |
| SC_3097 | cis-8-Dimethylamino-1-[(1-hydroxy-cyclobutyl)-methyl]-3-(2-morpholin-4-yl-pyrimidin-5-yl)-8-phenyl-1,3-diazaspiro[4.5]decan-2-one |
| SC_3098 | cis-8-Dimethylamino-1-[(1-hydroxy-cyclobutyl)-methyl]-3-[2-(4-methyl-piperazin-1-yl)-pyrimidin-5-yl]-8-phenyl-1,3-diazaspiro[4.5]decan-2-one |
| SC_3099 | cis-1-[(1-Hydroxy-cyclobutyl)-methyl]-8-methylamino-3-(2-morpholin-4-yl-pyrimidin-5-yl)-8-phenyl-1,3-diazaspiro[4.5]decan-2-one |
| SC_3100 | cis-8-Dimethylamino-1-[(1-hydroxy-cyclobutyl)-methyl]-8-phenyl-3-(2-piperazin-1-yl-pyrimidin-5-yl)-1,3-diazaspiro[4.5]decan-2-one hydrochloride |
| SC_3101 | cis-1-[(1-Hydroxy-cyclobutyl1)-methyl]-8-methylamino-3-[2-(4-methyl-piperazin-1-yl)-pyrimidin-5-yl]-8-phenyl-1,3-diazaspiro[4.5]decan-2-one |
| SC_3102 | cis-1-[(1-Hydroxy-cyclobutyl)-methyl]-8-methylamino-8-phenyl-3-(2-piperazin-1-yl-pyrimidin-5-yl)-1,3-diazaspiro[4.5]decan-2-one dihydrochloride |
| SC_3103 | cis-1-(Cyclobutyl-methyl)-8-dimethylamino-3-[4-methyl-6-(trifluoromethyl)-pyridin-3-yl]-8-phenyl-1,3-diazaspiro[4.5]decan-2-one |
| SC_3104 | cis-1-(Cyclobutyl-methyl)-8-methylamino-3-[4-methyl-6-(trifluoromethyl)-pyridin-3-yl]-8-phenyl-1,3-diazaspiro[4.5]decan-2-one |
| SC_3105 | cis-1-(Cyclopropyl-methyl)-8-dimethylamino-3-(4-methylsulfonyl-phenyl)-8-phenyl-1,3-diazaspiro[4.5]decan-2-one |
| SC_3106 | cis-1-(Cyclopropyl-methyl)-8-methylamino-3-(4-methylsulfonyl-phenyl)-8-phenyl-1,3-diazaspiro[4.5]decan-2-one |
| SC_3107 | cis-1-(Cyclopropyl-methyl)-8-dimethylamino-3-(2-fluoro-4-methylsulfonyl-phenyl)-8-phenyl-1,3-diazaspiro[4.5]decan-2-one |
| SC_3108 | cis-2-[8-Dimethylamino-1-[(1-hydroxy-cyclobutyl)-methyl]-2-oxo-8-phenyl-1,3-diazaspiro[4.5]decan-3-yl]-benzamide; formic acid |
| SC_3109 | cis-2-[8-Dimethylamino-1-[2-(1-methoxy-cyclobutyl)-ethyl]-2-oxo-8-phenyl-1,3-diazaspiro[4.5]decan-3-yl]-benzamide |
| SC_3110 | cis-8-Dimethylamino-1-[2-(1-methoxy-cyclobutyl)-ethyl]-3-(2-methyl-pyrimidin-5-yl)-8-phenyl-1,3-diazaspiro[4.5]decan-2-one |
| SC_3111 | cis-5-[1-[(1-Hydroxy-cyclobutyl)-methyl]-8-methylamino-2-oxo-8-phenyl-1,3-diazaspiro[4.5]decan-3-yl]-pyrimidine-2-carbonitrile |
| SC_3112 | cis-2-[1-[(1-Hydroxy-cyclobutyl)-methyl]-8-methylamino-2-oxo-8-phenyl-1,3-diazaspiro[4.5]decan-3-yl]-benzonitrile |
| SC_3113 | cis-4-[1-[(1-Hydroxy-cyclobutyl)-methyl]-8-methylamino-2-oxo-8-phenyl-1,3-diazaspiro[4.5]decan-3-yl]-3-methoxy-benzonitrile |
| SC_3114 | cis-4-[8-Ethylamino-1-[(1-hydroxy-cyclobutyl)-methyl]-2-oxo-8-phenyl-1,3-diazaspiro[4.5]decan-3-yl]-3-methoxy-benzonitrile |
| SC_3115 | cis-2-[8-Ethylamino-1-[(1-hydroxy-cyclobutyl)-methyl]-2-oxo-8-phenyl-1,3-diazaspiro[4.5]decan-3-yl]-benzonitrile |
| SC_3116 | cis-5-[1-[(1-Hydroxy-cyclobutyl)-methyl]-8-methylamino-2-oxo-8-phenyl-1,3-diazaspiro[4.5]decan-3-yl]-4-methoxy-pyrimidine-2-carbonitrile |
| SC_3117 | cis-2-[8-Dimethylamino-1-(oxetan-3-yl-methyl)-2-oxo-8-phenyl-1,3-diazaspiro[4.5]decan-3-yl]-benzamide |
| SC_3118 | cis-4-Methoxy-5-(8-methylamino-2-oxo-8-phenyl-1,3-diazaspiro[4.5]decan-3-yl)-pyrimidine-2-carbonitrile |
| SC_3119 | cis-2-(8-Methylamino-2-oxo-8-phenyl-1,3-diazaspiro[4.5]decan-3-yl)-benzamide |
| SC_3120 | cis-8-Dimethylamino-3-[2-(3-oxo-piperazin-1-yl)-pyrimidin-5-yl]-8-phenyl-1,3-diazaspiro[4.5]decan-2-one |
| SC_3121 | cis-3-(2-Cyclopropyl-pyrimidin-5-yl)-8-dimethylamino-8-phenyl-1,3-diazaspiro[4.5]decan-2-one |
| SC_3122 | cis-8-Dimethylamino-3-[4-methyl-6-(trifluoromethyl)-pyridin-3-yl]-8-phenyl-1,3-diazaspiro[4.5]decan-2-one |
| SC_3123 | cis-8-Dimethylamino-3-(2-methylsulfonyl-phenyl)-8-phenyl-1,3-diazaspiro[4.5]decan-2-one |
| SC_3124 | cis-8-Dimethylamino-8-phenyl-3-(2-piperazin-1-yl-pyrimidin-5-yl)-1,3-diazaspiro[4.5]decan-2-one |
| SC_3125 | trans-2-(8-Ethylamino-2-oxo-8-phenyl-1,3-diazaspiro[4.5]decan-3-yl)-benzamide |
| SC_3126 | cis--2-(8-Ethylamino-2-oxo-8-phenyl-1,3-diazaspiro[4.5]decan-3-yl)-benzamide |
| SC_3127 | cis-2-(8-Ethylamino-2-oxo-8-phenyl-1,3-diazaspiro[4.5]decan-3-yl)-benzamide |
| SC_3128 | cis-2-(8-Ethylamino-2-oxo-8-phenyl-1,3-diazaspiro[4.5]decan-3-yl)-benzamide |
| SC_3129 | cis-3-[5-(8-Dimethylamino-2-oxo-8-phenyl-1,3-diazaspiro[4.5]decan-3-yl)-pyrimidin-2-yl]-benzonitrile |
| SC_3130 | cis-8-Dimethylamino-3-[2-(4-methylsulfonyl-piperazin-1-yl)-pyrimidin-5-yl]-8-phenyl-1,3-diazaspiro[4.5]decan-2-one |
| SC_3131 | cis-3-[5-(8-Dimethylamino-2-oxo-8-phenyl-1,3-diazaspiro[4.5]decan-3-yl)-pyrimidin-2-yl]-benzamide |
| SC_3132 | cis-8-[(Cyclopropyl-methyl)-methyl-amino]-8-phenyl-3-[2-(trifluoromethyl)-pyrimidin-5-yl]-1,3-diazaspiro[4.5]decan-2-one |
| SC_3133 | cis-8-Dimethylamino-3-[2-(4-methyl-piperazine-1-carbonyl)-pyrimidin-5-yl]-8-phenyl-1,3-diazaspiro[4.5]decan-2-one |
| SC_3134 | trans-4-(8-Ethylamino-2-oxo-8-phenyl-1,3-diazaspiro[4.5]decan-3-yl)-3-methoxy-benzonitrile |

| | |
|---|---|
| SC_3135 | cis-4-(8-Ethylamino-2-oxo-8-phenyl-1,3-diazaspiro[4.5]decan-3-yl)-3-methoxy-benzonitrile |
| SC_3136 | cis-3-[2-(4-Acetyl-piperazin-1-yl)-pyrimidin-5-yl]-8-dimethylamino-8-phenyl-1,3-diazaspiro[4.5]decan-2-one |
| SC_3137 | cis-8-Dimethylamino-8-phenyl-3-(2-pyridin-4-yl-pyrimidin-5-yl)-1,3-diazaspiro[4.5]decan-2-one |
| SC_3138 | cis-8-Dimethylamino-8-phenyl-3-(2-pyridin-3-yl-pyrimidin-5-yl)-1,3-diazaspiro[4.5]decan-2-one |
| SC_3139 | cis-5-(8-Dimethylamino-2-oxo-8-phenyl-1,3-diazaspiro[4.5]decan-3-yl)-N-(2-hydroxy-ethyl)-pyrimidine-2-carboxylic acid amide |
| SC_3140 | cis-5-(8-Dimethylamino-2-oxo-8-phenyl-1,3-diazaspiro[4.5]decan-3-yl) pyrimidine-2-carboxylic acid amide |
| SC_3141 | cis-8-Dimethylamino-3-[2-morpholin-4-yl-4-(trifluoromethyl)-pyrimidin-5-yl]-8-phenyl-1,3-diazaspiro[4.5]decan-2-one |
| SC_3142 | cis-4-[5-(8-Dimethylamino-2-oxo-8-phenyl-1,3-diazaspiro[4.5]decan-3-yl)-pyrimidin-2-yl]-benzonitrile |
| SC_3143 | cis-5-(8-Ethylamino-2-oxo-8-phenyl-1,3-diazaspiro[4.5]decan-3-yl)-4-methoxy-pyrimidine-2-carbonitrile |
| SC_3144 | trans-5-(8-Ethylamino-2-oxo-8-phenyl-1,3-diazaspiro[4.5]decan-3-yl)-4-methoxy-pyrimidine-2-carbonitrile |
| SC_3145 | cis-8-Dimethylamino-3-[2-(morpholine-4-carbonyl)-pyrimidin-5-yl]-8-phenyl-1,3-diazaspiro[4.5]decan-2-one |
| SC_3146 | cis-2-[4-[5-(8-Dimethylamino-2-oxo-8-phenyl-1,3-diazaspiro[4.5]decan-3-yl)-pyrimidin-2-yl]-piperazin-1-yl]-acetic acid methyl ester |
| SC_3147 | cis-8-Dimethylamino-3-[2-(methylsulfonyl-methyl)-phenyl]-8-phenyl-1,3-diazaspiro[4.5]decan-2-one |
| SC_3148 | cis-8-Dimethylamino-3-(4-methyl-2-morpholin-4-yl-pyrimidin-5-yl)-8-phenyl-1,3-diazaspiro[4.5]decan-2-one |
| SC_3149 | cis-8-Dimethylamino-3-[2-(1,1-dioxo-[1,4]thiazinan-4-yl)-pyrimidin-5-yl]-8-phenyl-1,3-diazaspiro[4.5]decan-2-one |
| SC_3150 | cis-8-Dimethylamino-3-(4-fluoro-pyridin-3-yl)-8-phenyl-1,3-diazaspiro[4.5]decan-2-one |
| SC_3151 | cis-5-(8-Dimethylamino-2-oxo-8-phenyl-1,3-diazaspiro[4.5]decan-3-yl)-N-(2-hydroxy-ethyl)-N-methyl-pyrimidine-2-carboxylic acid amide |
| SC_3152 | cis-5-(8-Dimethylamino-2-oxo-8-phenyl-1,3-diazaspiro[4.5]decan-3-yl)-2-morpholin-4-yl-isonicotinonitrile |
| SC_3153 | cis-4-(8-Dimethylamino-2-oxo-8-phenyl-1,3-diazaspiro[4.5]decan-3-yl)-benzamide |
| SC_3154 | cis-8-Dimethylamino-3-(2-fluoro-4-methylsulfonyl-phenyl)-8-phenyl-1,3-diazaspiro[4.5]decan-2-one |
| SC_3155 | cis-4-(8-Dimethylamino-2-oxo-8-phenyl-1,3-diazaspiro[4.5]decan-3-yl)-3-fluoro-benzonitrile |
| SC_3156 | cis-4-(8-Dimethylamino-2-oxo-8-phenyl-1,3-diazaspiro[4.5]decan-3-yl)-3,5-difluoro-benzonitrile |
| SC_3157 | cis-8-Dimethylamino-3-(2-methoxy-pyrimidin-5-yl)-8-phenyl-1,3-diazaspiro[4.5]decan-2-one |
| SC_3158 | cis-3-[2-(Benzylamino)-pyrimidin-5-yl]-8-dimethylamino-8-phenyl-1,3-diazaspiro[4.5]decan-2-one |
| SC_3159 | cis-8-Dimethylamino-3-[2-(4-fluorophenyl)-pyrimidin-5-yl]-8-phenyl-1,3-diazaspiro[4.5]decan-2-one |
| SC_3160 | trans-8-Benzyl-8-dimethylamino-3-(2-morpholin-4-yl-pyrimidin-5-yl)-1,3-diazaspiro[4.5]decan-2-one |
| SC_3161 | cis-8-Benzyl-8-dimethylamino-3-(2-morpholin-4-yl-pyrimidin-5-yl)-1,3-diazaspiro[4.5]decan-2-one |
| SC_3162 | cis-8-Dimethylamino-8-phenyl-3-(2-pyridin-2-yl-pyrimidin-5-yl)-1,3-diazaspiro[4.5]decan-2-one |
| SC_3163 | cis-4-(8-Dimethylamino-2-oxo-8-phenyl-1,3-diazaspiro[4.5]decan-3-yl)-3,5-difluoro-benzamide |
| SC_3164 | cis-4-(8-Dimethylamino-2-oxo-8-phenyl-1,3-diazaspiro[4.5]decan-3-yl)-3-fluoro-benzamide |
| SC_3165 | cis-8-Benzyl-8-dimethylamino-3-[2-(trifluoromethyl)-pyrimidin-5-yl]-1,3-diazaspiro[4.5]decan-2-one |
| SC_3166 | trans-8-Benzyl-8-dimethylamino-3-[2-(trifluoromethyl)-pyrimidin-5-yl]-1,3-diazaspiro[4.5]decan-2-one |
| SC_3167 | cis-8-Dimethylamino-8-thiophen-2-yl-3-[2-(trifluoromethyl)-pyrimidin-5-yl]-1,3-diazaspiro[4.5]decan-2-one |
| SC_3168 | trans-8-Dimethylamino-8-thiophen-2-yl-3-[2-(trifluoromethyl)-pyrimidin-5-yl]-1,3-diazaspiro[4.5]decan-2-one |
| SC_3169 | cis-2-[2-(8-Dimethylamino-2-oxo-8-phenyl-1,3-diazaspiro[4.5]decan-3-yl) phenoxy]-acetic acid |
| SC_3170 | cis-8-Dimethylamino-8-phenyl-3-(2-piperidin-1-yl-pyrimidin-5-yl)-1,3-diazaspiro[4.5]decan-2-one |
| SC_3171 | cis-8-Dimethylamino-8-phenyl-3-(2-pyrrolidin-1-yl-pyrimidin-5-yl)-1,3-diazaspiro[4.5]decan-2-one |
| SC_3172 | cis-8-Dimethylamino-8-phenyl-3-(2-pyrimidin-5-yl-pyrimidin-5-yl)-1,3-diazaspiro[4.5]decan-2-one |
| SC_3173 | cis-8-Dimethylamino-8-phenyl-3-[2-(piperazine-1-carbonyl)-pyrimidin-5-yl]-1,3-diazaspiro[4.5]decan-2-one |
| SC_3174 | trans-8-Benzyl-8-dimethylamino-3-[4-methyl-6-(trifluoromethyl)-pyridin-3-yl]-1,3-diazaspiro[4.5]decan-2-one |

| | |
|---|---|
| SC_3175 | cis-5-(8-Dimethylamino-2-oxo-8-phenyl-1,3-diazaspiro[4.5]decan-3-yl)-2-morpholin-4-yl-pyridine-4-carboxylic acid amide |
| SC_3176 | cis-8-Dimethylamino-3-[2-(3,5-dimethyl-isoxazol-4-yl)-pyrimidin-5-yl]-8-phenyl-1,3-diazaspiro[4.5]decan-2-one |
| SC_3177 | cis-3-[2-(Benzothiazol-6-yl)-pyrimidin-5-yl]-8-dimethylamino-8-phenyl-1,3-diazaspiro[4.5]decan-2-one |
| SC_3178 | cis-8-Dimethylamino-3-[2-fluoro-4-(trifluoromethyl)-phenyl]-8-phenyl-1,3-diazaspiro[4.5]decan-2-one |
| SC_3179 | cis-8-Dimethylamino-3-(6-morpholin-4-yl-pyridin-3-yl)-8-phenyl-1,3-diazaspiro[4.5]decan-2-one |
| SC_3180 | cis-8-Dimethylamino-8-phenyl-3-(2-phenyl-thiazol-4-yl)-1,3-diazaspiro[4.5[decan-2-one |
| SC_3181 | cis-8-Dimethylamino-8-phenyl-3-[2-(tetrahydro-pyran-4-ylamino)-pyrimidin-5-yl]-1,3-diazaspiro[4.5]decan-2-one |
| SC_3182 | cis-8-Dimethylamino-3-[2-(4-hydroxy-piperidin-1-yl)-pyrimidin-5-yl]-8-phenyl-1,3-diazaspiro[4.5]decan-2-one |
| SC_3183 | cis-8-Dimethylamino-8-phenyl-3-(4-phenyl-thiazol-2-yl)-1,3-diazaspiro[4.5]decan-2-one |
| SC_3184 | cis-8-Dimethylamino-8-phenyl-3-[2-(1H-pyrrolo[2,3-b]pyridin-1-yl)-pyrimidin-5-yl]-1,3-diazaspiro[4.5]decan-2-one |
| SC_3185 | cis-8-Dimethylamino-8-phenyl-3-[2-(3,4,5-trifluoro-phenyl)-pyrimidin-5-yl]-1,3-diazaspiro[4.5]decan-2-one |
| SC_3186 | cis-8-Dimethylamino-3-o-tolyl-8-phenyl-1,3-diazaspiro[4.5]decan-2-one |
| SC_3187 | cis-8-Dimethylamino-3-m-tolyl-8-phenyl-1,3-diazaspiro[4.5]decan-2-one |
| SC_3188 | cis-8-Dimethylamino-8-phenyl-3-p-tolyl-1,3-diazaspiro[4.5]decan-2-one |
| SC_3189 | cis-8-Dimethylamino-8-phenyl-3-[4-(trifluoromethyl)-phenyl]-1,3-diazaspiro[4.5]decan-2-one |
| SC_3190 | cis-8-Dimethylamino-8-phenyl-3-[3-(trifluoromethyloxy)-phenyl]-1,3-diazaspiro[4.5]decan-2-one |
| SC_3191 | cis-8-Dimethylamino-8-phenyl-3-[4-(trifluoromethyloxy)-phenyl]-1,3-diazaspiro[4.5]decan-2-one |
| SC_3192 | cis-2-(8-Dimethylamino-2-oxo-8-phenyl-1,3-diazaspiro[4.5]decan-3-yl)-benzoic acid methyl ester |
| SC_3193 | cis-3-(8-Dimethylamino-2-oxo-8-phenyl-1,3-diazaspiro[4.5]decan-3-yl)-benzoic acid methyl ester |
| SC_3194 | cis-4-(8-Dimethylamino-2-oxo-8-phenyl-1,3-diazaspiro[4.5]decan-3-yl)-benzoic acid methyl ester |
| SC_3195 | cis-3-(1,3-Benzodioxol-5-yl)-8-dimethylamino-8-phenyl-1,3-diazaspiro[4.5]decan-2-one |
| SC_3196 | cis-8-Dimethylamino-8-phenyl-3-quinolin-5-yl-1,3-diazaspiro[4.5]decan-2-one |
| SC_3197 | cis-3-(2,3-Dihydro-1H-indol-6-yl)-8-dimethylamino-8-phenyl-1,3-diazaspiro[4.5]decan-2-one |
| SC_3198 | cis-5-(8-Dimethylamino-2-oxo-8-phenyl-1,3-diazaspiro[4.5]decan-3-yl)-4-methyl-pyridine-2-carboxylic acid methyl ester |
| SC_3199 | cis-8-Dimethylamino-3-(6-methoxy-4-methyl-pyridin-3-yl)-8-phenyl-1,3-diazaspiro[4.5]decan-2-one |
| SC_3200 | cis-8-Dimethylamino-3-[2-methyl-5-(trifluoromethyl)-2H-pyrazol-3-yl]-8-phenyl-1,3-diazaspiro[4.5]decan-2-one |
| SC_3201 | cis-8-Dimethylamino-3-(3-methoxy-pyridin-2-yl)-8-phenyl-1,3-diazaspiro[4.5]decan-2-one |
| SC_3202 | cis-8-Dimethylamino-8-phenyl-3-[5-(trifluoromethyl)-pyridin-2-yl]-1,3-diazaspiro[4.5]decan-2-one |
| SC_3203 | cis-5-(8-Dimethylamino-2-oxo-8-phenyl-1,3-diazaspiro[4.5]decan-3-yl)-nicotinonitrile |
| SC_3204 | cis-8-Dimethylamino-3-(3-methyl-pyridin-2-yl)-8-phenyl-1,3-diazaspiro[4.5]decan-2-one |
| SC_3205 | cis-8-Dimethylamino-3-(6-methoxy-pyridin-3-yl)-8-phenyl-1,3-diazaspiro[4.5]decan-2-one |
| SC_3206 | cis-8-Dimethylamino-8-phenyl-3-[3-(trifluoromethyl)phenyl]-1,3-diazaspiro[4.5]decan-2-one |
| SC_3207 | cis-3-(1,3-Benzodioxol-4-yl)-8-dimethylamino-8-phenyl-1,3-diazaspiro[4.5]decan-2-one |
| SC_3208 | cis-8-Dimethylamino-3-[2-(2-oxo-1,3-dihydro-indol-4-yl)-pyrimidin-5-yl]-8-phenyl-1,3-diazaspiro[4.5]decan-2-one |
| SC_3209 | cis-8-Dimethylamino-3-[2-(3,5-dimethyl-1H-pyrazol-1-yl)-pyrimidin-5-yl]-8-phenyl-1,3-diazaspiro[4.5]decan-2-one |
| SC_3210 | cis-8-Dimethylamino-3-[2-(3-hydroxy-piperidin-1-yl)-pyrimidin-5-yl]-8-phenyl-1,3-diazaspiro[4.5]decan-2-one |
| SC_3211 | cis-8-Dimethylamino-3-[2-(3-hydroxy-piperidin-1-yl)-pyrimidin-5-yl]-8-phenyl-1,3-diazaspiro[4.5]decan-2-one |
| SC_3212 | cis-8-Dimethylamino-3-[2-[4-(2-hydroxy-ethyl)-piperazin-1-yl]-pyrimidin-5-yl]-8-phenyl-1,3-diazaspiro[4.5]decan-2-one |
| SC_3213 | cis-2-[4-[5-(8-Dimethylamino-2-oxo-8-phenyl-1,3-diazaspiro[4.5]decan-3-yl)-pyrimidin-2-yl]-piperazin-1-yl]-acetic acid |
| SC_3214 | cis-8-Dimethylamino-3-[2-(1-methyl-1H-pyrrolo[2,3-b]pyridin-4-yl)-pyrimidin-5-yl]-8-phenyl-1,3-diazaspiro[4.5]decan-2-one |
| SC_3215 | cis-8-Benzyl-8-dimethylamino-3-[4-methyl-6-(trifluoromethyl)-pyridin-3-yl]-1,3-diazaspiro[4.5]decan-2-one |

| | |
|---|---|
| SC_3216 | trans-8-Dimethylamino-3-[4-methyl-6-(trifluoromethyl)-pyridin-3-yl]-8-thiophen-2-yl-1,3-diazaspiro[4.5]decan-2-one |
| SC_3217 | cis-8-Dimethylamino-3-[4-methyl-6-(trifluoromethyl)-pyridin-3-yl]-8-thiophen-2-y1-1,3-diazaspiro[4.5]decan-2-one |
| SC_3218 | cis-8-Dimethylamino-3-[2-(1,1-dioxo-[1,4]thiazinan-4-yl)-4-(trifluoromethyl)-pyrimidin-5-yl]-8-phenyl-1,3-diazaspiro[4.5]decan-2-one |
| SC_3219 | cis-8-Dimethylamino-8-(1-methyl-1H-benzoimidazol-2-yl)-3-[2-(trifluoromethyl)-pyrimidin-5-yl]-1,3-diazaspiro[4.5]decan-2-one |
| SC_3220 | cis-8-Dimethylamino-8-(1-methyl-1H-benzoimidazol-2-yl)-3-[4-methyl-6-(trifluoromethyl)-pyridin-3-yl]-1,3-diazaspiro[4.5]decan-2-one |
| SC_3221 | cis-8-Dimethylamino-3-[2-(2-hydroxy-ethylamino)-pyrimidin-5-yl]-8-phenyl-1,3-diazaspiro[4.5]decan-2-one |
| SC_3222 | cis-3-[2-(Benzyl-methyl-amino)-pyrimidin-5-yl]-8-dimethylamino-8-phenyl-1,3-diazaspiro[4.5]decan-2-one |
| SC_3223 | cis-5-(8-Dimethylamino-2-oxo-8-phenyl-1,3-diazaspiro[4.5]decan-3-yl)-N-[2-[2-[2-(2-methoxy-ethoxy)-ethoxy]-ethoxy]-ethyl]-pyrimidine-2-carboxylic acid amide |
| SC_3224 | cis-8-Dimethylamino-3-[2-(1H-indazol-1-yl)-pyrimidin-5-yl]-8-phenyl-1,3 diazaspiro[4.5]decan-2-one |
| SC_3225 | cis-8-Dimethylamino-3-[2-[(2-hydroxy-ethyl)-methyl-amino]-pyrimidin-5-yl]-8-phenyl-1,3-diazaspiro[4.5]decan-2-one |
| SC_3226 | cis-3-(8-Dimethylamino-2-oxo-8-phenyl-1,3-diazaspiro[4.5]decan-3-yl)-benzamide |
| SC_3227 | cis-8-Dimethylamino-3-[3-fluoro-5-(trifluoromethyl)-pyridin-2-yl]-8-phenyl-1,3-diazaspiro[4.5]decan-2-one |
| SC_3228 | cis-8-Dimethylamino-3-(5-methyl-pyrazin-2-yl)-8-phenyl-1,3-diazaspiro[4.5]decan-2-one |
| SC_3229 | cis-8-Dimethylamino-3-(5-fluoro-pyrimidin-4-yl)-8-phenyl-1,3-diazaspiro[4.5]decan-2-one |
| SC_3230 | cis-8-Dimethylamino-3-(5-fluoro-pyrimidin-2-yl)-8-pheny1-1,3-diazaspiro[4.5]decan-2-one |
| SC_3231 | cis-8-Dimethylamino-8-phenyl-3-pyrazin-2-yl-1,3-diazaspiro[4.5]decan-2-one |
| SC_3232 | cis-3-([2,1,3]Benzoxadiazol-5-yl)-8-dimethylamino-8-phenyl-1,3-diazaspiro[4.5]decan-2-one |
| SC_3233 | cis-2-[2-(8-Dimethylamino-2-oxo-8-phenyl-1,3-diazaspiro[4.5]decan-3-yl)-phenoxy]-acetamide |
| SC_3234 | cis-8-Dimethylamino-8-phenyl-3-(5-pyridin-4-yl-thiophen-2-yl)-1,3-diazaspiro[4.5]decan-2-one |
| SC_3235 | cis-2-[2-(8-Dimethylamino-2-oxo-8-phenyl-1,3-diazaspiro[4.5]decan-3-yl)-phenoxy]-acetic acid methyl ester |
| SC_3236 | cis-8-Dimethylamino-3-(2-morpholin-4-yl-pyrimidin-4-yl)-8-phenyl-1,3-diazaspiro[4.5]decan-2-one |
| SC_3237 | cis-3-[2-(3,4-Difluoro-phenyl)-pyrimidin-5-yl]-8-dimethylamino-8-phenyl-1,3-diazaspiro[4.5]decan-2-one |
| SC_3238 | cis-2-[5-(8-Dimethylamino-2-oxo-8-phenyl-1,3-diazaspiro[4.5]decan-3-yl)-pyrimidin-2-yl]-benzonitrile |
| SC_3239 | cis-3-(2-Amino-pyrimidin-5-yl)-8-dimethylamino-8-phenyl-1,3-diazaspiro[4.5]decan-2-one |
| SC_3240 | cis-N-[5-(8-Dimethylamino-2-oxo-8-phenyl-1,3-diazaspiro[4.5]decan-3-yl)-pyrimidin-2-yl]-cyclopropanecarboxylic acid amide |
| SC_3241 | cis-2-[4-[5-(8-Dimethylamino-2-oxo-8-phenyl-1,3-diazaspiro[4.5]decan-3-yl)-pyrimidin-2-yl]-piperazin-1-yl]-acetamide |
| SC_3242 | cis-8-Dimethylamino-8-phenyl-3-(6-piperazin-1-yl-pyridin-3-yl)-1,3-diazaspiro[4.5]decan-2-one |
| SC_3243 | cis-8-Dimethylamino-3-[6-(4-methyl-piperazin-1-yl)-pyridin-3-yl]-8-phenyl-1,3-diazaspiro[4.5]decan-2-one |
| SC_3244 | cis-8-Dimethylamino-3-[2-(1,1-dioxo-[1,4]thiazinan-4-yl)-4-methyl-pyrimidin-5-yl]-8-phenyl-1,3-diazaspiro[4.5]decan-2-one |
| SC_3245 | cis-8-Dimethylamino-8-phenyl-3-[2-(trifluoromethyl)-pyrimidin-5-yl]-1,3-diazaspiro[4.5]decan-2-one |
| SC_3246 | cis-2-[8-Dimethylamino-1-(3-methoxy-propyl)-2-oxo-8-phenyl-1,3-diazaspiro[4.5]decan-3-yl]-pyrimidine-5-carbonitrile |
| SC_3247 | cis-8-Dimethylamino-3-[2-(4-methyl-piperazin-1-yl)-pyrimidin-5-yl]-8-phenyl-1,3-diazaspiro[4.5]decan-2-one |
| SC_3248 | cis-8-Dimethylamino-1-[(1-hydroxy-cyclobutyl)-methyl]-8-phenyl-3-[2-(trifluoromethyl)-pyrimidin-5-yl]-1,3-diazaspiro[4.5]decan-2-one |
| SC_3249 | cis-2-[1-(3-Methoxy-propyl)-8-methylamino-2-oxo-8-phenyl-1,3-diazaspiro[4.5]decan-3-yl]-pyrimidine-5-carbonitrile |
| SC_3250 | cis-8-Dimethylamino-8-phenyl-3-[6-(trifluoromethyl)-pyridin-3-yl]-1,3-diazaspiro[4.5]decan-2-one |
| SC_3251 | cis-5-(8-Dimethylamino-2-oxo-8-phenyl-1,3-diazaspiro[4.5]decan-3-yl)-pyridine-2-carbonitrile |
| SC_3252 | cis-8-Dimethylamino-3-(2-morpholin-4-yl-pyrimidin-5-yl)-8-phenyl-1,3-diazaspiro[4.5]decan-2-one |
| SC_3253 | cis-8-Dimethylamino-3-(2-methyl-pyrimidin-5-yl)-8-phenyl-1,3-diazaspiro[4.5]decan-2-one |
| SC_3254 | cis-8-Dimethylamino-1-[(2-methoxyphenyl)-methyl]-3-(2-methyl-pyrimidin-5-yl)-8-phenyl-1,3-diazaspiro[4.5]decan-2-one |
| SC_3255 | cis-1-[(1-Hydroxy-cyclobutyl)-methyl]-8-methylamino-8-phenyl-3-[2-(trifluoromethyl)-pyrimidin-5-yl]-1,3-diazaspiro[4.5]decan-2-one |

-continued

| | |
|---|---|
| SC_3256 | cis-8-Dimethylamino-1-[(1-hydroxy-cyclobutyl)-methyl]-3-(2-methyl-pyrimidin-5-yl)-8-phenyl-1,3-diazaspiro[4.5]decan-2-one |
| SC_3257 | cis-1-[(1-Hydroxy-cyclobutyl)-methyl]-8-methylamino-8-phenyl-3-pyrimidin-5-yl 1,3-diazaspiro[4.5]decan-2-one |
| SC_3258 | cis-5-(8-Dimethylamino-2-oxo-8-phenyl-1,3-diazaspiro[4.5]decan-3-yl)-4-methyl-pyridine-2-carbonitrile |
| SC_3259 | cis-8-Dimethylamino-3-(2-methyl-pyrimidin-5-yl)-8-phenyl-1-(pyridin-2-yl-methyl)-1,3-diazaspiro[4.5]decan-2-one |
| SC_3260 | cis-8-Dimethylamino-8-phenyl-3-pyrimidin-5-yl-1,3-diazaspiro[4.5]decan-2-one |
| SC_3261 | cis-8-Dimethylamino-1-[(1-hydroxy-cyclobutyl)-methyl]-8-phenyl-3-pyrimidin-5-yl-1,3-diazaspiro[4.5]decan-2-one |
| SC_3262 | cis-8-Amino-1-[(1-hydroxy-cyclobutyl)-methyl]-8-phenyl-3-[2-(trifluoromethyl)-pyrimidin-5-yl]-1,3-diazaspiro[4.5]decan-2-one |
| SC_3263 | cis-8-Dimethylamino-3-(3-fluorophenyl)-8-phenyl-1,3-diazaspiro[4.5]decan-2-one |
| SC_3264 | cis-8-Dimethylamino-3-(3-methylsulfonyl-phenyl)-8-phenyl-1,3-diazaspiro[4.5]decan-2-one |
| SC_3265 | cis-8-Dimethylamino-3-(4-methylsulfonyl-phenyl)-8-phenyl-1,3-diazaspiro[4.5]decan-2-one |
| SC_3266 | cis-8-Dimethylamino-8-phenyl-3-pyridazin-3-yl-1,3-diazaspiro[4.5]decan-2-one |
| SC_3267 | cis-3-Methoxy-4-(8-methylamino-2-oxo-8-phenyl-1,3-diazaspiro[4.5]decan-3-yl)-benzonitrile |
| SC_3268 | cis-8-Dimethylamino-3-(2-fluorophenyl)-8-phenyl-1,3-diazaspiro[4.5]decan-2-one |
| SC_3269 | cis-8-Dimethylamino-8-phenyl-3-(2-phenyl-pyrimidin-5-yl)-1,3-diazaspiro[4.5]decan-2-one |
| SC_3270 | cis-8-Methylamino-1-(oxetan-3-yl-methyl)-8-phenyl-3-[2-(trifluoromethyl)-pyrimidin-5-yl]-1,3-diazaspiro[4.5]decan-2-one |
| SC_3271 | cis-1-(Cyclopropyl-methyl)-8-methylamino-8-phenyl-3-[2-(trifluoromethyl)-pyrimidin-5-yl]-1,3-diazaspiro[4.5]decan-2-one |
| SC_3272 | cis-4-(8-Dimethylamino-2-oxo-8-phenyl-1,3-diazaspiro[4.5]decan-3-yl)-benzonitrile |
| SC_3273 | cis-8-Dimethylamino-3-(4-fluorophenyl)-8-phenyl-1,3-diazaspiro[4.5]decan-2-one |
| SC_3274 | cis-2-(8-Dimethylamino-2-oxo-8-phenyl-1,3-diazaspiro[4.5]decan-3-yl)-benzonitrile |
| SC_3275 | cis-8-Ethylamino-1-[(1-hydroxy-cyclobutyl)-methyl]-8-phenyl-3-[2-(trifluoromethyl)-pyrimidin-5-yl]-1,3-diazaspiro[4.5]decan-2-one |
| SC_3276 | cis-1-[(1-Hydroxy-cyclobutyl)-methyl]-8-methylamino-3-(2-methyl-pyrimidin-5-yl)-8-phenyl-1,3-diazaspiro[4.5]decan-2-one |
| SC_3277 | cis-8-Dimethylamino-3-[2-(morpholin-4-yl-methyl)-pyrimidin-5-yl]-8-phenyl-1,3-diazaspiro[4.5]decan-2-one |
| SC_3278 | cis-8-Dimethylamino-3-[2-(methyl-tetrahydro-pyran-4-yl-amino)-pyrimidin-5-yl]-8-phenyl-1,3-diazaspiro[4.5]decan-2-one |
| SC_3279 | cis-5-[8-Dimethylamino-1-[(1-hydroxy-cyclobutyl)-methyl]-2-oxo-8-phenyl-1,3-diazaspiro[4.5]decan-3-yl]-N-[2-[2-(2-methoxy-ethoxy)-ethoxyl-ethoxyl-ethyl]-pyrimidine-2-carboxylic acid amide |
| SC_3280 | cis-1-(Cyclopropyl-methyl)-3-(2-fluoro-4-methylsulfonyl-phenyl)-8-methylamino-8-phenyl-1,3-diazaspiro[4.5]decan-2-one |
| SC_3281 | cis-2-[[5-(8-Dimethylamino-2-oxo-8-phenyl-1,3-diazaspiro[4.5]decan-3-yl)-pyrimidin-2-yl]-methyl-aminol-acetamide |
| SC_3282 | cis-2-[[5-(8-Dimethylamino-2-oxo-8-phenyl-1,3-diazaspiro[4.5]decan-3-yl)-pyrimidin-2-yl]amino]-acetamide |
| SC_3283 | cis-1-(Cyclopropyl-methyl)-8-methylamino-3-[4-methyl-6-(trifluoromethyl)-pyridin-3-yl]-8-phenyl-1,3-diazaspiro[4.5]decan-2-one |
| SC_3284 | cis-1-(Cyclopropyl-methyl)-8-dimethylamino-3-[4-methyl-6-(trifluoromethyl)-pyridin-3-yl]-8-phenyl-1,3-diazaspiro[4.5]decan-2-one |
| SC_3285 | cis-N-[5-(8-Dimethylamino-2-oxo-8-phenyl-1,3-diazaspiro[4.5]decan-3-yl)-pyrimidin-2-yl]-thiophene-2-carboxylic acid amide |
| SC_3286 | cis-N-[5-(8-Dimethylamino-2-oxo-8-phenyl-1,3-diazaspiro[4.5]decan-3-yl)-pyrimidin-2-yl]-benzamide |
| SC_3287 | cis-8-Dimethylamino-8-phenyl-3-(5-phenyl-thiophen-2-yl)-1,3-diazaspiro[4.5]decan-2-one |
| SC_3288 | cis-1-(Cyclopropyl-methyl)-8-methylamino-3-[2-(methylsulfonyl-methyl)-phenyl]-8-phenyl-1,3-diazaspiro[4.5]decan-2-one |
| SC_3289 | cis-1-(Cyclopropyl-methyl)-8-dimethylamino-3-[2-(methylsulfonyl-methyl)-phenyl]-8-phenyl-1,3-diazaspiro[4.5]decan-2-one |
| SC_3290 | cis-8-Dimethylamino-8-(3-fluorophenyl)-3-[2-(methylsulfonyl-methyl)-phenyl]-1,3-diazaspiro[4.5]decan-2-one |
| SC_3291 | cis-8-Dimethylamino-8-(4-fluorophenyl)-3-[2-(methylsulfonyl-methyl)-phenyl]-1,3-diazaspiro[4.5]decan-2-one |
| SC_3292 | cis-8-[Methyl-(tetrahydro-furan-3-yl-methyl)-amino]-8-phenyl-3-[2-(trifluoromethyl)-pyrimidin-5-yl]-1,3-diazaspiro[4.5]decan-2-one (enantiomer 1) |
| SC_3293 | cis-8-[Methyl-(tetrahydro-furan-3-yl-methyl)-amino]-8-phenyl-3-[2-(trifluoromethyl)-pyrimidin-5-yl]-1,3-diazaspiro[4.5]decan-2-one (enantiomer 2) |
| SC_3294 | cis-8-Dimethylamino-8-(3-fluorophenyl)-3-(4-methyl-2-morpholin-4-yl-pyrimidin-5-yl)-1,3-diazaspiro[4.5]decan-2-one |
| SC_3295 | cis-3-[6-(4-Acetyl-piperazin-1-yl)-4-methyl-pyridin-3-yl]-8-dimethylamino-8-phenyl-1,3-diazaspiro[4.5]decan-2-one |
| SC_3296 | cis-3-[2-(4-Acetyl-piperazin-1-yl)-4-methyl-pyrimidin-5-yl]-8-dimethylamino-8-phenyl-1,3-diazaspiro[4.5]decan-2-one |

| | |
|---|---|
| SC_3297 | cis-8-Dimethylamino-3-(4-methyl-6-pyridin-4-yl-pyridin-3-yl)-8-phenyl-1,3-diazaspiro[4.5]decan-2-one |
| SC_3298 | cis-3-[2-(4-Acetyl-piperazin-1-yl)-4-(trifluoromethyl)-pyrimidin-5-yl]-8-dimethylamino-8-phenyl-1,3-diazaspiro[4.5]decan-2-one |
| SC_3299 | cis-8-Dimethylamino-3-[2-(3-oxo-piperazin-1-yl)-4-(trifluoromethyl)-pyrimidin-5-yl]-8-phenyl-1,3-diazaspiro[4.5]decan-2-one |
| SC_3300 | cis-8-Dimethylamino-3-isoquinolin-4-yl-8-phenyl-1,3-diazaspiro[4.5]decan-2-one |
| SC_3301 | cis-8-Dimethylamino-3-isoquinolin-5-yl-8-phenyl-1,3-diazaspiro[4.5]decan-2-one |
| SC_3302 | cis-8-Dimethylamino-8-phenyl-3-(1H-pyrrolo[2,3-b]pyridin-4-yl)-1,3-diazaspiro[4.5]decan-2-one |
| SC_3303 | cis-8-Dimethylamino-8-phenyl-3-(2-pyridin-4-yl-thiazol-4-yl)-1,3-diazaspiro[4.5]decan-2-one |
| SC_3304 | cis-8-[Methyl-(tetrahydro-furan-3-yl-methyl)-amino]-3-(2-morpholin-4-yl-pyrimidin-5-yl)-8-phenyl-1,3-diazaspiro[4.5]decan-2-one (enantiomer 1) |
| SC_3305 | cis-8-[Methyl-(tetrahydro-furan-3-yl-methyl)-amino]-3-(2-morpholin-4-yl-pyrimidin-5-yl)-8-phenyl-1,3-diazaspiro[4.5]decan-2-one (enantiomer 2) |
| SC_3306 | cis-3-[2-(Azetidin-1-yl)-pyrimidin-5-yl]-8-dimethylamino-8-phenyl-1,3-diazaspiro[4.5]decan-2-one |
| SC_3307 | cis-3-[2-(3,3-Difluoro-azetidin-1-yl)-pyrimidin-5-yl]-8-dimethylamino-8-phenyl-1,3-diazaspiro[4.5]decan-2-one |
| SC_3308 | cis-8-Dimethylamino-3-[6-morpholin-4-yl-5-(trifluoromethyl)-pyridin-3-yl]-8-phenyl-1,3-diazaspiro[4.5]decan-2-one |
| SC_3309 | cis-8-Methylamino-3-[6-morpholin-4-yl-5-(trifluoromethyl)-pyridin-3-yl]-8-phenyl-1,3-diazaspiro[4.5]decan-2-one |
| SC_3310 | cis-8-Dimethylamino-8-phenyl-3-[5-(trifluoromethyloxy)-pyridin-2-yl]-1,3-diazaspiro[4.5]decan-2-one |
| SC_3311 | cis-8-Dimethylamino-3-(5-methylsulfonyl-pyridin-2-yl)-8-phenyl-1,3-diazaspiro[4.5]decan-2-one |
| SC_3312 | cis-6-(8-Dimethylamino-2-oxo-8-phenyl-1,3-diazaspiro[4.5]decan-3-yl)-nicotinonitrile |
| SC_3313 | cis-3-[2-(4-Cyclopropyl-1H-[1,2,3]triazol-1-yl)-pyrimidin-5-yl]-8-dimethylamino-8-phenyl-1,3-diazaspiro[4.5]decan-2-one |
| SC_3314 | cis-8-Dimethylamino-3-[4-methyl-2-(3-oxo-piperazin-1-yl)-pyrimidin-5-yl]-8-phenyl-1,3-diazaspiro[4.5]decan-2-one |
| SC_3315 | cis-5-(8-Dimethylamino-2-oxo-8-phenyl-1,3-diazaspiro[4.5]decan-3-yl)-pyridine-2-carboxylic acid amide |
| SC_3316 | cis-3-[4-(Azetidin-1-yl)-2-methyl-pyrimidin-5-yl]-8-dimethylamino-8-phenyl-1,3-diazaspiro[4.5]decan-2-one |
| SC_3317 | cis-2-(8-Dimethylamino-2-oxo-8-phenyl-1,3-diazaspiro[4.5]decan-3-yl)-benzamide |
| SC_3318 | cis-8-Dimethylamino-3-[2-(methylsulfonyl-methyl)-phenyl]-8-thiophen-2-yl-1,3-diazaspiro[4.5]decan-2-one |
| SC_3319 | cis-8-Dimethylamino-8-(3-fluorophenyl)-3-[2-methyl-5-(trifluoromethyl)-2H-pyrazol-3-yl]-1,3-diazaspiro[4.5]decan-2-one |
| SC_3320 | cis-8-Dimethylamino-3-(4-methyl-2-morpholin-4-yl-pyrimidin-5-yl)-8-thiophen-2-yl-1,3-diazaspiro[4.5]decan-2-one |
| SC_3321 | cis-8-Dimethylamino-3-(6-methylsulfonyl-pyridin-3-yl)-8-phenyl-1,3-diazaspiro[4.5]decan-2-one |
| SC_3322 | cis-8-Dimethylamino-8-phenyl-3-(1H-pyrrolo[2,3-b]pyridin-5-yl)-1,3-diazaspiro[4.5]decan-2-one |
| SC_3323 | cis-N-[5-(8-Dimethylamino-2-oxo-8-phenyl-1,3-diazaspiro[4.5]decan-3-yl)-pyrimidin-2-yl]-acetamide |
| SC_3324 | cis-3-[2-(4-Methyl-piperazin-1-yl)-pyrimidin-5-yl]-8-[methyl-(tetrahydro-furan-3-yl-methyl)-amino]-8-phenyl-1,3-diazaspiro[4.5]decan-2-one (enantiomer 1) |
| SC_3325 | cis-3-[2-(4-Methyl-piperazin-1-yl)-pyrimidin-5-yl]-8-[methyl-(tetrahydro-furan-3-yl-methyl)-amino]-8-phenyl-1,3-diazaspiro[4.5]decan-2-one (enantiomer 2) |
| SC_3326 | cis-8-Dimethylamino-3-(4,6-dimethyl-2-morpholin-4-yl-pyrimidin-5-yl)-8-phenyl-1,3-diazaspiro[4.5]decan-2-one |
| SC_3327 | cis-8-Dimethylamino-3-(2-morpholin-4-yl-pyrimidin-5-yl)-8-thiophen-2-yl-1,3-diazaspiro[4.5]decan-2-one |
| SC_3328 | cis-6-(8-Dimethylamino-2-oxo-8-phenyl-1,3-diazaspiro[4.5]decan-3-yl)-pyridine-3-carboxylic acid amide |
| SC_3329 | cis-8-Dimethylamino-3-[2-methyl-5-(trifluoromethyl)-2H-pyrazol-3-yl]-8-thiophen-2-yl-1,3-diazaspiro[4.5]decan-2-one |
| SC_3330 | cis-8-Dimethylamino-3-[2-[(2-hydroxy-ethyl)-methyl-amino]-pyrimidin-5-yl]-8-thiophen-2-yl-1,3-diazaspiro[4.5]decan-2-one |
| SC_3331 | cis-8-Dimethylamino-3-[2-(2-oxo-1,3-dihydro-indol-4-yl)-pyrimidin-5-yl]-8-thiophen-2-yl-1,3-diazaspiro[4.5]decan-2-one |
| SC_3332 | cis-8-Dimethylamino-3-[4-methyl-6-(3-oxo-piperazin-1-yl)-pyridin-3-yl]-8-phenyl-1,3-diazaspiro[4.5]decan-2-one |
| SC_3333 | cis-8-Dimethylamino-3-(4-methyl-6-pyridin-2-yl-pyridin-3-yl)-8-phenyl-1,3-diazaspiro[4.5]decan-2-one |
| SC_3334 | cis-8-Dimethylamino-3-(4-methylsulfonyl-pyridin-3-yl)-8-phenyl-1,3-diazaspiro[4.5]decan-2-one |
| SC_3335 | cis-3-(Benzothiazol-7-yl)-8-dimethylamino-8-phenyl-1,3-diazaspiro[4.5]decan-2-one |
| SC_3336 | cis-8-Dimethylamino-8-(4-fluorophenyl)-3-(4-methyl-2-morpholin-4-yl-pyrimidin-5-yl)-1,3-diazaspiro[4.5]decan-2-one |
| SC_3337 | cis-2-[8-Dimethylamino-3-[4-methyl-6-(trifluoromethyl)-pyridin-3-yl]-2-oxo-8-phenyl-1,3-diazaspiro[4.5]decan-1-yl]-N,N-dimethyl-acetamide |

| | -continued |
|---|---|
| SC_3338 | cis-8-Dimethylamino-3-[2-(2-methyl-1-oxo-2,3-dihydro-isoindol-4-yl)-pyrimidin-5-yl]-8-phenyl-1,3-diazaspiro[4.5]decan-2-one |
| SC_3339 | cis-2-[[5-(8-Dimethylamino-2-oxo-8-phenyl-1,3-diazaspiro[4.5]decan-3-yl)-2-methyl-pyrimidin-4-yl]amino]-acetamide |
| SC_3340 | cis-2-[3-(8-Dimethylamino-2-oxo-8-phenyl-1,3-diazaspiro[4.5]decan-3-yl)-pyridin-4-yl]-acetamide |
| SC_3341 | cis-8-Dimethylamino-3-[4-(methylsulfonyl-methyl)-pyridin-3-yl]-8-phenyl-1,3-diazaspiro[4.5]decan-2-one |
| SC_3342 | cis-8-Dimethylamino-3-[6-(4-methyl-3-oxo-piperazin-1-yl)-pyridin-3-yl]-8-phenyl-1,3-diazaspiro[4.5]decan-2-one |
| SC_3343 | cis-8-Dimethylamino-3-(2,4-dimethyl-pyrimidin-5-yl)-8-phenyl-1,3-diazaspiro[4.5]decan-2-one |
| SC_3344 | cis-8-Dimethylamino-3-[2-(1-oxo-2,3-dihydro-isoindol-4-yl)-pyrimidin-5-yl]-8-phenyl-1,3-diazaspiro[4.5]decan-2-one; 2,2,2-trifluoro-acetic acid |
| SC_3345 | cis-8-Dimethylamino-3-[6-[(2-hydroxy-ethyl)-methyl-amino]-5-(trifluoromethyl)-pyridin-3-yl]-8-phenyl-1,3-diazaspiro[4.5]decan-2-one |
| SC_3346 | cis-8-Dimethylamino-8-phenyl-3-[2-[4-(trifluoromethyl)-1H-[1,2,3]triazol-1-yl]-pyrimidin-5-yl]-1,3-diazaspiro[4.5]decan-2-one |
| SC_3347 | cis-8-Dimethylamino-3-[2-(4-isopropyl-1H-[1,2,3]triazol-1-yl)-pyrimidin-5-yl]-8-phenyl-1,3-diazaspiro[4.5]decan-2-one |
| SC_3348 | cis-8-Dimethylamino-3-[6-(1,1-dioxo-[1,4]thiazinan-4-yl)-pyridin-3-yl]-8-phenyl-1,3-diazaspiro[4.5]decan-2-one |
| SC_3349 | cis-5-(8-Dimethylamino-2-oxo-8-phenyl-1,3-diazaspiro[4.5]decan-3-yl)-2-morpholin-4-yl-nicotinonitrile |
| SC_3350 | cis-8-Dimethylamino-3-(1-methylsulfonyl-1H-pyrrolo[2,3-b]pyridin-5-yl)-8-phenyl-1,3-diazaspiro[4.5]decan-2-one |
| SC_3351 | cis-8-Dimethylamino-3-(1H-indol-4-yl)-8-phenyl-1,3-diazaspiro[4.5]decan-2-one |
| SC_3352 | cis-8-Dimethylamino-3-(2-hydroxy-benzooxazol-7-yl)-8-phenyl-1,3 diazaspiro[4.5]decan-2-one |
| SC_3353 | cis-8-Dimethylamino-3-[2-fluoro-4-(trifluoromethyloxy)-phenyl]-8-phenyl-1,3-diazaspiro[4.5]decan-2-one |
| SC_3354 | cis-4-[5-(8-Dimethylamino-2-oxo-8-phenyl-1,3-diazaspiro[4.5]decan-3-yl)-pyrimidin-2-yl]-benzamide; 2,2,2-trifluoro-acetic acid |
| SC_3355 | cis-8-Dimethylamino-3-(1-methyl-1H-pyrrolo[2,3-b]pyridin-4-yl)-8-phenyl-1,3-diazaspiro[4.5]decan-2-one |
| SC_3356 | cis-3-(1-Acetyl-1H-indol-4-yl)-8-dimethylamino-8-phenyl-1,3-diazaspiro[4.5]decan-2-one |
| SC_3357 | cis-8-Dimethylamino-3-(1H-indol-3-yl)-8-phenyl-1,3-diazaspiro[4.5]decan-2-one |
| SC_3358 | cis-6-(8-Dimethylamino-2-oxo-8-phenyl-1,3-diazaspiro[4.5]decan-3-yl)-5-methyl nicotinonitrile |
| SC_3359 | cis-6-(8-Dimethylamino-2-oxo-8-phenyl-1,3-diazaspiro[4.5]decan-3-yl)-5-fluoro nicotinonitrile |
| SC_3360 | cis-8-Dimethylamino-3-[4-methyl-6-(trifluoromethyl)-pyridin-3-yl]-1-(2-oxo-2-pyrrolidin-1-yl-ethyl)-8-phenyl-1,3-diazaspiro[4.5]decan-2-one |
| SC_3361 | cis-6-(8-Dimethylamino-2-oxo-8-phenyl-1,3-diazaspiro[4.5]decan-3-yl)-5-methyl pyridine-3-carboxylic acid amide |
| SC_3362 | cis-6-(8-Dimethylamino-2-oxo-8-phenyl-1,3-diazaspiro[4.5]decan-3-yl)-5-fluoro-pyridine-3-carboxylic acid amide |
| SC_3363 | cis-8-Dimethylamino-3-[4-methyl-6-(trifluoromethyl)-pyridin-3-yl]-8-m-tolyl-1,3-diazaspiro[4.5]decan-2-one |
| SC_3364 | cis-3-(8-Dimethylamino-2-oxo-8-phenyl-1,3-diazaspiro[4.5]decan-3-yl)-isonicotinonitrile |
| SC_3365 | cis-8-Dimethylamino-3-[3-fluoro-5-(2-oxo-1,3-dihydro-indol-4-yl)-pyridin-2-yl]-8-phenyl-1,3-diazaspiro[4.5]decan-2-one |
| SC_3366 | cis-8-Dimethylamino-3-[4-methyl-6-(trifluoromethyl)-pyridin-3-yl]-8-[3-(trifluoromethyloxy)-phenyl]-1,3-diazaspiro[4.5]decan-2-one |
| SC_3367 | cis-8-Dimethylamino-3-[4-methyl-6-(trifluoromethyl)-pyridin-3-yl]-8-[3-(trifluoromethyl)phenyl]-1,3-diazaspiro[4.5]decan-2-one |
| SC_3368 | cis-8-Dimethylamino-8-(3-methoxyphenyl)-3-[4-methyl-6-(trifluoromethyl)-pyridin-3-yl]-1,3-diazaspiro[4.5]decan-2-one |
| SC_3369 | cis-8-(5-Chloro-thiophen-2-yl)-8-dimethylamino-3-[4-methyl-6-(trifluoromethyl)-pyridin-3-yl]-1,3-diazaspiro[4.5]decan-2-one |
| SC_3370 | cis-8-Dimethylamino-8-(3-fluorophenyl)-3-[4-methyl-6-(trifluoromethyl)-pyridin-3-yl]-1,3-diazaspiro[4.5]decan-2-one |
| SC_3371 | cis-8-Dimethylamino-3-(2-methylamino-pyrimidin-5-yl)-8-phenyl-1,3-diazaspiro[4.5]decan-2-one |
| SC_3372 | cis-8-(5-Chloro-thiophen-2-yl)-8-dimethylamino-3-(4-methyl-2-morpholin-4-yl-pyrimidin-5-yl)-1,3-diazaspiro[4.5]decan-2-one |
| SC_3373 | cis-N-[5-(8-Dimethylamino-2-oxo-8-phenyl-1,3-diazaspiro[4.5]decan-3-yl)-pyrimidin-2-yl]-N-methyl-cyclopropanecarboxylic acid amide |
| SC_3374 | cis-N-[5-(8-Dimethylamino-2-oxo-8-phenyl-1,3-diazaspiro[4.5]decan-3-yl)-pyrimidin-2-yl]-N,2,5-trimethyl-2H-pyrazole-3-carboxylic acid amide |
| SC_3375 | cis-3-[4,6-Bis(trifluoromethyl)-pyridin-3-yl]-8-dimethylamino-8-phenyl-1,3-diazaspiro[4.5]decan-2-one |
| SC_3376 | cis-8-Dimethylamino-3-[2-[(2-hydroxy-ethyl)-methyl-amino]-quinazolin-6-yl]-8-phenyl-1,3-diazaspiro[4.5]decan-2-one |
| SC_3377 | cis-8-Dimethylamino-3-(2-morpholin-4-yl-quinazolin-6-yl)-8-phenyl-1,3-diazaspiro[4.5]decan-2-one |

-continued

| | |
|---|---|
| SC_3378 | cis-8-[Methyl-(oxetan-3-yl-methyl)-amino]-8-phenyl-3-[2-(trifluoromethyl)-pyrimidin-5-yl]-1,3-diazaspiro[4.5]decan-2-one |
| SC_3379 | cis-3-(1-Acetyl-1H-indol-3-yl)-8-dimethylamino-8-phenyl-1,3-diazaspiro[4.5]decan-2-one |
| SC_3380 | cis-8-Dimethylamino-8-phenyl-3-quinazolin-6-yl-1,3-diazaspiro[4.5]decan-2-one |
| SC_3381 | cis-5-(8-Dimethylamino-2-oxo-8-phenyl-1,3-diazaspiro[4.5]decan-3-yl)-2-(2-oxo-1,3-dihydro-indol-4-yl)-isonicotinonitrile |
| SC_3382 | cis-N-[5-(8-Dimethylamino-2-oxo-8-phenyl-1,3-diazaspiro[4.5]decan-3-yl)-pyrimidin-2-yl]-N-methyl-tetrahydro-pyran-4-carboxylic acid amide |
| SC_3383 | cis-N-[5-(8-Dimethylamino-2-oxo-8-phenyl-1,3-diazaspiro[4.5]decan-3-yl)-pyrimidin-2-yl]-N,2,2-trimethyl-propionamide |
| SC_3384 | cis-8-Dimethylamino-3-[2-(1-methyl-2-oxo-1,3-dihydro-indol-4-yl)-pyrimidin-5-yl]-8-phenyl-1,3-diazaspiro[4.5]decan-2-one |
| SC_3385 | cis-8-Dimethylamino-3-(2-morpholin-4-yl-1H-benzoimidazol-5-yl)-8-phenyl-1,3-diazaspiro[4.5]decan-2-one |
| SC_3386 | cis-8-Dimethylamino-8-(3-fluoro-5-methyl-phenyl)-3-[4-methyl-6-(trifluoromethyl)-pyridin-3-yl]-1,3-diazaspiro[4.5]decan-2-one |
| SC_3387 | cis-8-Dimethylamino-3-[6-(2-oxo-1,3-dihydro-indol-4-yl)-pyridin-3-yl]-8-phenyl-1,3-diazaspiro[4.5]decan-2-one |
| SC_3388 | cis-8-Dimethylamino-8-(3-hydroxyphenyl)-3-[4-methyl-6-(trifluoromethyl)-pyridin-3-yl]-1,3-diazaspiro[4.5]decan-2-one |
| SC_3389 | cis-3-[6-(Azetidin-1-yl)-5-(trifluoromethyl)-pyridin-3-yl]-8-dimethylamino-8-phenyl-1,3-diazaspiro[4.5]decan-2-one |
| SC_3390 | cis-3-[1-(Cyclopropyl-methyl)-8-dimethylamino-2-oxo-8-phenyl-1,3-diazaspiro[4.5]decan-3-yl]-isonicotinonitrile |
| SC_3391 | cis-3-[3,5-Bis(trifluoromethyl)-pyridin-2-yl]-8-dimethylamino-8-phenyl-1,3-diazaspiro[4.5]decan-2-one |
| SC_3392 | cis-8-Dimethylamino-3-(5-fluoro-6-morpholin-4-yl-pyridin-3-yl)-8-phenyl-1,3-diazaspiro[4.5]decan-2-one |
| SC_3393 | cis-8-(3-Chlorophenyl)-8-dimethylamino-3-[4-methyl-6-(trifluoromethyl)-pyridin-3-yl]-1,3-diazaspiro[4.5]decan-2-one |
| SC_3394 | cis-8-Dimethylamino-3-[5-(2-oxo-1,3-dihydro-indol-4-yl)-pyridin-2-yl]-8-phenyl-1,3-diazaspiro[4.5]decan-2-one |
| SC_3395 | cis-8-Dimethylamino-8-phenyl-3-[5-(trifluoromethyl)-[1,3,4]thiadiazol-2-yl]-1,3-diazaspiro[4.5]decan-2-one |
| SC_3396 | cis-8-Dimethylamino-3-(2-oxo-1,3-dihydro-indol-4-yl)-8-phenyl-1,3-diazaspiro[4.5]decan-2-one |
| SC_3397 | cis-8-Dimethylamino-3-[2-[(2-hydroxy-ethyl)-methyl-amino]-1H-benzoimidazol-5-yl]-8-phenyl-1,3-diazaspiro[4.5]decan-2-one |
| SC_3398 | cis-8-Dimethylamino-3-(5-methyl-6-morpholin-4-yl-pyridin-3-yl)-8-phenyl-1,3-diazaspiro[4.5]decan-2-one |
| SC_3399 | cis-1-(Cyclopropyl-methyl)-8-dimethylamino-8-(3-fluorophenyl)-3-(5-methylsulfonyl-pyridin-2-yl)-1,3-diazaspiro[4.5]decan-2-one |
| SC_3400 | cis-1-(Cyclopropyl-methyl)-8-(3-fluorophenyl)-8-methylamino-3-(5-methylsulfonyl-pyridin-2-yl)-1,3-diazaspiro[4.5]decan-2-one |
| SC_3401 | cis-1-(Cyclobutyl-methyl)-8-(3-fluorophenyl)-8-methylamino-3-[2-(trifluoromethyl)-pyrimidin-5-yl]-1,3-diazaspiro[4.5]decan-2-one |
| SC_3402 | cis-1-(Cyclopropyl-methyl)-8-dimethylamino-8-(3-fluorophenyl)-3-[2-(trifluoromethyl)-pyrimidin-5-yl]-1,3-diazaspiro[4.5]decan-2-one |
| SC_3403 | cis-1-(Cyclopropyl-methyl)-8-(3-fluorophenyl)-8-methylamino-3-[2-(trifluoromethyl)-pyrimidin-5-yl]-1,3-diazaspiro[4.5]decan-2-one |
| SC_3404 | cis-8-Dimethylamino-8-(3-fluorophenyl)-3-[2-(trifluoromethyl)-pyrimidin-5-yl]-1,3-diazaspiro[4.5]decan-2-one |
| SC_3405 | cis-1-(Cyclopropyl-methyl)-8-dimethylamino-8-(3-fluorophenyl)-3-[2-methyl-5-(trifluoromethyl)-2H-pyrazol-3-yl]-1,3-diazaspiro[4.5]decan-2-one |
| SC_3406 | cis-1-(Cyclopropyl-methyl)-8-(3-fluorophenyl)-8-methylamino-3-[2-methyl-5-(trifluoromethyl)-2H-pyrazol-3-yl]1-1,3-diazaspiro[4.5]decan-2-one |
| SC_3407 | cis-8-Methylamino-3-(4-methyl-2-morpholin-4-yl-pyrimidin-5-yl)-8-phenyl-1,3-diazaspiro[4.5]decan-2-one |
| SC_3408 | cis-3-[5-(Azetidin-1-yl)-3-methyl-pyridin-2-yl]-8-dimethylamino-8-(3-fluorophenyl)-1,3-diazaspiro[4.5]decan-2-one |
| SC_3409 | cis-8-Dimethylamino-8-(3-fluorophenyl)-3-(5-methylsulfonyl-pyridin-2-yl)-1,3-diazaspiro[4.5]decan-2-one |
| SC_3410 | cis-3-(6-(azetidin-1-yl)-4-fluoropyridin-3-yl)-8-(dimethylamino)-8-phenyl-1,3-diazaspiro[4.5]decan-2-one |
| SC_3411 | cis-3-(6-(azetidin-1-yl)pyridin-3-yl)-8-(dimethylamino)-8-(3-fluorophenyl)-1,3-diazaspiro[4.5]decan-2-one |
| SC_3412 | cis-3-(1-(cyclopropanecarbonyl)-3-(trifluoromethyl)-1H-pyrazol-5-yl)-8-(dimethylamino)-8-(3-fluorophenyl)-1,3-diazaspiro[4.5]decan-2-one |
| SC_3413 | cis-8-(dimethylamino)-8-(3-fluorophenyl)-3-(1-(2-hydroxyethyl)-3-(trifluoromethyl)-1H-pyrazol-5-yl)-1,3-diazaspiro[4.5]decan-2-one |
| SC_3414 | cis-3-(1-(cyclopropylmethyl)-3-(trifluoromethyl)-1H-pyrazol-5-yl)-8-(dimethylamino)-8-(3-fluorophenyl)-1,3-diazaspiro[4.5]decan-2-one |
| SC_3415 | cis-8-(dimethylamino)-8-(3-fluorophenyl)-3-(1-(methylsulfonyl)-3-(trifluoromethyl)-1H-pyrazol-5-yl)-1,3-diazaspiro[4.5]decan-2-one |
| SC_3416 | cis-1-(cyclopropylmethyl)-8-(dimethylamino)-8-(3-fluorophenyl)-3-(1-(methylsulfonyl)-3-(trifluoromethyl)-1H-pyrazol-5-yl)-1,3-diazaspiro[4.5]decan-2-one |

-continued

| | |
|---|---|
| SC_3417 | cis-2-(5-(8-(dimethylamino)-8-(3-fluorophenyl)-2-oxo-1,3-diazaspiro[4.5]decan-3-yl)-3-(trifluoromethyl)-1H-pyrazol-1-yl)-N,N-dimethylacetamide |
| SC_3418 | cis-2-(5-(1-(cyclopropylmethyl)-8-(dimethylamino)-8-(3-fluorophenyl)-2-oxo-1,3-diazaspiro[4.5]decan-3-yl)-3-(trifluoromethyl)-1H-pyrazol-1-yl)-N,N-dimethylacetamide |
| SC_3419 | cis-8-(dimethylamino)-3-(1-methyl1-1H-pyrrolo[2,3-b]pyridin-5-yl)-8-phenyl-1,3-diazaspiro[4.5]decan-2-one |
| SC_3420 | cis-8-(dimethylamino)-3-(3-fluoro-1H-pyrrolo[2,3-b]pyridin-5-yl)-8-phenyl-1,3-diazaspiro[4.5]decan-2-one |
| SC_3421 | cis-8-(dimethylamino)-8-phenyl-3-(1H-pyrrolo[2,3-c]pyridin-4-yl)-1,3-diazaspiro[4.5]decan-2-one |
| SC_3422 | cis-8-(dimethylamino)-8-phenyl-3-(2-(pyridazin-4-yl)pyrimidin-5-yl)-1,3-diazaspiro[4.5]decan-2-one |
| SC_3423 | cis-8-(dimethylamino)-3-(2-(2-oxo-1,2-dihydropyridin-4-yl)pyrimidin-5-yl)-8-phenyl-1,3-diazaspiro[4.5]decan-2-one |
| SC_3424 | cis-8-(dimethylamino)-8-(3-fluorophenyl)-3-(1-methyl-3-(thiophen-2-yl)-1H-pyrazol-5-yl)-1,3-diazaspiro[4.5]decan-2-one |
| SC_3425 | cis-8-(dimethylamino)-8-(3-fluorophenyl)-3-(1-methyl-3-morpholino-1H-pyrazol-5-yl)-1,3-diazaspiro[4.5]decan-2-one |
| SC_3426 | cis-8-(dimethylamino)-8-phenyl-1-(2,2,2-trifluoroethyl)-3-(2-(trifluoromethyl)pyrimidin-5-yl)-1,3-diazaspiro[4.5]decan-2-one |
| SC_3427 | cis-8-(dimethylamino)-8-phenyl-3-(2-(trifluoromethyl)pyrimidin-5-yl)-1-(3,3,3-trifluoropropyl)-1,3-diazaspiro[4.5]decan-2-one |
| SC_3428 | cis-3-(4-methyl-6-(trifluoromethyl)pyridin-3-yl)-8-(methylamino)-8-phenyl-1,3-diazaspiro[4.5]decan-2-one |
| SC_3429 | cis-3-(1-methyl-3-(trifluoromethyl)-1H-pyrazol-5-yl)-8-(methylamino)-8-phenyl-1,3-diazaspiro[4.5]decan-2-one |
| SC_3430 | cis-8-(dimethylamino)-8-(3-fluorophenyl)-3-(4-(methylsulfonyl)pyridin-3-yl)-1,3-diazaspiro[4.5]decan-2-one |
| SC_3431 | cis-8-(dimethylamino)-3-(1-ethyl-3-(trifluoromethyl)-1H-pyrazol-5-yl)-8-(3-fluorophenyl)-1,3-diazaspiro[4.5]decan-2-one |
| SC_3432 | cis-3-(1-cyclopropyl-3-(trifluoromethyl)-1H-pyrazol-5-yl)-8-(dimethylamino)-8-(3-fluorophenyl)-1,3-diazaspiro[4.5]decan-2-one |
| SC_3433 | cis-8-(dimethylamino)-8-(3-fluorophenyl)-3-(1-(oxetan-3-ylmethyl)-3-(trifluoromethyl)-1H-pyrazol-5-yl)-1,3-diazaspiro[4.5]decan-2-one |
| SC_3434 | cis-8-(dimethylamino)-8-(3-fluorophenyl)-3-(1-(2-(methylsulfonyl)ethyl)-3-(trifluoromethyl)-1H-pyrazol-5-yl)-1,3-diazaspiro[4.5]decan-2-one |
| SC_3435 | cis-8-(dimethylamino)-8-(3-fluorophenyl)-3-(4-methyl-2-(methylamino)pyrimidin-5-yl)-1,3-diazaspiro[4.5]decan-2-one |
| SC_3436 | cis-3-(2-cyclopropoxy-4-methylpyrimidin-5-yl)-8-(dimethylamino)-8-(3-fluorophenyl)-1,3-diazaspiro[4.5]decan-2-one |
| SC_3437 | cis-N-(5-(8-(dimethylamino)-8-(3-fluorophenyl)-2-oxo-1,3-diazaspiro[4.5]decan-3-yl)-4-methylpyrimidin-2-yl)-N-methylcyclopropanecarboxamide |
| SC_3438 | cis-N-(5-(8-(dimethylamino)-8-(3-fluorophenyl)-2-oxo-1,3-diazaspiro[4.5]decan-3-yl)-4-methylpyrimidin-2-yl)-N-methylpivalamide |
| SC_3439 | cis-3-(4-(azetidin-1-yl)-2-(trifluoromethyl)pyrimidin-5-yl)-8-(dimethylamino)-8-(3-fluorophenyl)-1,3-diazaspiro[4.5]decan-2-one |
| SC_3440 | cis-8-(dimethylamino)-8-(3-fluorophenyl)-3-(4-(oxetan-3-ylmethoxy)-2-(trifluoromethyl)pyrimidin-5-yl)-1,3-diazaspiro[4.5]decan-2-one |
| SC_3441 | cis-3-(2-cyclopropyl-4-(2,2,2-trifluoroethoxy)pyrimidin-5-yl)-8-(dimethylamino)-8-(3-fluorophenyl)-1,3-diazaspiro[4.5]decan-2-one |
| SC_3442 | cis-3-(2-cyclopropyl-4-((2-hydroxyethyl)(methyl)amino)pyrimidin-5-yl)-8-(dimethylamino)-8-(3-fluorophenyl)-1,3-diazaspiro[4.5]decan-2-one | and the physiologically acceptable salts thereof.

According to the invention, unless expressly stated otherwise, "—$C_1$-$C_4$-alkyl", "—$C_1$-$C_6$-alkyl" and any other alkyl residues can be linear or branched, saturated or unsaturated. Linear saturated alkyl includes methyl, ethyl, n-propyl, n-butyl, n-pentyl and n-hexyl. Examples of branched saturated alkyl include but are not limited to iso-propyl, sec-butyl, and tert-butyl. Examples of linear unsaturated alkyl include but are not limited to vinyl, propenyl, allyl, and propargyl.

According to the invention, unless expressly stated otherwise, "—$C_1$-$C_4$-alkyl", "—$C_1$-$C_6$-alkyl" and any other alkyl residues can be unsubstituted, mono- or polysubstituted. Examples of substituted alkyl include but are not limited to —$CH_2CH_2OH$, —$CH_2CH_2OCH_3$, —$CH_2CH_2CH_2OCH_3$, —$CH_2CH_2S(=O)_2CH_3$, —$CH_2C(=O)NH_2$, —$C(CH_3)_2C(=O)NH_2$, —$CH_2C(CH_3)_2C(=O)NH_2$, and —$CH_2CH_2C(=O)N(CH_3)_2$.

According to the invention, unless expressly stated otherwise, "—$C_1$-$C_6$-alkylene-", "—$C_1$-$C_4$-alkylene" and any other alkylene residue can be unsubstituted, mono- or polysubstituted. Examples of saturated alkylene include but are not limited to —$CH_2$—, —$CH(CH_3)$—, —$C(CH_3)_2$—, —$CH_2CH_2$—, —$CH(CH_3)CH_2$—, —$CH_2CH(CH_3)$—, —$CH(CH_3)$—$CH(CH_3)$—, —$C(CH_3)_2CH_2$—, —$CH_2C(CH_3)_2$—, —$CH(CH_3)C(CH_3)_2$—, —$C(CH_3)_2CH(CH_3)$—, $C(CH_3)_2C(CH_3)_2$—, —$CH_2CH_2CH_2$—, and —$C(CH_3)_2CH_2CH_2$—. Examples of unsaturated alkylene include but are not limited to —$CH=CH$—, —$C\equiv C$—, —$C(CH_3)=CH$—, —$CH=C(CH_3)$—, —$C(CH_3)=C(CH_3)$—, —$CH_2CH=CH$—, —$CH=CHCH_2$—, —$CH=CH$—$CH=CH$—, and —$CH=CH$—$C\equiv C$—.

According to the invention, unless expressly stated otherwise, "—$C_1$-$C_6$-alkylene-", "—$C_1$-$C_4$-alkylene" and any other alkylene residue can be unsubstituted, mono- or polysubstituted. Examples of substituted —$C_1$-$C_6$-alkylene- include but are not limited to —$CHF$—, —$CF_2$—, —$CHOH$— and —$C(=O)$—.

According to the invention, moieties may be connected through —$C_1$-$C_6$-alkylene-, i.e. the moieties may not be directly bound to the core structure of compound according to general formula (I), but may be connected to the core structure of compound according to general formula (I) or its periphery through a —$C_1$-$C_6$-alkylene- linker.

According to the invention, "3-12-membered cycloalkyl moiety" means a non-aromatic, monocyclic, bicyclic or tricyclic moiety comprising 3 to 12 ring carbon atoms but no heteroatoms in the ring. Examples of preferred saturated 3-12-membered cycloalkyl moieties according to the invention include but are not limited to cyclopropane, cyclobutane, cyclopentane, cyclohexane, cycloheptane, cyclooctane, hydrindane, and decaline. Examples of preferred unsaturated 3-12-membered cycloalkyl moiety moieties according to the invention include but are not limited to cyclopropene, cyclobutene, cyclopentene, cyclopentadiene, cyclohexene, 1,3-cyclohexadiene, and 1,4-cyclohexadiene. The 3-12-membered cycloalkyl moiety, which is bonded to the compound according to the invention, in its periphery may optionally be condensed with a 3-12-membered heterocycloalkyl moiety, saturated or unsaturated, unsubstituted, mono- or polysubstituted; and/or with a 6-14-membered aryl moiety, unsubstituted, mono- or polysubstituted; and/or with a 5-14-membered heteroaryl moiety, unsubstituted, mono- or polysubstituted. Under these circumstances, the ring atoms of the condensed moieties are not included in the 3 to 12 ring atoms of the 3-12-membered cycloalkyl moiety. Examples of 3-12-membered cycloalkyl moieties condensed with 3-12-membered heterocycloalkyl moieties include but are not limited to octahydro-1H-indol, decahydroquinoline, decahydroisoquinoline, octahydro-2H-benzo[b][1,4]oxazin, and decahydro-quinoxalin, which in each case are connected through the 3-12-membered cycloalkyl moiety. Examples of 3-12-membered cycloalkyl moieties condensed with 6-14-membered aryl moieties include but are not limited to 2,3-dihydro-1H-indene and tetraline, which in each case are connected through the 3-12-membered cycloalkyl moiety. Examples of 3-12-membered cycloalkyl moieties condensed with 5-14-membered heteroaryl moieties include but are not limited to 5,6,7,8-tetrahydroquinoline and 5,6,7,8-tetrahydroquinazoline, which in each case are connected through the 3-12-membered cycloalkyl moiety.

According to the invention, the 3-12-membered cycloalkyl moiety may optionally be connected through —$C_1$-$C_6$-alkylene-, i.e. the 3-12-membered cycloalkyl moiety may not be directly bound to the compound according to general formula (I) but may be connected thereto through a —$C_1$-$C_6$-alkylene- linker. Examples include but are not limited to —$CH_2$-cyclopropyl, —$CH_2$-cyclobutyl, —$CH_2$-cyclopentyl, —$CH_2$-cyclohexyl, —$CH_2CH_2$-cyclopropyl, —$CH_2CH_2$-cyclobutyl, —$CH_2CH_2$-cyclopentyl, and —$CH_2CH_2$-cyclohexyl.

According to the invention, unless expressly stated otherwise, the 3-12-membered cycloalkyl moiety can be unsubstituted, mono- or polysubstituted. Examples of substituted 3-12-membered cycloalkyl moieties include but are not limited to —$CH_2$—1-hydroxy-cyclobutyl.

According to the invention, "3-12-membered heterocycloalkyl moiety" means a non-aromatic, monocyclic, bicyclic or tricyclic moiety comprising 3 to 12 ring atoms, wherein each cycle comprises independently of one another 1, 2, 3, 4 or more heteroatoms independently of one another selected from the group consisting of nitrogen, oxygen and sulfur, whereas sulfur may be oxidized (S(=O) or (S(=O)$_2$), whereas the remaining ring atoms are carbon atoms, and whereas bicyclic or tricyclic systems may share common heteroatom(s). Examples of preferred saturated 3-12-membered heterocycloalkyl moieties according to the invention include but are not limited to aziridin, azetidine, pyrrolidine, imidazolidine, pyrazolidine, piperidine, piperazine, triazolidine, tetrazolidine, oxiran, oxetane, tetrahydrofurane, tetrahydropyrane, thiirane, thietane, tetra-hydrothiophene, diazepane, oxazolidine, isoxazolidine, thiazolidine, isothiazolidine, thiadiazoli-dine, morpholine, thiomorpholine. Examples of preferred unsaturated 3-12-membered heterocycloalkyl moiety moieties according to the invention include but are not limited to oxazoline, pyrazoline, imidazoline, isoxazoline, thiazoline, isothiazoline, and dihydropyran. The 3-12-membered heterocycloalkyl moiety, which is bonded to the compound according to the invention, in its periphery may optionally be condensed with a 3-12-membered cycloalkyl moiety, saturated or unsaturated, unsubstituted, mono- or polysubstituted; and/or with a 6-14-membered aryl moiety, unsubstituted, mono- or polysubstituted; and/or with a 5-14-membered heteroaryl moiety, unsubstituted, mono- or polysubstituted. Under these circumstances, the ring atoms of the condensed moieties are not included in the 3 to 12 ring atoms of the 3-12-membered heterocycloalkyl moieties. Examples of 3-12-membered heterocycloalkyl moieties condensed with 3-12-membered cycloalkyl moieties include but are not limited to octahydro-1H-indol, decahydroquinoline, decahydroisoquinoline, octahydro-2H-benzo[b][1,4]oxazin, and decahydro-quinoxalin, which in each case are connected through the 3-12-membered heterocycloalkyl moiety. An examples of a 3-12-membered heterocycloalkyl moiety condensed with a 6-14-membered aryl moiety includes but is not limited to 1,2,3,4-tetrahydroquinoline, which is connected through the 3-12-membered heterocycloalkyl moiety. An example of a 3-12-membered heterocycloalkyl moiety condensed with a 5-14-membered heteroaryl moieties includes but is not limited to 5,6,7,8-tetrahydro-[1,2,4]triazolo[1,5-a]pyrazine, which is connected through the 3-12-membered heterocycloalkyl moiety.

According to the invention, the 3-12-membered heterocycloalkyl moiety may optionally be connected through —$C_1$-$C_6$-alkylene-, i.e. the 3-12-membered heterocycloalkyl moiety may not be directly bound to the compound according to general formula (I) but may be connected thereto through a —$C_1$-$C_6$-alkylene- linker. Said linker may be connected to a carbon ring atom or to a hetero ring atom of the 3-12-membered heterocycloalkyl moiety. Examples include but are not limited to —$CH_2$-oxetane, —$CH_2$-pyrrolidine, —$CH_2$-piperidine, —$CH_2$-morpholine, —$CH_2CH_2$-oxetane, —$CH_2CH_2$-pyrrolidine, —$CH_2CH_2$-piperidine, and —$CH_2CH_2$-morpholine.

According to the invention, unless expressly stated otherwise, the 3-12-membered heterocycloalkyl moiety can be unsubstituted, mono- or polysubstituted. Examples of substituted 3-12-membered heterocycloalkyl moieties include but are not limited to 2-carboxamido-N-pyrrolidinyl-, 3,4-dihydroxy-N-pyrrolidinyl, 3-hydroxy-N-pyrimidinyl, 3,4-dihydroxy-N-pyrimidinyl, 3-oxo-N-piperazinyl, -tetrahydro-2H-thiopyranyl dioxide and thiomorpholinyl dioxide.

According to the invention, "6-14-membered aryl moiety" means an aromatic, monocyclic, bicyclic or tricyclic moiety comprising 6 to 14 ring carbon atoms but no heteroatoms in the ring. Examples of preferred 6-14-membered aryl moieties according to the invention include but are not limited to benzene, naphthalene, anthracen, and phenanthren. The 6-14-membered aryl moiety, which is bonded to the compound according to the invention, in its periphery may optionally be condensed with a 3-12-membered cycloalkyl moiety, saturated or unsaturated, unsubstituted, mono- or polysubstituted; and/or with a 3-12-membered heterocycloalkyl moiety, saturated or unsaturated, unsubstituted, mono- or polysubstituted; and/or with a 5-14-membered heteroaryl moiety, unsubstituted, mono- or polysubstituted. Under these circumstances, the ring atoms of the condensed moieties are not included in the 6 to 14 ring carbon atoms of the 6-14-membered heterocycloalkyl moieties. Examples of 6-14-membered aryl moieties condensed with 3-12-membered cycloalkyl moieties include but are not limited to 2,3-dihydro-1H-indene and tetraline, which in each case are connected through the 6-14-membered aryl moiety. An example of a 6-14-membered aryl moiety condensed with a 3-12-membered heterocycloalkyl moiety includes but is not limited to 1,2,3,4-tetrahydroquinoline, which is connected through the 6-14-membered aryl moiety. Examples of 6-14-membered aryl moieties condensed with 5-14-membered heteroaryl moieties include but are not limited to quinoline, isoquinoline, phenazine and phenoxacine, which in each case are connected through the 6-14-membered aryl moiety.

According to the invention, the 6-14-membered aryl moiety may optionally be connected through —$C_1$-$C_6$-alkylene-, i.e. the 6-14-membered aryl moiety may not be directly bound to the compound according to general formula (I) but may be connected thereto through a —$C_1$-$C_6$-alkylene- linker. Said linker may be connected to a carbon ring atom or to a hetero ring atom of the 6-14-membered aryl moiety. Examples include but are not limited to —$CH_2$—$C_6H_5$, —$CH_2CH_2$—$C_6H_5$ and —$CH=CH$—$C_6H_5$.

According to the invention, unless expressly stated otherwise, the 6-14-membered aryl moiety can be unsubstituted, mono- or polysubstituted. Examples of substituted 6-14-membered aryl moieties include but are not limited to 2-fluorophenyl, 3-fluorophenyl, 2-methoxyphenyl and 3-methoxyphenyl.

According to the invention, "5-14-membered heteroaryl moiety" means an aromatic, monocyclic, bicyclic or tricyclic moiety comprising 6 to 14 ring atoms, wherein each cycle comprises independently of one another 1, 2, 3, 4 or more heteroatoms independently of one another selected from the group consisting of nitrogen, oxygen and sulfur, whereas the remaining ring atoms are carbon atoms, and whereas bicyclic or tricyclic systems may share common heteroatom(s). Examples of preferred 5-14-membered heteroaryl moieties according to the invention include but are not limited to pyrrole, pyrazole, imidazole, triazole, tetrazole, furane, thiophene, oxazole, isoxazole, thiazole, isothiazole, pyridine, pyridazine, pyrimidine, pyrazine, indolicine, 9H-chinolicine, 1,8-naphthyridine, purine, imidazo[1,2-a]pyrazine, and pteridine. The 5-14-membered heteroaryl moiety, which is bonded to the compound according to the invention, in its periphery may optionally be condensed with a 3-12-membered cycloalkyl moiety, saturated or unsaturated, unsubstituted, mono- or polysubstituted; and/or with a 3-12-membered heterocycloalkyl moiety, saturated or unsaturated, unsubstituted, mono- or polysubstituted; and/or with a 6-14-membered aryl moiety, unsubstituted, mono- or polysubstituted. Under these circumstances, the ring atoms of the condensed moieties are not included in the 6 to 14 ring carbon atoms of the 6-14-membered heterocycloalkyl moieties. Examples of 5-14-membered heteroaryl moieties condensed with 3-12-membered cycloalkyl moieties include but are not limited to 5,6,7,8-tetrahydroquinoline and 5,6,7,8-tetrahydroquinazoline, which in each case are connected through the 5-14-membered heteroaryl moiety. An examples of a 5-14-membered heteroaryl moiety condensed with a 3-12-membered heterocycloalkyl moiety includes but is not limited to 5,6,7,8-tetrahydro-[1,2,4]triazolo[1,5-a]pyrazine, which is connected through the 5-14-membered heteroaryl moiety. Examples of 5-14-membered heteroaryl moieties condensed with 6-14-membered aryl moieties include but are not limited to quinoline, isoquinoline, phenazine and phenoxacine, which in each case are connected through the 5-14-membered heteroaryl moiety.

According to the invention, the 5-14-membered heteroaryl moiety may optionally be connected through —$C_1$-$C_6$-alkylene-, i.e. the 5-14-membered heteroaryl moiety may not be directly bound to the compound according to general formula (I) but may be connected thereto through a —$C_1$-$C_6$-alkylene- linker. Said linker may be connected to a carbon ring atom or to a hetero ring atom of the 5-14-membered heteroaryl moiety. Examples include but are not limited to —$CH_2$-oxazole, —$CH_2$-isoxazole, —$CH_2$-imidazole, —$CH_2$-pyridine, —$CH_2$-pyrimidine, —$CH_2$-pyridazine, —$CH_2CH_2$-oxazole, —$CH_2CH_2$-isoxazole, —$CH_2CH_2$-imidazole, —$CH_2CH_2$-pyridine, —$CH_2CH_2$-pyrimidine, and —$CH_2CH_2$-pyridazine.

According to the invention, unless expressly stated otherwise, the 5-14-membered heteroaryl moiety can be unsubstituted, mono- or polysubstituted. Examples of 5-14-membered heteroaryl moieties include but are not limited to 2-methoxy-4-pyridinyl, 2-methoxy-5-pyridinyl, 3-methoxy-4-pyridinyl, 3-methoxy-6-pyridinyl, 4-methoxy-2-pyridinyl, 2-methylsulfonyl-5-pyridinyl, 3-methylsulfonyl-6-pyridinyl, 3-methoxy-6-pyridazinyl, 2-nitrilo-5-pyrimidinyl, 4-hydroxy-2-pyrimidinyl, 4-methoxy-pyrimidinyl, and 2-methoxy-6-pyrazinyl.

Preferably, the compound according to the invention has a structure according to general formula (I')

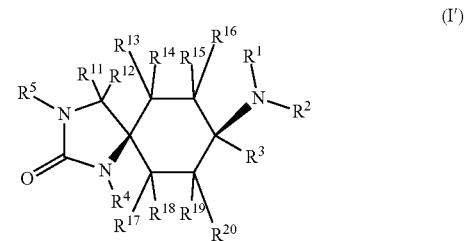

wherein $R^1$ to $R^5$, $R^{11}$ to $R^{20}$ are defined as above, or a physiologically acceptable salt thereof.

In one preferred embodiment, the excess of the cis-isomer so designated is at least 50% de, more preferably at least 75% de, yet more preferably at least 90% de, most preferably at least 95% de and in particular at least 99% de.

In a preferred embodiment, the compound according to the invention has a structure according to general formula (IX) or (X)

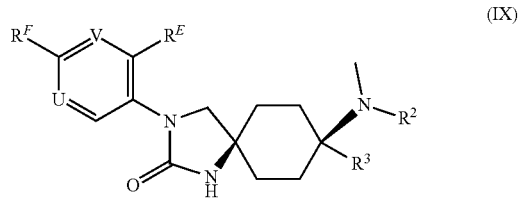

-continued (X)

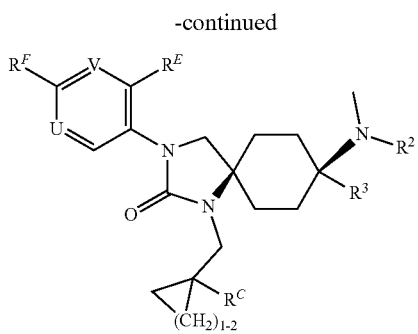

wherein
R² means —H or —CH₃;
R³ means -phenyl or -3-fluorophenyl;
$R^C$ means —H or —OH;
$R^E$ means —H, —CH₃, —F, —CF₃, -cyclopropyl, -aziridinyl, —OH; —O—$C_1$-$C_4$-alkyl; —OCF₃; —O—$C_1$-$C_4$-alkyl-CO₂H; —O—$C_1$-$C_4$-alkyl-C(=O)O—$C_1$-$C_4$-alkyl; or —O—$C_1$-$C_4$-alkyl-CONH₂;
$R^F$ means
—CF₃, -cyclopropyl, —S(=O)₂CH₃,
—NH₂; —NHC₁-C₄-alkyl; —N(C₁-C₄-alkyl)₂; —NHC₁-C₄-alkyl-OH; —NCH₃C₁-C₄-alkyl-OH; —NH—C₁-C₄-alkyl-C(=O)NH₂; —NCH₃—C₁-C₄-alkyl-C(=O)NH₂; —NHC(=O)—C₁-C₄-alkyl; —NCH₃C(=O)—C₁-C₄-alkyl;
-6-14-membered aryl, unsubstituted, mono- or polysubstituted; or
-5-14-membered heteroaryl, unsubstituted, mono- or polysubstituted;
U means =CH— or =N—; and
V means =CH— or =N—;
or a physiologically acceptable salt thereof In a preferred embodiment, the compound according to the invention has a structure according to general formula (XI)

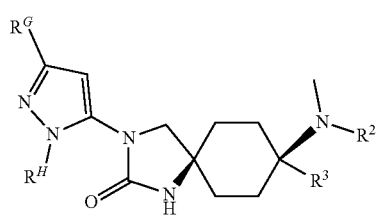

(XI)

wherein
R² means —H or —CH₃;
R³ means -phenyl or -3-fluorophenyl;
$R^H$ means
—CN; —C₁-C₄-alkyl; —CF₃; —C₁-C₄-alkyl-C(=O)NH₂; —C₁-C₄-alkyl-S(=O)₂—C₁-C₄-alkyl; —C(=O)—C₁-C₄-alkyl; —C(=O)OH; —C(=O)O—C₁-C₄-alkyl; —C(=O)NH₂; —C(=O)NHC₁-C₄-alkyl; —C(=O)N(C₁-C₄-alkyl)₂; —C(=O)NH(C₁-C₄-alkyl-OH); —C(=O)N(C₁-C₄-alkyl)(C₁-C₄-alkyl-OH); —C(=O)NH—(CH₂CH₂O)₁₋₃₀—CH₃;
-3-12-membered cycloalkyl, saturated or unsaturated, unsubstituted, mono- or polysubstituted; wherein said 3-12-membered cycloalkyl is optionally connected through —CH₂—, —NH—, —NCH₃—, —NH—(CH₂)₁₋₃—, —NCH₃(CH₂)₁₋₃—, —(C=O)—, —NHC(=O)—, —NCH₃C(=O)—, —C(=O)NH—(CH₂)₁₋₃—, —C(=O)NCH₃—(CH₂)₁₋₃—; or -3-12-membered heterocycloalkyl, saturated or unsaturated, unsubstituted, mono- or polysubstituted; 6-14-membered aryl, unsubstituted, mono- or polysubstituted; wherein said 3-12-membered heterocycloalkyl is optionally connected through —CH₂—, —NH—, —NCH₃—, —NH—(CH₂)₁₋₃—, —NCH₃(CH₂)₁₋₃—, —(C=O)—, —NHC(=O)—, —NCH₃C(=O)—, —C(=O)NH—(CH₂)₁₋₃—, —C(=O)NCH₃—(CH₂)₁₋₃—;
$R^G$ means
—CF₃, —S(=O)₂CH₃;
—NH₂; —NHC₁-C₄-alkyl; —N(C₁-C₄-alkyl)₂; —NHC₁-C₄-alkyl-OH; —NCH₃C₁-C₄-alkyl-OH; —NH—C₁-C₄-alkyl-C(=O)NH₂; —NCH₃—C₁-C₄-alkyl-C(=O)NH₂; —NHC(=O)—C₁-C₄-alkyl; —NCH₃C(=O)—C₁-C₄-alkyl;
-3-12-membered cycloalkyl, saturated or unsaturated, unsubstituted, mono- or polysubstituted; wherein said 3-12-membered cycloalkyl is optionally connected through —CH₂—, —NH—, —NCH₃—, —NH—(CH₂)₁₋₃—, —NCH₃(CH₂)₁₋₃—, —(C=O)—, —NHC(=O)—, —NCH₃C(=O)—, —C(=O)NH—(CH₂)₁₋₃—, —C(=O)NCH₃—(CH₂)₁₋₃—; or
-3-12-membered heterocycloalkyl, saturated or unsaturated, unsubstituted, mono- or polysubstituted; 6-14-membered aryl, unsubstituted, mono- or polysubstituted; wherein said 3-12-membered heterocycloalkyl is optionally connected through —CH₂—, —NH—, —NCH₃—, —NH—(CH₂)₁₋₃—, —NCH₃(CH₂)₁₋₃—, —(C=O)—, —NHC(=O)—, —NCH₃C(=O)—, —C(=O)NH—(CH₂)₁₋₃—, —C(=O)NCH₃—(CH₂)₁₋₃—,
or a physiologically acceptable salt thereof.

In a preferred embodiment, the compounds according to the invention are in the form of the free bases.

In another preferred embodiment, the compounds according to the invention are in the form of the physiologically acceptable salts.

For the purposes of the description, a "salt" is to be understood as being any form of the compound in which it assumes an ionic form or is charged and is coupled with a counter-ion (a cation or anion) or is in solution. The term is also to be understood as meaning complexes of the compound with other molecules and ions, in particular complexes which are associated via ionic interactions. Preferred salts are physiologically acceptable, in particular physiologically acceptable salts with anions or acids or also a salt formed with a physiologically acceptable acid.

Physiologically acceptable salts with anions or acids are salts of the particular compound in question with inorganic or organic acids which are physiologically acceptable, in particular when used in humans and/or mammals. Examples of physiologically acceptable salts of particular acids include but are not limited to salts of hydrochloric acid, sulfuric acid, and acetic acid.

The invention also includes isotopic isomers of a compound according to the invention, wherein at least one atom of the compound is replaced by an isotope of the respective atom which is different from the naturally predominantly occurring isotope, as well as any mixtures of isotopic isomers of such a compound. Preferred isotopes are ²H (deuterium), ³H (tritium), ¹³C and ¹⁴C.

Certain compounds according to the invention are useful for modulating a pharmacodynamic response from one or more opioid receptors (mu, delta, kappa, NOP/ORL-1) either centrally or peripherally, or both. The pharmacodynamic response may be attributed to the compound either stimulating (agonizing) or inhibiting (antagonizing) the one or more receptors. Certain compounds according to the invention may antagonize one opioid receptor, while also agonizing one or more other receptors. Compounds according to the invention having agonist activity may be either full agonists or partial agonists.

As used herein, compounds that bind to receptors and mimic the regulatory effects of endogenous ligands are defined as "agonists". Compounds that bind to a receptor but produce no regulatory effect, but rather block the binding of ligands to the receptor, are defined as "antagonists".

In certain embodiments, the compounds according to the invention are agonists at the mu opioid (MOP) and/or kappa opioid (KOP) and/or delta opioid (DOP) and/or nociceptin opioid (NOP/ORL-1) receptors.

The compounds according to the invention potently bind to the MOP and/or KOP and/or DOP and/or NOP receptors.

The compounds according to the invention can be modulators at the MOP and/or KOP and/or DOP and/or NOP receptors, and therefore the compounds according to the invention can be used/administered to treat, ameliorate, or prevent pain.

In some embodiments, the compounds according to the invention are agonists of one or more opioid receptors. In some embodiments, the compounds according to the invention are agonists of the MOP and/or KOP and/or DOP and/or NOP receptors.

In some embodiments, the compounds according to the invention are antagonists of one or more opioid receptors. In some embodiments, the compounds according to the invention are antagonists of the MOP and/or KOP and/or DOP and/or NOP receptors.

In some embodiments, the compounds according to the invention have both, (i) agonist activity at the NOP receptor; and (ii) agonist activity at one or more of the MOP, KOP, and DOP receptors.

In some embodiments, the compounds according to the invention have both, (i) agonist activity at the NOP receptor; and (ii) antagonist activity at one or more of the MOP, KOP, and DOP receptors.

In some embodiments, the compounds according to the invention have both, (i) antagonist activity at the NOP receptor; and (ii) agonist activity at one or more of the MOP, KOP, and DOP receptors.

In some embodiments, the compounds according to the invention have both, (i) antagonist activity at the NOP receptor; and (ii) antagonist activity at one or more of the MOP, KOP, and DOP receptors.

In some embodiments, preferably with respect to receptors of the peripheral nervous system, the compounds according to the invention have selective agonist activity at the NOP receptor. In some embodiments, preferably with respect to receptors of the peripheral nervous system, the compounds according to the invention have agonist activity at the NOP receptor, but no significant activity at the MOP receptor;

have agonist activity at the NOP receptor, but no significant activity at the KOP receptor;

have agonist activity at the NOP receptor, but no significant activity at the DOP receptor;

have agonist activity at the NOP receptor, but no significant activity at the MOP receptor as well as no significant activity at the KOP receptor;

have agonist activity at the NOP receptor, but no significant activity at the MOP receptor as well as no significant activity at the DOP receptor; or have agonist activity at the NOP receptor, but no significant activity at the MOP receptor as well as no significant activity at the KOP receptor as well as no significant activity at the DOP receptor.

In some embodiments, preferably with respect to receptors of the peripheral nervous system, the compounds according to the invention have balanced agonist activity at the NOP receptor as well as at the MOP receptor. In some embodiments, preferably with respect to receptors of the peripheral nervous system, the compounds according to the invention have agonist activity at the NOP receptor as well as agonist activity at the MOP receptor;

have agonist activity at the NOP receptor as well as agonist activity at the MOP receptor as well as agonist activity at the KOP receptor;

have agonist activity at the NOP receptor as well as agonist activity at the MOP receptor as well as agonist activity at the DOP receptor;

can be regarded as opioid pan agonists, i.e. have agonist activity at the NOP receptor as well as agonist activity at the MOP receptor as well as agonist activity at the KOP receptor as well as agonist activity at the DOP receptor;

have agonist activity at the NOP receptor as well as agonist activity at the MOP receptor, but no significant activity at the KOP receptor;

have agonist activity at the NOP receptor as well as agonist activity at the MOP receptor, but no significant activity at the DOP receptor; or have agonist activity at the NOP receptor as well as agonist activity at the MOP receptor, but no significant activity at the KOP receptor as well as no significant activity at the DOP receptor.

In some embodiments, preferably with respect to receptors of the peripheral nervous system, the compounds according to the invention have balanced agonist activity at the NOP receptor as well as at the KOP receptor. In some embodiments, preferably with respect to receptors of the peripheral nervous system, the compounds according to the invention have agonist activity at the NOP receptor as well as agonist activity at the KOP receptor;

have agonist activity at the NOP receptor as well as agonist activity at the KOP receptor as well as agonist activity at the MOP receptor;

have agonist activity at the NOP receptor as well as agonist activity at the KOP receptor as well as agonist activity at the DOP receptor;

have agonist activity at the NOP receptor as well as agonist activity at the KOP receptor, but no significant activity at the MOP receptor;

have agonist activity at the NOP receptor as well as agonist activity at the KOP receptor, but no significant activity at the DOP receptor; or have agonist activity at the NOP receptor as well as agonist activity at the KOP receptor, but no significant activity at the MOP receptor as well as no significant activity at the DOP receptor.

In some embodiments, preferably with respect to receptors of the peripheral nervous system, the compounds according to the invention have balanced agonist activity at the NOP receptor as well as at the DOP receptor. In some embodiments, preferably with respect to receptors of the peripheral nervous system, the compounds according to the invention have agonist activity at the NOP receptor as well as agonist activity at the DOP receptor;

have agonist activity at the NOP receptor as well as agonist activity at the DOP receptor, but no significant activity at the MOP receptor;

have agonist activity at the NOP receptor as well as agonist activity at the DOP receptor, but no significant activity at the KOP receptor; or have agonist activity at the NOP receptor as well as agonist activity at the DOP receptor, but no significant activity at the MOP receptor as well as no significant activity at the KOP receptor.

In some embodiments, preferably with respect to receptors of the peripheral nervous system, the compounds according to the invention have selective agonist activity at the KOP receptor. In some embodiments, preferably with respect to receptors of the peripheral nervous system, the compounds according to the invention have agonist activity at the KOP receptor, but no significant activity at the MOP receptor;

have agonist activity at the KOP receptor, but no significant activity at the NOP receptor;

have agonist activity at the KOP receptor, but no significant activity at the DOP receptor;

have agonist activity at the KOP receptor, but no significant activity at the MOP receptor as well as no significant activity at the NOP receptor;

have agonist activity at the KOP receptor, but no significant activity at the MOP receptor as well as no significant activity at the DOP receptor; or have agonist activity at the KOP receptor, but no significant activity at the MOP receptor as well as no significant activity at the NOP receptor as well as no significant activity at the DOP receptor.

In some embodiments, preferably with respect to receptors of the peripheral nervous system, the compounds according to the invention have agonist activity at the MOP receptor, agonist activity at the KOP receptor, and antagonist activity at the DOP receptor. In some embodiments, preferably with respect to receptors of the peripheral nervous system, the compounds according to the invention have agonist activity at the MOP receptor as well as agonist activity at the KOP receptor as well as antagonist activity at the DOP receptor;

have agonist activity at the MOP receptor as well as agonist activity at the KOP receptor as well as antagonist activity at the DOP receptor as well as agonist activity at the NOP receptor;

have agonist activity at the MOP receptor as well as agonist activity at the KOP receptor as well as antagonist activity at the DOP receptor as well as antagonist activity at the NOP receptor; or have agonist activity at the MOP receptor as well as agonist activity at the KOP receptor as well as antagonist activity at the DOP receptor, no significant activity at the NOP receptor.

In some embodiments, preferably with respect to receptors of the central nervous system, the compounds according to the invention have selective agonist activity at the NOP receptor. In some embodiments, preferably with respect to receptors of the central nervous system, the compounds according to the invention have agonist activity at the NOP receptor, but no significant activity at the MOP receptor;

have agonist activity at the NOP receptor, but no significant activity at the KOP receptor;

have agonist activity at the NOP receptor, but no significant activity at the DOP receptor;

have agonist activity at the NOP receptor, but no significant activity at the MOP receptor as well as no significant activity at the KOP receptor;

have agonist activity at the NOP receptor, but no significant activity at the MOP receptor as well as no significant activity at the DOP receptor; or have agonist activity at the NOP receptor, but no significant activity at the MOP receptor as well as no significant activity at the KOP receptor as well as no significant activity at the DOP receptor.

In some embodiments, preferably with respect to receptors of the central nervous system, the compounds according to the invention have selective antagonist activity at the NOP receptor. In some embodiments, preferably with respect to receptors of the central nervous system, the compounds according to the invention have antagonist activity at the NOP receptor, but no significant activity at the MOP receptor;

have antagonist activity at the NOP receptor, but no significant activity at the KOP receptor;

have antagonist activity at the NOP receptor, but no significant activity at the DOP receptor;

have antagonist activity at the NOP receptor, but no significant activity at the MOP receptor as well as no significant activity at the KOP receptor;

have antagonist activity at the NOP receptor, but no significant activity at the MOP receptor as well as no significant activity at the DOP receptor; or have antagonist activity at the NOP receptor, but no significant activity at the MOP receptor as well as no significant activity at the KOP receptor as well as no significant activity at the DOP receptor.

In some embodiments, preferably with respect to receptors of the central nervous system, the compounds according to the invention have antagonist activity at the NOP receptor as well as agonist activity at the DOP receptor. In some embodiments, preferably with respect to receptors of the central nervous system, the compounds according to the invention have antagonist activity at the NOP receptor as well as agonist activity at the DOP receptor;

have antagonist activity at the NOP receptor as well as agonist activity at the DOP receptor, but no significant activity at the MOP receptor;

have antagonist activity at the NOP receptor as well as agonist activity at the DOP receptor, but no significant activity at the KOP receptor; or have antagonist activity at the NOP receptor as well as agonist activity at the DOP receptor, but no significant activity at the MOP receptor as well as no significant activity at the KOP receptor.

For the purpose of the specification, "no significant activity" means that the activity (agonist/antagonist) of the given compound at this receptor is lower by a factor of 1000 or more compared to its activity (agonist/antagonist) at one or more of the other opioid receptors.

A further aspect of the invention relates to the compounds according to the invention as medicaments.

A further aspect of the invention relates to the compounds according to the invention for use in the treatment of pain. A further aspect of the invention relates to a method of treating pain comprising the administration of a pain alleviating amount of a compound according to the invention to a subject in need thereof, preferably to a human. The pain is preferably acute or chronic. The pain is preferably nociceptive or neuropathic.

A further aspect of the invention relates to the compounds according to the invention for use in the treatment of neurodegenerative disorders, neuroinflammatory disorders, neuropsychiatric disorders, and substance abuse/dependence. A further aspect of the invention relates to a method of treating any one of the aforementioned disorders, diseases or conditions comprising the administration of a therapeutically effective amount of a compound according to the invention to a subject in need thereof, preferably to a human.

Another aspect of the invention relates to a pharmaceutical composition which contains a physiologically acceptable carrier and at least one compound according to the invention.

Preferably, the composition according to the invention is solid, liquid or pasty; and/or contains the compound according to the invention in an amount of from 0.001 to 99 wt. %, preferably from 1.0 to 70 wt. %, based on the total weight of the composition.

The pharmaceutical composition according to the invention can optionally contain suitable additives and/or auxiliary substances and/or optionally further active ingredients.

Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik and angrenzende Gebiete, Editio Cantor Aulendoff).

The pharmaceutical composition according to the invention contains the compound according to the invention in an amount of preferably from 0.001 to 99 wt. %, more preferably from 0.1 to 90 wt. %, yet more preferably from 0.5 to 80 wt. %, most preferably from 1.0 to 70 wt. % and in particular from 2.5 to 60 wt. %, based on the total weight of the pharmaceutical composition.

The pharmaceutical composition according to the invention is preferably for systemic, topical or local administration, preferably for oral administration.

Another aspect of the invention relates to a pharmaceutical dosage form which contains the pharmaceutical composition according to the invention.

In one preferred embodiment, the pharmaceutical dosage form according to the invention is produced for administration twice daily, for administration once daily or for administration less frequently than once daily. Administration is preferably systemic, in particular oral.

The pharmaceutical dosage form according to the invention can be administered, for example, as a liquid dosage form in the form of injection solutions, drops or juices, or as a semi-solid dosage form in the form of granules, tablets, pellets, patches, capsules, plasters/spray-on plasters or aerosols. The choice of auxiliary substances etc. and the amounts thereof to be used depend on whether the form of administration is to be administered orally, perorally, parenterally, intravenously, intraperitoneally, intradermally, intramuscularly, intranasally, buccally, rectally or locally, for example to the skin, the mucosa or into the eyes.

Pharmaceutical dosage forms in the form of tablets, dragees, capsules, granules, drops, juices and syrups are suitable for oral administration, and solutions, suspensions, readily reconstitutable dry preparations and also sprays are suitable for parenteral, topical and inhalatory administration. Compounds according to the invention in a depot, in dissolved form or in a plaster, optionally with the addition of agents promoting penetration through the skin, are suitable percutaneous administration preparations.

The amount of the compounds according to the invention to be administered to the patient varies in dependence on the weight of the patient, on the type of administration, on the indication and on the severity of the disease. Usually, from 0.00005 mg/kg to 50 mg/kg, preferably from 0.001 mg/kg to 10 mg/kg, of at least one compound according to the invention is administered.

Another aspect of the invention relates to a process for the preparation of the compounds according to the invention. Suitable processes for the synthesis of the compounds according to the invention are known in principle to the person skilled in the art.

Preferred synthesis routes are described below:

The compounds according to the invention can be obtained via different synthesis routes. Depending on the synthesis route, different intermediates are prepared and subsequently further reacted.

In a preferred embodiment, the synthesis of the compounds according to the invention proceeds via a synthesis route which comprises the preparation of an intermediate according to general formula (IIIa):

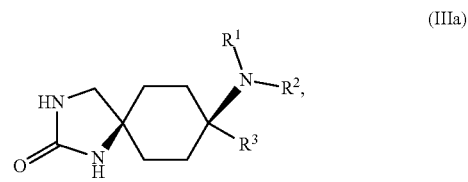

(IIIa)

wherein $R^1$, $R^2$ and $R^3$ are defined as above.

In another preferred embodiment, the synthesis of the compounds according to the invention proceeds via a synthesis route which comprises the preparation of an intermediate according to general formula (IIIb):

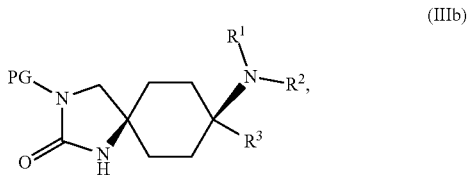

(IIIb)

wherein $R^1$, $R^2$ and $R^3$ are defined as above and PG is a protecting group.

Preferably the protecting group is -p-methoxybenzyl. Therefore, in another preferred embodiment, the synthesis of the compounds according to the invention proceeds via a synthesis route which comprises the preparation of an intermediate according to general formula (IIIc):

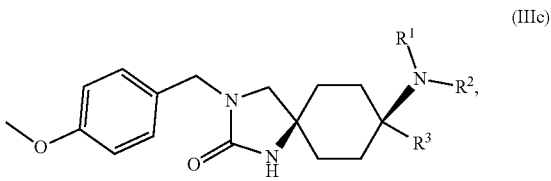

(IIIc)

wherein $R^1$, $R^2$ and $R^3$ are defined as above.

As already indicated, in general formula (IIIc), the -p-methoxybenzyl moiety represents a protecting group which can be cleaved in the course of the synthesis route.

In yet another preferred embodiment, the synthesis of the compounds according to the invention proceeds via a synthesis route which comprises the preparation of
- an intermediate according to general formula (IIIa) and according to general formula (IIIb); or
- an intermediate according to general formula (IIIa) and according to general formula (IIIc); or
- an intermediate according to general formula (IIIb) and according to general formula (IIIc); or
- an intermediate according to general formula (IIIa), according to general formula (IIIb) and according to general formula (IIIc).

The following examples further illustrate the invention but are not to be construed as limiting its scope.

EXAMPLES

"RT" means room temperature (23±7° C.), "M" are indications of concentration in mol/l, "aq." means aqueous, "sat." means saturated, "sol." means solution, "conc." means concentrated.

Further Abbreviations brine saturated aqueous sodium chloride solution
CC column chromatography
cHex cyclohexane
dba dibenzylideneacetone
DCM dichloromethane
DIPEA N,N-diisopropylethylamine
DMF N,N-dimethylformamide
Et ethyl
ether diethyl ether
EE ethyl acetate
EtOAc ethyl acetate
EtOH ethanol
h hour(s)
H$_2$O water
HATU O-(7-aza-benzotriazol-1-yl)-N,N,N',N'-tetramethyl-uroniumhexafluorophosphate
LDA lithium diisoproylamide
Me methyl
m/z mass-to-charge ratio
MeOH methanol
MeCN acetonitrile
min minutes
MS mass spectrometry
NBS N-bromosuccinimide
NIS N-iodosuccinimide
NEt$_3$ triethylamine
PE petroleum ether (60-80° C.)
RM reaction mixture
RT room temperature
TFA trifluoroacetic acid
T3P 2,4,6-tripropyl-1,3,5,2,4,6-trioxatriphosphorinane-2,4,6-trioxide
tBME tert-butyl methyl ether
THF tetrahydrofurane
v/v volume to volume
w/w weight to weight
Xantphos 4,5-bis(diphenylphosphino)-9,9-dimethylxanthene The yields of the compounds prepared were not optimised. All temperatures are uncorrected.

All starting materials, which are not explicitly described, were either commercially available (the details of suppliers such as for example Acros, Aldrich, Bachem, Butt park, Enamine, Fluka, Lancaster, Maybridge, Merck, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The mixing ratios of solvents or eluents for chromatography are specified in v/v.

All the intermediate products and exemplary compounds were analytically characterised by mass spectrometry (MS, m/z for [M+H]+). In addition $^1$H-NMR and $^{13}$C spectroscopy was carried out for all the exemplary compounds and selected intermediate products.

Remark Regarding Stereochemistry

CIS refers to the relative configuration of compounds described herein, in which both nitrogen atoms are drawn on the same face of the cyclohexane ring as described in the following exemplary structure. Two depictions are possible:

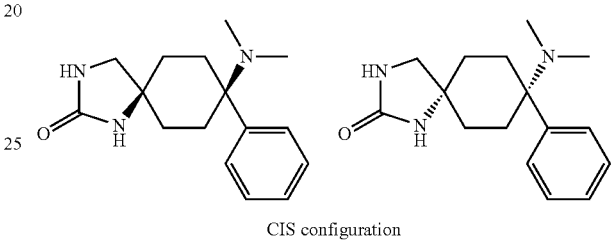

CIS configuration

TRANS refers to compounds, in which both nitrogen atoms are on opposite faces of the cyclohexane ring as described in the following exemplary structure. Two depictions are possible:

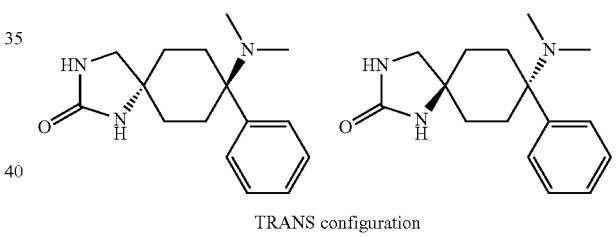

TRANS configuration

Synthesis of Intermediates

Synthesis of INT-600: 5-(cis-8-(Dimethylamino)-2-oxo-8-phenyl-1,3-diazaspiro[4.5]decan-3-yl)pyrimidine-2-carbonitrile

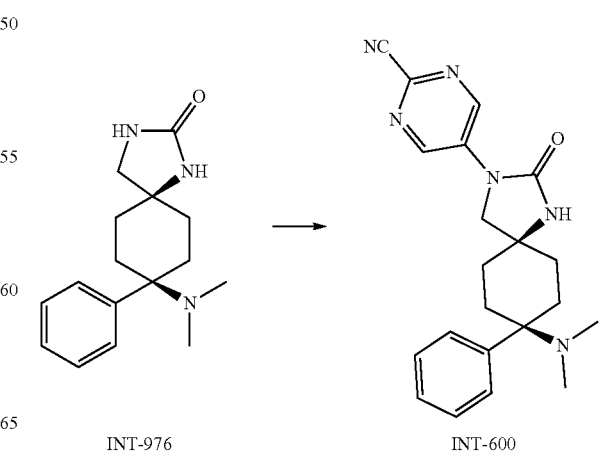

INT-976      INT-600

Cs₂CO₃ (1.1 g, 3.66 mmol) was added to the solution of CIS-8-(dimethylamino)-8-phenyl-1,3-diazaspiro[4.5]decan-2-one (INT-976) (0.5 g, 1.83 mmol), Xanthphos (0.158 g, 0.274 mmol), Pd₂(dba)₃ (0.083 g, 0.091 mmol) and 5-bromopyrimidine-2-carbonitrile (0.52 g, 2.74 mmol) in 1,4-dioxane (20 mL) under argon atmosphere. The reaction mixture was stirred for 16 h at 90° C., then cooled to RT and concentrated under reduced pressure. The residue was suspended in EtOAc (20 mL) and filtered through a plug of celite. The filtrate was concentrated under reduced pressure and the resulting residue was purified by flash chromatography on silica gel to afford 5-(cis-8-(dimethylamino)-2-oxo-8-phenyl-1,3-diazaspiro[4.5]decan-3-yl)pyrimidine-2-carbonitrile (INT-600) (0.4 g) as a white solid.

Synthesis of INT-799: CIS-8-Dimethylamino-1-[(1-hydroxy-cyclobutyl)-methyl]-8-phenyl-1,3-diazaspiro[4.5]decan-2-one

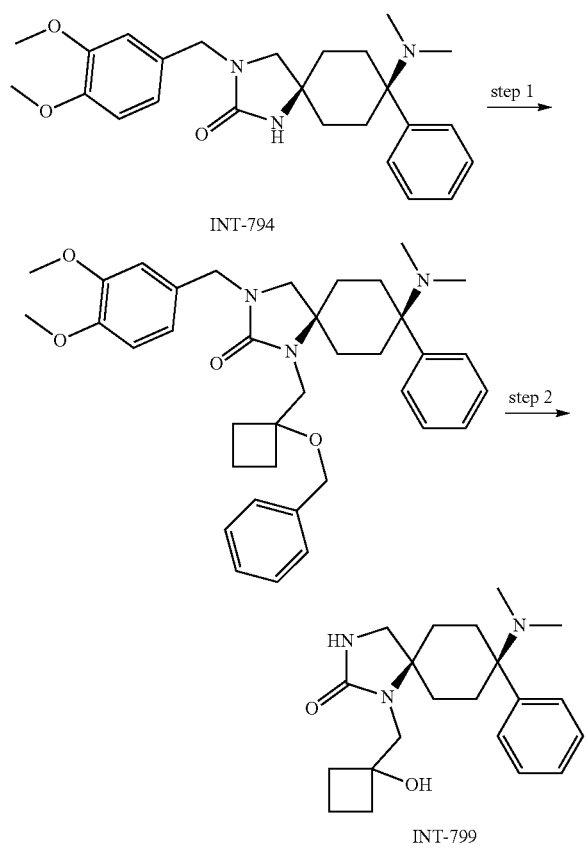

Step 1: CIS-1-((1-(benzyloxy)cyclobutyl)methyl)-3-(3,4-dimethoxybenzyl)-8-(dimethylamino)-8-phenyl-1,3-diazaspiro[4.5]decan-2-one NaOH (1.42 g, 35.5 mmol) was added to a solution of CIS-3-(3,4-dimethoxybenzyl)-8-(dimethylamino)-8-phenyl-1,3-diazaspiro[4.5]decan-2-one (INT-794) (3 g, 7.09 mmol) in DMSO (90 mL) under argon atmosphere and the reaction mixture was stirred at 80° C. for 30 min. ((1-(Bromomethyl)cyclobutoxy)methyl)benzene (5.4 g, 21.3 mmol) was added and stirring was continued for 2 days at 80° C. The reaction completion was monitored by TLC. The reaction mixture was diluted with water (500 mL) and extracted with diethyl ether (4×300 mL). The combined organic extracts were dried over anhydrous Na₂SO₄ and concentrated under reduced pressure. The residue was purified by column chromatography (230-400 mesh silica gel; 65-70% EtOAc in petroleum ether as eluent) to afford 2.5 g (59%) of CIS-1-((1-(benzyloxy)cyclobutyl)methyl)-3-(3,4-dimethoxybenzyl)-8-(dimethylamino)-8-phenyl-1,3-diazaspiro[4.5]decan-2-one (TLC system: 10% MeOH in DCM; Rf: 0.8).

Step 2: CIS-8-Dimethylamino-1-[(1-hydroxy-cyclobutyl)-methyl]-8-phenyl-1,3-diazaspiro[4.5]decan-2-one TFA (12 mL) was added to CIS-1-((1-(benzyloxy)cyclobutyl)methyl)-3-(3,4-dimethoxybenzyl)-8-(dimethylamino)-8-phenyl-1,3-diazaspiro[4.5]decan-2-one (2.5 g, 4.18 mmol) at 0° C. and the resulting mixture was stirred at 70° C. for 6 h. The reaction completion was monitored by LCMS. The reaction mixture was concentrated under reduced pressure. To the residue sat. aq. NaHCO₃ was added (until pH 10) and the organic product was extracted with DCM (3×150 mL). The combined organic extracts were dried over anhydrous Na₂SO₄ and concentrated under reduced pressure. The residue was purified by column chromatography (230-400 mesh silica gel; 5% MeOH in DCM as eluent) to afford 500 mg (33%) of CIS-8-dimethylamino-1-[(1-hydroxy-cyclobutyl)-methyl]-8-phenyl-1,3-diazaspiro[4.5]decan-2-one (INT-799) (TLC system: 10% MeOH in DCM; Rf: 0.5). [M+H]⁺ 358.2

Synthesis of INT-951: CIS-1-[(8-Dimethylamino-2-oxo-8-phenyl-1,3-diazaspiro[4.5]decan-1-yl)-methyl]-cyclobutane-1-carbonitrile

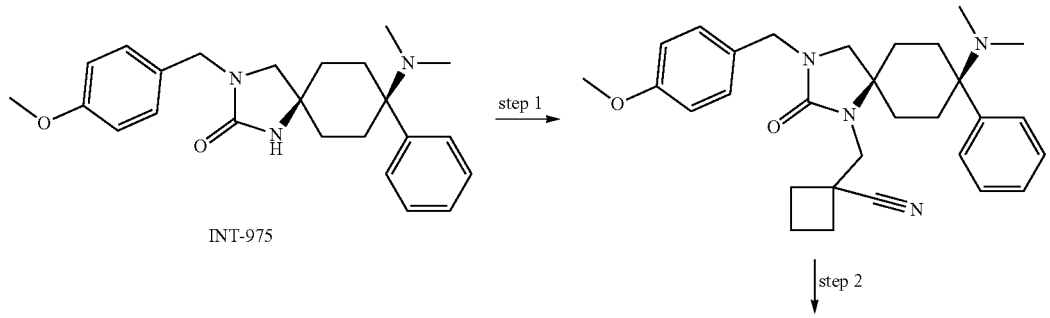

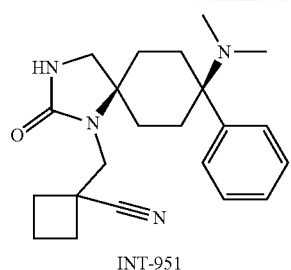 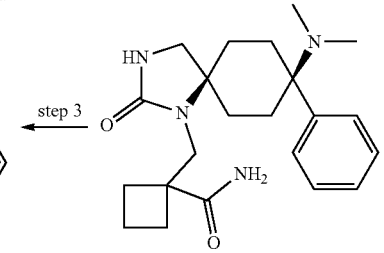

step 3

INT-951

Step 1: 1-((CIS-8-(dimethylamino)-3-(4-methoxybenzyl)-2-oxo-8-phenyl-1,3-diazaspiro[4.5]decan-1-yl)methyl)cyclobutanecarbonitrile NaH (50% in mineral oil) (2.44 g, 50.89 mmol) was added to a solution of CIS-8-dimethylamino-3-[(4-methoxyphenyl)-methyl]-8-phenyl-1,3-diazaspiro [4.5]decan-2-one (INT-975) (5 g, 12.72 mmol) in DMF (100 mL) at 0° C. portionwise over 10 min. 1-(Bromomethyl)cyclobutanecarbonitrile (4.4 g, 25.44 mmol) was added dropwise over 10 minutes at 0° C. The reaction mixture was allowed to stir at RT for 3 h, then quenched with water and the organic product was extracted with ethyl acetate (3×200 mL). The combined organic extracts were dried over anhydrous $Na_2SO_4$ and concentrated under reduced pressure to afford 5 g (crude) of 1-((CIS-8-(dimethylamino)-3-(4-methoxybenzyl)-2-oxo-8-phenyl-1,3-diazaspiro[4.5]decan-1-yl)methyl)cyclobutane-carbonitrile as gummy brown liquid. The material was used for the next step without further purification.

Step 2: 1-((CIS-8-(dimethylamino)-2-oxo-8-phenyl-1,3-diazaspiro[4.5]decan-1-yl)methyl) cyclobutanecarboxamide TFA (100 mL) was added to 1-((CIS-8-(dimethylamino)-3-(4-methoxybenzyl)-2-oxo-8-phenyl-1,3-diazaspiro[4.5]decan-1-yl)methyl)cyclobutanecarbonitrile (5 g, 10.28 mmol) at 0° C. and the reaction mixture at mixture was stirred at RT for 2 days. The reaction mixture was concentrated in vacuo. To the residue sat. aq. $NaHCO_3$ was added (until pH 10) and the organic product was extracted with dichloromethane (3×150 mL). The combined organic extracts were dried over anhydrous $Na_2SO_4$ and concentrated under reduced pressure to afford 3.5 g (crude) of 1-((CIS-8-(dimethylamino)-2-oxo-8-phenyl-1,3-diazaspiro[4.5]decan-1-yl)methyl) cyclobutanecarboxamide. The material was used for the next step without further purification.

Step 3: 1-((cis-8-(dimethylamino)-2-oxo-8-phenyl-1,3-diazaspiro[4.5]decan-1-yl)methyl)cyclobutane carbonitrile Thionyl chloride (35 mL) was added to 1-((cis-8-(dimethylamino)-2-oxo-8-phenyl-1,3-diazaspiro[4.5]decan-1-yl) methyl)cyclobutanecarboxamide (3.5 g, 9.11 mmol) at RT and the resulting mixture was stirred at reflux for 2 h. The reaction mixture was concentrated in vacuo. To the residue sat. aq. $NaHCO_3$ was added (until pH 10) and the organic product was extracted with dichloromethane (3×150 mL). The combined organic layer was dried over anhydrous $Na_2SO_4$ and concentrated in vacuo. The residue was purified by column chromatography to afford 1.3 g (34% after three steps) of CIS-1-[(8-dimethylamino-2-oxo-8-phenyl-1,3-diazaspiro[4.5]decan-1-yl)-methyl]-cyclobutane-1-carbonitrile (INT-951). $[M+H]^+$ 367.2.

Synthesis of INT-952: CIS-1-(Cyclobutyl-methyl)-8-dimethylamino-8-phenyl-3-[(4-methoxyphenyl)-methyl]-1,3-diazaspiro[4.5]decan-2-one

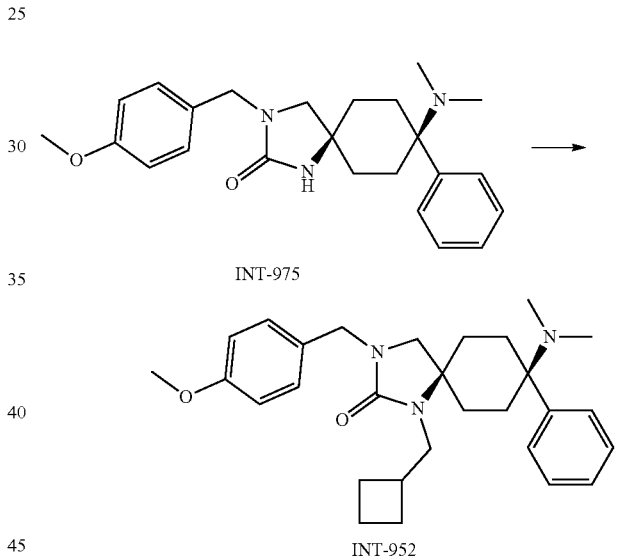

To a solution of CIS-8-dimethylamino-3-[(4-methoxyphenyl)-methyl]-8-phenyl-1,3-diazaspiro [4.5]decan-2-one (INT-975) (10 g, 25 mmol) in THF (500 mL) was added KOtBu (7.1 g, 63 mmol) at 50° C. The reaction mixture was heated up to reflux, cyclobutylmethylbromide (11.3 g, 76 mmol) was added in one portion, and stirring was continued at reflux for 12 h. KOtBu (7.1 g) and cyclobutylmethylbromide (11.3 g) were added again. The reaction mixture was allowed to stir another 2 h at reflux, then cooled to RT, diluted with water (150 mL) and the layers partitioned. The aqueous layer was extracted with EtOAc (3×300 mL). The combined organic layers were dried over $Na_2SO_4$ and then concentrated in vacuo. The residue was filtered through a plug of silica gel using a DCM/MeOH (19/1 v/v) mixture. The filtrate was concentrated in vacuo and the resulting solid was recrystallized from hot ethanol to yield 7.8 g of CIS-1-(cyclobutyl-methyl)-8-dimethylamino-8-phenyl-3-[(4-methoxyphenyl)-methyl]-1,3-diazaspiro[4.5]decan-2-one (INT-952). $[M+H]^+$ 461.3.

Synthesis of INT-953: CIS-1-(Cyclobutyl-methyl)-8-(methyl-(2-methyl-propyl)-amino)-8-phenyl-1,3-diazaspiro[4.5]decan-2-one

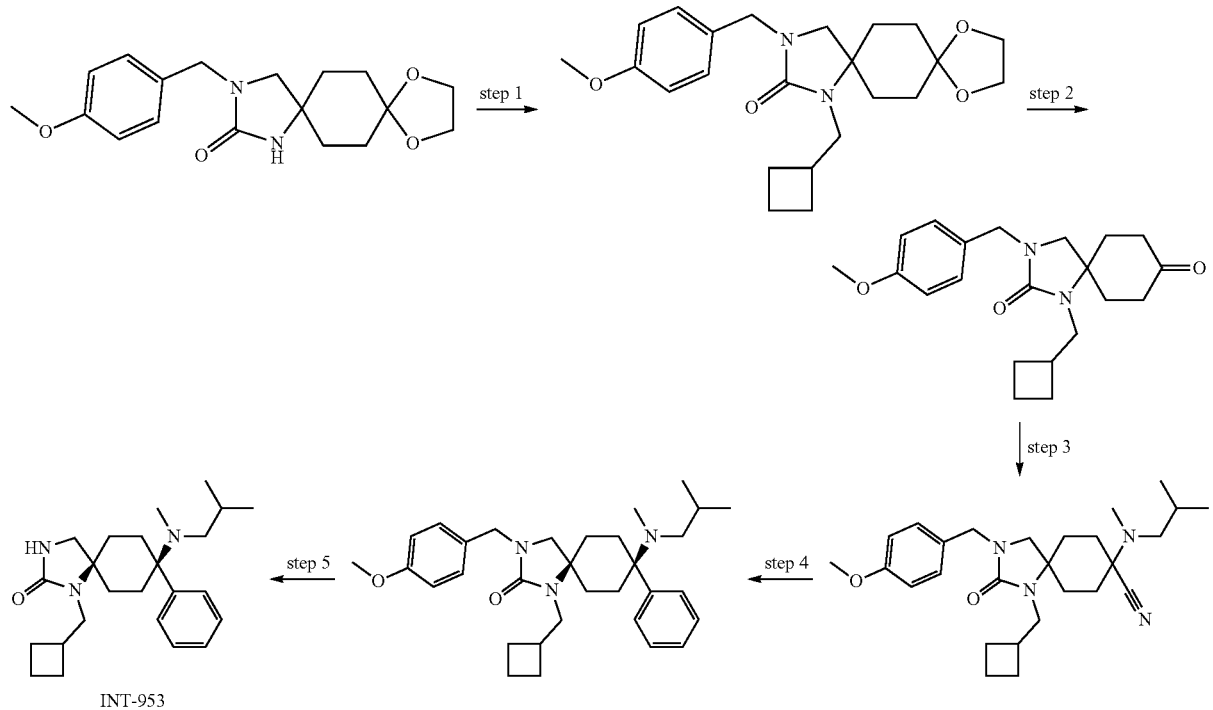

INT-953

Step 1: 1-Cyclobutylmethyl-3-(4-methoxy-benzyl)-9,12-dioxa-1,3-diazadispiro[4.2.4.2]tetradecan-2-one To a stirred solution of 3-(4-methoxy-benzyl)-9,12-dioxa-1,3-diazadispiro[4.2.4.2]tetradecan-2-one (4 g, 12.04 mmol) in anhydrous DMF (60 ml) was added NaH (1.38 g, 60% dispersion in oil, 36.14 mmol) at RT. The reaction mixture was stirred for 10 min, bromomethylcyclobutane (3 ml, 26.5 mmol) was added dropwise and stirring was continued for 50 h. TLC analysis showed complete consumption of the starting material. The reaction mixture was quenched with sat. aq. $NH_4Cl$ (50 ml) and extracted with EtOAc (3×200 ml). The combined organic phase was dried over $Na_2SO_4$ and concentrated under reduced pressure. The resulting residue was purified column chromatography (neutral aluminum oxide, EtOAc—petroleum ether (2:8)) to give 1-cyclobutylmethyl-3-(4-methoxy-benzyl)-9,12-dioxa-1,3-diazadispiro[4.2.4.2]tetradecan-2-one (2.4 g, 50%, white solid). TLC system:EtOAc—pet ether (6:4); $R_f$=0.48.

Step 2: 1-Cyclobutylmethyl-3-(4-methoxy-benzyl)-1,3-diaza-spiro[4.5]decane-2,8-dione To a stirred solution of 1-cyclobutylmethyl-3-(4-methoxy-benzyl)-9,12-dioxa-1,3-diazadispiro[4.2.4.2]tetradecan-2-one (1 g, 2.5 mmol) in MeOH (7 ml) was added 10% aq. HCl (8 ml) at 0° C. The reaction mixture was warmed up to RT and stirred for 16 h. TLC analysis showed complete consumption of the starting material. The reaction mixture was quenched with sat. aq. $NaHCO_3$ (30 ml) and extracted with EtOAc (3×50 ml). The combined organic phase was dried over $Na_2SO_4$ and concentrated under reduced pressure. The resulting residue was purified by column chromatography (silica gel, 230-400 mesh, EtOAc—pet ether (1:3)→(3:7)) to give 1-cyclobutylmethyl-3-(4-methoxy-benzyl)-1,3-diaza-spiro[4.5]decane-2,8-dione (650 mg, 73%, colorless viscous oil). TLC system: EtOAc—pet ether (6:4); R=0.40.

Step 3: 1-(cyclobutylmethyl)-8-(isobutyl(methyl)amino)-3-(4-methoxybenzyl)-2-oxo-1,3-diazaspiro[4.5]decane-8-carbonitrile To a stirred solution of N-isobutyl-N-methylamine (1.34 ml, 11.23 mmol) and $MeOH/H_2O$ (8 ml, 1:1, v/v) was added 4N aq. HCl (1.5 ml) and the reaction mixture was stirred for 10 min at 0° C. (ice bath). A solution of 1-cyclobutylmethyl-3-(4-methoxy-benzyl)-1,3-diaza-spiro[4.5]decane-2,8-dione (1 g, 2.80 mmol) in MeOH (7 ml) and KCN (548 mg, 8.42 mmol) were added and the reaction mixture was stirred at 45° C. for 20 h. TLC analysis showed complete consumption of the starting material. The reaction mixture was diluted with water (30 ml), extracted with EtOAc (3×30 ml), the combined organic phase was dried over $Na_2SO_4$ and concentrated under reduced pressure to give 1-(cyclobutylmethyl)-8-(isobutyl(methyl)amino)-3-(4-methoxybenzyl)-2-oxo-1,3-diazaspiro[4.5]decane-8-carbonitrile (1.3 g, viscous yellow oil). TLC system:EtOAc—pet ether (1:1); $R_f$=0.45. The product was used for the next step without additional purification.

Step 4: CIS-1-(cyclobutylmethyl)-8-(isobutyl(methyl)amino)-3-(4-methoxybenzyl)-8-phenyl-1,3-diazaspiro[4.5]decan-2-one A round bottom flask containing 1-(cyclobutylmethyl)-8-(isobutyl(methyl)amino)-3-(4-methoxybenzyl)-2-oxo-1,3-diazaspiro[4.5]decane-8-carbonitrile (1.3 g, 2.81 mmol) was cooled in an ice bath (~0° C.) and a solution of phenylmagnesium bromide (26 ml, ~2M in THF) was added slowly at 0° C.-5° C. The ice bath was removed and the reaction mixture was stirred for 30 min, then diluted with sat. aq. NH₄Cl (25 ml) and extracted with EtOAc (4×30 ml). The combined organic phase was dried over Na₂SO₄ and concentrated under reduced pressure to give pale yellow viscous oil. This residue was purified by column chromatography (silica gel, 230-400 mesh, eluent: EtOAc—pet ether (15:85)→(2:4)) to give CIS-1-(cyclobutylmethyl)-8-(isobutyl(methyl)amino)-3-(4-methoxybenzyl)-8-phenyl-1,3-diazaspiro[4.5]decan-2-one (135 mg, 10%, white solid). TLC system:EtOAc—pet ether (1:1); $R_f$=0.6

Step 5: CIS-1-(Cyclobutyl-methyl)-8-(methyl-(2-methyl-propyl)-amino)-8-phenyl-1,3-diazaspiro[4.5]decan-2-one A round bottom flask containing CIS-1-(cyclobutylmethyl)-8-(isobutyl(methyl)amino)-3-(4-methoxybenzyl)-8-phenyl-1,3-diazaspiro[4.5]decan-2-one (130 mg, 0.25 mmol) was cooled in an ice bath and a mixture of TFA/CH₂Cl₂ (2.6 ml, 1:1, v/v) was added slowly at 0° C.-5° C. The reaction mixture was warmed to RT and stirred for 20 h, then quenched with methanolic NH₃ (10 ml, ~10% in MeOH) and concentrated under reduced pressure to give pale yellow viscous oil. This residue was purified twice by column chromatography (silica gel, 230-400 mesh, eluent: MeOH—CHCl₃ (1:99)→(2:98)) to give CIS-1-(cyclobutyl-methyl)-8-(methyl-(2-methyl-propyl)-amino)-8-phenyl-1,3-diazaspiro[4.5]decan-2-one (INT-953) (65 mg, 66%, white solid). TLC system:MeOH—CHCl₃ (5:95); $R_f$=0.25; [M+H]⁺ 384.3

Synthesis of INT-958:
4-Oxo-1-pyridin-2-yl-cyclohexane-1-carbonitrile

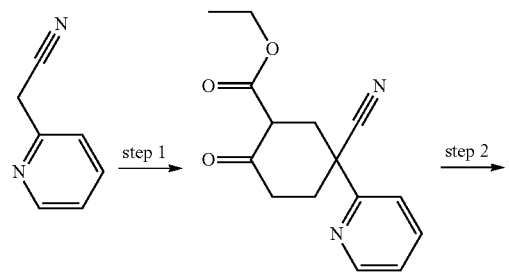

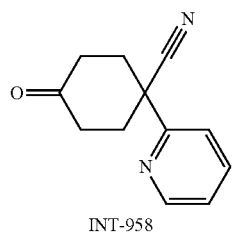

INT-958

Step 1: Ethyl 5-cyano-2-oxo-5-(pyridin-2-yl)cyclohexanecarboxylate

KOtBu (57.0 g, 508.4 mmol) was added to the solution of 2-(pyridin-2-yl)acetonitrile (50.0 g, 423.7 mmol) and ethyl acrylate (89.0 g, 889.8 mmol) in THF (500 mL) at 0° C. and stirred for 16 h at RT. The reaction mixture was quenched with sat. aq. NH₄Cl and extracted with EtOAc (2×500 mL). The combined organic layer was washed with brine, dried over Na₂SO₄ and concentrated under reduced pressure to afford 68.0 g (60%; crude) of ethyl 5-cyano-2-oxo-5-(pyridin-2-yl)cyclohexanecarboxylate as a brown liquid (TLC system: 50% ethyl acetate in petroleum ether; Rf: 0.65).

Step 2:
4-Oxo-1-pyridin-2-yl-cyclohexane-1-carbonitrile

A solution of ethyl 5-cyano-2-oxo-5-(pyridin-2-yl)cyclohexanecarboxylate (68.0 g, 250.0 mmol) was added to a mixture of conc. aq. HCl and glacial acetic acid (170 mL/510 mL) at 0° C. The reaction mixture was heated to 100° C. for 16 h. All volatiles were evaporated under reduced pressure. The residue was diluted with sat. aq. NaHCO₃ and extracted with ethyl acetate (3×300 mL). The combined organic layer was washed with brine, dried over Na₂SO₄ and concentrated under reduced pressure to afford 44.0 g (88%) of 4-oxo-1-pyridin-2-yl-cyclohexane-1-carbonitrile INT-958 as a brown solid (TLC system: 50% ethyl acetate in pet ether; Rf: 0.45). [M+H]⁺ 201.1

Synthesis of INT-961:
4-Dimethylamino-4-pyridin-2-yl-cyclohexan-1-one

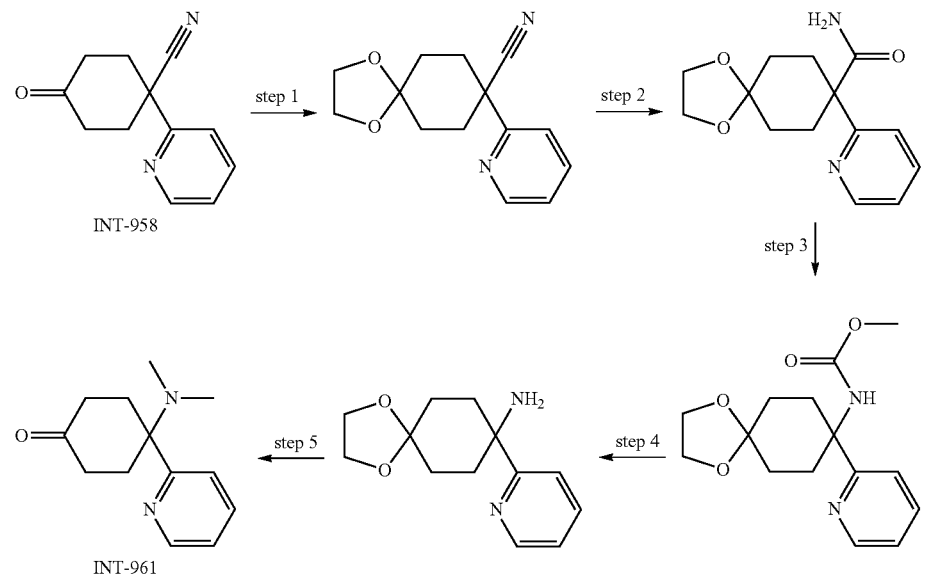 [SMILES: N#CC1(c2ccccn2)CCC(=O)CC1 ; N#CC1(c2ccccn2)CCC2(CC1)OCCO2 ; NC(=O)C1(c2ccccn2)CCC2(CC1)OCCO2 ; CN(C)C1(c2ccccn2)CCC(=O)CC1 ; NC1(c2ccccn2)CCC2(CC1)OCCO2 ; COC(=O)NC1(c2ccccn2)CCC2(CC1)OCCO2]

Step 1: 8-(pyridin-2-yl)-1,4-dioxaspiro[4.5]decane-8-carbonitrile

A solution of 4-oxo-1-pyridin-2-yl-cyclohexane-1-carbonitrile (INT-958) (44.0 g, 220.0 mmol), ethylene glycol (27.0 g, 440.0 mmol) and PTSA (4.2 g, 22.0 mmol) in toluene (450 mL) was heated to 120° C. for 16 h using Dean Stark apparatus. All volatiles were evaporated under reduced pressure. The residue was diluted with sat. aq. NaHCO₃ and extracted with ethyl acetate (3×300 mL). The combined organic layer was washed with brine, dried over Na₂SO₄ and concentrated under reduced pressure to afford 45.0 g (85%) of 8-(pyridin-2-yl)-1,4-dioxaspiro[4.5]decane-8-carbonitrile as a light brown solid (TLC system: 50% ethyl acetate in petroleum ether; Rf: 0.55).

Step 2: 8-(pyridin-2-yl)-1,4-dioxaspiro[4.5]decane-8-carboxamide

Potassium carbonate (50.0 g, 368.84 mmol) and 30% aq. H₂O₂ (210.0 mL, 1844.2 mmol) were added to the solution of 8-(pyridin-2-yl)-1,4-dioxaspiro[4.5]decane-8-carbonitrile (45.0 g, 184.42 mmol) in DMSO (450 mL) at 0° C. and the resulting mixture was stirred at RT for 14 h. The reaction mixture was diluted with water (1.5 L) and stirred for 1 h. The precipitated solid was separated by filtration, washed with water, petroleum ether and dried under reduced pressure to get 32.0 g (66%) of 8-(pyridin-2-yl)-1,4-dioxaspiro[4.5]decane-8-carboxamide as a white solid. (TLC system: 10% MeOH in DCM R$_f$: 0.35).

Step 3: methyl 8-(pyridin-2-yl)-1,4-dioxaspiro[4.5]decan-8-ylcarbamate

A mixture of 8-(pyridin-2-yl)-1,4-dioxaspiro[4.5]decane-8-carboxamide (25.0 g, 95.41 mmol), sodium hypochlorite (5 wt % aq. solution, 700 mL, 477.09 mmol) and KF—Al₂O₃ (125.0 g) in methanol (500 mL) was heated to 80° C. for 16 h. The reaction mixture was filtered through celite and the solid residue was washed with methanol. The combined filtrate was concentrated under reduced pressure. The residue was diluted with water and extracted with ethyl acetate (3×500 mL). The combined organic layer was washed with brine, dried over Na₂SO₄ and concentrated under reduced pressure to afford 18.0 g (66%) of methyl 8-(pyridin-2-yl)-1,4-dioxaspiro[4.5]decan-8-ylcarbamate as a light brown solid. (TLC system: 5% MeOH in DCM R$_f$: 0.52.)

Step 4: 8-(pyridin-2-yl)-1,4-dioxaspiro[4.5]decan-8-amine

A suspension of methyl 8-(pyridin-2-yl)-1,4-dioxaspiro[4.5]decan-8-ylcarbamate (18.0 g, 61.64 mmol) in 10 wt % aq. NaOH (200 mL) was heated to 100° C. for 24 h. The reaction mixture was filtered through celite pad, the solid residue was washed with water and the combined filtrate was extracted with EtOAc (4×200 mL). The combined organic layer washed with brine, dried over Na₂SO₄ and concentrated under reduced pressure to afford 12.5 g (88%) of 8-(pyridin-2-yl)-1,4-dioxaspiro[4.5]decan-8-amine as a light brown semi-solid. (TLC system: 5% MeOH in DCM R$_f$: 0.22.).

Step 5: 4-Dimethylamino-4-pyridin-2-yl-cyclohexan-1-one

Sodium cyanoborohydride (13.7 g, 0.213 mol) was added portionwise to a solution of 8-(pyridin-2-yl)-1,4-dioxaspiro[4.5]decan-8-amine (12.5 g, 53.418 mmol) and 35 wt % aq. formaldehyde (45 mL, 0.534 mol) in acetonitrile (130 mL) at 0° C. The reaction mixture was warmed up to room temperature and stirred for 16 h. The reaction mixture was quenched with sat. aq. NH₄Cl and concentrated under reduced pressure. The residue was dissolved in water and extracted with EtOAc (3×200 mL). The combined organic layer was washed with brine, dried over Na₂SO₄ and concentrated under reduced pressure to afford 10.5 g (72%) of 4-dimethylamino-4-pyridin-2-yl-cyclohexan-1-one (INT-961) as a light brown solid. (TLC system: 5% MeOH in DCM R$_f$: 0.32.). [M+H]⁺ 219.1

Synthesis of INT-965: 4-Dimethylamino-4-phenyl-cyclohexan-1-one

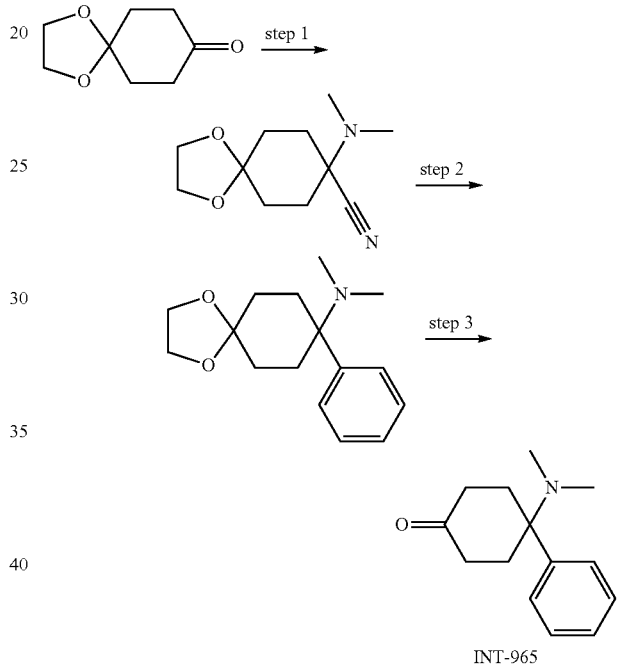

INT-965

Step 1: 8-(Dimethylamino)-1,4-dioxaspiro 4.5]decane-8-carbonitrile

Dimethylamine hydrochloride (52 g, 0.645 mol) was added to the solution of 1,4-dioxaspiro-[4.5]-decan-8-one (35 g, 0.224 mmol) in MeOH (35 mL) at RT under argon atmosphere. The solution was stirred for 10 min and 40 wt % aq. dimethylamine (280 mL, 2.5 mol) and KCN (32 g, 0.492 mol) were sequentially added. The reaction mixture was stirred for 48 h at RT, then diluted with water (100 mL) and extracted with EtOAc (2×200 mL). The combined organic layer was dried over anhydrous Na₂SO₄ and concentrated under reduced pressure to afford 44 g of 8-(dimethylamino)-1,4-dioxaspiro-[4.5]-decane-8-carbonitrile (93%) as a white solid.

Step 2: N,N-dimethyl-8-phenyl-1,4-dioxaspiro[4.5]decan-8-amine 8-(Dimethylamino)-1,4-dioxaspiro[4.5]decane-8-carbonitrile (35 g, 0.167 mol) in THF (350 mL) was added to the solution of 3M phenylmagnesium bromide in diethyl ether (556 mL, 1.67 mol) dropwise at −10° C. under argon atmosphere. The reaction mixture was stirred for 4 h at −10° C. to 0° C. and then at RT for 18 h. The reaction completion was monitored by TLC. The reaction mixture was cooled to 0° C., diluted with sat. aq. NH$_4$Cl (1 L) and extracted with EtOAc (2×600 mL). The combined organic layer was dried over anhydrous Na$_2$SO$_4$ and concentrated under reduced pressure to afford 60 g of, N N-dimethyl-8-phenyl-1, 4-dioxaspiro-[4.5]-decan-8-amine as a liquid.

Step 3: 4-(dimethylamino)-4-phenylcyclohexanone

A solution of N,N-dimethyl-8-phenyl-1,4-dioxaspiro[4.5]decan-8-amine (32 g, 0.123 mol) in 6N aq. HCl (320 mL) was stirred at 0° C. for 2 h and then at RT for 18 h. The reaction completion was monitored by TLC. The reaction mixture was extracted with DCM (2×150 mL). The aqueous layer was basified to pH 10 with solid NaOH and extracted with ethyl acetate (2×200 mL). The combined organic layer was dried over anhydrous Na$_2$SO$_4$ and concentrated under reduced pressure. The solid residue was washed with hexane and dried in vacuo to afford 7 g of 4-dimethylamino-4-phenyl-cyclohexan-1-one (INT-965) (25% over 2 steps) as a brown solid. [M+H]$^+$ 218.1

Synthesis of INT-966: 3-[(4-Methoxyphenyl)-methyl]-1,3-diazaspiro[4.5]decane-2,8-dione

Step 2: 2-[(4-Methoxyphenyl)-methyl]-9,12-dioxa-2,4-diazadispiro[4.2.4^{8}.2^{5}]tetradecane-1,3-dione Cs$_2$CO$_3$ (258.7 g, 796.1 mmol) was added to the solution of 73a (150 g, 663.4 mmol) in MeCN (1.5 L) under argon atmosphere and the reaction mixture was stirred for 30 min. A solution of p-methoxybenzyl bromide (96 mL, 663.4 mmol) was added. The reaction mixture was stirred at RT for 48 h. The reaction completion was monitored by TLC. The reaction mixture was quenched with sat. aq. NH$_4$Cl (1.0 L) and the organic product was extracted with EtOAc (2×1.5 L). The combined organic layer was dried over anhydrous Na$_2$SO$_4$ and concentrated under reduced pressure. The residue was washed with diethyl ether and pentane and dried under reduced pressure to afford 151 g (65%) of 2-[(4-Methoxyphenyl)-methyl]-9,12-dioxa-2,4-diazadispiro[4.2.4^{8}.2^{5}]tetradecane-1,3-dione as an off white solid (TLC system: 10% MeOH in DCM; Rf: 0.6).

Step 3: 2-[(4-Methoxyphenyl)-methyl]-9,12-dioxa-2,4-diazadispiro[4.2.4^{8}.2^{5}]tetradecan-3-one AlCl$_3$ (144.3 g, 1082.6 mmol) was added to a solution of LiAlH$_4$ (2M in THF) (433 mL, 866.10 mmol) in THF (4.5 L) at 0° C. under argon atmosphere and the resulting mixture was stirred at RT for 1 h. 2-[(4-Methoxyphenyl)-methyl]-9,12-dioxa-2,4-diazadispiro[4.2.4^{8}.2^{5}]tetradecane-1,3-dione (150 g, 433.05 mmol) was added at 0° C. The reaction mixture was stirred at RT for 16 h. The reaction completion was monitored by TLC. The reaction mixture was cooled to

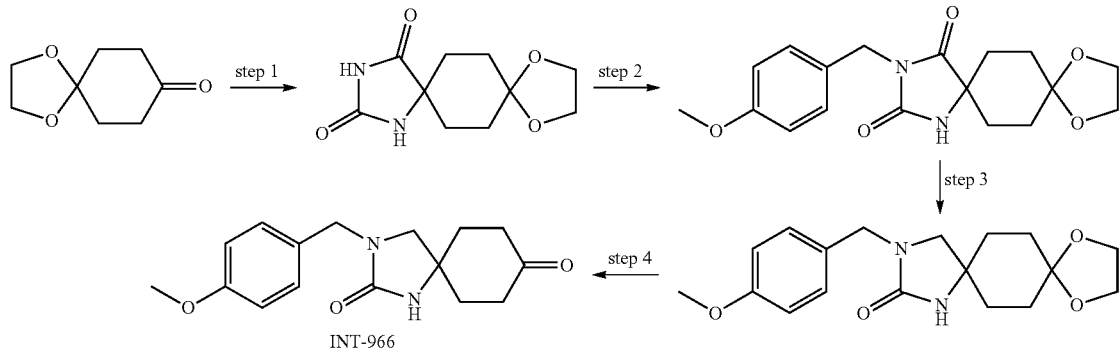

INT-966

Step 1: 9,12-Dioxa-2,4-diazadispiro[4.2.4^{8}.2^{5}]tetradecane-1,3-dione

KCN (93.8 g, 1441.6 mmol) and (NH$_4$)$_2$CO$_3$ (271.8 g, 1729.9 mmol) were added to the solution of 1,4-dioxaspiro[4.5]decan-8-one (150 g, 961 mmol) in MeOH:H$_2$O (1:1 v/v) (1.92 L) at RT under argon atmosphere. The reaction mixture was stirred at 60° C. for 16 h. The reaction completion was monitored by TLC. The reaction mixture was cooled to 0° C., the precipitated solid was filtered off and dried in vacuo to afford 120 g (55%) of 9,12-dioxa-2,4-diazadispiro[4.2.4^{8}.2^{(5)}]tetradecane-1,3-dione. The filtrate was extracted with DCM (2×1.5 L). The combined organic layer was dried over anhydrous Na$_2$SO$_4$ and concentrated under reduced pressure to afford additional 30 g (14%) of 9,12-dioxa-2,4-diazadispiro[4.2.4^{8}.2^{5}]tetradecane-1,3-dione (TLC system: 10% Methanol in DCM; Rf: 0.4).

0° C., quenched with sat. aq. NaHCO$_3$ (500 mL) and filtered through celite pad. The filtrate was extracted with EtOAc (2×2.0 L). The combined organic layer was dried over anhydrous Na$_2$SO$_4$ and concentrated in vacuo to afford 120 g (84%) of 2-[(4-methoxyphenyl)-methyl]-9,12-dioxa-2,4-diazadispiro[4.2.4^{8}.2^{5}]tetradecan-3-one as an off-white solid. (TLC system: 10% MeOH in DCM, Rf: 0.5).

Step 4: 3-[(4-Methoxyphenyl)-methyl]-1,3-diazaspiro[4.5]decane-2,8-dione

A solution of 2-[(4-methoxyphenyl)-methyl]-9,12-dioxa-2,4-diazadispiro[4.2.4^{8}.2^{5}] tetradecan-3-one (120 g, 361.03 mmol) in 6N aq. HCl (2.4 L) was stirred at 0° C. for 2 h and then at RT for 18 h. The reaction completion was monitored by TLC. The reaction mixture was extracted with DCM (2×2.0 L). The aqueous layer was basified to pH 10 with 50% aq. NaOH and then extracted with DCM (2×2.0

L). Combined organic extracts were dried over anhydrous Na$_2$SO$_4$ and concentrated under reduced pressure. The solid residue was washed with hexane and dried in vacuo to afford 90 g of 3-[(4-Methoxyphenyl)-methyl]-1,3-diazaspiro[4.5] decane-2,8-dione (INT-966) as an off-white solid (TLC system: 10% MeOH in DCM; Rf: 0.4) [M+H]$^+$ 289.11.

Synthesis of INT-971: CIS-1-(Cyclobutyl-methyl)-8-dimethylamino-8-(3-hydroxyphenyl)-3-[(4-methoxyphenyl)-methyl]-1,3-diazaspiro [4.5]decan-2-one

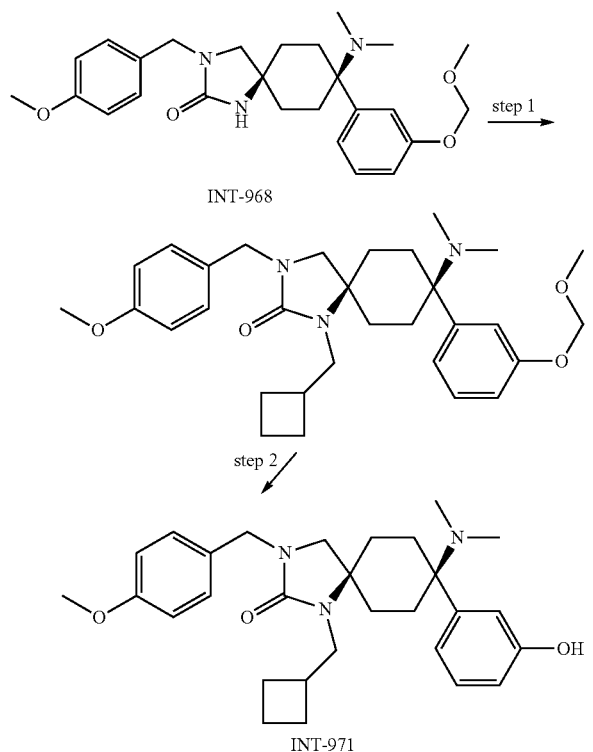

Step 1: CIS-8-(dimethylamino)-1-isobutyl-3-(4-methoxybenzyl)-8-phenyl-1,3-diazaspiro[4.5]decan-2-one In analogy to the method described for INT-951 step 1 CIS-8-Dimethylamino-8-[3-(methoxymethyloxy)-phenyl]-3-[(4-methoxyphenyl)-methyl]-1,3-diazaspiro[4.5]decan-2-one (INT-968) was converted into CIS-1-(cyclobutylmethyl)-8-(dimethylamino)-3-(4-methoxybenzyl)-8-(3-(methoxymethoxy)phenyl)-1,3-diazaspiro[4.5]decan-2-one.

Step 2: CIS-1-(Cyclobutyl-methyl)-8-dimethyl-amino-8-(3-hydroxyphenyl)-3-[(4-methoxyphenyl)-methyl]-1,3-diazaspiro[4.5]decan-2-one TFA (0.2 mL) was added to the solution of CIS-1-(cyclobutylmethyl)-8-(dimethylamino)-3-(4-methoxybenzyl)-8-(3-methoxyphenyl)-1,3-diazaspiro[4.5]decan-2-one (300 mg, 0.57 mmol) in DCM (1.5 mL) at 0° C. The reaction mixture was stirred at 0° C. for 3 h. The reaction completion was monitored by TLC. The reaction mixture was quenched with sat. aq. NaHCO$_3$ and the organic product was extracted with DCM (3×10 mL). The combined organic extracts were dried over anhydrous Na$_2$SO$_4$ and concentrated under reduced pressure. Purification of the residue by preparative TLC (3% MeOH in DCM as mobile phase) yielded 50 mg (18%) of CIS-1-(Cyclobutyl-methyl)-8-dimethylamino-8-(3-hydroxyphenyl)-3-[(4-methoxyphenyl)-methyl]-1,3-diazaspiro[4.5]decan-2-one (INT-971) as an off white solid. (TLC system: 10% MeOH in DCM; Rf: 0.20) [M+H]$^+$ 478.3

Synthesis of INT-974: CIS-8-Dimethylamino-8-(3-fluorophenyl)-3-[(4-methoxyphenyl)-methyl]-1,3-diazaspiro[4.5]decan-2-one

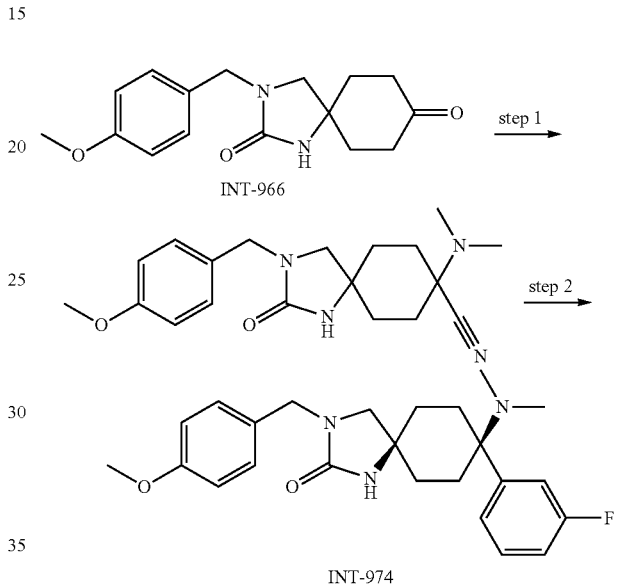

Step 1: 8-(dimethylamino)-3-(4-methoxybenzyl)-2-oxo-1,3-diazaspiro[4.5]decane-8-carbonitrile Dimethylamine hydrochloride (76.4 g, 936.4 mmol) was added to a solution of 3-[(4-methoxyphenyl)-methyl]-1,3-diazaspiro[4.5]decane-2,8-dione (INT-966) (90 g, 312.13 mmol) in MeOH (180 mL) at RT under argon atmosphere. The solution was stirred for 15 min and 40 wt % aq. dimethylamine (780 mL) and KCN (48.76 g, 749.11 mmol) were sequentially added. The reaction mixture was stirred for 48 h and the completion of the reaction was monitored by NMR. The reaction mixture was diluted with water (1.0 L) and the organic product was extracted with ethyl acetate (2×2.0 L). The combined organic layer was dried over anhydrous Na$_2$SO$_4$ and concentrated under reduced pressure to afford 90 g (85%) of 8-(dimethylamino)-3-(4-methoxybenzyl)-2-oxo-1,3-diazaspiro[4.5]decane-8-carbonitrile as an off white solid (TLC system: TLC system: 10% MeOH in DCM; Rf: 0.35, 0.30).

Step 2: CIS-8-Dimethylamino-8-(3-fluorophenyl)-3-[(4-methoxyphenyl)-methyl]-1,3-diazaspiro[4.5] decan-2-one 3-Fluorophenylmagnesium bromide (1M in THF) (220 mL, 219.17 mmol) was added dropwise to a solution of 8-(dimethylamino)-3-(4-methoxybenzyl)-2-oxo-1,3-diazaspiro[4.5]decane-8-carbonitrile (15 g, 43.83 mmol) in THF (300 mL) at 0° C. under argon atmosphere. The reaction mixture was stirred for 16 h at RT. The reaction completion was monitored by TLC. The reaction mixture was cooled to 0° C., quenched with sat. aq. NH₄Cl (200 mL) and the organic product was extracted with EtOAc (2×200 mL). The combined organic layer was dried over anhydrous Na₂SO₄ and concentrated under reduced pressure. The reaction was carried out in 4 batches (15 g×2 and 5 g×2) and the batches were combined for purification. Purification of the crude product by flash column chromatography on silica gel (230-400 mesh) (2 times) (0-20% methanol in DCM) eluent and subsequently by washing with pentane yielded 5.6 g (11%) of CIS-8-dimethylamino-8-(3-fluorophenyl)-3-[(4-methoxyphenyl)-methyl]-1,3-diazaspiro[4.5]decan-2-one (INT-974) as an off-white solid. (TLC system: 5% MeOH in DCM in presence of ammonia; Rf: 0.1). [M+H]⁺ 412.2

Synthesis of INT-975: CIS-8-Dimethylamino-3-[(4-methoxyphenyl)-methyl]-8-phenyl-1,3-diazaspiro[4.5]decan-2-one

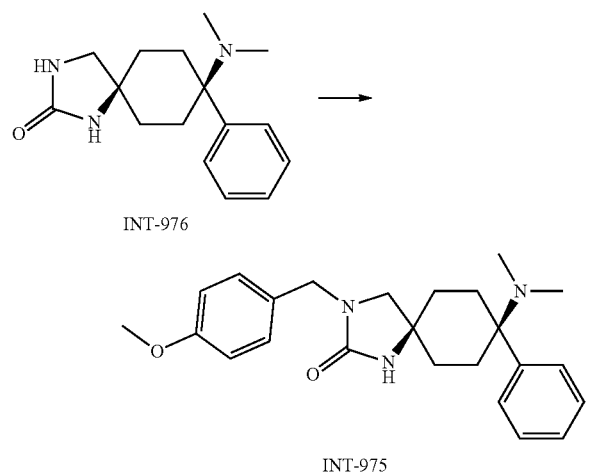

KOtBu (1M in THF) (29.30 mL, 29.30 mmol) was added to the solution of CIS-8-Dimethylamino-8-phenyl-1,3-diazaspiro[4.5]decan-2-one INT-976 (8.0 g, 29.30 mmol) in THF (160 mL) under argon atmosphere and the reaction mixture was stirred for 30 min. 4-Methoxybenzyl bromide (4.23 mL, 29.30 mmol) was added and stirring was continued at RT for 4 h. The reaction completion was monitored by TLC. The reaction mixture was diluted with sat. aq. NH₄Cl (150 mL) and the organic product was extracted with EtOAc (2×150 mL). The combined organic layer was dried over anhydrous Na₂SO₄ and concentrated in vacuo. The reaction was carried out in 2 batches (8 g×2) and the batches were combined for purification. Purification of the crude product by flash column chromatography on silica gel (0-10% methanol in DCM) and subsequently by washing with pentane yielded 11 g (47%) of CIS-8-Dimethylamino-3-[(4-methoxyphenyl)-methyl]-8-phenyl-1,3-diazaspiro[4.5]decan-2-one (INT-975) as a white solid. [M+H]⁺ 394.2

Synthesis of INT-976: CIS-8-Dimethylamino-8-phenyl-1,3-diazaspiro[4.5]decan-2-one

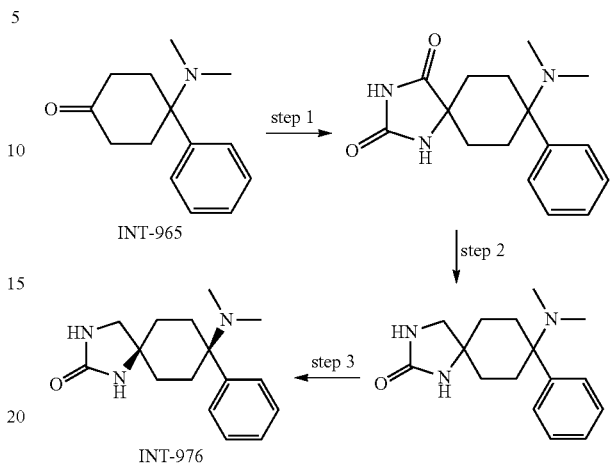

Step 1: 8-(dimethylamino)-8-phenyl-1,3-diazaspiro[4,5]decane-2,4-dione

In a sealed tube 4-dimethylamino-4-phenyl-cyclohexan-1-one (INT-965) (2 g, 9.22 mmol) was suspended in 40 mL EtOH/H₂O (1:1 v/v) at RT under argon atmosphere. (NH₄)₂CO₃ (3.62 g, 23.04 mmol) and KCN (0.6 g, 9.22 mmol) were added. The reaction mixture was stirred at 60° C. for 18 h. The reaction mixture was cooled to 0° C. and diluted with ice-water and filtered through a glass filter. The solid residue was dried under reduced pressure to afford 8-(dimethylamino)-8-phenyl-1,3-diazaspiro[4,5]decane-2,4-dione (1.8 g, 86%) as an off white crystalline solid (TLC: 80% EtOAc in hexane; Rf: 0.25).

Step 2: 8-(dimethylamino)-8-phenyl-1, 3-diazaspiro[4, 5] decan-2-one

LiAlH₄ (2M in THF) (70 mL, 139.4 mmol) was added to the solution of 8-(dimethylamino)-8-phenyl-1,3-diazaspiro[4,5]decane-2,4-dione (10 g, 34.8 mmol) in THF/Et₂O (2:1 v/v) (400 mL) at 0° C. under argon atmosphere. The reaction mixture was stirred for 4 h at 60° C. The reaction completion was monitored by TLC. The reaction mixture was cooled to 0° C., quenched with saturated Na₂SO₄ solution (100 mL) and filtered through Celite pad. The filtrate was dried over anhydrous Na₂SO₄ and concentrated in vacuo to afford 5.7 g (59%) of 8-(dimethylamino)-8-phenyl-1, 3-diazaspiro [4, 5] decan-2-one as an off white solid. (TLC system: 10% MeOH in DCM, Rf: 0.3).

Step 3: CIS-8-Dimethylamino-8-phenyl-1,3-diazaspiro[4.5]decan-2-one

A mixture of CIS- and TRANS-8-(dimethylamino)-8-phenyl-1,3-diazaspiro[4,5]decan-2-one (8 g, 29.30 mmol) was purified by preparative chiral SFC (column: Chiralcel AS-H, 60% CO₂, 40% (0.5% DEA in MeOH)) to get 5 g of CIS-8-Dimethylamino-8-phenyl-1,3-diazaspiro[4.5]decan-2-one (INT-976) as a white solid. [M+H]⁺ 274.2.

Synthesis of INT-977: CIS-2-(8-Dimethylamino-2-oxo-8-phenyl-1,3-diazaspiro[4.5]decan-1-yl)-acetic acid; 2,2,2-trifluoro-acetic acid salt

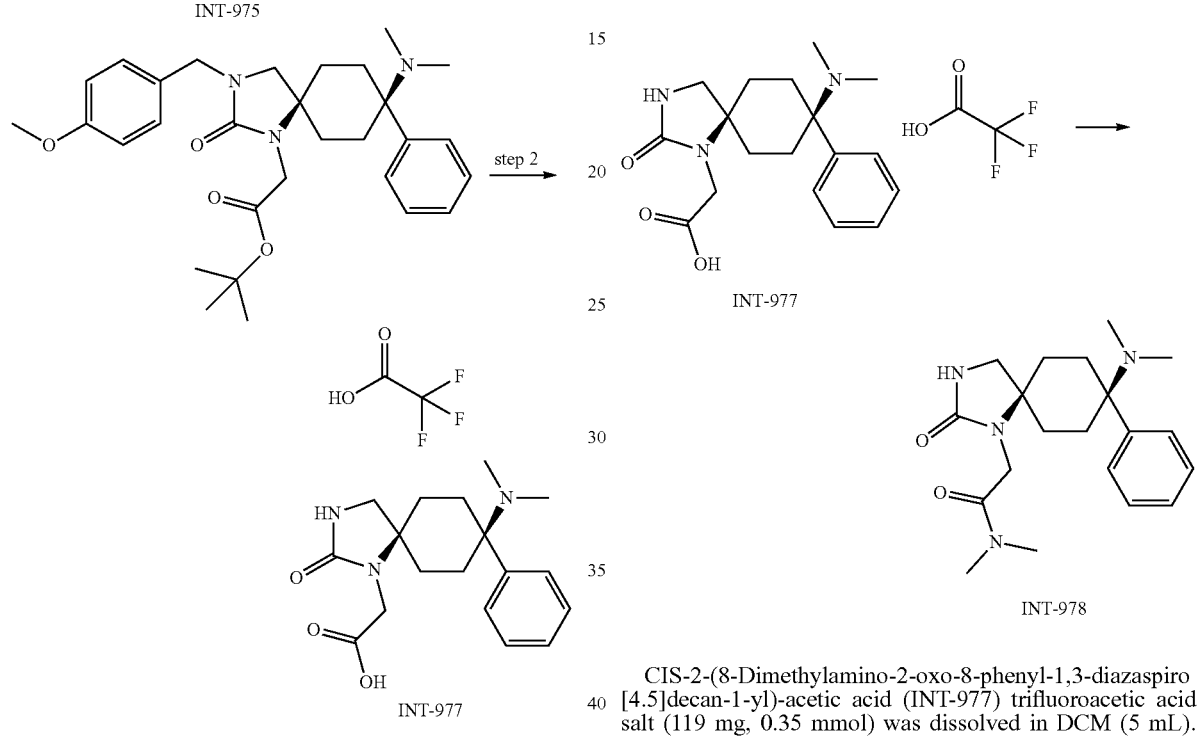

Step 1: CIS-2-[8-Dimethylamino-3-[(4-methoxyphenyl)-methyl]-2-oxo-8-phenyl-1,3-diazaspiro[4.5]decan-1-yl]-acetic acid tert-butyl ester A solution of CIS-8-Dimethylamino-3-[(4-methoxyphenyl)-methyl]-8-phenyl-1,3-diazaspiro[4.5]decan-2-one (INT-975) (5.0 g, 12.7 mmol) in THF (18 mL) was cooled to 0° C. and treated with LDA solution (2M in THF/heptane/ether, 25.4 mL, 50.8 mmol). The resulting mixture was was allowed to warm up to RT over 30 min. The solution was then cooled to 0° C. again and tert-butyl-bromoacetate (5.63 mL, 38.1 mmol) was added. The reaction mixture was stirred at RT for 16 h, quenched with water and extracted with DCM (3×). The combined organic layers were dried over Na₂SO₄, filtered and concentrated inder reduced pressure. Purification of the residue by column chromatography on silica gel provided CIS-2-[8-dimethylamino-3-[(4-methoxyphenyl)-methyl]-2-oxo-8-phenyl-1,3-diazaspiro[4.5]decan-1-yl]-acetic acid tert-butyl ester (4.4 g).

Step 2: cis-2-(8-Dimethylamino-2-oxo-8-phenyl-1,3-diazaspiro[4.5]decan-1-yl)-acetic acid trifluoroacetic acid salt CIS-2-[8-Dimethylamino-3-[(4-methoxyphenyl)-methyl]-2-oxo-8-phenyl-1,3-diazaspiro[4.5]decan-1-yl]-acetic acid tert-butyl ester (200 mg, 0.4 mmol) was dissolved in TFA (5 mL) and heated to reflux overnight. After cooling to RT all volatiles are removed in vacuo. The residue was taken up in THF (1 mL) and added dropwise to diethyl ether (20 mL). The resulting precipitate was filtered off and dried under reduced pressure to give CIS-2-(8-dimethylamino-2-oxo-8-phenyl-1,3-diazaspiro[4.5]decan-1-yl)-acetic acid; 2,2,2-trifluoro-acetic acid salt (INT-977) (119 mg) as a white solid. [M+H]⁺ 332.2

Synthesis of INT-978: CIS-2-(8-Dimethylamino-2-oxo-8-phenyl-1,3-diazaspiro[4.5]decan-1-yl)-N,N-dimethyl-acetamide

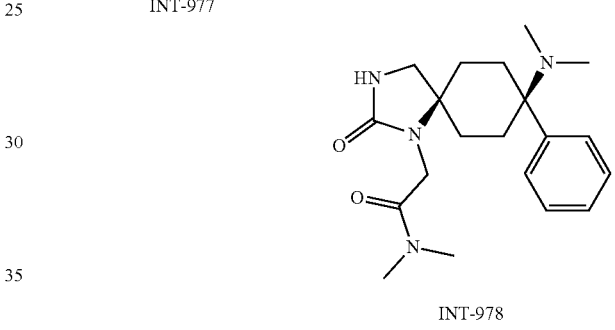

CIS-2-(8-Dimethylamino-2-oxo-8-phenyl-1,3-diazaspiro[4.5]decan-1-yl)-acetic acid (INT-977) trifluoroacetic acid salt (119 mg, 0.35 mmol) was dissolved in DCM (5 mL). Triethylamine (0.21 mL, 1.6 mmol), dimethylamine (0.54 mL, 1.1 mmol) and T3P (0.63 mL, 1.1 mmol) were sequentially added. The reaction mixture was stirred at RT overnight, then diluted with 1 M aq. Na₂CO₃ (5 mL). The aqueous layer was extracted with DCM (3×5 mL), the combined organic layers were dried over Na₂SO₄ and concentrated under reduced pressure. The residue was purified by flash chromatography on silica gel to yield CIS-2-(8-dimethylamino-2-oxo-8-phenyl-1,3-diazaspiro[4.5]decan-1-yl)-N,N-dimethyl-acetamide (INT-978) (39 mg) as a white solid. [M+H]⁺ 359.2

Synthesis of INT-982: CIS-8-Dimethylamino-1-[(1-methyl-cyclobutyl)-methyl]-8-phenyl-1,3-diazaspiro[4.5]decan-2-one

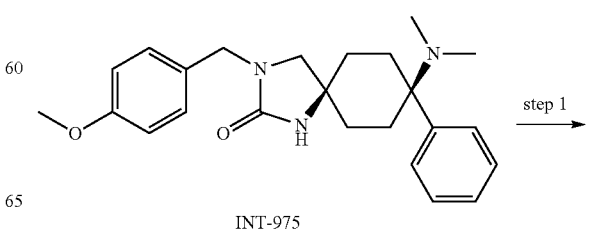

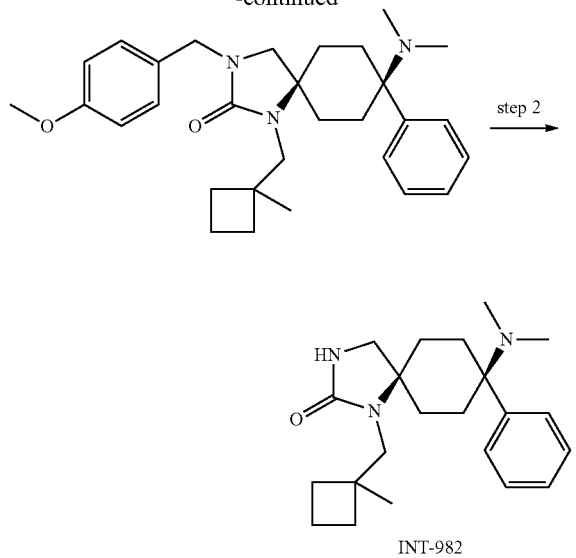

INT-982

Step 1: CIS-8-(dimethylamino)-3-(4-methoxybenzyl)-1-((1-methylcyclobutyl)methyl)-8-phenyl-1,3-diazaspiro[4.5]decan-2-one A solution of NaOH (2.85 g, 71.2 mmol) in DMSO (25 mL) was stirred at RT for 10 min. CIS-8-Dimethylamino-3-[(4-methoxyphenyl)-methyl]-8-phenyl-1,3-diazaspiro[4.5]decan-2-one (INT-975) (7.00 g, 17.8 mmol) was added and stirring was continued for 15 min. 1-(Bromo-methyl)-1-methyl-cyclobutane (8.7 g, 53.4 mmol) was added at 0° C. The reaction mixture was heated to 60° C. for 16 h. After cooling down to RT, water (100 mL) was added and the mixture was extracted with DCM (3×150 mL). The combined organic layers were washed with water (70 mL), brine (100 mL), dried over $Na_2SO_4$ and concentrated under reduced pressure. Purification of the residue by column chromatography on silica gel provided CIS-8-(dimethylamino)-3-(4-methoxybenzyl)-1-((1-methylcyclobutyl)methyl)-8-phenyl-1,3-diazaspiro[4.5]decan-2-one (6.5 g) as a light yellow solid.

Step 2: CIS-8-Dimethylamino-1-[(1-methyl-cyclobutyl)-methyl]-8-phenyl-1,3-diazaspiro[4.5]decan-2-one To the solution of CIS-8-Dimethylamino-1-[(1-methyl-cyclobutyl)-methyl]-8-phenyl-1,3-diazaspiro[4.5]decan-2-one (6.66 g, 14.0 mmol) in DCM (65 mL) was added TFA (65 mL) and the resulting mixture was stirred at RT for 16 h. The reaction mixture was concentrated under reduced pressure. The residue was taken up in DCM (100 mL) and water (60 mL) and basified with 2M aq. NaOH to pH 10. The organic layer was separated and washed with brine (40 mL), dried over $MgSO_4$, filtered and concentrated under reduced pressure. Crystallization of the residue from EtOAc provided CIS-8-Dimethylamino-1-[(1-methyl-cyclobutyl)-methyl]-8-phenyl-1,3-diazaspiro[4.5]decan-2-one (INT-982) (3.41 g) as an off-white solid. [M+H]+ 356.3

Synthesis of INT-984: CIS-1-(Cyclobutyl-methyl)-8-(ethyl-methyl-amino)-8-phenyl-1,3-diazaspiro[4.5]decan-2-one

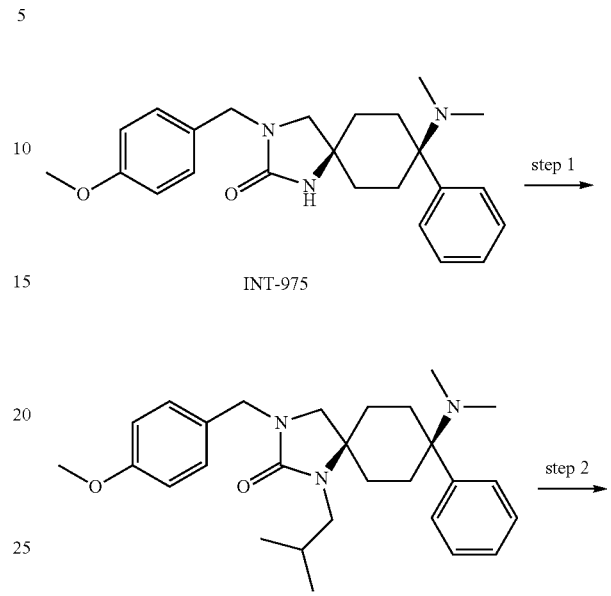

INT-984

Step 1: CIS-8-(dimethylamino)-1-isobutyl-3-(4-methoxybenzyl)-8-phenyl-1,3-diazaspiro[4.5]decan-2-one In analogy to the method described for INT-951 step 1 CIS-8-Dimethylamino-3-[(4-methoxyphenyl)-methyl]-8-phenyl-1,3-diazaspiro[4.5]decan-2-one (INT-975) was converted into CIS-8-(dimethylamino)-1-isobutyl-3-(4-methoxybenzyl)-8-phenyl-1,3-diazaspiro [4.5]decan-2-one.

Step 2: CIS-1-(Cyclobutyl-methyl)-8-(ethyl-methyl-amino)-8-phenyl-1,3-diazaspiro[4.5]decan-2-one In analogy to the method described for INT-982 step 2 CIS-8-(dimethylamino)-1-isobutyl-3-(4-methoxybenzyl)-8-phenyl-1,3-diazaspiro[4.5]decan-2-one was converted into CIS-1-(Cyclobutyl-methyl)-8-(ethyl-methyl-amino)-8-phenyl-1,3-diazaspiro[4.5]decan-2-one (INT-984).

Synthesis of INT-986: CIS-1-(Cyclobutyl-methyl)-8-(ethyl-methyl-amino)-8-phenyl-1,3-diazaspiro[4.5]decan-2-one

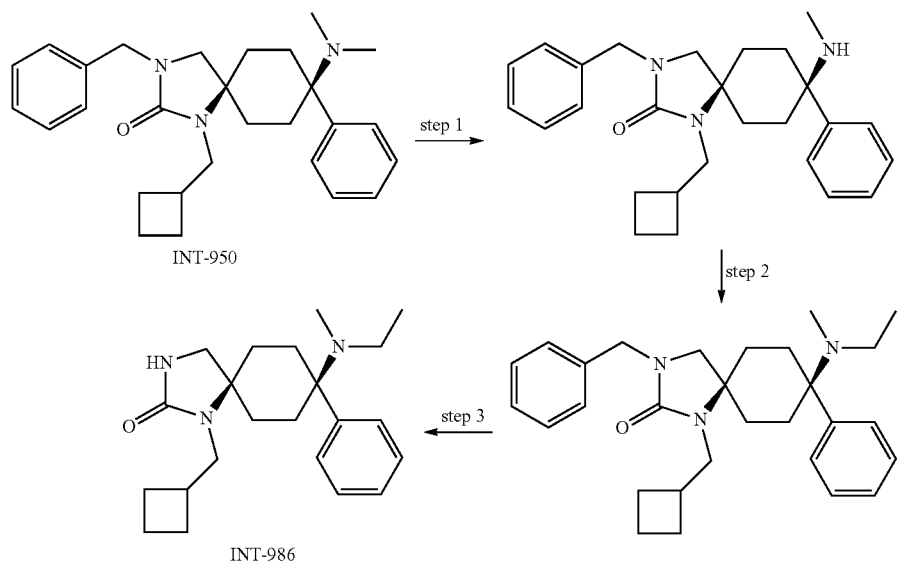

Step 1: CIS-3-benzyl-1-(cyclobutylmethyl)-8-(methylamino)-8-phenyl-1,3-diazaspiro[4.5]decan-2-one N-Iodosuccinimide (3.1 g, 13.92 mmol) was added to the solution of CIS-1-(Cyclobutyl-methyl)-8-dimethylamino-8-phenyl-3-[phenyl-methyl]-1,3-diazaspiro[4.5]decan-2-one (INT-950) (4 g, 9.28 mmol) in a mixture of acetonitrile and THF (1:1 v/v, 80 mL) and the resulting mixture was stirred at RT for 16 h. The reaction mixture was basified with 2N aq. NaOH to pH-10 and the organic product was extracted with DCM (3×10 mL). The combined organic extracts were dried over anhydrous $Na_2SO_4$ and concentrated in vacuo. The residue was stirred vigorously with a mixture of 10 wt % aq. citric acid (5 mL) and DCM (10 mL) at RT for 10 min. The reaction mixture was basified with 5N aq. NaOH to pH-10 and extracted with DCM (3×10 mL). The combined organic layer was dried over anhydrous $Na_2SO_4$ and concentrated in vacuo to give 3.5 g (crude) of CIS-3-benzyl-1-(cyclobutylmethyl)-8-(methylamino)-8-phenyl-1,3-diazaspiro[4.5]decan-2-one as semi solid (TLC system: 10% MeOH in DCM; $R_f$: 0.60.).

Step 2: CIS-3-benzyl-1-(cyclobutylmethyl)-8-(ethyl(methyl)amino)-8-phenyl-1,3-diazaspiro [4.5]decan-2-one Sodium cyanoborohydride (1.56 g, 25.17 mmol, 3 equiv.) was added to the solution of CIS-3-benzyl-1-(cyclobutylmethyl)-8-(methylamino)-8-phenyl-1,3-diazaspiro[4.5]decan-2-one (3.5 g, 8.39 mmol), acetaldehyde (738 mg, 16.78 mmol, 2 equiv.) and acetic acid (0.5 mL) in methanol (20 mL). The reaction mixture was stirred at RT for 3 h, then quenched with sat. aq. $NaHCO_3$ and the organic product was extracted with DCM (3×50 mL). The combined organic extracts were dried over anhydrous $Na_2SO_4$ and concentrated in vacuo. Purification of the residue by flash column chromatography on silica gel (230-400 mesh) (20-25% ethyl acetate in petroleum ether) yielded 2.3 g (62%) of CIS-3-benzyl-1-(cyclobutylmethyl)-8-(ethyl(methyl)amino)-8-phenyl-1,3-diazaspiro [4.5]decan-2-one as a solid. (TLC system: 50% EtOAc in Pet. Ether; $R_f$: 0.65).

Step 3: CIS-1-(Cyclobutyl-methyl)-8-(ethyl-methyl-amino)-8-phenyl-1,3-diazaspiro[4.5]decan-2-one (INT-986)

Sodium metal (1.18 g, 51.68 mmol, 10 equiv.) was added to liquid ammonia (~25 mL) at −78° C. The resulting mixture was stirred for 10 min at −78° C. A solution of CIS-3-benzyl-1-(cyclobutylmethyl)-8-(ethyl(methyl)amino)-8-phenyl-1,3-diazaspiro[4.5]decan-2-one (2.3 g, 5.16 mmol) in THF (25 mL) was added at −78° C. The reaction mixture was stirred for 15 min, then quenched with sat. aq. $NH_4Cl$, warmed to RT and stirred for 1 h. The organic product was extracted with DCM (3×50 mL). The combined organic layer was washed with water, brine and concentrated under reduced pressure to afford 1.30 g (72%) of CIS-1-(cyclobutylmethyl)-8-(ethyl(methyl)amino)-8-phenyl-1,3-diazaspiro[4.5]decan-2-one (INT-986) as an off-white solid. (TLC system: 10% MeOH in DCM $R_f$: 0.15). $[M+H]^+$ 356.3

Synthesis of INT-987: CIS-1-(Cyclobutyl-methyl)-8-dimethylamino-8-phenyl-1,3-diazaspiro[4.5]decan-2-one

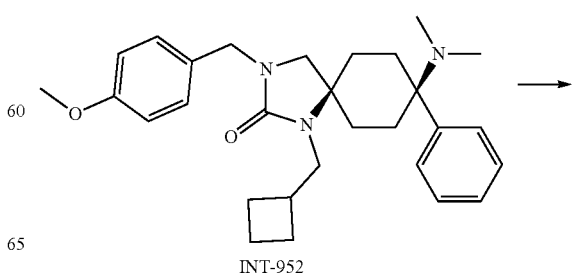

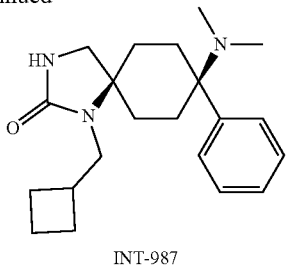

INT-987

In analogy to the method as described for INT-982 step 2 CIS-1-(Cyclobutyl-methyl)-8-dimethylamino-8-phenyl-3-[(4-methoxyphenyl)-methyl]-1,3-diazaspiro[4.5]decan-2-one (INT-952) was converted into CIS-1-(Cyclobutyl-methyl)-8-dimethylamino-8-phenyl-1,3-diazaspiro[4.5]decan-2-one (INT-987).

Synthesis of INT-988: CIS-8-(dimethylamino)-1-(2-(1-methoxycyclobutyl)ethyl)-8-phenyl-1,3-diazaspiro[4.5]decan-2-one

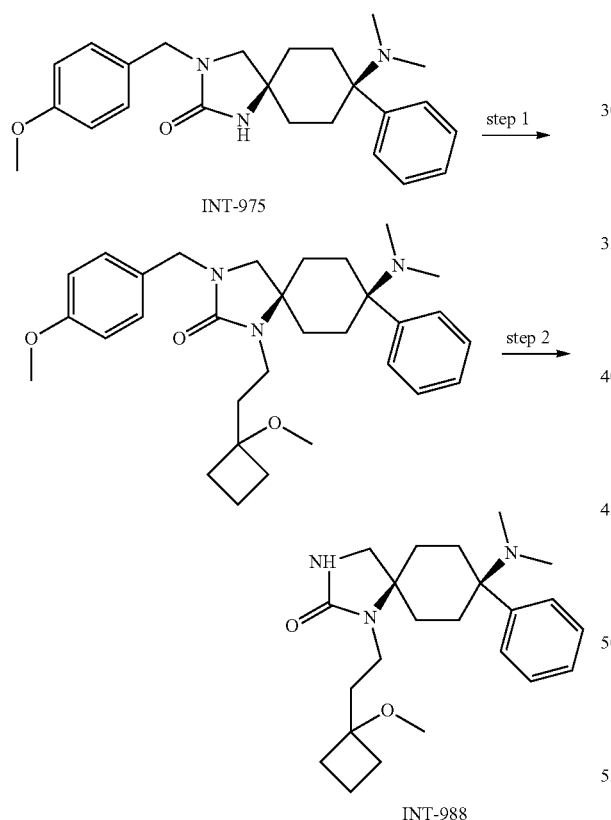

Step 1: CIS-8-(dimethylamino)-1-[2-(1-methoxycyclobutyl)ethyl]-3-[(4-methoxyphenyl)methyl]-8-phenyl-1,3-diazaspiro[4.5]decan-2-one Sodium hydroxide (78.06 mg, 4.0 equiv.) was suspended in DMSO (3.5 mL), stirred for 10 minutes, 8-(dimethylamino)-3-[(4-methoxyphenyl)methyl]-8-phenyl-1,3-diazaspiro[4.5]decan-2-one (INT-975) (192.0 mg, 1.0 equiv.) was added, the reaction mixture was stirred for 5 min followed by addition of 2-(1-methoxycyclobutyl)ethyl 4-methylbenzenesulfonate (416.2 mg, 3.0 equiv.) in DMSO (1.5 mL). The resulting mixture was stirred overnight at 50° C. The reaction mixture was quenched with water and extracted with DCM (3×20 mL). The combined organic phases were washed with brine, dried over $Na_2SO_4$ and concentrated under reduced pressure. The residue (283 mg yellow oil) was purified by column chromatography on silica gel (eluent DCM/EtOH 98/2 to 96/4) to give 8-(dimethylamino)-1-[2-(1-methoxycyclobutyl)ethyl]-3-[(4-methoxyphenyl)methyl]-8-phenyl-1,3-diazaspiro[4.5]decan-2-one 163 mg (66%).

Step 2: CIS-8-(dimethylamino)-1-(2-(1-methoxycyclobutyl)ethyl)-8-phenyl-1,3-diazaspiro[4.5]decan-2-one (INT-988)

In analogy to the method described for INT-982 step 2 CIS-8-(dimethylamino)-1-[2-(1-methoxycyclobutyl)ethyl]-3-[(4-methoxyphenyl)methyl]-8-phenyl-1,3-diazaspiro[4.5]decan-2-one was converted into CIS-8-(dimethylamino)-1-(2-(1-methoxycyclobutyl)ethyl)-8-phenyl-1,3-diazaspiro[4.5]decan-2-one (INT-988). Mass: m/z 386.3 $(M+H)^+$.

Synthesis of INT-989: CIS-3-(2-chloropyrimidin-5-yl)-8-(dimethylamino)-8-phenyl-1,3-diazaspiro[4.5]decan-2-one

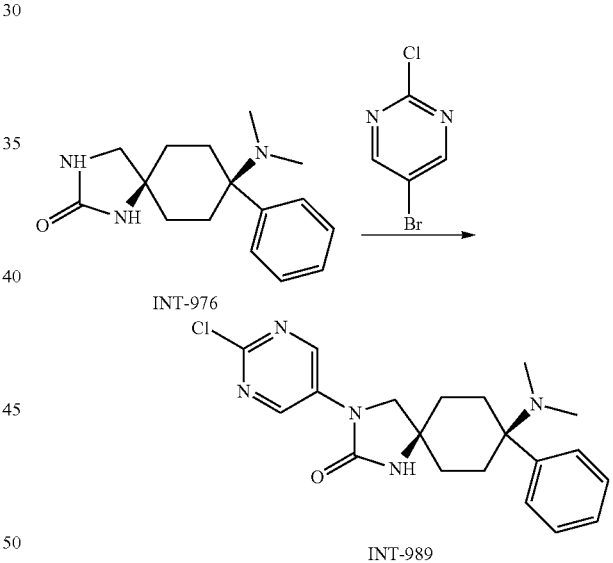

CIS-8-(dimethylamino)-8-phenyl-1,3-diazaspiro[4.5]decan-2-one (INT-976) (1250 mg, 4.6 mmol), 5-bromo-2-chloro-pyrimidine (1.5 equiv., 6.7 mmol, 1327 mg), $Cs_2CO_3$ (2 equiv., 9.15 mmol, 2980 mg), XantPhos (0.15 equiv., 0.69 mmol, 397 mg) and $Pd_2(dba)_3$ (0.05 equiv., 0.23 mmol, 209 mg) were dissolved in dry 1,4-dioxane (120 equiv., 549 mmol, 47 mL) under nitrogen atmosphere and stirred at 90° C. overnight. The reaction mixture was cooled down, diluted with water (50 mL), extracted with DCM (3×70 mL), the combined organic phases were dried over $Na_2SO_4$ and concentrated under reduced pressure. The residue (2.8 g) was suspended in 10 mL DCM and stirred for 10 min. The resulting precipitate was filtered off and washed with small amount of DCM to give 1213 mg of CIS-3-(2-chloropyrimidin-5-yl)-8-(dimethylamino)-8-phenyl-1,3-diazaspiro

[4.5]decan-2-one (INT-989) as a white solid. The mother liquor was concentrated under reduced pressure (1428 mg), suspended in 3 mL DCM, 3 mL pentane were slowly added and the mixture was stirred for 30 min. The precipitate was filtered off, washed with small amounts of pentane and DCM to give second portion of INT-989 (215 mg) as a light yellow solid. $^1$H NMR (600 MHz, DMSO) δ 8.94 (s, 2H), 7.88 (s, 1H), 7.41-7.33 (m, 4H), 7.27 (tt, 1H), 3.65 (s, 2H), 2.49-2.32 (m, 2H), 1.98-1.88 (m, 2H), 1.96 (s, 6H), 1.87-1.73 (m, 2H), 1.53-1.47 (m, 2H). Mass: m/z 386.2 (M+H)$^+$.

Synthesis of INT-991: lithium CIS-5-(8-(dimethylamino)-2-oxo-8-phenyl-1,3-diazaspiro[4.5]decan-3-yl)pyrimidine-2-carboxylate

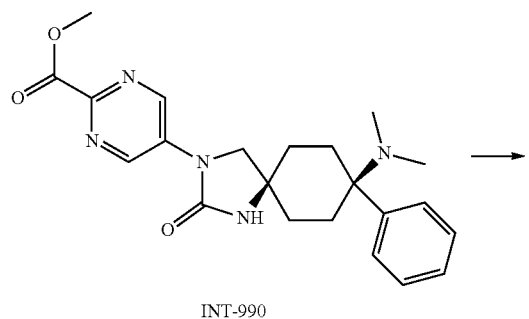

INT-990

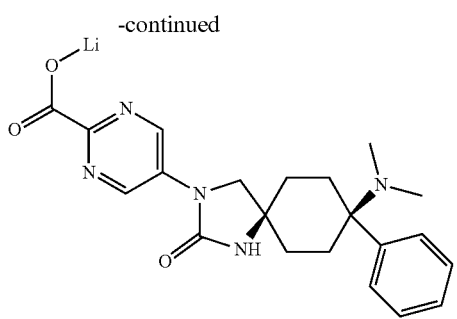

INT-991

Methyl CIS-5-[8-(dimethylamino)-2-oxo-8-phenyl-1,3-diazaspiro[4.5]decan-3-yl]pyrimidine-2-carboxylate (INT-990) (950 mg, 2.32 mmol) was suspended in a mixture of MeOH (140 equiv., 325 mmol, 13 mL) and THF (70 equiv., 162 mmol, 13 mL). Lithium hydroxide 2M aq. sol. (1.3 mL) was added. The reaction mixture was stirred 5 days at RT. Additional 1.3 mL of lithium hydroxide 2M aq. sol. were added and the reaction mixture was stirred for 2 h at RT. The solvents were removed under reduced pressure. The residue was suspended in EtOAc (10 mL) and stirred overnight. The precipitate was filtered off (1.07 g) and washed with DCM (3 mL), pentane and dried under reduced pressure. The resulting solid (960 mg) containing INT-990 and residual lithium salts was used directly in the next steps. Mass: m/z 394.2 (M-Li)$^-$.

Synthesis of INT-1008: CIS-8-ethylamino-8-phenyl-1,3-diaza-spiro[4.5]decan-2-one

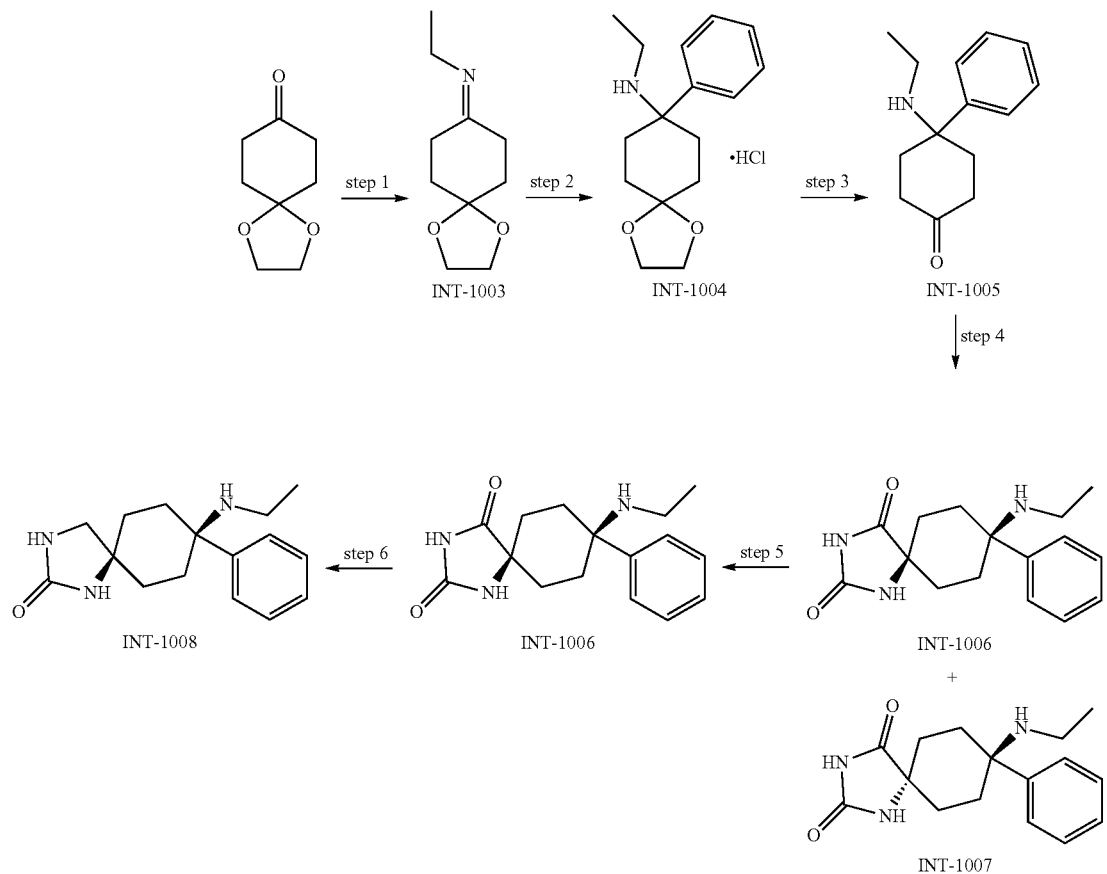

Step 1 and step 2: ethyl-(8-phenyl-1,4-dioxa-spiro[4.5]dec-8-yl)-amine hydrochloride (INT-1004)

A mixture of 1,4-dioxa-spiro[4.5]decan-8-one (25.0 g, 160.25 mmol, 1.0 eq.) and 2M solution of $EtNH_2$ in THF (200 ml, 2.5 eq. 400.64 mmol) in EtOH (30 ml) was stirred at RT for 48 h. The reaction mixture was concentrated under argon atmosphere and the residue was diluted with ether (60 ml), and a freshly prepared PhLi solution was added [prepared by addition of 2.5M n-BuLi in THF (70.5 ml, 1.1 eq. 176.27 mmol) to a solution of bromobenzene (27.675 g, 1.1 eq. 176.275 mmol) in ether (100 ml) at −30° C. and stirred at RT for 1 h). The reaction mixture was stirred at RT for 1.5 h, quenched with saturated $NH_4Cl$ solution (100 ml) at 0° C. and extracted with ethyl acetate (2×750 ml). The combined organic layer was washed with water (3×350 ml), brine (300 ml), dried over $Na_2SO_4$ and concentrated under reduced pressure. The resulting residue was dissolved in ethyl methyl ketone (100 ml) and trimethylsilyl chloride (37.5 ml) was added at 0° C. The resulting mixture was stirred at RT for 16 h. The precipitated solid was filtered off and washed with acetone followed by THF to get ethyl-(8-phenyl-1,4-dioxa-spiro[4.5]dec-8-yl)-amine hydrochloride as an off white solid. This reaction was done in 2 batches of 25 g scale and the yield is given for 2 combined batches. Yield: 18% (17.1 g, 57.575 mmol). LCMS: m/z 262.2 (M+H)+.

Step 3: 4-ethylamino-4-phenyl-cyclohexanone (INT-1005)

To a solution of ethyl-(8-phenyl-1,4-dioxa-spiro[4.5]dec-8-yl)-amine hydrochloride (10.1 g, 34.0 mmol, 1 eq.) in water (37.5 ml) was added conc. aq. HCl (62.5 ml) at 0° C. and the resulting mixture was stirred at RT for 16 h. The reaction mixture was basified with aq. NaOH (pH ~14) at 0° C. and extracted with DCM (2×750 ml). Organic layer was washed with water (400 ml), brine (400 ml), dried over $Na_2SO_4$ and concentrated under reduced pressure to yield 4-ethylamino-4-phenyl-cyclohexanone which was used in the next step without further purification. This reaction was carried out in another batch of 15.1 g scale and the yield is given for 2 combined batches. Yield: 92% (17.0 g, 78.34 mmol).

Step 4: cis and trans mixture of 8-ethylamino-8-phenyl-1,3-diaza-spiro[4.5]decane-2,4-dione (INT-1006 and INT-1007)

To a solution of 4-ethylamino-4-phenyl-cyclohexanone (17 g, 78.341 mmol, 1.0 eq.) in EtOH (250 ml) and water (200 ml) was added $(NH_4)_2CO_3$ (18.8 g, 195.85 mmol, 2.5 eq.) and the reaction mixture was stirred at RT for 15 min. KCN (5.09 g, 78.341 mmol, 1.0 eq.) was added and stirring was continued at 60° C. for 18 h. The reaction mixture was cooled down to RT. The precipitated solid was filtered off, washed with water (250 ml), EtOH (300 ml), hexane (200 ml) and dried under reduced pressure to yield cis and trans mixture of 8-ethylamino-8-phenyl-1,3-diaza-spiro[4.5]decane-2,4-dione (13.0 g, 45.29 mmol, 58%) as a white solid. Yield: 58% (13 g, 45.296 mmol). LC-MS: m/z $[M+1]^+$= 288.2.

Step 5: CIS-8-ethylamino-8-phenyl-1,3-diaza-spiro[4.5]decane-2,4-dione (INT-1006)

To a solution of cis and trans mixture of 8-ethylamino-8-phenyl-1,3-diaza-spiro[4.5]decane-2,4-dione (12 g) in MeOH-DCM (1:1, 960 ml) was added a solution of L-tartaric acid in MeOH (25 ml) and the resulting mixture stirred at RT for 2 h and then kept in refrigerator for 16 h. The precipitated solid was filtered off and washed with MeOH-DCM (1:5, 50 ml) to get tartrate salt of 8-ethylamino-8-phenyl-1,3-diaza-spiro[4.5]decane-2,4-dione (7.5 g) as a white solid. To this solid sat. aq. $NaHCO_3$ was added (pH-8) and the resulting mixture was extracted with 25% MeOH-DCM (2×800 ml). Combined organic layer was washed with water (300 ml), brine (300 ml), dried over anhydrous $Na_2SO_4$ and concentrated under reduced pressure. The residue was triturated with 20% DCM-hexane and the resulting solid was dried under reduced pressure to afford CIS-8-ethylamino-8-phenyl-1,3-diaza-spiro[4.5]decane-2,4-dione as white solid. This step was done in 2 batches (12 g & 2.4 g) and the yield is given for 2 combined batches. Yield: 31.2% (5.0 g, 17.421 mmol). LC-MS: m/z $[M+1]^+$=288.0.

Step 6: CIS-8-ethylamino-8-phenyl-1,3-diaza-spiro[4.5]decan-2-one (INT-1008)

To a slurry of $LiAlH_4$ (793 mg, 20.91 mmol, 3.0 eq.) in THF (15 ml) was added a suspension of CIS-8-ethylamino-8-phenyl-1,3-diaza-spiro[4.5]decane-2,4-dione (2.0 g, 6.97 mmol, 1.0 eq.) in THF (60 ml) at 0° C. and the reaction mixture was heated to 65° C. for 16 h. The reaction mixture was cooled to 0° C., quenched with sat. aq. $Na_2SO_4$ (20 ml), stirred at RT for 1 h and filtered through celite pad. The residue was washed with 15% MeOH-DCM (500 ml). The combined filtrate was dried over anhydrous $Na_2SO_4$ and concentrated under reduced pressure to give crude product which was triturated with 15% DCM-Hexane to afford CIS-8-ethylamino-8-phenyl-1,3-diaza-spiro[4.5]decan-2-one (INT-1008) (1.6 g, 5.86 mmol, 84%) as a white solid. Yield: 84% (1.6 g, 5.86 mmol). LC-MS: m/z $[M+1]^+$=274.2.

Synthesis of INT-1026: CIS-8-(methyl((tetrahydrofuran-3-yl)methyl)amino)-8-phenyl-1,3-diazaspiro[4.5]decan-2-one

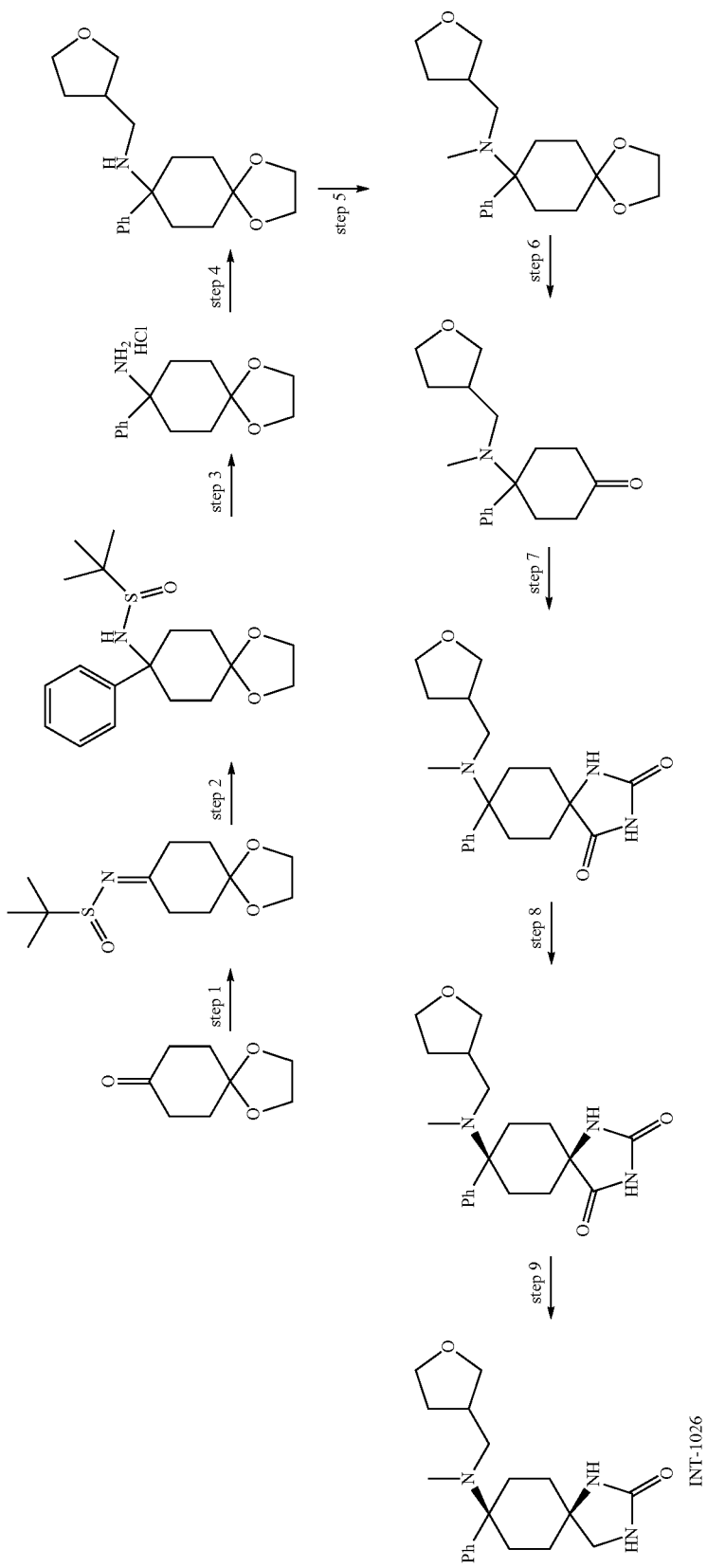

Step 1: 2-methyl-N-(1,4-dioxaspiro[4.5]decan-8-ylidene)propane-2-sulfinamide Titanium ethoxide (58.45 g, 256.4 mmol) was added to a solution of 1,4-dioxaspiro[4.5]decan-8-one (20 g, 128.20 mmol) and 2-methylpropane-2-sulfinamide (15.51 g, 128.20 mmol) in THF (200 mL) at RT and the reaction mixture was stirred at RT for 18 h. The reaction mixture was cooled to 0° C. and quenched by dropwise addition of sat. aq. NaHCO$_3$ (500 mL) over a period of 30 min. The organic product was extracted with EtOAc (3×100 mL). The combined organic extracts were dried over anhydrous Na$_2$SO$_4$ and concentrated in vacuo to afford 10 g (crude) of 2-methyl-N-(1,4-dioxaspiro[4.5]decan-8-ylidene)propane-2-sulfinamide as a white solid (TLC system: 30% Ethyl acetate in hexane; Rf: 0.30).

Step 2: 2-methyl-N-(8-phenyl-1,4-dioxaspiro[4.5]decan-8-yl)propane-2-sulfinamide Phenylmagnesium bromide (1M in THF, 116 mL, 116 mmol) was added dropwise to a solution of 2-methyl-N-(1,4-dioxaspiro[4.5]decan-8-ylidene)propane-2-sulfinamide (10 g, 38.61 mmol) in THF (500 mL) at −10° C. under argon atmosphere. The reaction mixture was stirred for 2 h at −10° C. to 0° C. The reaction completion was monitored by TLC. The reaction mixture was quenched with sat. aq. NH$_4$Cl (50 mL) at 0° C. and the organic product was extracted with EtOAc (3×100 mL). The combined organic extracts were dried over anhydrous Na$_2$SO$_4$ and concentrated in vacuo. The residue was purified by column chromatography (silica gel 230-400 mesh; 40-60% ethyl acetate in hexane) to yield 6.0 g (46%) of 2-methyl-N-(8-phenyl-1,4-dioxaspiro[4.5]decan-8-yl)propane-2-sulfinamide as a liquid (TLC system: 70% Ethyl acetate in hexane; Rf: 0.30).

Step 3: 8-phenyl-1,4-dioxaspiro[4.5]decan-8-amine hydrochloride 2N solution of HCl in diethyl ether (17.80 mL, 35.60 mmol) was added to a solution of 2-methyl-N-(8-phenyl-1,4-dioxaspiro[4.5]decan-8-yl)propane-2-sulfinamide (6.0 g, 17.80 mmol) in DCM (60 mL) at 0° C. The reaction mixture was stirred at RT for 2 h. The reaction mixture was concentrated in vacuo. The residue was washed with diethyl ether to yield 3 g (crude) of 8-phenyl-1,4-dioxaspiro[4.5]decan-8-amine hydrochloride as a brown solid (TLC system: 5% MeOH in DCM; Rf: 0.10).

Step 4: 8-phenyl-N-((tetrahydrofuran-3-yl)methyl)-1,4-dioxaspiro[4.5]decan-8-amine Sodium cyanoborohydride (2.17 g, 33.45 mmol) was added to a solution of 8-phenyl-1,4-dioxaspiro[4.5]decan-8-amine hydrochloride (3.0 g, 11.15 mmol) and tetrahydrofuran-3-carbaldehyde (4.46 mL, 22.30 mmol) and acetic acid (0.05 mL) in methanol (30 mL) at 0° C. The reaction mixture was stirred at RT for 16 h. The reaction mixture was concentrated in vacuo at 30° C. and to the residue sat. aq. NaHCO$_3$ was added. The organic product was extracted with DCM (3×30 mL). The combined organic extracts were dried over anhydrous Na$_2$SO$_4$ and solvent was concentrated under reduced pressure to get 3 g (crude) of 8-phenyl-N-((tetrahydrofuran-3-yl)methyl)-1,4-dioxaspiro[4.5]decan-8-amine as a semi-solid (TLC system: 10% MeOH in DCM; Rf: 0.22).

Step 5: N-methyl-8-phenyl-N-((tetrahydrofuran-3-yl)methyl)-1,4-dioxaspiro[4.5]decan-8-amine)

Sodium cyanoborohydride (1.76 g, 28.39 mmol) was added to a solution of 8-phenyl-N-((tetrahydrofuran-3-yl)methyl)-1,4-dioxaspiro[4.5]decan-8-amine (3.0 g, 9.46 mmol), 37% formaldehyde in water (7.70 mL, 94.60 mmol) and acetic acid (0.05 mL) in methanol (30 mL) at 0° C. The reaction mixture was stirred at RT for 16 h. The reaction mixture was concentrated in vacuo and to the residue sat. aq. NaHCO$_3$ was added. The organic product was extracted with DCM (3×30 mL). The combined organic extracts were dried over anhydrous Na$_2$SO$_4$ and solvent was concentrated under reduced pressure. The resulting residue was purified by column chromatography (silica gel 230-400 mesh; 5-6% MeOH in DCM) to yield 2.50 g (83%) of N-methyl-8-phenyl-N-((tetrahydrofuran-3-yl)methyl)-1,4-dioxaspiro[4.5]decan-8-amine as a semi solid (TLC system: 10% MeOH in DCM; Rf: 0.25).

Step 6: 4-(methyl((tetrahydrofuran-3-yl)methyl)amino)-4-phenylcyclohexanone

5% sulfuric acid in water (25 mL) was added to N-methyl-8-phenyl-N-((tetrahydrofuran-3-yl)methyl)-1,4-dioxaspiro[4.5]decan-8-amine (2.50 g, 7.55 mmol) at 0° C. and the resulting mixture was stirred at RT for 24 h. The reaction mixture was quenched with sat. aq. NaHCO$_3$ and the organic product was extracted with DCM (2×50 mL). The combined organic layers were dried over anhydrous Na$_2$SO$_4$ and concentrated in vacuo to afford 2.0 g (crude) of 4-(methyl((tetrahydrofuran-3-yl)methyl)amino)-4-phenylcyclohexanone as a thick liquid (TLC system: 10% MeOH in DCM, Rf: 0.20).

Step 7: 8-(methyl((tetrahydrofuran-3-yl)methyl)amino)-8-phenyl-1,3-diazaspiro[4.5]decane-2,4-dione 4-(methyl((tetrahydrofuran-3-yl)methyl)amino)-4-phenylcyclohexanone (1.50 g, 5.22 mmol) was suspended in 30 mL of EtOH:H$_2$O (1:1 v/v) at RT under argon atmosphere. (NH$_4$)$_2$CO$_3$ (1.9 g, 13.05 mmol) and KCN (0.34 g, 5.22 mmol) were added. The reaction mixture was heated to 70° C. for 16 h. The reaction mixture was diluted with ice-water and the organic product was extracted with DCM (2×50 mL). The combined organic layer was dried over anhydrous Na$_2$SO$_4$ and concentrated in vacuo to give 1.0 g (crude) of 8-(methyl((tetrahydrofuran-3-yl)methyl)amino)-8-phenyl-1,3-diazaspiro[4.5]decane-2,4-dione as a solid (TLC system: 70% Ethyl acetate in hexane; Rf: 0.18).

Step 8: CIS-8-(methyl((tetrahydrofuran-3-yl)methyl)amino)-8-phenyl-1,3-diazaspiro[4.5]decane-2,4-dione Diastereomeric mixture of 8-(methyl((tetrahydrofuran-3-yl)methyl)amino)-8-phenyl-1,3-diazaspiro[4.5]decane-2,4-dione (1.0 g) was separated by reverse phase preparative HPLC to afford 400 mg of isomer 1 (CIS-8-(methyl((tetrahydrofuran-3-yl)methyl)amino)-8-phenyl-1,3-diazaspiro[4.5]decane-2,4-dione) and 60 mg of isomer 2 (TRANS-8-(methyl((tetrahydrofuran-3-yl)methyl)amino)-8-phenyl-1,3-diazaspiro[4.5]decane-2,4-dione) and 300 mg of mixture of both isomers. Reverse phase preparative HPLC conditions: mobile phase: 10 mM ammonium bicarbonate in H$_2$O/acetonitrile, column: X-BRIDGE-C18 (150*30), 5 µm, gradient (T/B %): 0/35, 8/55, 8.1/98, 10/98, 10.1/35, 13/35, flow rate: 25 ml/min, diluent: mobile phase+THF.

Step 9: CIS-8-(methyl((tetrahydrofuran-3-yl)methyl) amino)-8-phenyl-1,3-diazaspiro[4.5]decan-2-one (INT-1026)

LiAlH$_4$ (1M in THF) (4.48 mL, 4.48 mmol) was added to a solution of CIS-8-(methyl((tetrahydrofuran-3-yl)methyl)amino)-8-phenyl-1,3-diazaspiro[4.5]decane-2,4-dione (isomer-1) (0.4 g, 1.12 mmol) in THF:Et$_2$O (2:1 v/v, 15 mL) at 0° C. under argon atmosphere. The reaction mixture was stirred at 65° C. for 16 h. The mixture was cooled to 0° C., quenched with sat. aq. Na$_2$SO$_4$ (1000 mL) and filtered through celite pad. The filtrate was dried over anhydrous Na$_2$SO$_4$ and concentrated in vacuo. The residue was purified by column chromatography (silica gel 230-400 mesh; 5-6% MeOH in DCM) to yield 0.3 g (78%) of CIS-8-(methyl((tetrahydrofuran-3-yl)methyl)amino)-8-phenyl-1,3-diazaspiro[4.5]decan-2-one (INT-1026) as an off white solid. (TLC system: 10% MeOH in DCM, Rf: 0.2). LC-MS: m/z [M+1]$^+$=344.2.

Synthesis of INT-1031: CIS-1-(Cyclobutyl-methyl)-8-dimethylamino-8-(3-fluorophenyl)-1,3-diazaspiro[4.5]decan-2-one

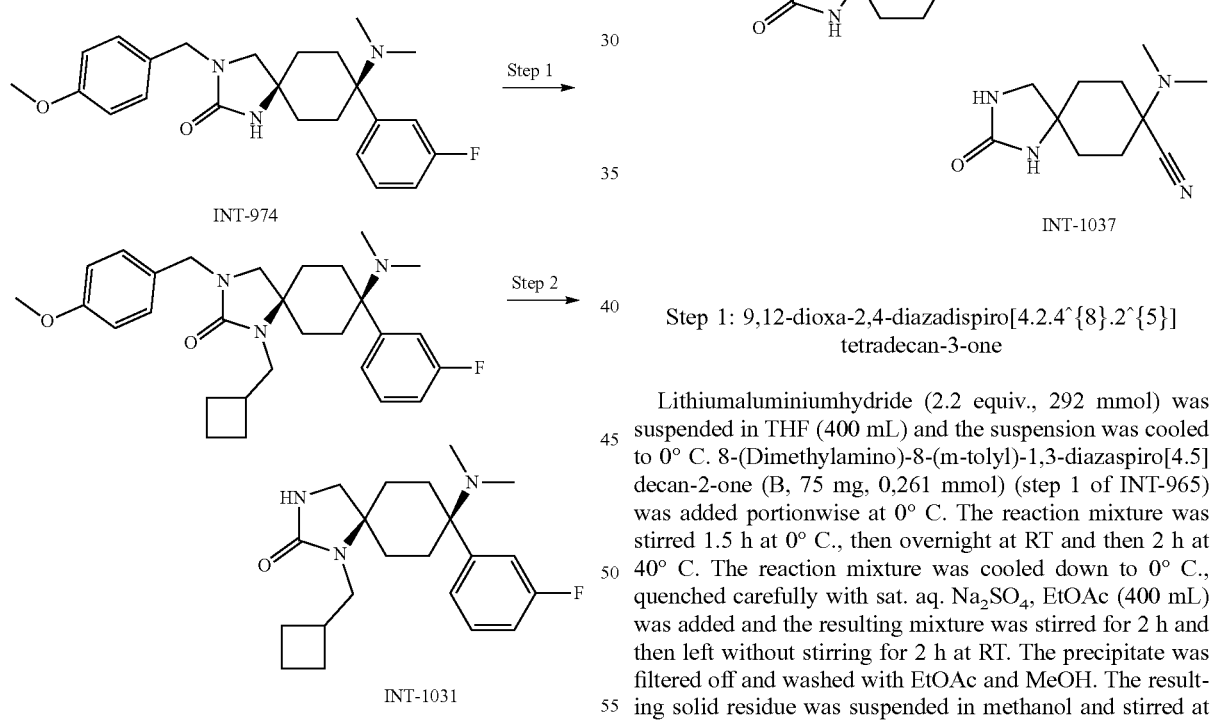

Step 1: CIS-1-(Cyclobutyl-methyl)-8-dimethyl-amino-8-(3-fluorophenyl)-3-[(4-methoxyphenyl)-methyl]-1,3-diazaspiro[4.5]decan-2-one In analogy to the method described for INT-952 CIS-8-dimethylamino-8-(3-fluorophenyl)-3-[(4-methoxyphenyl)-methyl]-1,3-diazaspiro[4.5]decan-2-one (INT-974) was converted into CIS-1-(cyclobutyl-methyl)-8-dimethylamino-8-(3-fluorophenyl)-3-[(4-methoxyphenyl)-methyl]-1,3-diazaspiro[4.5]decan-2-one.

Step 2: CIS-1-(Cyclobutyl-methyl)-8-dimethyl-amino-8-(3-fluorophenyl)-1,3-diazaspiro[4.5]decan-2-one In analogy to the method described for INT-982 step 2 1-(cyclobutyl-methyl)-8-dimethylamino-8-(3-fluorophenyl)-3-[(4-methoxyphenyl)-methyl]-1,3-diazaspiro[4.5]decan-2-one was converted into 1-(cyclobutyl-methyl)-8-dimethylamino-8-(3-fluorophenyl)-1,3-diazaspiro[4.5]decan-2-one (INT-1031).

Synthesis of INT-1037: 8-(dimethylamino)-2-oxo-1,3-diazaspiro[4.5]decane-8-carbonitrile

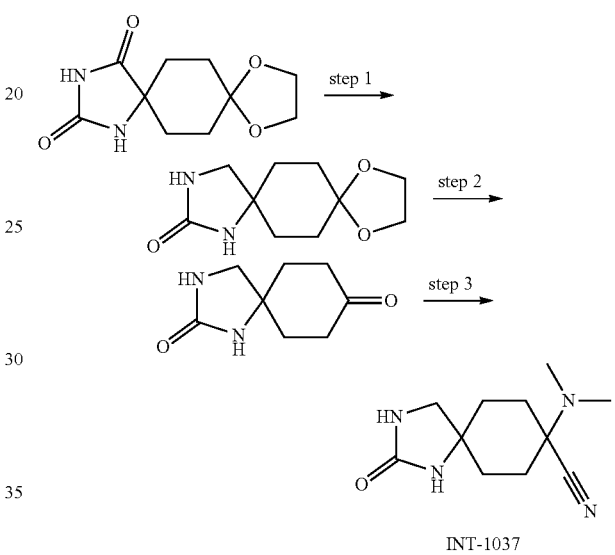

Step 1: 9,12-dioxa-2,4-diazadispiro[4.2.4^{8}.2^{5}]tetradecan-3-one

Lithiumaluminiumhydride (2.2 equiv., 292 mmol) was suspended in THF (400 mL) and the suspension was cooled to 0° C. 8-(Dimethylamino)-8-(m-tolyl)-1,3-diazaspiro[4.5]decan-2-one (B, 75 mg, 0,261 mmol) (step 1 of INT-965) was added portionwise at 0° C. The reaction mixture was stirred 1.5 h at 0° C., then overnight at RT and then 2 h at 40° C. The reaction mixture was cooled down to 0° C., quenched carefully with sat. aq. Na$_2$SO$_4$, EtOAc (400 mL) was added and the resulting mixture was stirred for 2 h and then left without stirring for 2 h at RT. The precipitate was filtered off and washed with EtOAc and MeOH. The resulting solid residue was suspended in methanol and stirred at RT overnight. The precipitate was filtered off and disposed. The filtrate was concentrated under reduced pressure, the residue was suspended thoroughly in water (50 mL) at 40° C., the precipitate was filtered off and dried under reduced pressure to yield 9,12-dioxa-2,4-diazadispiro[4.2.4^{8}.2^{5}]tetradecan-3-one (11.4 g, 41%). Mass: m/z 213.2 (M+H)$^+$.

Step 2: 1,3-diazaspiro[4.5]decane-2,8-dione

In analogy to the method described for INT-1003 step 3 9,12-dioxa-2,4-diazadispiro[4.2.4^{8}.2^{5}]tetradecan-3- one was treated with conc. aq. HCl to be converted into 1,3-diazaspiro[4.5]decane-2,8-dione. Mass: m/z 169.1 (M+H)⁺.

Step 3: 8-(dimethylamino)-2-oxo-1,3-diazaspiro[4.5]decane-8-carbonitrile (INT-1037)

In analogy to the method described for INT-965 step 1 1,3-diazaspiro[4.5]decane-2,8-dione was treated with dimethyl amine and potassium cyanide to be converted into 8-(dimethylamino)-2-oxo-1,3-diazaspiro[4.5]decane-8-carbonitrile (INT-1037). Mass: m/z 223.2 (M+H)+.

Synthesis of INT-1038: CIS-8-(dimethylamino)-8-(m-tolyl)-1,3-diazaspiro[4.5]decan-2-one

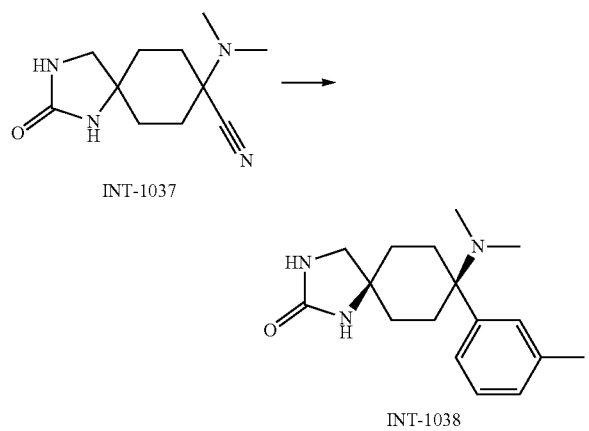

To the suspension of 8-(dimethylamino)-2-oxo-1,3-diazaspiro[4.5]decane-8-carbonitrile (200 mg, 0.90 mmol) in THF (4 mL) at RT was added dropwise 1M bromo(m-tolyl)magnesium in THF (4 equiv., 3.6 mmol, 3.6 mL) and the reaction mixture was stirred for 1 h at RT. Additional portion of 1M bromo(m-tolyl)magnesium in THF (1 equiv., 0.8 mL) was added. The reaction mixture was stirred at RT overnight, then quenched with methanol/water. Solid NH₄Cl and DCM were added to the resulting mixture and the precipitate was filtered off. The organic phase of the filtrate was separated and the aqueous phase was extracted with DCM (3×). The combined organic phases were dried over anhydr. Na₂SO₄ and concentrated under reduced pressure. The residue was purified by flash chromatography on silica gel (DCM/MeOH, 100/0 to 65/35) to yield CIS-8-(dimethylamino)-8-(m-tolyl)-1,3-diazaspiro[4.5]decan-2-one (INT-1038) (81 mg, 31%). Mass: m/z 288.2 (M+H)⁺.

Synthesis of INT-1059: TRANS-8-(dimethylamino)-8-phenyl-1,3-diazaspiro[4.5]decan-2-one

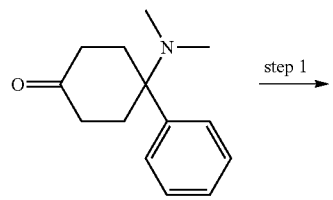

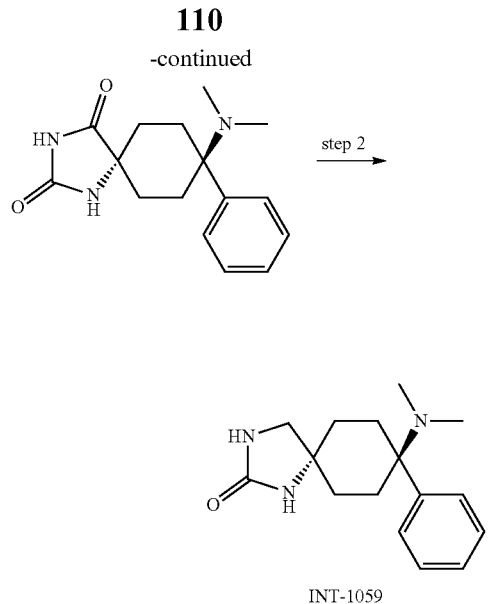

Step 1: TRANS-8-(dimethylamino)-8-phenyl-1,3-diazaspiro[4.5]decane-2,4-dione

To a stirred solution of 4-dimethylamino-4-phenyl-cyclohexanone (250.0 g, 1.15 mol, 1.0 eq.) in EtOH (2.5 L) and water (2.1 L) was added (NH₄)₂CO₃ (276.2 g, 2.87 mol, 2.5 eq.) and the reaction mixture was stirred at RT for 15 min. KCN (74.92 g, 1.15 mol, 1.0 eq.) was added. The reaction mixture was stirred at 60° C. for 18 h and then filtered in hot condition to get white solid which was washed with water (2.5 L), ethanol (1 L) and hexane (2.5 L). The resulting solid was dried under reduced pressure to get CIS-8-dimethylamino-8-phenyl-1,3-diaza-spiro[4.5]decane-2,4-dione (223 g, 0.776 mol, 65%) as a white solid. The filtrate was collected from multiple batches (~450 g) which contained a mixture of cis and trans isomers. The filtrate was concentrated under reduced pressure and solid obtained was filtered and washed with water (1 L) and hexane (1 L). Solid material was dried under reduced pressure to get ~100 g of a mixture of cis and trans (major) isomers. Crude material was partially dissolved in hot MeOH (600 mL) and cooled to RT, filtered through sintered funnel, washed with MeOH (200 mL) followed by ether (150 mL) and dried to get TRANS-8-dimethylamino-8-phenyl-1,3-diaza-spiro[4.5]decane-2,4-dione (50 g, 0.174 mmol, ~9-10%).

Step 2: TRANS-8-(dimethylamino)-8-phenyl-1,3-diazaspiro[4.5]decan-2-one (INT-1059)

In analogy to the method described for INT-976 step 2 TRANS-8-dimethylamino-8-phenyl-1,3-diaza-spiro[4.5]decane-2,4-dione was treated with LiAlH₄ to be converted into TRANS-8-(dimethylamino)-8-phenyl-1,3-diazaspiro[4.5]decan-2-one (INT-1059). Mass: m/z 274.2 (M+H)⁺.

Synthesis of INT-1068 and INT-1069: CIS- and TRANS-8-(dimethylamino)-8-phenyl-1-(2,2,2-trifluoroethyl)-1,3-diazaspiro[4.5]decan-2-one

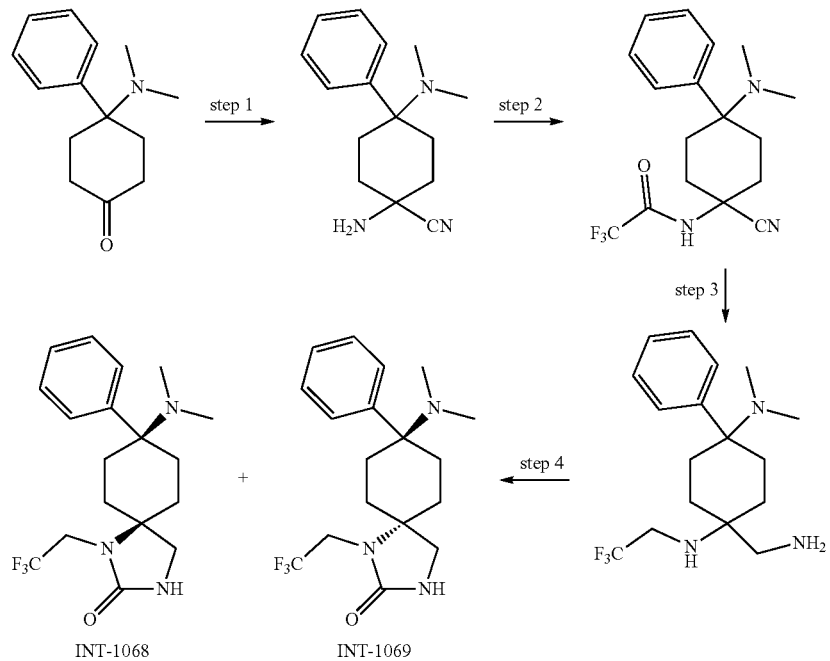

INT-1068      INT-1069

Step 1: 1-amino-4-dimethylamino-4-phenyl-cyclohexanecarbonitrile

To a stirred solution of 4-dimethylamino-4-phenyl-cyclohexanone (50 g, 230.096 mmol) in MeOH (400 mL) was added NH$_4$Cl (24.6 g, 460.8 mmol) followed by NH$_4$OH (400 mL) at RT and the reaction mixture was stirred for 15 min. NaCN (22.5 g, 460.83 mmol) was added and the resulting mixture was stirred for 16 h at RT. The reaction mixture was extracted with DCM (3×750 mL). Combined organic layer was washed with water (750 mL), brine (750 mL), dried over Na$_2$SO$_4$ and concentrated under reduced pressure. The residue was triturated with DCM/hexane to get crude 1-amino-4-dimethylamino-4-phenyl-cyclohexanecarbonitrile (50 g, 90%) as an off white solid which was used in next step without further purification. LC-MS: m/z [M+H]+=244.2 (MW calc. 244.09).

Step 2: N-(1-cyano-4-dimethylamino-4-phenyl-cyclohexyl)-2,2,2-trifluoroacetamide To a solution of 1-amino-4-dimethylamino-4-phenyl-cyclohexanecarbonitrile (5.0 g, 20.57 mmol, 1.0 eq.) in THF (100 ml) were added DIPEA (10.72 ml, 61.71 mmol, 3.0 eq), trifluoroacetic acid (1.89 ml, 24.69 mmol, 1.2 eq) and T3P (18.2 ml, 30.85 mmol, 1.5 eq) at 0° C. The reaction mixture was stirred at RT for 16 h, then diluted with water (100 ml) and extracted with 10% MeOH in DCM (2×250 mL). Combined organic layer was washed with brine (100 mL), dried over Na$_2$SO$_4$ and concentrated under reduced pressure to get crude N-(1-cyano-4-dimethylamino-4-phenyl-cyclohexyl)-2,2,2-trifluoroacetamide as a light yellow sticky material which was used in the next step without further purification. LC-MS: m/z [M+1]+=339.9 (MW calc. 339.36).

Step 3: 1-aminomethyl-N',N'-dimethyl-4-phenyl-N-(2,2,2-trifluoroethyl)cyclohexane-1,4-diamine To suspension of LiAlH$_4$ (4.03 g, 106.19 mmol, 6.0 eq.) in dry THF (40 mL) was added N-(1-cyano-4-dimethylamino-4-phenyl-cyclohexyl)-2,2,2-trifluoro-acetamide (6.0 g, 17.69 mmol, 1.0 eq.) in dry THF (100 mL) dropwise at 0° C. The reaction mixture was stirred at RT for 16 h, then quenched with sat. aq. Na$_2$SO$_4$ at 0° C., excess THF was added and the resulting mixture was stirred at RT for 2 h. The resulting suspension was filtered through celite and the filter cake was washed with 10% MeOH in DCM (150 mL). Combined filtrate was concentrated under reduced pressure to yield crude 1-aminomethyl-N',N'-dimethyl-4-phenyl-N-(2,2,2-trifluoro-ethyl)-cyclohexane-1,4-diamine (4.2 g, crude) as a light yellow sticky material which was directly used in the next step without further purification. LC-MS: m/z [M+1]+=330.0 (MW calc. 329.40).

Step 4: CIS- and TRANS-8-dimethylamino-8-phenyl-1-(2,2,2-trifluoro-ethyl)-1,3-diaza-spiro[4.5]decan-2-one (INT-1068 and INT-1069)

To a solution of 1-aminomethyl-N',N'-dimethyl-4-phenyl-N-(2,2,2-trifluoro-ethyl)-cyclohexane-1,4-diamine (4.2 g, 12.76 mmol, 1.0 eq.) in toluene (60 ml) was added KOH (4.29 g, 76.56 mmol, 6.0 eq.) in water (120 ml) at 0° C. followed by addition of COCl$_2$ (15.6 ml, 44.66 mmol, 3.5 eq., 20% in toluene) at 0° C. and stirred at RT for 16 h. Reaction mixture was basified with sat NaHCO$_3$ solution and extracted with DCM (2×200 ml). Combined organic layer was dried over Na$_2$SO$_4$ and concentrated under reduced pressure to get crude product which was purified by prep HPLC to get CIS-8-dimethylamino-8-phenyl-1-(2,2,2- trifluoro-ethyl)-1,3-diaza-spiro[4.5]decan-2-one (INT-1068) (1.5 g) (major isomer, polar spot on TLC) and TRANS-8-dimethylamino-8-phenyl-1-(2,2,2-trifluoro-ethyl)-1,3-diaza-spiro[4.5]decan-2-one (INT-1069) as minor isomer (non-polar spot on TLC) (120 mg, 92.93% by HPLC) as off-white solids. CIS-isomer: LC-MS: m/z [M+1]$^+$=356.2 (MW calc.=355.40). HPLC: 98.53%, Column: Xbridge C-18 (100×4.6), 5μ, Diluent: MeOH, Mobile phase: A) 0.05% TFA in water; B) ACN flow rate: 1 ml/min, Rt=5.17 min. $^1$HNMR (DMSO-d$_6$, 400 MHz), δ (ppm)=7.43-7.27 (m, 5H), 6.84 (s, 1H), 3.30-3.25 (m, 4H), 2.66-2.63 (d, 2H, J=12.72 Hz), 1.89 (s, 6H), 1.58-1.51 (m, 2H), 1.46-1.43 (m, 2H), 1.33-1.23 (m, 2H).

For further intermediates the synthesis in analogy to previously described methods is given in the following table. The syntheses of the building blocks and intermediates have either been described previously within this application or can be performed in analogy to the herein described methods or by methods known to the person, skilled in the art. Such a person will also know which building blocks and intermediates need to be chosen for synthesis of each exemplary compound.

| Intermediate | Chemical Name | Chemical Structure | in analogy to method | m/z [M + H]$^+$ |
| --- | --- | --- | --- | --- |
| INT-601 | CIS-5-(-8-(dimethylamino)-8-(3-fluorophenyl)-2-oxo-1,3-diazaspiro[4.5]decan-3-yl)pyrimidine-2-carbonitrile | 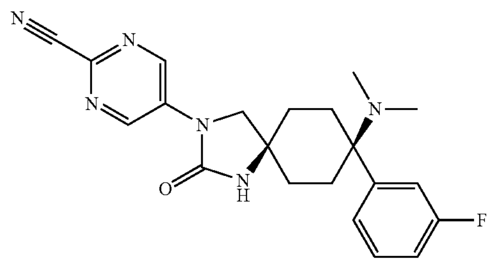 [SMILES: CN(C)[C@]1(c2cccc(F)c2)CC[C@]2(CC1)CN(c1cnc(C#N)nc1)C(=O)N2] | INT-600 | 395.1 |
| INT-794 | CIS-3-(3,4-dimethoxybenzyl)-8-(dimethylamino)-8-phenyl-1,3-diazaspiro[4.5]decan-2-one | 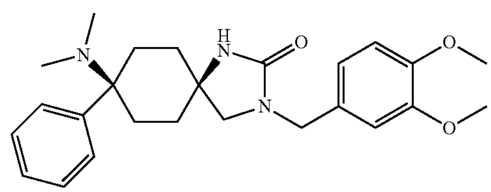 [SMILES: COc1ccc(CN2C[C@]3(CC[C@](c4ccccc4)(N(C)C)CC3)NC2=O)cc1OC] | INT-975 | 424.3 |
| INT-796 | CIS-8-Dimethylamino-3-[(4-methoxyphenyl)-methyl]-8-(3-methoxy-propyl)-1,3-diazaspiro[4.5]decan-2-one | 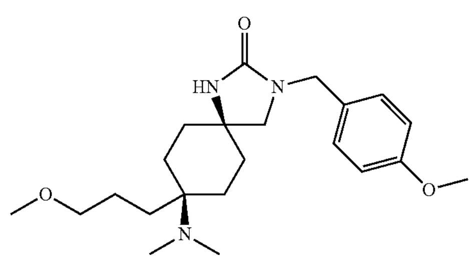 | INT-974 | 390.3 |
| INT-797 | CIS-8-(Ethyl-methyl-amino)-8-phenyl-1,3-diazaspiro[4.5]decan-2-one | 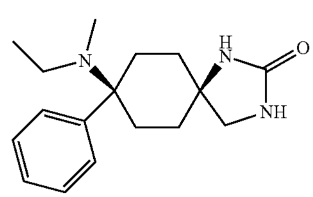 [SMILES: CCN(C)[C@]1(c2ccccc2)CC[C@]2(CC1)CNC(=O)N2] | INT-976 | 288.2 |
| INT-949 | CIS-8-Dimethylamino-1-ethyl-8-phenyl-1,3-diazaspiro[4.5]decan-2-one | 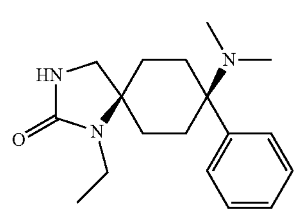 [SMILES: CCN1C(=O)NC[C@]12CC[C@](c1ccccc1)(N(C)C)CC2] | INT-984 | 302.2 |

-continued

| Intermediate | Chemical Name | Chemical Structure | in analogy to method | m/z [M + H]+ |
|---|---|---|---|---|
| INT-950 | CIS-1-(Cyclobutyl-methyl)-8-dimethylamino-8-phenyl-3-[phenyl-methyl]-1,3-diazaspiro[4.5]decan-2-one | 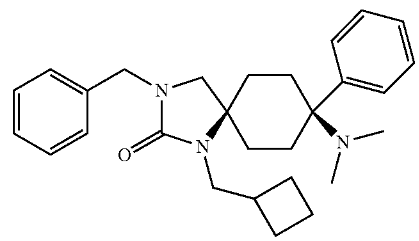 [SMILES: CN(C)[C@]1(c2ccccc2)CC[C@]2(CC1)CN(Cc1ccccc1)C(=O)N2CC1CCC1] | INT-952 | 432.3 |
| INT-954 | 4-Dimethylamino-4-(5-methyl-thiophen-2-yl)-cyclohexan-1-one | 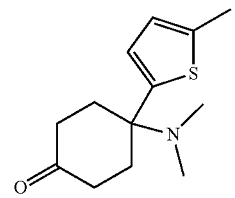 [SMILES: Cc1ccc(C2(N(C)C)CCC(=O)CC2)s1] | INT-965 | 238.1 |
| INT-955 | 4-Dimethylamino-4-thiophen-2-yl-cyclohexan-1-one | 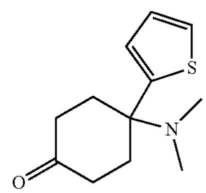 | INT-965 | 224.1 |
| INT-956 | 1-(1-Methyl-1H-pyrazol-3-yl)-4-oxo-cyclohexane-1-carbonitrile | 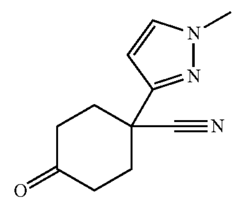 | INT-958 | 204.1 |
| INT-957 | 4-Oxo-1-pyrazin-2-yl-cyclohexane-1-carbonitrile | 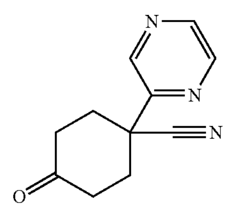 [SMILES: N#CC1(c2cnccn2)CCC(=O)CC1] | INT-958 | 202.1 |
| INT-959 | 4-Dimethylamino-4-(1-methyl-1H-pyrazol-3-yl)-cyclohexan-1-one | 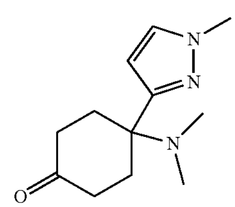 [SMILES: CN(C)C1(c2ccn(C)n2)CCC(=O)CC1] | INT-961 | 222.2 |
| INT-960 | 4-Dimethylamino-4-pyrazin-2-yl-cyclohexan-1-one | 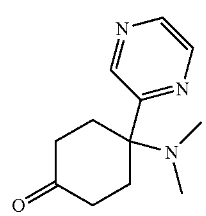 [SMILES: CN(C)C1(c2cnccn2)CCC(=O)CC1] | INT-961 | 220.1 |

-continued

| Intermediate | Chemical Name | in analogy to method | m/z [M + H]+ |
|---|---|---|---|
| INT-962 | 4-Dimethylamino-4-(3-methoxyphenyl)-cyclohexan-1-one | INT-965 | 248.2 |
| INT-963 | CIS-3-Benzyl-8-dimethylamino-8-phenyl-1,3-diazaspiro[4.5]decan-2-one | INT-975 | 364.2 |
| INT-964 | 4-(Ethyl-methyl-amino)-4-phenyl-cyclohexan-1-one | INT-965 | 232.2 |
| INT-967 | CIS-8-Dimethylamino-8-[4-(methoxymethyloxy)-phenyl]-3-[(4-methoxyphenyl)-methyl]-1,3-diazaspiro[4.5]decan-2-one | INT-974 | 454.3 |
| INT-968 | CIS-8-Dimethylamino-8-[3-(methoxymethyloxy)-phenyl]-3-[(4-methoxyphenyl)-methyl]-1,3-diazaspiro[4.5]decan-2-one | INT-974 | 454.3 |
| INT-969 | CIS-1-(Cyclobutyl-methyl)-8-dimethylamino-8-(4-hydroxyphenyl)-3-[(4-methoxyphenyl)-methyl]-1,3-diazaspiro[4.5]decan-2-one | INT-971 | 478.3 |
| INT-970 | CIS-8-Dimethylamino-8-(4-methoxyphenyl)-3-[(4-methoxyphenyl)-methyl]-1,3-diazaspiro[4.5]decan-2-one | SC_2017 | 424.3 |
| INT-972 | CIS-8-Dimethylamino-8-(3-methoxyphenyl)-3-[(4-methoxyphenyl)-methyl]-1,3-diazaspiro[4.5]decan-2-one | SC_2017 | 424.3 |

-continued

| Intermediate | Chemical Name | Chemical Structure | in analogy to method | m/z [M + H]+ |
|---|---|---|---|---|
| INT-973 | CIS-8-Dimethylamino-8-(4-fluorophenyl)-3-[(4-methoxyphenyl)-methyl]-1,3-diazaspiro[4.5]decan-2-one | 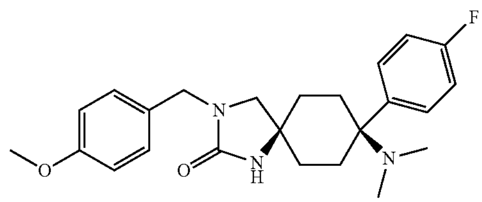 [SMILES: COc1ccc(CN2C[C@]3(CC[C@](c4ccc(F)cc4)(N(C)C)CC3)NC2=O)cc1] | INT-974 | 412.2 |
| INT-979 | CIS-8-Dimethylamino-1-(3-methoxy-propyl)-8-phenyl-1,3-diazaspiro[4.5]decan-2-one | 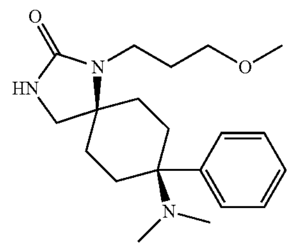 [SMILES: COCCCN1C(=O)NC[C@]12CC[C@](c1ccccc1)(N(C)C)CC2] | INT-984 | 346.2 |
| INT-980 | CIS-8-Dimethylamino-1-(2-methoxy-ethyl)-8-phenyl-1,3-diazaspiro[4.5]decan-2-one | 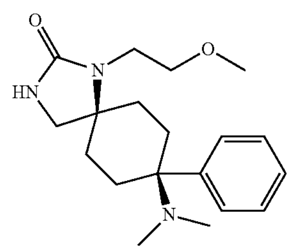 [SMILES: COCCN1C(=O)NC[C@]12CC[C@](c1ccccc1)(N(C)C)CC2] | INT-984 | 332.2 |
| INT-981 | CIS-8-Dimethylamino-8-phenyl-1-propyl-1,3-diazaspiro[4.5]decan-2-one | 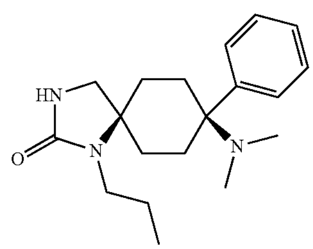 [SMILES: CCCN1C(=O)NC[C@]12CC[C@](c1ccccc1)(N(C)C)CC2] | INT-984 | 316.2 |
| INT-983 | CIS-1-(Cyclopropyl-methyl)-8-dimethylamino-8-phenyl-1,3-diazaspiro[4.5]decan-2-one | 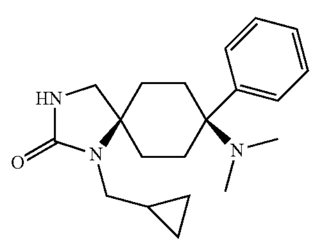 [SMILES: CN(C)[C@]1(c2ccccc2)CC[C@]2(CC1)CNC(=O)N2CC1CC1] | INT-984 | 328.2 |
| INT-985 | CIS-1-(Cyclobutyl-methyl)-8-(methyl-propyl-amino)-8-phenyl-1,3-diazaspiro[4.5]decan-2-one | 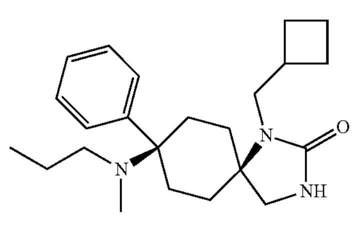 [SMILES: CCCN(C)[C@]1(c2ccccc2)CC[C@]2(CC1)CNC(=O)N2CC1CCC1] | INT-986 | 370.3 |

-continued

| Intermediate | Chemical Name | in analogy to method | m/z [M + H]+ |
|---|---|---|---|
| INT-990 | methyl CIS-5-(8-(dimethylamino)-2-oxo-8-phenyl-1,3-diazaspiro[4.5]decan-3-yl)pyrimidine-2-carboxylate | INT-989 | 410.2 |
| INT-992 | CIS-3-(2-chloro-4-methylpyrimidin-5-yl)-8-(dimethylamino)-8-phenyl-1,3-diazaspiro[4.5]decan-2-one | INT-989 | 400.2 |
| INT-993 | 4-benzyl-4-(dimethylamino)cyclohexanone | INT-965 | 232.3 |
| INT-994 | CIS-8-benzyl-8-(dimethylamino)-1,3-diazaspiro[4.5]decan-2-one | INT-976 | 288.2 |
| INT-995 | TRANS-8-benzyl-8-(dimethylamino)-1,3-diazaspiro[4.5]decan-2-one | INT-976 | 288.2 |
| INT-997 | CIS-8-(dimethylamino)-8-(thiophen-2-yl)-1,3-diazaspiro[4.5]decan-2-one | INT-976 | 280.1 |

-continued

| Intermediate | Chemical Name | Chemical Structure | in analogy to method | m/z [M + H]+ |
|---|---|---|---|---|
| INT-998 | TRANS-8-(dimethylamino)-8-(thiophen-2-yl)-1,3-diazaspiro[4.5]decan-2-one | 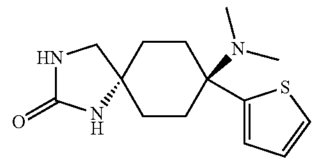 [SMILES: CN(C)[C@]1(c2cccs2)CC[C@@]2(CC1)CNC(=O)N2] | INT-976 | 280.1 |
| INT-999 | 4-(dimethylamino)-4-(1-methyl-1H-benzo[d]imidazol-2-yl)cyclohexanone | 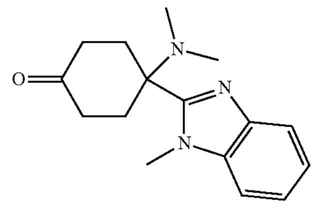 [SMILES: CN(C)C1(c2nc3ccccc3n2C)CCC(=O)CC1] | INT-965 | 272.2 |
| INT-1000 | CIS-8-(dimethylamino)-8-(1-methyl-1H-benzo[d]imidazol-2-yl)-1,3-diazaspiro[4.5]decan-2-one | 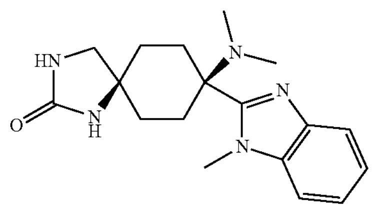 [SMILES: Cn1c2ccccc2nc1[C@]1(N(C)C)CC[C@@]2(CC1)CNC(=O)N2] | INT-976 | 328.2 |
| INT-1001 | TRANS-8-(dimethylamino)-8-(1-methyl-1H-benzo[d]imidazol-2-yl)-1,3-diazaspiro[4.5]decan-2-one | 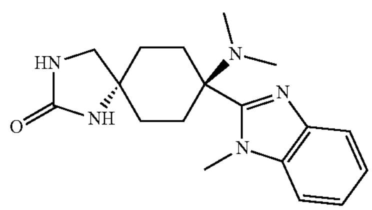 [SMILES: Cn1c2ccccc2nc1[C@]1(N(C)C)CC[C@]2(CC1)CNC(=O)N2] | INT-976 | 328.2 |
| INT-1002 | CIS-3-(2-chloropyrimidin-4-yl)-8-(dimethylamino)-8-phenyl-1,3-diazaspiro[4.5]decan-2-one | 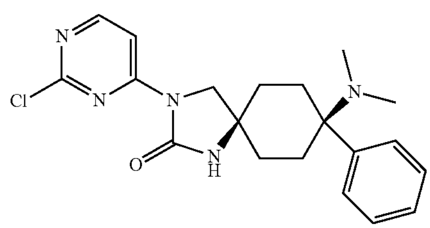 [SMILES: CN(C)[C@]1(c2ccccc2)CC[C@]2(CC1)CN(c1ccnc(Cl)n1)C(=O)N2] | INT-989 | 386.9 |
| INT-1009 | TRANS-8-ethylamino-8-phenyl-1,3-diaza-spiro[4.5]decan-2-one | 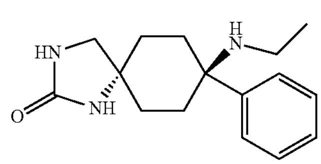 [SMILES: CCN[C@]1(c2ccccc2)CC[C@@]2(CC1)CNC(=O)N2] | INT-1008 | 274.2 |
| INT-1024 | CIS-8-(dimethylamino)-8-(3-fluorophenyl)-1,3-diazaspiro[4.5]decan-2-one | 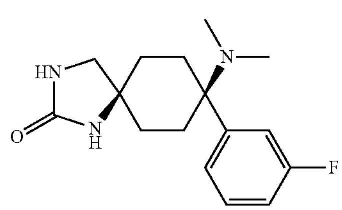 [SMILES: CN(C)[C@]1(c2cccc(F)c2)CC[C@]2(CC1)CNC(=O)N2] | INT-977 (step 2) | 292.2 |

-continued

| Intermediate | Chemical Name | in analogy to method | m/z [M + H]+ |
|---|---|---|---|
| INT-1025 | CIS-8-(dimethylamino)-8-(4-fluorophenyl)-1,3-diazaspiro[4.5]decan-2-one | INT-974, INT-977 (step 2) | 292.2 |
| INT-1027 | CIS-3-(2-chloropyrimidin-5-yl)-8-(dimethylamino)-8-(thiophen-2-yl)-1,3-diazaspiro[4.5]decan-2-one | INT-989 | 392.1 |
| INT-1039 | CIS-8-(dimethylamino)-8-(3-(trifluoromethoxy)phenyl)-1,3-diazaspiro[4.5]decan-2-one | INT-1038 | 358.2 |
| INT-1040 | (CIS)-8-(dimethylamino)-8-(3-(trifluoromethyl)phenyl)-1,3-diazaspiro[4.5]decan-2-one | INT-1038 | 342.2 |
| INT-1041 | (CIS)-8-(dimethylamino)-8-(3-methoxyphenyl)-1,3-diazaspiro[4.5]decan-2-one | INT-1038 | 304.2 |
| INT-1042 | (CIS)-8-(5-chlorothiophen-2-yl)-8-(dimethylamino)-1,3-diazaspiro[4.5]decan-2-one | INT-1038 | 314.1 |
| INT-1043 | (CIS)-8-(dimethylamino)-8-(3-fluoro-5-methylphenyl)-1,3-diazaspiro[4.5]decan-2-one | INT-1038 | 306.2 |

-continued

| Intermediate | Chemical Name | Chemical Structure | in analogy to method | m/z [M + H]+ |
|---|---|---|---|---|
| INT-1044 | (CIS)-8-(3-chlorophenyl)-8-(dimethylamino)-1,3-diazaspiro[4.5]decan-2-one | 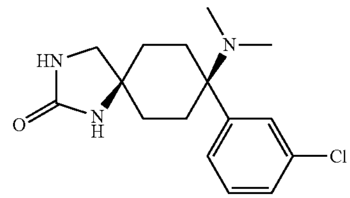 [SMILES: CN(C)[C@]1(c2cccc(Cl)c2)CC[C@]2(CC1)CNC(=O)N2] | INT-1038 | 308.2 |
| INT-1045 | (CIS)-3-(5-chloro-3-fluoropyridin-2-yl)-8-(dimethylamino)-8-phenyl-1,3-diazaspiro[4.5]decan-2-one | 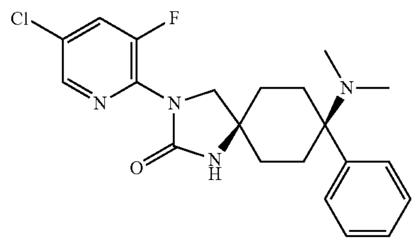 [SMILES: CN(C)[C@]1(c2ccccc2)CC[C@]2(CC1)CN(c1ncc(Cl)cc1F)C(=O)N2] | INT-989 | 403.2 |
| INT-1047 | (CIS)-8-(methyl(oxetan-3-ylmethyl)amino)-8-phenyl-1,3-diazaspiro[4.5]decan-2-one | 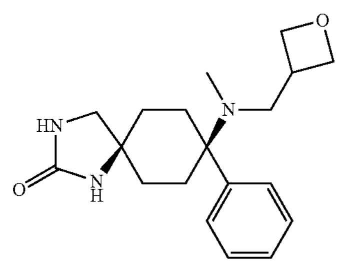 [SMILES: CN(CC1COC1)[C@]1(c2ccccc2)CC[C@]2(CC1)CNC(=O)N2] | INT-1026 | 330.5 |
| INT-1048 | (CIS)-3-(6-chloropyridin-3-yl)-8-(dimethylamino)-8-phenyl-1,3-diazaspiro[4.5]decan-2-one | 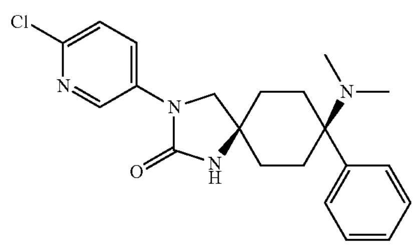 [SMILES: CN(C)[C@]1(c2ccccc2)CC[C@]2(CC1)CN(c1ccc(Cl)nc1)C(=O)N2] | INT-989 | 385.2 |
| INT-1049 | (CIS)-3-(5-chloropyridin-2-yl)-8-(dimethylamino)-8-phenyl-1,3-diazaspiro[4.5]decan-2-one | 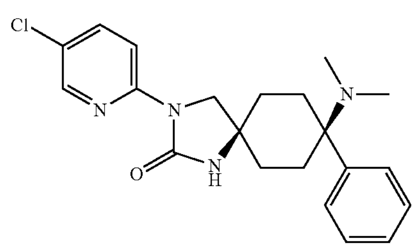 [SMILES: CN(C)[C@]1(c2ccccc2)CC[C@]2(CC1)CN(c1ccc(Cl)cn1)C(=O)N2] | INT-989 | 385.2 |
| INT-1061 | TRANS-1-(cyclopropyl-methyl)-8-dimethylamino-8-phenyl-1,3-diazaspiro[4.5]decan-2-one | 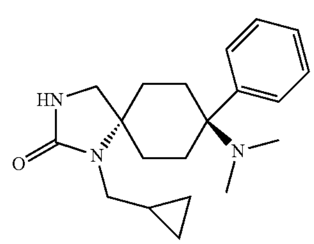 [SMILES: CN(C)[C@]1(c2ccccc2)CC[C@@]2(CC1)CNC(=O)N2CC1CC1] | INT-984 | 328.2 |

-continued

| Intermediate | Chemical Name | Chemical Structure | in analogy to method | m/z [M + H]+ |
|---|---|---|---|---|
| INT-1063 | CIS-1-(cyclopropylmethyl)-8-(dimethylamino)-8-(3-fluorophenyl)-1,3-diazaspiro[4.5]decan-2-one | 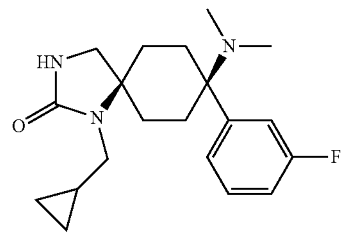 [SMILES: CN(C)[C@]1(c2cccc(F)c2)CC[C@]2(CC1)CNC(=O)N2CC1CC1] | INT-1031 | 346.2 |
| INT-1066 | TRANS-1-(cyclobutylmethyl)-8-(dimethylamino)-8-phenyl-1,3-diazaspiro[4.5]decan-2-one | 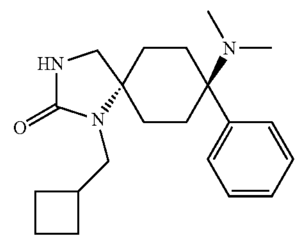 [SMILES: CN(C)[C@]1(c2ccccc2)CC[C@@]2(CC1)CNC(=O)N2CC1CCC1] | INT-987 | 342.3 |
| INT-1070 | CIS-8-(dimethylamino)-8-phenyl-1-(3,3,3-trifluoropropyl)-1,3-diazaspiro[4.5]decan-2-one | 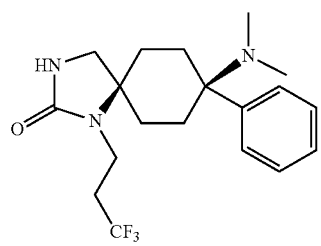 [SMILES: CN(C)[C@]1(c2ccccc2)CC[C@]2(CC1)CNC(=O)N2CCC(F)(F)F] | INT-1068 | 360.2 |
| INT-1074 | CIS-8-(dimethylamino)-8-(3-fluorophenyl)-1-((1-hydroxycyclobutyl)methyl)-1,3-diazaspiro[4.5]decan-2-one | 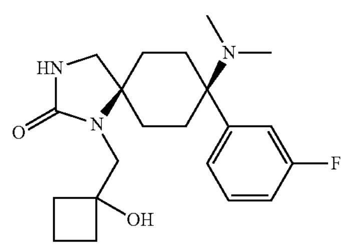 [SMILES: CN(C)[C@]1(c2cccc(F)c2)CC[C@]2(CC1)CNC(=O)N2CC1(O)CCC1] | INT-1031 | 376.2 |
| INT-1076 | CIS-3-(2-chloro-4-methylpyrimidin-5-yl)-8-(dimethylamino)-8-(3-fluorophenyl)-1,3-diazaspiro[4.5]decan-2-one | 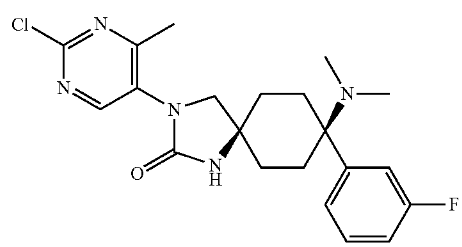 [SMILES: Cc1nc(Cl)ncc1N1C[C@]2(CC[C@](c3cccc(F)c3)(N(C)C)CC2)NC1=O] | INT-989 | 418.2 |
| INT-1077 | CIS-3-(4-chloro-2-(trifluoromethyl)pyrimidin-5-yl)-8-(dimethylamino)-8-(3-fluorophenyl)-1,3-diazaspiro[4.5]decan-2-one | 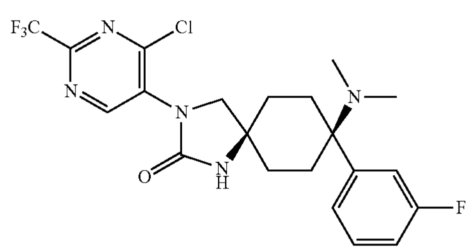 [SMILES: CN(C)[C@]1(c2cccc(F)c2)CC[C@]2(CC1)CN(c1cnc(C(F)(F)F)nc1Cl)C(=O)N2] | INT-989 | 472.2 |

| Intermediate | Chemical Name | Chemical Structure | in analogy to method | m/z [M + H]+ |
|---|---|---|---|---|
| INT-1078 | CIS-3-(4-chloro-2-cyclopropylpyrimidin-5-yl)-8-(dimethylamino)-8-(3-fluorophenyl)-1,3-diazaspiro[4.5]decan-2-one | 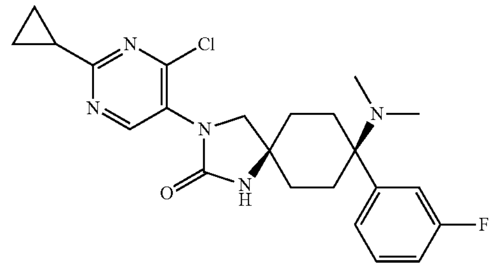 [SMILES: CN(C)[C@]1(c2cccc(F)c2)CC[C@]2(CC1)CN(c1cnc(C3CC3)nc1Cl)C(=O)N2] | INT-989 | 444.2 |

Synthesis of Exemplary Compounds

Synthesis of SC_3013: cis-5-[8-Dimethylamino-1-[(1-hydroxy-cyclobutyl)-methyl]-2-oxo-8-phenyl-1,3-diazaspiro[4.5]decan-3-yl]-pyrimidine-2-carbonitrile

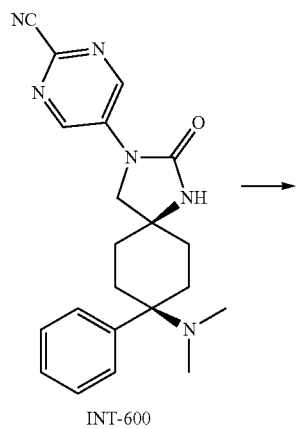

INT-600

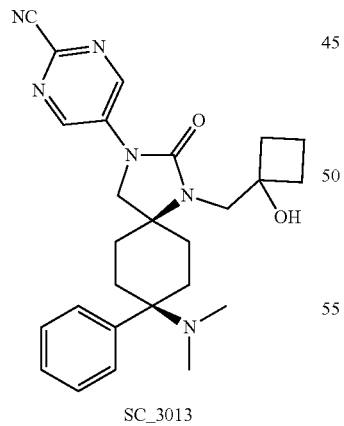

SC_3013

NaH (60% in mineral oil, 0.076 g, 3.19 mmol, 3 equiv.) was added to a solution of 5-(cis-8-(dimethylamino)-2-oxo-8-phenyl-1,3-diazaspiro[4.5]decan-3-yl)pyrimidine-2-carbonitrile INT_600 (0.4 g, 1.06 mmol) in DMF (5 mL) at 0° C. The mixture was stirred for 30 min at RT and then cooled to 0° C. (1-(Tert-butyldimethylsilyloxy)cyclobutyl)methyl 4-methylbenzenesulfonate (1.18 g, 3.19 mmol, 3 equiv.) was added dropwise over a period of 5 min and the reaction mixture was allowed to warm up to RT and further heated to 70° C. for 16 h. The reaction mixture was diluted with water (10 mL) and extracted with EtOAc (3×20 mL). The combined organic layers were dried over anhydrous Na$_2$SO$_4$ and the solvent was removed in vacuo. The residue was purified by silica gel flash chromatography to afford CIS-5-[8-dimethylamino-1-[(1-hydroxy-cyclobutyl)-methyl]-2-oxo-8-phenyl-1,3-diazaspiro[4.5]decan-3-yl]-pyrimidine-2-carbonitrile (0.25 g).

Synthesis of SC_3014: cis-2-[1-(Cyclobutyl-methyl)-8-dimethylamino-2-oxo-8-phenyl-1,3-diazaspiro[4.5]decan-3-yl]-pyrimidine-5-carbonitrile

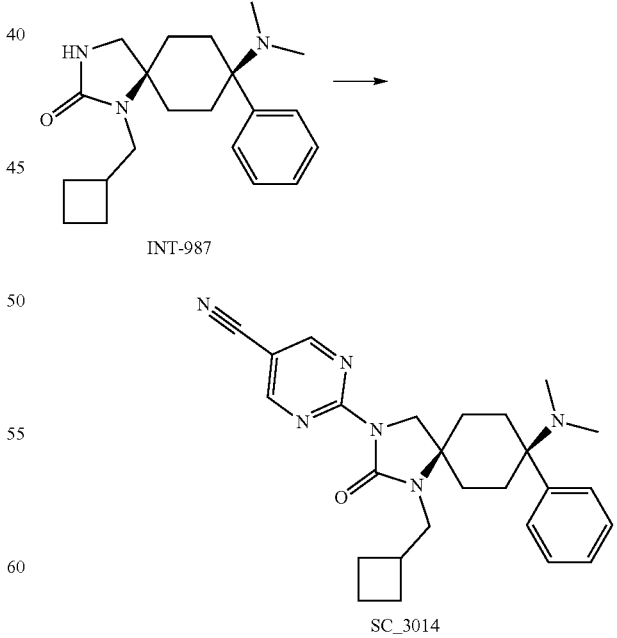

INT-987

SC_3014 cis-1-(Cyclobutylmethyl)-8-(dimethylamino)-8-phenyl-1,3-diazaspiro[4.5]decan-2-one INT-987 (500 mg, 1.464 mmol), 2-chloropyrimidine-5-carbonitrile (409 mg, 2.928 mmol) and Cs$_2$CO$_3$ (954 mg, 2.928 mmol) in 1,4-dioxane (6 ml) were stirred under an nitrogen atmosphere for 18 h at 105° C. The reaction mixture was cooled to RT, 2N aqueous NaOH solution (3 ml) was added and stirring was continued for 10 min. The mixture was extracted first with EtOAc and then with a blend of DCM (30 ml) and methanol (5 ml). The organic layers were combined and concentrated under reduced pressure. The residue was purified by flash chromatography on silica gel (elution with a DCM/EtOAc gradient) provided cis-2-[1-(cyclobutyl-methyl)-8-dimethyl-amino-2-oxo-8-phenyl-1,3-diazaspiro[4.5]decan-3-yl]-pyrimidine-5-carbonitrile SC_3014 (57 mg).

Synthesis of SC_3016: cis-2-[1-(Cyclobutyl-methyl)-8-dimethylamino-2-oxo-8-phenyl-1,3-diaz-aspiro[4.5]decan-3-yl]-pyrimidine-5-carboxylic acid amide

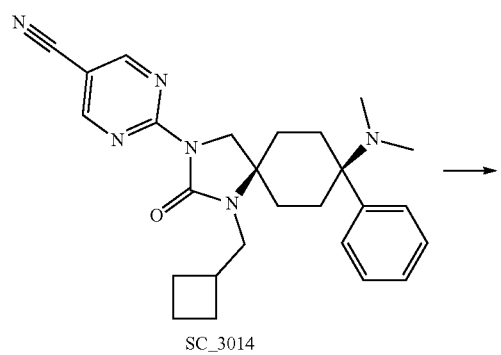

SC_3014

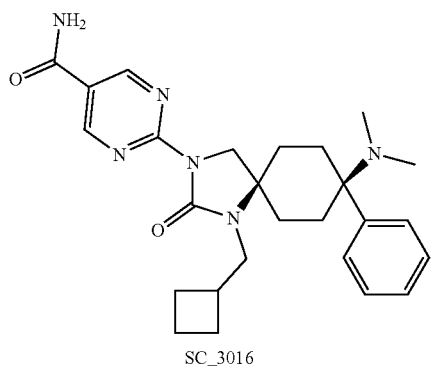

SC_3016 cis-2-[1-(Cyclobutylmethyl)-8-(dimethylamino)-2-oxo-8-phenyl-1,3-diazaspiro[4.5]decan-3-yl]pyrimidine-5-carbonitrile SC_3014 (40 mg, 0.09 mmol) was dissolved in DMSO (1.2 mL) and K$_2$CO$_3$ (25 mg, 0.18 mmol) and hydrogen peroxide (30%, 0.13 mL 1.260 mmol) were added. The reaction mixture was stirred at RT for 20 h, then diluted with 2N NaOH (10 mL) and extracted with DCM (3×20 mL). The combined organic layers were dried over Na$_2$SO$_4$, concentrated in vacuo. The residue was purified by flash chromatography to yield cis-2-[1-(cyclobutyl-methyl)-8-dimethylamino-2-oxo-8-phenyl-1,3-diazaspiro[4.5]decan-3-yl]-pyrimidine-5-carboxylic acid amide SC_3016 (40 mg) as a white solid.

Synthesis of SC_3022: cis-1-(Cyclobutylmethyl)-8-(dimethylamino)-8-phenyl-3-[2-(trifluoromethyl)pyrimidin-5-yl]-1,3-diazaspiro[4.5]decan-2-one

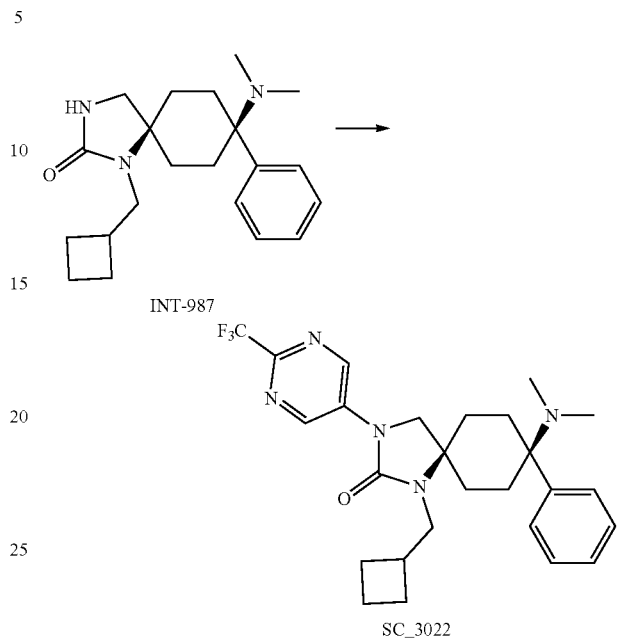

SC_3022 cis-1-(Cyclobutylmethyl)-8-(dimethylamino)-8-phenyl-1,3-diazaspiro[4.5]decan-2-one INT-987 (240 mg, 0.7 mmol), Pd-XPhos Generation 2 (138 mg, 0.17 mmol), Cs$_2$CO$_3$ (457 mg, 1.4 mmol) and 5-bromo-2-(trifluoromethyl)pyrimidine (319 mg, 1.4 mmol) were suspended in anhydrous 1,4-dioxane (3 mL) under nitrogen atmosphere and the resulting mixture was stirred at 100° C. overnight. The reaction mixture was cooled to RT and water (3 mL) was added. The aqueous layer was extracted with DCM (3×10 mL), the combined organic layers were dried over Na$_2$SO$_4$ and concentrated in vacuo. The residue was purified by flash chromatography on silica gel to yield the title compound. Final purification using a strong cation exchange resin gave cis-1-(cyclobutylmethyl)-8-(dimethylamino)-8-phenyl-3-[2-(trifluoromethyl)pyrimidin-5-yl]-1,3-diazaspiro[4.5]decan-2-one SC_3022 (145 mg) as a white solid.

Synthesis of SC_3028: cis-4-[1-(cyclobutyl-methyl)-8-dimethylamino-2-oxo-8-phenyl-1,3-diaz-aspiro[4.5]decan-3-yl]-N,N-dimethyl-benzamide

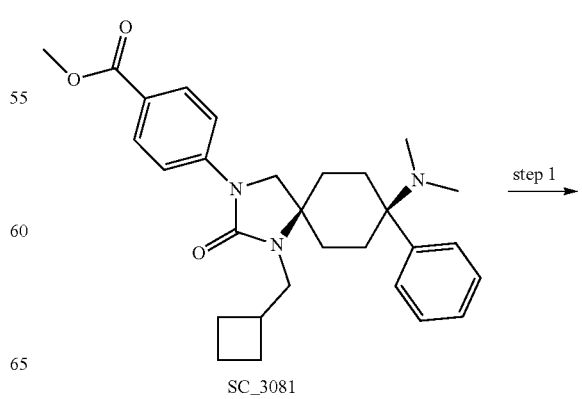

SC_3081    step 1

135

-continued

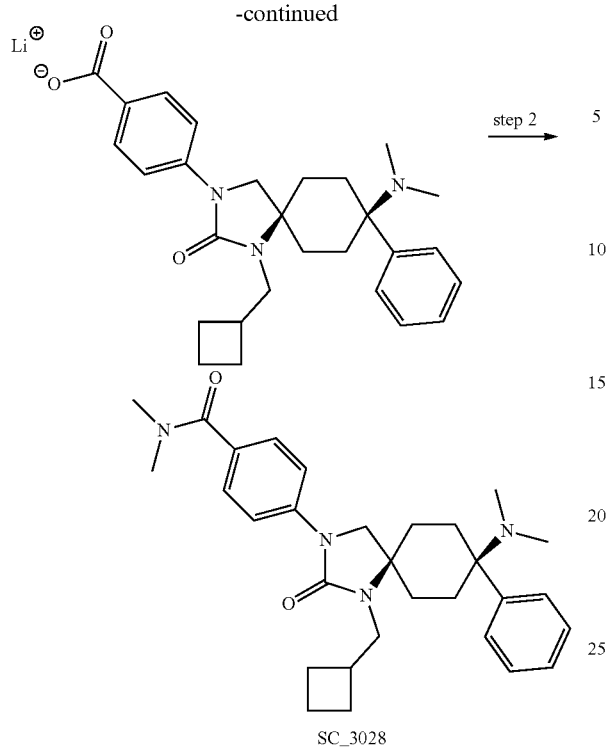

SC_3028

Step 1: Lithium 4-(cis-1-(cyclobutylmethyl)-8-(dimethylamino)-2-oxo-8-phenyl-1,3-diazaspiro[4.5]decan-3-yl)benzoate Methyl 4-(cis-1-(cyclobutylmethyl)-8-(dimethylamino)-2-oxo-8-phenyl-1,3-diazaspiro [4,5]decan-3-yl)benzoate SC_3081 (400 mg) was dissolved in methanol (5 mL) and DCM (5 mL). Lithium hydroxide solution (2 M in water, 1 mL) was added and the resulting mixture was stirred overnight at RT. All volatiles were removed in vacuo to yield lithium 4-(cis-1-(cyclobutylmethyl)-8-(dimethylamino)-2-oxo-8-phenyl-1,3-diazaspiro[4.5]decan-3-yl)benzoate (403 mg).

Step 2 cis-4-[1-(Cyclobutyl-methyl)-8-dimethyl-amino-2-oxo-8-phenyl-1,3-diazaspiro [4,5]decan-3-yl]-N,N-dimethyl-benzamide (SC_3028)

Lithium 4-(cis-1-(cyclobutylmethyl)-8-(dimethylamino)-2-oxo-8-phenyl-1,3-diazaspiro [4,5]decan-3-yl)benzoate (80 mg, 0.17 mmol) was suspended in DCM (1 mL) and triethylamine (0.23 mL, 1.7 mmol) and dimethylamine (2M solution in THF, 0.17 mL) and T3P (0.20 mL, 0.34 mmol) were sequentially added. The resulting mixture was stirred for 18 h at RT. Water (10 mL) was added and the mixture was extracted with DCM (3×20 mL). The combined organic layers were dried over Na₂SO₄, concentrated in vacuo and the residue was purified by flash chromatography to yield cis-4-[1-(cyclobutyl-methyl)-8-dimethylamino-2-oxo-8-phenyl-1,3-diazaspiro[4.5]decan-3-yl]-N,N-dimethyl-benzamide SC_3028 (28 mg) as white solid.

136

Synthesis of SC_3045: cis-4-Methoxy-5-[1-(3-methoxypropyl)-8-(methylamino)-2-oxo-8-phenyl-1,3-diazaspiro[4.5]decan-3-yl]pyrimidine-2-carbonitrile

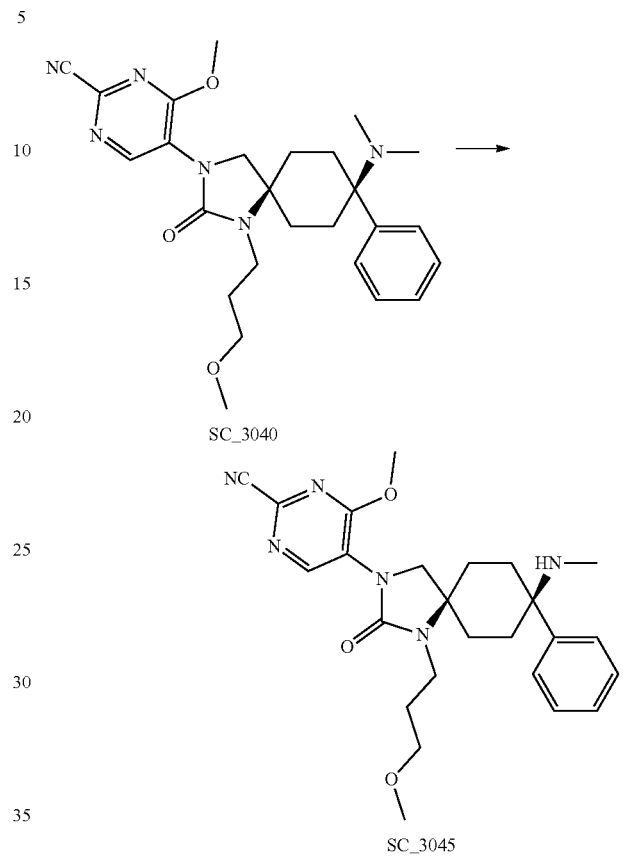

N-iodosuccinimide (150 mg, 0.67 mmol) was added to a suspension of cis-5-[8-(dimethylamino)-1-(3-methoxypropyl)-2-oxo-8-phenyl-1,3-diazaspiro[4.5]decan-3-yl]-4-methoxy-pyrimidine-2-carbonitrile SC_3040 (214 mg, 0.44 mmol) in acetonitrile/THF (2/1 v/v, 10 mL) at RT and the resulting mixture was stirred for 16 h at RT. The reaction mixture was basified with 2N NaOH solution to pH-10 and the organic product was extracted with DCM (10 mL×3). The combined organic extracts were dried over anhydrous Na₂SO₄, the solvent was removed in vacuo and the residue was purified by preparative flash chromatography to give cis-4-methoxy-5-[1-(3-methoxypropyl)-8-(methylamino)-2-oxo-8-phenyl-1,3-diazaspiro[4.5]decan-3-yl]pyrimidine-2-carbonitrile SC_3045 (81 mg) as a solid.

Synthesis of SC_3064: cis-2-[3-(2-cyano-pyrimidin-5-yl)-8-dimethylamino-2-oxo-8-phenyl-1,3-diazaspiro[4.5]decan-1-yl]-N-propyl-acetamide

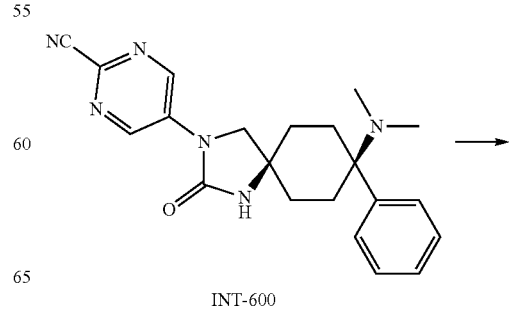

INT-600

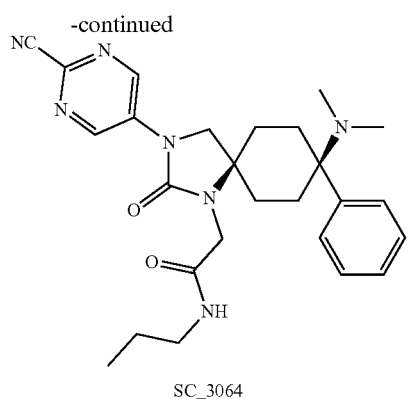

SC_3064

Sodium hydroxide (51 mg, 1.3 mmol) was added to anhydrous DMSO (4.5 mL) and stirred for 10 minutes at room temperature. cis-5-[8-(Dimethylamino)-2-oxo-8-phenyl-1,3-diazaspiro[4.5]decan-3-yl]pyrimidine-2-carbonitrile INT_600 (80 mg, 0.21 mmol) was added and the resulting mixture was stirred at room temperature for 5 min and then heated to 50° C. 2-Bromo-N-propyl-acetamide (153 mg, 0.85 mmol) was added and stirring was continued at 50° C. for one hour. The reaction mixture was quenched with water (25 mL) and extracted with ethyl acetate (2×10 mL). The combined organic layers were washed with water (5 mL) and brine (5 mL), dried over $Na_2SO_4$ and concentrated under reduced pressure. The residue was purified by flash chromatography on silica gel to yield cis-2-[3-(2-cyano-pyrimidin-5-yl)-8-dimethylamino-2-oxo-8-phenyl-1,3-diazaspiro[4.5]decan-1-yl]-N-propyl-acetamide SC 3064 (22 mg) as a solid.

Synthesis of SC_3065: 5-(cis-1-(Cyclobutylmethyl)-8-(ethyl(methyl)amino)-2-oxo-8-phenyl-1,3-diazaspiro[4.5]decan-3-yl)-4-methoxypyrimidine-2-carbonitrile

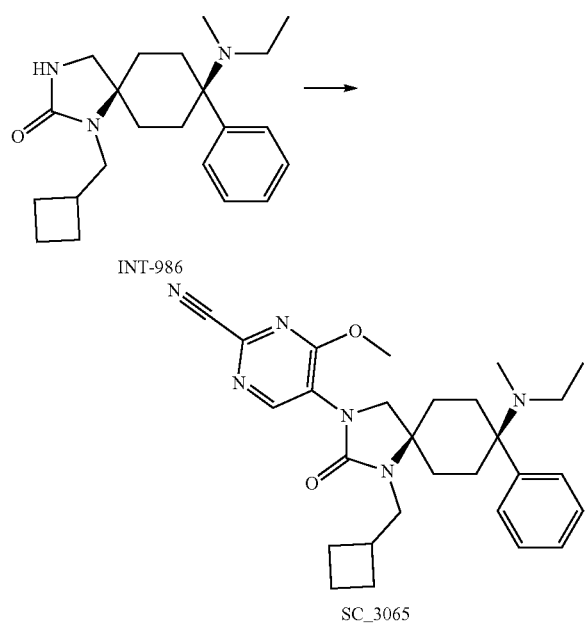

INT-986

SC_3065

$Cs_2CO_3$ (274 mg, 0.84 mmol) was added to the solution of cis-1-(cyclobutylmethyl)-8-(ethyl(methyl)amino)-8-phenyl-1,3-diazaspiro[4.5]decan-2-one INT_986 (150 mg, 0.42 mmol), Xanthphos (36 mg, 0.063 mmol), $Pd_2(dba)_3$ (19 mg, 0.0211 mmol) and 5-bromo-4-methoxypyrimidine-2-carbonitrile (135 mg, 0.633 mmol) in 1,4-dioxane (10 mL) under argon atmosphere. The mixture was flushed again with argon for 5 min and the reaction mixture was stirred at 90° C. for 5 h. The reaction mixture was cooled to room temperature. The residue was diluted with water (20 mL) and the organic product was extracted with ethyl acetate (3×10 mL). The combined organic extracts were dried over anhydrous $Na_2SO_4$ and the solvent was concentrated under reduced pressure. The residue was purified by preparative TLC (EtOAc/petroleum ether 1/9) to afford a white solid (0.15 g), which was further washed with n-pentane to give 0.1 g of 5-(cis-1-(cyclobutylmethyl)-8-(ethyl(methyl)amino)-2-oxo-8-phenyl-1,3-diazaspiro[4.5]decan-3-yl)-4-methoxypyrimidine-2-carbonitrile SC_3065.

Synthesis of SC_3008: cis-2-[1-(Cyclobutylmethyl)-8-dimethylamino-2-oxo-8-phenyl-1,3-diazaspiro[4.5]decan-3-yl]-5-methylsulfoylsulfonyl-benzonitrile

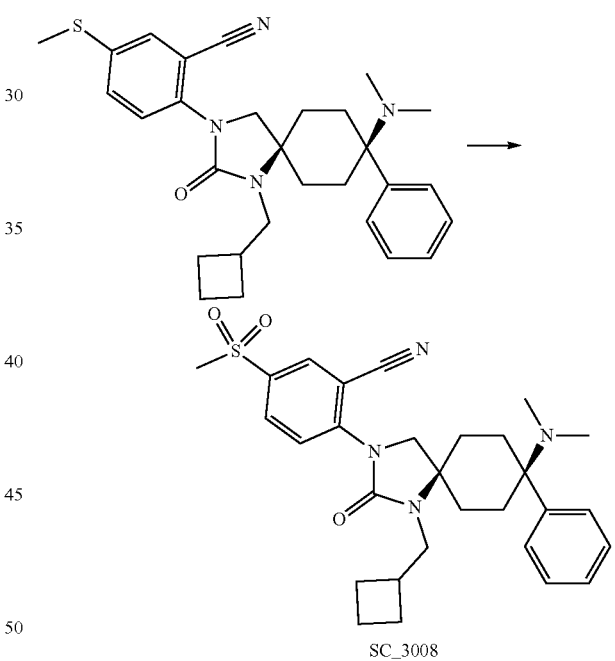

SC_3008 cis-2-[1-(Cyclobutylmethyl)-8-(dimethylamino)-2-oxo-8-phenyl-1,3-diazaspiro[4.5]decan-3-yl]-5-methylsulfanyl-benzonitrile (320 mg, 0.66 mmol, prepared from 2-iodo-5-(methylthio)benzonitrile and INT-987 analogously to SC_3022) was dissolved in a mixture of methanol (9 mL) and water (8 mL). Oxone® (807 mg, 1.3 mmol) was added at RT and the resulting mixture was stirred at RT for 18 h. Water (10 mL) was added and the mixture was extracted with DCM (3×20 mL). The combined organic layers were dried over $Na_2SO_4$, concentrated in vacuo. The residue was purified by flash chromatography on silica gel to yield cis-2-[1-(cyclobutylmethyl)-8-(dimethylamino)-2-oxo-8-phenyl-1,3-diazaspiro[4.5]decan-3-yl]-5-methylsulfonyl-benzonitrile SC_3008 (66 mg) as a white solid.

Synthesis of SC_3023: cis-8-Dimethylamino-1-[(1-hydroxy-cyclobutyl)-methyl]-3-(2-hydroxy-pyrimidin-5-yl)-8-phenyl-1,3-diazaspiro[4.5]decan-2-one

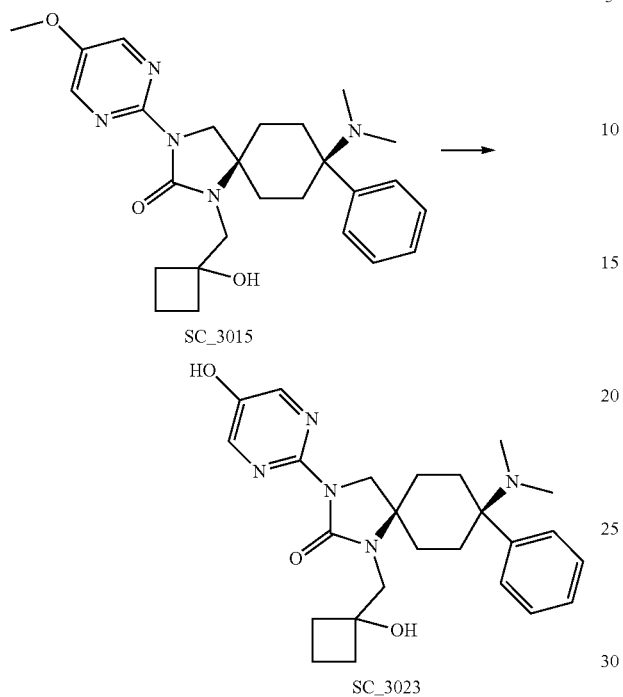

Boron tribromide (1M in DCM, 0.38 mL, 0.387 mmol) was added to the solution of cis-8-dimethylamino-1-[(1-hydroxy-cyclobutyl)-methyl]-3-(2-methoxy-pyrimidin-5-yl)-8-phenyl-1,3-diazaspiro[4.5]decan-2-one SC_3015 (180 mg, 0.387 mmol) in DCM (2 mL) at 0° C. The reaction mixture was stirred for 30 min at 0° C. and then for 16 h at room temperature, quenched with methanol (2 mL), the solvents were removed under reduced pressure and the residue was purified by normal phase preparative HPLC to yield cis-8-dimethylamino-1-[(1-hydroxy-cyclobutyl)-methyl]-3-(2-hydroxy-pyrimidin-5-yl)-8-phenyl-1,3-diazaspiro[4.5]decan-2-one SC_3023 (60 mg, 34%) as a white solid. $^1$H NMR (400 MHz, DMSO-d6, δ in ppm): δ 8.43 (s, 2H), 7.35-7.25 (m, 5H), 5.50 (s, 1H), 3.67 (s, 2H), 3.19 (s, 2H), 2.69-2.65 (m, 2H), 2.19-2.10 (m, 4H), 1.98-1.85 (m, 8H), 1.68-1.61 (m, 1H), 1.51-1.39 (m, 5H).

Synthesis of SC_3025: cis-5-[8-Dimethylamino-1-(2-hydroxy-ethyl)-2-oxo-8-phenyl-1,3-diazaspiro[4.5]decan-3-yl]-pyrimidine-2-carbonitrile

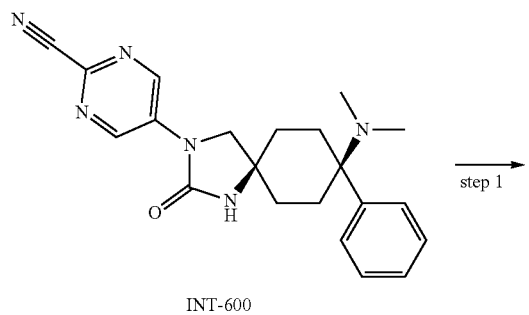

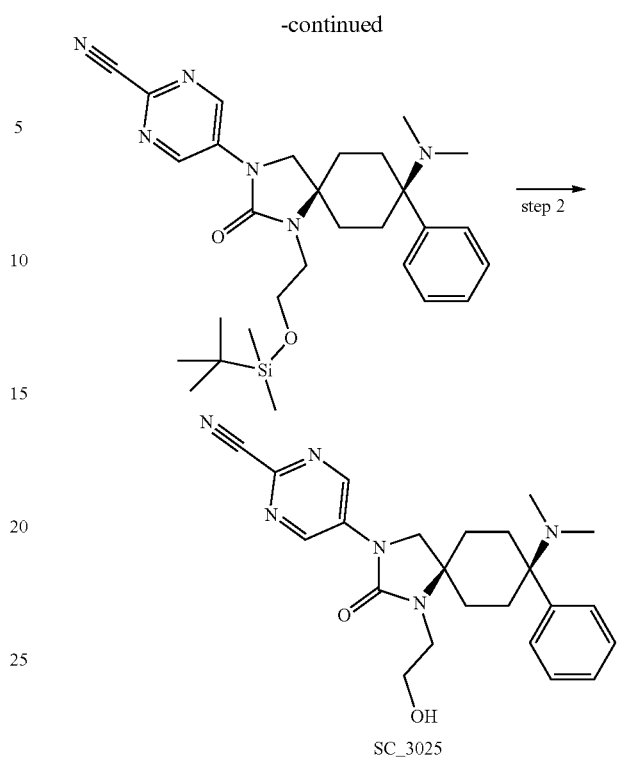

Step 1: 5-(cis-1-(2-(tert-Butyldimethylsilyloxy)ethyl)-8-(dimethylamino)-2-oxo-8-phenyl-1,3-diazaspiro[4.5]decan-3-yl)pyrimidine-2-carbonitrile NaH (60% in mineral oil, 63.8 mg, 1.59 mmol) was added at 0° C. to the solution of 5-(cis-8-(dimethylamino)-2-oxo-8-phenyl-1,3-diazaspiro[4.5]decan-3-yl)pyrimidine-2-carbonitrile INT-600 (0.2 g, 0.53 mmol) in DMF (8 mL) for 10 min at 0° C. The reaction mixture was stirred at RT for 30 min, (3-bromopropoxy)(tert-butyl)dimethylsilane (252 mg, 1.06 mmol) was added dropwise over 5 min at 0° C. and the mixture was stirred for further 16 h at RT. The reaction mixture was diluted with water (15 mL) and extracted with diethyl ether (3×25 mL). The combined organic extracts were dried over anhydrous Na$_2$SO$_4$, the solvents were removed under reduced pressure and the residue was purified by flash chromatography on silica gel to afford 5-(cis-1-(2-(tert-butyldimethylsilyloxy)ethyl)-8-(dimethylamino)-2-oxo-8-phenyl-1,3-diazaspiro[4.5]decan-3-yl)pyrimidine-2-carbonitrile (100 mg, 34%) as a white solid.

Step 2: cis-5-[8-Dimethylamino-1-(2-hydroxy-ethyl)-2-oxo-8-phenyl-1,3-diazaspiro[4.5]decan-3-yl]-pyrimidine-2-carbonitrile (SC_3025)

1M TBAF solution in THF (0.36 mL, 0.36 mmol) was added to 5-(cis-1-(2-(tert-butyldimethylsilyloxy)ethyl)-8-(dimethylamino)-2-oxo-8-phenyl-1,3-diazaspiro[4.5]decan-3-yl)pyrimidine-2-carbonitrile (0.1 g, 0.18 mmol) in THF (5 mL) at 0° C. The reaction mixture was stirred at RT for 30 min, diluted with water (10 mL) and extracted with diethyl ether (3×25 mL). The combined organic extracts were washed with sat. aq. NaHCO$_3$, water and brine and dried over anhydrous Na$_2$SO$_4$. The solvents were evaporated under reduced pressure and the residue was purified by preparative TLC (ethyl acetate/n-hexane=45:55) and then washed with n-pentane (5 mL) to give of cis-5-[8-dimethylamino-1-(2-hydroxy-ethyl)-2-oxo-8-phenyl-1,3-diazaspiro[4.5]decan-3-yl]-pyrimidine-2-carbonitrile (70 mg, 80%) as a white solid. ¹H NMR (400 MHz, DMSO-d6, δ in ppm): δ 9.18 (s, 2H), 7.38-7.26 (m, 5H), 4.84 (t, 1H), 3.82 (s, 2H), 3.55-3.51 (m, 2H), 3.26-3.20 (m, 2H), 2.73-2.70 (m, 2H), 2.17-2.11 (m, 2H), 2.00 (s, 6H), 1.57-1.43 (m, 4H).

Synthesis of SC_3097: CIS-8-dimethylamino-1-[(1-hydroxy-cyclobutyl)-methyl]-3-(2-morpholin-4-yl-pyrimidin-5-yl)-8-phenyl-1,3-diazaspiro[4.5]decan-2-one

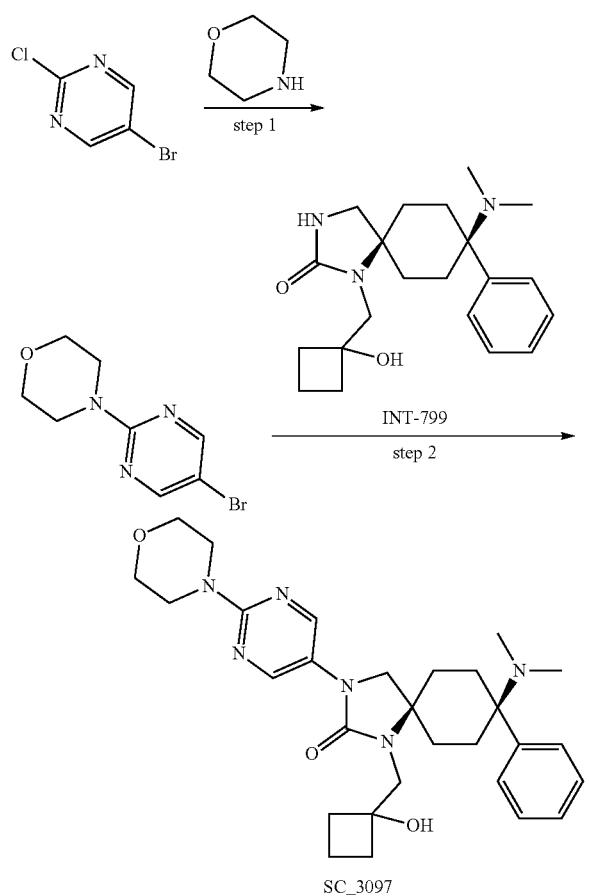

starting from here until the end of the section all procedures were added

Step 1: 4-(5-bromopyrimidin-2-yl)morpholine

K₂CO₃ (14.2 g, 103 mmol) was added to the solution of morpholine (9.0 g, 103 mmol) in acetonitrile (900 mL) and the resulting suspension was stirred at RT for 1 h. 5-Bromo-2-chloropyrimidine (20 g, 103 mmol) was added portionwise. The reaction mixture was stirred for 16 h at 80° C., then cooled down to RT and diluted with EtOAc (100 mL) and water (50 mL). The organic product was extracted with EtOAc (2×100 mL). The combined organic layer was washed with brine (100 mL), dried over anhydrous Na₂SO₄ and concentrated under reduced pressure. The resulting residue was purified by column chromatography on silica gel (100-200 mesh) (20% EtOAc in petroleum ether) to afford 18.0 g (71%) of 4-(5-bromopyrimidin-2-yl)morpholine as an off white solid (TLC system: 30% EtOAc in pet ether, Rf: 0.6).

Step 2: CIS-8-dimethylamino-1-[(1-hydroxy-cyclobutyl)-methyl]-3-(2-morpholin-4-yl-pyrimidin-5-yl)-8-phenyl-1,3-diazaspiro[4.5]decan-2-one (SC_3097)

K₂CO₃ (0.53 g, 3.85 mmol, 2.5 equiv.) was added to the suspension of CIS-8-(dimethylamino)-1-((1-hydroxycyclobutyl)methyl)-8-phenyl-1,3-diazaspiro[4.5]decan-2-one (INT-799) (0.55 g, 1.54 mmol, 1 equiv.) and 4-(5-bromopyrimidin-2-yl)morpholine (0.37 g, 1.54 mmol, 1 equiv.) in dioxane (20 mL) and the resulting suspension was purged with nitrogen for 5 min. Copper(I) iodide (0.29 g, 1.54 mmol, 1 equiv.) and trans-1,2-diaminocyclohexane (0.35 g, 3.085 mmol, 2 equiv.) were sequentially added, the reaction vessel was sealed and the reaction mixture was stirred at 130° C. for 4 h. The reaction mixture was cooled down to RT and diluted with EtOAc (20 mL) and aq. ammonia (10 mL). The organic product was extracted with EtOAc (2×50 mL). The combined organic layer was washed with brine (50 mL), dried over anhydrous Na₂SO₄ and concentrated under reduced pressure. Purification of the resulting residue by column chromatography on silica gel (100-200 mesh) (60-70% EtOAc in petroleum ether) afforded 0.35 g (48%) of CIS-8-(dimethylamino)-1-((1-hydroxycyclobutyl)methyl)-3-(2-morpholin-4-yl-pyrimidin-5-yl)-8-phenyl-1,3-diazaspiro[4.5]decan-2-one (SC_3097) as an off white solid (TLC system:EtOAc, Rf: 0.7). ¹H NMR (DMSO-d6): δ 8.60 (s, 2H), 7.36-7.35 (m, 4H), 7.27-7.24 (m, 1H), 5.50 (s, 1H), 3.72 (s, 2H), 3.62-3.61 (m, 8H), 3.21 (s, 2H), 2.70-2.66 (m, 2H), 2.19-2.11 (m, 4H), 1.98 (s, 6H), 1.93-1.85 (m, 2H), 1.66-1.64 (m, 1H), 1.53-1.42 (m, 5H). Mass: m/z 521.3 (M+H)+.

Synthesis of SC_3099: CIS-1-[(1-hydroxy-cyclobutyl)-methyl]-8-methylamino-3-(2-morpholin-4-yl-pyrimidin-5-yl)-8-phenyl-1,3-diazaspiro[4.5]decan-2-one

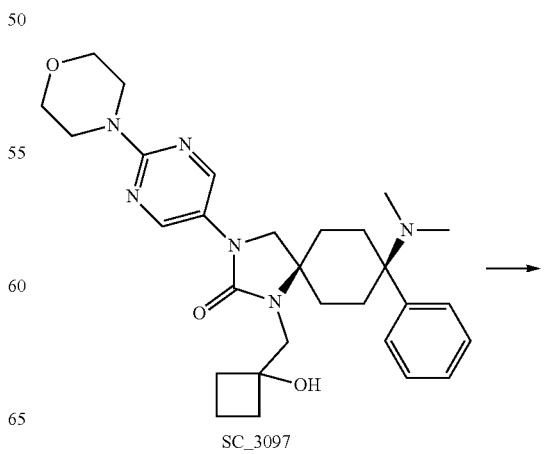

-continued

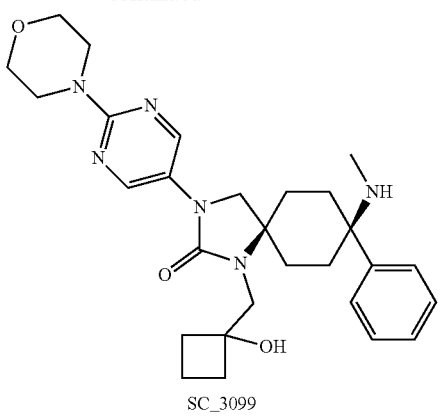

SC_3099

N-Iodosuccinimide (162 mg, 0.72 mmol) was added to the solution CIS-8-(dimethylamino)-1-((1-hydroxycyclobutyl)methyl)-3-(2-morpholinopyrimidin-5-yl)-8-phenyl-1,3-diazaspiro[4.5]decan-2-one (SC-3097) (250 mg, 0.48 mmol) in acetonitrile (8.0 mL) and THF (8.0 mL) at 0° C. and the resulting mixture was stirred for 16 h at RT. The reaction mixture was concentrated under reduced pressure. The residue was dissolved in EtOAc (2×30 mL), the organic layer was washed with 2N aq. NaOH solution, dried over anhydrous $Na_2SO_4$ and concentrated under reduced pressure. The residue was purified by reverse phase prep. HPLC to yield 0.12 g (49%) of CIS-1-((1-hydroxycyclobutyl)methyl)-8-(methylamino)-3-(2-morpholinopyrimidin-5-yl)-8-phenyl-1,3-diazaspiro[4.5]decan-2-one (SC_3099) as an off white solid (TLC system 5% MeOH in DCM $R_f$: 0.5.). Preparative reverse phase HPLC conditions: column: Luna-Phenyl-Hexyl-C18 (150*19 mm) 5 μm; mobile phase: 10 mM ammonium bicarbonate/acetonitrile, gradient (T/% B): 0/50, 7/85, 7.1/98, 9/98, 9.1/50, 12/50; flow Rate: 25 ml/min; diluent: mobile phase+THF. $^1$H NMR (DMSO-d6): δ 8.63 (s, 2H), 7.49-7.47 (m, 2H), 7.34-7.30 (t, 2H), 7.21-7.17 (m, 1H), 5.60 (s, 1H), 3.76 (s, 2H), 3.64-3.62 (m, 8H), 3.35 (m, 2H), 2.26-2.20 (m, 3H), 2.12-2.08 (m, 2H), 1.90-1.88 (m, 7H), 1.79-1.73 (m, 2H), 1.65-1.63 (m, 1H), 1.52-1.44 (m, 3H). Mass: m/z 507.3 (M+H)+.

Synthesis of SC_3100: CIS-8-dimethylamino-1-[(1-hydroxy-cyclobutyl)-methyl]-8-phenyl-3-(2-piperazin-1-yl-pyrimidin-5-yl)-1,3-diazaspiro[4.5]decan-2-one hydrochloride

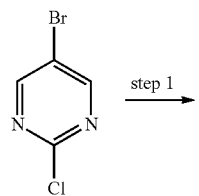
step 1

-continued

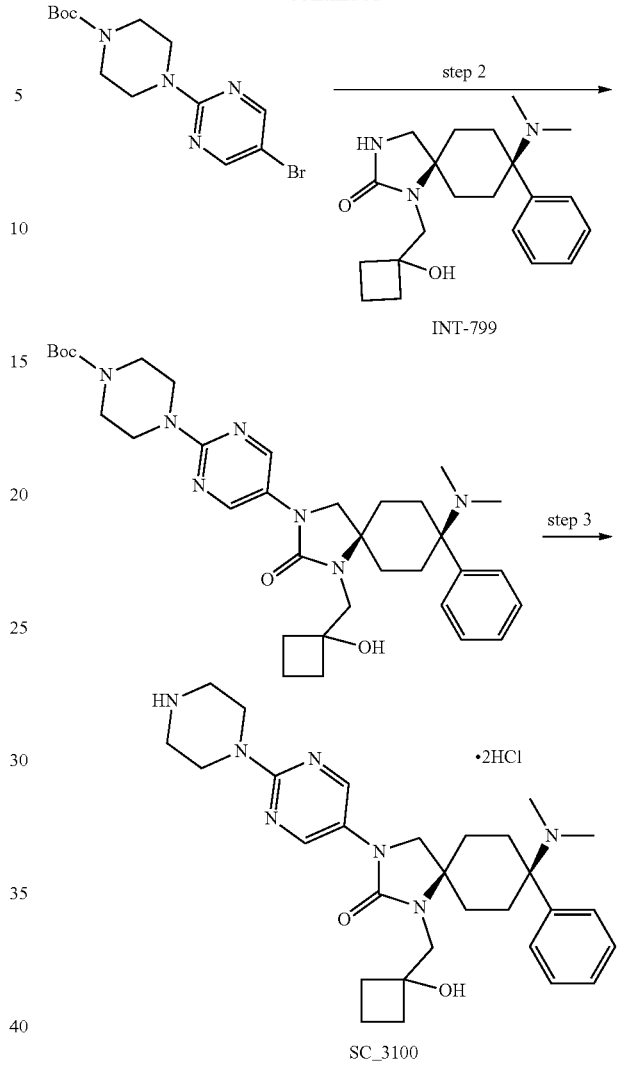

Step 1: tert-butyl 4-(5-bromopyrimidin-2-yl)piperazine-1-carboxylate

In analogy to the method described for SC_3097 step 1 tert-butyl piperazine-1-carboxylate was reacted with 5-bromo-2-chloropyrimidine to be converted into tert-butyl 4-(5-bromopyrimidin-2-yl)piperazine-1-carboxylate.

Step 2: tert-butyl 4-(5-((cis)-8-(dimethylamino)-1-((1-hydroxycyclobutyl)methyl)-2-oxo-8-phenyl-1,3-diazaspiro[4.5]decan-3-yl)pyrimidin-2-yl)piperazine-1-carboxylate $K_2CO_3$ (0.38 g, 2.8 mmol, 2.5 equiv.) was added to the suspension of CIS-8-(dimethylamino)-1-((1-hydroxycyclobutyl)methyl)-8-phenyl-1,3-diazaspiro[4.5]decan-2-one (0.4 g, 1.12 mmol, 1 equiv.) (INT-799) and tert-butyl 4-(5-bromopyrimidin-2-yl)piperazine-1-carboxylate (0.38 g, 1.12 mmol, 1 equiv.) in dioxane (25 mL) and the resulting mixture was purged with nitrogen for 5 min. Copper(I) iodide (0.21 g, 1.12 mmol, 1 equiv.) and trans-1,2-diaminocyclohexane (0.25 g, 2.24 mmol, 2 equiv.) were sequentially added, the reaction vessel was sealed and the reaction mixture was stirred for 10 h at 130° C. The reaction mixture was cooled down to RT and diluted with EtOAc (20 mL) and aq. ammonia (10 mL). The organic product was extracted with e EtOAc (2×50 mL). The combined organic layer was washed with brine (50 mL), dried over anhydrous $Na_2SO_4$ and concentrated under reduced pressure. Purification of the residue by column chromatography on silica gel (100-200 mesh) (60-70% EtOAc in petroleum ether) afforded 0.5 g (72%) of tert-butyl 4-(5-((cis)-8-(dimethylamino)-1-((1-hydroxycyclobutyl)methyl)-2-oxo-8-phenyl-1,3-diazaspiro[4.5]decan-3-yl)pyrimidin-2-yl)piperazine-1-carboxylate as an off white solid (TLC system: 1:1 EtOAc/pet ether, Rf: 0.3).

Step 3: CIS-8-(dimethylamino)-1-((1-hydroxycyclobutyl)methyl)-8-phenyl-3-(2-(piperazin-1-yl)pyrimidin-5-yl)-1,3-diazaspiro[4.5]decan-2-one hydrochloride (SC_3100)

4N HCl in dioxane (2 mL) was added to tert-butyl 4-(5-(cis-8-(dimethylamino)-1-((1-hydroxycyclobutyl) methyl)-2-oxo-8-phenyl-1,3-diazaspiro[4.5]decan-3-yl)pyrimidin-2-yl)piperazine-1-carboxylate (0.15 g, 0.24 mmol). The resulting mixture was stirred at 0° C. for 6 h and then concentrated under reduced pressure to give a pale yellow solid which was triturated with n-pentane and lyophilized with water for 16 h to yield 0.14 g of CIS-8-(dimethylamino)-1-((1-hydroxycyclobutyl)methyl)-8-phenyl-3-(2-(piperazin-1-yl)pyrimidin-5-yl)-1,3-diazaspiro[4.5]decan-2-one hydrochloride (SC_3100) as a pale yellow solid. $^1$H NMR (DMSO-d6): δ 10.42 (br s, 1H), 9.34 (br s, 2H), 8.63 (s, 2H), 7.70-7.68 (m, 2H), 7.54-7.50 (m, 3H), 3.88-3.86 (m, 4H), 3.77 (m, 4H), 3.16-3.11 (m, 6H), 2.52-2.49 (m, 6H), 2.47 (m, 2H), 2.10-2.07 (m, 2H), 2.00-1.95 (t, 2H), 1.87-1.81 (m, 3H), 1.70-1.68 (m, 2H), 1.58 (m, 1H). Mass: m/z 520.3 (M+H)+.

Synthesis of SC_3103: CIS-1-(cyclobutyl-methyl)-8-dimethylamino-3-[4-methyl-6-(trifluoromethyl)-pyridin-3-yl]-8-phenyl-1,3-diazaspiro[4.5]decan-2-one

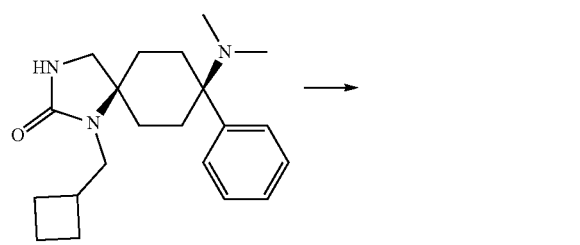

INT-987

$Cs_2CO_3$ (2 g, 6.451 mmol) was added to an argon purged solution of CIS-1-(cyclobutylmethyl)-8-(dimethylamino)-8-phenyl-1,3-diazaspiro[4.5]decan-2-one (INT-987) (1.1 g, 3.225 mmol, 1 equiv.), Xantphos (279 mg, 0.483 mmol, 0.15 equiv.), $Pd_2(dba)_3$ (295 mg, 0.322 mmol, 0.1 equiv.) and 5-bromo-4-methyl-2-(trifluoromethyl)pyridine (774 mg, 3.225 mmol, 1 equiv.) in 1,4-dioxane (55 mL). The mixture was purged again with argon for 15 min. The reaction mixture was stirred at 90° C. for 18 h, then cooled down to RT, filtered through Celite and washed with EtOAc (80 mL). The filtrate was concentrated under reduced pressure. The resulting residue was purified by flash chromatography (neutral alumina, 0-3% methanol in DCM) to afford 0.6 g (37%) of CIS-1-(cyclobutylmethyl)-8-(dimethylamino)-3-(4-methyl-6-(trifluoromethyl)pyridin-3-yl)-8-phenyl-1,3-diazaspiro[4.5]decan-2-one (SC_3103) as an off white solid. (TLC system: 5% MeOH in DCM; Rf: 0.5). $^1$H NMR (DMSO-d6): δ 8.56 (s, 1H), 7.80 (s, 1H), 7.34-7.24 (m, 5H), 3.71 (s, 2H), 3.17 (d, 2H), 2.70-2.56 (m, 3H), 2.31 (s, 3H), 2.17-2.11 (m, 2H), 2.03-2.00 (m, 8H), 1.82-1.73 (m, 4H), 1.54-1.41 (m, 4H). Mass: m/z 501.3 (M+H)+.

Synthesis of SC_3105: CIS-1-(cyclopropyl-methyl)-8-dimethylamino-3-(4-methylsulfonyl-phenyl)-8-phenyl-1,3-diazaspiro[4.5]decan-2-one

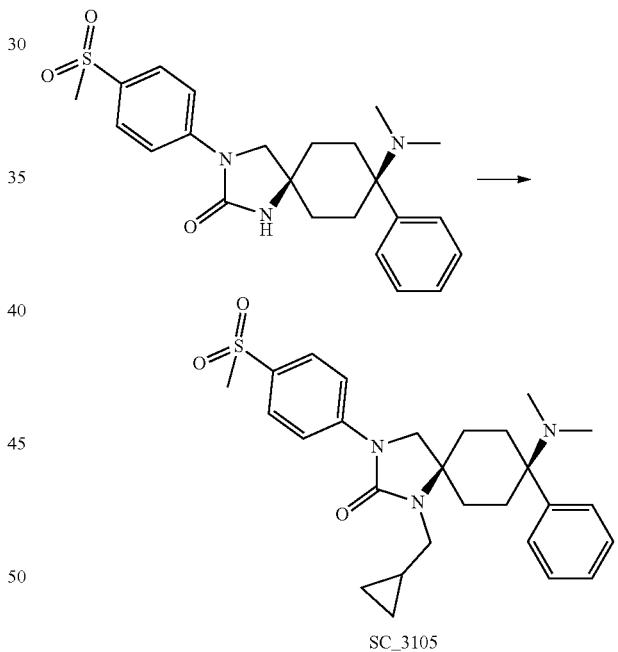

SC_3105

NaH (60% in mineral oil) (36.80 mg, 0.92 mmol) was added portionwise to the solution of CIS-8-(dimethylamino)-3-(4-(methylsulfonyl)phenyl)-8-phenyl-1,3-diazaspiro[4.5]decan-2-one (200 mg, 0.46 mmol, prepared from INT-976 and 1-bromo-4-(methylsulfonyl)benzene by analogy with SC_3103) in DMF (30 mL) at 0° C. under argon atmosphere and the resulting mixture was stirred for 10 min. (Bromomethyl)cyclopropane (122 mg, 0.92 mmol) was added dropwise at 0° C., ice bath was removed and the reaction mixture was further stirred for 4 h at room temperature. The reaction progress was monitored by TLC. The reaction mixture was diluted with water (30 mL) and the precipitated solid was filtered. Purification by column chromatography (silica gel 100-200 mesh, 50-60% ethyl acetate in hexane as eluent) to get 80 mg (35%) of CIS-1-(cyclopropylmethyl)-8-(dimethylamino)-3-(4-(methylsulfonyl)phenyl)-8-phenyl-1,3-diazaspiro[4.5]decan-2-one (SC_3105) as off white solid (TLC system: 10% MeOH in DCM; Rf: 0.70). 1H NMR (CDCl3): δ 7.85-7.83 (d, 2H), 7.73-7.71 (d, 2H), 7.39-7.36 (m, 2H), 7.32-7.27 (m, 3H), 3.64 (s, 2H), 3.20 (d, 2H), 3.00 (s, 3H), 2.75-2.71 (m, 2H), 2.43-2.36 (m, 2H), 2.07 (s, 6H), 1.57 (m, 2H), 1.50 (m, 2H), 1.11-1.06 (m, 1H), 0.59-0.54 (m, 2H), 0.41-0.37 (m, 2H). Mass: m/z 482.2 (M+H)+.

Synthesis of SC_3109: CIS-2-[8-Dimethylamino-1-[2-(1-methoxy-cyclobutyl)-ethyl]-2-oxo-8-phenyl-1,3-diazaspiro[4.5]decan-3-yl]-benzamide

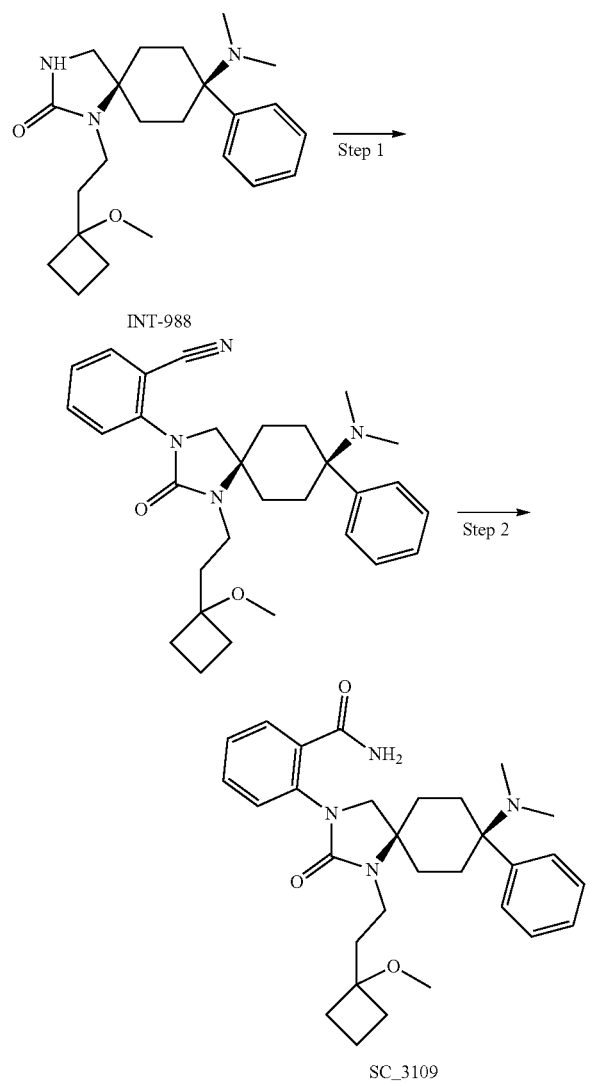

Step 1: CIS-2-(8-(dimethylamino)-1-(2-(1-methoxycyclobutyl)ethyl)-2-oxo-8-phenyl-1,3-diazaspiro[4.5]decan-3-yl)benzonitrile In analogy to the method described for SC_3103 CIS-8-(dimethylamino)-1-(2-(1-methoxycyclobutyl)ethyl)-8-phenyl-1,3-diazaspiro[4.5]decan-2-one was reacted with 2-bromobenzonitrile to be converted into CIS-2-(8-(dimethylamino)-1-(2-(1-methoxycyclobutyl)ethyl)-2-oxo-8-phenyl-1,3-diazaspiro[4.5]decan-3-yl)benzonitrile.

Step 2: CIS-2-[8-Dimethylamino-1-[2-(1-methoxycyclobutyl)-ethyl]-2-oxo-8-phenyl-1,3-diazaspiro[4.5]decan-3-yl]-benzamide SC_3109

CIS-2-[8-(dimethylamino)-1-[2-(1-methoxycyclobutyl)ethyl]-2-oxo-8-phenyl-1,3-diazaspiro[4.5]decan-3-yl]benzonitrile (57.0 mg, 1.0 equiv.) was dissolved in DMSO (1.6 mL), hydrogen peroxide (0.167 mL, 14.0 equiv., 30 mass % in water solution) and $K_2CO_3$ (32.4 mg, 2.0 equiv.) were added and the reaction mixture was stirred at RT for 18 h. The reaction mixture was then quenched with 10 mL water, extracted with DCM (3×10 mL), the combined organic extracts were dried over $Na_2SO_4$ and concentrated under reduced pressure (24 mg crude product). The aqueous phase was concentrated to dryness (91 mg), suspended in DCM, the precipitate was filtered off and the organic solution was concentrated under reduced pressure to give additional 56 mg of the crude product. The combined crude product was purified by column chromatography on silica gel (DCM/EtOH 95/5) to give 37 mg (62%) of CIS-2-[8-dimethylamino-1-[2-(1-methoxy-cyclobutyl)-ethyl]-2-oxo-8-phenyl-1,3-diazaspiro[4.5]decan-3-yl]-benzamide (SC_3109) as a white solid. $^1$H NMR (600 MHz, DMSO) δ 7.52-7.48 (s, 1H), 7.47-7.31 (m, 7H), 7.29-7.23 (m, 1H), 7.25-7.22 (s, 1H), 7.24-7.18 (m, 1H), 3.68-3.65 (s, 3H), 3.13-3.10 (s, 2H), 3.09-3.02 (m, 2H), 2.71-2.65 (m, 2H), 2.21-2.12 (m, 2H), 2.09-1.99 (m, 2H), 2.02-1.98 (s, 6H), 1.97-1.86 (m, 4H), 1.77-1.67 (m, 1H), 1.64-1.52 (m, 3H), 1.44-1.36 (td, 2H). Mass: m/z 505.32 (M+H)$^+$.

Synthesis of SC_3112: CIS-2-(1-((1-hydroxycyclobutyl)methyl)-8-(methylamino)-2-oxo-8-phenyl-1,3-diazaspiro[4.5]decan-3-yl)benzonitrile

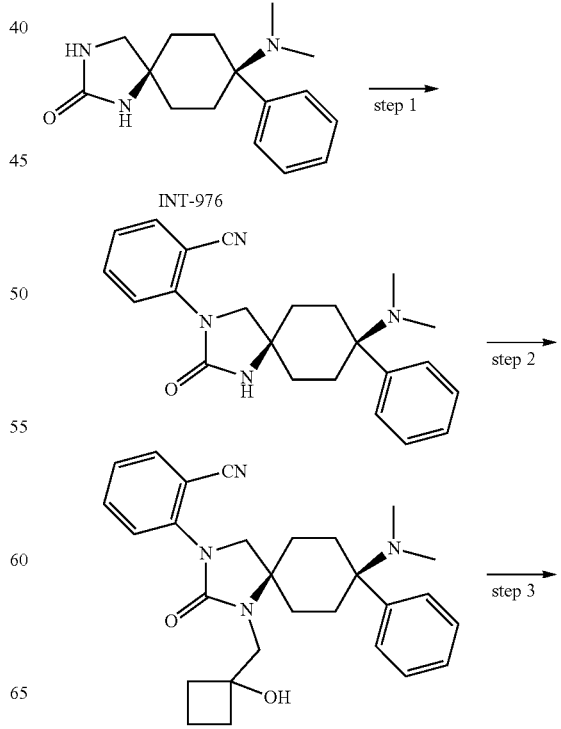

-continued

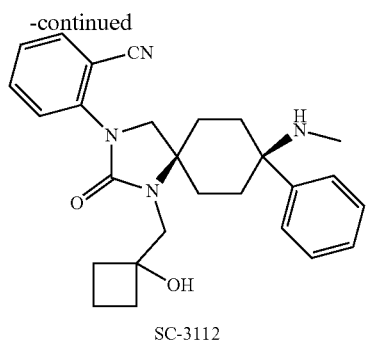

SC-3112

Step 1: CIS-2-(8-(dimethylamino)-2-oxo-8-phenyl-1,3-diazaspiro[4.5]decan-3-yl)benzonitrile In analogy to the method described for SC_3103 1-bromo-2-cyanobenzene was reacted with CIS-8-(dimethylamino)-8-phenyl-1,3-diazaspiro[4.5]decan-2-one (INT-976) to be converted into CIS-2-(8-(dimethylamino)-2-oxo-8-phenyl-1,3-diazaspiro[4.5]decan-3-yl)benzonitrile.

Step 2: CIS-2-(8-(dimethylamino)-1-((1-hydroxycyclobutyl)methyl)-2-oxo-8-phenyl-1,3-diazaspiro[4.5]decan-3-yl)benzonitrile To a solution of CIS-2-(8-(dimethylamino)-2-oxo-8-phenyl-1,3-diazaspiro[4.5]decan-3-yl)benzonitrile (500 mg, 1.336 mmol, 1.0 equiv.) in DMSO (16 ml) was added sodium hydroxide (213 mg, 5.334 mmol, 4.0 equiv.) and the mixture was stirred at 60° C. for 30 min. A solution of 1-oxa-spiro[2.3]hexane (237 mg, 6.68 mmol, 5.0 equiv.) in DMSO (4 ml) was added at RT and the reaction mixture was stirred at 55° C. for 16 h. The reaction mixture was diluted with water (100 ml) and extracted with EtOAc (100 ml). The organic layer was washed with water (50 ml) and brine (50 ml), dried over anhydrous $Na_2SO_4$ and concentrated under reduced pressure. The residue was purified by column chromatography on silica gel (EtOAc/Hexane, 7/3) to yield CIS-2-(8-(dimethylamino)-1-((1-hydroxycyclobutyl)methyl)-2-oxo-8-phenyl-1,3-diazaspiro[4.5]decan-3-yl)benzonitrile (200 mg, 0.436 mmol, 32%) as an off white solid. Mass: m/z 459.4 (M+H)+

Step 3: CIS-2-(1-((1-hydroxycyclobutyl)methyl)-8-(methylamino)-2-oxo-8-phenyl-1,3-diazaspiro[4.5]decan-3-yl)benzonitrile (SC_3112)

In analogy to the method described for SC_3099 CIS-2-(8-(dimethylamino)-1-((1-hydroxycyclobutyl)methyl)-2-oxo-8-phenyl-1,3-diazaspiro[4.5]decan-3-yl)benzonitrile was reacted with N-iodosuccinimide to be converted into CIS-2-(1-((1-hydroxycyclobutyl)methyl)-8-(methylamino)-2-oxo-8-phenyl-1,3-diazaspiro[4.5]decan-3-yl)benzonitrile (SC_3112). Yield: 29%. $^1$H NMR (DMSO-d6, 400 MHz), δ (ppm)=7.75 (dd, 1H, J=7.76 Hz, 1.16 Hz), 7.70-7.65 (m, 1H), 7.50 (d, 1H, J=8.16 Hz), 7.44-7.42 (m, 2H), 7.35-7.25 (m, 3H), 7.17-7.15 (m, 1H), 5.49 (s, 1H), 3.85 (s, 2H), 3.32 (s, 2H), 2.29-2.23 (m, 2H), 2.12-2.23 (m, 2H), 1.87 (bs, 6H), 1.73-1.46 (m, 6H). Mass: m/z 445.26 (M+H)$^+$.

Synthesis of SC_3120: CIS-8-(dimethylamino)-3-(2-(3-oxopiperazin-1-yl)pyrimidin-5-yl)-8-phenyl-1,3-diazaspiro[4.5]decan-2-one

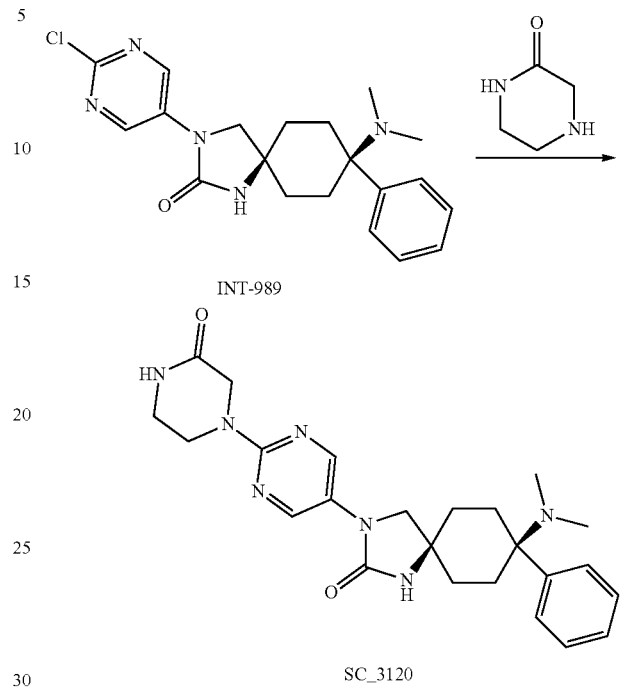

INT-989

SC_3120

CIS-3-(2-chloropyrimidin-5-yl)-8-(dimethylamino)-8-phenyl-1,3-diazaspiro[4.5]decan-2-one (INT-989) (100 mg, 0.259 mmol) was placed into a reaction vial for microwave reactor (5 mL), the vial was flushed with nitrogen, anhydrous n-butanol (50 equiv., 13.0 mmol, 1.2 mL), diisopropylethylamine (5 equiv., 1.30 mmol, 0.224 mL) and piperazine-2-one (1.2 equiv., 0.311 mmol, 31 mg) were added, the vial was sealed and the reaction mixture was stirred for 2.5 h at 140° C. (conventional heating). The reaction mixture was cooled down, transferred into a 1-neck flask and concentrated under reduced pressure. The resulting residue (128 mg) was purified by flash chromatography on aluminium oxide (neutral) (DCM/MeOH gradient 100/0 to 97/3) to yield 65 mg (56%) CIS-8-(dimethylamino)-3-(2-(3-oxopiperazin-1-yl)pyrimidin-5-yl)-8-phenyl-1,3-diazaspiro-[4.5]decan-2-one (SC_3120). $^1$H NMR (600 MHz, DMSO) δ 8.60 (s, 2H), 8.01 (s, 1H), 7.46 (s, 1H), 7.43-7.30 (m, 4H), 7.27 (td, 1H), 4.09 (s, 2H), 3.91-3.75 (m, 2H), 3.62-3.40 (m, 2H), 3.30-3.09 (m, 2H), 2.61-2.51 (m, 2H), 2.44-2.25 (m, 2H), 1.97 (s, 6H), 1.93-1.80 (m, 2H), 1.55-1.41 (m, 2H). Mass: m/z 437.27 (M+H)$^+$.

Synthesis of SC_3129: CIS-3-(5-(8-(dimethylamino)-2-oxo-8-phenyl-1,3-diazaspiro[4.5]decan-3-yl)pyrimidin-2-yl)benzonitrile

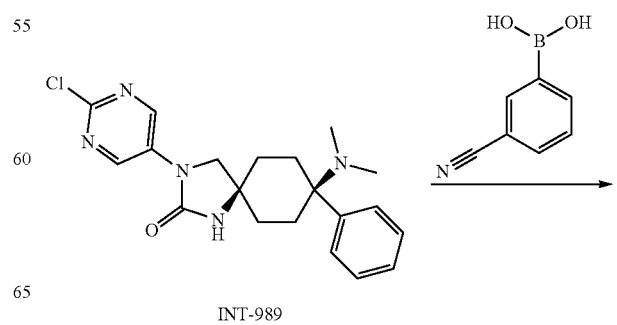

INT-989

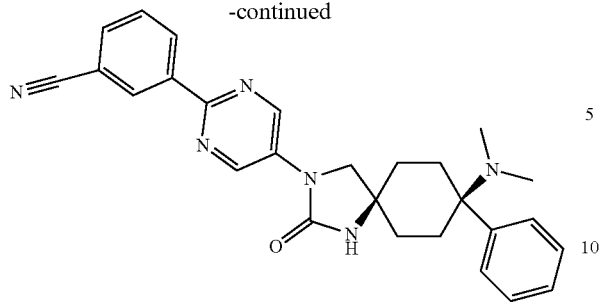

SC_3129

CIS-3-(2-chloropyrimidin-5-yl)-8-(dimethylamino)-8-phenyl-1,3-diazaspiro[4.5]decan-2-one (INT-989) (1 equiv., 0.47 mmol, 180 mg), Pd(PPh$_3$)$_4$ (0.1 equiv., 0,047 mmol, 54 mg) and (3-cyanophenyl)boronic acid (1.5 equiv., 0.70 mmol, 103 mg) were dissolved in degassed dry tetrahydrofurane (9.5 mL) and sodium carbonate 1M aq. sol. (1.9 equiv., 0.89 mmol, 0.89 mL) was added. The resulting clear reaction mixture was stirred overnight at 70° C. Additional portion of Pd(PPh$_3$)$_4$ (0.1 equiv., 0,047 mmol, 54 mg) was added and the reaction was stirred further 12 h at 70° C. The reaction mixture was diluted with EtOAc (50 mL), stirred for 10 min, the precipitate was filtered off and the filtrate was concentrated under reduced pressure. The resulting residue (285 mg) was purified by flash chromatography on silica gel (gradient DCM/MeOH, 100/0 to 80/20) to yield 130 mg (62%) of CIS-3-(5-(8-(dimethylamino)-2-oxo-8-phenyl-1,3-diazaspiro[4.5]decan-3-yl)pyrimidin-2-yl)benzonitrile (SC_3129). $^1$H NMR (600 MHz, DMSO) δ 9.13 (s, 2H), 8.60 (dp, 2H), 7.93 (dt, 1H), 7.88 (s, 1H), 7.72 (dd, 1H), 7.42-7.35 (m, 5H), 7.28 (d, 1H), 3.73 (s, 2H), 2.01-1.91 (m, 2H), 1.98 (s, 10H), 1.57-1.48 (m, 2H). Mass: m/z 453.24 (M+H)+.

Synthesis of SC_3130: CIS-8-(dimethylamino)-3-(2-(4-(methylsulfonyl)piperazin-1-yl)pyrimidin-5-yl)-8-phenyl-1,3-diazaspiro[4.5]decan-2-one

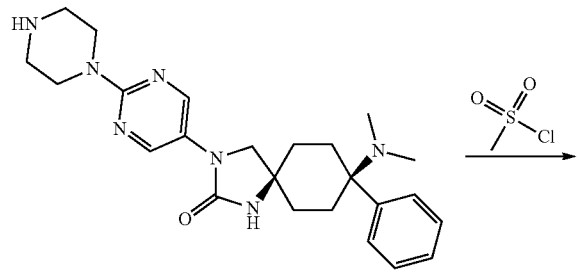

SC_3130

CIS-8-(dimethylamino)-8-phenyl-3-(2-(piperazin-1-yl)pyrimidin-5-yl)-1,3-diazaspiro[4.5]decan-2-one (SC_3124) (100 mg, 0.23 mmol) was dissolved in DCM (150 equiv., 34 mmol, 2.2 mL) under nitrogen atmosphere. To the resulting solution 4-dimethylaminopyridine (0.05 equiv., 0.012 mmol, 1.4 mg) and diisopropylethylamine (3 equiv., 0.67 mmol, 0.119 mL) were added and the mixture was cooled to 0° C. Methansulfonylchloride (2 equiv., 0.46 mmol, 0.036 mL) was added, ice bath was removed and the reaction mixture was stirred for 2 h at RT. The reaction mixture was quenched with water (5 mL), diluted with DCM (10 mL), the resulting brown suspension was filtered through a glass filter, the filtrate transferred to a separating funnel, the organic phase separated and the aqueous phase extracted with DCM (2×10 mL). The combined organic phases were dried over MgSO$_4$ and concentrated under reduced pressure. The resulting residue (81 mg) was purified by flash chromatography on aluminium oxide (gradient DCM/EtOH 97/3 to 96/4) to yield 51 mg (43%) of CIS-8-(dimethylamino)-3-(2-(4-(methylsulfonyl)piperazin-1-yl)pyrimidin-5-yl)-8-phenyl-1,3-diazaspiro-[4.5]decan-2-one (SC_3130). $^1$H NMR (600 MHz, DMSO) δ 8.59 (s, 2H), 7.46 (s, 1H), 7.39 (d, 1H), 7.37 (s, 3H), 7.28 (d, 1H), 3.79-3.74 (m, 4H), 3.54 (s, 2H), 3.18-3.13 (m, 4H), 2.87 (s, 3H), 2.43-2.32 (m, 2H), 1.97 (s, 6H), 1.92-1.87 (m, 2H), 1.51-1.41 (m, 2H). Mass: m/z 514.26 (M+H)$^+$.

Synthesis of SC_3132: CIS-8-((cyclopropylmethyl)(methyl)amino)-8-phenyl-3-(2-(trifluoromethyl)pyrimidin-5-yl)-1,3-diazaspiro[4.5]decan-2-one

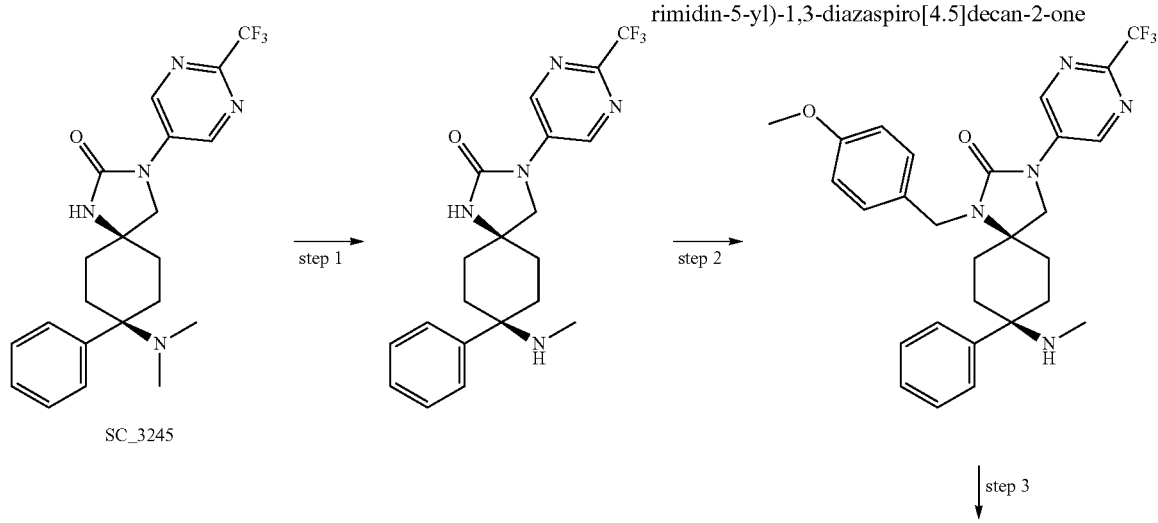

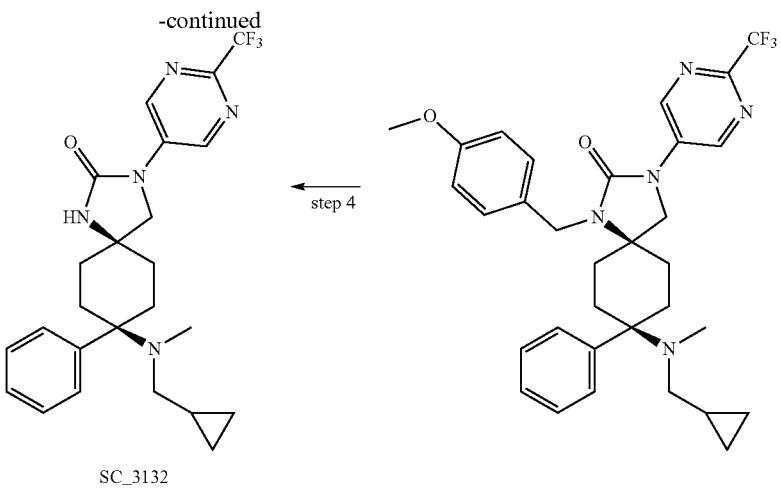

Step 1: CIS-8-(methylamino)-8-phenyl-3-(2-(trifluoromethyl)pyrimidin-5-yl)-1,3-diazaspiro[4.5]decan-2-one In analogy to the method described for SC_3099 CIS-8-(dimethylamino)-8-phenyl-3-(2-(trifluoromethyl)pyrimidin-5-yl)-1,3-diazaspiro[4.5]decan-2-one (SC_3245) was reacted with N-iodosuccinimide to be converted into CIS-8-(methylamino)-8-phenyl-3-(2-(trifluoromethyl)pyrimidin-5-yl)-1,3-diazaspiro[4.5]decan-2-one.

Step 2: CIS-1-(4-methoxybenzyl)-8-(methylamino)-8-phenyl-3-(2-(trifluoromethyl)pyrimidin-5-yl)-1,3-diazaspiro[4.5]decan-2-one NaH (60% in mineral oil) (296.3 mg, 7.407 mmol, 1.5 equiv.) was added portionwise to the solution CIS-8-(methylamino)-8-phenyl-3-(2-(trifluoromethyl)pyrimidin-5-yl)-1,3-diazaspiro[4.5]decan-2-one (2 g, 4.938 mmol, 1 equiv.) in DMF (20 mL) at 0° C. under argon atmosphere and the resulting mixture was stirred for 10 min. 1-(Bromomethyl)-4-methoxybenzene (1.092 g, 5.432 mmol, 1.1 equiv.) was added dropwise. The reaction mixture was allowed to warm up to RT and stirred for 16 h. The reaction progress was monitored by LCMS. The reaction mixture was diluted with water (150 mL) and the organic product was extracted with EtOAc (3×60 mL). The combined organic extracts were dried over anhydrous $Na_2SO_4$ and concentrated under reduced pressure. The resulting residue was purified by flash chromatography (silica gel 230-400 mesh; 0-4% MeOH/DCM) to afford 2 g (77%) of CIS-1-(4-methoxybenzyl)-8-(methylamino)-8-phenyl-3-(2-(trifluoromethyl)pyrimidin-5-yl)-1,3-diazaspiro[4.5]decan-2-one as an off white solid (TLC system 5% MeOH in DCM Rf: 0.55).

Step 3: CIS-8-((cyclopropylmethyl)(methyl)amino)-1-(4-methoxybenzyl)-8-phenyl-3-(2-(trifluoromethyl)pyrimidin-5-yl)-1,3-diazaspiro[4.5]decan-2-one (Bromomethyl)cyclopropane (0.461 mL, 4.762 mmol, 5 equiv.) was added dropwise to a mixture of CIS-1-(4-methoxybenzyl)-8-(methylamino)-8-phenyl-3-(2-(trifluoromethyl)pyrimidin-5-yl)-1,3-diazaspiro-[4.5]decan-2-one (500 mg, 0.952 mmol, 1 equiv.) and $K_2CO_3$ (657 mg, 4.762 mmol, 5 equiv.) in acetonitrile (20 mL) at RT under argon atmosphere. The reaction vessel was sealed and the mixture was stirred at 95° C. for 24 h. Reaction progress was monitored by LCMS. The reaction mixture was diluted with water (50 mL) and the organic product was extracted with EtOAc (2×50 mL). The combined organic extracts were dried over anhydrous $Na_2SO_4$ and concentrated under reduced pressure. The resulting residue was purified by flash chromatography (silica gel 230-400 mesh; 0-40% EtOAc/petroleum ether) to afford 220 mg (39%) of CIS-8-((cyclopropylmethyl)(methyl)amino)-1-(4-methoxybenzyl)-8-phenyl-3-(2-(trifluoromethyl)pyrimidin-5-yl)-1,3-diazaspiro[4.5]decan-2-one as an off white solid (TLC 50% EtOAc in petroleum ether, Rf: 0.65) and 230 mg of the unreacted starting material.

Step 4: CIS-8-((cyclopropylmethyl)(methyl)amino)-8-phenyl-3-(2-(trifluoromethyl)pyrimidin-5-yl)-1,3-diazaspiro[4.5]decan-2-one (SC_3132)

TFA (4.2 mL) was added drop wise to a solution of CIS-8-((cyclopropylmethyl)(methyl)amino)-1-(4-methoxybenzyl)-8-phenyl-3-(2-(trifluoromethyl)pyrimidin-5-yl)-1,3-diazaspiro[4.5]decan-2-one (210 mg, 0.363 mmol) in DCM (0.05 mL) at 0° C. under argon atmosphere. The reaction mixture was allowed to warm up to RT and stirred for 16 h. The reaction progress was monitored by LCMS. The excess of TFA was evaporated under reduced pressure and the residual amount of TFA was removed as an azeotropic mixture with DCM (2×5 mL). The crude product was purified by preparative HPLC to yield 105 mg (63%) of CIS-8-((cyclopropylmethyl)(methyl)amino)-8-phenyl-3-(2-(trifluoromethyl)pyrimidin-5-yl)-1,3-diazaspiro[4.5]decan-2-one (SC_3132) as an off white solid (TLC system 50% EtOAc in pe ether, Rf: 0.35). $^1$H NMR (DMSO-d6): δ 9.17 (s, 2H), 8.10 (br s, 1H), 7.35-7.33 (m, 4H), 7.25-7.22 (m, 1H), 3.72 (s, 2H), 2.43 (m, 2H), 2.13 (s, 3H), 1.97-1.82 (m, 6H), 1.49 (m, 2H), 0.75-0.71 (m, 1H), 0.41-0.39 (m, 2H), 0.06-0.01 (m, 2H). Mass: m/z=460.2 (M+H).

Synthesis of SC_3133: CIS-8-Dimethylamino-3-[2-(4-methyl-piperazine-1-carbonyl)-pyrimidin-5-yl]-8-phenyl-1,3-diazaspiro[4.5]decan-2-one

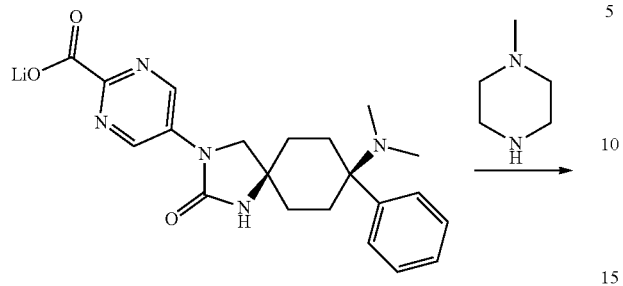

INT-990

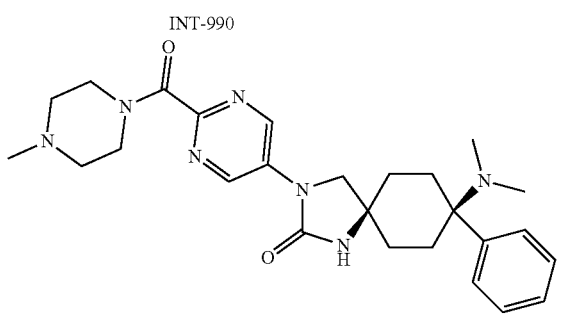

SC_3133

1-Methylpiperazine (2 equiv., 0.5 mmol, 55 μL) and [5-[8-(dimethylamino)-2-oxo-8-phenyl-1,3-diazaspiro[4.5]decan-3-yl]pyrimidine-2-carbonyl]oxylithium (INT-990) (100 mg, 0.25 mmol) were suspended in DCM (1.6 mL), triethylamine (10 equiv., 2.5 mmol, 336 μL) and propylphosphonic anhydride (>50 wt. % solution in ethyl acetate) (2 equiv., 0.5 mmol, 297 μL) were sequentially added and the reaction mixture was stirred at RT for 2 h. The resulting mixture was quenched with 2M aq. NaOH (2 mL), organic phase was separated and aqueous phase was extracted with dichloromethane (3×10 mL). The combined organic extracts were dried over Na₂SO₄ and concentrated under reduced pressure. The residue (88 mg) was dissolved in 3 mL DCM and 6 mL pentane were slowly added. The resulting mixture was stirred for 30 min. The precipitate was filtered off and dried under reduced pressure to give 69 mg (58%) of CIS-8-dimethylamino-3-[2-(4-methyl-piperazine-1-carbonyl)-pyrimidin-5-yl]-8-phenyl-1,3-diazaspiro[4.5]decan-2-one (SC_3133). ¹H NMR (600 MHz, DMSO) δ 9.03 (s, 2H), 7.87 (s, 1H), 7.42-7.34 (m, 5H), 7.28 (d, 1H), 3.69 (s, 2H), 3.62 (dd, 2H), 3.17-3.12 (m, 2H), 2.57-2.51 (m, 2H), 2.36 (t, 2H), 2.25-2.21 (m, 2H), 2.21 (s, 3H), 1.98-1.89 (m, 2H), 1.96 (s, 6H), 1.56-1.46 (m, 2H). Mass: m/z 478.29 (M+H)⁺.

Synthesis of SC_3146: CIS-5-(8-(dimethylamino)-2-oxo-8-phenyl-1,3-diazaspiro[4.5]decan-3-yl)pyrimidine-2-carboxamide

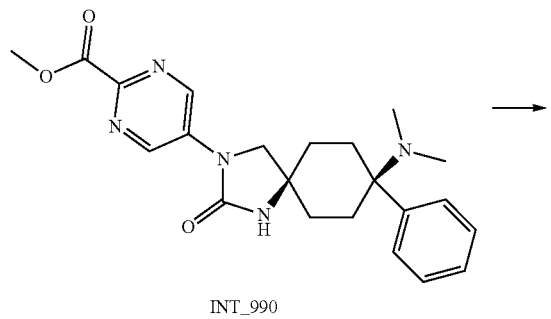

INT_990

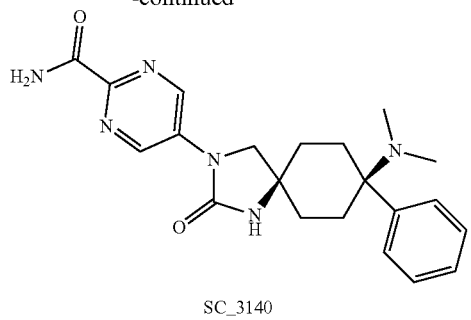

SC_3140

Methyl CIS-5-(8-(dimethylamino)-2-oxo-8-phenyl-1,3-diazaspiro[4.5]decan-3-yl)pyrimidine-2-carboxylate (INT-990) (100 mg, 0.244 mmol) was dissolved in 7N NH₃ in methanol (25 equiv. NH₃, 0.9 mL) in a microwave reactor vial. The reaction vessel was sealed, the reaction mixture was stirred for 5 days at RT and then concentrated under reduced pressure. The residue was purified by flash chromatography on neutral aluminum oxide (DCM/EtOH, gradient 90/10 to 74/26) to yield 38 mg (39%) of CIS-5-(8-(dimethylamino)-2-oxo-8-phenyl-1,3-diazaspiro[4.5]decan-3-yl)pyrimidine-2-carboxamide (SC_3140). ¹H NMR (600 MHz, DMSO) δ 9.07 (s, 2H), 8.02 (d, 1H), 7.93 (s, 1H), 7.59-7.55 (m, 1H), 7.38 (d, 4H), 7.28 (ddd, 1H), 3.72 (s, 2H), 2.49-2.37 (m, 2H), 1.99-1.92 (m, 8H), 1.88-1.75 (m, 2H), 1.56-1.45 (m, 2H). Mass: m/z 395.22 (M+H)⁺.

Synthesis of SC_3146: methyl CIS-2-(4-(5-(8-(dimethylamino)-2-oxo-8-phenyl-1,3-diazaspiro[4.5]decan-3-yl)pyrimidin-2-yl)piperazin-1-yl)acetate

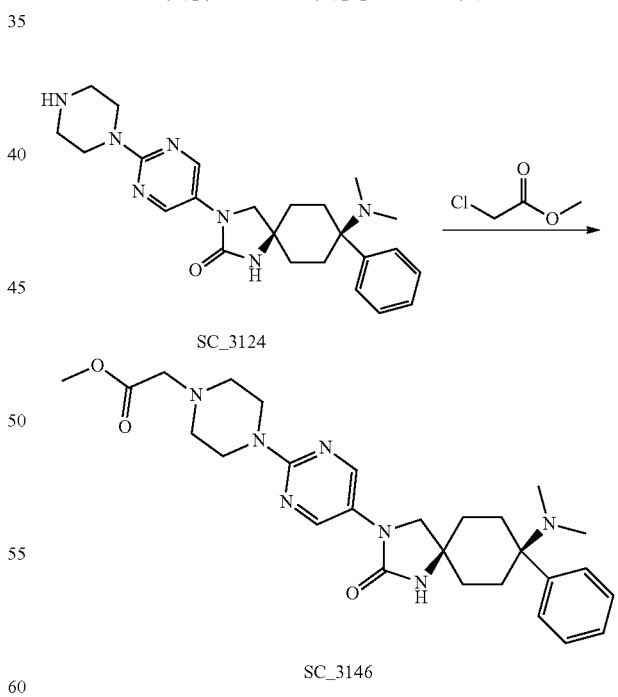

CIS-8-(dimethylamino)-8-phenyl-3-(2-(piperazin-1-yl)pyrimidin-5-yl)-1,3-diazaspiro[4.5]decan-2-one (SC_3124) (200 mg, 0.46 mmol) was dissolved in dry acetonitrile (5 mL) under nitrogen atmosphere, K₂CO₃ (1.2 equiv., 0.55 mmol, 76 mg) and methyl-2-chloroacetate (1.5 equiv., 0.69 mmol, 0.06 mL) were sequentially added and the reaction mixture was stirred at reflux for 5 h. A new portion of methyl-2-chloroacetate (1.5 equiv., 0.69 mmol, 0.06 mL) was added and the reaction mixture was stirred at reflux overnight. The reaction mixture was concentrated under reduced pressure. The residue was suspended in DCM, the precipitate was filtered off and washed with DCM. The combined filtrate was concentrated under reduced pressure to give 106 mg of crude product. Flash chromatography on silica gel (eluent DCM/EtOH gradient 98/2 to 96/4) yielded 168 mg (72%) of methyl CIS-2-(4-(5-(8-(dimethylamino)-2-oxo-8-phenyl-1,3-diazaspiro[4.5]decan-3-yl)pyrimidin-2-yl)piperazin-1-yl)acetate (SC_3146). $^1$H NMR (600 MHz, DMSO) δ 8.54 (s, 2H), 7.42 (s, 1H), 7.37 (m, 4H), 7.27 (m, 1H), 3.63 (t, 7H), 3.52 (s, 2H), 3.27 (s, 2H), 2.54 (t, 4H), 2.45-2.30 (m, 2H), 1.96 (s, 6H), 1.93-1.83 (m, 4H), 1.52-1.42 (m, 2H). Mass: m/z 508.4 (M+H)$^+$.

Synthesis of SC_3162: CIS-8-(dimethylamino)-8-phenyl-3-(2-(pyridin-2-yl)pyrimidin-5-yl)-1,3-diazaspiro[4.5]decan-2-one

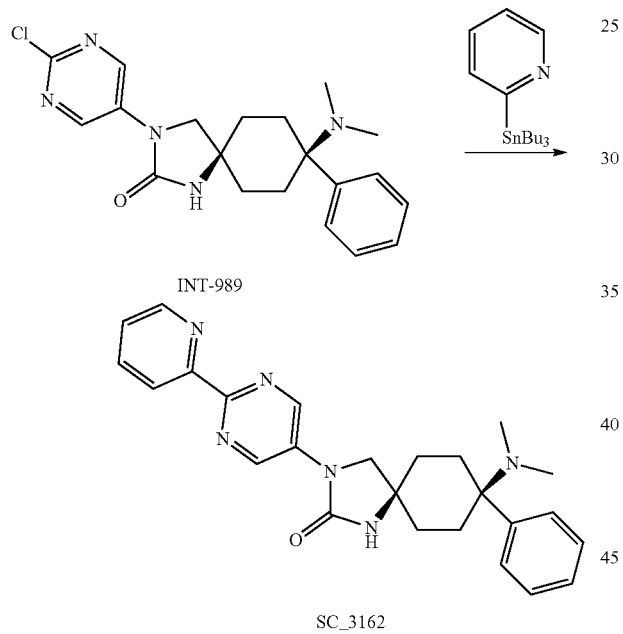

SC_3162

CIS-3-(2-chloropyrimidin-5-yl)-8-(dimethylamino)-8-phenyl-1,3-diazaspiro[4.5]decan-2-one (INT-989) (200 mg, 0.52 mmol), tributyl(2-pyridyl)stannane (1.5 equiv., 0.78 mmol, 286 mg) and Pd(PPh3)$_4$ (0.1 equiv., 0.052 mmol, 60 mg) were dissolved in degassed anhydrous DMF (150 equiv., 77.7 mmol, 6 mL) under nitrogen atmosphere. Cesium fluoride (2.2 equiv., 1.14 mmol, 173 mg) was added and the reaction mixture was stirred at 90° C. overnight. The resulting suspension was cooled down to RT, diluted with water (10 mL), extracted with ethylacetate (30 mL), then DCM (30 mL), the DCM phase was dried over MgSO$_4$ and concentrated under reduced pressure to give 320 mg of crude product. Flash chromatography on silica gel (eluent DCM/0.1N NH$_3$ in MeOH, gradient 95/5 to 70/30) yielded 72 mg (33%) of CIS-8-(dimethylamino)-8-phenyl-3-(2-(pyridin-2-yl)pyrimidin-5-yl)-1,3-diazaspiro[4.5]decan-2-one (SC_3162). $^1$H NMR (600 MHz, DMSO) δ 9.13 (s, 2H), 8.71-8.67 (m, 1H), 8.30 (d, 1H), 7.92 (td, 1H), 7.86 (s, 1H), 7.46 (dd, 1H), 7.43-7.35 (m, 5H), 7.31-7.25 (m, 1H), 3.73 (s, 2H), 2.48-2.33 (m, 2H), 2.00-1.78 (m, 10H), 1.57-1.47 (m, 2H). Mass: m/z 429.2 (M+H)$^+$.

Synthesis of SC_3169: CIS-2-(2-(8-(dimethylamino)-2-oxo-8-phenyl-1,3-diazaspiro[4.5]decan-3-yl)phenoxy)acetic acid

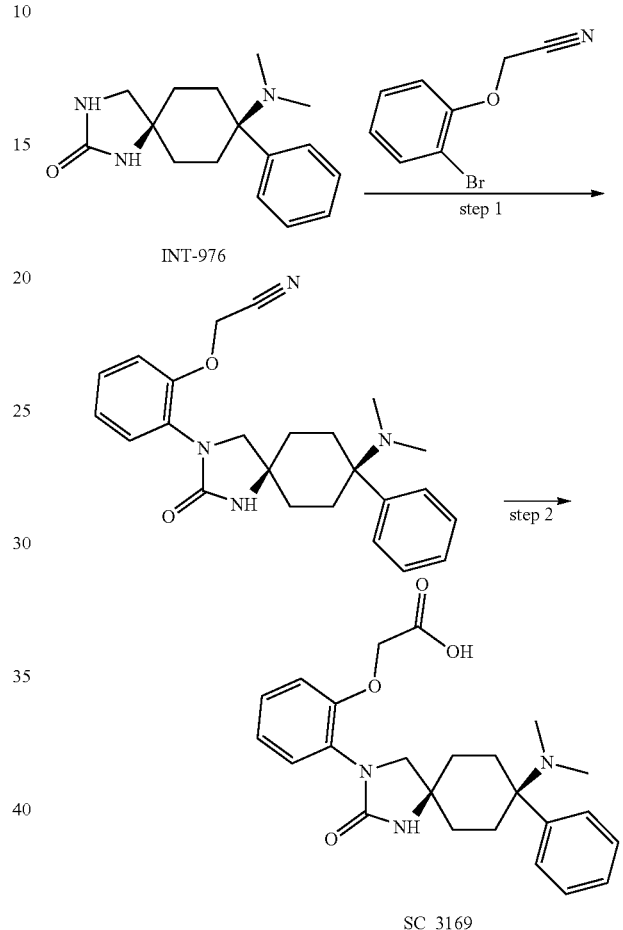

SC_3169

Step 1: CIS-2-(2-(8-(dimethylamino)-2-oxo-8-phenyl-1,3-diazaspiro[4.5]decan-3-yl)phenoxy)acetonitrile In analogy to the method described for SC_3103 CIS-8-(dimethylamino)-8-phenyl-1,3-diazaspiro[4.5]decan-2-one (INT-976) was reacted with 2-(2-bromophenoxy)acetonitrile to be converted into CIS-2-(2-(8-(dimethylamino)-2-oxo-8-phenyl-1,3-diazaspiro[4.5]decan-3-yl)phenoxy)acetonitrile.

Step 2: CIS-2-(2-(8-(dimethylamino)-2-oxo-8-phenyl-1,3-diazaspiro[4.5]decan-3-yl)phenoxy)acetic acid (SC_3169)

CIS-2-(2-(8-(dimethylamino)-2-oxo-8-phenyl-1,3-diazaspiro[4.5]decan-3-yl)phenoxy)acetonitrile (134 mg, 0.331 mmol) was dissolved in conc. aq. HCl (1.4 mL, 50 equiv.). The reaction mixture was heated to 100° C. for 2 h and cooled down to RT. The precipitate was filtered off, washed with water (2x) and dried under reduced pressure to give 31 mg (22%) of CIS-2-(2-(8-(dimethylamino)-2-oxo-8-phenyl-1,3-diazaspiro[4.5]decan-3-yl)phenoxy)acetic acid (SC_3169). ¹H NMR (600 MHz, DMSO) δ 7.75-7.71 (m, 1H), 7.59-7.48 (m, 4H), 7.27 (dd, 1H), 7.15 (ddd, 1H), 6.97-6.90 (m, 2H), 4.65 (s, 2H), 3.43 (s, 2H), 2.70 (d, 2H), 2.56 (s, 6H), 2.31 (t, 2H), 1.93-1.86 (m, 2H), 1.33-1.22 (m, 2H). Mass: m/z 424.2 (M+H)⁺.

Synthesis of SC_3173: CIS-8-(dimethylamino)-8-phenyl-3-(2-(piperazine-1-carbonyl)pyrimidin-5-yl)-1,3-diazaspiro[4.5]decan-2-one

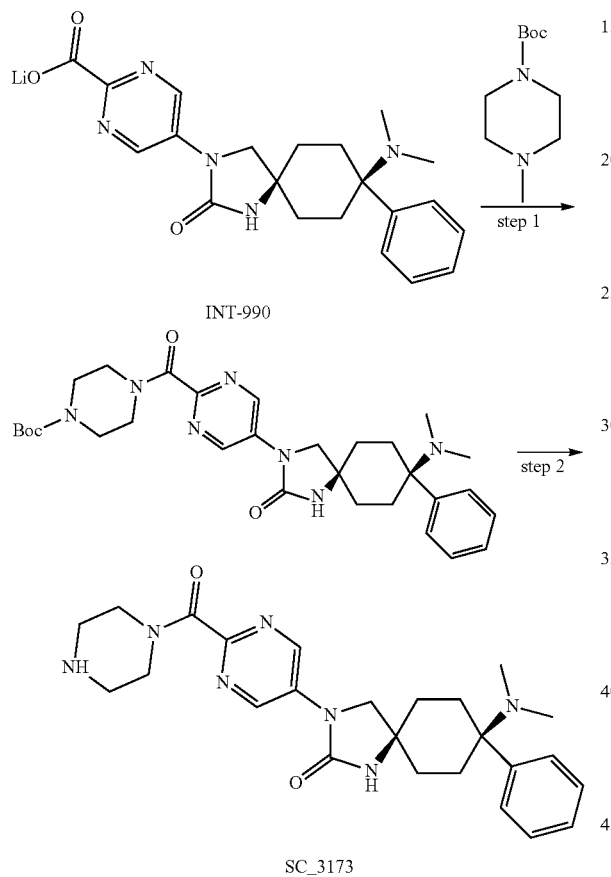

Step 1: CIS-tert-butyl 4-(5-(8-(dimethylamino)-2-oxo-8-phenyl-1,3-diazaspiro[4.5]decan-3-yl)pyrimidine-2-carbonyl)piperazine-1-carboxylate In analogy to the method described for SC_3133 lithium CIS-5-(8-(dimethylamino)-2-oxo-8-phenyl-1,3-diazaspiro[4.5]decan-3-yl)pyrimidine-2-carboxylate (INT-990) was reacted with 1-(tert-butoxycarbonyl)piperazine to be converted into CIS-tert-butyl 4-(5-(8-(dimethylamino)-2-oxo-8-phenyl-1,3-diazaspiro[4.5]decan-3-yl)pyrimidine-2-carbonyl)piperazine-1-carboxylate.

Step 2: CIS-8-(dimethylamino)-8-phenyl-3-(2-(piperazine-1-carbonyl)pyrimidin-5-yl)-1,3-diazaspiro[4.5]decan-2-one (SC_3173)

CIS-tert-butyl 4-(5-(8-(dimethylamino)-2-oxo-8-phenyl-1,3-diazaspiro[4.5]decan-3-yl)pyrimidine-2-carbonyl)piperazine-1-carboxylate (230 mg, 0.41 mmol) was dissolved in TFA (2.2 mL, 28.6 mmol, 70 equiv.). The reaction mixture was stirred at RT for 2.5 h and then concentrated under reduced pressure. The residue was dissolved in DCM and aq. sat Na₂CO₃ was added (until pH 10). The organic phase was separated and the aq. phase was extracted with DCM (2×). The combined organic extracts were dried over MgSO₄ and concentrated under reduced pressure. Recrystallization of the residue from DCM/pentane gave 105 mg (56%) of CIS-8-(dimethylamino)-8-phenyl-3-(2-(piperazine-1-carbonyl)pyrimidin-5-yl)-1,3-diazaspiro[4.5]decan-2-one (SC_3173). ¹H NMR (600 MHz, DMSO) δ 9.04 (s, 2H), 7.89 (s, 1H), 7.42-7.32 (m, 4H), 7.31-7.26 (m, 1H), 3.69 (s, 2H), 3.65 (t, 2H), 3.21 (t, 2H), 2.90 (t, 2H), 2.79-2.74 (m, 2H), 2.43 (s, 2H), 1.98 (s, 9H), 1.89-1.75 (m, 1H), 1.53-1.47 (m, 2H). Mass: m/z 464.3 (M+H)⁺.

Synthesis of SC_3182: CIS-8-(dimethylamino)-3-(2-(4-hydroxypiperidin-1-yl)pyrimidin-5-yl)-8-phenyl-1,3-diazaspiro[4.5]decan-2-one

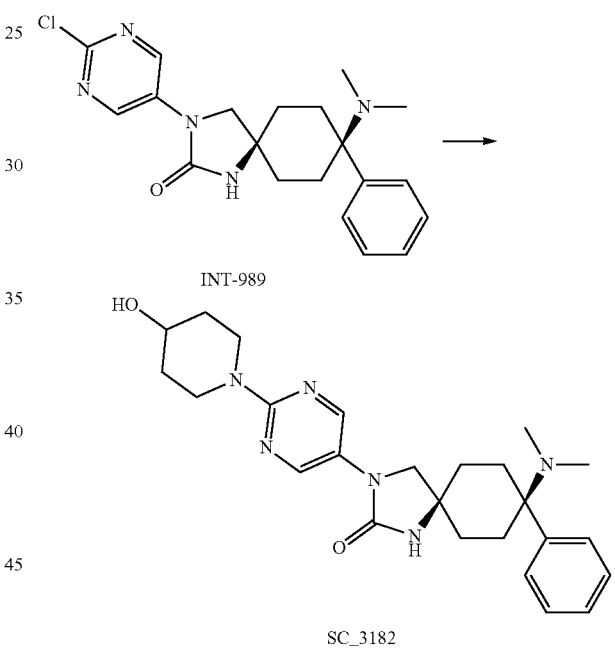

Et₃N (0.39 g, 3.89 mmol) was added to the solution of CIS-3-(2-chloropyrimidin-5-yl)-8-(dimethylamino)-8-phenyl-1,3-diazaspiro[4.5]decan-2-one (INT-989) (0.5 g, 1.29 mmol) and piperidin-4-ol (0.32 g, 3.24 mmol) in DMF (10 mL) at RT. The reaction mixture was stirred at 130° C. for 16 h, cooled down to RT and concentrated under reduced pressure. The residue was diluted with 10% aq. NaOH and the organic product was extracted with 1/9 v/v MeOH/DCM. The combined organic layer was dried over anhydrous Na₂SO₄ and concentrated in vacuo. The residue was purified by preparative TLC using 10% MeOH/DCM as eluent to afford 130 mg of CIS-8-(dimethylamino)-3-(2-(4-hydroxypiperidin-1-yl)pyrimidin-5-yl)-8-phenyl-1,3-diazaspiro[4.5]decan-2-one (SC_3182) as an off-white solid (TLC system: 10% MeOH in DCM; Rf: 0.1). ¹H NMR (DMSO-d6): δ 8.50 (s, 2H), 7.39-7.26 (m, 6H), 4.68 (d, 1H), 4.19-4.16 (m, 2H), 3.69-3.67 (m, 1H), 3.51 (s, 2H), 3.14 (t, 2H), 2.33 (m, 2H), 1.94-1.71 (m, 12H), 1.45 (m, 2H), 1.30-1.23 (m, 2H). Mass: m/z 451.2 (M+H)+.

Synthesis of SC_3186: CIS-8-(dimethylamino)-3-(3-methylpyridin-2-yl)-8-phenyl-1,3-diazaspiro[4.5]decan-2-one

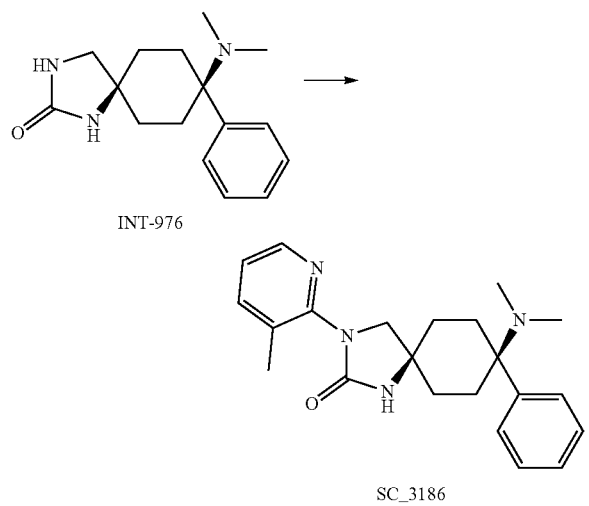

Compound was synthesized within a parallel array. An argon-flushed dry reaction vessel equipped with a septum was loaded with the solutions of INT-976 (0.1 M, 1 mL) and 1-bromo-2-methylbenzene (0.15 M, 1 mL) in dioxane. To the resulting mixture Cs$_2$CO$_3$ (200 µmol), XantPhos (10 µmol) and Pd$_2$(dba)$_3$ (5 µmol) were added. The reaction vessel was flushed with argon once again, sealed and the reaction mixture was shaken at 100° C. overnight. The resulting mixture was cooled down to RT and the solvent was removed under reduced pressure. The residue was taken up in 3 mL dichloromethane and 3 mL water, the organic phase was separated, the aqueous phase was extracted with dichloromethane (2×3 mL). Combined organic phases were concentrated under reduced pressure. The residue was purified by HPLC to give CIS-8-(dimethylamino)-3-(3-methylpyridin-2-yl)-8-phenyl-1,3-diazaspiro[4.5]decan-2-one (SC_3186). Mass: m/z 363.2 (M+H)+.

Synthesis of SC_3208: CIS-4-(5-(8-(dimethylamino)-2-oxo-8-phenyl-1,3-diazaspiro[4.5]decan-3-yl)pyrimidin-2-yl)indolin-2-one

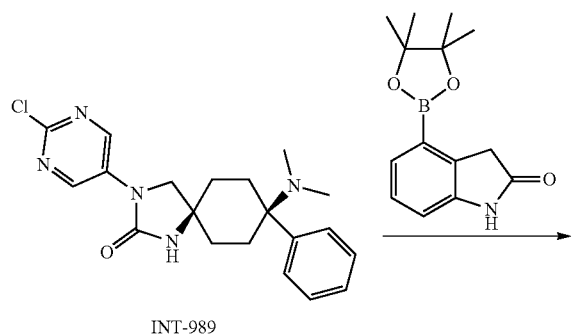

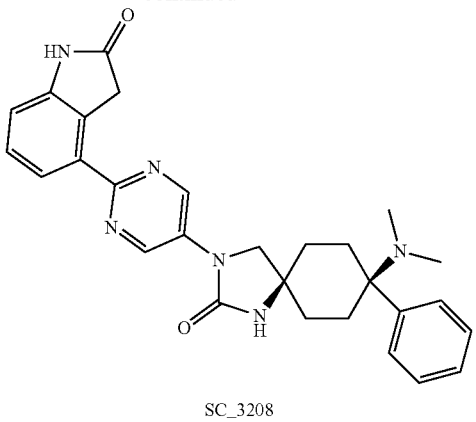

CIS-3-(2-chloropyrimidin-5-yl)-8-(dimethylamino)-8-phenyl-1,3-diazaspiro[4.5]decan-2-one (INT-989) (150 mg, 0.38 mmol), Pd(t-Bu$_3$P)$_2$ (0.1 equiv., 0.02 mmol, 10 mg) and 4-(4,4,5,5-tetramethyl-1,3,2-dioxaborolan-2-yl)indolin-2-one (2 equiv., 0.78 mmol, 201 mg) were dissolved in degassed anhydrous THF (80 equiv., 31 mmol, 2.5 mL) and 1M aq. Na$_2$CO$_3$ (5.5 equiv., 2.14 mmol, 2.14 mL) was added. The resulting mixture was stirred at 60° C. for 8 h and then at RT overnight. The reaction mixture was diluted with water until precipitation occurred. The precipitate was filtered off, suspended in 30 mL DCM, filtered off again, washed with pentane (5 mL) and dried under reduced pressure to give 143 mg (76%) of CIS-4-(5-(8-(dimethylamino)-2-oxo-8-phenyl-1,3-diazaspiro[4.5]decan-3-yl)pyrimidin-2-yl)indolin-2-one (SC_3208). $^1$H NMR (600 MHz, DMSO) δ 10.45 (s, 1H), 9.10 (s, 2H), 7.87 (d, 1H), 7.84-7.80 (m, 1H), 7.39 (d, 5H), 7.29 (dt, 2H), 6.91 (d, 1H), 3.82 (s, 2H), 3.72 (s, 2H), 2.41 (d, 2H), 2.03-1.74 (m, 9H), 1.60-1.44 (m, 3H). Mass: m/z 484.26 (M+H)+.

Synthesis of SC_3221: CIS-8-(dimethylamino)-3-(2-((2-hydroxyethyl)amino)pyrimidin-5-yl)-8-phenyl-1,3-diazaspiro[4.5]decan-2-one

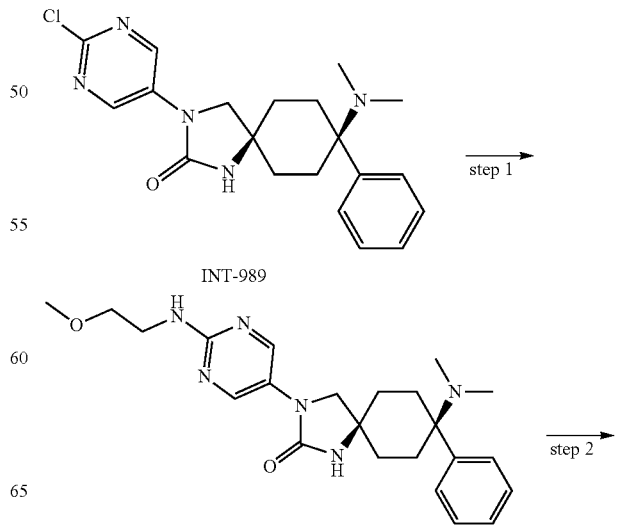

-continued

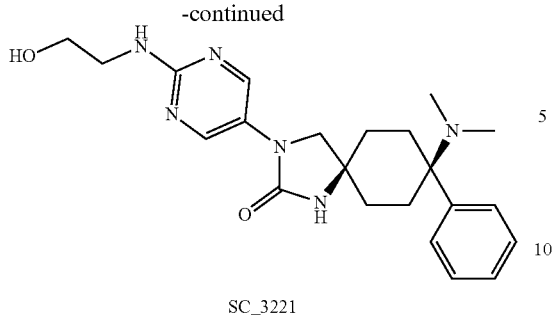

SC_3221

Step 1: CIS-8-(dimethylamino)-3-(2-((2-methoxyethyl)amino)pyrimidin-5-yl)-8-phenyl-1,3-diazaspiro[4.5]decan-2-one In analogy to the method described for SC_3103 2-methoxyethanamine was reacted with CIS-3-(2-chloropyrimidin-5-yl)-8-(dimethylamino)-8-phenyl-1,3-diazaspiro[4.5]decan-2-one (INT-989) to be converted into CIS-8-(dimethylamino)-3-(2-((2-methoxyethyl)amino)pyrimidin-5-yl)-8-phenyl-1,3-diazaspiro[4.5]decan-2-one.

Step 2: CIS-8-(dimethylamino)-3-(2-((2-hydroxyethyl)amino)pyrimidin-5-yl)-8-phenyl-1,3-diazaspiro[4.5]decan-2-one (SC_3221)

BBr$_3$ (1M in DCM) (2.2 mL, 2.22 mmol) was added to the solution of CIS-8-(dimethylamino)-3-(2-((2-methoxyethyl)amino)pyrimidin-5-yl)-8-phenyl-1,3-diazaspiro[4.5]decan-2-one (0.55 g, 1.06 mmol) in DCM (20 mL) at −78° C. over 15 min. The reaction mixture was stirred at RT for 4 h, then quenched with water and concentrated under reduced pressure. The residue was purified by preparative reverse phase HPLC to afford 82 mg (19%) of CIS-8-(dimethylamino)-3-(2-((2-hydroxyethyl)amino)pyrimidin-5-yl)-8-phenyl-1,3-diazaspiro[4.5]decan-2-one (SC_3221) (TLC system: 10% MeOH in DCM (Ammonia atmosphere); Rf: 0.3). $^1$H NMR (DMSO-d6): δ 8.41 (s, 2H), 7.39-7.24 (m, 6H), 6.70 (t, 1H), 4.64 (br, s, 1H), 3.50-3.45 (m, 4H), 3.28-3.25 (m, 2H), 2.37 (br m, 2H), 1.94-1.86 (m, 10H), 1.45 (m, 2H). Mass: m/z 411.2 (M+H)$^+$

Synthesis of SC_3224: CIS-3-(2-(1H-indazol-1-yl)pyrimidin-5-yl)-8-(dimethylamino)-8-phenyl-1,3-diazaspiro[4.5]decan-2-one

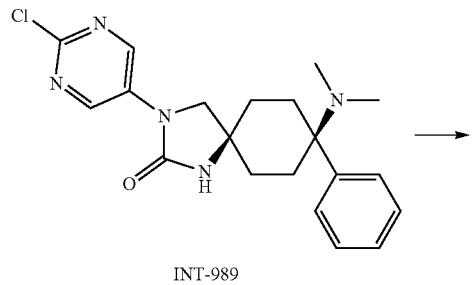

INT-989

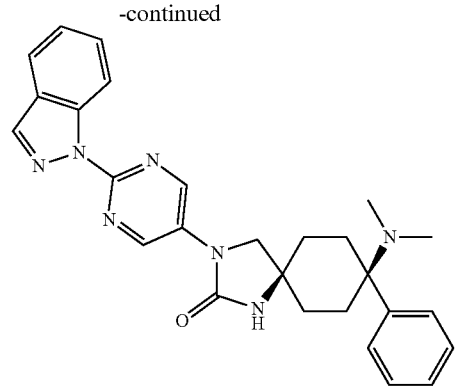

SC_3224

K$_2$CO$_3$ (0.53 g, 3.89 mmol) was added to the solution of CIS-3-(2-chloropyrimidin-5-yl)-8-(dimethylamino)-8-phenyl-1,3-diazaspiro[4.5]decan-2-one (500 mg, 1.29 mmol) and 1H-indazole (306 mg, 2.59 mmol) in DMF (10 mL). The reaction mixture was stirred at 140° C. for 48 h, cooled down to RT and concentrated under reduced pressure. The residue was diluted with DCM (50 mL), filtered through Celite and the filtrate was concentrated under reduced pressure. The residue was purified by flash chromatography using neutral alumina (0-10% MeOH/DCM) followed by reverse phase HPLC to afford 77 mg (13%) of CIS-3-(2-(1H-indazol-1-yl)pyrimidin-5-yl)-8-(dimethylamino)-8-phenyl-1,3-diazaspiro[4.5]decan-2-one (SC_3224) as off-white solid (TLC system: 10% MeOH in DCM; Rf: 0.6). $^1$H NMR (DMSO-d6): δ 9.10 (s, 2H), 8.57-8.55 (d, 1H), 8.41 (s, 1H), 7.89-7.87 (d, 1H), 7.82 (br s, 1H), 7.57-7.53 (t, 1H), 7.39-7.28 (m, 6H), 3.72 (s, 2H), 2.45 (m, 2H), 1.98-1.93 (m, 10H), 1.52 (m, 2H). Mass: m/z 468.2 (M+H)$^+$.

Synthesis of SC_3235: CIS-methyl 2-(2-(8-(dimethylamino)-2-oxo-8-phenyl-1,3-diazaspiro[4.5]decan-3-yl)phenoxy)acetate

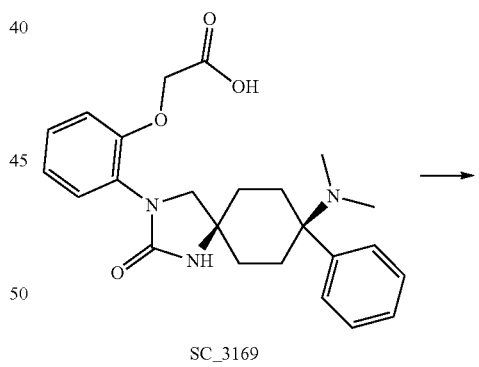

SC_3169

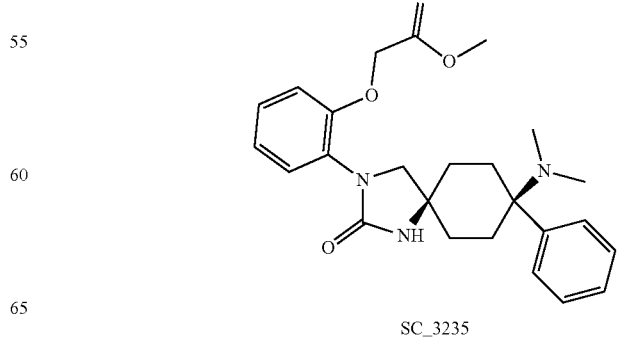

SC_3235

CIS-2-(2-(8-(dimethylamino)-2-oxo-8-phenyl-1,3-diazaspiro[4.5]decan-3-yl)phenoxy)acetic acid (120 mg, 0.28 mmol) was dissolved in methanol (1.4 mL, 125 equiv.) and thionyl chloride (4 equiv., 1.13 mmol, 83 µL) was added dropwise. The reaction mixture was stirred at RT overnight, diluted with aq. sat. NaHCO$_3$ and extracted with DCM (3×). The combined organic phases were dried over MgSO$_4$ and concentrated under reduced pressure. The residue (112 mg) was purified by flash chromatography on silica gel (gradient DCM/MeOH 97/3 to 88/12) to give 92 mg (74%) of CIS-methyl 2-(2-(8-(dimethylamino)-2-oxo-8-phenyl-1,3-diazaspiro[4.5]decan-3-yl)phenoxy)acetate (SC_3235). $^1$H NMR (600 MHz, DMSO) δ 7.40-7.33 (m, 4H), 7.29 (dd, 1H), 7.28-7.24 (m, 1H), 7.13 (td, 1H), 6.99-6.91 (m, 2H), 4.76 (s, 2H), 3.67 (s, 3H), 3.55 (s, 2H), 2.45-2.26 (m, 2H), 2.07 (s, 2H), 1.98 (s, 6H), 1.94-1.75 (m, 4H), 1.52-1.45 (m, 2H). Mass: m/z 438.2 (M+H)$^+$.

Synthesis of SC_3238: CIS-2-(5-(8-(dimethylamino)-2-oxo-8-phenyl-1,3-diazaspiro[4.5]decan-3-yl)pyrimidin-2-yl)benzonitrile

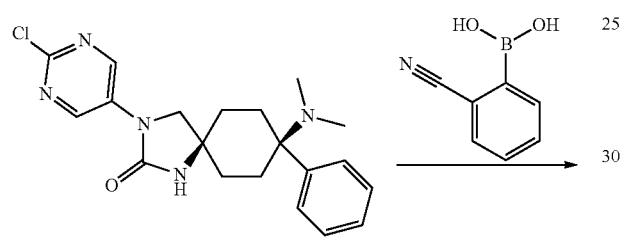

CIS-3-(2-chloropyrimidin-5-yl)-8-(dimethylamino)-8-phenyl-1,3-diazaspiro[4.5]decan-2-one (INT-989) (240 mg, 0.56 mmol), [1,1'-bis(diphenylphosphino)ferrocene]dichloropalladium(II) complex with dichloromethane (0.05 equiv., 0.028 mmol, 23 mg) and (2-cyanophenyl)boronic acid (1.125 equiv., 0.63 mmol, 92 mg) were dissolved in degassed 1,2-dimethoxyethane (100 equiv., 56 mmol, 5.8 mL) and Cs$_2$CO$_3$ (3.3 equiv., 1.84 mmol, 600 mg) in water (175 equiv., 98 mmol, 1.8 mL) was added. The resulting clear reaction mixture was stirred 3 days at 60° C. The reaction mixture was diluted with water (15 mL) and extracted with EtOAc (2×15 mL). Combined organic phases were dried over MgSO$_4$ and concentrated under reduced pressure. The residue (355 mg) was purified by flash chromatography on silica gel (gradient DCM/MeOH 95/5 to 70/30) to give 60 mg of product, which was further purified by HPLC to give 15.4 mg (6%) of CIS-2-(5-(8-(dimethylamino)-2-oxo-8-phenyl-1,3-diazaspiro[4.5]decan-3-yl)pyrimidin-2-yl)benzonitrile (SC_3238). $^1$H NMR (600 MHz, DMSO) δ 9.17 (s, 2H), 8.27 (dd, 1H), 7.94 (dd, 1H), 7.81 (td, 1H), 7.65 (td, 1H), 7.42-7.35 (m, 5H), 7.28 (ddt, 1H), 3.75 (s, 2H), 2.49-2.34 (m, 1H), 2.00-1.76 (m, 11H), 1.55-1.51 (m, 2H). Mass: m/z 453.24 (M+H)$^+$.

Synthesis of SC_3239: CIS-3-(2-aminopyrimidin-5-yl)-8-(dimethylamino)-8-phenyl-1,3-diazaspiro[4.5]decan-2-one

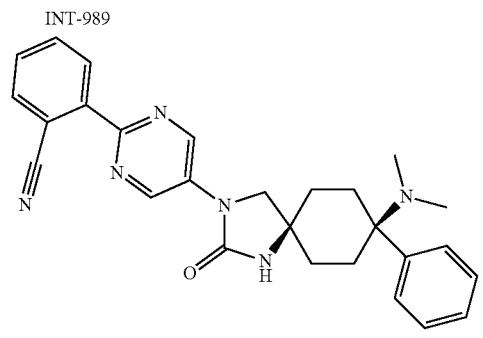

Microwave reactor vial was loaded with CIS-3-(2-chloropyrimidin-5-yl)-8-(dimethylamino)-8-phenyl-1,3-diazaspiro[4.5]decan-2-one (INT-989) (250 mg, 0.65 mmol), flushed with nitrogen, 7N solution of NH$_3$ in methanol (108 equiv., 70 mmol, 10 mL) and dioxane (37 equiv., 24 mmol, 2 mL) were added, the vial was sealed and the reaction mixture was stirred at 115° C. for 12 h in the microwave reactor. The reaction mixture was then cooled down to 4° C. overnight. The precipitate formed was filtered off, washed with DCM (small amount), water (2×), ether (2×) and dried under reduced pressure to give 180 mg (76%) of CIS-3-(2-aminopyrimidin-5-yl)-8-(dimethylamino)-8-phenyl-1,3-diazaspiro[4.5]decan-2-one (SC_3239) as an off-white solid. $^1$H NMR (600 MHz, DMSO) δ 8.39 (s, 2H), 7.40-7.32 (m, 5H), 7.26 (tt, 1H), 6.25 (s, 2H), 3.51 (s, 2H), 2.37 (s, 2H), 2.07 (s, 2H), 1.96 (s, 6H), 1.94-1.68 (m, 4H), 1.47 (d, 2H). Mass: m/z 367.23 (M+H)+.

Synthesis of SC_3240: CIS-N-(5-(8-(dimethylamino)-2-oxo-8-phenyl-1,3-diazaspiro[4.5]decan-3-yl)pyrimidin-2-yl)cyclopropanecarboxamide

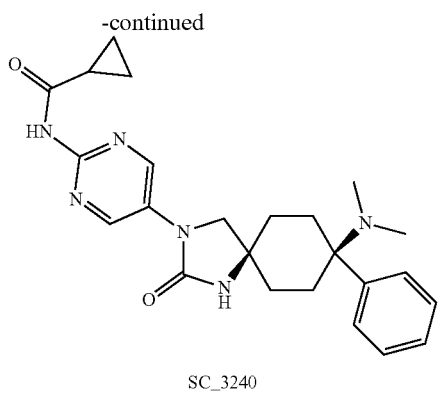

SC_3240

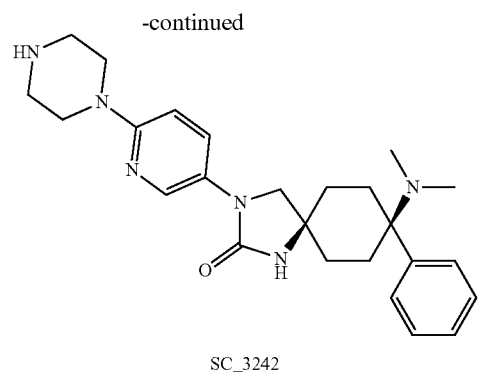

SC_3242

CIS-3-(2-aminopyrimidin-5-yl)-8-(dimethylamino)-8-phenyl-1,3-diazaspiro[4.5]decan-2-one (SC_3239) (50 mg, 0.14 mmol) and 4-dimethylaminopyridine (1.3 equiv., 0.18 mmol, 22 mg) were dissolved in dry pyridine (200 equiv., 27 mmol, 2.2 mL) under nitrogen atmosphere. Cyclopropancarbonyl chloride (1.3 equiv., 0.18 mmol, 16 µL) was added in one portion and the reaction mixture was stirred at RT for 3 h. Additional portion of cyclopropancarbonyl chloride (3 equiv., 0.42 mmol, 37 µL) was added and the reaction mixture was stirred at 90° C. for 1 h. The reaction mixture was diluted with water (5 mL) and aq. sat. NaHCO$_3$ (5 mL), extracted with DCM (3×10 mL), organic phases were washed with brine, dried over Na$_2$SO$_4$ and the solvent was removed under reduced pressure. The residue was suspended thoroughly in 3 mL DCM, the precipitate was filtered off, washed with ether and dried under reduced pressure to give 47 mg (79%) of CIS-N-(5-(8-(dimethylamino)-2-oxo-8-phenyl-1,3-diazaspiro[4.5]decan-3-yl)pyrimidin-2-yl)cyclopropanecarboxamide (SC_3240) as a white solid. $^1$H NMR (600 MHz, DMSO) δ 10.66 (s, 1H), 8.81 (s, 2H), 7.67 (s, 1H), 7.41-7.33 (m, 4H), 7.31-7.21 (m, 1H), 3.62 (s, 2H), 2.45-2.32 (m, 2H), 2.01 (td, 1H), 1.96 (s, 6H), 1.93-1.78 (m, 3H), 1.52-1.47 (m, 2H), 0.82-0.72 (m, 4H). Mass: m/z 435.3 (M+H)$^+$.

Synthesis of SC_3242: CIS-8-(dimethylamino)-8-phenyl-3-(6-(piperazin-1-yl)pyridin-3-yl)-1,3-diazaspiro[4.5]decan-2-one Step 1: 4-(5-bromopyrimidin-2-yl)piperazine In analogy to the method described for SC_3097 step 1 5-bromo-2-chloro-pyridine was reacted with piperazine to be converted into 4-(5-bromopyrimidin-2-yl)piperazine.

Step 2: CIS-8-(dimethylamino)-8-phenyl-3-(6-(piperazin-1-yl)pyridin-3-yl)-1,3-diazaspiro[4.5]decan-2-one (SC_3242)

CIS-8-(dimethylamino)-8-phenyl-1,3-diazaspiro[4.5]decan-2-one (INT-976) (80 mg, 0.29 mmol), 4-(5-bromopyrimidin-2-yl)piperazine (2 equiv., 0.56 mmol, 142 mg) and potassium phosphate (4 equiv., 1.17 mmol, 248 mg) were suspended in N,N'-dimethylethylenediamine (18 equiv., 5.27 mmol, 0.6 mL) under nitrogen atmosphere. The reaction mixture was stirred at 80° C. for 2 h, diluted with water (10 mL) and extracted with DCM (3×15 mL). The combined organic phases contained a precipitate which was filtered off, washed with isopropanol and dried under reduced pressure to give 79 mg (62%) of CIS-8-(dimethyl-amino)-8-phenyl-3-(6-(piperazin-1-yl)pyridin-3-yl)-1,3-diazaspiro[4.5]decan-2-one (SC_3242). $^1$H NMR (600 MHz, DMSO) δ 8.15 (d, 1H), 7.85 (dd, 1H), 7.41-7.33 (m, 4H), 7.32-7.23 (m, 2H), 6.74 (d, 1H), 3.51 (s, 2H), 3.30-3.25 (m, 4H), 2.78-2.73 (m, 4H), 2.43-2.31 (m, 2H), 1.96 (s, 6H), 1.93-1.79 (m, 4H), 1.50-1.42 (m, 2H). Mass: m/z 435.3 (M+H)$^+$.

Synthesis of SC_3275: CIS-8-(ethylamino)-1-((1-hydroxycyclobutyl)methyl)-8-phenyl-3-(2-(trifluoromethyl)pyrimidin-5-yl)-1,3-diazaspiro[4.5]decan-2-one

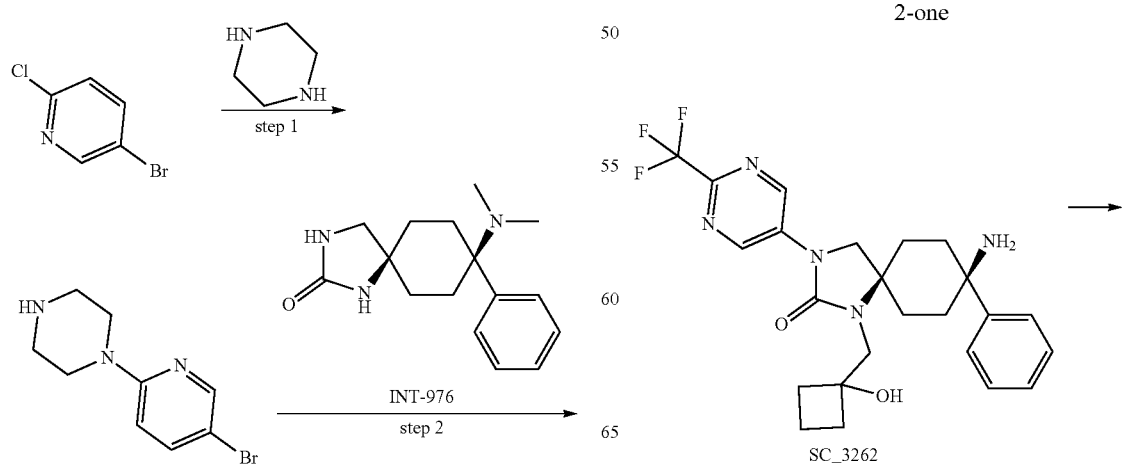

SC_3262

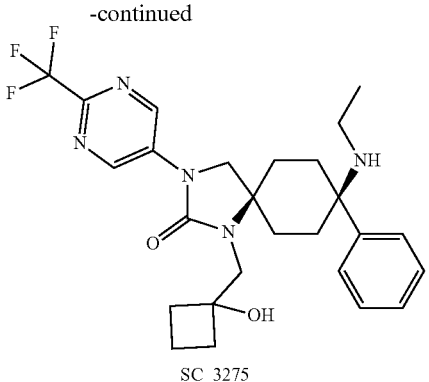

SC_3275

CIS-8-amino-1-((1-hydroxycyclobutyl)methyl)-8-phenyl-3-(2-(trifluoromethyl)pyrimidin-5-yl)-1,3-diazaspiro[4.5]decan-2-one (70 mg, 0.15 mmol) was dissolved in anhydrous DCM (3.8 mL) under nitrogen atmosphere. Acetic acid (0.1 equiv., 0.015 mmol, 0.8 μL) and acetaldehyde (1.1 equiv., 0.16 mmol, 9 μL) were sequentially added and the resulting mixture was stirred at RT for 1 h. Sodium triacetoxyborohydride (2 equiv., 0.29 mmol, 62 mg) was added and the reaction mixture was stirred at RT overnight and then at 50° C. for 5 h. Additional amounts of acetaldehyde (1.1 equiv., 0.16 mmol, 9 μL) and sodium triacetoxyborohydride (2 equiv., 0.29 mmol, 62 mg) were added and the reaction mixture was stirred further 24 h at 50° C. The resulting mixture was cooled down to RT, quenched with aq. sat. NaHCO$_3$ until pH>7, diluted with water and extracted with DCM (3×). The combined organic layers were dried over Na$_2$SO$_4$ and concentrated under reduced pressure. The residue (70 mg) was purified by flash chromatography on silica gel (DCM/EtOH gradient 99/1 to 95/5) to yield 43 mg (58%) of CIS-8-(ethylamino)-1-((1-hydroxycyclobutyl)methyl)-8-phenyl-3-(2-(trifluoromethyl)pyrimidin-5-yl)-1,3-diazaspiro[4.5]decan-2-one (SC_3275). $^1$H NMR (600 MHz, DMSO) δ 9.26 (s, 2H), 7.55-7.49 (m, 2H), 7.33 (t, 2H), 7.21 (d, 1H), 3.92 (s, 2H), 2.38 (td, 2H), 2.17-2.06 (m, 3H), 2.00-1.87 (m, 4H), 1.81 (td, 2H), 1.72-1.64 (m, 1H), 1.60-1.50 (m, 1H), 1.49-1.43 (m, 2H), 0.99 (t, 3H). Mass: m/z 504.3 (M+H)+

Synthesis of SC_3292 and SC_3293: enantiomer 1 and enantiomer 2 of CIS-8-(methyl((tetrahydrofuran-3-yl)methyl)amino)-8-phenyl-3-(2-(trifluoromethyl)pyrimidin-5-yl)-1,3-diazaspiro[4.5]decan-2-one

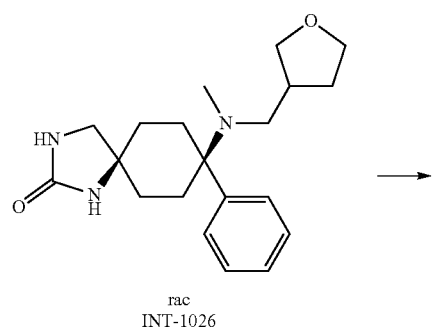

rac
INT-1026

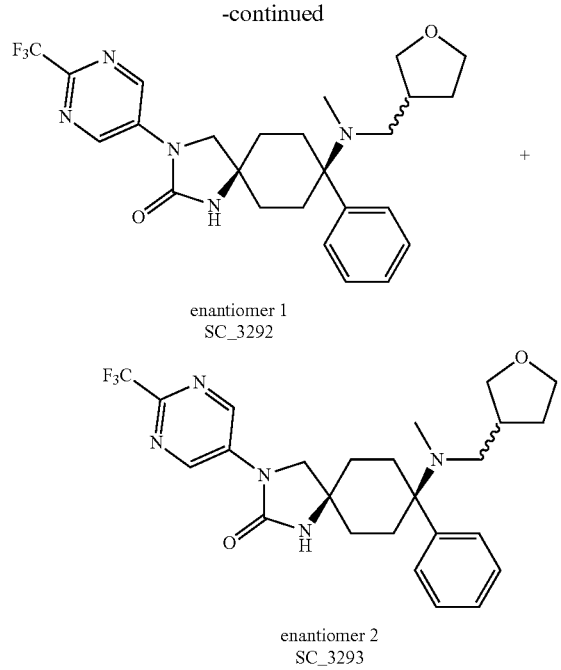

enantiomer 1
SC_3292 enantiomer 2
SC_3293

Cs$_2$CO$_3$ (0.85 g, 2.61 mmol) was added to an argon purged solution of CIS-8-(methyl((tetrahydrofuran-3-yl)methyl)amino)-8-phenyl-1,3-diazaspiro[4.5]decan-2-one (INT-1026) (0.3 g, 0.87 mmol), Xanthphos (45 mg, 0.087 mmol), Pd$_2$(dba)$_3$ (80 mg, 0.087 mmol) and 5-bromo-2-(trifluoromethyl)pyrimidine (0.29 g, 1.30 mmol) in 1,4-dioxane (15 mL). The mixture was purged with argon for 5 min and stirred at 90° C. for 16 h. The reaction mixture was cooled to RT, diluted with EtOAc (20 mL), filtered through Celite and the filtrate was concentrated under reduced pressure. The crude product was purified by flash chromatography (silica gel 230-400 mesh; 3% MeOH in DCM) to get the compound which was further purified by reverse phase preparative HPLC to afford 0.1 g (23%) of CIS-8-(methyl((tetrahydrofuran-3-yl)methyl)amino)-8-phenyl-3-(2-(trifluoromethyl)pyrimidin-5-yl)-1,3-diazaspiro[4.5]decan-2-one (TLC system: 10% MeOH in DCM; Rf: 0.4) as a mixture of enantiomers. Reverse phase preparative HPLC conditions: mobile phase: 10 mM ammonium bicarbonate in H$_2$O/acetonitrile; column: X-BRIDGE-C18 (150*19), 5 μm; mobile phase gradient (min/% B): 0/30, 8/82, 8.1/100, 10/100, 10.1/30, 12/30; flow rate: 19 ml/min; diluent: mobile phase+THF. Enantiomeric mixture of CIS-8-(methyl((tetrahydrofuran-3-yl)methyl)amino)-8-phenyl-3-(2-(trifluoromethyl)pyrimidin-5-yl)-1,3-diazaspiro[4.5]decan-2-one (100 mg) was separated by chiral SFC to afford 35 mg of enantiomer 1 (SC-3292) and 40 mg of enantiomer 2 (SC-3293) as off-white solids. Preparative SFC conditions: column: Chiralpak IA (250×30) mm, 5 μm; % CO$_2$: 50.0%; % co-solvent: 50.0% (100% Methanol); total flow: 70.0 g/min; back pressure: 100.0 bar; UV: 256 nm; stack time: 13.5 min; load/inj.: 9.5 mg; no. of injections: 11. SC-3292: $^1$H NMR (DMSO-d6): δ 9.15 (s, 2H), 8.23 (broad s, 1H), 7.37-7.25 (m, 5H), 3.68-3.58 (m, 5H), 3.37-3.36 (m, 1H), 2.32 (m, 3H), 2.13-1.89 (m, 10H), 1.47 (m, 3H). SC-3293: $^1$H NMR (DMSO-d6): δ 9.15 (s, 2H), 8.23 (broad s, 1H), 7.37-7.36 (m, 4H), 7.26-7.24 (m, 1H), 3.68-3.56 (m, 5H), 3.37-3.36 (m, 1H), 2.31-2.28 (m, 3H), 2.13-1.86 (m, 10H), 1.48 (m, 3H). Mass: m/z 490.3 (M+H)+.

Synthesis of SC_3313: CIS-3-(2-(4-cyclopropyl-1H-1,2,3-triazol-1-yl)pyrimidin-5-yl)-8-(dimethyl-amino)-8-phenyl-1,3-diazaspiro[4.5]decan-2-one

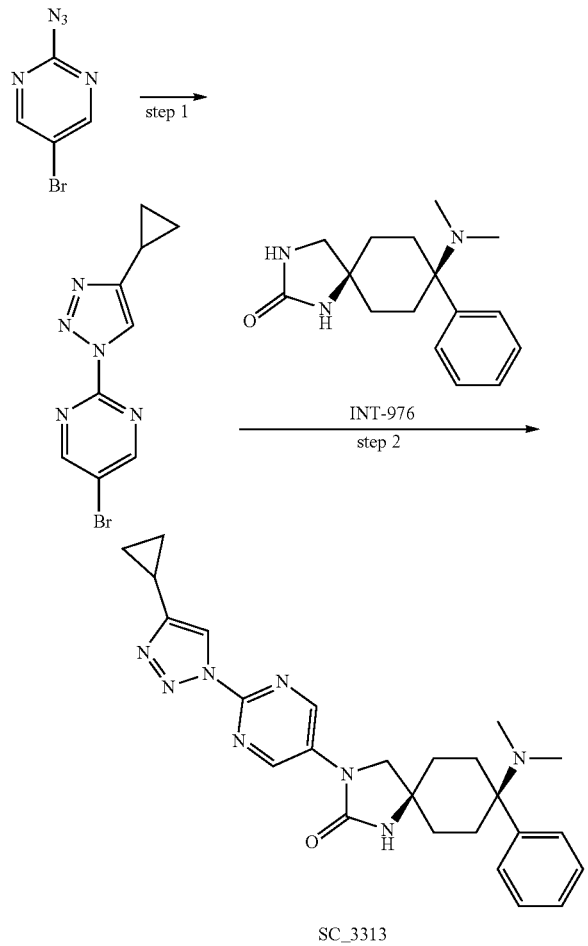

SC_3313

Step 1: 5-bromo-2-(4-cyclopropyl-1H-1,2,3-triazol-1-yl)pyrimidine

2-Azido-5-bromo-pyrimidine (400 mg, 1.94 mmol) and ethynylcyclopropane (1.3 equiv., 2.522 mmol, 0.21 mL) were dissolved in tert-butanol (5 mL). The solutions of sodium ascorbate (0.1 equiv., 0.194 mmol, 38 mg) in water (2.5 mL) and copper(II) sulfate pentahydrate (0.1 equiv., 0.194 mmol, 48 mg) in water (2.5 mL) were sequentially added. The reaction mixture was stirred under ambient conditions for 18 h, then diluted with 20 mL 1M aq. $NH_4OH$ and extracted with EtOAc (3×30 mL). The combined organic extracts were washed with brine, dried over $Na_2SO_4$ and concentrated under reduced pressure. Crude product (510 mg) was purified by flash chromatography on silica gel (DCM/EtOH 99/1) to yield 143 mg of 5-bromo-2-(4-cyclopropyl-1H-1,2,3-triazol-1-yl)pyrimidine as a white solid. Mass: m/z 266.0 (M+H)$^+$.

Step 2: CIS-3-(2-(4-cyclopropyl-1H-1,2,3-triazol-1-yl)pyrimidin-5-yl)-8-(dimethylamino)-8-phenyl-1,3-diazaspiro[4.5]decan-2-one (SC_3313)

In analogy to the method described for SC_3103 CIS-8-(dimethylamino)-8-phenyl-1,3-diazaspiro[4.5]decan-2-one (INT-976) was reacted with 5-bromo-2-(4-cyclopropyl-1H-1,2,3-triazol-1-yl)pyrimidine to be converted into CIS-3-(2-(4-cyclopropyl-1H-1,2,3-triazol-1-yl)pyrimidin-5-yl)-8-(dimethylamino)-8-phenyl-1,3-diazaspiro[4.5]decan-2-one (SC_3313). $^1$H NMR (600 MHz, DMSO) δ 9.09 (d, 2H), 8.50 (d, 1H), 7.91 (s, 1H), 7.42-7.34 (m, 2H), 7.38 (s, 3H), 7.31-7.25 (m, 1H), 3.72 (s, 2H), 2.48-2.31 (m, 2H), 2.10-2.01 (m, 1H), 1.99-1.77 (m, 10H), 1.58-1.46 (m, 2H), 1.00-0.91 (m, 2H), 0.84 (tt, 2H). Mass: m/z 459.3 (M+H)$^+$.

Synthesis of SC_3319: CIS-8-(methyl((tetrahydro-furan-3-yl)methyl)amino)-8-phenyl-3-(2-(trifluorom-ethyl)pyrimidin-5-yl)-1,3-diazaspiro[4.5]decan-2-one

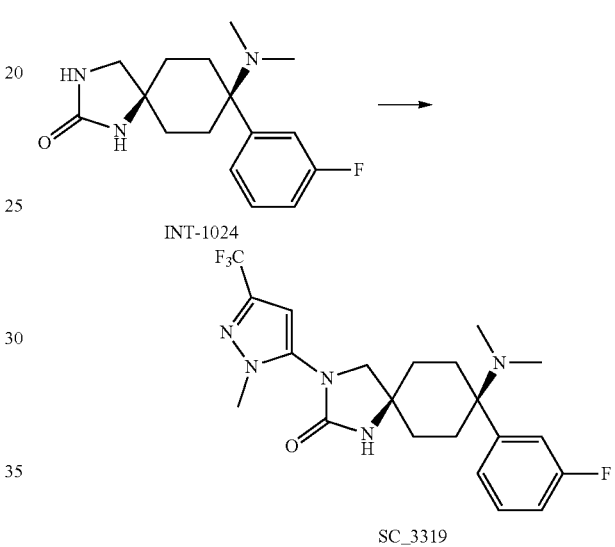

SC_3319

$Cs_2CO_3$ (145 mg, 0.45 mmol, 2 equiv.), CIS-8-(dimethylamino)-8-(3-fluorophenyl)-1,3-diazaspiro[4.5]decan-2-one (INT-1024) (65 mg, 0.223 mmol, 1 equiv.), Xantphos (19 mg, 0.033 mmol, 0.15 equiv.), $Pd_2(dba)_3$ (10 mg, 0.011 mmol, 0.05 equiv.) and 5-bromo-1-methyl-3-(trifluorom-ethyl)pyrazole (102 mg, 0.446 mmol, 2 equiv.) were loaded into a microwave reactor vial (2-5 mL), the vial was sealed and flushed with nitrogen (3×). 1,4-Dioxane (1.5 mL) was added via syringe and the reaction mixture was stirred at 110° C. in the microwave reactor for 10 h. The resulting mixture was cooled down to RT, solution of Xantphos (19 mg, 0.033 mmol, 0.15 equiv.) and $Pd_2(dba)_3$ (10 mg, 0.011 mmol, 0.05 equiv.) in 1,4 dioxane (1 mL) was added, and the reaction mixture was stirred at 130° C. in the microwave reactor for further 10 h. The resulting suspension was cooled to RT, quenched with water and extracted with DCM (3×). The combined organic layer was dried over $Na_2SO_4$ and concentrated under reduced pressure. The resulting residue was purified by flash chromatography (gradient 0% to 16% MeOH in DCM) to yield 41 mg (42%) of CIS-8-(methyl ((tetrahydrofuran-3-yl)methyl)amino)-8-phenyl-3-(2-(trifluoromethyl)pyrimidin-5-yl)-1,3-diazaspiro[4.5]decan-2-one (SC_3319). $^1$H NMR (600 MHz, DMSO) δ 7.71 (s, 1H), 7.41 (q, 1H), 7.21-7.12 (m, 2H), 7.09 (td, 1H), 6.63 (s, 1H), 3.75 (s, 2H), 3.55 (s, 2H), 2.42-2.27 (m, 2H), 1.99-1.89 (m, 8H), 1.88-1.73 (m, 2H), 1.56-1.49 (m, 2H). Mass: m/z 440.2 (M+H)$^+$.

Synthesis of SC_3340: CIS-2-(3-(8-(dimethylamino)-2-oxo-8-phenyl-1,3-diazaspiro[4.5]decan-3-yl)pyridin-4-yl)acetamide

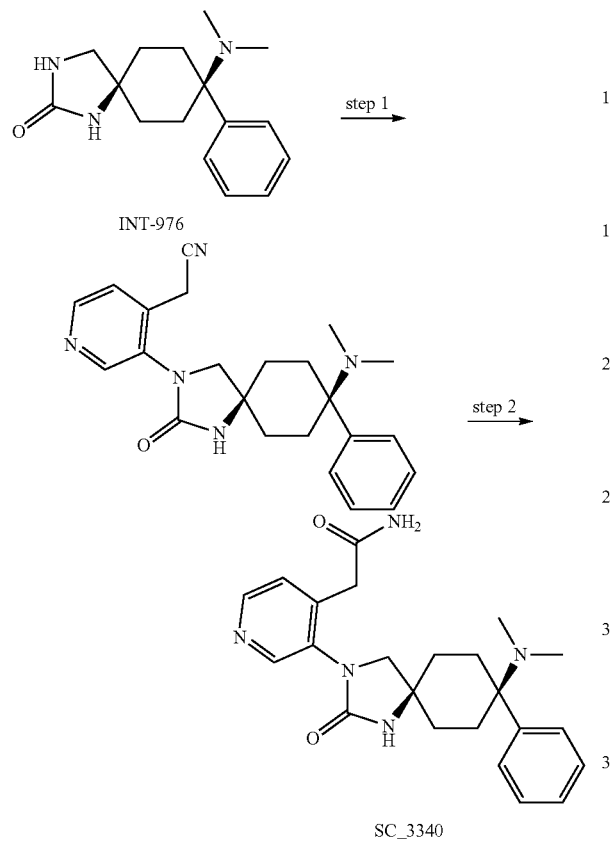

Step 1: CIS-2-(3-(8-(dimethylamino)-2-oxo-8-phenyl-1,3-diazaspiro[4.5]decan-3-yl)pyridin-4-yl)acetonitrile In analogy to the method described for SC_3097 step 2 CIS-8-(dimethylamino)-8-phenyl-1,3-diazaspiro[4.5]decan-2-one (INT-976) was reacted with (3-bromo-pyridin-4-yl)-acetonitrile to be converted into CIS-2-(3-(8-(dimethylamino)-2-oxo-8-phenyl-1,3-diazaspiro[4.5]decan-3-yl)pyridin-4-yl)acetonitrile.

Step 2: CIS-2-(3-(8-(dimethylamino)-2-oxo-8-phenyl-1,3-diazaspiro[4.5]decan-3-yl)pyridin-4-yl)acetamide (SC_3340)

To a solution of CIS-2-(3-(8-(dimethylamino)-2-oxo-8-phenyl-1,3-diazaspiro[4.5]decan-3-yl)pyridin-4-yl)acetonitrile (600 mg, 1.54 mmol, 1.0 equiv.) in EtOH (50 ml) was added NaOH (247 mg, 6.16 mmol, 4.0 equiv.). The reaction mixture was stirred at reflux for 16 h and then concentrated under reduced pressure. The resulting residue was purified by column chromatography (neutral alumina; 4% MeOH in DCM) and finally by preparative HPLC (column: Gemini NX-C18 (50×4.6), 3 μm, diluent: DMSO, mobile phase: gradient 0.05% HCOOH in water/ACN flow rate: 1 ml/min) to yield CIS-2-(3-(8-(dimethylamino)-2-oxo-8-phenyl-1,3-diazaspiro[4.5]decan-3-yl)pyridin-4-yl)acetamide (SC_3340) (40 mg, 0,098 mmol, 4% yield after two steps) as an off white solid. $^1$HNMR (DMSO, 400 MHz) δ 8.40 (s, 1H), 8.32 (d, 1H, J=4.92 Hz), 7.49 (s, 1H), 7.36-7.24 (m, 7H), 6.99 (s, 1H), 3.49-3.46 (m, 4H), 2.32 (bs, 2H), 1.94-1.77 (m, 10H), 1.52 (bs, 2H). Mass: m/z 408.2 (M+H)$^+$.

Synthesis of SC_3352: CIS-8-(dimethylamino)-3-(2-hydroxybenzo[d]oxazol-7-yl)-8-phenyl-1,3-diazaspiro[4.5]decan-2-one

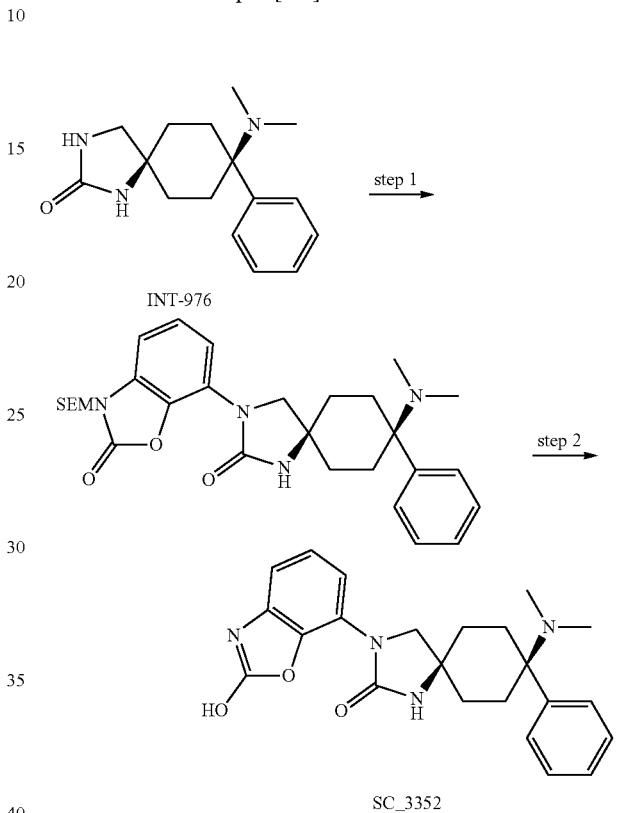

Step 1: CIS-7-(8-(dimethylamino)-2-oxo-8-phenyl-1,3-diazaspiro[4.5]decan-3-yl)-3-((2-(trimethylsilyl)ethoxy)methyl)benzo[d]oxazol-2(3H)-one In analogy to the method described for SC_3103 CIS-8-(dimethylamino)-8-phenyl-1,3-diazaspiro[4.5]decan-2-one (INT-976) was reacted with 7-bromo-3-(2-trimethylsilanyl-ethoxymethyl)-3H-benzooxazol-2-one (prepared from 7-bromobenzo[d]oxazol-2(3H)-one and trimethylsilylethoxymethylchloride following a standart procedure) to be converted into CIS-7-(8-(dimethylamino)-2-oxo-8-phenyl-1,3-diazaspiro[4.5]decan-3-yl)-3-((2-(trimethylsilyl)ethoxy)methyl)benzo[d]oxazol-2(3H)-one. Mass: m/z 537.2 (M+H)$^+$.

Step 2: CIS-8-(dimethylamino)-3-(2-hydroxybenzo[d]oxazol-7-yl)-8-phenyl-1,3-diazaspiro[4.5]decan-2-one (SC_3352)

To a solution of CIS-7-[8-dimethylamino-2-oxo-8-phenyl-1-(2-trimethylsilanyl-ethoxymethyl)-1,3-diaza-spiro[4.5]dec-3-yl]-3H-benzooxazol-2-one (350 mg, 0.65 mmol, 1.0 eq) in 1,4-dioxane (2 mL) was added 4M HCl in dioxane (6 mL) dropwise at 0° C. The reaction mixture was stirred at RT for 48 h and then concentrated under reduced pressure.

The residue was taken in DCM (200 mL) and washed with sat. aq. NaHCO₃ (100 mL). Organic layer was dried over Na₂SO₄ and concentrated under reduced pressure to get the crude product which was purified by column chromatography (neutral alumina; 2% MeOH/DCM) to yield CIS-7-(8-dimethylamino-2-oxo-8-phenyl-1,3-diaza-spiro[4.5]dec-3-yl)-3H-benzooxazol-2-one (SC_3352) (85 mg, 0.21 mmol, 32%) as an off white solid. ¹HNMR (DMSO-d6, 400 MHz at 100° C.), δ (ppm)=11.19 (bs, 1H), 7.37-7.23 (m, 6H), 7.14 (s, 1H), 7.04 (t, 1H, J=8.06), 6.76 (d, 1H, J=7.68 Hz), 3.69 (s, 2H), 2.38-2.26 (m, 2H), 2.08-1.76 (m, 10H), 1.56-1.51 (m, 2H). Mass: m/z 407.1 (M+H)⁺.

Synthesis of SC_3354: CIS-4-(5-(8-(dimethylamino)-2-oxo-8-phenyl-1,3-diazaspiro[4.5]decan-3-yl)pyrimidin-2-yl)benzamide trifluoroacetate salt

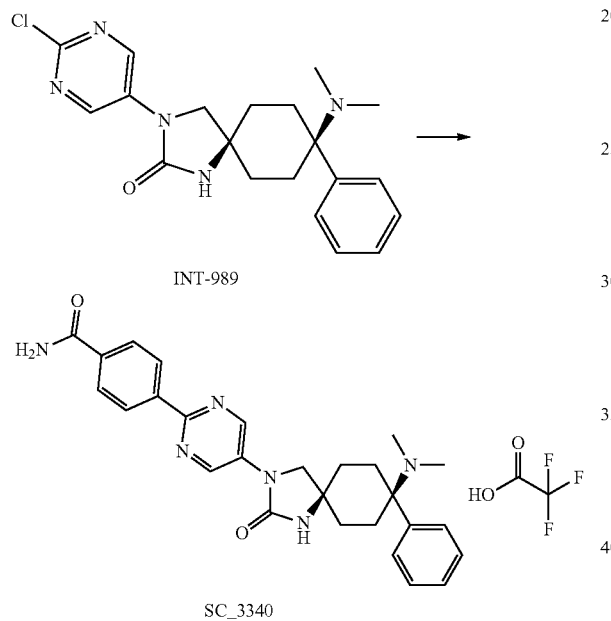

INT-989

SC_3340

3-(2-chloropyrimidin-5-yl)-8-(dimethylamino)-8-phenyl-1,3-diazaspiro[4.5]decan-2-one (INT 989) (200 mg, 0.52 mmol, 1 equiv.), 4-(4,4,5,5-tetramethyl-1,3,2-dioxaborolan-2-yl)benzamide (129 mg, 0.52 mmol, 1 equiv.), Pd₂(dba)₃ (95 mg, 0.10 mmol, 0.2 equiv.), 2-dicyclohexylphosphino-2',4',6'-triisopropylbiphenyl (X-Phos) (99 mg, 0.21 mmol, 0.4 equiv.) were loaded into microwave reactor vessel and flushed with nitrogen (2×). Anhydrous 1,4-dioxane (9 mL) and sodium carbonate (213 mg, 2.07 mmol, 4 equiv.) were sequentially added. The reaction mixture was stirred 8 h at 120° C. in the microwave reactor and then concentrated under reduced pressure. The residue was suspended in EtOAc/water (1/1, v/v) and filtered through a glass filter. The solid residue was dissolved in MeOH/DCM/TFA, filtered through Celite pad and the filtrate was concentrated under reduced pressure to give 75 mg (25%) of CIS-4-(5-(8-(dimethylamino)-2-oxo-8-phenyl-1,3-diazaspiro[4.5]decan-3-yl)pyrimidin-2-yl)benzamide trifluoroacetate salt (SC_3354). ¹H NMR (600 MHz, DMSO) δ 9.05 (s, 2H), 8.42 (s, 1H), 8.34 (d, 2H), 8.03 (s, 1H), 7.98 (d, 2H), 7.74-7.65 (m, 2H), 7.58 (t, 2H), 7.56-7.52 (m, 1H), 7.40 (s, 1H), 3.58 (s, 2H), 2.70 (d, 2H), 2.60 (s, 6H), 2.25 (t, 2H), 1.91 (d, 2H), 1.39 (t, 2H). Mass: m/z 471.3 (M+H)+.

Synthesis of SC_3357: CIS-8-(dimethylamino)-3-(1H-indol-3-yl)-8-phenyl-1,3-diazaspiro[4.5]decan-2-one

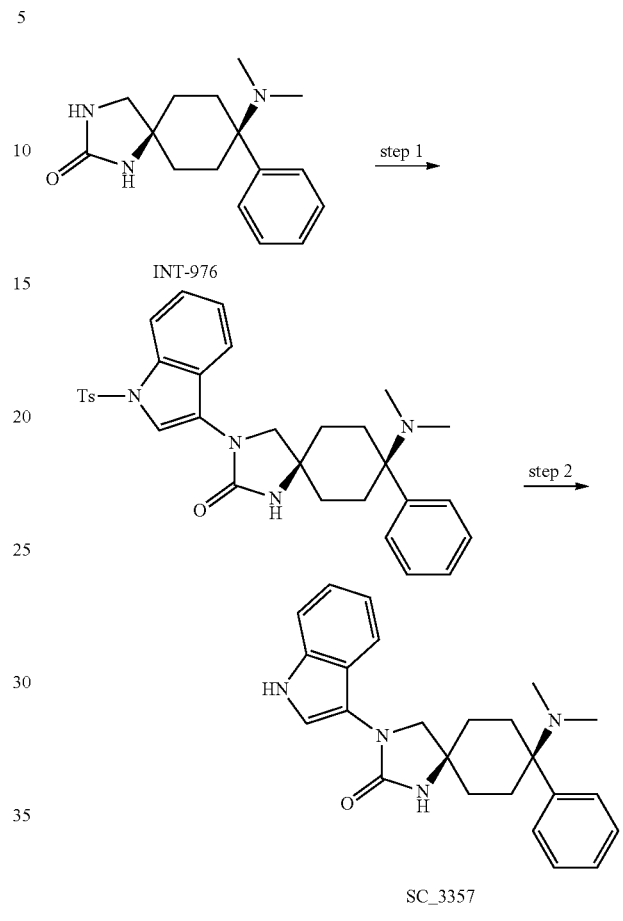

INT-976

SC_3357

Step 1: CIS-8-(dimethylamino)-8-phenyl-3-(1-tosyl-1H-indol-3-yl)-1,3-diazaspiro[4.5]decan-2-one In analogy to the method described for SC_3103 CIS-8-(dimethylamino)-8-phenyl-1,3-diazaspiro[4.5]decan-2-one (INT-976) was reacted with 3-bromo-1-(toluene-4-sulfonyl)-1H-indole to be converted into CIS-8-(dimethylamino)-8-phenyl-3-(1-tosyl-1H-indol-3-yl)-1,3-diazaspiro[4.5]decan-2-one. Mass: m/z 543.1 (M+H)⁺.

Step 2: CIS-8-(dimethylamino)-3-(1H-indol-3-yl)-8-phenyl-1,3-diazaspiro[4.5]decan-2-one (SC_3357)

To a solution of 8-dimethylamino-8-phenyl-3-[1-(toluene-4-sulfonyl)-1H-indol-3-yl]-1,3-diaza-spiro[4.5]decan-2-one (275 mg, 0.51 mmol, 1.0 eq.) in EtOH (24 mL) was added 10N aq. NaOH (1.2 mL) at RT. The reaction mixture was heated to reflux for 1.5 h, then concentrated, diluted with water (50 mL) and extracted with EtOAc (150 mL). Organic layer was dried over Na₂SO₄ and concentrated under reduced pressure. The residue was purified by column chromatography (neutral alumina; 2% MeOH/DCM) to afford CIS-8-dimethylamino-3-(1H-indol-3-yl)-8-phenyl-1,3-diaza-spiro[4.5]decan-2-one (SC_3357) (130 mg, 0.33 mmol, 65%) as light brown solid. ¹H NMR (DMSO-d6, 400 MHz at 100° C.), δ (ppm)=10.55 (bs, 1H), 7.62-7.60 (d, 1H, J=7.96 Hz), 7.37-7.23 (m, 7H), 7.04 (t, 1H, J=7.48 Hz), 6.92

(t, 1H, J=7.44 Hz), 6.71 (bs, 1H), 3.61 (s, 2H), 2.38-2.33 (m, 2H), 2.04-1.82 (m, 10H), 1.59-1.54 (m, 2H). Mass: m/z 389.3 (M+H)+.

Synthesis of SC_3379: CIS-3-(1-acetyl-1H-indol-3-yl)-8-(dimethylamino)-8-phenyl-1,3-diazaspiro[4.5]decan-2-one

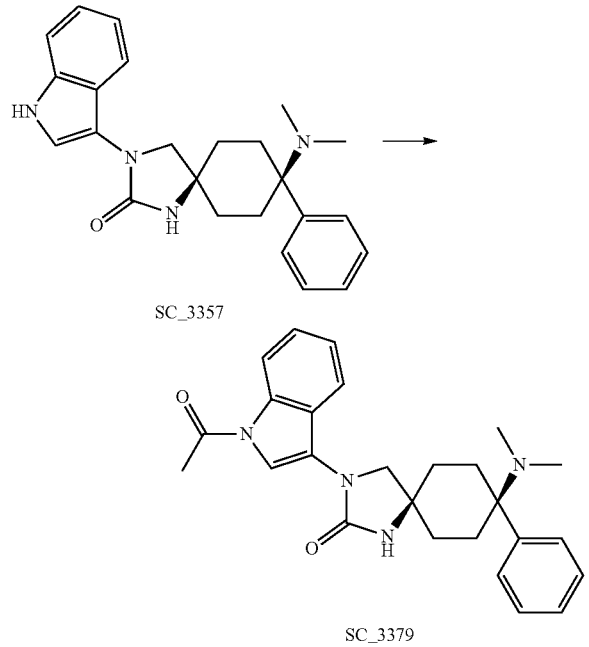

SC_3357

SC_3379

To a solution of 8-dimethylamino-3-(1H-indol-3-yl)-8-phenyl-1,3-diaza-spiro[4.5]decan-2-one (SC_3357) (150 mg, 0.38 mmol, 1.0 eq.) in DCM (6 mL) were added NaOH (39 mg, 0.96 mmol, 2.5 eq.) and Bu₄NHSO₄ (129 mg, 0.38 mmol, 1.0 eq.) at 0° C. and the reaction mixture was stirred for 30 min followed by addition of acetyl chloride (54 μl, 0.76 mmol, 2.0 eq.). The reaction mixture was stirred at RT for 16 h, then diluted with DCM (150 ml) and washed with water (50 mL) and brine (50 mL). Organic layer was dried over Na₂SO₄ and concentrated under reduced pressure. The residue was purified by column chromatography (neutral alumina; 1% MeOH/DCM) followed by prep HPLC to afford 3-(1-acetyl-1H-indol-3-yl)-8-dimethylamino-8-phenyl-1,3-diaza-spiro[4.5]decan-2-one (SC_3379) as off white solid. Note: Two batches of same reactions were done and yield was calculated accordingly. Yield: 13% (45 mg, 0.1 mmol). 1HNMR (DMSO-d6, 400 MHz at 100° C.), δ (ppm)=8.34-8.32 (d, 1H, J=7.88 Hz), 7.90 (d, 1H, J=7.36 Hz), 7.67 (s, 1H), 7.37-7.10 (m, 8H), 3.71 (s, 2H), 2.57 (s, 3H), 2.38-2.32 (m, 2H), 2.04-1.88 (m, 10H), 1.61-1.59 (m, 2H). Mass: m/z 431.2 (M+H)⁺.

Synthesis of SC_3388: CIS-8-(dimethylamino)-8-(3-hydroxyphenyl)-3-(4-methyl-6-(trifluoromethyl)pyridin-3-yl)-1,3-diazaspiro[4.5]decan-2-one

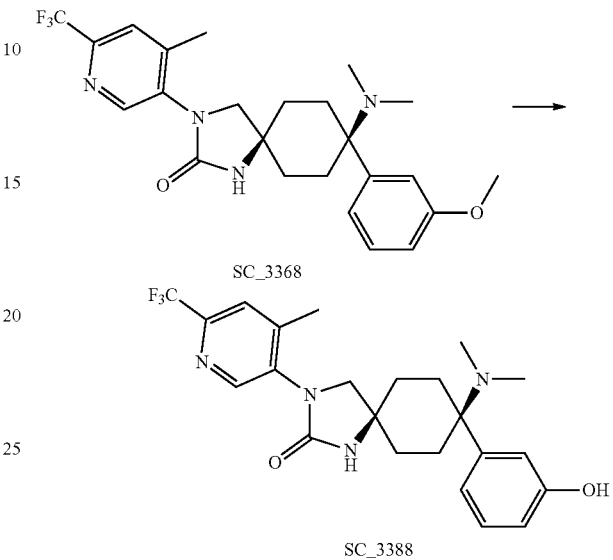

SC_3368

SC_3388

CIS-8-(dimethylamino)-8-(3-methoxyphenyl)-3-[4-methyl-6-(trifluoromethyl)-3-pyridyl]-1,3-diazaspiro[4.5]decan-2-one (SC_3368) (42 mg, 0.091 mmol) was dissolved in DCM (2 mL) and the solution was cooled to 0° C. Boron tribromide (1M sol. in DCM, 4 equiv., 0.36 mmol, 0.36 mL) was added in one portion. The reaction mixture was allowed to stir at RT overnight, then quenched with methanol and diluted with water. The resulting mixture was extracted with DCM (2×), the combined organic phases weres dried over Na₂SO₄ and concentrated under reduced pressure. The residue was purified by flash chromatography on silica gel (eluent gradient DCM/EtOH) to yield 16 mg (39%) of CIS-8-(dimethylamino)-8-(3-hydroxyphenyl)-3-(4-methyl-6-(trifluoromethyl)pyridin-3-yl)-1,3-diazaspiro[4.5]decan-2-one (SC_3388). ¹H NMR (600 MHz, DMSO) δ 8.57 (s, 1H), 7.80 (s, 1H), 7.52 (s, 1H), 7.14 (t, 1H), 6.77 (d, 1H), 6.74 (s, 1H), 6.66 (dd, 1H), 3.61 (s, 2H), 2.32 (s, 3H), 2.31-2.19 (m, 2H), 2.01-1.89 (m, 8H), 1.88-1.70 (m, 2H), 1.54 (t, 2H). Mass: m/z 449.2 (M+H)⁺.

Synthesis of SC_3396: CIS-4-(8-(dimethylamino)-2-oxo-8-phenyl-1,3-diazaspiro[4.5]decan-3-yl)indolin-2-one

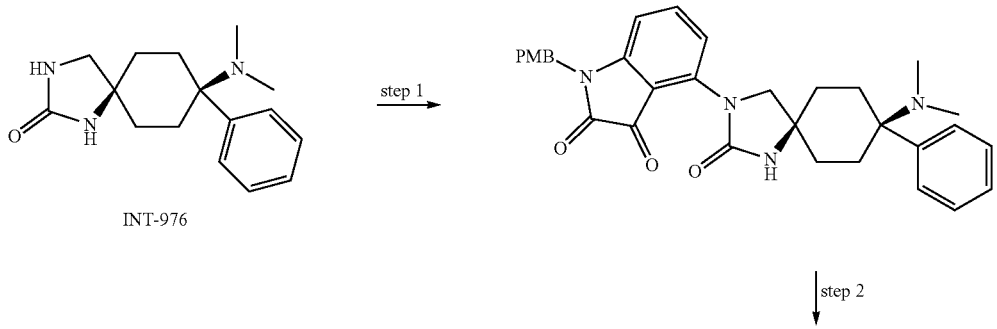

INT-976 step 1 step 2

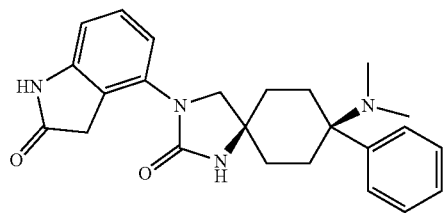 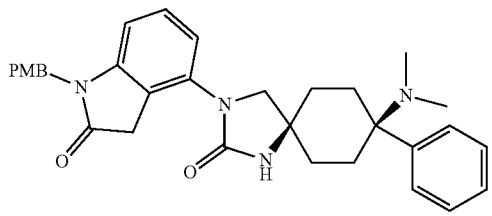

SC_3396

Step 1: CIS-4-(8-(dimethylamino)-2-oxo-8-phenyl-1,3-diazaspiro[4.5]decan-3-yl)-1-(4-methoxybenzyl)indoline-2,3-dione In analogy to the method described for SC_3242 CIS-8-(dimethylamino)-8-phenyl-1,3-diazaspiro[4.5]decan-2-one (INT-976) was reacted with 4-bromo-1-(4-methoxy-benzyl)-1H-indole-2,3-dione to be converted into CIS-4-(8-(dimethylamino)-2-oxo-8-phenyl-1,3-diazaspiro[4.5]decan-3-yl)-1-(4-methoxybenzyl)indoline-2,3-dione. Mass: m/z 539.2 (M+H)⁺.

Step 2: CIS-4-(8-(dimethylamino)-2-oxo-8-phenyl-1,3-diazaspiro[4.5]decan-3-yl)-1-(4-methoxybenzyl)indolin-2-one To a solution of CIS-4-(8-dimethylamino-2-oxo-8-phenyl-1,3-diaza-spiro[4.5]dec-3-yl)-1-(4-methoxy-benzyl)-1H-indole-2,3-dione (600 mg, 1.11 mmol, 1.0 eq) in EtOH (9 mL) was added hydrazine hydrate (9 mL) at RT. The reaction mixture was stirred at reflux for 16 h, then concentrated, diluted with water (50 mL) and extracted with EtOAc (200 mL). Organic layer was dried over Na₂SO₄, filtered and concentrated under reduced pressure. The resulting residue was purified by column chromatography (neutral alumina, 0.5% MeOH/DCM) to afford 8-dimethylamino-3-[1-(4-methoxy-benzyl)-2-oxo-2,3-dihydro-1H-indol-4-yl]-8-phenyl-1,3-diaza-spiro[4.5]decan-2-one (275 mg, 0.52 mmol, 47%) as a brown solid. Mass: m/z 525.2 (M+H)⁺.

Step 3: CIS-4-(8-(dimethylamino)-2-oxo-8-phenyl-1,3-diazaspiro[4.5]decan-3-yl)indolin-2-one (SC_3396)

A solution of CIS-8-dimethylamino-3-[1-(4-methoxybenzyl)-2-oxo-2,3-dihydro-1H-indol-4-yl]-8-phenyl-1,3-diaza-spiro[4.5]decan-2-one (275 mg, 0.52 mmol, 1.0 eq.) in TFA (4 mL) was stirred at 90° C. in a sealed tube for 16 h. The reaction mixture was cooled to RT, concentrated under reduced pressure, diluted with water (50 mL), basified with sat. aq. NaHCO₃ and extracted with EtOAc (200 mL). The organic phase was washed with brine (50 mL), dried over Na₂SO₄, filtered and concentrated under reduced pressure. The resulting residue was purified by column chromatography (neutral alumina, 5% MeOH in DCM) to afford CIS-8-dimethylamino-3-(2-oxo-2,3-dihydro-1H-indol-4-yl)-8-phenyl-1,3-diaza-spiro[4.5]decan-2-one (SC_3396) (60 mg, 0.14 mmol, 28%) as an off-white solid. $^1$H NMR (DMSO-d6, 400 MHz, 100° C.): δ (ppm)=9.98 (bs, 1H), 7.36-7.22 (m, 5H), 7.09 (t, 1H, J=7.94 Hz), 6.95-6.88 (m, 2H), 6.59 (d, 1H, J=7.52 Hz), 3.57 (s, 2H), 3.49 (s, 2H), 2.36-2.31 (m, 2H), 2.03 (s, 6H), 1.97-1.85 (m, 4H), 1.55-1.51 (m, 2H). Mass: m/z 405.3 (M+H)⁺.

The following compounds were prepared in analogy and by combining previously described methods:

| Example | Chemical Name | Reactant I | Reactant II | in analogy to method | m/z [M + H]⁺ |
|---|---|---|---|---|---|
| SC_3001 | cis-5-[1-(Cyclobutyl-methyl)-8-dimethylamino-2-oxo-8-phenyl-1,3-diazaspiro[4.5]decan-3-yl]-pyrimidine-2-carbonitrile | INT-987 | 5-bromopyrimidine-2-carbonitrile | SC_3022 | 445.3 |
| SC_3002 | cis-5-[1-(Cyclobutyl-methyl)-8-dimethylamino-2-oxo-8-phenyl-1,3-diazaspiro[4.5]decan-3-yl]-pyrazine-2-carbonitrile | INT-987 | 5-bromopyrazine-2-carbonitrile | SC_3022 | 445.3 |
| SC_3003 | cis-5-[1-(Cyclobutyl-methyl)-8-dimethylamino-2-oxo-8-phenyl-1,3-diazaspiro[4.5]decan-3-yl]-4-methoxy-pyrimidine-2-carbonitrile | INT-987 | 5-bromo-4-methoxypyrimidine-2-carbonitrile | SC_3022 | 475.3 |
| SC_3004 | cis-5-[8-Dimethylamino-1-(2-methoxy-ethyl)-2-oxo-8-phenyl-1,3-diazaspiro[4.5]decan-3-yl]-pyrimidine-2-carbonitrile | INT-980 | 5-bromopyrimidine-2-carbonitrile | SC_3022 | 435.2 |
| SC_3005 | cis-5-[1-(Cyclobutyl-methyl)-8-dimethylamino-2-oxo-8-phenyl-1,3-diazaspiro[4.5]decan-3-yl]-pyrimidine-2-carboxylic acid amide | SC_3001 | — | SC_3016 | 463.3 |
| SC_3006 | cis-5-[1-(Cyclobutyl-methyl)-8-dimethylamino-2-oxo-8-phenyl-1,3-diazaspiro[4.5]decan-3-yl]-2-methylsulfonyl-pyrimidine-4-carbonitrile | INT-987 | 5-bromo-2-(methylthio)-pyrimidine-4-carbonitrile | SC_3022 (step 1); SC_3008 (step 2) | 523.2 |
| SC_3007 | cis-5-[1-(2-Methoxy-ethyl)-8-methylamino-2-oxo-8-phenyl-1,3-diazaspiro[4.5]decan-3-yl]-pyrimidine-2-carbonitrile | SC_3004 | — | SC_3045 | 421.2 |
| SC_3008 | cis-2-[1-(Cyclobutyl-methyl)-8-dimethylamino-2-oxo-8-phenyl-1,3-diazaspiro[4.5]decan-3-yl]-5-methylsulfonyl-benzonitrile | INT-987 | 2-iodo-5-(methylthio)benzonitrile (step 1) | SC_3022 (step 1); SC_3008 (step 2) | 521.3 |
| SC_3009 | cis-2-[1-(Cyclobutyl-methyl)-8-dimethylamino-2-oxo-8-phenyl-1,3-diazaspiro[4.5]decan-3-yl]-benzamide | SC_3090 | — | SC_3016 | 461.3 |
| SC_3010 | cis-3-[1-(Cyclobutyl-methyl)-8-dimethylamino-2-oxo-8-phenyl-1,3-diazaspiro[4.5]decan-3-yl]-benzamide | SC_3072 | — | SC_3016 | 461.3 |

-continued

| Example | Chemical Name | Reactant I | Reactant II | in analogy to method | m/z [M + H]+ |
|---|---|---|---|---|---|
| SC_3011 | cis-5-[8-Dimethylamino-1-[(1-hydroxy-cyclobutyl)-methyl]-2-oxo-8-phenyl-1,3-diazaspiro[4.5]decan-3-yl]-pyrimidine-2-carboxylic acid amide | SC_3013 | — | SC_3016 | 479.3 |
| SC_3012 | cis-5-[1-(Cyclobutyl-methyl)-8-methylamino-2-oxo-8-phenyl-1,3-diazaspiro[4.5]decan-3-yl]-4-methoxy-pyrimidine-2-carbonitrile | SC_3003 | — | SC_3045 | 461.3 |
| SC_3013 | cis-5-[8-Dimethylamino-1-[(1-hydroxy-cyclobutyl)-methyl]-2-oxo-8-phenyl-1,3-diazaspiro[4.5]decan-3-yl]-pyrimidine-2-carbonitrile | INT-600 | — | SC_3013 | 461.3 |
| SC_3014 | cis-2-[1-(Cyclobutyl-methyl)-8-dimethylamino-2-oxo-8-phenyl-1,3-diazaspiro[4.5]decan-3-yl]-pyrimidine-5-carbonitrile | INT-987 | 2-chloropyrimidine-5-carbonitrile | SC_3014 | 445.3 |
| SC_3015 | cis-8-Dimethylamino-1-[(1-hydroxy-cyclobutyl)-methyl]-3-(2-methoxy-pyrimidin-5-yl)-8-phenyl-1,3-diazaspiro[4.5]decan-2-one | INT-976 | 5-bromo-2-methoxypyrimidine (step 1); 1-(tert-butyldimethyl-silyloxy)cyclobutyl)methyl 4-methylbenzene-sulfonate (step 2) | SC_3013 | 466.3 |
| SC_3016 | cis-2-[1-(Cyclobutyl-methyl)-8-dimethylamino-2-oxo-8-phenyl-1,3-diazaspiro[4.5]decan-3-yl]-pyrimidine-5-carboxylic acid amide | SC_3014 | — | SC_3016 | 463.3 |
| SC_3017 | cis-4-[1-(Cyclobutyl-methyl)-8-dimethylamino-2-oxo-8-phenyl-1,3-diazaspiro[4.5]decan-3-yl]-N-methyl-benzamide | SC_3081 | methanamine | SC_3028 | 475.3 |
| SC_3018 | cis-5-(8-Dimethylamino-2-oxo-8-phenyl-1-propyl-1,3-diazaspiro[4.5]decan-3-yl)-pyrimidine-2-carbonitrile | INT-600 | 1-bromopropane | SC_3013 | 419.2 |
| SC_3019 | cis-5-[8-Dimethylamino-1-(3-methoxy-propyl)-2-oxo-8-phenyl-1,3-diazaspiro[4.5]decan-3-yl]-pyrimidine-2-carbonitrile | INT-600 | 1-bromo-3-methoxypropane | SC_3013 | 449.3 |
| SC_3020 | cis-5-[1-(Cyclopropyl-methyl)-8-dimethylamino-2-oxo-8-phenyl-1,3-diazaspiro[4.5]decan-3-yl]-pyrimidine-2-carbonitrile | INT-600 | (bromomethyl)cyclopropane | SC_3013 | 431.2 |
| SC_3021 | cis-4-[1-(Cyclobutyl-methyl)-8-dimethylamino-2-oxo-8-phenyl-1,3-diazaspiro[4.5]decan-3-yl]-benzamide | SC_3081 | ammonia | SC_3028 | 461.3 |
| SC_3022 | cis-1-(Cyclobutyl-methyl)-8-dimethylamino-8-phenyl-342-(trifluoromethyl)-pyrimidin-5-yl]-1,3-diazaspiro[4.5]decan-2-one | INT-987 | 5-bromo-2-(trifluoromethyl)pyrimidine | SC_3022 | 488.3 |
| SC_3023 | cis-8-Dimethylamino-1-[(1-hydroxy-cyclobutyl)-methyl]-3-(2-hydroxy-pyrimidin-5-yl)-8-phenyl-1,3-diazaspiro[4.5]decan-2-one | SC_3015 | — | SC_3023 | 452.3 |
| SC_3024 | cis-5-[8-Dimethylamino-1-(2-methyl-propyl)-2-oxo-8-phenyl-1,3-diazaspiro[4.5]decan-3-yl]-pyrimidine-2-carbonitrile | INT-600 | 1-bromo-2-methylpropane | SC_3013 | 433.3 |
| SC_3025 | cis-5-[8-Dimethylamino-1-(2-hydroxy-ethyl)-2-oxo-8-phenyl-1,3-diazaspiro[4.5]decan-3-yl]-pyrimidine-2-carbonitrile | INT-600 | (3-bromopropoxy)(tert-butyl)dimethylsilane | SC-3025 | 421.2 |
| SC_3026 | cis-5-[1-(Cyclobutyl-methyl)-8-methylamino-2-oxo-8-phenyl-1,3-diazaspiro[4.5]decan-3-yl]-4-methyl-pyridine-2-carbonitrile | SC_3078 | — | SC_3045 | 444.3 |
| SC_3027 | cis-1-(Cyclobutyl-methyl)-3-(5-methoxy-pyrazin-2-yl)-8-methylamino-8-phenyl-1,3-diazaspiro[4.5]decan-2-one | SC_3075 | — | SC_3045 | 436.3 |
| SC_3028 | cis-4-[1-(Cyclobutyl-methyl)-8-dimethylamino-2-oxo-8-phenyl-1,3-diazaspiro[4.5]decan-3-yl]-N,N-dimethyl-benzamide | SC_3081 | — | SC_3028 | 489.3 |
| SC_3029 | cis-4-[1-(Cyclobutyl-methyl)-8-dimethylamino-2-oxo-8-phenyl-1,3-diazaspiro[4.5]decan-3-yl]-N-ethyl-N-(2-hydroxy-ethyl)-benzamide | SC_3081 | — | SC_3028 | 533.3 |
| SC_3030 | cis-2-[1-(Cyclobutyl-methyl)-8-methylamino-2-oxo-8-phenyl-1,3-diazaspiro[4.5]decan-3-yl]-5-methylsulfonyl-benzonitrile | SC_3008 | — | SC_3045 | 507.2 |
| SC_3031 | cis-1-(Cyclobutyl-methyl)-8-methylamino-3-[2-methylsulfonyl-4-(trifluoromethyl)-phenyl]-8-phenyl-1,3-diazaspiro[4.5]decan-2-one | SC_3084 | — | SC_3031 | 550.2 |
| SC_3032 | cis-4-[1-(Cyclobutyl-methyl)-8-methylamino-2-oxo-8-phenyl-1,3-diazaspiro[4.5]decan-3-yl]-N,N-dimethyl-3-(trifluoromethyl)-benzenesulfonic acid amide | SC_3089 | — | SC_3032 | 579.3 |
| SC_3033 | cis-4-[1-(Cyclobutyl-methyl)-8-(ethyl-methyl-amino)-2-oxo-8-phenyl-1,3-diazaspiro[4.5]decan-3-yl]-benzonitrile | INT-797 | 4-bromobenzonitrile (step 1); (bromomethyl)cyclobutane (step 2) | SC_3013 | 457.3 |
| SC_3034 | cis-1-(Cyclobutyl-methyl)-8-(ethyl-methyl-amino)-8-phenyl-3-[2-(trifluoromethyl)-pyrimidin-5-yl]-1,3-diazaspiro[4.5]decan-2-one | INT-797 | 5-bromo-2-(trifluoromethyl)pyrimidine (step 1); (bromomethyl)cyclobutane (step 2) | SC-3013 | 502.3 |
| SC_3035 | cis-5-[1-(Cyclobutyl-methyl)-8-(ethyl-methyl-amino)-2-oxo-8-phenyl-1,3-diazaspiro[4.5]decan-3-yl]-pyrimidine-2-carbonitrile | INT-797 | 5-bromopyrimidine-2-carbonitrile (step 1); (bromomethyl)cyclobutane (step 2) | SC_3013 | 459.3 |

-continued

| Example | Chemical Name | Reactant I | Reactant II | in analogy to method | m/z [M + H]+ |
|---|---|---|---|---|---|
| SC_3036 | cis-5-[8-Dimethylamino-1-[(1-methyl-cyclobutyl)-methyl]-2-oxo-8-phenyl-1,3-diazaspiro[4.5]decan-3-yl]-pyrimidine-2-carbonitrile | INT-982 | 5-bromopyrimidine-2-carbonitrile | SC_3022 | 459.3 |
| SC_3037 | cis-2-[3-(2-Cyano-pyrimidin-5-yl)-8-dimethylamino-2-oxo-8-phenyl-1,3-diazaspiro[4.5]decan-1-yl]-N,N-dimethyl-acetamide | INT-978 | 5-bromopyrimidine-2-carbonitrile | SC_3065 | 462.3 |
| SC_3038 | cis-1-(Cyclobutyl-methyl)-8-methylamino-8-phenyl-3-[2-(trifluoromethyl)-pyrimidin-5-yl]-1,3-diazaspiro[4.5]decan-2-one | SC_3022 | — | SC_3038 | 474.2 |
| SC_3039 | cis-5-[8-Dimethylamino-8-(3-fluorophenyl)-1-(4-methoxy-butyl)-2-oxo-1,3-diazaspiro[4.5]decan-3-yl]-pyrimidine-2-carbonitrile | INT-601 | 1-bromo-4-methoxybutane | SC_3064 | 481.3 |
| SC_3040 | cis-5-[8-Dimethylamino-1-(3-methoxy-propyl)-2-oxo-8-phenyl-1,3-diazaspiro[4.5]decan-3-yl]-4-methoxy-pyrimidine-2-carbonitrile | INT-979 | 5-bromo-4-methoxypyrimidine-2-carbonitrile | SC_3022 | 479.3 |
| SC_3041 | cis-5-[1-[(1-Cyano-cyclobutyl)-methyl]-8-dimethylamino-2-oxo-8-phenyl-1,3-diazaspiro[4.5]decan-3-yl]-pyrimidine-2-carbonitrile | INT_600 | (1-cyanocyclobutyl)methyl 4-methylbenzenesulfonate | SC_3013 | 470.3 |
| SC_3042 | cis-N-(Cyclobutyl-methyl)-5-[1-(cyclobutyl-methyl)-8-dimethylamino-8-(3-fluorophenyl)-2-oxo-1,3-diazaspiro[4.5]decan-3-yl]-pyrimidine-2-carboxylic acid amide | INT-601 | (bromomethyl)cyclobutane | SC_3064 | 549.3 |
| SC_3043 | cis-5-[1-(3-Methoxy-propyl)-8-methylamino-2-oxo-8-phenyl-1,3-diazaspiro[4.5]decan-3-yl]-pyrimidine-2-carbonitrile | SC_3019 | — | SC_3043 | 435.2 |
| SC_3044 | cis-5-[8-Dimethylamino-8-(3-fluorophenyl)-1-methyl-2-oxo-1,3-diazaspiro[4.5]decan-3-yl]-pyrimidine-2-carbonitrile | INT_600 | iodomethane | SC_3013 | 409.2 |
| SC_3045 | cis-4-Methoxy-5-[1-(3-methoxy-propyl)-8-methylamino-2-oxo-8-phenyl-1,3-diazaspiro[4.5]decan-3-yl]-pyrimidine-2-carbonitrile | SC_3040 | — | SC_3045 | 465.3 |
| SC_3046 | cis-4-[8-Dimethylamino-1-(2-methoxy-ethyl)-2-oxo-8-phenyl-1,3-diazaspiro[4.5]decan-3-yl]-pyrimidine-2-carbonitrile | INT-980 | 4-bromopyrimidine-2-carbonitrile | SC_3022 | 435.2 |
| SC_3047 | cis-5-[8-Dimethylamino-1-(2-methoxy-ethyl)-2-oxo-8-phenyl-1,3-diazaspiro[4.5]decan-3-yl]-4-methoxy-pyrimidine-2-carbonitrile | INT-980 | 5-bromo-4-methoxypyrimidine-2-carbonitrile | SC_3022 | 465.3 |
| SC_3048 | cis-4-[1-(Cyclobutyl-methyl)-8-dimethylamino-2-oxo-8-phenyl-1,3-diazaspiro[4.5]decan-3-yl]-pyrimidine-2-carbonitrile | INT-987 | 4-bromopyrimidine-2-carbonitrile | SC_3022 | 445.3 |
| SC_3049 | cis-1-(Cyclobutyl-methyl)-8-dimethylamino-3-(6-methylsulfanyl-pyrimidin-4-yl)-8-phenyl-1,3-diazaspiro[4.5]decan-2-one | INT-987 | 4-bromo-6-(methylthio)-pyrimidine | SC_3022 | 466.3 |
| SC_3050 | cis-2-[3-(2-Cyano-pyrimidin-4-yl)-8-dimethylamino-2-oxo-8-phenyl-1,3-diazaspiro[4.5]decan-1-yl]-N,N-dimethyl-acetamide | SC_3022 | 4-bromopyrimidine-2-carbonitrile | SC_3022 | 462.3 |
| SC_3051 | cis-6-[1-(Cyclobutyl-methyl)-8-dimethylamino-2-oxo-8-phenyl-1,3-diazaspiro[4.5]decan-3-yl]-pyrimidine-4-carbonitrile | INT-987 | 6-bromopyrimidine-4-carbonitrile | SC_3022 | 445.3 |
| SC_3052 | cis-2-(8-Dimethylamino-2-oxo-3,8-diphenyl-1,3-diazaspiro[4.5]decan-1-yl)-N,N-dimethyl-acetamide | INT-987 | bromobenzene | SC_3022 | 435.3 |
| SC_3053 | cis-1-(Cyclobutyl-methyl)-8-dimethylamino-3,8-diphenyl-1,3-diazaspiro[4.5]decan-2-one | INT-987 | bromobenzene | SC_3022 | 418.3 |
| SC_3054 | cis-2-[8-Dimethylamino-1-(2-methoxy-ethyl)-2-oxo-8-phenyl-1,3-diazaspiro[4.5]decan-3-yl]-pyrimidine-5-carbonitrile | INT-980 | 5-chloropyrimidine-2-carbonitrile | SC_3022 | 435.2 |
| SC_3055 | cis-8-Dimethylamino-1-(2-methoxy-ethyl)-3,8-diphenyl-1,3-diazaspiro[4.5]decan-2-one | INT-980 | bromobenzene | SC_3022 | 408.3 |
| SC_3056 | cis-5-[8-Dimethylamino-1-(2-methoxy-ethyl)-2-oxo-8-phenyl-1,3-diazaspiro[4.5]decan-3-yl]-4-methyl-pyridine-2-carbonitrile | INT-980 | 5-bromo-4-methylpicolinonitrile | SC_3022 | 448.3 |
| SC_3057 | cis-N,N-Dimethyl-2-(8-methylamino-2-oxo-3,8-diphenyl-1,3-diazaspiro[4.5]decan-1-yl)-acetamide | SC_3052 | — | SC_3045 | 421.3 |
| SC_3058 | cis-5-[1-[(1-Cyano-cyclobutyl)-methyl]-8-methylamino-2-oxo-8-phenyl-1,3-diazaspiro[4.5]decan-3-yl]-pyrimidine-2-carbonitrile | SC_3041 | — | SC_3058 | 456.2 |
| SC_3059 | cis-5-[1-[(1-Cyano-cyclobutyl)-methyl]-8-(ethyl-methyl-amino)-2-oxo-8-phenyl-1,3-diazaspiro[4.5]decan-3-yl]-pyrimidine-2-carbonitrile | INT-797 | 5-bromopyrimidine-2-carbo-nitrile (step 1); 1-(bromo-methyl)cyclobutane-carbonitrile (step 2) | SC_3013 | 484.3 |
| SC_3060 | CIS-4-[8-Dimethylamino-1-[(1-hydroxy-cyclobutyl)-methyl]-2-oxo-8-phenyl-1,3-diazaspiro[4.5]decan-3-yl]-benzonitrile | INT-987 | 4-bromobenzonitrile (step 1); (1-(tert-butyldimethylsilyloxy) cyclobutyl)methyl 4-methylbenzene-sulfonate (2 step) | SC_3013 | 459.3 |

| Example | Chemical Name | Reactant I | Reactant II | in analogy to method | m/z [M + H]+ |
|---|---|---|---|---|---|
| SC_3061 | cis-3-[8-Dimethylamino-1-[(1-hydroxy-cyclobutyl)-methyl]-2-oxo-8-phenyl-1,3-diazaspiro[4.5]decan-3-yl]-benzonitrile | INT-987 | 3-bromobenzonitrile (step 1); (1-(tert-butyldimethylsilyloxy)cyclobutyl)methyl 4-methylbenzene-sulfonate (step 2) | SC_3013 | 459.3 |
| SC_3063 | cis-5-[1-[(1-Cyano-cyclobutyl)-methyl]-8-dimethylamino-2-oxo-8-phenyl-1,3-diazaspiro[4.5]decan-3-yl]-pyridine-2-carbonitrile | INT-987 | 5-bromopicolinonitrile (step 1); 1-(bromomethyl)cyclo-butanecarbonitrile (step 2) | SC_3013 | 469.3 |
| SC_3064 | cis-2-[3-(2-Cyano-pyrimidin-5-yl)-8-dimethylamino-2-oxo-8-phenyl-1,3-diazaspiro[4.5]decan-1-yl]-N-propyl-acetamide | INT-600 | 2-bromo-N-propylacetamide | SC_3064 | 476.3 |
| SC_3065 | cis-5-[1-(Cyclobutyl-methyl)-8-(ethyl-methyl-amino)-2-oxo-8-phenyl-1,3-diazaspiro[4.5]decan-3-yl]-4-methoxy-pyrimidine-2-carbonitrile | INT-986 | 5-bromo-4-methoxypyrimidine-2-carbonitrile | SC_3065 | 489.3 |
| SC_3066 | cis-4-[1-(Cyclobutyl-methyl)-8-methylamino-2-oxo-8-phenyl-1,3-diazaspiro[4.5]decan-3-yl]-3-methoxy-benzonitrile | SC_3080 | — | SC_3066 | 459.3 |
| SC_3067 | cis-5-[8-Dimethylamino-1-(3-methoxy-propyl)-2-oxo-8-phenyl-1,3-diazaspiro[4.5]decan-3-yl]-6-methoxy-pyridine-2-carbonitrile | INT-979 | 5-bromo-6-methoxypicolinonitrile | SC_3022 | 478.3 |
| SC_3068 | cis-4-[8-Dimethylamino-1-[(1-hydroxy-cyclobutyl)-methyl]-2-oxo-8-phenyl-1,3-diazaspiro[4.5]decan-3-yl]-benzamide | SC_3060 | — | SC_3016 | 477.3 |
| SC_3069 | cis-5-[8-Dimethylamino-1-[(1-hydroxy-cyclobutyl)-methyl]-2-oxo-8-phenyl-1,3-diazaspiro[4.5]decan-3-yl]-pyridine-2-carbonitrile | INT-976 | 5-bromopicolinonitrile (step 1); 1-(tert-butyldimethyl-silyloxy)cyclobutyl)methyl 4-methylbenzene-sulfonate (step 2) | SC_3013 | 460.3 |
| SC_3070 | cis-5-[8-Dimethylamino-1-[(1-hydroxy-cyclobutyl)-methyl]-2-oxo-8-phenyl-1,3-diazaspiro[4.5]decan-3-yl]-N-[(1-hydroxy-cyclobutyl)-methyl]-pyridine-2-carboxylic acid amide | INT-976 | 5-bromopicolinonitrile (step 1); 1-(tert-butyldimethyl-silyloxy)cyclobutyl)methyl 4-methylbenzene-sulfonate (step 2) | SC_3013 | 562.3 |
| SC_3071 | cis-2-[8-Dimethylamino-1-[(1-hydroxy-cyclobutyl)-methyl]-2-oxo-8-phenyl-1,3-diazaspiro[4.5]decan-3-yl]-benzonitrile | INT-976 | 2-bromobenzonitrile (step 1); 1-(tert-butyldimethyl-silyloxy)cyclobutyl)methyl 4-methylbenzene-sulfonate (step 2) | SC_3013 | 459.3 |
| SC_3072 | cis-3-[1-(Cyclobutyl-methyl)-8-dimethylamino-2-oxo-8-phenyl-1,3-diazaspiro[4.5]decan-3-yl]-benzonitrile | INT-987 | 3-iodobenzonitrile | SC_3022 | 443.3 |
| SC_3073 | cis-1-(Cyclobutyl-methyl)-8-dimethylamino-8-phenyl-3-[2-(trifluoromethyl)-pyrimidin-5-yl]-1,3-diazaspiro[4.5]decan-2-one | INT-987 | 5-bromo-2-(trifluoromethyl)pyrimidine | SC_3022 | 488.3 |
| SC_3074 | cis-5-[1-(Cyclobutyl-methyl)-8-dimethylamino-2-oxo-8-phenyl-1,3-diazaspiro[4.5]decan-3-yl]-4-methyl-pyridine-2-carboxylic acid methyl ester | INT-987 | methyl 5-bromo-4-methyl-picolinate | SC_3022 | 491.3 |
| SC_3075 | cis-1-(Cyclobutyl-methyl)-8-dimethylamino-3-(5-methoxy-pyrazin-2-yl)-8-phenyl-1,3-diazaspiro[4.5]decan-2-one | INT-987 | 2-bromo-5-methoxypyrazine | SC_3022 | 450.3 |
| SC_3076 | cis-1-(Cyclobutyl-methyl)-8-dimethylamino-3-(2-methoxy-pyrimidin-5-yl)-8-phenyl-1,3-diazaspiro[4.5]decan-2-one | INT-987 | 5-bromo-2-methoxypyrimidine | SC_3022 | 450.3 |
| SC_3077 | cis-4-[1-(Cyclobutyl-methyl)-8-dimethylamino-2-oxo-8-phenyl-1,3-diazaspiro[4.5]decan-3-yl]-benzonitrile | INT-987 | 4-iodobenzonitrile | SC_3022 | 443.3 |
| SC_3078 | cis-5-[1-(Cyclobutyl-methyl)-8-dimethylamino-2-oxo-8-phenyl-1,3-diazaspiro[4.5]decan-3-yl]-4-methyl-pyridine-2-carbonitrile | INT-987 | 5-bromo-4-methylpicolinonitrile | SC_3022 | 458.3 |
| SC_3079 | cis-1-(Cyclobutyl-methyl)-8-dimethylamino-3-(5-fluoro-pyrimidin-2-yl)-8-phenyl-1,3-diazaspiro[4.5]decan-2-one | INT-987 | 2-bromo-5-fluoropyrimidine | SC_3022 | 438.3 |
| SC_3080 | cis-4-[1-(Cyclobutyl-methyl)-8-dimethylamino-2-oxo-8-phenyl-1,3-diazaspiro[4.5]decan-3-yl]-3-methoxy-benzonitrile | INT-987 | 4-bromo-3-methoxybenzonitrile | SC_3022 | 473.3 |
| SC_3081 | cis-4-[1-(Cyclobutyl-methyl)-8-dimethylamino-2-oxo-8-phenyl-1,3-diazaspiro[4.5]decan-3-yl]-benzoic acid methyl ester | INT-987 | methyl 4-iodobenzoate | SC_3022 | 476.3 |
| SC_3082 | cis-1-(Cyclobutyl-methyl)-8-dimethylamino-8-phenyl-3-(2-pyrrolidin-1-yl-pyrimidin-4-yl)-1,3-diazaspiro[4.5]decan-2-one | INT-987 | 4-iodo-2-(pyrrolidin-1-yl)pyrimidine | SC_3022 | 489.3 |
| SC_3083 | cis-1-(Cyclobutyl-methyl)-8-dimethylamino-8-phenyl-3-(5-pyridin-2-yl-thiophen-2-yl)-1,3-diazaspiro[4.5]decan-2-one | INT-987 | 2-(5-bromothiophen-2-yl)pyridine | SC_3022 | 501.3 |
| SC_3084 | cis-1-(Cyclobutyl-methyl)-8-dimethylamino-3[2-methylsulfonyl-4-(trifluoromethyl)-phenyl]-8-phenyl-1,3-diazaspiro[4.5]decan-2-one | INT-987 | 1-bromo-2-(methylsulfonyl)-4-(trifluoromethyl)benzene | SC_3022 | 564.2 |
| SC_3085 | cis-1-(Cyclobutyl-methyl)-8-dimethylamino-8-phenyl-346-(trifluoromethyl)-pyridin-3-yl]-1,3-diazaspiro[4.5]decan-2-one | INT-987 | 5-bromo-2-(trifluoromethyl)pyridine | SC_3022 | 487.3 |
| SC_3086 | cis-1-(Cyclobutyl-methyl)-3-(2,4-dimethoxy-phenyl)-8-dimethylamino-8-phenyl-1,3-diazaspiro[4.5]decan-2-one | INT-987 | 1-bromo-2,4-dimethoxybenzene | SC_3022 | 478.3 |
| SC_3087 | cis-2-[1-(Cyclobutyl-methyl)-8-dimethylamino-2-oxo-8-phenyl-1,3-diazaspiro[4.5]decan-3-yl]-4-methylsulfonyl-benzonitrile | INT 987 | 2-iodo-4-(methylthio)-benzonitrile (SC_3022) | SC_3022/ SC_3008 | 521.3 |
| SC_3088 | cis-5-[1-(Cyclobutyl-methyl)-8-dimethylamino-2-oxo-8-phenyl-1,3-diazaspiro[4.5]decan-3-yl]-2-fluoro-benzonitrile | INT-987 | 5-bromo-2-fluorobenzonitrile | SC_3022 | 461.3 |

| Example | Chemical Name | Reactant I | Reactant II | in analogy to method | m/z [M + H]+ |
|---|---|---|---|---|---|
| SC_3089 | cis-4-[1-(Cyclobutyl-methyl)-8-dimethylamino-2-oxo-8-phenyl-1,3-diazaspiro[4.5]decan-3-yl]-N,N-dimethyl-3-(trifluoromethyl)-benzenesulfonic acid amide | INT-987 | 4-bromo-N,N-dimethyl-3-(trifluoromethyl) benzenesulfonamide | SC_3022 | 593.3 |
| SC_3090 | cis-2-[1-(Cyclobutyl-methyl)-8-dimethylamino-2-oxo-8-phenyl-1,3-diazaspiro[4.5]decan-3-yl]-benzonitrile | INT-987 | 2-bromobenzonitrile | SC_3022 | 443.3 |
| SC_3091 | cis-1-(Cyclobutyl-methyl)-8-dimethylamino-3-(2-methyl-imidazo[1,2-a]pyrazin-6-yl)-8-phenyl-1,3-diazaspiro[4.5]decan-2-one | INT-987 | 6-bromo-2-methylimidazo[1,2-a]pyrazine | SC_3022 | 473.3 |
| SC_3092 | cis-1-(Cyclobutyl-methyl)-8-dimethylamino-3-(4-methylsulfonyl-phenyl)-8-phenyl-1,3-diazaspiro[4.5]decan-2-one | INT-987 | (4-iodophenyl)(methyl)sulfane | SC_3022/ SC_3008 | 496.3 |
| SC_3093 | cis-2-[1-(Cyclobutyl-methyl)-8-dimethylamino-2-oxo-8-phenyl-1,3-diazaspiro[4.5]decan-3-yl]-5-methoxy-benzonitrile | INT-987 | 2-bromo-5-methoxybenzonitrile | SC_3022 | 473.3 |
| SC_3094 | cis-1-(Cyclobutyl-methyl)-8-dimethylamino-3,8-diphenyl-1,3-diazaspiro[4.5]decan-2-one | INT-987 | bromobenzene | SC_3022 | 418.3 |
| SC_3096 | cis-1-(Cyclobutyl-methyl)-8-dimethylamino-8-phenyl-3-pyrazin-2-yl-1,3-diazaspiro[4.5]decan-2-one | INT-987 | 2-bromopyrazine | SC_3022 | 420.3 |

| Example | Chemical name | Reactant I | Reactant II | in analogy to method | ¹H NMR data | m/z (M + H)⁺ |
|---|---|---|---|---|---|---|
| SC_3098 | cis-8-Dimethylamino-1-[(1-hydroxy-cyclobutyl)-methyl]-3-[2-(4-methyl-piperazin-1-yl)-pyrimidin-5-yl]-8-phenyl-1,3-diazaspiro[4.5]decan-2-one | INT-799 | 5-bromo-2-(4-methylpiperazin-1-yl)pyrimidine | SC_3097 | 1H NMR (DMSO-d6): δ 8.56 (s, 2H), 7.36-7.35 (m, 4H), 7.27-7.24 (m, 1H), 5.52 (s, 1H), 3.71 (s, 2H), 3.64 (m, 4H), 3.21 (s, 2H), 2.69-2.67 (m, 2H), 2.32 (m, 4H), 2.19-2.11 (m, 7H), 1.98 (s, 6H), 1.92-1.86 (m, 2H), 1.66-1.64 (m, 1H), 1.52-1.42 (m, 5H). | 534.4 |
| SC_3101 | cis-1-[(1-Hydroxy-cyclobutyl)-methyl]-8-methylamino-3-[2-(4-methyl-piperazin-1-yl)-pyrimidin-5-yl]-8-phenyl-1,3-diazaspiro[4.5]decan-2-one | SC_3098 | | SC_3099 | 1H NMR (DMSO-d6): δ 8.58 (s, 2H), 7.48 (d, 2H), 7.32 (t, 2H), 7.19 (t, 1H), 5.61 (s, 1H), 3.75 (s, 2H), 3.66-3.64 (m, 4H), 3.30 (s, 2H), 2.35-2.32 (m, 4H), 2.25-2.19 (m, 5H), 2.12-2.07 (m, 2H), 1.90-1.88 (m, 7H), 1.79-1.73 (m, 1H), 1.65-1.63 (m, 1H), 1.50-1.44 (m, 3H). | 520.4 |
| SC_3102 | cis-1-[(1-Hydroxy-cyclobutyl)-methyl]-8-methylamino-8-phenyl-3-(2-piperazin-1-yl-pyrimidin-5-yl)-1,3-diazaspiro[4.5]decan-2-one dihydrochloride | SC_3100 | | SC_3099 | 1H NMR (DMSO-d6): δ 9.51 (br s, 2H), 9.15 (br s, 2H), 8.65 (s, 2H), 7.69-7.68 (m, 2H), 7.50-7.41 (m, 3H), 3.88-3.86 (m, 4H), 3.79 (m, 2H), 3.65 (m, 2H), 3.16-3.13 (m, 4H), 2.64-2.62 (m, 2H), 2.38-2.33 (m, 2H), 2.16-2.04 (m, 7H), 1.90-1.84 (m, 2H), 1.76-1.70 (m, 3H), 1.60-1.58 (m, 1H). | 506.3 |
| SC_3104 | cis-1-(Cyclobutyl-methyl)-8-methylamino-3-[4-methyl-6-(trifluoromethyl)-pyridin-3-yl]-8-phenyl-1,3-diazaspiro[4.5]decan-2-one | SC_3103 | | SC_3099 | 1H NMR (DMSO-d6): δ 8.59 (s, 1H), 7.81 (s, 1H), 7.44 (d, 2H), 7.30 (t, 2H), 7.17 (t, 1H), 3.76 (s, 2H), 3.21 (d, 2H), 2.61-2.57 (m, 1H), 2.32 (s, 3H), 2.29-2.17 (m, 3H), 2.03-1.97 (m, 2H), 1.91-1.88 (m, 5H), 1.84-1.67 (m, 6H), 1.51-1.48 (m, 2H). | 487.3 |
| SC_3106 | cis-1-(Cyclopropyl-methyl)-8-methylamino-3-(4-methylsulfonyl-phenyl)-8-phenyl-1,3-diazaspiro[4.5]decan-2-one | SC_3105 | | SC_3099 | 1H NMR (DMSO-d6): δ 7.90-7.88 (d, 2H), 7.82-7.80 (d, 2H), 7.50-7.48 (d, 2H), 7.35-7.32 (m, 2H), 7.22-7.19 (m, 1H), 3.80 (s, 2H), 3.14-3.10 (m, 5H), 2.29-2.23 (m, 3H), 1.91-1.79 (m, 7H), 1.42-1.39 (m, 2H), 1.05-1.04 (m, 1H), 0.50-0.47 (m, 2H), 0.34-0.32 (m, 2H). | 468.2 |
| SC_3107 | cis-1-(Cyclopropyl-methyl)-8-dimethylamino-3-(2-fluoro-4-methylsulfonyl-phenyl)-8-phenyl-1,3-diazaspiro[4.5]decan-2-one | INT-983 | 1-bromo-2-fluoro-4-(methylsulfonyl)benzene (step 1), (Bromomethyl)cyclopropane (step 2) | SC3103 (step 1), SC_3105 (step 2) | 1H NMR (DMSO-d6): δ 7.85 (t, 1H), 7.79-7.76 (m, 1H), 7.72-7.69 (m, 1H), 7.37-7.33 (m, 4H), 7.27-7.24 (m, 1H), 3.81 (s, 2H), 3.24 (s, 3H), 3.07 (d, 2H), 2.71-2.68 (m, 2H), 2.28-2.22 (m, 2H), 1.99 (s, 6H), 1.53-1.42 (m, 4H), 1.00-0.99 (m, 1H), 0.53-0.49 (m, 2H), 0.34-0.30 (m, 2H). | 500.2 |
| SC_3108 | cis-2-[8-Dimethylamino-1-[(1-hydroxy-cyclobutyl)-methyl]-2-oxo-8-phenyl-1,3-diazaspiro[4.5]decan-3-yl]-benzamide; formic acid | SC_3071 | | SC_3016 | 1H NMR (600 MHz, DMSO) δ 7.59-7.55 (s, 1H), 7.47-7.39 (m, 2H), 7.39-7.31 (m, 5H), 7.30-7.21 (m, 3H), 3.77-3.73 (s, 2H), 3.21-3.17 (s, 1H), 2.72-2.66 (d, 2H), 2.17-2.09 (m, 2H), 2.02-1.99 (s, 6H), 1.95-1.86 (m, 2H), 1.71-1.60 (m, 3H), 1.49-1.37 (m, 3H). | 477.3 |

-continued

| Example | Chemical name | Reactant I | Reactant II | in analogy to method | 1H NMR data | m/z (M + H)+ |
|---|---|---|---|---|---|---|
| SC_3109 | cis-2-[Dimethylamino-1-[2-(1-methoxy-cyclobutyl)-ethyl]-2-oxo-8-phenyl-1,3-diazaspiro[4.5]decan-3-yl]-benzamide | INT988 | 2-bromobenzonitrile | SC_3097 (step 1), SC_3109 (step 2) | 1H NMR (600 MHz, DMSO) δ 7.52-7.48 (s, 1H), 7.47-7.31 (m, 7H), 7.29-7.23 (m, 1H), 7.25-7.22 (s, 1H), 7.24-7.18 (m, 1H), 3.68-3.65 (s, 3H), 3.13-3.10 (s, 2H), 3.09-3.02 (m, 2H), 2.71-2.65 (m, 2H), 2.21-2.12 (m, 2H), 2.09-1.99 (m, 2H), 2.02-1.98 (s, 6H), 1.97-1.86 (m, 4H), 1.77-1.67 (m, 1H), 1.64-1.52 (m, 3H), 1.44-1.36 (td, 2H). | 505.3 |
| SC_3110 | cis-8-Dimethylamino-1-[2-(1-methoxy-cyclobutyl)-ethyl]-3-(2-methyl-pyrimidin-5-yl)-8-phenyl-1,3-diazaspiro[4.5]decan-2-one | INT-988 | 5-bromo2-methyl-pyrimidine | SC_3103 | 1H NMR (600 MHz, DMSO) δ 8.94-8.90 (s, 2H), 7.41-7.34 (d, 4H), 7.32-7.24 (ddd, 1H), 3.76-3.72 (s, 2H), 3.15-3.08 (m, 5H), 2.72-2.65 (m, 2H), 2.57-2.52 (s, 3H), 2.25-2.16 (m, 2H), 2.11-2.02 (m, 2H), 2.03-1.99 (s, 6H), 1.99-1.86 (m, 4H), 1.78-1.68 (tq, 1H), 1.65-1.51 (m, 3H), 1.50-1.44 (d, 2H). | 478.3 |
| SC_3111 | cis-5-[1-[(1-Hydroxy-cyclobutyl)-methyl]-8-methylamino-2-oxo-8-phenyl-1,3-diazaspiro[4.5]decan-3-yl]-pyrimidine-2-carbonitrile | INT-799 | 5-bromo-2-cyanopyrimidine | SC_3103 (step 1), SC_3099 (step 2) | 1H NMR (600 MHz, DMSO) δ 9.24-9.20 (s, 2H), 7.53-7.48 (m, 2H), 7.37-7.31 (t, 2H), 7.25-7.19 (t, 1H), 3.93-3.89 (s, 2H), 3.42-3.36 (m, 2H), 2.35-2.26 (td, 2H), 2.18-2.10 (tt, 2H), 2.09-2.04 (s, 1H), 1.97-1.88 (m, 2H), 1.93-1.90 (s, 6H), 1.86-1.77 (td, 2H), 1.72-1.62 (s, 1H), 1.59-1.54 (d, 1H), 1.48-1.43 (d, 2H). | 447.3 |
| SC_3112 | cis-4-[1-[(1-Hydroxy-cyclobutyl)-methyl]-8-methylamino-2-oxo-8-phenyl-1,3-diazaspiro[4.5]decan-3-yl]-3-methoxy-benzonitrile | INT-976 | 1-bromo-4-cyano-2-methoxybenzene (step 1) | SC_3112 | 1HNMR (DMSO-d6, 400 MHz), δ (ppm) = 7.54 (s, 1H), 7.50 (d, 1H, J = 8.16 Hz), 7.46-7.39 (m, 3H), 7.30 (t, 2H, J = 7.48 Hz), 7.18 (t, 1H, J = 7.16 Hz), 5.59 (s, 1H), 3.85 (s, 3H), 3.73 (s, 2H), 3.30 (s, 2H, merged with DMSO-water), 2.32-2.08 (m, 4H), 1.91-1.87 (m, 7H), 1.68-1.47 (m, 6H). | 475.3 |
| SC_3114 | cis-4-[8-Ethylamino-1-[(1-hydroxy-cyclobutyl)-methyl]-2-oxo-8-phenyl-1,3-diazaspiro[4.5]decan-3-yl]-3-methoxy-benzonitrile | INT-1008 | 4-Bromo-3-methoxy-benzonitrile (step 1) | SC_3112 (step 1, step 2) | 1HNMR (DMSO-d6, 400 MHz), δ (ppm) = 7.54 (s, 1H), 7.51-7.45 (m, 3H), 7.40 (d, 1H, J = 8.24 Hz), 7.29 (t, 2H, J = 7.58 Hz), 7.17 (t, 1H, J = 7.12 (Hz), 5.60 (s, 1H), 3.85 (s, 3H), 3.73 (s, 2H), 3.21 (s, 2H, merged with DMSO-H2O), 2.32-2.27 (m, 2H), 2.08 (bs, 5H), 1.96-1.87 (m, 4H), 1.68-1.46 (m, 6H), 0.97 (t, 3H, J = 4.0 Hz). | 489.1 |
| SC_3115 | cis-2-[8-Ethylamino-1-[(1-hydroxy-cyclobutyl)-methyl]-2-oxo-8-phenyl-1,3-diazaspiro[4.5]decan-3-yl]-benzonitrile | INT-1008 | 2-bromo-benzonitrile (step 1) | SC_3112 (step 1, step 2) | 1HNMR (DMSO-d6, 400 MHz), δ (ppm) = 7.82 (d, 1H, J = 7.56 Hz), 7.71 (t, 1H, J = 6.98 Hz), 7.53-7.47 (m, 3H), 7.37-7.27 (m, 3H), 7.19-7.17 (m, 1H), 5.55 (s, 1H), 3.87 (s, 2H), 3.38 (s, 2H), 2.36-2.32 (m, 2H), 2.10 (bs, 4H), 1.94-1.86 (m, 4H), 1.75-1.48 (6H), 0.98 (bs, 3H). | 458.9 |

| Example | Chemical name | Reactant I | Reactant II | in analogy to method | 1H NMR data | m/z (M + H)+ |
|---|---|---|---|---|---|---|
| SC_3116 | cis-5-[1-[(1-Hydroxy-cyclobutyl)-methyl]-8-methylamino-2-oxo-8-phenyl-1,3-diazaspiro[4.5]decan-3-yl]-4-methoxy-pyrimidine-2-carbonitrile | INT-799 | 5-bromo-4-methoxy-pyrimidine-2-carbonitrile (step 1) | SC_3103 (step 1), SC_3099 (step 2) | 1HNMR (DMSO-d6, 400 MHz, at 100° C.), δ (ppm) = 8.79 (s, 1H), 7.46 (d, 2H, J = 7.84 Hz), 7.32 (t, 2H, J = 7.12 Hz), 7.19 (t, 1H, J = 7.28 Hz), 5.09 (bs, 1H), 4.05 (s, 3H), 3.85 (s, 2H), 3.38 (s, 2H), 2.31-2.15 (m, 4H), 1.98 (m, 7H), 1.74-1.51 (m, 6H). | 477.2 |
| SC_3117 | cis-2-[8-Dimethylamino-1-(oxetan-3-yl-methyl)-2-oxo-8-phenyl-1,3-diazaspiro[4.5]decan-3-yl]-benzamide | SC_3274 | toluene-4-sulfonic acid oxetan-3-ylmethyl ester (step 1) | SC_3105 (step 1), SC_3016 (step 2) | 1HNMR (DMSO-d6, 400 MHz), δ (ppm) = 7.52 (s, 1H), 7.43-7.33 (m, 6H), 7.30-7.17 (m, 4H), 4.63 (t, 2H, J = 6.9 Hz), 4.39 (t, 2H, J = 6.08 Hz), 3.64 (s, 2H), 3.38 (d, 2H, J = 7.32 Hz), 3.21-3.15 (m, 1H), 2.70-2.66 (m, 2H), 2.08-1.98 (m, 8H), 1.54-1.35 (m, 4H). | 463.4 |
| SC_3118 | cis-4-Methoxy-5-(8-methylamino-2-oxo-8-phenyl-1,3-diazaspiro[4.5]decan-3-yl)-pyrimidine-2-carbonitrile | INT-976 | 5-bromo-4-methoxy-pyrimidine-2-carbonitrile (step 1) | SC_3103 (step 1), SC_3099 (step 2) | 1HNMR (DMSO-d6, 400 MHz), δ (ppm) = 8.80 (s, 1H), 7.86 (bs, 1H), 7.43 (d, 2H, J = 7.84 Hz), 7.32 (t, 2H, J = 7.32 Hz), 7.21-7.18 (m, 1H), 4.02 (s, 3H), 3.83 (s, 2H), 2.07-2.00 (m, 3H), 1.90-1.74 (m, 7H), 1.48 (d, 2H, J = 13.8 Hz). | 393.0 |
| SC_3119 | cis-2-(8-Methylamino-2-oxo-8-phenyl-1,3-diazaspiro[4.5]decan-3-yl)-benzamide | INT-976 | 2-bromo-benzonitrile (step 1) | SC_3103 (step 1), SC_3099 (step 2), SC_3016 (step 3) | 1HNMR (DMSO-d6, 400 MHz) δ 7.51 (bs, 1H), 7.43-7.37 (m, 4H), 7.33-2.29 (m, 3H, J = 8.28 Hz), 7.22-7.16 (m, 3H), 6.93 (bs, 1H), 3.64 (s, 2H), 2.03-1.97 (m, 2H), 1.86 (bs, 5H), 1.73-1.58 (m, 4H). | 379.4 |
| SC_3121 | cis-3-(2-Cyclopropyl-pyrimidin-5-yl)-8-dimethylamino-8-phenyl-1,3-diazaspiro[4.5]decan-2-one | INT-976 | 5-bromo-2-cyclopropyl-pyrimidine | SC_3103 | 1H NMR (600 MHz, DMSO) δ 8.80 (s, 2H), 7.67 (s, 1H), 7.41-7.32 (m, 4H), 7.31-7.22 (ddt, 1H), 3.60 (s, 2H), 2.42-2.36 (m, 2H), 2.18-2.08 (m, 1H), 1.98-1.85 (m, 4H), 1.96 (s, 6H), 1.47 (s, 2H). | 392.3 |
| SC_3122 | cis-8-Dimethylamino-3-[4-methyl-6-(trifluoromethyl)-pyridin-3-yl]-8-phenyl-1,3-diazaspiro[4.5]decan-2-one | INT-976 | 5-bromo-4-methyl-2-(trifluoromethyl)pyridine | SC_3103 | 1H NMR (600 MHz, DMSO) δ 8.57 (s, 1H), 7.79 (s, 1H), 7.52 (s, 1H), 7.40-7.32 (m, 4H), 7.30-7.22 (tt, 1H), 3.61 (s, 2H), 2.39-2.30 (m, 5H), 1.96 (s, 6H), 2.00-1.91 (m, 2H), 1.84 (s, 2H), 1.57-1.53 (s, 2H). | 433.2 |
| SC_3123 | cis-8-Dimethylamino-3-(2-methylsulfonyl-phenyl)-8-phenyl-1,3-diazaspiro[4.5]decan-2-one | INT-976 | 1-bromo-2-methylsulfonyl-benzene | SC_3103 | 1H NMR (600 MHz, DMSO) δ 7.98-7.92 (dd, 1H), 7.81-7.74 (td, 1H), 7.61-7.54 (td, 1H), 7.52-7.46 (m, 2H), 7.41-7.31 (m, 2H), 7.35 (s, 2H), 7.29-7.22 (tt, 1H), 3.49 (s, 2H), 3.25 (s, 3H), 2.37 (s, 2H), 1.99-1.96 (m, 1H), 1.98-1.94 (s, 6H), 1.95-1.91 (d, 1H), 1.83-1.79 (m, 2H), 1.58-1.55 (s, 2H). | 428.2 |
| SC_3124 | cis-8-Dimethylamino-8-phenyl-3-(2-piperazin-1-yl-pyrimidin-5-yl)-1,3-diazaspiro[4.5]decan-2-one | INT-989 | Piperazine-2-one | SC_3120 | 1H NMR (600 MHz, DMSO) δ 8.52 (s, 2H), 7.41-7.31 (m, 5H), 3.59-3.54 (m, 4H), 3.52 (s, 2H), 2.76-2.70 (m, 4H), 2.55 (s, 3H), 2.49-2.33 (m, 2H), 1.96 (s, 6H), 1.93-1.83 (m, 4H), 1.51-1.43 (s, 2H). | 436.3 |
| SC_3125 | trans-2-(8-Ethylamino-2-oxo-8-phenyl-1,3-diazaspiro[4.5]decan-3-yl)-benzamide | SC_3127 | | SC_3016 | 1HNMR (DMSO-d6, 400 MHz), δ (ppm) = 7.56-7.20 (m, 12H), 3.60 (s, 2H), 2.08-1.92 (m, 6H), 1.69 (bs, 2H), 1.56 (bs, 2H), 0.93 (t, 3H). | 393.1 |

| Example | Chemical name | Reactant I | Reactant II | in analogy to method | 1H NMR data | m/z (M + H)+ |
|---|---|---|---|---|---|---|
| SC_3126 | cis-2-(8-Ethylamino-2-oxo-8-phenyl-1,3-diazaspiro[4.5]decan-3-yl)-benzamide | SC_3128 | | SC_3016 | 1HNMR (DMSO-d6, 400 MHz), δ (ppm) = 7.51-2.38 (m, 5H), 7.32-7.30 (m, 3H), 7.22-7.18 (m, 3H), 6.93 (s, 1H), 3.63 (s, 2H), 2.07-1.98 (m, 4H), 1.86-1.72 (m, 4H), 1.60-1.57 (m, 2H), 0.93 (t, 3H). | 393.4 |
| SC_3127 | cis-2-(8-Ethylamino-2-oxo-8-phenyl-1,3-diazaspiro[4.5]decan-3-yl)-benzonitrile | INT-1009 | 2-bromo-benzonitrile | SC_3103 | 1HNMR (DMSO-d6, 400 MHz), δ (ppm) = 7.77 (d, 1H, J = 6.8 Hz), 7.69-7.65 (m, 1H), 7.51 (d, 1H, J = 8.4 Hz), 7.44 (d, 2H, J = 7.6 Hz), 7.39 (s, 1H), 7.34-7.28 (m, 3H), 7.17 (t, 1H, 7.2 Hz), 3.77 (s, 2H), 2.10-2.04 (m, 4H), 1.91-1.88 (m, 2H), 1.80-1.74 (m, 3H), 1.61-1.58 (m, 2H), 0.94 (t, 3H, J = 6.8 Hz). | 375.1 |
| SC_3128 | cis-2-(8-Ethylamino-2-oxo-8-phenyl-1,3-diazaspiro[4.5]decan-3-yl)-benzonitrile | INT-1008 | 2-bromo-benzonitrile | SC_3103 | 1HNMR (DMSO-d6, 400 MHz), δ (ppm) = 7.89 (bs, 1H), 7.79 (d, 1H, J = 7.6), 7.69 (t, 1H, J = 7.6 Hz), 7.54-7.50 (m, 3H), 7.36-7.30 (m, 3H), 7.18 (t, 1H, J = 7.2 Hz), 3.73 (s, 2H), 2.08-1.92 (m, 7H), 1.71 (bs, 2H), 1.59 (bs, 2H), 0.93 (t, 3H, J = 6.4 Hz). | 375.1 |
| SC_3131 | cis-3-[5-(8-Dimethylamino-2-oxo-8-phenyl-1,3-diazaspiro[4.5]decan-3-yl)-pyrimidin-2-yl]-benzamide | SC_3129 | | SC_3016 | 1H NMR (600 MHz, DMSO) δ 9.11 (s, 2H), 8.79 (t, 1H), 8.43 (dt, 1H), 8.09 (s, 1H), 7.94 (dt, 1H), 7.84 (s, 1H), 7.56 (t, 1H), 7.41-7.35 (m, 4H), 7.28 (ddd, 1H), 3.72 (s, 2H), 2.00-1.84 (m, 2H), 1.98 (s, 6H), 1.53 (s, 2H). | 471.3 |
| SC_3134 | trans-4-(8-Ethylamino-2-oxo-8-phenyl-1,3-diazaspiro[4.5]decan-3-yl)-3-methoxy-benzonitrile | INT-1009 | 4-Bromo-3-methoxy-benzonitrile | SC_3103 | 1HNMR (DMSO-d6, 400 MHz), δ (ppm) = 7.71 (bs, 1H), 7.56-7.49 (m, 4H), 7.37 (d, 1H, J = 6.6 Hz), 7.31 (t, 2H, J = 7.10 Hz), 7.19-7.17 (m, 1H), 3.87 (s, 3H), 3.62 (s, 2H), 2.06-1.90 (m, 7H), 1.69-1.53 (m, 4H), 0.92 (t, 3H, J = 6.70 Hz). | 405.3 |
| SC_3135 | cis-4-(8-Ethylamino-2-oxo-8-phenyl-1,3-diazaspiro[4.5]decan-3-yl)-3-methoxy-benzonitrile | INT-1008 | 4-Bromo-3-methoxy-benzonitrile | SC_3103 | 1HNMR (DMSO-d6, 400 MHz), δ (ppm) = 7.52-7.50 (m, 2H), 7.44-7.43 (m, 2H), 736 (d, 1H, J = 8.04 Hz), 7.30-7.19 (m, 4H), 3.83 (s, 3H), 3.63 (s, 2H), 2.05-1.72 (m, 8H), 1.53-1.50 (m, 2H), 0.92 (t, 3H). | 405.2 |
| SC_3136 | cis-3-[2-(4-Acetyl-piperazin-1-yl)-pyrimidin-5-yl]-8-dimethylamino-8-phenyl-1,3-diazaspiro[4.5]decan-2-one | SC_3124 | acetyl chloride | SC_3130 | | 478.3 |
| SC_3137 | cis-8-Dimethylamino-8-phenyl-3-(2-pyridin-4-yl-pyrimidin-5-yl)-1,3-diazaspiro[4.5]decan-2-one | INT-989 | pyridine-4-boronic acid | SC_3129 | 1H NMR (600 MHz, DMSO) δ 9.16 (s, 2H), 8.70 (d, 1H), 8.18 (s, 1H), 7.91 (s, 1H), 7.42-7.35 (m, 4H), 3.73 (s, 2H), 2.49-2.37 (m, 2H), 1.98 (s, 6H), 2.01-1.87 (m, 2H), 1.58-1.47 (m, 2H). | 429.2 |
| SC_3138 | cis-8-Dimethylamino-8-phenyl-3-(2-pyridin-3-yl-pyrimidin-5-yl)-1,3-diazaspiro[4.5]decan-2-one | INT-989 | pyridine-3-boronic acid | SC_3129 | 1H NMR (600 MHz, DMSO) δ 9.43 (dd, 1H), 9.13 (s, 2H), 8.65 (dd, 1H), 8.58 (dt, 1H), 7.52 (ddd, 1H), 7.42-7.36 (m, 4H), 7.28 (ddd, 1H), 3.72 (s, 2H), 1.98 (s, 6H), 2.02-1.89 (m, 4H), 1.57-1.46 (m, 4H). | 429.2 |

| Example | Chemical name | Reactant I | Reactant II | in analogy to method | $^1$H NMR data | m/z (M + H)$^+$ |
|---|---|---|---|---|---|---|
| SC_3139 | cis-5-(8-Dimethylamino-2-oxo-8-phenyl-1,3-diazaspiro[4.5]decan-3-yl)-N-(2-hydroxy-ethyl)-pyrimidine-2-carboxylic acid amide | INT-991 | 2-aminoethanol | SC_3133 | 1H NMR (600 MHz, DMSO) δ 9.08 (s, 2H), 8.59 (t, 1H), 7.94 (s, 1H), 7.43-7.30 (m, 5H), 7.30-7.21 (m, 1H), 3.72 (s, 2H), 3.51 (q, 2H), 2.49-2.37 (m, 2H), 2.00-1.90 (m, 10H), 1.89-1.74 (m, 2H), 1.57-1.48 (m, 2H), 1.38-1.32 (m, 1H). | 439.3 |
| SC_3141 | cis-8-Dimethylamino-3-[2-morpholin-4-yl-4-(trifluoromethyl)-pyrimidin-5-yl]-8-phenyl-1,3-diazaspiro[4.5]decan-2-one | INT-976 | 4-[5-bromo-4-(trifluoromethyl)pyrimidin-2-yl]morpholine | SC_3103 | 1H NMR (600 MHz, DMSO) δ 8.59 (d, 1H), 7.39-7.35 (m, 5H), 7.27 (d, 1H), 3.73 (t, 4H), 3.67 (q, 4H), 3.28-3.22 (m, 1H), 2.41-2.28 (m, 2H), 1.98 (s, 6H), 1.94-1.80 (m, 3H), 1.53-1.42 (m, 2H). | 505.3 |
| SC_3142 | cis-4-[5-(8-Dimethylamino-2-oxo-8-phenyl-1,3-diazaspiro[4.5]decan-3-yl)-pyrimidin-2-yl]-benzonitrile | INT-989 | 4-cyanophenylboronic acid | SC_3129 | 1H NMR (600 MHz, DMSO) δ 9.15 (s, 2H), 8.49-8.43 (m, 2H), 7.99-7.92 (m, 2H), 7.89 (s, 1H), 7.38 (m, 4H), 7.28 (td, 1H), 3.73 (s, 2H), 2.48-2.35 (m, 1H), 2.03-1.90 (m, 10H), 1.55-1.48 (m, 2H). | 453.2 |
| SC_3143 | cis-5-(8-Dimethylamino-2-oxo-8-phenyl-1,3-diazaspiro[4.5]decan-3-yl)-4-methoxy-pyrimidine-2-carbonitrile | INT-1008 | 5-Bromo-4-methoxy-pyrimidine-2-carbonitrile | SC_3103 | (DMSO-d6, 400 MHz), δ (ppm) = 8.79 (s, 1H), 7.60 (s, 1H), 7.41 (d, 2H, J = 7.72 Hz), 7.28 (t, 2H, J = 7.54 Hz), 7.16 (t, 1H, J = 7.32 Hz), 3.97 (s, 3H), 3.72 (s, 2H), 2.02 (bs, 4H), 1.90-1.69 (m, 5H), 1.51-1.48 (m, 2H), 0.89 (t, 3H, J = 6.56 Hz). | 407.2 |
| SC_3144 | trans-5-Ethylamino-2-oxo-8-phenyl-1,3-diazaspiro[4.5]decan-3-yl)-4-methoxy-pyrimidine-2-carbonitrile | INT-1009 | 5-Bromo-4-methoxy-pyrimidine-2-carbonitrile | SC_3103 | 1HNMR (DMSO-d6, 400 MHz), δ (ppm) = 8.87 (s, 1H), 8.10 (bs, 1H), 7.50 (d, 2H, J = 7.52 Hz), 7.31 (t, 2H, J = 7.20 Hz), 7.18 (t, 1H, J = 6.88 Hz), 4.04 (s, 3H), 3.74 (s, 2H), 2.07-1.95 (m, 6H), 1.70-1.54 (m, 4H), 0.93 (t, 3H, J = 6.62 Hz). | 407.3 |
| SC_3145 | cis-8-Dimethylamino-3-[2-(morpholine-4-carbonyl)-pyrimidin-5-yl]-8-phenyl-1,3-diazaspiro[4.5]decan-2-one | INT-991 | morpholine | SC_3133 | 1H NMR (600 MHz, DMSO) δ 9.04 (s, 2H), 7.88 (s, 1H), 7.42-7.30 (m, 5H), 7.30-7.22 (m, 1H), 3.75-3.58 (m, 6H), 3.51 (t, 2H), 3.20 (t, 2H), 2.50-2.33 (m, 2H), 1.99-1.90 (m, 8H), 1.89-1.74 (m, 2H), 1.54-1.44 (m, 2H). | 478.3 |
| SC_3147 | cis-8-Dimethylamino-3-[2-(methylsulfonyl-methyl)-phenyl]-8-phenyl-1,3-diazaspiro[4.5]decan-2-one | INT-976 | 1-bromo-2-(methylsulfonylmethyl)benzene | SC_3103 | 1H NMR (600 MHz, DMSO) δ 7.47 (d, 1H), 7.42-7.31 (m, 6H), 7.30-7.22 (m, 3H), 4.50 (s, 2H), 3.56 (s, 2H), 2.88 (s, 3H), 2.42-2.28 (m, 2H), 2.07 (s, 2H), 1.98-1.90 (m, 8H), 1.89-1.69 (m, 2H), 1.61-1.48 (d, 2H). | 442.2 |
| SC_3148 | cis-8-Dimethylamino-3-(4-methyl-2-morpholin-4-yl-pyrimidin-5-yl)-8-phenyl-1,3-diazaspiro[4.5]decan-2-one | INT-992 | morpholine | SC_3120 | 1H NMR (600 MHz, DMSO) δ 8.14 (s, 1H), 7.40-7.32 (m, 4H), 7.26 (td, 1H), 7.21 (s, 1H), 3.69-3.60 (m, 8H), 3.38 (s, 2H), 2.41-2.27 (m, 2H), 2.20 (s, 3H), 1.97 (s, 6H), 1.95-1.76 (m, 4H), 1.54-1.45 (s, 2H). | 451.3 |
| SC_3149 | cis-8-Dimethylamino-3-[2-(1,1-dioxo-[1,4]thiazinan-4-yl)-pyrimidin-5-yl]-8-phenyl-1,3-diazaspiro[4.5]decan-2-one | INT-989 | thiomorpholine-1,1-dioxide hydrochloride | SC_3120 | 1H NMR (600 MHz, DMSO) δ 8.63 (s, 2H), 7.50 (br s, 1H), 7.41-7.33 (m, 4H), 7.27 (td, 1H), 4.17-4.12 (m, 4H), 3.55 (s, 2H), 3.12-3.06 (m, 4H), 2.47-2.27 (m, 2H), 2.04-1.74 (m, 10H), 1.51-1.42 (m, 2H). | 485.2 |

-continued

| Example | Chemical name | Reactant I | Reactant II | in analogy to method | 1H NMR data | m/z (M + H)+ |
|---------|---------------|------------|-------------|---------------------|-------------|--------------|
| SC_3150 | cis-8-Dimethylamino-3-(4-fluoro-pyridin-3-yl)-8-phenyl-1,3-diazaspiro[4.5]decan-2-one | INT-976 | 3-bromo-4-fluoro-pyridine | SC_3103 | 1H NMR (600 MHz, DMSO) δ 8.70 (d, 1H), 8.36 (dd, 1H), 7.54 (s, 1H), 7.36 (td, 5H), 7.26 (s, 1H), 3.61 (s, 2H), 2.44-2.28 (m, 2H), 2.01-1.74 (m, 10H), 1.92 (d, 2H), 1.56-1.45 (m, 2H). | 369.2 |
| SC_3151 | cis-5-(8-Dimethylamino-2-oxo-8-phenyl-1,3-diazaspiro[4.5]decan-3-yl)-N-(2-hydroxy-ethyl)-N-methyl-pyrimidine-2-carboxylic acid amide | INT-991 | 2-(methylamino)ethanol | SC_3133 | 1H NMR (600 MHz, DMSO) δ 9.03 (d, 2H), 7.86 (s, 1H), 7.40-7.23 (m, 5H), 3.69 (s, 2H), 3.61 (q, 1H), 3.50 (t, 1H), 3.45 (d, 1H), 3.17 (t, 1H), 3.01 and 2.83 (both s, together 3H, amide rotamers), 2.49-2.36 (m, 2H), 2.00-1.89 (m, 8H), 1.89-1.73 (m, 2H), 1.55-1.47 (m, 2H). | 453.2 |
| SC_3152 | cis-5-(8-Dimethylamino-2-oxo-8-phenyl-1,3-diazaspiro[4.5]decan-3-yl)-2-morpholin-4-yl-isonicotinonitrile | INT-976 | 5-bromo-2-morpholino-pyridine-4-carbonitrile | SC_3103 | 1H NMR (600 MHz, DMSO) δ 8.24 (s, 1H), 7.67-7.30 (m, 5H), 7.29 (s, 1H), 3.70-3.65 (m, 4H), 3.51-3.44 (m, 4H), 2.37-2.22 (m, 2H), 2.10-1.87 (m, 10H), 1.53-1.31 (m, 2H). | 461.3 |
| SC_3153 | cis-4-(8-Dimethylamino-2-oxo-8-phenyl-1,3-diazaspiro[4.5]decan-3-yl)-benzamide | SC_3272 | | SC_3016 | 1H NMR (600 MHz, DMSO) δ 7.79 (d, 2H), 7.62 (d, 2H), 7.41-7.34 (m, 4H), 7.27 (td, 1H), 7.13-7.09 (m, 1H), 3.62 (s, 2H), 2.46-2.35 (m, 2H), 1.97 (s, 6H), 1.93-1.76 (m, 4H), 1.51-1.45 (m, 2H). | 393.2 |
| SC_3154 | cis-8-Dimethylamino-3-(2-fluoro-4-methylsulfonyl-phenyl)-8-phenyl-1,3-diazaspiro[4.5]decan-2-one | INT-976 | 1-bromo-2-fluoro-4-methylsulfonyl-benzene | SC_3103 | 1H NMR (600 MHz, DMSO) δ 7.89-7.83 (m, 1H), 7.76 (dd, 1H), 7.70 (dd, 1H), 7.40-7.32 (m, 5H), 7.29-7.23 (m, 1H), 3.69 (s, 2H), 3.23 (s, 3H), 2.43-2.30 (m, 2H), 1.96 (s, 6H), 1.94-1.88 (m, 2H), 1.53-1.47 (m, 2H). | 446.2 |
| SC_3155 | cis-4-(8-Dimethylamino-2-oxo-8-phenyl-1,3-diazaspiro[4.5]decan-3-yl)-3-fluoro-benzonitrile | INT-976 | 4-bromo-3-fluoro-benzonitrile | SC_3103 | 1H NMR (600 MHz, DMSO) δ 7.85-7.79 (m, 2H), 7.73 (s, 1H), 7.62 (dd, 1H), 7.40-7.31 (m, 4H), 7.26 (tt, 1H), 3.69 (s, 2H), 2.40-2.31 (m, 2H), 1.95 (s, 6H), 1.94-1.87 (m, 2H), 1.87-1.75 (m, 2H), 1.52-1.46 (m, 2H). | 393.2 |
| SC_3156 | cis-4-(8-Dimethylamino-2-oxo-8-phenyl-1,3-diazaspiro[4.5]decan-3-yl)-3,5-difluoro-benzonitrile | INT-976 | 4-bromo-3,5-difluoro-benzonitrile | SC_3103 | 1H NMR (600 MHz, DMSO) δ 7.85 (d, 2H), 7.61 (s, 1H), 7.39-7.31 (m, 4H), 7.25 (tt, 1H), 3.53 (s, 2H), 2.42-2.33 (m, 2H), 1.98-1.89 (m, 8H), 1.82-1.78 (m, 2H), 1.54-1.47 (m, 2H). | 411.2 |
| SC_3157 | cis-8-Dimethylamino-3-(2-methoxy-pyrimidin-5-yl)-8-phenyl-1,3-diazaspiro[4.5]decan-2-one | INT-989 | methanol instead of n-butanol as a solvent | SC_3120 | 1H NMR (600 MHz, DMSO) δ 8.76 (s, 2H), 7.41-7.33 (m, 5H), 7.27 (ddt, 1H), 3.86 (s, 3H), 3.60 (s, 2H), 2.47-2.30 (m, 2H), 2.01-1.74 (m, 10H), 1.52-1.45 (m, 2H). | 382.2 |
| SC_3158 | cis-3-[2-(Benzylamino)-pyrimidin-5-yl]-8-dimethylamino-8-phenyl-1,3-diazaspiro[4.5]decan-2-one | INT-989 | benzylamine | SC_3120 | 1H NMR (600 MHz, DMSO) δ 8.43 (s, 2H), 7.50-7.45 (m, 1H), 7.46-7.33 (m, 5H), 7.31-7.23 (m, 4H), 7.19 (tq, 1H), 4.46 (d, 2H), 4.02 (s, 1H), 3.50 (s, 2H), 2.41-2.31 (m, 2H), 1.97 (s, 6H), 1.88 (s, 2H), 1.49-1.41 (m, 2H). | 457.3 |

| Example | Chemical name | Reactant I | Reactant II | in analogy to method | 1H NMR data | m/z (M + H)+ |
|---|---|---|---|---|---|---|
| SC_3159 | cis-8-Dimethylamino-3-[2-(4-fluorophenyl)-pyrimidin-5-yl]-8-phenyl-1,3-diazaspiro[4.5]decan-2-one | INT-989 | (4-fluorophenyl)boronic acid | SC_3129 | 1H NMR (600 MHz, DMSO) δ 9.07 (s, 2H), 8.37-8.30 (m, 2H), 7.83 (s, 1H), 7.44-7.35 (m, 4H), 7.34-7.25 (m, 3H), 3.69 (s, 2H), 2.47-2.30 (m, 2H), 2.08-1.80 (m, 10H), 1.55-1.46 (m, 2H). | 446.2 |
| SC_3160 | trans-8-Benzyl-8-dimethylamino-3-(2-morpholin-4-yl-pyrimidin-5-yl)-1,3-diazaspiro[4.5]decan-2-one | INT-995 | 4-(5-bromopyrimidin-2-yl)morpholine | SC_3103 | 1H NMR (600 MHz, DMSO) δ 8.57 (s, 2H), 7.60 (s, 1H), 7.27 (t, 2H), 7.22-7.15 (m, 3H), 3.68-3.62 (m, 4H), 3.64-3.57 (m, 4H), 3.49 (s, 2H), 2.66 (s, 2H), 2.22 (s, 6H), 1.80-1.70 (m, 4H), 1.51-1.43 (m, 4H). | 451.3 |
| SC_3161 | cis-8-Benzyl-8-dimethylamino-3-(2-morpholin-4-yl-pyrimidin-5-yl)-1,3-diazaspiro[4.5]decan-2-one | INT-994 | 4-(5-bromopyrimidin-2-yl)morpholine | SC_3103 | 1H NMR (600 MHz, DMSO) δ 8.45 (s, 2H), 7.27 (t, 2H), 7.22-7.15 (m, 3H), 7.11 (s, 1H), 3.68-3.56 (m, 8H), 2.64 (s, 2H), 2.26 (s, 6H), 1.87-1.77 (m, 4H), 1.42 (d, 2H), 1.15 (dt, 2H). | 451.3 |
| SC_3163 | cis-4-(8-Dimethylamino-2-oxo-8-phenyl-1,3-diazaspiro[4.5]decan-3-yl)-3,5-difluoro-benzamide | SC_3156 | | SC_3016 | 1H NMR (600 MHz, DMSO) δ 8.08 (s, 1H), 7.65-7.58 (m, 2H), 7.48 (br s, 1H), 7.39-7.31 (m, 4H), 7.28-7.22 (m, 1H), 3.49 (s, 2H), 2.40-2.32 (m, 2H), 1.96 (s, 6H), 1.95-1.90 (m, 2H), 1.87-1.77 (m, 2H), 1.54-1.49 (m, 2H). | 429.2 |
| SC_3164 | cis-4-(8-Dimethylamino-2-oxo-8-phenyl-1,3-diazaspiro[4.5]decan-3-yl)-3-fluoro-benzamide | SC_3155 | | SC_3016 | 1H NMR (600 MHz, DMSO) δ 7.95 (s, 1H), 7.72-7.64 (m, 2H), 7.61 (t, 1H), 7.54-7.50 (m, 1H), 7.40-7.32 (m, 5H), 7.26 (tt, 1H), 3.62 (s, 2H), 2.41-2.31 (m, 2H), 1.96 (s, 6H), 1.93-1.88 (m, 2H), 1.86-1.75 (m, 2H), 1.53-1.45 (m, 2H). | 411.2 |
| SC_3165 | cis-8-Benzyl-8-dimethylamino-3-[2-(trifluoromethyl)-pyrimidin-5-yl]-1,3-diazaspiro[4.5]decan-2-one | INT-994 | 5-bromo-2-(trifluoromethyl)pyrimidine | SC_3103 | 1H NMR (600 MHz, DMSO) δ 9.07 (s, 2H), 7.77 (s, 1H), 7.29 (t, 2H), 7.24-7.17 (m, 3H), 3.55 (s, 2H), 2.66 (s, 2H), 2.26 (s, 6H), 1.86 (dt, 4H), 1.44 (d, 2H), 1.25-1.17 (m, 2H). | 434.2 |
| SC_3166 | trans-8-Benzyl-8-dimethylamino-3-[2-(trifluoromethyl)-pyrimidin-5-yl]-1,3-diazaspiro[4.5]decan-2-one | INT-995 | 5-bromo-2-(trifluoromethyl)pyrimidine | SC_3103 | 1H NMR (600 MHz, DMSO) δ 9.16 (s, 2H), 8.28 (s, 1H), 7.27 (t, 2H), 7.22-7.16 (m, 3H), 3.67 (s, 2H), 2.66 (s, 2H), 2.24 (s, 6H), 1.84-1.72 (m, 4H), 1.49 (q, 4H). | 434.2 |
| SC_3167 | cis-8-Dimethylamino-8-thiophen-2-yl-3-[2-(trifluoromethyl)-pyrimidin-5-yl]-1,3-diazaspiro[4.5]decan-2-one | INT-997 | 5-bromo-2-(trifluoromethyl)pyrimidine | SC_3103 | 1H NMR (600 MHz, DMSO) δ 9.19 (d, 2H), 7.97 (s, 1H), 7.43 (t, 1H), 7.07 (dd, 1H), 6.97 (d, 1H), 3.78 (s, 2H), 2.40-2.27 (m, 2H), 2.04 (s, 6H), 1.96 (t, 2H), 1.90-1.79 (m, 2H), 1.60-1.52 (m, 2H). | 426.1 |
| SC_3168 | trans-8-Dimethylamino-8-thiophen-2-yl-3-[2-(trifluoromethyl)-pyrimidin-5-yl]-1,3-diazaspiro[4.5]decan-2-one | INT-998 | 5-bromo-2-(trifluoromethyl)pyrimidine | SC_3103 | 1H NMR (600 MHz, DMSO) δ 9.20 (s, 2H), 8.00 (s, 1H), 7.45 (dd, 1H), 7.09 (dd, 1H), 7.02-6.97 (m, 1H), 3.81 (s, 2H), 2.12 (d, 4H), 2.03 (s, 6H), 1.85 (t, 2H), 1.62-1.54 (m, 2H). | 426.1 |
| SC_3170 | cis-8-dimethylamino-3-phenyl-3-(2-piperidin-1-yl-pyrimidin-5-yl)-1,3-diazaspiro[4.5]decan-2-one | INT-989 | piperidine | SC_3120 | 1H NMR (DMSO-d6): δ 8.49 (s, 2H), 7.39-7.24 (m, 6H), 3.65-3.63 (m, 4H), 3.50 (s, 2H), 2.36-2.32 (m, 2H), 1.95-1.86 (m, 10H), 1.61-1.56 (m, 2H), 1.50-1.44 (m, 6H). | 435.3 |

-continued

| Example | Chemical name | Reactant I | Reactant II | in analogy to method | 1H NMR data | m/z (M + H)+ |
|---|---|---|---|---|---|---|
| SC_3171 | cis-8-Dimethylamino-8-phenyl-3-(2-pyrrolidin-1-yl-pyrimidin-5-yl)-1,3-diazaspiro[4.5]decan-2-one | INT-989 | pyrrolidine | SC_3120 | 1H NMR (CDCl3): δ 8.43 (s, 2H), 7.41-7.38 (m, 2H), 7.32-7.30 (m, 3H), 5.05 (br s, 1H), 3.53 (t, 4H), 3.45 (s, 2H), 2.30-2.06 (m, 10H), 1.99-1.96 (m, 6H), 1.62-1.58 (m, 2H). | 421.3 |
| SC_3172 | cis-8-Dimethylamino-8-phenyl-3-(2-pyrimidin-5-yl-pyrimidin-5-yl)-1,3-diazaspiro[4.5]decan-2-one | INT-989 | pyrimidin-5-ylboronic acid | SC_3129 | 1H NMR (600 MHz, DMF) δ 9.56 (s, 2H), 9.27 (s, 1H), 9.17 (s, 2H), 8.35 (s, 1H), 7.89 (d, 2H), 7.63 (dq, 3H), 3.73 (s, 2H), 3.04 (d, 2H), 2.81 (s, 6H), 2.57 (td, 2H), 2.06 (d, 2H), 1.58 (td, 2H). | 430.2 |
| SC_3174 | trans-8-Benzyl-8-dimethylamino-3-[4-methyl-6-(trifluoromethyl)-pyridin-3-yl]-1,3-diazaspiro[4.5]decan-2-one | INT-995 | 5-bromo-4-methyl-2-(trifluoromethyl)pyridine | SC_3103 | 1H NMR (600 MHz, DMSO) δ 8.57 (s, 1H), 7.80 (s, 1H), 7.67 (s, 1H), 7.27 (t, 2H), 7.23-7.15 (m, 3H), 3.58 (d, 2H), 2.67 (s, 2H), 2.31 (s, 3H), 2.22 (d, 6H), 1.82-1.72 (m, 4H), 1.56 (dd, 2H), 1.48 (td, 2H). | 447.2 |
| SC_3175 | cis-5-(8-Dimethylamino-2-oxo-8-phenyl-1,3-diazaspiro[4.5]decan-3-yl)-2-morpholin-4-yl-pyridine-4-carboxylic acid amide | SC_3152 | | SC_3016 | | 480.6 |
| SC_3176 | cis-8-Dimethylamino-3-[2-(3,5-dimethyl-isoxazol-4-yl)-pyrimidin-5-yl]-8-phenyl-1,3-diazaspiro[4.5]decan-2-one | INT-989 | (3,5-dimethylisoxazol-4-yl)boronic acid | SC_3129 | 1H NMR (600 MHz, DMSO) δ 9.05 (s, 2H), 7.80 (s, 1H), 7.43-7.34 (m, 4H), 7.28 (tt, 1H), 3.68 (s, 2H), 2.69 (s, 3H), 2.47 (s, 3H), 2.43-2.35 (m, 2H), 2.01-1.79 (m, 10H), 1.50 (s, 2H). | 447.2 |
| SC_3177 | cis-3-[2-(Benzothiazol-6-yl)-pyrimidin-5-yl]-8-dimethylamino-8-phenyl-1,3-diazaspiro[4.5]decan-2-one | INT-989 | 1,3-benzothiazol-6-ylboronic acid | SC_3129 | 1H NMR (600 MHz, DMSO) δ 9.46 (s, 1H), 9.12 (s, 2H), 9.07 (s, 1H), 8.49 (d, 1H), 8.16 (d, 1H), 7.84 (s, 1H), 7.39 (d, 4H), 7.29 (d, 1H), 3.73 (s, 2H), 2.42 (d, 2H), 1.97 (d, 10H), 1.54 (d, 2H). | 485.2 |
| SC_3178 | cis-8-Dimethylamino-3-[2-fluoro-4-(trifluoromethyl)-phenyl]-8-phenyl-1,3-diazaspiro[4.5]decan-2-one | INT-976 | 1-bromo-2-fluoro-4-(trifluoromethyl)benzene | SC_3103 | 1H NMR (600 MHz, DMSO) δ 7.80 (t, 1H), 7.65 (dd, 1H), 7.53 (dd, 1H), 7.40-7.32 (m, 4H), 7.29-7.23 (m, 1H), 3.66 (s, 2H), 2.36 (s, 2H), 1.97-1.88 (m, 8H), 1.85-1.75 (m, 2H), 1.53-1.46 (m, 2H). | 436.2 |
| SC_3179 | cis-8-Dimethylamino-3-(6-morpholin-4-yl-pyridin-3-yl)-8-phenyl-1,3-diazaspiro[4.5]decan-2-one | INT-976 | 4-(5-bromo-2-pyridyl)morpholine | as SC_3097 step 2 | 1H NMR (600 MHz, DMSO) δ 8.20 (d, 1H), 7.89 (dd, 1H), 7.37 (p, 5H), 7.27 (d, 1H), 6.79 (d, 1H), 3.71-3.66 (m, 4H), 3.53 (s, 2H), 2.43-2.32 (m, 2H), 1.96 (s, 7H), 1.91-1.85 (m, 5H), 1.49-1.42 (m, 2H). | 436.3 |
| SC_3180 | cis-8-Dimethylamino-8-phenyl-3-(2-phenyl-thiazol-4-yl)-1,3-diazaspiro[4.5]decan-2-one | INT-976 | 4-bromo-2-phenylthiazole | SC_3103 | 1H NMR (DMSO-d6): δ 7.89-7.87 (m, 2H), 7.55 (br s, 1H), 7.43-7.35 (m, 8H), 7.29-7.26 (m, 1H), 3.82 (s, 2H), 2.45 (br m, 2H), 1.96-1.79 (m, 10H), 1.53-1.50 (m, 2H). | 433.2 |
| SC_3181 | cis-8-Dimethylamino-8-phenyl-3-[2-(tetrahydro-pyran-4-ylamino)-pyrimidin-5-yl]-1,3-diazaspiro[4.5]decan-2-one | INT-989 | tetrahydro-2H-pyran-4-amine | SC_3103 | 1H NMR (DMSO-d6): δ 8.42 (s, 2H), 7.39-7.35 (m, 5H), 7.27-7.24 (m, 1H), 6.83 (d, 1H), 3.84-3.79 (m, 3H), 3.50 (s, 2H), 3.38-3.35 (m, 2H), 2.36-2.32 (m, 2H), 1.94-1.77 (m, 12H), 1.50-1.40 (m, 4H). | 451.3 |

-continued

| Example | Reactant I | Reactant II | Chemical name | in analogy to method | ¹H NMR data | m/z (M + H)⁺ |
|---|---|---|---|---|---|---|
| SC_3183 | INT-976 | 2-bromo-4-phenylthiazole | cis-8-Dimethylamino-8-phenyl-3-(4-phenyl-thiazol-2-yl)-1,3-diazaspiro[4.5]decan-2-one | SC_3103 | 1H NMR (DMSO-d6): δ 8.09 (br s, 1H), 7.87 (d, 2H), 7.51 (s, 1H), 7.37-7.24 (m, 8H), 3.87 (s, 2H), 2.43 (m, 2H), 1.96-1.84 (m, 10H), 1.54 (m, 2H). | 433.2 |
| SC_3184 | INT-976 | 1H-pyrrolo[2,3-b]pyridine | cis-8-Dimethylamino-8-phenyl-3-[2-(1H-pyrrolo[2,3-b]pyridin-1-yl)-pyrimidin-5-yl]-1,3-diazaspiro[4.5]decan-2-one | SC_3103 | 1H NMR (DMSO-d6): δ 9.07 (s, 2H), 8.35-8.33 (m, 1H), 8.10-8.04 (m, 2H), 7.83 (br s, 1H), 7.41-7.37 (m, 4H), 7.29-7.21 (m, 2H), 6.72-6.71 (d, 1H), 3.71 (s, 2H), 2.49 (m, 2H), 1.97 (m, 10H), 1.52 (m, 2H). | 468.2 |
| SC_3185 | INT-989 | (3,4,5-trifluorophenyl)boronic acid | cis-8-Dimethylamino-8-phenyl-3-[2-(3,4,5-trifluoro-phenyl)-pyrimidin-5-yl]-1,3-diazaspiro[4.5]decan-2-one | SC_3129 | 1H NMR (600 MHz, DMSO) δ 9.11 (s, 2H), 8.12-8.03 (m, 2H), 7.89 (s, 1H), 7.42-7.34 (m, 4H), 7.28 (dq, 1H), 3.71 (s, 2H), 2.48-2.35 (m, 2H), 1.99-1.79 (m, 10H), 1.58-1.47 (m, 2H). | 481.2 |
| SC_3187 | INT-976 | 1-bromo-3-methylbenzene | cis-8-Dimethylamino-3-m-tolyl-8-phenyl-1,3-diazaspiro[4.5]decan-2-one | SC_3186 | | 363.2 |
| SC_3188 | INT-976 | 1-bromo-4-methylbenzene | cis-8-Dimethylamino-8-phenyl-3-p-tolyl-1,3-diazaspiro[4.5]decan-2-one | SC_3186 | | 363.2 |
| SC_3189 | INT-976 | 1-bromo-4-(trifluoromethyl)benzene | cis-8-Dimethylamino-8-phenyl-3-[4-(trifluoromethyl)-phenyl]-1,3-diazaspiro[4.5]decan-2-one | SC_3186 | | 417.2 |
| SC_3190 | INT-976 | 1-bromo-3-(trifluoromethoxy)benzene | cis-8-Dimethylamino-8-phenyl-3-[3-(trifluoromethyoxy)-phenyl]-1,3-diazaspiro[4.5]decan-2-one | SC_3186 | | 433.2 |
| SC_3191 | INT-976 | 1-bromo-4-(trifluoromethoxy)benzene | cis-8-Dimethylamino-8-phenyl-3-[4-(trifluoromethyoxy)-phenyl]-1,3-diazaspiro[4.5]decan-2-one | SC_3186 | | 433.2 |
| SC_3192 | INT-976 | methyl 2-bromobenzoate | cis-2-(8-Dimethylamino-2-oxo-8-phenyl-1,3-diazaspiro[4.5]decan-3-yl)-benzoic acid methyl ester | SC_3186 | | 407.2 |
| SC_3193 | INT-976 | methyl 3-bromobenzoate | cis-3-(8-Dimethylamino-2-oxo-8-phenyl-1,3-diazaspiro[4.5]decan-3-yl)-benzoic acid methyl ester | SC_3186 | | 407.2 |
| SC_3194 | INT-976 | methyl 4-bromobenzoate | cis-4-(8-Dimethylamino-2-oxo-8-phenyl-1,3-diazaspiro[4.5]decan-3-yl)-benzoic acid methyl ester | SC_3186 | | 407.2 |
| SC_3195 | INT-976 | 5-bromobenzo[d][1,3]dioxole | cis-3-(1,3-Benzodioxol-5-yl)-8-dimethylamino-8-phenyl-1,3-diazaspiro[4.5]decan-2-one | SC_3186 | | 393.2 |
| SC_3196 | INT-976 | 5-bromoquinoline | cis-8-Dimethylamino-8-phenyl-3-quinolin-5-yl-1,3-diazaspiro[4.5]decan-2-one | SC_3186 | | 400.2 |
| SC_3197 | INT-976 | 6-bromoindoline | cis-3-(2,3-Dihydro-1H-indol-6-yl)-8-dimethylamino-8-phenyl-1,3-diazaspiro[4.5]decan-2-one | SC_3186 | | 390.2 |

-continued

| Example | Chemical name | Reactant I | Reactant II | in analogy to method | 1H NMR data | m/z (M + H)+ |
|---|---|---|---|---|---|---|
| SC_3198 | cis-5-(8-Dimethylamino-2-oxo-8-phenyl-1,3-diazaspiro[4.5]decan-3-yl)-4-methyl-pyridine-2-carboxylic acid methyl ester | INT-976 | methyl 5-bromo-4-methylpicolinate | SC_3186 | | 422.2 |
| SC_3199 | cis-8-Dimethyl amino-3-(6-methoxy-4-methyl-pyridin-3-yl)-8-phenyl-1,3-diazaspiro[4.5]decan-2-one | INT-976 | 5-bromo-2-methoxy-4-methylpyridine | SC_3186 | | 394.2 |
| SC_3200 | cis-8-Dimethylamino-3-[2-methyl-5-(trifluoromethyl)-2H-pyrazol-3-yl]-8-phenyl-1,3-diazaspiro[4.5]decan-2-one | INT-976 | 5-bromo-1-methyl-3-(trifluoromethyl)-1H-pyrazole | SC_3186 | | 421.2 |
| SC_3201 | cis-8-Dimethylamino-3-(3-methoxy-pyridin-2-yl)-8-phenyl-1,3-diazaspiro[4.5]decan-2-one | INT-976 | 2-bromo-3-methoxypyridine | SC_3186 | | 380.2 |
| SC_3202 | cis-8-Dimethylamino-8-phenyl-3-[5-(trifluoromethyl)-pyridin-2-yl]-1,3-diazaspiro[4.5]decan-2-one | INT-976 | 2-bromo-5-trifluoromethylpyridine | SC_3186 | | 418.2 |
| SC_3203 | cis-5-(8-Dimethylamino-2-oxo-8-phenyl-1,3-diazaspiro[4.5]decan-3-yl)-nicotinonitrile | INT-976 | 3-bromo-5-cyanopyridine | SC_3186 | | 375.2 |
| SC_3204 | cis-8-Dimethylamino-3-(3-methyl-pyridin-2-yl)-8-phenyl-1,3-diazaspiro[4.5]decan-2-one | INT-976 | 2-bromo-3-methylpyridine | SC_3186 | | 364.2 |
| SC_3205 | cis-8-Dimethylamino-3-(6-methoxy-pyridin-3-yl)-8-phenyl-1,3-diazaspiro[4.5]decan-2-one | INT-976 | 5-bromo-2-methoxypyridine | SC_3186 | | 380.2 |
| SC_3206 | cis-8-Dimethylamino-8-phenyl-3-[3-(trifluoromethyl)phenyl]-1,3-diazaspiro[4.5]decan-2-one | INT-976 | 1-bromo-3-trifluoromethylbenzene | SC_3186 | | 417.2 |
| SC_3207 | cis-3-(1,3-Benzodioxol-4-yl)-8-dimethylamino-8-phenyl-1,3-diazaspiro[4.5]decan-2-one | INT-976 | 4-bromobenzo[d][1,3]dioxole | SC_3186 | | 393.2 |
| SC_3209 | cis-8-Dimethylamino-3-[2-(3,5-dimethyl-1H-pyrazol-1-yl)-pyrimidin-5-yl]-8-phenyl-1,3-diazaspiro[4.5]decan-2-one | INT-976 | 3,5-dimethyl-1H-pyrazole | SC_3103 | 1H NMR (DMSO-d6): δ 9.00 (s, 2H), 7.81 (br s, 1H), 7.38-7.27 (m, 5H), 6.07 (s, 1H), 3.69 (s, 2H), 2.45 (m, 5H), 2.17 (s, 3H), 1.96-1.91 (m, 10H), 1.51 (br m, 2H). | 446.2 |
| SC_3210 | cis-8-Dimethylamino-3-[2-(3-hydroxy-piperidin-1-yl)-pyrimidin-5-yl]-8-phenyl-1,3-diazaspiro[4.5]decan-2-one | INT-989 | rac-piperidin-3-ol | SC_3182 | 1H NMR (DMSO-d6): 8.48 (s, 2H), 7.39-7.35 (m, 5H), 7.27-7.24 (m, 1H), 4.82 (d, 1H), 4.39-4.36 (m, 1H), 4.24-4.21 (m, 1H), 3.51 (s, 2H), 3.41-3.36 (m, 1H), 2.92-2.87 (m, 1H), 2.77-2.72 (m, 1H), 2.42-2.32 (m, 2H), 2.00-1.66 (m, 12H), 1.46-1.39 (m, 2H), 1.34 (t, 2H). | 451.2 |
| SC_3211 | cis-8-Dimethylamino-3-[2-(3-hydroxy-piperidin-1-yl)-pyrimidin-5-yl]-8-phenyl-1,3-diazaspiro[4.5]decan-2-one | INT-989 | rac-piperidin-3-ol | SC_3182 | 1H NMR (DMSO-d6): 8.48 (s, 2H), 7.35 (m, 5H), 7.25 (m, 1H), 4.82 (d, 1H), 4.39-4.37 (m, 1H), 4.24-4.21 (m, 1H), 3.51 (s, 2H), 3.40-3.39 (m, 1H), 2.90-2.87 (m, 1H), 2.77-2.72 (m, 1H), 2.37 (m, 2H), 2.00-1.66 (m, 12H), 1.45 (m, 2H), 1.34 (t, 2H). | 451.3 |

-continued

| Example | Chemical name | Reactant I | Reactant II | in analogy to method | 1H NMR data | m/z (M + H)+ |
|---|---|---|---|---|---|---|
| SC_3212 | cis-8-Dimethylamino-3-[2-[4-(2-hydroxy-ethyl)-piperazin-1-yl]-pyrimidin-5-yl]-8-phenyl-1,3-diazaspiro[4.5]decan-2-one | INT-989 | 2-piperazin-1-ylethanol | SC_3120 | 1H NMR (600 MHz, DMSO) δ 8.53 (s, 2H), 7.37 (p, 5H), 7.27 (d, 1H), 3.62 (t, 4H), 3.53 (q, 4H), 2.49-2.27 (m, 7H), 1.96 (s, 6H), 1.94-1.73 (m, 4H), 1.51-1.40 (m, 2H). | 480.3 |
| SC_3213 | cis-2-[4-[5-(8-Dimethylamino-2-oxo-8-phenyl-1,3-diazaspiro[4.5]decan-3-yl)-pyrimidin-2-yl]-piperazin-1-yl]-acetic acid | SC_3146 | | INT-991 | 1H NMR (600 MHz, DMSO) δ 8.53 (s, 2H), 7.57 (s, 1H), 7.42 (d, 4H), 7.33 (d, 1H), 3.68 (t, 4H), 3.19 (s, 2H), 2.62 (t, 4H), 2.37 (d, 2H), 2.20-1.96 (m, 8H), 1.88 (d, 2H), 1.43 (t, 2H). | 494.3 |
| SC_3214 | cis-8-Dimethylamino-3-[2-(1-methyl-1H-pyrrolo[2,3-b]pyridin-4-yl)-pyrimidin-5-yl]-8-phenyl-1,3-diazaspiro[4.5]decan-2-one | INT-989 | 1-methyl-4-(4,4,5,5-tetramethyl-1,3,2-dioxaborolan-2-yl)-2,3-dihydropyrrolo[2,3-b]pyridine | SC_3208 | 1H NMR (600 MHz, DMSO + 2 vol % TFA) δ 9.85 (s, 1H), 9.13 (s, 2H), 8.41 (d, 2H), 7.99 (s, 1H), 7.72 (s, 2H), 7.66-7.46 (m, 4H), 7.30 (s, 1H), 3.88 (s, 2H), 3.60 (s, 6H), 2.77-2.71 (m, 2H), 2.30-2.26 (m, 2H), 1.94-1.89 (m, 2H), 1.75 (s, 3H), 1.41-1.35 (m, 2H). | 484.3 |
| SC_3215 | cis-8-Benzyl-8-dimethylamino-3-[4-methyl-6-(trifluoromethyl)-pyridin-3-yl]-1,3-diazaspiro[4.5]decan-2-one | INT-994 | 5-bromo-4-methyl-2-(trifluoromethyl)pyridine | SC_3103 | 1H NMR (600 MHz, DMSO) δ 8.52 (s, 1H), 7.76 (s, 1H), 7.23 (dd, 2H), 7.19-7.11 (m, 4H), 2.62 (s, 2H), 2.27 (s, 6H), 2.25 (s, 3H), 1.86 (td, 2H), 1.80 (dt, 2H), 1.57-1.49 (m, 2H), 1.09 (td, 2H). | 447.2 |
| SC_3216 | trans-8-Dimethylamino-3-[4-methyl-6-(trifluoromethyl)-pyridin-3-yl]-8-thiophen-2-yl-1,3-diazaspiro[4.5]decan-2-one | INT-998 | 5-bromo-4-methyl-2-(trifluoromethyl)pyridine | SC_3103 | 1H NMR (600 MHz, DMSO) δ 8.61 (s, 1H), 7.83 (s, 1H), 7.53-7.49 (m, 1H), 7.45 (dd, 1H), 7.09 (dd, 1H), 6.99 (dd, 1H), 3.70 (s, 2H), 2.35 (s, 3H), 2.19-2.05 (m, 4H), 2.02 (s, 6H), 1.93-1.85 (m, 2H), 1.64 (dt, 2H). | 439.2 |
| SC_3217 | cis-8-Dimethylamino-3-[4-methyl-6-(trifluoromethyl)-pyridin-3-yl]-8-thiophen-2-yl-1,3-diazaspiro[4.5]decan-2-one | INT-997 | 5-bromo-4-methyl-2-(trifluoromethyl)pyridine | SC_3103 | 1H NMR (600 MHz, DMSO) δ 8.58 (s, 1H), 7.80 (s, 1H), 7.45 (s, 1H), 7.42 (dd, 1H), 7.05 (dd, 1H), 6.95 (dd, 1H), 3.67 (s, 2H), 2.33 (s, 3H), 2.32-2.25 (m, 2H), 2.04 (s, 6H), 2.00-1.92 (m, 2H), 1.89-1.76 (m, 2H), 1.62 (dt, 2H). | 439.2 |
| SC_3218 | cis-8-Dimethylamino-3-[2-(1,1-dioxo-[1,4]thiazinan-4-yl)-4-(trifluoromethyl)-pyrimidin-5-yl]-8-phenyl-1,3-diazaspiro[4.5]decan-2-one | INT-976 | 4-[5-bromo-4-(trifluoromethyl)pyrimidin-2-yl]-1,4-thiazinane 1,1-dioxide (prepared as SC_3097 step 1) | SC_3103 | 1H NMR (600 MHz, DMSO) δ 8.65 (s, 1H), 7.42 (m, 1H), 7.41-7.31 (m, 5H), 7.25 (tt, 1H), 4.23 (t, 4H), 3.22 (t, 4H), 2.40-2.26 (m, 2H), 1.97-1.88 (m, 8H), 1.87-1.75 (m, 2H), 1.54-1.42 (m, 2H). | 553.2 |
| SC_3219 | cis-8-Dimethylamino-8-(1-methyl-1H-benzoimidazol-2-yl)-3-[2-(trifluoromethyl)-pyrimidin-5-yl]-1,3-diazaspiro[4.5]decan-2-one | INT-1000 | 5-bromo-2-(trifluoromethyl)pyrimidine | SC_3103 | 1H NMR (600 MHz, DMSO) δ 9.14 (s, 2H), 8.65 (s, 1H), 7.63 (d, 1H), 7.51 (d, 1H), 7.25 (ddd, 1H), 7.19 (ddd, 1H), 4.02 (s, 3H), 3.61 (s, 2H), 2.26 (d, 2H), 2.18 (s, 6H), 2.16-2.09 (m, 2H), 1.87 (s, 2H), 1.78 (d, 2H). | 474.2 |
| SC_3220 | cis-8-Dimethylamino-8-(1-methyl-1H-benzoimidazol-2-yl)-3-[4-methyl-6-(trifluoromethyl)-pyridin-3-yl]-1,3-diazaspiro[4.5]decan-2-one | INT-1000 | 5-bromo-4-methyl-2-(trifluoromethyl)pyridine | SC_3103 | 1H NMR (600 MHz, DMSO) δ 8.56 (s, 1H), 8.10 (s, 1H), 7.80 (s, 1H), 7.60 (d, 1H), 7.50 (d, 1H), 7.23 (ddd, 1H), 7.17 (td, 1H), 4.02 (s, 3H), 3.50 (s, 2H), 2.34-2.25 (m, 5H), 2.19-2.09 (m, 8H), 1.90-1.74 (m, 4H). | 487.3 |

-continued

| Example | Chemical name | Reactant I | Reactant II | in analogy to method | 1H NMR data | m/z (M + H)+ |
|---|---|---|---|---|---|---|
| SC_3222 | cis-3-[2-(Benzyl-methyl-amino)-pyrimidin-5-yl]-8-dimethylamino-8-phenyl-1,3-diazaspiro[4.5]decan-2-one | INT-976 | N-benzyl-5-bromo-N-methylpyrimidin-2-amine | SC_3103 | 1H NMR (DMSO-d6): δ 8.52 (s, 2H), 7.39-7.33 (m, 5H), 7.30-7.17 (m, 6H), 4.81 (s, 2H), 3.52 (s, 2H), 3.03 (s, 3H), 2.45-2.32 (m, 2H), 1.95-1.86 (m, 10H), 1.47-1.43 (m, 2H). | 471.2 |
| SC_3223 | cis-5-(8-Dimethylamino-2-oxo-8-phenyl-1,3-diazaspiro[4.5]decan-3-yl)-N-[2-[2-[2-(2-methoxy-ethoxy)-ethoxy]-ethoxy]-ethyl]-pyrimidine-2-carboxylic acid amide | INT-976 | ethyl 5-bromopyrimidine-2-carboxylate (step 1), INT-991 (step 2), SC_3133 (step 3) | SC_3103 (step 1), INT-991 (step 2), SC_3133 (step 3) | 1H NMR (DMSO-d6): δ 9.04 (s, 2H), 8.24-8.23 (m, 1H), 7.42-7.39 (m, 2H), 7.32-7.31 (m, 3H), 5.70 (s, 1H), 3.70-3.60 (m, 16H), 3.54-3.52 (m, 2H), 3.35 (s, 3H), 2.21-2.00 (m, 12H), 1.66-1.64 (m, 2H). | 585.3 |
| SC_3225 | cis-8-Dimethylamino-3-[2-[(2-hydroxy-ethyl)-methyl-amino]-pyrimidin-5-yl]-8-phenyl-1,3-diazaspiro[4.5]decan-2-one | INT-989 | 2-(methylamino)ethanol | SC_3182 | 1H NMR (DMSO-d6): δ 8.46 (s, 2H), 7.39-7.33 (m, 5H), 7.27-7.24 (m, 1H), 4.62 (t, 1H), 3.61-3.50 (m, 6H), 3.08 (s, 3H), 2.36-2.33 (m, 2H), 1.95-1.86 (m, 10H), 1.47-1.45 (m, 2H). | 425.2 |
| SC_3226 | cis-3-(8-Dimethylamino-2-oxo-8-phenyl-1,3-diazaspiro[4.5]decan-3-yl)-benzamide | INT-976 | 5-bromo-4-methyl-2-(trifluoromethyl)pyridine | SC_3103 (step 1), SC_3016 (step 2) |  | 487.3 |
| SC_3227 | cis-8-Dimethylamino-3-[3-fluoro-5-(trifluoromethyl)-pyridin-2-yl]-8-phenyl-1,3-diazaspiro[4.5]decan-2-one | INT-976 | 2-bromo-3-fluoro-5-(trifluoromethyl)pyridine | SC_3186 |  | 417.1 |
| SC_3228 | cis-8-Dimethylamino-3-(5-methyl-pyrazin-2-yl)-8-phenyl-1,3-diazaspiro[4.5]decan-2-one | INT-976 | 2-bromo-5-methylpyrazine | SC_3186 |  | 459.1 |
| SC_3229 | cis-8-Dimethylamino-3-(5-fluoro-pyrimidin-4-yl)-8-phenyl-1,3-diazaspiro[4.5]decan-2-one | INT-976 | 4-bromo-5-fluoropyrimidine | SC_3186 |  | 433.2 |
| SC_3230 | cis-8-Dimethylamino-3-(5-fluoro-pyrimidin-2-yl)-8-phenyl-1,3-diazaspiro[4.5]decan-2-one | INT-976 | 2-bromo-5-fluoropyrimidine | SC_3186 |  | 458.1 |
| SC_3231 | cis-8-Dimethylamino-8-phenyl-3-pyrazin-2-yl-1,3-diazaspiro[4.5]decan-2-one | INT-976 | 2-bromopyrazine | SC_3186 |  | 471.1 |
| SC_3232 | cis-3-([2,1,3]Benzoxadiazol-5-yl)-8-dimethylamino-8-phenyl-1,3-diazaspiro[4.5]decan-2-one | INT-976 | 5-bromobenzo[c][1,2,5]oxadiazole | SC_3186 |  | 444.1 |
| SC_3233 | cis-2-(8-Dimethylamino-2-oxo-8-phenyl-1,3-diazaspiro[4.5]decan-3-yl)-phenoxy]-acetamide | SC_3169 | ammonium chloride | SC_3133 | 1H NMR (600 MHz, DMSO) δ 7.73 (s, 1H), 7.40-7.32 (m, 4H), 7.31 (s, 1H), 7.26 (dd, 1H), 7.18 (td, 1H), 6.98-6.91 (m, 2H), 4.50 (s, 2H), 3.52 (s, 2H), 2.42-2.29 (m, 2H), 2.01-1.71 (m, 10H), 1.55-1.48 (m, 2H). | 423.2 |
| SC_3234 | cis-8-Dimethylamino-8-phenyl-3-(5-pyridin-4-yl-thiophen-2-yl)-1,3-diazaspiro[4.5]decan-2-one | INT-976 | 4-(5-bromothiophen-2-yl)pyridine | SC_3103 | 1H NMR (DMSO-d6): δ 8.45-8.43 (d, 2H), 7.87 (br s, 1H), 7.54-7.53 (d, 1H), 7.49-7.48 (m, 2H), 7.38-7.27 (m, 5H), 6.35-6.34 (d, 2H), 3.64 (s, 2H), 2.42 (m, 2H), 1.96-1.90 (m, 10H), 1.51-1.49 (m, 2H). | 433.2 |

-continued

| Example | Chemical name | Reactant I | Reactant II | in analogy to method | $^1$H NMR data | m/z (M + H)$^+$ |
|---|---|---|---|---|---|---|
| SC_3236 | cis-8-Dimethylamino-3-(2-morpholin-4-yl-pyrimidin-4-yl)-8-phenyl-1,3-diazaspiro[4.5]decan-2-one | INT-1002 | morpholine | SC_3120 | 1H NMR (600 MHz, DMSO) δ 8.07 (d, 1H), 7.93 (s, 1H), 7.37 (dt, 5H), 7.27 (t, 1H), 3.65 (s, 2H), 3.58 (s, 8H), 2.40-2.27 (m, 2H), 1.94 (s, 6H), 1.92-1.80 (m, 4H), 1.43 (d, 2H). | 437.3 |
| SC_3237 | cis-3-[2-(3,4-Difluoro-phenyl)-pyrimidin-5-yl]-8-dimethylamino-8-phenyl-1,3-diazaspiro[4.5]decan-2-one | INT-989 | (3,4-difluorophenyl)boronic acid | SC_3129 | 1H NMR (600 MHz, DMSO) δ 9.08 (s, 2H), 8.22-8.12 (m, 2H), 7.54 (dt, 1H), 7.41-7.37 (m, 4H), 7.29 (s, 1H), 3.70 (s, 2H), 2.06-1.75 (m, 12H), 1.50 (d, 2H). | 463.2 |
| SC_3241 | cis-2-[4-[5-(8-Dimethylamino-2-oxo-8-phenyl-1,3-diazaspiro[4.5]decan-3-yl)-pyrimidin-2-yl]-piperazin-1-yl]-acetamide | SC_3213 | ammonium chloride | SC_3133 | 1H NMR (600 MHz, DMSO) δ 8.53 (s, 2H), 7.38 (d, 5H), 7.27 (s, 1H), 7.23 (s, 1H), 7.11 (s, 1H), 3.67 (t, 4H), 3.54-3.50 (m, 2H), 2.89 (s, 2H), 2.47 (t, 4H), 2.39-2.35 (m, 2H), 1.96 (s, 7H), 1.93-1.82 (m, 3H), 1.48-1.44 (m, 2H). | 493.3 |
| SC_3243 | cis-8-Dimethylamino-3-[6-(4-methyl-piperazin-1-yl)-pyridin-3-yl]-8-phenyl-1,3-diazaspiro[4.5]decan-2-one | INT-976 | 1-(5-bromo-2-pyridyl)-4-methyl-piperazine | SC_3242 (step 2) | 1H NMR (600 MHz, DMSO) δ 8.16 (d, 1H), 7.86 (dd, 1H), 7.41-7.33 (m, 4H), 7.32 (s, 1H), 7.27 (t, 1H), 6.78 (d, 1H), 3.51 (s, 2H), 2.55-2.45 (m, 4H), 2.42-2.27 (m, 6H), 2.21 (s, 3H), 1.96 (s, 6H), 1.93-1.73 (m, 4H), 1.46 (t, 2H). | 449.3 |
| SC_3244 | cis-8-Dimethylamino-3-[2-(1,1-dioxo-[1,4]thiazinan-4-yl)-4-methyl-pyrimidin-5-yl]-8-phenyl-1,3-diazaspiro[4.5]decan-2-one | INT-976 | 4-(5-bromo-4-methyl-pyrimidin-2-yl)-1,4-thiazinane 1,1-dioxide | SC_3103 | 1H NMR (600 MHz, DMSO) δ 8.20 (s, 1H), 7.36 (h, 4H), 7.30-7.17 (m, 2H), 4.23-4.17 (m, 4H), 3.13 (t, 4H), 2.44-2.28 (m, 2H), 2.24 (s, 3H), 1.97 (s, 6H), 1.91 (d, 4H), 1.55-1.44 (m, 2H). | 499.3 |
| SC_3245 | cis-8-Dimethylamino-8-phenyl-3-[2-(trifluoromethyl)-pyrimidin-5-yl]-1,3-diazaspiro[4.5]decan-2-one | INT-976 | 5-bromo-2-(trifluoromethyl)-pyrimidine | SC_3103 | 1H NMR (600 MHz, DMSO) δ 9.17 (s, 2H), 8.03 (s, 1H), 7.38 (s, 4H), 7.28 (tt, 1H), 3.73 (s, 2H), 2.49-2.35 (m, 2H), 1.97 (s, 6H), 1.97-1.92 (m, 2H), 1.90-1.73 (m, 2H), 1.55-1.49 (m, 2H). | 419.2 |
| SC_3246 | cis-2-[8-Dimethylamino-1-(3-methoxy-propyl)-2-oxo-8-phenyl-1,3-diazaspiro[4.5]decan-3-yl]-pyrimidine-5-carbonitrile | INT-979 | 2-chloropyrimidine-5-carbonitrile | SC_3103 | 1H NMR (600 MHz, DMSO) δ 9.02 (s, 2H), 7.40-7.31 (m, 5H), 3.86 (s, 2H), 3.26 (s, 3H), 3.29-3.19 (m, 2H), 2.73-2.67 (m, 2H), 2.16 (td, 2H), 2.00 (s, 7H), 1.83 (dt, 2H), 1.50-1.40 (m, 5H). | 449.3 |
| SC_3247 | cis-8-Dimethylamino-3-[2-(4-methyl-piperazin-1-yl)-pyrimidin-5-yl]-8-phenyl-1,3-diazaspiro[4.5]decan-2-one | INT-989 | 1-Methylpiperazin | SC_3120 | 1H NMR (600 MHz, DMSO) δ 8.54 (s, 2H), 7.48-7.33 (m, 5H), 7.31-7.21 (m, 1H), 3.63 (dd, 4H), 2.45-2.29 (m, 6H), 2.20 (s, 3H), 1.96 (s, 6H), 1.94-1.78 (m, 4H), 1.51-1.42 (m, 2H). | 450.3 |
| SC_3248 | cis-8-Dimethylamino-1-[(1-hydroxy-cyclobutyl)-methyl]-8-phenyl-3-[2-(trifluoromethyl)-pyrimidin-5-yl]-1,3-diazaspiro[4.5]decan-2-one | SC_3245 | [1-[tert-butyl(dimethyl)silyl]-oxycyclobutyl]methyl 4-methylbenzenesulfonate | INT-988 (step 1) | 1H NMR (600 MHz, DMSO) δ 9.24 (s, 2H), 7.38 (d, 4H), 7.27 (p, 1H), 3.89 (s, 2H), 2.73-2.67 (m, 2H), 2.26 (ddd, 2H), 2.19 (tt, 2H), 2.08 (s, 1H), 2.00 (s, 6H), 1.92 (qd, 2H), 1.73-1.64 (m, 1H), 1.60-1.50 (m, 3H), 1.50-1.45 (m, 2H). | 504.3 |

-continued

| Example | Chemical name | Reactant I | Reactant II | in analogy to method | 1H NMR data | m/z (M + H)+ |
|---|---|---|---|---|---|---|
| SC_3249 | cis-2-[1-(3-Methoxy-propyl)-8-methylamino-2-oxo-8-phenyl-1,3-diazaspiro[4.5]decan-3-yl]-pyrimidine-5-carbonitrile | SC_3246 | | SC_3099 | 1H NMR (600 MHz, DMSO) δ 9.05 (s, 2H), 7.49-7.44 (m, 2H), 7.34 (t, 2H), 7.21 (t, 1H), 3.90 (s, 2H), 3.26 (s, 3H), 2.23 (td, 2H), 2.07 (s, 1H), 1.91 (d, 5H), 1.86-1.78 (m, 2H), 1.73 (tt, 2H), 1.42 (d, 2H). | 435.3 |
| SC_3250 | cis-8-Dimethylamino-8-phenyl-3-[6-(trifluoromethyl)-pyridin-3-yl]-1,3-diazaspiro[4.5]decan-2-one | INT-976 | 5-bromo-2-(trifluoromethyl)pyridine | SC_3103 | 1H NMR (600 MHz, DMSO) δ 8.88 (d, 1H), 8.24 (dd, 1H), 7.86 (s, 1H), 7.78 (d, 1H), 7.41-7.34 (m, 4H), 7.27 (t, 1H), 3.69 (s, 2H), 2.42 (s, 2H), 1.97 (s, 6H), 1.96-1.74 (m, 4H), 1.53-1.47 (m, 2H). | 419.3 |
| SC_3251 | cis-5-(8-Dimethylamino-2-oxo-8-phenyl-1,3-diazaspiro[4.5]decan-3-yl)-pyridine-2-carbonitrile | INT-976 | 5-bromopyridine-2-carbonitrile | SC_3103 | 1H NMR (600 MHz, DMSO) δ 8.92 (d, 1H), 8.15 (dd, 1H), 7.95 (br s, 1H), 7.90 (d, 1H), 7.41-7.34 (m, 4H), 7.27 (t, 1H), 3.69 (s, 2H), 2.44-2.40 (m, 2H), 1.97 (s, 6H), 1.96-1.89 (m, 3H), 1.90-1.70 (m, 1H), 1.53-1.46 (m, 2H). | 376.2 |
| SC_3252 | cis-8-Dimethylamino-3-(2-morpholin-4-yl-pyrimidin-5-yl)-8-phenyl-1,3-diazaspiro[4.5]decan-2-one | INT-989 | morpholine | SC_3120 | 1H NMR (600 MHz, DMSO) δ 8.57 (s, 2H), 7.46-7.42 (m, 1H), 7.40-7.34 (m, 4H), 7.27 (td, 1H), 3.64 (dd, 4H), 3.59 (dd, 4H), 3.54 (s, 2H), 2.46-2.29 (m, 2H), 1.96 (s, 7H), 1.93-1.73 (m, 3H), 1.50-1.44 (m, 2H). | 437.3 |
| SC_3253 | ci s-8-Dimethylamino-3-(2-methyl-pyrimidin-5-yl)-8-phenyl-1,3-diazaspiro[4.5]decan-2-one | INT-976 | 5-bromo-2-methyl-pyrimidine | SC_3103 | 1H NMR (600 MHz, DMSO) δ 8.86 (s, 2H), 7.69 (s, 1H), 7.41-7.33 (m, 5H), 7.31-7.19 (m, 1H), 3.62 (s, 2H), 2.53 (s, 3H), 2.48-2.31 (m, 2H), 1.97 (s, 6H), 1.95-1.77 (m, 4H), 1.52-1.46 (m, 2H). | 366.3 |
| SC_3254 | cis-8-Dimethylamino-1-(2-methoxyphenyl)-methyl]-3-(2-methyl-pyrimidin-5-yl)-8-phenyl-1,3-diazaspiro[4.5]decan-2-one | SC_3248 | 2-methoxybenzyl bromide | SC_3105 | 1H NMR (DMSO-d6): δ 8.90 (s, 2H), 7.39-7.34 (m, 3H), 7.28-7.22 (m, 4H), 6.95-6.87 (m, 2H), 4.58 (s, 2H), 3.89 (s, 3H), 3.63 (s, 2H), 2.68-2.64 (m, 5H), 2.35-2.28 (m, 2H), 2.01 (s, 6H), 1.49-1.43 (m, 4H). | 486.2 |
| SC_3255 | cis-1-[(1-Hydroxy-cyclobutyl)-methyl]-8-methylamino-8-phenyl-3-[2-(trifluoromethyl)-pyrimidin-5-yl]-1,3-diazaspiro[4.5]decan-2-one | SC_3253 | | SC_3099 | 1H NMR (600 MHz, DMSO) δ 9.26 (s, 2H), 7.51 (d, 2H), 7.34 (t, 2H), 7.22 (t, 1H), 3.92 (s, 2H), 3.41 (s, 1H), 2.31 (td, 2H), 2.15 (td, 2H), 2.07 (d, 1H), 1.93 (d, 7H), 1.83 (dt, 2H), 1.67 (t, 1H), 1.56 (q, 1H), 1.47 (d, 2H). | 490.3 |
| SC_3256 | cis-8-Dimethylamino-1-[(1-hydroxy-cyclobutyl)-methyl]-3-(2-methyl-pyrimidin-5-yl)-8-phenyl-1,3-diazaspiro[4.5]decan-2-one | SC_3253 | [1-[tert-butyl(dimethyl)silyl]-oxycyclobutyl]methyl 4-methylbenzenesulfonate | INT-988 (step 1) | 1H NMR (600 MHz, DMSO) δ 8.92 (s, 2H), 7.37 (d, 4H), 7.27 (td, 1H), 3.79 (s, 2H), 3.27 (s, 1H), 2.72-2.65 (m, 2H), 2.54 (s, 3H), 2.25-2.19 (m, 2H), 2.16 (tt, 2H), 2.07 (s, 2H), 2.00 (s, 6H), 1.95-1.86 (m, 7H), 1.67 (qd, 1H), 1.55 (td, 2H), 1.51-1.42 (m, 3H). | 450.3 |
| SC_3257 | cis-1-[(1-Hydroxy-cyclobutyl)-methyl]-8-methylamino-8-phenyl-3-pyrimidin-5-yl-1,3-diazaspiro[4.5]decan-2-one | SC_3260 | | SC_3099 | 1H NMR (600 MHz, DMSO) δ 9.07 (s, 2H), 8.81 (s, 1H), 7.53-7.48 (m, 2H), 7.33 (t, 2H), 7.24-7.18 (m, 1H), 3.86 (s, 2H), 2.29 (td, 2H), 2.14 (tt, 2H), 2.07 (s, 1H), 1.96-1.87 (m, 8H), 1.82 (td, 2H), 1.71-1.62 (m, 1H), 1.54 (dp, 1H), 1.49-1.43 (m, 2H). | 422.3 |

-continued

| Example | Chemical name | Reactant I | Reactant II | in analogy to method | $^1$H NMR data | m/z (M + H)$^+$ |
|---|---|---|---|---|---|---|
| SC_3258 | cis-5-(8-Dimethylamino-2-oxo-8-phenyl-1,3-diazaspiro[4.5]decan-3-yl)-4-methyl-pyridine-2-carbonitrile | INT-976 | 5-bromo-4-methyl-pyridine-2-carbonitrile | SC_3103 | 1H NMR (600 MHz, DMSO) δ 8.57 (s, 1H), 7.92 (s, 1H), 7.61-7.57 (m, 1H), 7.42-7.32 (m, 4H), 7.25 (tt, 1H), 3.63 (s, 2H), 2.38 (d, 2H), 2.28 (s, 3H), 2.00-1.90 (m, 9H), 1.90-1.72 (m, 1H), 1.59-1.49 (m, 2H). | 390.2 |
| SC_3259 | cis-8-Dimethylamino-3-(2-methyl-pyrimidin-5-yl)-8-phenyl-1-(pyridin-2-yl-methyl)-1,3-diazaspiro[4.5]decan-2-one | SC_3253 | 2-(bromomethyl)pyridine | SC_3105 | 1H NMR (DMSO-d6) δ 8.94 (s, 2H), 8.52-8.51 (m, 1H), 7.77-7.74 (m, 1H), 7.45-7.42 (d, 1H), 7.38-7.22 (m, 6H), 4.47 (s, 2H), 3.84 (s, 2H), 2.66-2.63 (m, 2H), 2.54 (s, 3H), 2.06-2.03 (m, 2H), 1.92 (s, 6H), 1.57-1.42 (m, 4H). | 457.2 |
| SC_3260 | cis-8-Dimethylamino-3-phenyl-1,3-diazaspiro[4.5]decan-2-one | INT-976 | 5-bromopyrimidine | SC_3103 | 1H NMR (600 MHz, DMSO) δ 8.98 (s, 2H), 8.76 (s, 1H), 7.78 (s, 1H), 7.41-7.34 (m, 4H), 7.31-7.24 (m, 1H), 3.65 (s, 2H), 2.49-2.34 (m, 2H), 1.97 (s, 6H), 1.95-1.76 (m, 4H), 1.50 (t, 2H). | 352.2 |
| SC_3261 | cis-8-Dimethylamino-1-[(1-hydroxy-cyclobutyl)-methyl]-8-phenyl-3-pyrimidin-5-yl-1,3-diazaspiro[4.5]decan-2-one | SC_3260 | [1-[tert-butyl(dimethyl)silyl]-oxycyclobutyl]methyl 4-methylbenzenesulfonate | INT-988 (step 1) | 1H NMR (600 MHz, DMSO) δ 9.04 (s, 2H), 8.80 (s, 1H), 7.37 (d, 4H), 7.27 (p, 1H), 3.83 (s, 2H), 3.28 (s, 1H), 2.72-2.65 (m, 2H), 2.23 (td, 1H), 2.17 (tt, 1H), 2.07 (s, 2H), 2.00 (s, 6H), 1.91 (dt, 2H), 1.72-1.63 (m, 1H), 1.60-1.45 (m, 5H). | 436.3 |
| SC_3262 | cis-8-Amino-1-[(1-hydroxy-cyclobutyl)-methyl]-8-phenyl-3-[2-(trifluoromethyl)-pyrimidin-5-yl]-1,3-diazaspiro[4.5]decan-2-one | SC_3255 | | SC_3099 | 1H NMR (600 MHz, DMSO) δ 9.29 (s, 2H), 7.68-7.63 (m, 2H), 7.33 (t, 2H), 7.26-7.18 (m, 1H), 3.97 (s, 2H), 3.45 (s, 2H), 2.43 (td, 2H), 2.14 (tt, 2H), 1.99 (td, 2H), 1.96-1.90 (m, 2H), 1.71-1.54 (m, 4H), 1.52-1.47 (m, 2H). | 476.2 |
| SC_3263 | cis-8-Dimethylamino-3-(3-fluorophenyl)-8-phenyl-1,3-diazaspiro[4.5]decan-2-one | INT-976 | 1-bromo-3-fluoro-benzene | SC_3103 | 1H NMR (600 MHz, DMSO) δ 7.58-7.50 (m, 2H), 7.41-7.33 (m, 4H), 7.33-7.23 (m, 3H), 6.77-6.71 (m, 1H), 3.58 (s, 2H), 2.48-2.31 (m, 2H), 1.97 (s, 6H), 1.92-1.80 (m, 4H), 1.47 (t, 2H). | 368.2 |
| SC_3264 | cis-8-Dimethylamino-3-(3-methylsulfonyl-phenyl)-8-phenyl-1,3-diazaspiro[4.5]decan-2-one | INT-976 | 1-bromo-3-methylsulfonylbenzene | SC_3103 | 1H NMR (600 MHz, DMSO) δ 8.13 (t, 1H), 7.88 (d, 1H), 7.65 (s, 1H), 7.53 (t, 1H), 7.47 (dt, 1H), 7.41-7.35 (m, 4H), 7.28 (qd, 1H), 3.66 (s, 2H), 3.16 (s, 3H), 2.49-2.36 (m, 2H), 1.97 (s, 6H), 1.96-1.74 (m, 4H), 1.53-1.47 (m, 2H). | 428.2 |
| SC_3265 | cis-8-Dimethylamino-3-(4-methylsulfonyl-phenyl)-8-phenyl-1,3-diazaspiro[4.5]decan-2-one | INT-976 | 1-bromo-4-methylsulfonylbenzene | SC_3103 | 1H NMR (600 MHz, DMSO) δ 7.83-7.70 (m, 5H), 7.41-7.34 (m, 4H), 7.27 (tt, J = 7.1, 1.9 Hz, 1H), 3.65 (s, 2H), 3.12 (s, 3H), 2.49-2.31 (m, 2H), 1.97 (s, 6H), 1.95-1.75 (m, 4H), 1.49 (t, J = 8.6 Hz, 2H). | 428.2 |
| SC_3266 | cis-8-Dimethylamino-8-phenyl-3-pyridazin-3-yl-1,3-diazaspiro[4.5]decan-2-one | INT-976 | 3-bromopyridazine | SC_3103 | 1H NMR (600 MHz, DMSO) δ 8.82 (dd, J = 4.6, 1.4 Hz, 1H), 8.45 (dd, J = 9.2, 1.4 Hz, 1H), 7.95 (br s, 1H), 7.55 (dd, J = 9.2, 4.5 Hz, 1H), 7.42-7.34 (m, 4H), 7.28 (t, J = 6.8 Hz, 1H), 3.83 (s, 2H), 2.47-2.29 (m, 1H), 1.97 (s, 10H), 1.54-1.48 (m, 2H). | 352.2 |

| Example | Chemical name | Reactant I | Reactant II | in analogy to method | ¹H NMR data | m/z (M + H)⁺ |
|---|---|---|---|---|---|---|
| SC_3267 | cis-3-Methoxy-4-(8-methylamino-2-oxo-8-phenyl-1,3-diazaspiro[4.5]decan-3-yl)-benzonitrile | INT-976 | 4-bromo-3-methoxy-benzonitrile (step 1) | SC_3103 (for step 1), SC_3099 (for step 2) | 1HNMR (DMSO-d6, 400 MHz), δ (ppm) = 7.50-7.50 (m, 2H), 7.42-7.31 (m, 5H), 7.18 (bs, 2H), 3.83 (s, 3H), 3.64 (s, 2H), 2.05-21.99 (m, 2H), 1.85 (bs, 5H), 1.70 (bs, 2H), 1.53-1.50 (m, 2H). | 391.2 |
| SC_3268 | cis-8-Dimethylamino-3-(2-fluorophenyl)-8-phenyl-1,3-diazaspiro[4.5]decan-2-one | INT-976 | 1-bromo-2-fluorobenzene | SC_3103 | 1H NMR (600 MHz, DMSO) δ 7.46 (td, J = 8.0, 1.6 Hz, 1H), 7.40-7.32 (m, 5H), 7.26 (td, J = 6.7, 3.3 Hz, 1H), 7.24-7.12 (m, 3H), 3.53 (s, 2H), 2.37-2.33 (m, 2H), 1.96 (s, 6H), 1.95-1.74 (m, 4H), 1.49 (t, J = 9.3 Hz, 2H). | 368.2 |
| SC_3269 | cis-8-Dimethylamino-8-phenyl-3-(2-phenyl-pyrimidin-5-yl)-1,3-diazaspiro[4.5]decan-2-one | INT-976 | 5-bromo-2-phenyl-pyrimidine | SC_3103 | 1H NMR (600 MHz, DMSO) δ 9.07 (s, 2H), 8.34-8.28 (m, 1H), 7.82 (s, 1H), 7.52-7.42 (m, 4H), 7.39 (s, 1H), 7.38 (s, 3H), 7.28 (t, J = 4.8 Hz, 1H), 3.70 (s, 2H), 2.43-2.39 (m, 2H), 2.06-1.72 (m, 10H), 1.52 (d, J = 10.8 Hz, 2H). | 428.3 |
| SC_3270 | cis-8-Methylamino-1-(oxetan-3-yl-methyl)-8-phenyl-3-[2-(trifluoromethyl)-pyrimidin-5-yl]-1,3-diazaspiro[4.5]decan-2-one | SC_3245 | oxetan-3-ylmethyl 4-methylbenzenesulfonate (step 2) | SC_3099 (for step1), SC_3105 (for step 2) | 1H NMR (DMSO-d6): δ 9.24 (s, 2H), 7.49 (d, 2H), 7.34 (t, 2H), 7.21 (t, 1H), 4.66-4.62 (m, 2H), 4.44 (t, 2H), 3.87 (s, 2H), 3.55 (d, 2H), 3.28-3.23 (m, 1H), 2.36 (m, 1H), 2.20-2.14 (m, 2H), 1.95-1.91 (m, 5H), 1.84-1.77 (m, 2H), 1.43-1.40 (m, 2H). | 476.2 |
| SC_3271 | cis-1-(Cyclopropyl-methyl)-8-methylamino-8-phenyl-3-[2-(trifluoromethyl)-pyrimidin-5-yl]-1,3-diazaspiro[4.5]decan-2-one | SC_3245 | (bromomethyl)-cyclopropane | SC_3099 (for step1), SC_3105 (for step 2) | 1H NMR (DMSO-d6): δ 9.26 (s, 2H), 7.50 (d, 2H), 7.35 (t, 2H), 7.22 (t, 1H), 3.89 (s, 2H), 3.13 (d, 2H), 2.29-2.23 (m, 3H), 1.92-1.82 (m, 7H), 1.47-1.44 (m, 2H), 1.08-1.05 (m, 1H), 0.52-0.48 (m, 2H), 0.36-0.36-0.32 (m, 2H). | 460.1 |
| SC_3272 | cis-4-(8-Dimethylamino-2-oxo-8-phenyl-1,3-diazaspiro[4.5]decan-3-yl)-benzonitrile | INT-976 | 4-bromobenzonitrile | SC_3103 | 1H NMR (600 MHz, DMSO) δ 7.82-7.71 (m, 3H), 7.72-7.67 (m, 2H), 7.41-7.33 (m, 4H), 7.30-7.23 (m, 1H), 3.63 (s, 2H), 2.45-2.39 (m, 2H), 1.97 (s, 6H), 1.95-1.72 (m, 4H), 1.51-1.44 (m, 2H). | 375.2 |
| SC_3273 | cis-8-Dimethylamino-3-(4-fluorophenyl)-8-phenyl-1,3-diazaspiro[4.5]decan-2-one | INT-976 | 1-bromo-4-fluoro-benzene | SC_3103 | | 368.2 |
| SC_3274 | cis-2-(8-Dimethylamino-2-oxo-8-phenyl-1,3-diazaspiro[4.5]decan-3-yl)-benzonitrile | INT-976 | 2-bromobenzonitrile | SC_3103 | 1H NMR (600 MHz, DMSO) δ 7.77 (dd, J = 7.5, 1.6 Hz, 1H), 7.66 (ddd, J = 8.3, 7.5, 1.6 Hz, 1H), 7.60 (s, 1H), 7.48 (dd, J = 8.3, 1.1 Hz, 1H), 7.39-7.34 (m, 4H), 7.32 (td, J = 7.5, 1.1 Hz, 1H), 7.26 (t, J = 7.5, 1.6 Hz, 1H), 3.68 (s, 2H), 2.46-2.30 (m, 2H), 2.01-1.75 (m, 10H), 1.59-1.50 (m, 2H). | 375.2 |

| Example | Chemical name | Reactant I | Reactant II | in analogy to method | 1H NMR data | m/z (M + H)+ |
|---|---|---|---|---|---|---|
| SC_3276 | cis-1-[(1-Hydroxy-cyclobutyl)-methyl]-8-methylamino-3-(2-methyl-pyrimidin-5-yl)-8-phenyl-1,3-diazaspiro[4.5]decan-2-one | SC_3256 | | SC_3099 | 1H NMR (600 MHz, DMSO) δ 8.94 (s, 2H), 7.53-7.47 (m, 2H), 7.39-7.30 (m, 2H), 7.24-7.17 (m, 1H), 3.83 (s, 2H), 3.54-3.36 (m, 2H), 2.56 (s, 3H), 2.28 (td, 2H), 2.18-2.09 (m, 2H), 1.97-1.86 (m, 7H), 1.81 (td, 2H), 1.71-1.61 (m, 1H), 1.59-1.47 (m, 1H), 1.49-1.42 (m, 2H). | 436.3 |
| SC_3277 | cis-8-Dimethyl amino-3-[2-(morpholin-4-yl-methyl)-pyrimidin-5-yl]-8-phenyl-1,3-diazaspiro[4.5]decan-2-one | INT-976 | 4-[(5-bromopyrimidin-2-yl)methyl]morpholine | SC_3103 | 1H NMR (600 MHz, DMSO) δ 8.93 (s, 2H), 7.87-7.65 (m, 1H), 7.42-7.34 (m, 4H), 7.28 (dq, 1H), 3.66-3.62 (m, 2H), 3.61 (s, 2H), 3.54 (t, 4H), 2.43 (t, 4H), 1.98 (s, 6H), 1.96-1.74 (m, 4H), 1.52-1.46 (m, 2H). | 465.2 |
| SC_3278 | cis-8-Dimethylamino-3-[2-(methyl-tetrahydro-pyran-4-yl-amino)-pyrimidin-5-yl]-8-phenyl-1,3-diazaspiro[4.5]decan-2-one | INT-989 | N-methyltetrahydro-2H-pyran-4-amine | SC_3120 | 1H NMR (DMSO-d6): δ 8.50 (s, 2H), 7.39-7.35 (m, 5H), 7.27-7.24 (m, 1H), 4.74-4.67 (m, 1H), 3.94-3.90 (m, 2H), 3.50 (s, 2H), 3.39 (t, 2H), 2.93 (s, 3H), 2.35 (m, 2H), 1.99-1.71 (m, 12H), 1.50-1.44 (m, 4H). | |
| SC_3279 | cis-5-[8-Dimethylamino-1-[(1-hydroxy-cyclobutyl)-methyl]-2-oxo-8-phenyl-1,3-diazaspiro[4.5]decan-3-yl]-N-[2-[2-(2-methoxy-ethoxy)-ethoxy]-ethyl]-pyrimidine-2-carboxylic acid amide | INT-990 | (1-(tert-butyldimethylsilyloxy)cyclobutyl)methyl 4-methylbenzenesulfonate (step 1), 2,5,8,11-tetraoxatridecan-13-amine (step 2) | SC_3105 (step 1), SC_3133 (step 2) | 1H NMR (DMSO-d6): δ 9.12 (s, 2H), 8.63 (t, 1H), 7.36-7.33 (m, 4H), 7.26-7.23 (m, 1H), 5.25 (s, 1H), 3.85 (s, 2H), 3.52-3.34 (m, 16H), 3.35 (m, 2H), 3.19 (s, 3H), 2.69-2.66 (m, 2H), 2.25-2.13 (m, 4H), 1.97 (s, 6H), 1.92-1.87 (m, 2H), 1.57-1.44 (m, 6H). | 669.4 |
| SC_3280 | cis-1-(Cyclopropyl-methyl)-3-(2-fluoro-4-methylsulfonyl-phenyl)-8-methylamino-8-phenyl-1,3-diazaspiro[4.5]decan-2-one | INT-976 | 1-bromo-2-fluoro-4-(methylsulfonyl)benzene (step 1), (Bromomethyl)cyclopropane (step 2) | SC_3103 (for step 1), SC_3105 (step 2), SC_3099 (step 3) | 1H NMR (DMSO-d6): δ 7.86 (t, 1H), 7.81-7.77 (m, 1H), 7.73-7.70 (m, 1H), 7.45 (d, 2H), 7.31 (t, 2H), 7.19 (t, 1H), 3.85 (s, 2H), 3.24 (s, 3H), 3.09 (d, 2H), 2.29-2.22 (m, 3H), 1.93-1.90 (m, 5H), 1.74-1.68 (m, 2H), 1.49-1.46 (m, 2H), 1.04 (m, 1H), 0.51-0.46 (m, 2H), 0.34-0.30 (m, 2H). | 486.2 |
| SC_3281 | cis-2-[[5-(8-Dimethylamino-2-oxo-8-phenyl-1,3-diazaspiro[4.5]decan-3-yl)-pyrimidin-2-yl]-methyl-amino]-acetamide | INT-989 | 2-(methylamino)acetamide hydrochloride | SC_3120 | 1H NMR (DMSO-d6): δ 8.48 (s, 2H), 7.39-7.35 (m, 5H), 7.27-7.25 (m, 2H), 6.89 (s, 1H), 4.08 (s, 2H), 3.51 (s, 2H), 3.07 (s, 3H), 2.36-2.33 (m, 2H), 1.94-1.86 (m, 10H), 1.45 (m, 2H). | 438.2 |
| SC_3282 | cis-2-[[5-(8-Dimethylamino-2-oxo-8-phenyl-1,3-diazaspiro[4.5]decan-3-yl)-pyrimidin-2-yl]amino]-acetamide | INT-976 | tert-butyl (5-bromopyrimidin-2-yl)(cyanomethyl)carbamate (step 1) | SC_3103 (for step 1), SC_3100 step 3 (for step 2) | 1H NMR (DMSO-d6): δ 8.45 (s, 2H), 7.39-7.33 (m, 5H), 7.27-7.22 (m, 1H), 6.92 (s, 1H), 6.86 (t, 1H), 3.74 (d, 2H), 3.51 (s, 2H), 2.46-2.28 (m, 2H), 1.95-1.86 (m, 10H), 1.45 (m, 2H). | 424.2 |
| SC_3283 | cis-1-(Cyclopropyl-methyl)-8-methylamino-3-[4-methyl-6-(trifluoromethyl)-pyridin-3-yl]-8-phenyl-1,3-diazaspiro[4.5]decan-2-one | SC_3284 | | SC_3099 | 1H NMR (DMSO-d6): δ 8.61 (s, 1H), 7.82 (s, 1H), 7.46-7.44 (m, 2H), 7.30 (t, 2H), 7.18 (t, 1H), 3.80 (s, 2H), 3.08 (d, 2H), 2.33-2.25 (m, 6H), 1.92-1.89 (m, 5H), 1.72 (t, 2H), 1.56-1.53 (m, 2H), 1.04 (m, 1H), 0.51-0.46 (m, 2H), 0.33-0.30 (m, 2H). | 473.3 |

-continued

| Example | Chemical name | Reactant I | Reactant II | in analogy to method | 1H NMR data | m/z (M + H)+ |
|---|---|---|---|---|---|---|
| SC_3284 | cis-1-(Cyclopropyl-methyl)-8-dimethylamino-3-[4-methyl-6-(trifluoromethyl)-pyridin-3-yl]-8-phenyl-1,3-diazaspiro[4.5]decan-2-one | INT-984 | 5-bromo-4-methyl-2-(trifluoromethyl)pyridine | SC_3103 | 1H NMR (DMSO-d6): δ 8.59 (s, 1H), 7.82 (s, 1H), 7.35-7.34 (m, 4H), 7.27-7.23 (m, 1H), 3.75 (s, 2H), 3.06 (d, 2H), 2.71-2.68 (m, 2H), 2.33-2.24 (m, 5H), 2.00 (m, 6H), 1.59-1.56 (m, 2H), 1.46 (t, 2H), 1.02-0.99 (m, 1H), 0.53-0.48 (m, 2H), 0.33-0.30 (m, 2H). | 487.3 |
| SC_3285 | cis-N-[5-(8-Dimethylamino-2-oxo-8-phenyl-1,3-diazaspiro[4.5]decan-3-yl)-pyrimidin-2-yl]-thiophene-2-carboxylic acid amide | SC_3239 | thiophene-2-carbonyl chloride | SC_3240 | 1H NMR (600 MHz, DMSO) δ 8.90 (s, 2H), 8.08-8.04 (m, 1H), 7.84 (dd, 1H), 7.71 (s, 1H), 7.38 (d, 5H), 7.27 (t, 1H), 7.19 (dd, 1H), 3.66 (s, 2H), 2.48-2.34 (m, 2H), 1.99-1.75 (m, 10H), 1.54-1.48 (m, 2H). | 477.2 |
| SC_3286 | cis-N-[5-(8-Dimethylamino-2-oxo-8-phenyl-1,3-diazaspiro[4.5]decan-3-yl)-pyrimidin-2-yl]-benzamide | SC_3239 | benzoyl chloride | SC_3240 | 1H NMR (600 MHz, DMSO) δ 10.84 (s, 1H), 8.91 (s, 2H), 7.98-7.93 (m, 2H), 7.62-7.55 (m, 1H), 7.50 (t, 2H), 7.39 (d, 4H), 7.28 (dt, 1H), 3.67 (s, 2H), 2.48-2.32 (m, 2H), 2.05-1.76 (m, 10H), 1.55-1.49 (m, 2H). | 471.3 |
| SC_3287 | cis-8-Dimethylamino-8-phenyl-3-(5-phenyl-thiophen-2-yl)-1,3-diazaspiro[4.5]decan-2-one | INT-976 | 2-bromo-5-phenylthiophene | SC_3103 | 1H NMR (DMSO-d6): δ 7.80-7.70 (br s, 1H), 7.52 (d, 2H), 7.38-7.28 (m, 7H), 7.20-7.17 (m, 2H), 6.27 (d, 1H), 3.61 (s, 2H), 2.49 (m, 2H), 1.95-1.91 (m, 10H), 1.48 (m, 2H). | 432.2 |
| SC_3288 | cis-1-(Cyclopropyl-methyl)-8-dimethylamino-3-[2-(methylsulfonyl-methyl)-phenyl]-8-phenyl-1,3-diazaspiro[4.5]decan-2-one | INT-984 | 1-bromo-2-(methylsulfonylmethyl)benzene | SC_3103 | 1H NMR (CDCl3): δ 7.49 (d, 1H), 7.41-7.22 (m, 8H), 4.45 (s, 2H), 3.64 (s, 2H), 3.15 (d, 2H), 2.79 (s, 3H), 2.71-2.67 (m, 2H), 2.37 (t, 2H), 2.06 (s, 6H), 1.67-1.64 (m, 2H), 1.55-1.44 (m, 2H), 1.10-1.06 (m, 1H), 0.57-0.52 (m, 2H), 0.39-0.35 (m, 2H). | 496.3 |
| SC_3289 | cis-8-Dimethylamino-3-[2-(methylsulfonyl-methyl)-phenyl]-8-phenyl-1,3-diazaspiro[4.5]decan-2-one | SC_3288 | | SC_3099 | 1H NMR (DMSO-d6): δ 7.49-7.37 (m, 5H), 7.32-7.30 (m, 3H), 7.19-7.15 (m, 1H), 4.49 (s, 2H), 3.71 (s, 2H), 3.05 (d, 2H), 2.87 (s, 3H), 2.26-2.20 (m, 3H), 1.91-1.87 (m, 5H), 1.71-1.56 (m, 4H), 1.03-1.01 (m, 1H), 0.49-0.45 (m, 2H), 0.31-0.28 (m, 2H). | 482.3 |
| SC_3290 | cis-8-Dimethylamino-8-(3-fluorophenyl)-3-[2-(methylsulfonyl-methyl)-phenyl]-1,3-diazaspiro[4.5]decan-2-one | INT-1024 | 1-bromo-2-(methylsulfonylmethyl)benzene | SC_3103 | 1H NMR (600 MHz, DMSO) δ 7.46 (dd, 1H), 7.39 (td, 2H), 7.33 (dd, 1H), 7.31-7.21 (m, 1H), 7.18 (d, 1H), 7.15 (dd, 1H), 7.08 (td, 1H), 4.50 (s, 2H), 3.56 (s, 2H), 2.88 (s, 3H), 2.42-2.24 (m, 2H), 1.99-1.89 (m, 8H), 1.88-1.75 (m, 2H), 1.60-1.48 (m, 2H). | 460.3 |
| SC_3291 | cis-8-Dimethylamino-8-(4-fluorophenyl)-3-[2-(methylsulfonyl-methyl)-phenyl]-1,3-diazaspiro[4.5]decan-2-one | INT-1025 | 1-bromo-2-(methylsulfonylmethyl)benzene | SC_3103 | 1H NMR (600 MHz, DMSO) δ 7.46 (dd, 1H), 7.43-7.34 (m, 3H), 7.33 (dd, 1H), 7.28 (td, 2H), 7.16 (t, 2H), 4.49 (s, 2H), 3.55 (s, 2H), 2.88 (s, 3H), 2.35-2.32 (m, 2H), 1.95 (s, 6H), 1.94-1.88 (m, 2H), 1.88-1.65 (m, 2H), 1.59-1.47 (m, 2H). | 460.3 |

-continued

| Example | Reactant I | Reactant II | Chemical name | in analogy to method | ¹H NMR data | m/z (M + H)⁺ |
|---|---|---|---|---|---|---|
| SC_3294 | INT-1024 | 4-(5-bromo-4-methyl-pyrimidin-2-yl)morpholine | cis-8-Dimethylamino-8-(3-fluorophenyl)-3-(4-methyl-2-morpholin-4-yl-pyrimidin-5-yl)-1,3-diazaspiro[4.5]decan-2-one | SC_3103 | 1H NMR (600 MHz, DMSO) δ 8.13 (s, 1H), 7.40 (td, 1H), 7.22-7.11 (m, 4H), 7.08 (td, 1H), 3.69-3.60 (m, 8H), 2.34-2.31 (m, 2H), 2.20 (s, 3H), 1.96 (s, 6H), 1.96-1.70 (m, 4H), 1.56-1.43 (m, 2H). | 469.3 |
| SC_3295 | INT-976 | 1-[4-(5-bromo-4-methyl-pyridin-2-yl)-piperazin-1-yl]-ethanone | cis-3-[6-(4-Acetyl-piperazin-1-yl)-4-methyl-pyridin-3-yl]-8-dimethylamino-8-phenyl-1,3-diazaspiro[4.5]decan-2-one | SC_3103 | 1HNMR (DMSO-d6, 400 MHz at 100° C.) δ (ppm) = 7.88 (s, 1H), 7.35-7.22 (m, 5H), 6.73 (s, 1H), 6.64 (s, 1H), 3.53-3.50 (m, 8H), 3.38 (s, 2H), 2.33-2.30 (m, 2H), 2.14 (s, 3H), 2.03-1.88 (m, 13H), 1.56-1.51 (m, 2H). | 491.3 |
| SC_3296 | INT-976 | 1-[4-(5-bromo-4-methyl-pyrimidin-2-yl)-piperazin-1-yl]-ethanone | cis-3-[2-(4-Acetyl-piperazin-1-yl)-4-methyl-pyrimidin-5-yl]-8-dimethylamino-8-phenyl-1,3-diazaspiro[4.5]decan-2-one | SC_3103 | 1H-NMR (DMSO-d6, 400 MHz at 100° C.), δ (ppm) = 8.11 (s, 1H), 7.35-7.24 (m, 5H), 6.88 (s, 1H), 3.73 (bs, 4H), 3.52 (bs, 4H), 3.38 (s, 2H), 2.33 (bs, 2H), 2.22 (s, 3H), 2.03-1.87 (m, 13H), 1.56-1.53 (m, 2H). | 492.3 |
| SC_3297 | INT-976 | 5-bromo-2-chloro-4-methyl-pyridine (step 1), 4-pyridinylboronic acid (step 2) | cis-3-Dimethylamino-3-(4-methyl-6-pyridin-4-yl-pyridin-3-yl)-8-phenyl-1,3-diazaspiro[4.5]decan-2-one | SC_3103 (for step 1), SC_3129 (for step 2) | 1H-NMR (DMSO-d6, 400 MHz at 100° C.), δ (ppm) = 8.65 (d, 2H, J = 5.92 Hz), 8.50 (s, 1H), 7.96 (d, 2H, J = 5.96 Hz), 7.91 (s, 1H), 7.36-7.23 (m, 5H), 7.07 (s, 1H), 3.57 (s, 2H), 2.38-2.33 (m, 4H), 2.04 (s, 6H), 2.00-1.88 (m, 4H), 1.61-1.57 (m, 2H). | 442.3 |
| SC_3298 | INT-976 | 1-[4-(5-bromo-4-trifluoromethyl-pyrimidin-2-yl)-piperazin-1-yl]-ethanone | cis-3-[2-(4-Acetyl-piperazin-1-yl)-4-(trifluoromethyl)-pyrimidin-5-yl]-8-dimethylamino-8-phenyl-1,3-diazaspiro[4.5]decan-2-one | SC_3103 | 1H-NMR (DMSO-d6, 400 MHz at 100° C.), δ (ppm) = 8.52 (s, 1H), 7.35-7.22 (m, 5H), 7.07 (s, 1H), 3.79-3.78 (t, 4H, 5.08 Hz), 3.57 (t, 4H, 5.26 Hz), 3.39 (s, 2H), 2.36-2.32 (m, 2H), 2.04-1.85 (m, 13H), 1.54-1.50 (m, 2H). | 546.3 |
| SC_3299 | INT-976 | 4-(5-bromo-4-trifluoromethyl-pyrimidin-2-yl)-piperazin-2-one | cis-8-Dimethylamino-3-[2-(3-oxo-piperazin-1-yl)-4-(trifluoromethyl)-pyrimidin-5-yl]-8-phenyl-1,3-diazaspiro[4.5]decan-2-one | SC_3103 | 1HNMR (DMSO-d6, 400 MHz), δ (ppm) = 8.55 (s, 1H), 7.77 (bs, 1H), 7.35-7.23 (m, 5H), 7.09 (s, 1H), 4.20 (s, 2H), 3.92 (t, 2H, J = 5.04 Hz), 3.39 (s, 2H), 3.33 (bs, 2H), 2.36-2.33 (m, 2H), 2.03-1.85 (m, 10H), 1.54-1.39 (m, 2H). | 518.2 |
| SC_3300 | INT-976 | 4-bromo-isoquinoline | cis-8-Dimethylamino-3-isoquinolin-4-yl-8-phenyl-1,3-diazaspiro[4.5]decan-2-one | SC_3103 | 1HNMR (DMSO-d6, 400 MHz at 100° C.), δ (ppm) = 9.16 (s, 1H), 8.41 (s, 1H), 8.13 (d, 1H, J = 8.12 Hz), 7.91 (d, 1H, J = 8.64 Hz), 7.71 (t, 1H, J = 7.58 Hz), 7.67 (t, 1H, J = 7.46 Hz), 7.36-7.23 (m, 5H), 7.14 (s, 1H), 3.67 (s, 2H), 2.41-2.36 (m, 2H), 2.10-1.89 (m, 10H), 1.68-1.64 (m, 2H). | 401.2 |
| SC_3301 | INT-976 | 5-bromo-isoquinoline | cis-8-Dimethylamino-3-isoquinolin-5-yl-8-phenyl-1,3-diazaspiro[4.5]decan-2-one | SC_3103 | 1HNMR (DMSO-d6, 400 MHz at 100° C.), δ (ppm) = 9.29 (s, 1H), 8.48 (d, 1H, J = 5.92 Hz), 7.98-7.96 (m, 1H), 7.70-7.64 (m, 3H), 7.36-7.23 (m, 5H), 7.13 (s, 1H), 3.65 (s, 2H), 2.41-2.36 (m, 2H), 2.10-1.90 (m, 10H), 1.68-1.63 (m, 2H). | 401.2 |

-continued

| Example | Chemical name | Reactant I | Reactant II | in analogy to method | 1H NMR data | m/z (M + H)+ |
|---|---|---|---|---|---|---|
| SC_3302 | cis-8-Dimethylamino-8-phenyl-3-(1H-pyrrolo[2,3-b]pyridin-4-yl)-1,3-diazaspiro[4.5]decan-2-one | INT-976 | 4-bromo-1H-pyrrolo[2,3-b]pyridine | SC_3103 | 1H NMR (600 MHz, DMSO) δ 11.42 (s, 1H), 7.99 (d, 1H), 7.66 (br s, 1H), 7.43-7.33 (m, 5H), 7.27 (t, 1H), 7.22 (t, 1H), 6.65-6.60 (m, 1H), 3.91 (s, 2H), 2.45-2.27 (m, 2H), 1.98-1.82 (m, 10H), 1.56-1.49 (m, 2H). | 390.2 |
| SC_3303 | cis-8-Dimethylamino-8-phenyl-3-(2-pyridin-4-yl-thiazol-4-yl)-1,3-diazaspiro[4.5]decan-2-one | INT-976 | 4-bromo-2-(pyridin-4-yl)thiazole | SC_3103 | 1H NMR (DMSO-d6): δ 8.62 (d, 2H), 7.82 (d, 2H), 7.61 (broad s, 1H), 7.54 (s, 1H), 7.40-7.37 (m, 4H), 7.29-7.27 (m, 1H), 3.84 (s, 2H), 2.49 (m, 2H), 1.96-1.79 (m, 10H), 1.51 (m, 2H). | 434.1 |
| SC_3304 | cis-8-[Methyl-(tetrahydro-furan-3-yl-methyl)-amino]-3-(2-morpholin-4-yl-pyrimidin-5-yl)-8-phenyl-1,3-diazaspiro[4.5]decan-2-one (enantiomer 1) | INT-1026 | 4-(5-bromopyrimidin-2-yl)morpholine | step 2 of SC_3097 (for synthesis), SC_3292 and SC_3293 (for separation of enantiomers) | 1H NMR (DMSO-d6): δ 8.56 (s, 2H), 7.65 (broad s, 1H), 7.36-7.23 (m, 5H), 3.66-3.55 (m, 10H), 3.49 (s, 2H), 3.38 (m, 1H), 2.32-2.26 (m, 3H), 2.11-1.94 (m, 6H), 1.86-1.82 (m, 3H), 1.50-1.41 (m, 3H). | 507.3 |
| SC_3305 | cis-8-[Methyl-(tetrahydro-furan-3-yl-methyl)-amino]-3-(2-morpholin-4-yl-pyrimidin-5-yl)-8-phenyl-1,3-diazaspiro[4.5]decan-2-one (enantiomer 2) | INT-1026 | 4-(5-bromopyrimidin-2-yl)morpholine | step 2 of SC_3097 (for synthesis), SC_3292 and SC_3293 (for separation of enantiomers) | 1H NMR (DMSO-d6): δ 8.56 (s, 2H), 7.66 (broad s, 1H), 7.35-7.24 (m, 5H), 3.63-3.49 (m, 12H), 3.31 (m, 1H), 2.27 (m, 3H), 2.11-1.84 (m, 10H), 1.42 (m, 3H). | 507.2 |
| SC_3306 | cis-3-[2-(Azetidin-1-yl)pyrimidin-5-yl]-8-dimethylamino-8-phenyl-1,3-diazaspiro[4.5]decan-2-one | INT-976 | 2-azetidin-1-yl-5-bromo-pyrimidine | step 2 of SC_3242 | 1HNMR (DMSO-d6, 400 MHz at 100° C.), δ (ppm) = 8.48 (s, 2H), 7.36-7.26 (m, 5H), 7.07 (s, 1H), 3.99 (t, 4H, J = 7.18 Hz), 3.50 (s, 2H), 2.35-2.26 (m, 4H), 2.03 (s, 6H), 1.95-1.91 (m, 2H), 1.52-1.50 (m, 2H). | 407.2 |
| SC_3307 | cis-3-[2-(3,3-Difluoro-azetidin-1-yl)pyrimidin-5-yl]-8-dimethylamino-8-phenyl-1,3-diazaspiro[4.5]decan-2-one | INT-976 | 5-bromo-2-(3,3-difluoro-azetidin-1-yl)-pyrimidine | step 2 of SC_3242 | 1HNMR (DMSO-d6, 400 MHz at 100° C.), δ (ppm) = 8.62 (s, 2H), 7.37-7.25 (m, 5H), 7.20 (s, 1H), 4.38 (t, 4H, J = 12.40 Hz), 3.55 (s, 2H), 2.36-233 (m, 2H), 2.03 (s, 6H), 1.97-1.89 (m, 4H), 1.53-1.51 (m, 2H). | 443.2 |
| SC_3308 | cis-8-Dimethylamino-3-[6-morpholin-4-yl-5-(trifluoromethyl)-pyridin-3-yl]-8-phenyl-1,3-diazaspiro[4.5]decan-2-one | INT-976 | 4-(5-bromo-3-trifluoromethyl-pyridin-2-yl)morpholine | SC_3103 | 1HNMR (DMSO-d6, 400 MHz at 100° C.), δ (ppm) = 8.63 (s, 1H), 8.38 (s, 1H), 7.37-7.25 (m, 6H), 3.71 (bs, 4H), 3.65 (s, 2H), 3.03 (bs, 4H), 2.37-2.32 (m, 2H), 2.03 (s, 6H), 1.98-1.88 (m, 4H), 1.55-1.52 (m, 2H). | 504.3 |
| SC_3309 | cis-8-Methylamino-3-[6-morpholin-4-yl-5-(trifluoromethyl)-pyridin-3-yl]-8-phenyl-1,3-diazaspiro[4.5]decan-2-one | SC_3308 | | SC_3099 | 1HNMR (DMSO-d6, 400 MHz at 100° C.), δ (ppm) = 8.68 (s, 1H), 8.42 (s, 1H), 7.48 (d, 2H, J = 8.12 Hz), 7.33 (t, 2H, J = 7.62 Hz), 7.20 (t, 1H, J = 7.38 Hz), 7.14 (s, 1H), 3.75-3.71 (m, 6H), 3.03 (t, 4H, J = 8.88 Hz), 2.08-2.02 (m, 2H), 1.95-1.79 (m, 8H), 1.58-1.55 (m, 2H). | 490.4 |

-continued

| Example | Chemical name | Reactant I | Reactant II | in analogy to method | ¹H NMR data | m/z (M + H)⁺ |
|---|---|---|---|---|---|---|
| SC_3310 | cis-8-Dimethylamino-8-phenyl-3-[5-(trifluoromethyloxy)-pyridin-2-yl]-1,3-diazaspiro[4.5]decan-2-one | INT-976 | 2-bromo-5-(trifluoromethyloxy)-pyridine | SC_3103 | 1H NMR (600 MHz, DMSO) δ 8.32-8.26 (m, 2H), 7.86-7.82 (m, 1H), 7.79 (dd, 1H), 7.41-7.33 (m, 4H), 7.27 (t, 1H), 3.71 (s, 2H), 2.46-2.33 (m, 4H), 1.96 (s, 6H), 1.94-1.72 (m, 4H), 1.47 (t, 2H). | 435.2 |
| SC_3311 | cis-8-Dimethylamino-3-(5-methylsulfonyl-pyridin-2-yl)-8-phenyl-1,3-diazaspiro[4.5]decan-2-one | INT-976 | 2-bromo-5-methylsulfonylpyridine | SC_3103 | 1H NMR (600 MHz, DMSO) δ 8.66 (dd, 1H), 8.39 (dd, 1H), 8.14 (dd, 1H), 8.06 (s, 1H), 7.42-7.33 (m, 4H), 7.28 (t, 1H), 3.77 (s, 2H), 3.21 (s, 3H), 2.46-2.32 (m, 2H), 2.03-1.68 (m, 10H), 1.52-1.46 (m, 2H). | 429.2 |
| SC_3312 | cis-6-(8-Dimethylamino-2-oxo-8-phenyl-1,3-diazaspiro[4.5]decan-3-yl)-nicotinonitrile | INT-976 | 6-bromopyridine-3-carbonitrile | SC_3103 | 1H NMR (600 MHz, DMSO) δ 8.66 (d, 1H), 8.34 (d, 1H), 8.08 (dd, 1H), 7.41-7.33 (m, 4H), 7.28 (t, 1H), 3.74 (s, 2H), 2.46-2.30 (m, 2H), 1.96 (s, 6H), 1.94-1.73 (m, 4H), 1.51-1.44 (m, 2H). | 376.2 |
| SC_3314 | cis-8-Dimethylamino-3-[4-methyl-2-(3-oxo-piperazin-1-yl)-pyrimidin-5-yl]-8-phenyl-1,3-diazaspiro[4.5]decan-2-one | INT-976 | 4-(5-bromo-4-methyl-pyrimidin-2-yl)-piperazin-2-one | SC_3103 | 1HNMR (DMSO-d6, 400 MHz at 100° C.), δ (ppm) = 8.14 (s, 1H), 7.65 (bs, 1H), 7.34-7.23 (m, 5H), 6.89 (s, 1H), 4.16 (s, 2H), 3.88 (bs, 2H), 3.39 (s, 2H), 3.29 (bs, 2H), 2.33 (bs, 2H), 2.24 (s, 3H), 2.03-1.87 (m, 10H), 1.53 (bs, 2H). | 464.2 |
| SC_3315 | cis-5-(8-Dimethylamino-2-oxo-8-phenyl-1,3-diazaspiro[4.5]decan-3-yl)-pyridine-2-carboxylic acid amide | INT-976 | | SC_3016 | 1H NMR (600 MHz, DMSO) δ 8.80 (d, 1H), 8.10 (d, 1H), 7.95-7.89 (m, 2H), 7.79 (s, 1H), 7.42-7.35 (m, 5H), 7.28 (s, 1H), 3.67 (s, 2H), 2.48-2.28 (m, 2H), 1.95 (d, 10H), 1.53-1.46 (m, 2H). | 394.2 |
| SC_3316 | cis-3-[4-(Azetidin-1-yl)-2-methyl-pyrimidin-5-yl]-8-dimethylamino-8-phenyl-1,3-diazaspiro[4.5]decan-2-one | INT-976 | 4-azetidin-1-yl-5-bromo-2-methyl-pyrimidine | step 2 of SC_3242 | 1HNMR (DMSO-d6, 400 MHz at 100° C.), δ (ppm) = 7.85 (s, 1H), 7.34-7.23 (m, 5H), 6.93 (s, 1H), 4.11 (t, 4H, J = 7.40 Hz), 3.33 (s, 2H), 2.33-2.30 (m, 7H), 2.02 (s, 6H), 1.96-1.87 (m, 4H), 1.53-1.48 (m, 2H). | 421.2 |
| SC_3317 | cis-2-(8-Dimethylamino-2-oxo-8-phenyl-1,3-diazaspiro[4.5]decan-3-yl)-benzamide | INT-976 | 2-bromobenzonitrile | SC_3103 (step 1), SC_3016 (step 2) | 1H NMR (600 MHz, DMSO) δ 7.50 (s, 1H), 7.42 (dd, 1H), 7.42-7.32 (m, 5H), 7.31 (d, 1H), 7.26 (t, 1H), 7.23-7.13 (m, 3H), 3.53 (s, 2H), 2.41-2.27 (m, 2H), 1.96 (s, 6H), 1.90 (t, 2H), 1.86-1.68 (m, 2H), 1.52-1.48 (m, 2H). | 393.2 |
| SC_3318 | cis-8-Dimethylamino-3-[2-(methylsulfonyl-methyl)-phenyl]-8-thiophen-2-yl-1,3-diazaspiro[4.5]decan-2-one | INT-997 | 1-bromo-2-(methylsulfonylmethyl)-benzene | SC_3103 | 1H NMR (600 MHz, DMSO) δ 7.47 (dd, 1H), 7.43-7.36 (m, 2H), 7.34 (dd, 1H), 7.29 (ddd, 1H), 7.19 (s, 1H), 7.05 (ddd, 1H), 6.94 (d, 1H), 4.50 (s, 2H), 3.61 (s, 2H), 2.89 (s, 3H), 2.35-2.21 (m, 2H), 2.04 (s, 6H), 1.98-1.90 (m, 2H), 1.86-1.70 (m, 2H). | 448.2 |
| SC_3320 | cis-8-Dimethylamino-3-(4-methyl-2-morpholin-4-yl-pyrimidin-5-yl)-8-thiophen-2-yl-1,3-diazaspiro[4.5]decan-2-one | INT-997 | 4-(5-bromo-4-methyl-pyrimidin-2-yl)morpholine | SC_3319 | 1H NMR (600 MHz, DMSO) δ 8.15 (d, 1H), 7.41 (dt, 1H), 7.13 (s, 1H), 7.05 (ddd, 1H), 6.94 (dd, 1H), 3.71-3.60 (m, 8H), 3.44 (s, 2H), 2.32-2.24 (m, 2H), 2.21 (s, 3H), 2.04 (s, 6H), 1.98-1.88 (m, 2H), 1.87-1.75 (m, 2H), 1.62-1.54 (m, 2H). | 457.2 |

-continued

| Example | Chemical name | Reactant I | Reactant II | in analogy to method | ¹H NMR data | m/z (M + H)⁺ |
|---|---|---|---|---|---|---|
| SC_3321 | cis-8-Dimethylamino-3-(6-methylsulfonyl-pyridin-3-yl)-8-phenyl-1,3-diazaspiro[4.5]decan-2-one | INT-976 | 5-bromo-2-methylsulfonylpyridine | SC_3103 | 1H NMR (600 MHz, DMSO) δ 8.89 (d, J = 2.6 Hz, 1H), 8.28 (dd, J = 8.9, 2.6 Hz, 1H), 7.93 (d, 1H), 7.42-7.34 (m, 4H), 7.31-7.25 (m, 1H), 3.71 (s, 2H), 3.18 (s, 3H), 2.48-2.33 (m, 2H), 2.04-1.76 (m, 10H), 1.54-1.48 (m, 2H). | 429.2 |
| SC_3322 | cis-8-Dimethylamino-8-phenyl-3-(1H-pyrrolo[2,3-b]pyridin-5-yl)-1,3-diazaspiro[4.5]decan-2-one | INT-976 | tert-butyl 5-bromopyrrolo[2,3-b]pyridine-1-carboxylate (step 1) | SC_3103 (for step 1), SC_3173 (for step 2) | 1H NMR (600 MHz, DMSO) δ 11.45 (s, 1H), 8.38 (s, 1H), 8.00 (d, 1H), 7.85-7.81 (m, 1H), 7.70-7.66 (m, 2H), 7.57-7.53 (m, 3H), 7.41 (t, 1H), 6.35 (dd, 1H), 3.54 (s, 2H), 2.75-2.41 (m, 8H, overlapps with solvent residual peak), 2.30-2.26 (m, 2H), 1.89 (d, 2H), 1.41-1.37 (m, 2H). | 390.2 |
| SC_3323 | cis-N-[5-(8-Dimethylamino-2-oxo-8-phenyl-1,3-diazaspiro[4.5]decan-3-yl)-pyrimidin-2-yl]-acetamide (enantiomer 1) | SC_3239 | acetyl chloride | SC_3240 | 1H NMR (600 MHz, DMSO) δ 10.36 (s, 1H), 8.82 (s, 2H), 8.40 (s, rotamer), 7.67 (s, 1H), 7.44-7.31 (m, 4H), 7.27 (td, 1H), 3.62 (s, 2H), 2.46-2.30 (m, 2H), 2.11 (s, 3H), 2.08 (s, rotamer), 1.96 (s, 6H), 1.97 (s, rotamer), 1.95-1.75 (m, 4H), 1.52-1.47 (m, 2H). | 409.2 |
| SC_3324 | cis-3-[2-(4-Methyl-piperazin-1-yl)-pyrimidin-5-yl]-8-[methyl-(tetrahydro-furan-3-yl-methyl)-amino]-8-phenyl-1,3-diazaspiro[4.5]decan-2-one (enantiomer 2) | INT-1026 | 5-bromo-2-(4-methylpiperazin-1-yl)pyrimidine | step 2 of SC_3097 (for synthesis), SC_3292 and SC_3293 (for separation of enantiomers) | 1H NMR (DMSO-d6): δ 8.52 (s, 2H), 7.64 (broad s, 1H), 7.36-7.23 (m, 5H), 3.66-3.55 (m, 7H), 3.48 (s, 2H), 3.37-3.36 (m, 1H), 2.33-2.13 (m, 11H), 2.01-1.82 (m, 9H), 1.50-1.41 (m, 3H). | 518.3 |
| SC_3325 | cis-3-[2-(4-Methyl-piperazin-1-yl)-pyrimidin-5-yl]-8-[methyl-(tetrahydro-furan-3-yl-methyl)-amino]-8-phenyl-1,3-diazaspiro[4.5]decan-2-one | INT-1026 | 5-bromo-2-(4-methylpiperazin-1-yl)pyrimidine | step 2 of SC_3097 (for synthesis), SC_3292 and SC_3293 (for separation of enantiomers) | 1H NMR (DMSO-d6): δ 8.52 (s, 2H), 7.64 (broad s, 1H), 7.36-7.24 (m, 5H), 3.66-3.55 (m, 7H), 3.48 (s, 2H), 3.36 (m, 1H), 2.34-2.13 (m, 10H), 2.01-1.83 (m, 10H), 1.50-1.41 (m, 3H). | 518.3 |
| SC_3326 | cis-8-Dimethylamino-3-(4,6-dimethyl-2-morpholin-4-yl-pyrimidin-5-yl)-8-phenyl-1,3-diazaspiro[4.5]decan-2-one | INT-976 | 4-(5-bromo-4,6-dimethyl-pyrimidin-2-yl)morpholine | SC_3103 | — | 465.3 |
| SC_3327 | cis-8-Dimethylamino-3-(2-morpholin-4-yl-pyrimidin-5-yl)-8-thiophen-2-yl-1,3-diazaspiro[4.5]decan-2-one | INT-1027 | morpholine | SC_3120 | 1H NMR (600 MHz, DMSO) δ 8.58 (s, 2H), 7.43 (dd, 1H), 7.40-7.32 (m, 1H), 7.07 (dd, 1H), 6.96 (dd, 1H), 3.67-3.61 (m, 4H), 3.62-3.57 (m, 6H), 2.31-2.27 (m, 2H), 2.04 (s, 6H), 1.91 (t, 2H), 1.86-1.82 (m, 2H), 1.56-1.50 (m, 2H). | 443.2 |

-continued

| Example | Chemical name | Reactant I | Reactant II | in analogy to method | ¹H NMR data | m/z (M + H)⁺ |
|---|---|---|---|---|---|---|
| SC_3328 | cis-6-(8-Dimethylamino-2-oxo-8-phenyl-1,3-diazaspiro[4.5]decan-3-yl)-pyridine-3-carboxylic acid amide | SC_3312 | | SC_3016 | 1H NMR (600 MHz, DMSO) δ 8.71 (d, J = 2.3 Hz, 1H), 8.24 (d, J = 8.9 Hz, 1H), 8.12 (dd, J = 9.0, 2.4 Hz, 1H), 7.95 (s, 1H), 7.86 (s, 1H), 7.36 (dq, J = 13.7, 6.6, 5.6 Hz, 5H), 7.27 (t, J = 7.2 Hz, 1H), 3.74 (s, 2H), 2.41-2.37 (m, 2H), 1.96 (s, 6H), 1.94-1.87 (m, 2H), 1.86-1.80 (m, 2H), 1.51-1.44 (m, 2H). | 394.2 |
| SC_3329 | cis-8-Dimethylamino-3-[2-methyl-5-(trifluoromethyl)-2H-pyrazol-3-yl]-8-thiophen-2-yl-1,3-diazaspiro[4.5]decan-2-one | INT-997 | 5-bromo-1-methyl-3-(trifluoromethyl)pyrazole | SC_3319 | 1H NMR (600 MHz, DMSO) δ 7.66-7.63 (m, 1H), 7.42 (dd, 1H), 7.06 (dd, 1H), 6.95 (dd, 1H), 6.64 (s, 1H), 3.75 (s, 3H), 3.60 (s, 2H), 2.30-2.26 (m, 2H), 2.04 (s, 6H), 1.98-1.90 (m, 2H), 1.83-1.79 (m, 2H), 1.64-1.57 (m, 2H). | 428.2 |
| SC_3330 | cis-8-Dimethylamino-3-[2-[(2-hydroxy-ethyl)-methyl-amino]-pyrimidin-5-yl]-8-thiophen-2-yl-1,3-diazaspiro[4.5]decan-2-one | INT-1027 | 2-(methylamino)ethanol | SC_3120 | 1H NMR (600 MHz, DMSO) δ 8.48 (s, 2H), 7.43 (d, 1H), 7.30 (s, 1H), 7.07 (dd, 1H), 6.96 (d, 1H), 3.61 (dd, 2H), 3.58-3.51 (m, 4H), 3.09 (s, 3H), 2.34-2.22 (m, 2H), 2.04 (s, 6H), 1.96-1.76 (m, 4H), 1.56-1.50 (m, 2H). | 431.2 |
| SC_3331 | cis-8-Dimethylamino-3-[2-(2-oxo-1,3-dihydro-indol-4-yl)-pyrimidin-5-yl]-8-thiophen-2-yl-1,3-diazaspiro[4.5]decan-2-one | INT-1027 | 4-(4,4,5,5-tetramethyl-1,3,2-dioxaborolan-2-yl)indolin-2-one | SC_3208 | 1H NMR (600 MHz, DMSO) δ 10.46 (s, 1H), 9.12 (s, 2H), 7.87 (d, 1H), 7.47-7.42 (m, 1H), 7.31 (t, 1H), 7.08 (dd, 1H), 6.98 (dd, 1H), 6.92 (d, 1H), 3.83 (s, 2H), 3.77 (s, 2H), 2.35-2.30 (m, 2H), 2.05 (s, 6H), 1.96 (t, 2H), 1.88 (s, 2H), 1.60-1.54 (m, 2H). | 489.2 |
| SC_3332 | cis-8-Dimethylamino-3-[4-methyl-6-(3-oxo-piperazin-1-yl)-pyridin-3-yl]-8-phenyl-1,3-diazaspiro[4.5]decan-2-one | INT-976 | 4-(5-bromo-4-methyl-pyridin-2-yl)-piperazin-2-one | step 2 of SC_3097 | 1H-NMR (DMSO-d6, 400 MHz at 100° C.), δ (ppm) = 7.89 (s, 1H), 7.62 (bs, 1H), 7.35-7.22 (m, 5H), 6.73 (s, 1H), 6.62 (s, 1H), 3.96 (s, 2H), 3.68 (t, 2H, J = 5.2 Hz), 3.39 (s, 2H), 3.30 (bs, 2H), 2.35-2.30 (m, 2H), 2.15 (s, 3H), 2.03-1.86 (m, 10H), 1.56-1.51 (m, 2H). | 463.2 |
| SC_3333 | cis-8-Dimethylamino-3-(4-methyl-6-pyridin-2-yl-pyridin-3-yl)-8-phenyl-1,3-diazaspiro[4.5]decan-2-one | INT-976 | 5-bromo-2-chloro-4-methyl-pyridine (step 1), 2-tributylstannanyl-pyridine (step 2) | SC_3103 (for step 1), SC_3162 (for step 2) | 1H-NMR (DMSO-d6, 400 MHz at 100° C.), δ (ppm) = 8.64 (d, 1H, J = 4.0 Hz), 8.45 (s, 1H), 8.31 (d, 1H, J = 8.68 Hz), 8.22 (s, 1H), 7.88 (t, 1H, J = 7.04 Hz), 7.39-7.35 (m, 5H), 7.26-7.23 (m, 1H), 7.03 (s, 1H), 3.57 (s, 2H), 2.39-2.33 (m, 5H), 2.04 (s, 6H), 2.01-1.88 (m, 4H), 1.61-1.57 (m, 2H). | 442.3 |
| SC_3334 | cis-8-Dimethylamino-3-(4-methylsulfonyl-pyridin-3-yl)-8-phenyl-1,3-diazaspiro[4.5]decan-2-one | INT-976 | 3-bromo-4-methylsulfanyl-pyridine (step 1) | SC_3103 (for step 1), SC_3008 (for step 2) | 1HNMR at 100° C. (DMSO-d6, 400 MHz), δ (ppm) = 8.77-8.72 (m, 2H), 7.85-7.84 (m, 1H), 7.35-7.23 (m, 6H), 3.60 (s, 2H), 3.31 (s, 3H), 2.36 (bs, 2H), 2.03-1.82 (m, 10H), 1.60-1.58 (m, 2H). | 429.3 |
| SC_3335 | cis-3-(Benzothiazol-7-yl)-8-dimethylamino-8-phenyl-1,3-diazaspiro[4.5]decan-2-one | INT-976 | 7-bromo-benzothiazole | SC_3103 | | 407.1 |

-continued

| Example | Chemical name | Reactant I | Reactant II | in analogy to method | ¹H NMR data | m/z (M + H)⁺ |
|---|---|---|---|---|---|---|
| SC_3336 | cis-8-Dimethylamino-8-(4-fluorophenyl)-3-(4-methyl-2-morpholin-4-yl-pyrimidin-5-yl)-1,3-diazaspiro[4.5]decan-2-one | INT-1025 | 4-(5-bromo-4-methyl-pyrimidin-2-yl)morpholine | SC_3319 | 1H NMR (600 MHz, DMSO) δ 8.13 (s, 1H), 7.41-7.35 (m, 2H), 7.22-7.13 (m, 3H), 3.69-3.60 (m, 8H), 2.35-2.31 (m, 2H), 2.20 (s, 3H), 1.94 (s, 6H), 1.93-1.74 (m, 4H), 1.53-1.43 (m, 2H). | 469.3 |
| SC_3337 | cis-2-[8-Dimethylamino-3-[4-methyl-6-(trifluoromethyl)-pyridin-3-yl]-2-oxo-8-phenyl-1,3-diazaspiro[4.5]decan-1-yl]-N,N-dimethyl-acetamide | SC_3122 | 2-chloro-N,N-dimethyl-acetamide | INT-988 (step 1) | 1H NMR (600 MHz, DMSO) δ 8.59 (s, 1H), 7.82 (s, 1H), 7.37-7.32 (m, 4H), 7.25 (ddd, 1H), 4.00 (s, 2H), 3.80 (s, 2H), 3.07 (s, 3H), 2.87 (s, 3H), 2.71-2.64 (m, 2H), 2.55 (s, 3H), 2.34 (s, 3H), 2.03 (td, 2H), 1.98 (s, 6H), 1.67-1.58 (m, 2H), 1.49-1.40 (m, 2H). | 518.3 |
| SC_3338 | cis-8-Dimethylamino-3-[2-(2-methyl-1-oxo-2,3-dihydro-isoindol-4-yl)-pyrimidin-5-yl]-8-phenyl-1,3-diazaspiro[4.5]decan-2-one | INT-989 | 2-methyl-4-(4,4,5,5-tetramethyl-1,3,2-dioxaborolan-2-yl)isoindolin-1-one | SC_3208 | 1H NMR (600 MHz, DMSO) δ 9.57 (s, 1H), 9.08 (s, 2H), 8.52 (d, 1H), 8.43 (s, 1H), 7.77 (d, 1H), 7.72 (d, 2H), 7.63 (t, 1H), 7.59 (t, 2H), 7.55 (t, 1H), 4.86 (s, 2H), 3.59 (s, 2H), 3.13 (s, 3H), 2.72 (d, 2H), 2.61 (s, 6H). | 497.3 |
| SC_3339 | cis-2-[[5-(8-Dimethylamino-2-oxo-8-phenyl-1,3-diazaspiro[4.5]decan-3-yl)-2-methyl-pyrimidin-4-yl]amino]-acetonitrile | INT-976 | (5-bromo-2-methyl-pyrimidin-4-ylamino)-acetonitrile (step 1) | step 2 of SC_3242 (for step 1), SC_3016 (for step 2) | ¹HNMR at 100° C. (DMSO-d6, 400 MHz), δ (ppm) = 7.93 (s, 1H), 7.36-7.22 (m, 5H), 7.12 (s, 1H), 6.91 (bs, 2H), 6.58 (bs, 1H), 3.94 (d, 2H), 3.46 (s, 2H), 2.35-2.32 (m, 5H), 2.03-1.97 (m, 8H), 1.91-1.84 (m, 2H), 1.61-1.56 (m, 2H). | 438.4 |
| SC_3341 | cis-8-Dimethylamino-3-[4-(methylsulfonyl-methyl)-pyridin-3-yl]-8-phenyl-1,3-diazaspiro[4.5]decan-2-one | INT-976 | 3-bromo-4-methanesulfonylmethyl-pyridine | step 2 of SC_3097 | 1HNMR at 100° C. (DMSO-d6, 400 MHz), δ (ppm) = 8.53 (s, 1H), 8.43 (d, 1H, J = 4.88 Hz), 7.48 (d, 1H, J = 4.88 Hz), 7.36-7.23 (m, 5H), 7.15 (s, 1H), 4.55 (s, 2H), 3.64 (s, 2H), 2.95 (s, 3H), 2.38-2.33 (m, 2H), 2.04 (s, 6H), 1.99-1.83 (m, 4H), 1.62-1.57 (m, 2H). | 443.4 |
| SC_3342 | cis-8-Dimethylamino-3-[6-(4-methyl-3-oxo-piperazin-1-yl)-pyridin-3-yl]-8-phenyl-1,3-diazaspiro[4.5]decan-2-one | INT-976 | 4-(5-bromo-2-pyridyl)-1-methyl-piperazin-2-one | SC_3242 (step 2) | 1H NMR (600 MHz, CDCl3) δ 8.09 (d, 1H), 8.00 (dd, 1H), 7.45-7.39 (m, 2H), 7.37-7.28 (m, 3H), 6.61 (d, 1H), 5.71 (s, 1H), 4.04 (s, 2H), 3.87-3.82 (m, 2H), 3.51 (s, 2H), 3.45 (t, 2H), 3.03 (s, 3H), 2.32-2.02 (m, 10H), 2.02-1.94 (m, 2H), 1.64-1.53 (m, 2H). | 463.3 |
| SC_3343 | cis-8-Dimethylamino-3-(2,4-dimethyl-pyrimidin-5-yl)-8-phenyl-1,3-diazaspiro[4.5]decan-2-one | INT-976 | 5-bromo-2,4-dimethyl-pyrimidine | SC_3103 | 1H NMR (600 MHz, DMSO) δ 8.46 (s, 1H), 7.45-7.33 (m, 5H), 7.28-7.24 (m, 1H), 3.51 (s, 2H), 2.54 (s, 3H), 2.41-2.28 (m, 5H), 2.03-1.77 (m, 10H), 1.56-1.49 (m, 2H). | 380.3 |
| SC_3344 | cis-8-Dimethylamino-3-[2-(1-oxo-2,3-dihydro-isoindol-4-yl)-pyrimidin-5-yl]-8-phenyl-1,3-diazaspiro[4.5]decan-2-one; 2,2,2-trifluoro-acetic acid | INT-989 | 4-(4,4,5,5-tetramethyl-1,3,2-dioxaborolan-2-yl)isoindolin-1-one | SC_3208 | 1H NMR (600 MHz, DMSO) δ 9.06 (s, 2H), 8.67 (s, 1H), 8.52 (d, 1H), 8.39 (s, 1H), 7.75 (dd, 3H), 7.66-7.51 (m, 4H), 4.75 (s, 2H), 3.58 (s, 2H), 3.18 (s, 2H), 2.75 (d, 2H), 2.60 (s, 6H), 2.27 (t, 2H), 1.91 (d, 2H), 1.39 (t, 2H). | 483.3 |

-continued

| Example | Reactant I | Reactant II | Chemical name | in analogy to method | 1H NMR data | m/z (M + H)+ |
|---|---|---|---|---|---|---|
| SC_3345 | INT-976 | 2-[[5-bromo-3-(trifluoromethyl)-2-pyridyl]-methyl-amino]ethanol | cis-8-Dimethylamino-3-[6-[(2-hydroxy-ethyl)-methyl-amino]-5-(trifluoromethyl)-pyridin-3-yl]-8-phenyl-1,3-diazaspiro[4.5]decan-2-one | SC_3103 | 1H NMR (600 MHz, DMSO) δ 8.55-8.51 (m, 1H), 8.35 (d, 1H), 7.62 (s, 1H), 7.37 (td, 4H), 7.27 (td, 1H), 3.63 (s, 2H), 3.50 (td, 2H), 3.20 (t, 2H), 2.78 (s, 3H), 2.43-2.36 (m, 2H), 1.96 (s, 6H), 1.95-1.75 (m, 4H), 1.48 (t, 2H). | 492.3 |
| SC_3346 | INT-976 | 3,3,3-trifluoroprop-1-yne, 2-azido-5-bromo-pyrimidine | cis-8-Dimethylamino-3-[2-[4-[1,2,3]triazol-1-yl]-pyrimidin-5-yl]-1,3-diazaspiro[4.5]decan-2-one | SC_3313 | 1H NMR (600 MHz, DMSO) δ 9.56 (d, 1H), 9.16 (s, 2H), 7.99 (s, 1H), 7.42-7.35 (m, 4H), 7.31-7.25 (m, 1H), 3.75 (s, 2H), 2.49-2.34 (m, 2H), 2.05-1.75 (m, 10H), 1.60-1.47 (m, 2H). | 487.3 |
| SC_3347 | INT-976 | 3-methylbut-1-yne, 2-azido-5-bromo-pyrimidine | cis-8-Dimethylamino-3-[2-(4-isopropyl-1H-[1,2,3]triazol-1-yl)-pyrimidin-5-yl]-8-phenyl-1,3-diazaspiro[4.5]decan-2-one | SC_3313 | 1H NMR (600 MHz, DMSO) δ 9.10 (s, 2H), 8.50 (d, 1H), 7.91 (s, 1H), 7.42-7.35 (m, 5H), 7.28 (td, 1H), 3.73 (s, 2H), 3.08 (hept, 1H), 2.44 (s, 2H), 2.01-1.76 (m, 10H), 1.59-1.48 (m, 2H), 1.30 (d, 6H). | 461.3 |
| SC_3348 | INT-976 | 1,4-thiazinane 1,1-dioxo-[1,4]thiazinan-4-yl)-pyridin-3-yl]-8-phenyl-1,3-diazaspiro[4.5]decan-2-one (step 1) | cis-8-Dimethylamino-3-[6-(1,1-dioxo-[1,4]thiazinan-4-yl)-pyridin-3-yl]-8-phenyl-1,3-diazaspiro[4.5]decan-2-one | SC_3242 | 1H NMR (600 MHz, DMSO) δ 8.23 (d, 1H), 7.93 (dd, 1H), 7.41-7.33 (m, 5H), 7.27 (t, 1H), 6.98 (d, 1H), 3.97 (t, 4H), 3.53 (s, 2H), 3.04 (t, 4H), 2.43-2.28 (m, 2H), 1.96 (s, 6H), 1.92-1.72 (m, 4H), 1.51-1.40 (m, 2H). | 484.2 |
| SC_3349 | INT-976 | 5-bromo-2-chloropyridine-3-carbonitrile, morpholine | cis-5-(8-Dimethylamino-2-oxo-8-phenyl-1,3-diazaspiro[4.5]decan-3-yl)-2-morpholin-4-yl-nicotinonitrile | SC_3242 | 1H NMR (600 MHz, DMSO-d6) δ 8.66 (d, J = 2.9 Hz, 1H), 8.25 (d, J = 2.8 Hz, 1H), 7.60 (s, 1H), 7.41-7.33 (m, 4H), 7.30-7.24 (m, 1H), 3.74-3.69 (m, 4H), 3.60 (s, 2H), 2.48-2.29 (m, 2H), 1.96 (s, 6H), 1.94-1.68 (m, 4H), 1.52-1.41 (m, 2H). | 461.3 |
| SC_3350 | INT-976 | 5-bromo-1-methylsulfonyl-pyrrolo[2,3-b]pyridine | cis-8-Dimethylamino-3-(1-methylsulfonyl-1H-pyrrolo[2,3-b]pyridin-5-yl)-8-phenyl-1,3-diazaspiro[4.5]decan-2-one | SC_3103 | 1H NMR (600 MHz, DMSO) δ 8.64 (d, 1H), 8.28 (d, 1H), 7.65 (dd, 1H), 7.57 (s, 1H), 7.38 (dd, 4H), 7.28 (dt, 1H), 6.72 (dd, 1H), 3.68 (s, 2H), 3.65 (s, 3H), 2.48-2.29 (m, 2H), 1.98 (s, 10H), 1.53-1.44 (m, 2H). | 468.2 |
| SC_3351 | INT-976 | 4-bromo-1-(toluene-4-sulfonyl)-1H-indole (step 1) | cis-8-Dimethylamino-3-(1H-indol-4-yl)-8-phenyl-1,3-diazaspiro[4.5]decan-2-one | SC_3357 | 1H-NMR (DMSO-d6, 400 MHz at 100° C.), δ (ppm) = 10.77 (bs, 1H), 7.37 (bs, 4H), 7.24-7.18 (m, 3H), 7.02-6.94 (m, 2H), 6.81 (bs, 1H), 6.41 (s, 1H), 3.66 (s, 2H), 2.36-2.33 (m, 2H), 2.05-1.96 (m, 10H), 1.60-156 (m, 2H). | 389.3 |
| SC_3353 | INT-976 | 1-bromo-2-fluoro-4-(trifluoromethoxy)-benzene | cis-8-Dimethylamino-3-[2-fluoro-4-(trifluoromethyloxy)-phenyl]-8-phenyl-1,3-diazaspiro[4.5]decan-2-one | SC_3103 | 1H NMR (600 MHz, DMSO) δ 7.62 (t, 1H), 7.50-7.46 (m, 1H), 7.40 (dd, 1H), 7.38-7.31 (m, 4H), 7.25 (t, 1H), 7.21 (d, 1H), 3.57 (s, 2H), 2.38 (d, 2H), 1.97-1.88 (m, 8H), 1.84-1.79 (m, 2H), 1.53-1.46 (m, 2H). | 452.2 |
| SC_3355 | INT-976 | 4-bromo-1-methyl-pyrrolo[2,3-b]pyridine | cis-8-Dimethylamino-3-(1-methyl-1H-pyrrolo[2,3-b]pyridin-4-yl)-8-phenyl-1,3-diazaspiro[4.5]decan-2-one | SC_3103 | 1H NMR (600 MHz, DMSO) δ 8.04 (d, 1H), 7.70 (s, 1H), 7.47 (d, 1H), 7.41-7.33 (m, 4H), 7.31-7.24 (m, 2H), 6.65 (d, 1H), 3.91 (s, 3H), 3.74 (s, 3H), 2.44-2.25 (m, 2H), 2.08-1.74 (m, 10H), 1.52 (t, 2H). | 404.3 |

-continued

| Example | Chemical name | Reactant I | Reactant II | in analogy to method | ¹H NMR data | m/z (M + H)⁺ |
|---|---|---|---|---|---|---|
| SC_3356 | cis-3-(1-Acetyl-1H-indol-4-yl)-8-dimethylamino-8-phenyl-1,3-diazaspiro[4.5]decan-2-one | SC_3351 | acetyl chloride | SC_3379 | 1H-NMR (DMSO-d6, 400 MHz at 100° C.), δ (ppm) = 8.12 (d, 1H, J = 8.28 Hz), 7.68 (d, 1H, J = 3.64 Hz), 7.36-7.22 (m, 6H), 7.16 (d, 1H, J = 7.80 Hz), 7.01 (s, 1H), 6.69 (d, 1H, J = 3.8 Hz), 3.66 (s, 2H), 2.62 (s, 3H), 2.38-2.33 (m, 2H), 2.05-1.92 (m, 10H), 1.61-1.56 (m, 2H). | 431.2 |
| SC_3358 | cis-6-(8-Dimethylamino-2-oxo-8-phenyl-1,3-diazaspiro[4.5]decan-3-yl)-5-methyl-nicotinonitrile | INT-976 | 6-chloro-5-methyl-pyridine-3-carbonitrile | SC_3103 | 1H NMR (600 MHz, DMSO) δ 8.64 (s, 1H), 8.12 (s, 1H), 7.76 (s, 1H), 7.39-7.34 (m, 4H), 7.27 (s, 1H), 3.71 (s, 2H), 2.43-2.15 (m, 5H), 2.11-1.70 (m, 10H), 1.52 (s, 2H). | 390.2 |
| SC_3359 | cis-6-(8-Dimethylamino-2-oxo-8-phenyl-1,3-diazaspiro[4.5]decan-3-yl)-5-fluoro-nicotinonitrile | INT-976 | 6-chloro-5-fluoro-pyridine-3-carbonitrile | SC_3103 | 1H NMR (600 MHz, DMSO) δ 8.64 (d, 1H), 8.30 (dd, 1H), 7.95 (s, 1H), 7.40-7.31 (m, 4H), 7.29-7.23 (m, 1H), 3.72 (s, 2H), 2.36-2.33 (m, 2H), 1.96 (s, 6H), 1.94-1.79 (m, 4H), 1.52 (t, 2H). | 394.2 |
| SC_3361 | cis-6-(8-Dimethylamino-2-oxo-8-phenyl-1,3-diazaspiro[4.5]decan-3-yl)-5-methyl-pyridine-3-carboxylic acid amide | SC_3358 | | SC_3016 | 1H NMR (600 MHz, DMSO) δ 8.64 (d, 1H), 8.06-8.02 (m, 2H), 7.54 (s, 1H), 7.44 (s, 1H), 7.38-7.30 (m, 4H), 7.27-7.21 (m, 1H), 3.67 (s, 2H), 2.37-2.26 (m, 5H), 2.05-1.75 (m, 10H), 1.51 (t, 2H). | 408.2 |
| SC_3362 | cis-6-(8-Dimethylamino-2-oxo-8-phenyl-1,3-diazaspiro[4.5]decan-3-yl)-5-fluoro-pyridine-3-carboxylic acid amide | SC_3359 | | SC_3016 | 1H NMR (600 MHz, DMSO) δ 8.65-8.61 (m, 1H), 8.13 (s, 1H), 8.04 (dd, 1H), 7.76 (s, 1H), 7.59 (s, 1H), 7.39-7.30 (m, 4H), 7.28-7.21 (m, 1H), 3.70 (s, 2H), 2.41-2.23 (m, 2H), 1.96-1.76 (m, 10H), 1.50 (t, 2H). | 412.2 |
| SC_3363 | cis-8-Dimethylamino-3-[4-methyl-6-(trifluoromethyl)-pyridin-3-yl]-8-m-tolyl-1,3-diazaspiro[4.5]decan-2-one | INT-1038 | 5-bromo-4-methyl-2-(trifluoromethyl)pyridine | SC_3319 | 1H NMR (600 MHz, DMSO) δ 8.56 (s, 1H), 7.80 (s, 1H), 7.52 (s, 1H), 7.24 (t, 1H), 7.17-7.11 (m, 2H), 7.06 (d, 1H), 3.60 (s, 2H), 2.39-2.25 (m, 8H), 2.01-1.78 (m, 10H), 1.58-1.48 (m, 2H). | 447.2 |
| SC_3364 | cis-3-(8-Dimethylamino-2-oxo-8-phenyl-1,3-diazaspiro[4.5]decan-3-yl)-isonicotinonitrile | INT-976 | 3-bromopyridine-4-carbonitrile | SC_3242 | 1H NMR (600 MHz, DMSO) δ 8.79 (s, 1H), 8.50 (d, 1H), 7.84-7.80 (m, 1H), 7.37 (td, 4H), 7.26 (td, 1H), 3.79 (s, 2H), 2.43-2.36 (m, 2H), 1.97 (s, 7H), 1.96-1.91 (m, 2H), 1.88-1.81 (m, 2H), 1.61-1.45 (m, 2H). | 376.2 |
| SC_3365 | cis-8-Dimethylamino-3-[3-fluoro-5-(2-oxo-1,3-dihydro-indol-4-yl)-pyridin-2-yl]-8-phenyl-1,3-diazaspiro[4.5]decan-2-one | INT-1045 | 4-(4,4,5,5-tetramethyl-1,3,2-dioxaborolan-2-yl)indolin-2-one (step 2) | SC_3354 | 1H NMR (600 MHz, DMSO) δ 10.51 (s, 1H), 8.39 (d, 1H), 7.96 (dd, 1H), 7.41-7.32 (m, 4H), 7.28 (dt, 2H), 7.08 (d, 1H), 6.88 (d, 1H), 3.71 (s, 2H), 3.67 (s, 2H), 2.44-2.22 (m, 2H), 1.98-1.87 (m, 11H), 1.58-1.46 (m, 2H). | 500.2 |
| SC_3366 | cis-8-Dimethylamino-3-[4-methyl-6-(trifluoromethyl)-pyridin-3-yl]-8-[3-(trifluoromethyloxy)-phenyl]-1,3-diazaspiro[4.5]decan-2-one | INT-1039 | 5-bromo-4-methyl-2-(trifluoromethyl)pyridine | SC_3319 | 1H NMR (600 MHz, DMSO) δ 8.55 (s, 1H), 7.79 (s, 1H), 7.51 (t, 2H), 7.38 (dd, 1H), 7.26 (d, 2H), 3.62 (s, 2H), 2.40-2.34 (m, 2H), 2.31 (s, 3H), 2.01-1.77 (m, 10H), 1.58-1.49 (m, 2H). | 517.2 |

-continued

| Example | Chemical name | Reactant I | Reactant II | in analogy to method | 1H NMR data | m/z (M + H)+ |
|---|---|---|---|---|---|---|
| SC_3367 | cis-8-Dimethylamino-3-[4-methyl-6-(trifluoromethyl)-pyridin-3-yl]-8-[3-(trifluoromethyl)phenyl]-1,3-diazaspiro[4.5]decan-2-one | INT-1040 | 5-bromo-4-methyl-2-(trifluoromethyl)pyridine | SC_3319 | 1H NMR (600 MHz, DMSO) δ 8.55 (s, 1H), 7.79 (s, 1H), 7.69-7.56 (m, 5H), 7.52 (s, 1H), 3.61 (s, 2H), 2.44-2.36 (m, 2H), 2.31 (s, 3H), 2.02-1.80 (m, 10H), 1.60-1.47 (m, 2H). | 501.2 |
| SC_3368 | cis-8-Dimethylamino-8-(3-methoxyphenyl)-3-[4-methyl-6-(trifluoromethyl)-pyridin-3-yl]-1,3-diazaspiro[4.5]decan-2-one | INT-1041 | 5-bromo-4-methyl-2-(trifluoromethyl)pyridine | SC_3319 | 1H NMR (600 MHz, DMSO) δ 8.56 (s, 1H), 7.80 (s, 1H), 7.51 (s, 1H), 7.31-7.25 (m, 1H), 6.92 (dt, 1H), 6.87-6.82 (m, 2H), 3.75 (s, 3H), 3.61 (s, 2H), 2.35-2.30 (m, 5H), 1.98 (s, 7H), 1.96-1.90 (m, 2H), 1.88-1.80 (m, 2H), 1.60-1.49 (m, 2H). | 463.2 |
| SC_3369 | cis-8-(5-Chloro-thiophen-2-yl)-8-dimethylamino-3-[4-methyl-6-(trifluoromethyl)-pyridin-3-yl]-1,3-diazaspiro[4.5]decan-2-one | INT-1042 | 5-bromo-4-methyl-2-(trifluoromethyl)pyridine | SC_3319 | 1H NMR (600 MHz, DMSO) δ 8.56 (s, 1H), 7.79 (s, 1H), 7.39 (s, 1H), 7.04-7.00 (m, 1H), 6.80 (d, 1H), 3.64 (s, 2H), 2.31 (s, 3H), 2.22-2.15 (m, 2H), 2.04 (s, 6H), 1.95-1.87 (m, 2H), 1.83-1.77 (m, 2H), 1.63-1.57 (m, 2H). | 473.1 |
| SC_3370 | cis-8-Dimethylamino-8-(3-fluorophenyl)-3-[4-methyl-6-(trifluoromethyl)-pyridin-3-yl]-1,3-diazaspiro[4.5]decan-2-one | INT-1024 | 5-bromo-4-methyl-2-(trifluoromethyl)pyridine | SC_3319 | 1H NMR (600 MHz, DMSO) δ 8.56 (s, 1H), 7.80 (s, 1H), 7.51 (s, 1H), 7.41 (td, 1H), 7.21-7.12 (m, 2H), 7.12-7.06 (m, 1H), 3.61 (s, 2H), 2.38-2.30 (m, 5H), 1.97 (s, 6H), 1.96-1.90 (m, 2H), 1.90-1.73 (m, 2H), 1.61-1.45 (m, 2H). | 451.2 |
| SC_3371 | cis-8-Dimethylamino-3-(2-methylamino-pyrimidin-5-yl)-8-phenyl-1,3-diazaspiro[4.5]decan-2-one | INT-989 | methylamine | SC_3239 | 1H NMR (600 MHz, DMSO + TFA) δ 8.69 (s, 2H), 8.29 (s, 1H), 7.68 (d, 2H), 7.52 (dt, 3H), 2.90 (s, 3H), 2.68 (d, 2H), 2.59 (s, 6H), 2.24 (t, 2H), 1.86 (d, 2H), 1.39-1.31 (m, 2H) | 381.2 |
| SC_3372 | cis-8-(5-Chloro-thiophen-2-yl)-8-dimethylamino-3-(4-methyl-2-morpholin-4-yl-pyrimidin-5-yl)-1,3-diazaspiro[4.5]decan-2-one | INT-1042 | 4-(5-bromo-4-methyl-pyrimidin-2-yl)morpholine | SC_3242 | 1H NMR (600 MHz, DMSO) δ 8.15 (d, 1H), 7.15 (s, 1H), 7.05 (d, 1H), 6.82 (d, 1H), 3.70-3.61 (m, 8H), 3.44 (s, 2H), 2.31-2.12 (m, 5H), 2.06 (s, 6H), 1.93-1.85 (m, 2H), 1.82-1.69 (m, 2H), 1.64-1.49 (m, 2H). | 491.2 |
| SC_3373 | cis-N-[5-(8-Dimethylamino-2-oxo-8-phenyl-1,3-diazaspiro[4.5]decan-3-yl)-pyrimidin-2-yl]-N-methyl-cyclopropanecarboxylic acid amide | SC_3371 | Cyclopropancarbonyl chlorid | SC_3240 | 1H NMR (600 MHz, DMSO) δ 8.97 (s, 2H), 7.83-7.73 (m, 1H), 7.41-7.34 (m, 4H), 7.30-7.24 (m, 1H), 3.66 (s, 2H), 3.27 (s, 3H), 2.47-2.29 (m, 2H), 1.99-1.87 (m, 10H), 1.49 (t, 2H), 0.88-0.80 (m, 2H), 0.70 (dt, 2H). | 449.3 |
| SC_3374 | cis-N-[5-(8-Dimethylamino-2-oxo-8-phenyl-1,3-diazaspiro[4.5]decan-3-yl)-pyrimidin-2-yl]-N-2,5-trimethyl-2H-pyrazole-3-carboxylic acid amide | SC_3371 | 2,5-dimethylpyrazole-3-carbonyl chloride | SC_3240 | 1H NMR (600 MHz, DMSO) δ 8.83 (s, 2H), 7.77 (s, 1H), 7.41-7.32 (m, 4H), 7.27 (td, 1H), 5.48 (s, 1H), 3.80 (s, 3H), 3.61 (s, 2H), 3.40 (s, 3H), 2.46-2.31 (m, 2H), 1.96 (s, 3H), 1.96 (s, 6H), 1.94-1.74 (m, 5H), 1.52-1.42 (m, 2H). | 503.3 |
| SC_3375 | cis-3-[4,6-Bis(trifluoromethyl)-pyridin-3-yl]-8-dimethylamino-8-phenyl-1,3-diazaspiro[4.5]decan-2-one | INT-976 | 5-bromo-2,4-bis(trifluoromethyl)pyridine | SC_3103 | 1H NMR (600 MHz, DMSO) δ 8.98 (s, 1H), 8.20 (s, 1H), 7.79 (s, 1H), 7.40-7.32 (m, 4H), 7.26 (td, 1H), 3.62 (s, 2H), 2.44-2.24 (m, 2H), 1.98-1.91 (m, 8H), 1.86 (s, 2H), 1.53 (t, 2H). | 487.2 |

-continued

| Example | Reactant I | Reactant II | Chemical name | in analogy to method | 1H NMR data | m/z (M + H)+ |
|---|---|---|---|---|---|---|
| SC_3376 | INT-976 | 2-[(6-bromo-quinazolin-2-yl)-methyl-amino]-ethanol | cis-8-Dimethylamino-3-[2-[(2-hydroxy-ethyl)-methyl-amino]-quinazolin-6-yl]-8-phenyl-1,3-diazaspiro[4.5]decan-2-one | SC_3242 | 1HNMR at 100° C. (DMSO-d6, 400 MHz), δ (ppm) = 8.99 (s, 1H), 8.28 (d, 1H, J = 9.24 Hz), 7.63 (s, 1H), 7.43-7.26 (m, 6H), 7.13 (s, 1H), 4.31 (bs, 1H), 3.78-3.76 (m, 2H), 3.66 (bs, 4H), 3.24 (s, 3H), 2.43-2.38 (m, 2H), 2.05-1.90 (m, 10H), 1.56-1.54 (m, 2H), | 475.1 |
| SC_3377 | INT-976 | 6-bromo-2-morpholin-4-yl-quinazoline | cis-8-Dimethylamino-3-(2-morpholin-4-yl-quinazolin-6-yl)-8-phenyl-1,3-diazaspiro[4.5]decan-2-one | SC_3242 | 1HNMR at 100° C. (DMSO-d6, 400 MHz), δ (ppm) = 9.05 (s, 1H), 8.34 (d, 1H), 7.68 (s, 1H), 7.48 (d, 1H, J = 9.4 Hz), 7.38-7.27 (m, 5H), 7.18 (s, 1H), 3.81-3.67 (m, 10H), 2.40-2.38 (m, 2H), 2.05-1.90 (m, 10H), 1.57-1.54 (m, 2H). | 487.2 |
| SC_3378 | INT-1047 | 2-trifluoromethyl-5-bromopyrimidine | cis-8-[Methyl-(oxetan-3-yl-methyl)-amino]-8-phenyl-3-[2-(trifluoromethyl)-pyrimidin-5-yl]-1,3-diazaspiro[4.5]decan-2-one | SC_3103 | 1H NMR (DMSO-d6): δ 9.21-9.15 (s, 2H), 8.19-8.18 (broad s, 1H), 7.41-7.34 (m, 4H), 7.27-7.25 (m, 1H), 4.58-4.56 (m, 2H), 4.18 (s, 1H), 3.69 (s, 2H), 3.05-2.99 (m, 1H), 2.41-2.36 (m, 4H), 1.91 (m, 7H), 1.47 (s, 2H). | 476.2 |
| SC_3380 | INT-976 | 6-bromo-quinazoline | cis-8-Dimethylamino-8-phenyl-3-quinazolin-6-yl-1,3-diazaspiro[4.5]decan-2-one | SC_3103 | 1HNMR at 100° C. (DMSO-d6, 400 MHz), δ (ppm) = 9.35 (s, 1H), 9.10 (s, 1H), 8.65 (d, 1H, J = 9.04) 7.91-7.89 (m, 2H), 7.39-7.27 (m, 5H), 3.75 (s, 2H), 2.42-2.32 (m, 2H), 2.05 (s, 6H), 2.00-1.92 (m, 4H), 1.56 (bs, 2H). | 402.2 |
| SC_3381 | INT-976 | 5-bromo-2-chloro-pyridine-4-carbonitrile (step 1), 4-(4,4,5,5-tetramethyl-1,3,2-dioxaborolan-2-yl)indolin-2-one (step 2) | cis-5-[8-Dimethylamino-2-oxo-8-phenyl-1,3-diazaspiro[4.5]decan-3-yl]-2-(2-oxo-1,3-dihydro-indol-4-yl)-isonicotinonitrile | SC_3103 (for step 1), SC_3129 (for step 2) | 1H NMR (600 MHz, DMSO) δ 8.88 (s, 1H), 8.24 (s, 1H), 7.85 (s, 1H), 7.52-7.46 (m, 1H), 7.41-7.29 (m, 6H), 7.27 (td, 1H), 6.92 (d, 1H), 3.84 (s, 2H), 3.78 (s, 2H), 2.48-2.30 (m, 2H), 1.99-1.93 (m, 8H), 1.92-1.74 (m, 2H), 1.58-1.54 (m, 2H). | 507.3 |
| SC_3382 | SC_3371 | tetrahydropyran-4-carbonyl chloride | cis-N-[5-(8-Dimethylamino-2-oxo-8-phenyl-1,3-diazaspiro[4.5]decan-3-yl)-pyrimidin-2-yl]-N-methyl-tetrahydro-pyran-4-carboxylic acid amide | SC_3240 | 1H NMR (600 MHz, DMSO) δ 8.97 (s, 2H), 7.80 (s, 1H), 7.42-7.34 (m, 4H), 7.31-7.25 (m, 1H), 3.79 (ddd, 2H), 3.67 (s, 2H), 3.25 (s, 2H), 3.17 (td, 2H), 3.04-2.96 (m, 1H), 2.49-2.34 (m, 2H), 1.97 (s, 6H), 1.95-1.74 (m, 4H), 1.68-1.53 (m, 4H), 1.54-1.48 (m, 2H). | 493.3 |
| SC_3383 | SC_3371 | pivaloyl chloride | cis-N-[5-(8-Dimethylamino-2-oxo-8-phenyl-1,3-diazaspiro[4.5]decan-3-yl)-pyrimidin-2-yl]-N,2,2-trimethyl-propionamide | SC_3240 | 1H NMR (600 MHz, DMSO) δ 8.98 (s, 2H), 7.42-7.34 (m, 4H), 7.30-7.26 (m, 1H), 3.69 (s, 2H), 3.14 (s, 3H), 2.46-2.41 (m, 2H), 1.99-1.87 (m, 10H), 1.54-1.45 (m, 2H), 0.97 (s, 9H). | 465.3 |
| SC_3384 | INT-989 | 1-methyl-4-(4,4,5,5-tetramethyl-1,3,2-dioxaborolan-2-yl)indolin-2-one | cis-8-Dimethylamino-3-[2-(1-methyl-2-oxo-1,3-dihydro-indol-4-yl)-pyrimidin-5-yl]-8-phenyl-1,3-diazaspiro[4.5]decan-2-one | SC_3208 | 1H NMR (600 MHz, CDCl3) δ 9.05 (s, 2H), 8.08 (d, 1H), 7.47-7.39 (m, 3H), 7.38-7.31 (m, 3H), 6.91 (d, 1H), 5.46 (s, 1H), 4.04 (s, 2H), 3.64 (s, 2H), 3.27 (s, 3H), 2.35-2.14 (m, 4H), 2.10 (s, 6H), 2.08-2.01 (m, 3H), 1.73-1.64 (m, 2H), 1.28 (s, 6H). | 497.3 |

-continued

| Example | Chemical name | Reactant I | Reactant II | in analogy to method | $^1$H NMR data | m/z (M + H)$^+$ |
|---|---|---|---|---|---|---|
| SC_3385 | cis-8-Dimethylamino-3-(2-morpholin-4-yl-1H-benzoimidazol-5-yl)-8-phenyl-1,3-diazaspiro[4.5]decan-2-one | INT-976 | 6-bromo-1-(tert-butylsilanyl-methoxymethyl)-2-morpholin-4-yl-1H-benzoimidazole (step 1) | SC_3242 (for step 1), step 2 of SC_3352 (for step 2) | 1HNMR at 100° C. (DMSO-d6, 400 MHz), δ (ppm) = 10.94 (bs, 1H), 7.50 (bs, 1H), 7.39-7.27 (m, 5H), 7.06 (m, 2 H), 6.84 (bs, 1H), 3.72 (t, 4H, 4.56 Hz), 3.55 (s, 2H), 3.45 (t, 4H, 4.56 Hz), 2.372.24 (m, 2H), 1.95-1.81 (m, 10H), 1.52-1.50 (m, 2H) | 475.2 |
| SC_3386 | cis-8-Dimethylamino-8-(3-fluoro-5-methyl-phenyl)-3-[4-methyl-6-(trifluoromethyl)-pyridin-3-yl]-1,3-diazaspiro[4.5]decan-2-one | INT-1043 | 5-bromo-4-methyl-2-(trifluoromethyl)pyridine | SC_3319 | 1H NMR (600 MHz, DMSO) δ 8.57 (s, 1H), 7.80 (s, 1H), 7.51 (s, 1H), 6.99 (s, 1H), 6.96-6.89 (m, 2H), 3.61 (s, 2H), 2.34 (s, 3H), 2.32 (s, 3H), 2.07 (s, 1H), 1.97 (s, 6H), 1.96-1.89 (m, 2H), 1.88-1.78 (m, 2H), 1.54 (d, 2H). | 465.2 |
| SC_3387 | cis-8-Dimethylamino-3-[6-(2-oxo-1,3-dihydro-indol-4-yl)-pyridin-3-yl]-8-phenyl-1,3-diazaspiro[4.5]decan-2-one | INT-1048 | 4-(4,4,5,5-tetramethyl-1,3,2-dioxaborolan-2-yl)indolin-2-one | SC_3129 | 1H NMR (600 MHz, DMSO) δ 8.83 (d, 1H), 8.11 (dd, 1H), 7.77 (d, 1H), 7.64 (s, 1H), 7.43-7.34 (m, 5H), 7.31-7.24 (m, 2H), 6.84 (d, 1H), 3.73 (s, 2H), 3.68 (s, 2H), 2.45-2.31 (m, 2H), 1.99-1.79 (m, 10H), 1.51 (t, 2H). | 482.3 |
| SC_3389 | cis-3-[6-(Azetidin-1-yl)-5-(trifluoromethyl)pyridin-3-yl]-8-dimethylamino-8-phenyl-1,3-diazaspiro[4.5]decan-2-one | INT-976 | 5-bromo-2-chloro-3-(trifluoromethyl)pyridine (step 1), azetidine (step 2) | SC_3103 (for step 1), SC_3120 (for step 2, 160° C.) | 1H NMR (600 MHz, DMSO) δ 8.40 (d, 1H), 8.21 (d, 1H), 7.47 (s, 1H), 7.41-7.33 (m, 4H), 7.30-7.24 (m, 1H), 4.03 (t, 4H), 3.58 (s, 2H), 2.47-2.29 (m, 2H), 2.25 (p, 2H), 1.96 (s, 6H), 1.89 (s, 4H), 1.47 (t, 2H). | 453.2 |
| SC_3390 | cis-3-[1-(Cyclopropyl-methyl)-8-dimethylamino-2-oxo-8-phenyl-1,3-diazaspiro[4.5]decan-3-yl]-isonicotinonitrile | SC_3364 | bromomethylcyclopropane | INT-952 | 1H NMR (600 MHz, DMSO) δ 8.82 (s, 1H), 8.51 (dd, 1H), 7.81 (d, 1H), 7.40-7.33 (m, 4H), 7.29-7.23 (m, 1H), 3.93 (s, 2H), 3.10 (d, 2H), 2.76-2.70 (m, 2H), 2.29 (ddd, 2H), 2.02 (s, 6H), 1.58 (d, 2H), 1.52-1.44 (m, 2H), 1.01 (ddt, 2H), 0.55-0.49 (m, 2H), 0.37-0.31 (m, 2H). | 430.3 |
| SC_3391 | cis-3-[3,5-Bis(trifluoromethyl)-pyridin-2-yl]-8-dimethylamino-8-phenyl-1,3-diazaspiro[4.5]decan-2-one | INT-976 | 2-chloro-3,5-bis(trifluoromethyl)pyridine | SC_3103 | 1H NMR (600 MHz, DMSO) δ 9.04 (d, 1H), 8.58 (d, 1H), 7.96 (s, 1H), 7.41-7.32 (m, 4H), 7.29-7.23 (m, 1H), 3.75 (s, 2H), 2.41-2.25 (m, 2H), 1.98-1.89 (m, 10H), 1.52 (t, 2H). | 487.2 |
| SC_3392 | cis-8-Dimethylamino-3-(5-fluoro-6-morpholin-4-yl-pyridin-3-yl)-8-phenyl-1,3-diazaspiro[4.5]decan-2-one | INT-976 | 4-(5-bromo-3-fluoro-2-pyridyl)morpholine | SC_3103 | 1H NMR (600 MHz, CDCl3) δ 8.13 (dd, 1H), 7.76 (d, 1H), 7.42 (t, 2H), 7.33 (dd, 3H), 5.84 (s, 1H), 3.84 (t, 4H), 3.52 (s, 2H), 3.37 (t, 4H), 2.29-2.12 (m, 4H), 2.08 (s, 6H), 2.01-1.94 (m, 2H), 1.60 (t, 2H). | 454.3 |
| SC_3393 | cis-8-(3-Chlorophenyl)-8-dimethylamino-3-[4-methyl-6-(trifluoromethyl)-pyridin-3-yl]-1,3-diazaspiro[4.5]decan-2-one | INT-1044 | 5-bromo-4-methyl-2-(trifluoromethyl)pyridine | SC_3319 | 1H NMR (600 MHz, DMSO) δ 8.57 (s, 1H), 7.80 (s, 1H), 7.55-7.49 (m, 1H), 7.43-7.37 (m, 1H), 7.38-7.29 (m, 3H), 3.61 (s, 2H), 2.40-2.24 (m, 5H), 1.99-1.90 (m, 8H), 1.90-1.76 (m, 2H), 1.60-1.47 (m, 2H). | 467.2 |

-continued

| Example | Chemical name | Reactant I | Reactant II | in analogy to method | ¹H NMR data | m/z (M + H)⁺ |
|---|---|---|---|---|---|---|
| SC_3394 | cis-8-Dimethylamino-3-[5-(2-oxo-1,3-dihydro-indol-4-yl)-pyridin-2-yl]-8-phenyl-1,3-diazaspiro[4.5]decan-2-one | INT-1049 | 4-(4,4,5,5-tetramethyl-1,3,2-dioxaborolan-2-yl)indolin-2-one | SC_3354 | 1H NMR (600 MHz, DMSO) δ 8.41 (d, 1H), 8.26 (d, 1H), 7.92 (dd, 1H), 7.75 (s, 1H), 7.41-7.32 (m, 5H), 7.30-7.23 (m, 2H), 7.01 (d, 1H), 6.83 (d, 1H), 3.75 (s, 2H), 3.61 (s, 2H), 2.46-2.30 (m, 2H), 1.96 (s, 6H), 1.94-1.88 (m, 2H), 1.86-1.82 (m, 2H), 1.48 (t, 2H). | 482.3 |
| SC_3395 | cis-8-Dimethylamino-8-phenyl-3-[5-(trifluoromethyl)-[1,3,4]thiadiazol-2-yl]-1,3-diazaspiro[4.5]decan-2-one | INT-976 | 2-bromo-5-(trifluoromethyl)-1,3,4-thiadiazole | SC_3103 | 1H NMR (600 MHz, DMSO) δ 8.69 (s, 1H), 7.42-7.34 (m, 4H), 7.28 (t, 1H), 3.89 (s, 2H), 2.45-2.31 (m, 2H), 2.07-1.88 (m, 8H), 1.88-1.84 (m, 2H), 1.60-1.53 (m, 2H). | 426.2 |
| SC_3397 | cis-8-Dimethylamino-3-[2-[(2-hydroxy-ethyl)-methyl-amino]-1H-benzoimidazol-5-yl]-8-phenyl-1,3-diazaspiro[4.5]decan-2-one | INT-976 | 2-{[6-bromo-1-(2-trimethylsilanyl-ethoxymethyl)-1H-benzoimidazol-2-yl]-methyl-amino}-ethanol (step 1) | SC_3242 (for step 1), step 2 of SC_3352 (for step 2) | 1HNMR (DMSO-d6, 400 MHz at 100° C.), δ (ppm) = 10.62 (bs, 1H), 7.48-7.24 (m, 6H), 7.01-6.91 (m, 2H), 6.76 (s, 1H), 4.58 (bs, 1H), 3.66 (t, 2H, J = 5.62 Hz), 3.54-3.50 (m, 4H), 3.09 (s, 3H), 2.37-2.32 (m, 2H), 2.04 (s, 6H), 1.96-1.91 (m, 4H), 1.52-1.40 (m, 2H). | 463.3 |
| SC_3398 | cis-8-Dimethylamino-3-(5-methyl-6-morpholin-4-yl-pyridin-3-yl)-8-phenyl-1,3-diazaspiro[4.5]decan-2-one | INT-976 | 4-(5-bromo-3-methyl-2-pyridyl)morpholine | SC_3103 | 1H NMR (600 MHz, DMSO) δ 8.23 (s, 1H), 7.83 (s, 1H), 7.46-7.33 (m, 5H), 7.30-7.24 (m, 1H), 3.71 (t, 4H), 3.55 (s, 2H), 2.93 (t, 4H), 2.41-2.37 (m, 2H), 1.96 (s, 6H), 1.91-1.82 (m, 4H), 1.49-1.44 (m, 2H). | 450.3 |
| SC_3399 | cis-1-(Cyclopropyl-methyl)-8-dimethylamino-8-(3-fluorophenyl)-3-(5-methylsulfonyl-pyridin-2-yl)-1,3-diazaspiro[4.5]decan-2-one | SC_3409 | bromomethylcyclopropane | SC_3105 | 1HNMR (DMSO-d6, 400 MHz), δ (ppm) = 8.68-8.68 (d, 1H, J = 2.32 Hz), 8.42-8.40 (d, 1H, J = 9.04 Hz), 8.18-8.15 (m, 1H), 7.44-7.38 (m, 1H), 7.20-7.08 (m, 3H), 3.90 (s, 2H), 3.22 (s, 3H), 3.11-3.10 (d, 2H, J = 6.68 Hz), 2.71-2.68 (d, 2H, J = 13.6 Hz), 2.27-2.21 (m, 2H), 2.00 (s, 6H), 1.53-1.44 (m, 4H), 1.02-0.99 (m, 1H), 0.54-0.50 (m, 2H), 0.36-0.35 (m, 2H). | 501.4 |
| SC_3400 | cis-1-(Cyclopropyl-methyl)-8-(3-fluorophenyl)-8-methylamino-3-(5-methylsulfonyl-pyridin-2-yl)-1,3-diazaspiro[4.5]decan-2-one | SC_3399 | | SC_3105 | 1HNMR (DMSO-d6, 400 MHz), δ (ppm) = 8.72-8.71 (d, 1H, J = 2.28 Hz), 8.42-8.40 (d, 1H, J = 9.04 Hz), 8.18-8.15 (m, 1H), 7.40-7.31 (m, 3H), 7.05-7.01 (m, 1H), 3.93 (s, 2H), 3.23 (s, 3H), 3.14-3.13 (d, 2H, J = 6.76 Hz), 2.42 (bs, 1H), 2.28-2.23 (m, 2H), 1.96-1.88 (m, 5H), 1.79-1.73 (m, 2H), 1.44-1.41 (d, 2H, J = 12.2 Hz), 1.06-1.02 (m, 1H), 0.52-0.47 (m, 2H), 0.36-0.33 (m, 2H). | 487.2 |
| SC_3401 | cis-1-(Cyclobutyl-methyl)-8-(3-fluorophenyl)-8-methylamino-3-[2-(trifluoromethyl)-pyrimidin-5-yl]-1,3-diazaspiro[4.5]decan-2-one | SC_3404 | bromomethylcyclobutane (step 1) | SC_3105 (for step 1), SC_3099 (for step 2) | 1HNMR at 100° C. (DMSO-d6, 400 MHz), δ (ppm) = 9.23 (s, 2H), 7.38-7.26 (m, 3H), 7.00 (t, 1H, J = 8.1 Hz), 3.86 (s, 2H), 3.30-3.28 (d, 2H, J = 7.24 Hz), 2.68-2.65 (m, 1H), 2.27-2.16 (m, 3H), 2.06-1.78 (m, 13H), 1.46-1.43 (m, 2H). | 492.1 |

-continued

| Example | Chemical name | Reactant I | Reactant II | in analogy to method | ¹H NMR data | m/z (M + H)⁺ |
|---|---|---|---|---|---|---|
| SC_3402 | cis-1-(Cyclopropyl-methyl)-8-dimethylamino-8-(3-fluorophenyl)-3-[2-(trifluoromethyl)-pyrimidin-5-yl]-1,3-diazaspiro[4.5]decan-2-one | SC_3404 | bromomethylcyclopropane | SC_3105 | 1HNMR (DMSO-d6, 400 MHz), δ (ppm) = 9.21 (s, 2H), 7.45-7.39 (m, 1H), 7.22-7.18 (m, 2H), 7.14-7.09 (m, 1H), 3.84 (s, 2H), 3.09 (d, 2H, J = 6.4 Hz), 2.70 (d, 2H, J = 9.6 Hz), 2.32-2.21 (m, 2H), 2.01 (s, 6H), 1.59-1.46 (m, 4H), 1.01-1.00 (m, 1H), 0.54-0.49 (m, 2H), 0.35-0.33 (m, 2H). | 492.0 |
| SC_3403 | cis-1-(Cyclopropyl-methyl)-8-(3-fluorophenyl)-8-methylamino-3-[2-(trifluoromethyl)-pyrimidin-5-yl]-1,3-diazaspiro[4.5]decan-2-one | SC_3402 | | SC_3099 | 1HNMR (DMSO-d6, 400 MHz), δ (ppm) = 9.25 (s, 2H), 7.41-7.30 (m, 3H), 7.04 (t, 1H, J = 6.8 Hz), 3.89 (s, 2H), 3.12 (d, 2H, J = 6.8 Hz), 2.41 (bs, 1H), 2.27-2.22 (m, 2H), 1.93-1.78 (m, 7H), 1.46-1.43 (m, 2H), 1.08-1.03 (m, 1H), 0.51-0.47 (m, 2H), 0.33-0.29 (m, 2H). | 478.4 |
| SC_3404 | cis-8-Dimethylamino-8-(3-fluorophenyl)-3-[2-(trifluoromethyl)-pyrimidin-5-yl]-1,3-diazaspiro[4.5]decan-2-one | INT-1024 | 2-trifluoromethyl-5-bromopyrimidine | SC_3242 | 1HNMR at 100° C. (DMSO-d6, 400 MHz), δ (ppm) = 9.15 (s, 2H), 7.75 (s, 1H), 7.44-7.38 (m, 1H), 7.21-7.04 (m, 3H), 3.73 (s, 2H), 2.38-2.37 (m, 2H), 2.05 (s, 6H), 2.01-1.85 (m, 4H), 1.57-1.53 (m, 2H). | 437.9 |
| SC_3405 | cis-1-(Cyclopropyl-methyl)-8-dimethylamino-8-(3-fluorophenyl)-3-[2-methyl-5-(trifluoromethyl)-2H-pyrazol-3-yl]-1,3-diazaspiro[4.5]decan-2-one | SC_3319 | bromomethylcyclopropane | SC_3105 | 1HNMR at 100° C. (DMSO-d6, 400 MHz), δ (ppm) 7.39-7.36 (m, 1H), 7.19-7.05 (m, 3H), 6.56 (s, 1H), 3.78-3.67 (m, 5H), 3.10-3.08 (d, 2H, J = 6.12 Hz), 2.64-2.60 (d, 2H, J = 13.32 Hz), 2.37-2.26 (m, 2H), 2.09 (s, 6H), 1.61-1.49 (m, 4H), 1.10-1.02 (m, 1H), 0.54-0.52 (m, 2H), 0.36-0.33 (m, 2H). | 494.3 |
| SC_3406 | cis-1-(Cyclopropyl-methyl)-8-(3-fluorophenyl)-8-methylamino-3-[2-methyl-5-(trifluoromethyl)-2H-pyrazol-3-yl]-1,3-diazaspiro[4.5]decan-2-one | SC_3405 | | SC_3099 | 1HNMR at 100° C. (DMSO-d6, 400 MHz), δ (ppm) = 7.39-7.24 (m, 3H), 6.99-6.96 (m, 1H), 6.58 (s, 1H), 3.78-3.71 (m, 5H), 3.11-3.10 (d, 2H, J = 5.40 Hz), 2.30-2.23 (m, 2H), 1.99-1.92 (m, 5H), 1.79-1.72 (m, 2H), 1.58-1.56 (m, 2H), 1.10-1.00 (m, 1H), 0.54-0.52 (m, 2H), 0.36-0.33 (m, 2H). | 480.0 |
| SC_3407 | cis-8-Methylamino-3-(4-methyl-2-morpholin-4-yl-pyrimidin-5-yl)-8-phenyl-1,3-diazaspiro[4.5]decan-2-one | SC_3148 | | SC_3099 | | 437.3 |
| SC_3408 | cis-3-[5-(Azetidin-1-yl)-3-methyl-pyridin-2-yl]-8-dimethylamino-8-(3-fluorophenyl)-1,3-diazaspiro[4.5]decan-2-one | INT-1024 | 5-(azetidin-1-yl)-2-chloro-3-methyl-pyridine | SC_3103 | 1H NMR (600 MHz, DMSO) δ 7.44-7.36 (m, 2H), 7.20-7.05 (m, 4H), 6.69 (d, 1H), 3.82 (t, 4H), 3.51 (s, 2H), 2.36-2.26 (m, 4H), 2.15 (s, 3H), 1.96 (s, 6H), 1.94-1.76 (m, 4H), 1.49 (t, 2H). | 438.3 |
| SC_3409 | cis-8-Dimethylamino-8-(3-fluorophenyl)-3-(5-methylsulfonyl-pyridin-2-yl)-1,3-diazaspiro[4.5]decan-2-one | INT-1024 | 2-bromo-5-methylsulfonyl-pyridine | SC_3103 | 1H NMR (600 MHz, DMSO) δ 8.67 (dd, 1H), 8.39 (dd, 1H), 8.14 (dd, 1H), 8.04 (s, 1H), 7.42 (td, 1H), 7.19 (d, 1H), 7.15 (dt, 1H), 7.11 (td, 1H), 3.78 (s, 2H), 3.21 (s, 3H), 2.41-2.37 (m, 2H), 1.97 (s, 6H), 1.94-1.75 (m, 4H), 1.54-1.45 (m, 2H). | 447.2 |

-continued

| Example | Chemical name | Reactant I | Reactant II | in analogy to method | ¹H NMR data | m/z (M + H)⁺ |
|---|---|---|---|---|---|---|
| SC_3410 | cis-3-(6-(azetidin-1-yl)-4-fluoropyridin-3-yl)-8-(dimethylamino)-8-phenyl-1,3-diazaspiro[4.5]decan-2-one | INT-976 | 2-(azetidin-1-yl)-5-bromo-4-fluoropyridine | SC_3103 | | |
| SC_3411 | cis-3-(6-(azetidin-1-yl)pyridin-3-yl)-8-(dimethylamino)-1,3-diazaspiro[4.5]decan-2-one | INT-1024 | 2-(azetidin-1-yl)-5-bromopyridine | SC_3103 | | |
| SC_3412 | cis-3-(1-(cyclopropanecarbonyl)-3-(trifluoromethyl)-1H-pyrazol-5-yl)-8-(dimethylamino)-8-(3-fluorophenyl)-1,3-diazaspiro[4.5]decan-2-one | INT-1024 | (5-bromo-3-(trifluoromethyl)-1H-pyrazol-1-yl)(cyclopropyl)methanone | SC_3103 | | |
| SC_3413 | cis-8-(dimethylamino)-8-(3-fluorophenyl)-3-(1-(2-hydroxyethyl)-3-(trifluoromethyl)-1H-pyrazol-5-yl)-1,3-diazaspiro[4.5]decan-2-one | INT-1024 | 2-(5-bromo-3-(trifluoromethyl)-1H-pyrazol-1-yl)ethanol | SC_3242 | | |
| SC_3414 | cis-3-(1-(cyclopropylmethyl)-3-(trifluoromethyl)-1H-pyrazol-5-yl)-8-(dimethylamino)-8-(3-fluorophenyl)-1,3-diazaspiro[4.5]decan-2-one | INT-1024 | 5-bromo-1-(cyclopropylmethyl)-3-(trifluoromethyl)-1H-pyrazole | SC_3242 | | 480.2 |
| SC_3415 | cis-8-(dimethylamino)-8-(3-fluorophenyl)-3-(1-(methylsulfonyl)-3-(trifluoromethyl)-1H-pyrazol-5-yl)-1,3-diazaspiro[4.5]decan-2-one | INT-1024 | 5-bromo-1-(methylsulfonyl)-3-(trifluoromethyl)-1H-pyrazole | SC_3242 | | |
| SC_3416 | cis-1-(cyclopropylmethyl)-8-(dimethylamino)-8-(3-fluorophenyl)-3-(1-(methylsulfonyl)-3-(trifluoromethyl)-1H-pyrazol-5-yl)-1,3-diazaspiro[4.5]decan-2-one | SC_3415 | bromomethylcyclopropane | SC_3105 | | |
| SC_3417 | cis-2-(5-(8-(dimethylamino)-8-(3-fluorophenyl)-2-oxo-1,3-diazaspiro[4.5]decan-3-yl)-3-(trifluoromethyl)-1H-pyrazol-1-yl)-N,N-dimethylacetamide | INT-1024 | 2-(5-bromo-3-(trifluoromethyl)-1H-pyrazol-1-yl)-N,N-dimethylacetamide | SC_3242 | | |
| SC_3418 | cis-2-(5-(1-(cyclopropylmethyl)-8-(dimethylamino)-8-(3-fluorophenyl)-2-oxo-1,3-diazaspiro[4.5]decan-3-yl)-3-(trifluoromethyl)-1H-pyrazol-1-yl)-N,N-dimethylacetamide | SC_3417 | bromomethylcyclopropane | SC_3105 | | |
| SC_3419 | cis-8-(dimethylamino)-3-(1-methyl-1H-pyrrolo[2,3-b]pyridin-5-yl)-8-phenyl-1,3-diazaspiro[4.5]decan-2-one | INT-976 | 5-bromo-1-methyl-1H-pyrrolo[2,3-b]pyridine | SC_3103 | | 404.3 |

-continued

| Example | Chemical name | Reactant I | Reactant II | in analogy to method | ¹H NMR data | m/z (M + H)⁺ |
|---|---|---|---|---|---|---|
| SC_3420 | cis-8-(dimethylamino)-3-(3-fluoro-1H-pyrrolo[2,3-b]pyridin-5-yl)-8-phenyl-1,3-diazaspiro[4.5]decan-2-one | INT-976 | 5-bromo-3-fluoro-1-((2-(trimethylsilyl)ethoxy)methyl)-1H-pyrrolo[2,3-b]pyridine (step 1) | SC_3352 | | 408.2 |
| SC_3421 | cis-8-(dimethylamino)-8-phenyl-3-(1H-pyrrolo[2,3-c]pyridin-4-yl)-1,3-diazaspiro[4.5]decan-2-one | INT-976 | 4-bromo-1-((2-(trimethylsilyl)ethoxy)methyl)-1H-pyrrolo[2,3-c]pyridine | SC_3352 | | 390.2 |
| SC_3422 | cis-8-(dimethylamino)-8-phenyl-3-(2-(pyridazin-4-yl)pyrimidin-5-yl)-1,3-diazaspiro[4.5]decan-2-one | INT-989 | 4-(4,4,5,5-tetramethyl-1,3,2-dioxaborolan-2-yl)pyridazine | SC_3354 | | 430.2 |
| SC_3423 | cis-8-(dimethylamino)-3-(2-(2-oxo-1,2-dihydropyridin-4-yl)pyrimidin-5-yl)-8-phenyl-1,3-diazaspiro[4.5]decan-2-one | INT-989 | (2-oxo-1,2-dihydropyridin-4-yl)boronic acid | SC_3354 | | 445.2 |
| SC_3424 | cis-8-(dimethylamino)-8-(3-fluorophenyl)-3-(1-methyl-3-(thiophen-2-yl)-1H-pyrazol-5-yl)-1,3-diazaspiro[4.5]decan-2-one | INT-1024 | 3,5-dibromo-1-methyl-1H-pyrazole (step 1), thiophen-2-ylboronic acid (step 2) | SC_3103 (for step 1), SC_3354 (for step 2) | | |
| SC_3425 | cis-8-(dimethylamino)-8-(3-fluorophenyl)-3-(1-methyl-3-morpholino-1H-pyrazol-5-yl)-1,3-diazaspiro[4.5]decan-2-one | INT-1024 | 3,5-dibromo-1-methyl-1H-pyrazole (step 1), morpholine (step 2) | SC_3103 (for step 1), SC_3103 (for step 2) | | |
| SC_3426 | cis-8-(dimethylamino)-8-phenyl-1-(2,2,2-trifluoroethyl)-3-(2-(trifluoromethyl)pyrimidin-5-yl)-1,3-diazaspiro[4.5]decan-2-one | INT-1068 | 2-trifluoromethyl-5-bromopyrimidine | SC_3103 | | 502.2 |
| SC_3427 | cis-8-(dimethylamino)-8-phenyl-3-(2-(trifluoromethyl)pyrimidin-5-yl)-1-(3,3,3-trifluoropropyl)-1,3-diazaspiro[4.5]decan-2-one | INT-1070 | 2-trifluoromethyl-5-bromopyrimidine | SC_3103 | | |
| SC_3428 | cis-3-(4-methyl-6-(trifluoromethyl)pyridin-3-yl)-8-(methylamino)-8-phenyl-1,3-diazaspiro[4.5]decan-2-one | SC_3122 | | SC_3099 | | |
| SC_3429 | cis-3-(1-methyl-3-(trifluoromethyl)-1H-pyrazol-5-yl)-8-(methylamino)-8-phenyl-1,3-diazaspiro[4.5]decan-2-one | SC_3200 | | SC_3099 | | |
| SC_3430 | cis-8-(dimethylamino)-8-(3-fluorophenyl)-3-(4-(methylsulfonyl)pyridin-3-yl)-1,3-diazaspiro[4.5]decan-2-one | INT-1024 | 3-bromo-4-(methylsulfonyl)pyridine | SC_3103 | | |

| Example | Chemical name | Reactant I | Reactant II | in analogy to method | ¹H NMR data | m/z (M + H)⁺ |
|---|---|---|---|---|---|---|
| SC_3431 | cis-8-(dimethylamino)-3-(1-ethyl-3-(trifluoromethyl)-1H-pyrazole-5-yl)-8-(3-fluorophenyl)-1,3-diazaspiro[4.5]decan-2-one | INT-1024 | 5-bromo-1-ethyl-3-(trifluoromethyl)-1H-pyrazole | SC_3242 | | |
| SC_3432 | cis-3-(1-cyclopropyl-3-(trifluoromethyl)-1H-pyrazol-5-yl)-8-(dimethylamino)-8-(3-fluorophenyl)-1,3-diazaspiro[4.5]decan-2-one | INT-1024 | 5-bromo-1-cyclopropyl-3-(trifluoromethyl)-1H-pyrazole | SC_3242 | | |
| SC_3433 | cis-8-(dimethylamino)-8-(3-fluorophenyl)-3-(1-(oxetan-3-ylmethyl)-3-(trifluoromethyl)-1H-pyrazol-5-yl)-1,3-diazaspiro[4.5]decan-2-one | INT-1024 | 5-bromo-1-(oxetan-3-ylmethyl)-3-(trifluoromethyl)-1H-pyrazole | SC_3242 | | |
| SC_3434 | cis-8-(dimethylamino)-8-(3-fluorophenyl)-3-(1-(2-(methylsulfonyl)ethyl)-3-(trifluoromethyl)-1H-pyrazol-5-yl)-1,3-diazaspiro[4.5]decan-2-one | INT-1024 | 5-bromo-1-(2-(methylsulfonyl)ethyl)-3-(trifluoromethyl)-1H-pyrazole | SC_3242 | | |
| SC_3435 | cis-8-(dimethylamino)-8-(3-fluorophenyl)-3-(4-methyl-2-(methylamino)pyrimidin-5-yl)-1,3-diazaspiro[4.5]decan-2-one | INT-1076 | methylamine | SC_3239 | | |
| SC_3436 | cis-3-(2-cyclopropoxy-4-methylpyrimidin-5-yl)-8-(dimethylamino)-8-(3-fluorophenyl)-1,3-diazaspiro[4.5]decan-2-one | INT-1076 | cyclopropanol | SC_3224 | | 440.3 |
| SC_3437 | cis-N-(5-(8-(dimethylamino)-8-(3-fluorophenyl)-2-oxo-1,3-diazaspiro[4.5]decan-3-yl)-4-methylpyrimidin-2-yl)-N-methylcyclopropanecarboxamide | INT-1024 | N-(5-bromo-4-methylpyrimidin-2-yl)-N-methylcyclopropanecarboxamide | SC_3103 | | 481.3 |
| SC_3438 | cis-N-(5-(8-(dimethylamino)-8-(3-fluorophenyl)-2-oxo-1,3-diazaspiro[4.5]decan-3-yl)-4-methylpyrimidin-2-yl)-N-methylpivalamide | INT-1024 | N-(5-bromo-4-methylpyrimidin-2-yl)-N-methylpivalamide | SC_3103 | | 497.3 |
| SC_3439 | cis-3-(4-(azetidin-1-yl)-2-(trifluoromethyl)pyrimidin-5-yl)-8-(dimethylamino)-8-(3-fluorophenyl)-1,3-diazaspiro[4.5]decan-2-one | INT-1077 | azetidine | SC_3120 | | 493.2 |

-continued

| Example | Chemical name | Reactant I | Reactant II | in analogy to method | ¹H NMR data | m/z (M + H)⁺ |
|---|---|---|---|---|---|---|
| SC_3440 | cis-8-(dimethylamino)-3-(4-(oxetan-3-fluorophenyl)-3-(4-(oxetan-3-ylmethoxy)-2-(trifluoromethyl)pyrimidin-5-yl)-1,3-diazaspiro[4.5]decan-2-one | INT-1077 | oxetan-3-ylmethanol | SC_3224 | | 524.2 |
| SC_3441 | cis-3-(2-cyclopropyl-4-(2,2,2-trifluoroethoxy)pyrimidin-5-yl)-8-(dimethylamino)-8-(3-fluorophenyl)-1,3-diazaspiro[4.5]decan-2-one | INT-1078 | 2,2,2-trifluoroethanol | SC_3224 | | 508.2 |
| SC_3442 | cis-3-(2-cyclopropyl-4-((2-hydroxyethyl)(methyl)amino)pyrimidin-5-yl)-8-(dimethylamino)-8-(3-fluorophenyl)-1,3-diazaspiro[4.5]decan-2-one | INT-1078 | 2-(methylamino)ethanol | SC_3120 | | 483.3 |

Chemical Structures of all Examples
SC_3001
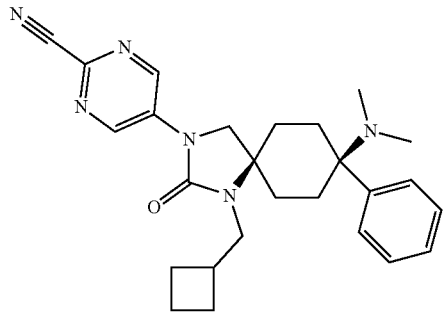
SC_3002
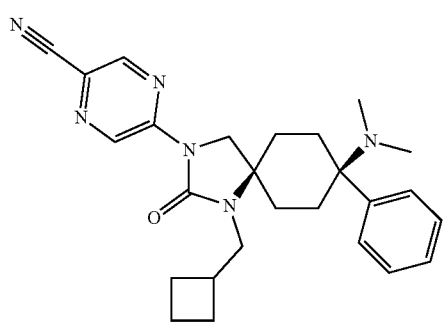
SC_3003
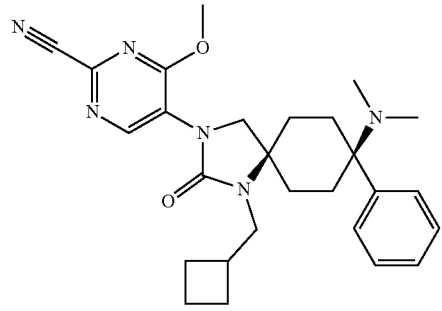
SC_3004
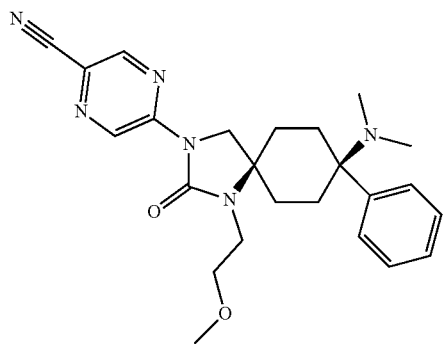
SC_3005
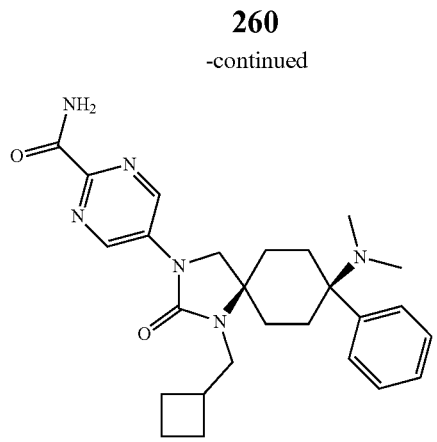
SC_3006
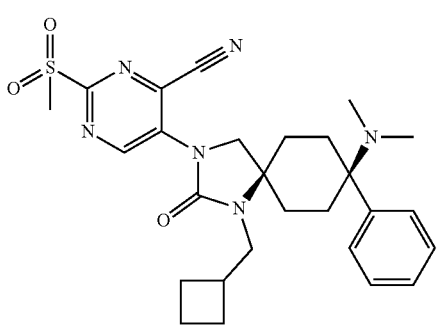
SC_3007
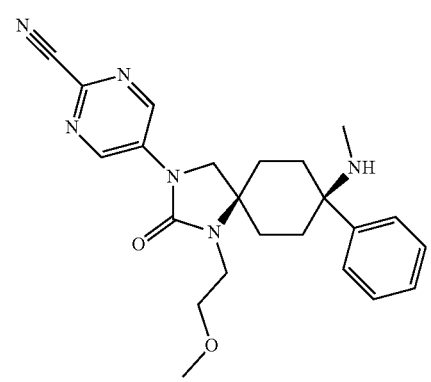
SC_3008
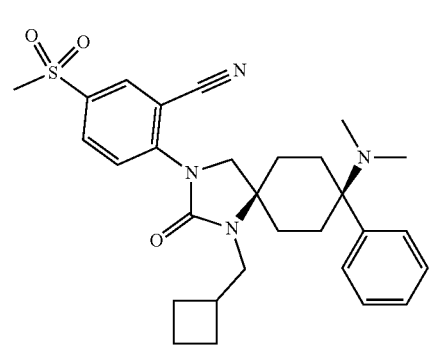

SC_3009
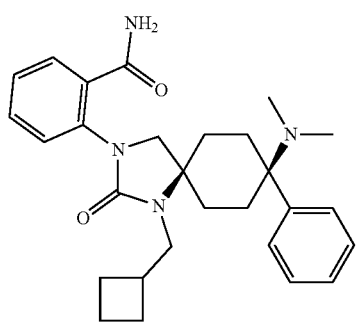
SC_3010
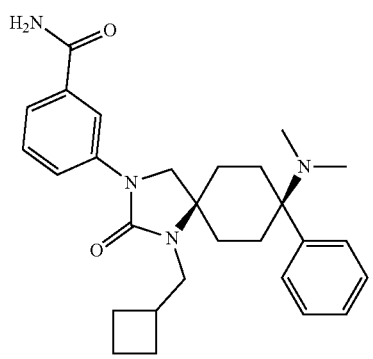
SC_3011
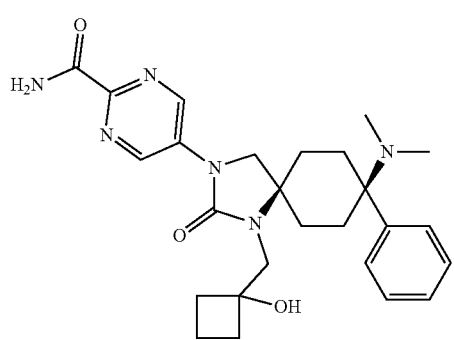
SC_3012
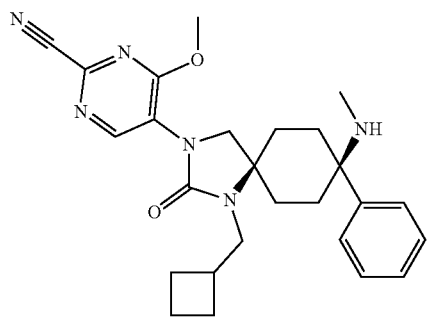
SC_3013
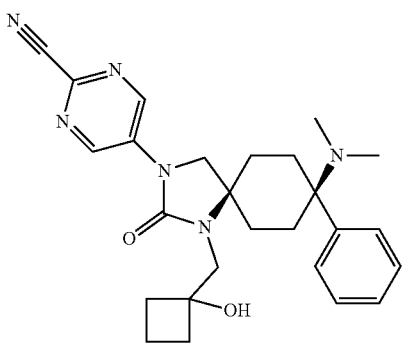
SC_3014
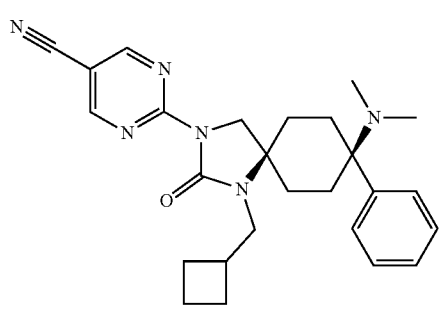
SC_3015
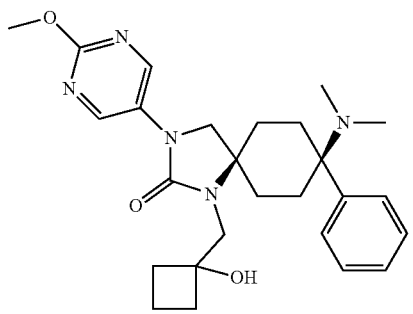
SC_3016
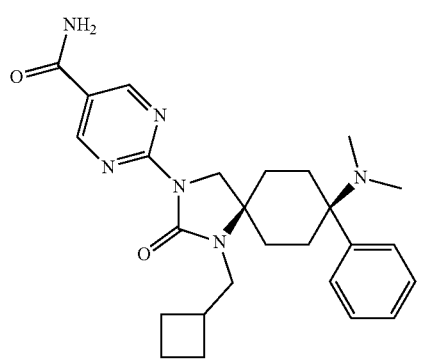

-continued
SC_3017
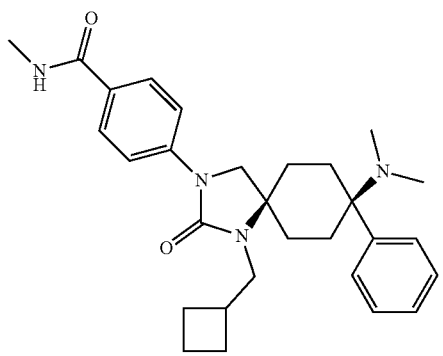
SC_3018
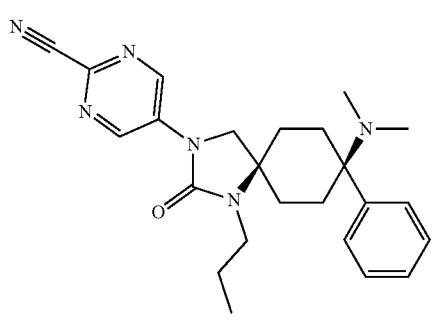
SC_3019
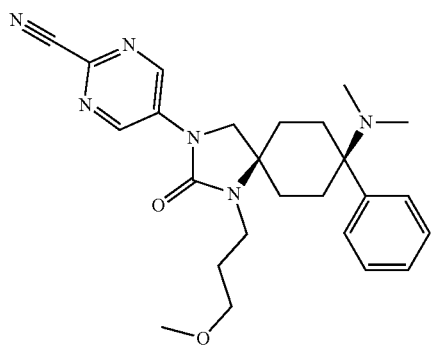
SC_3020
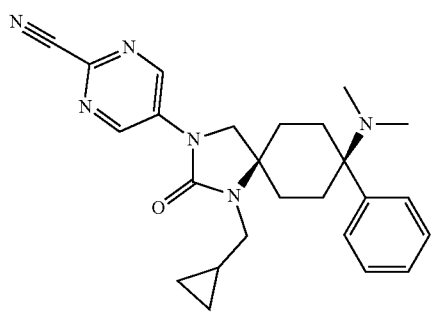
-continued
SC_3021
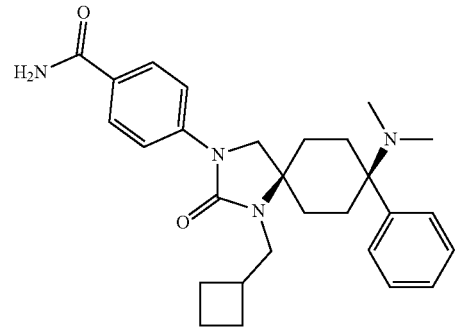
SC_3022
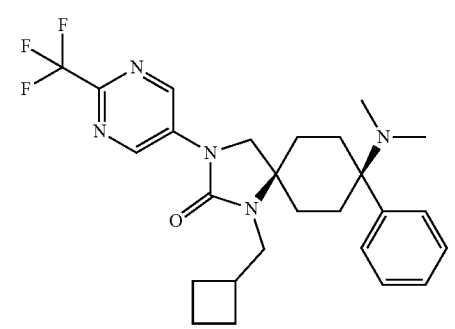
SC_3023
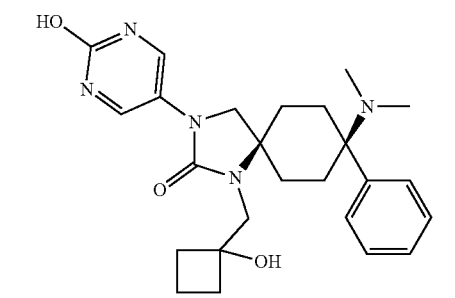
SC_3024
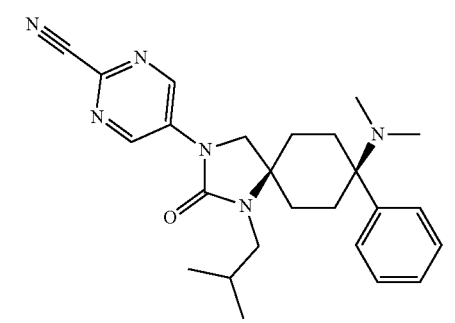
SC_3025
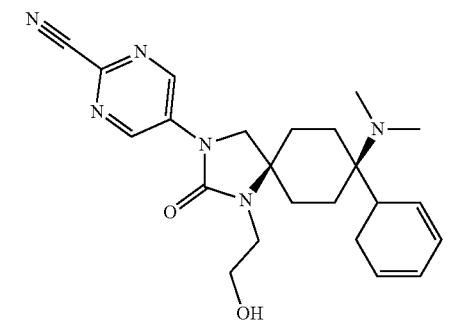

SC_3026
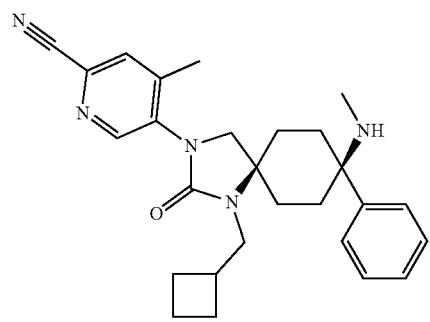
SC_3027
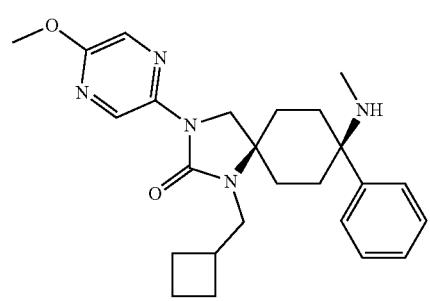
SC_3028
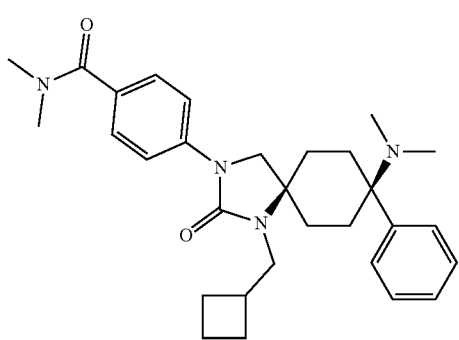
SC_3029
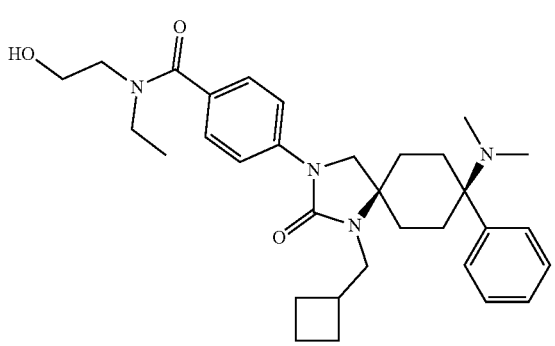
SC_3030
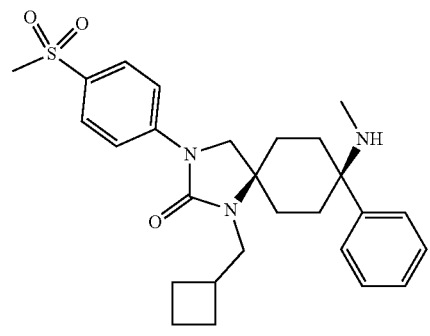
SC_3031
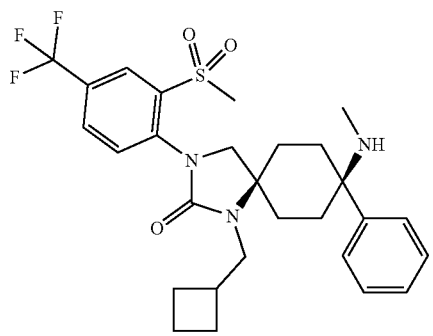
SC_3032
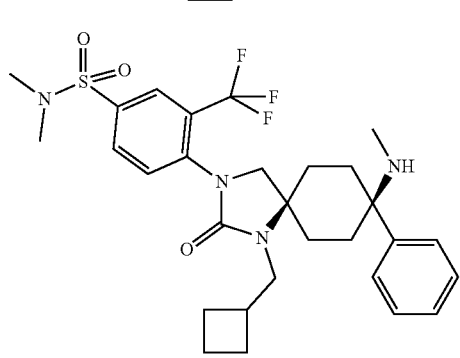
SC_3033
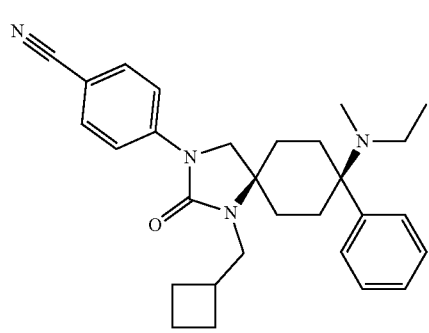
SC_3034
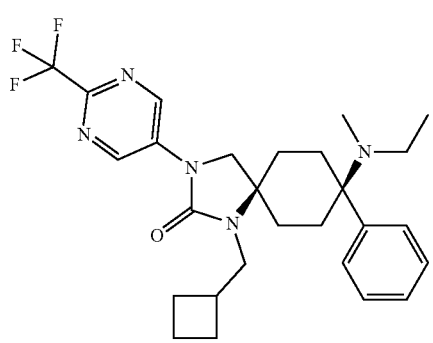
SC_3035
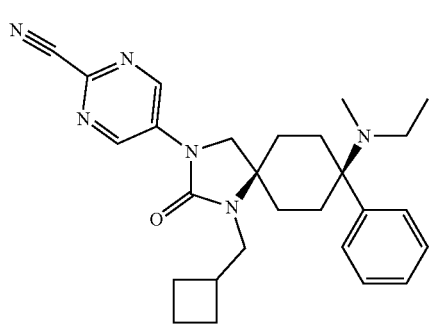

-continued
SC_3036
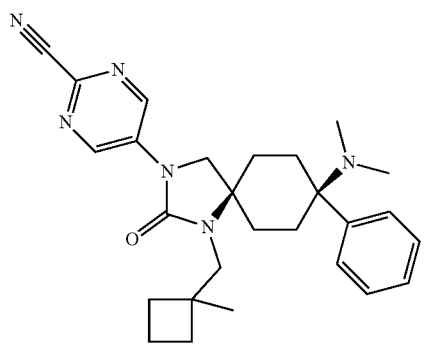
SC_3037
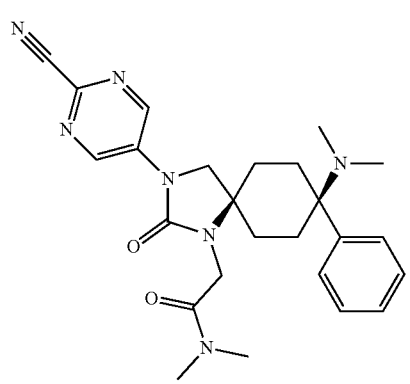
SC_3038
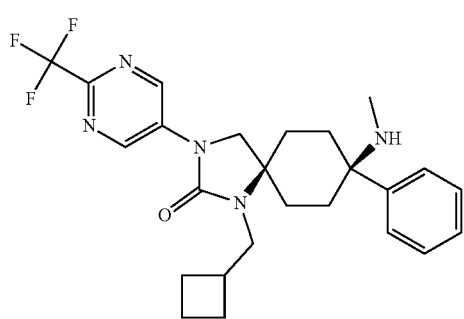
SC_3039
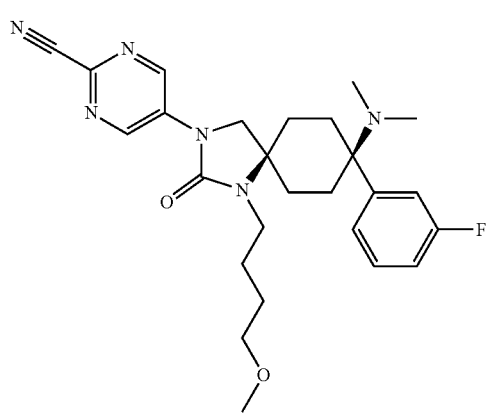
-continued
SC_3040
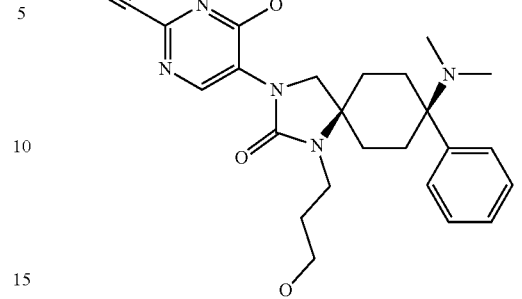
SC_3041
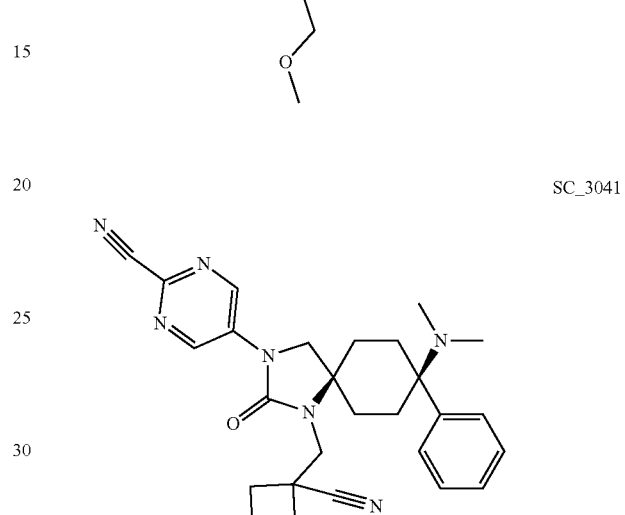
SC_3042
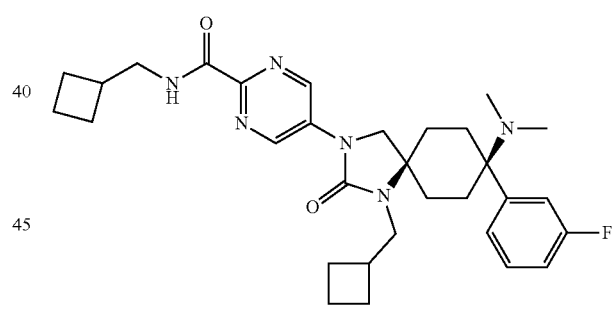
SC_3043
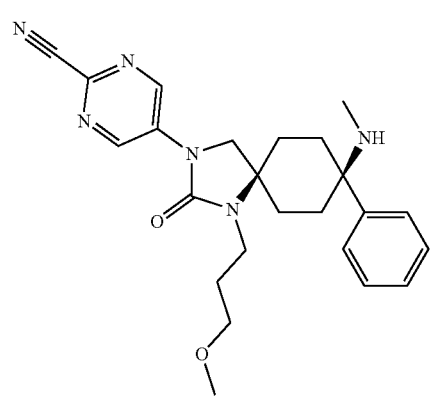

269
-continued
SC_3044
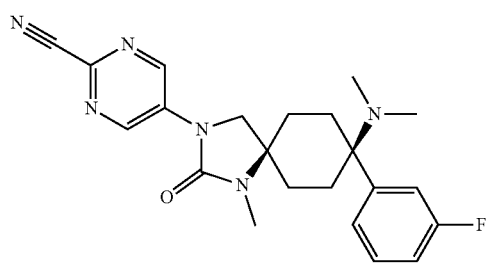
SC_3045
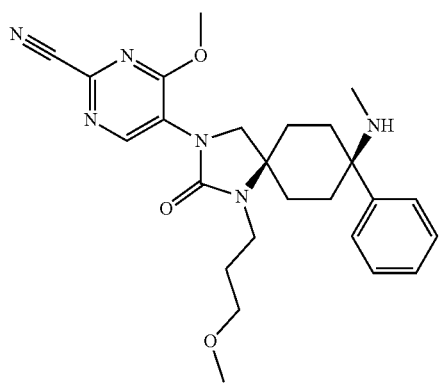
SC_3046
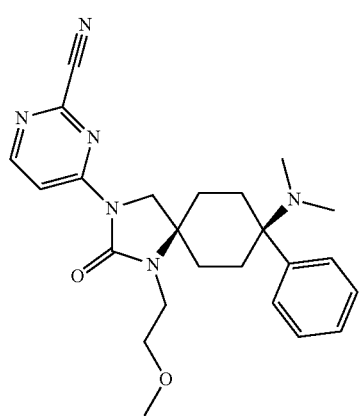
SC_3047
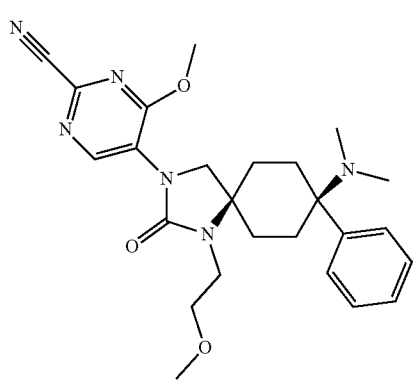
270
-continued
SC_3048
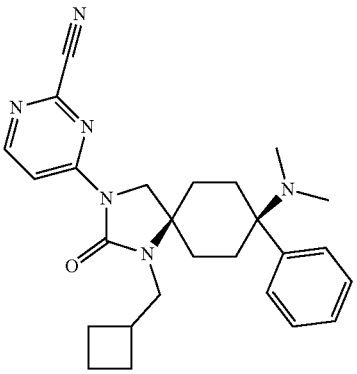
SC_3049
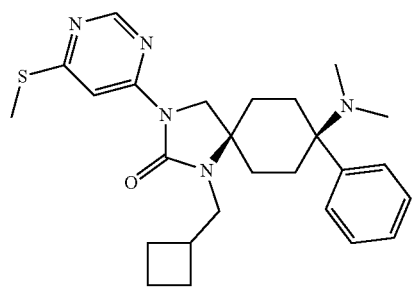
SC_3050
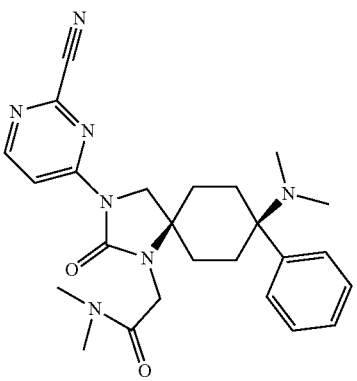
SC_3051
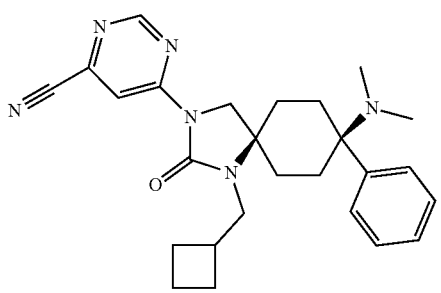
SC_3052
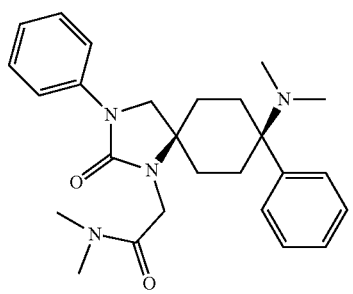

SC_3053
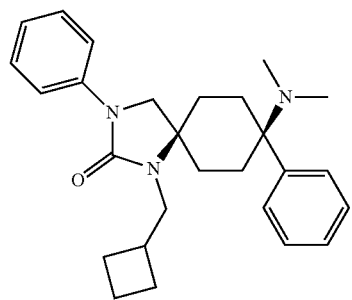
SC_3054
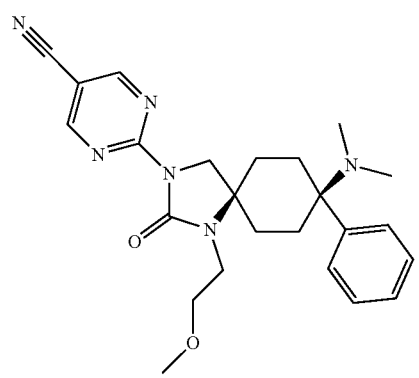
SC_3055
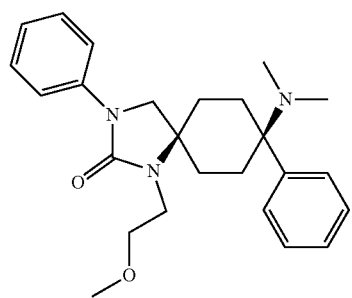
SC_3056
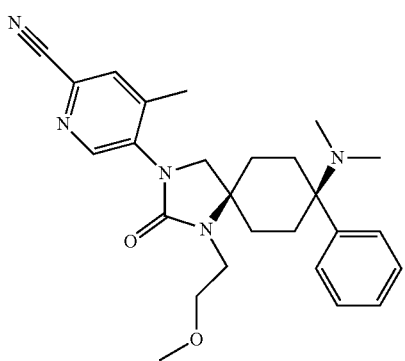
SC_3057
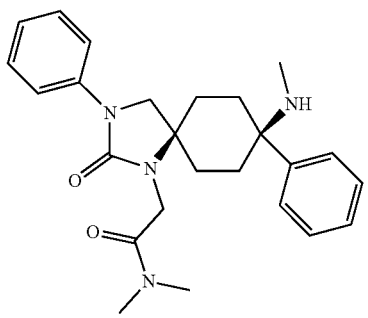
SC_3058
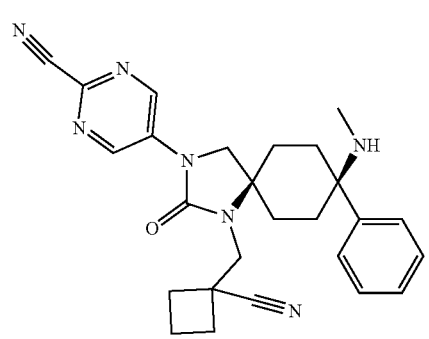
SC_3059
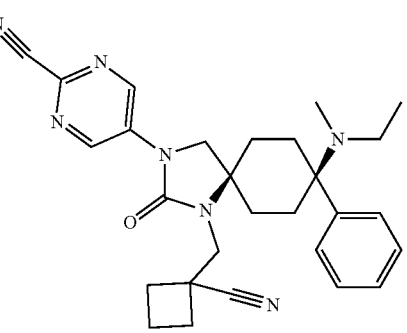
SC_3060
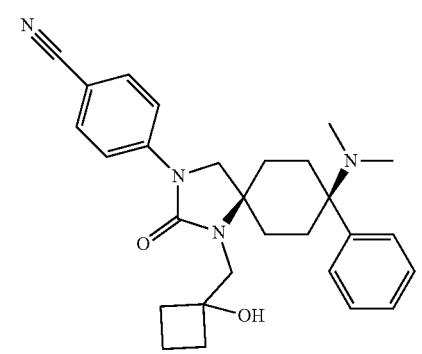
SC_3061

SC_3063
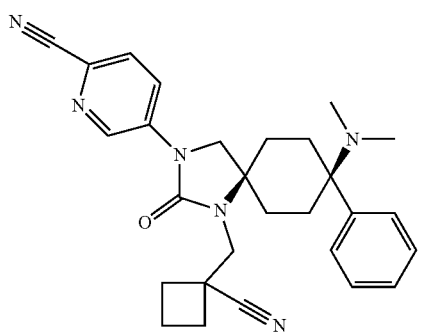
SC_3067
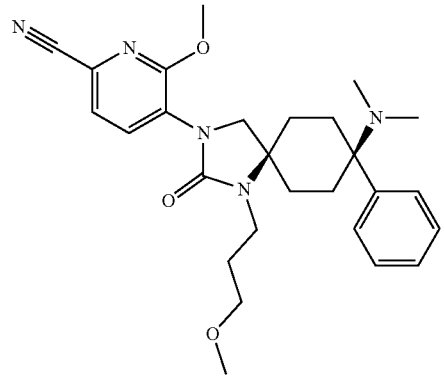
SC_3064
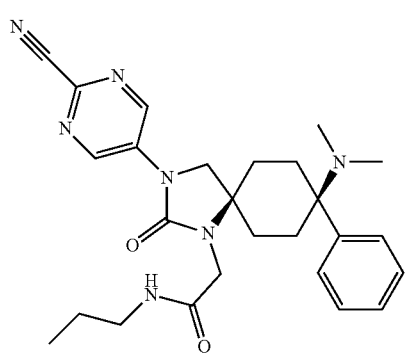
SC_3068
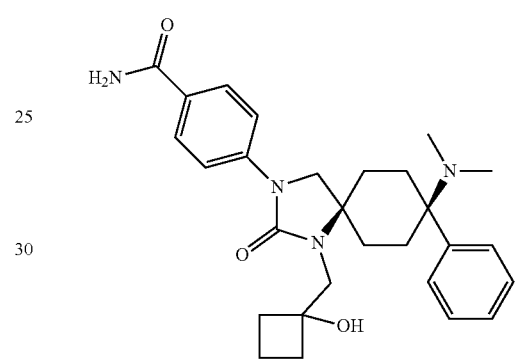
SC_3065
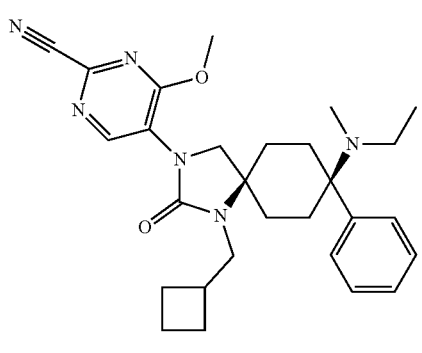
SC_3069
SC_3066
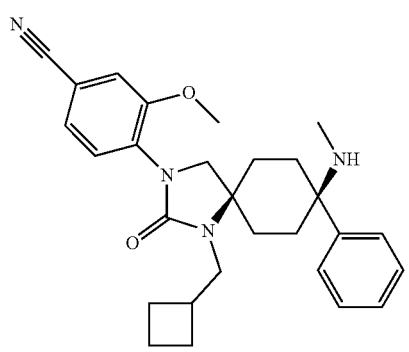
SC_3070
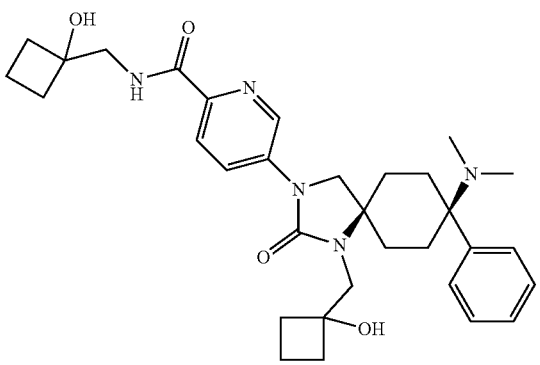

SC_3071
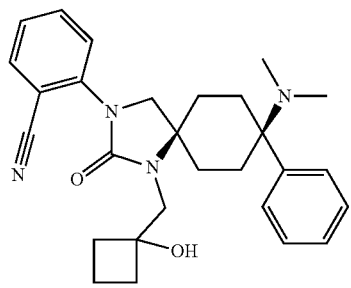
SC_3072
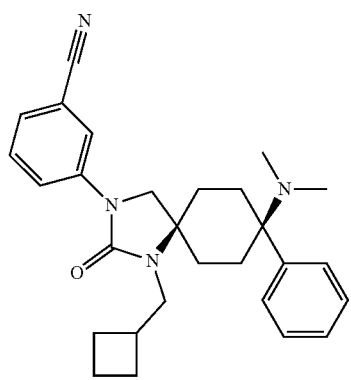
SC_3073
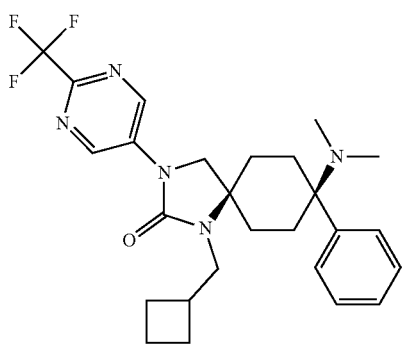
SC_3074
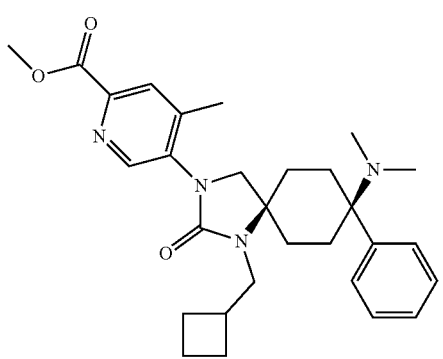
SC_3075
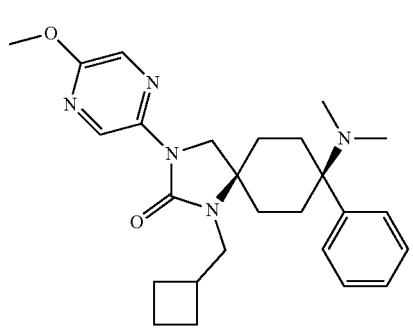
SC_3076
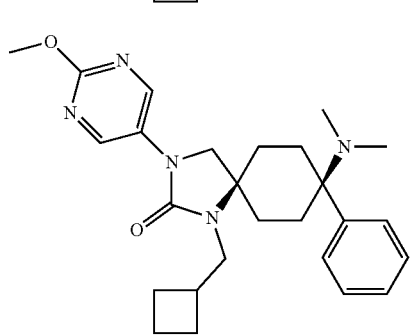
SC_3077
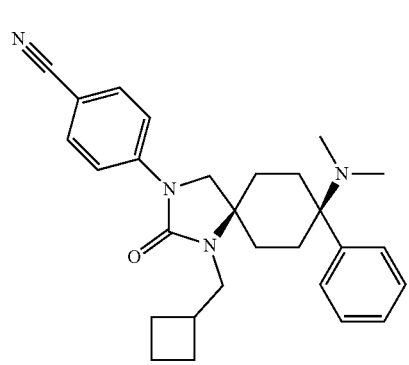
SC_3078
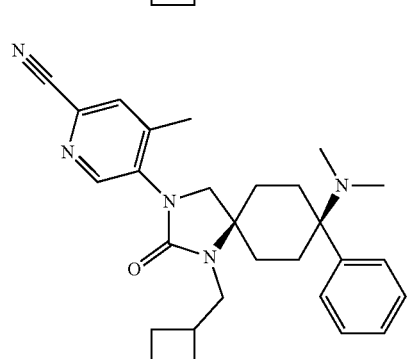
SC_3079
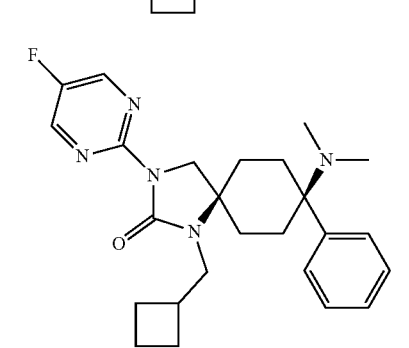

SC_3080
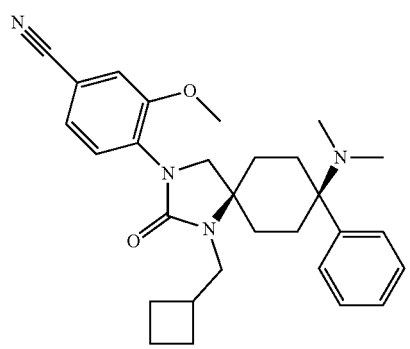
SC_3084
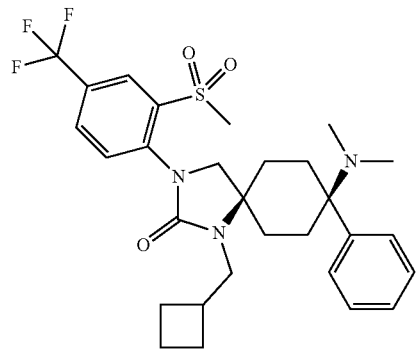
SC_3081
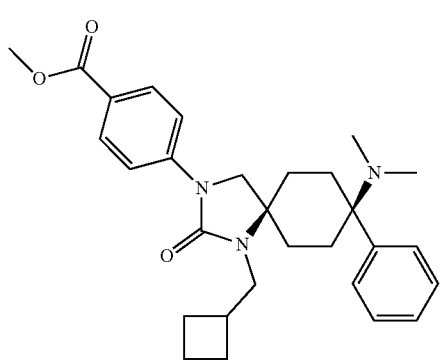
SC_3085
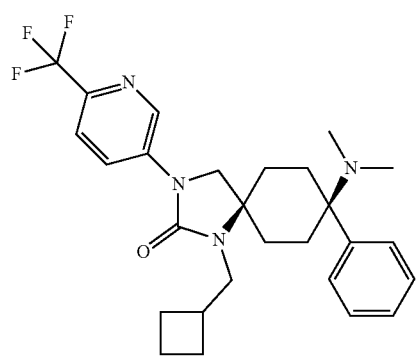
SC_3082
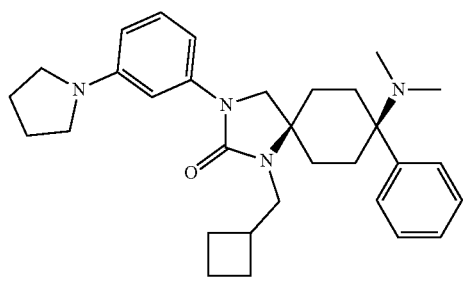
SC_3086
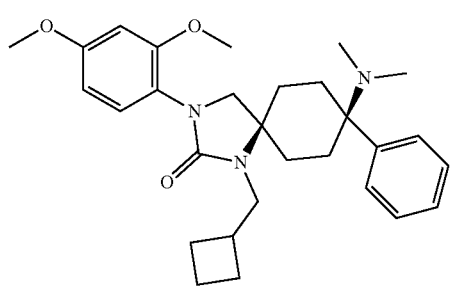
SC_3083
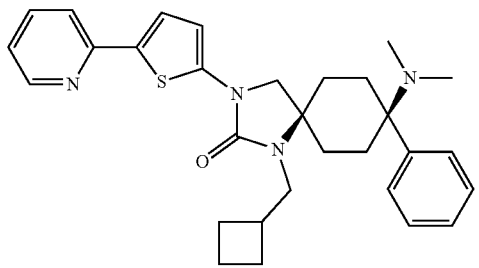
SC_3087
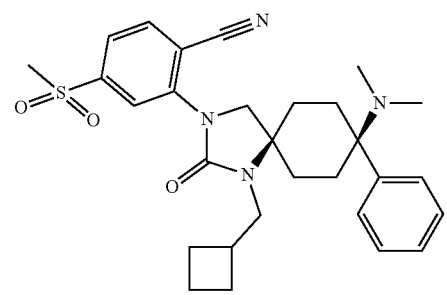

SC_3088
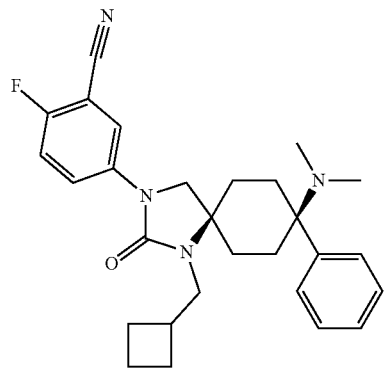
SC_3089
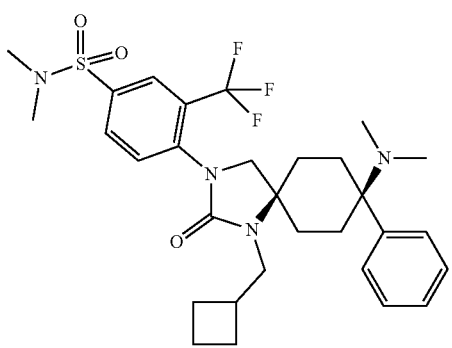
SC_3090
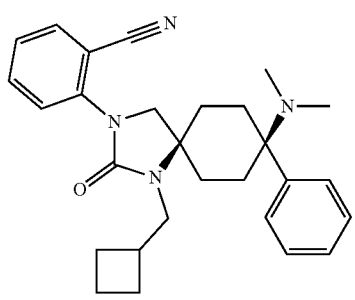
SC_3091
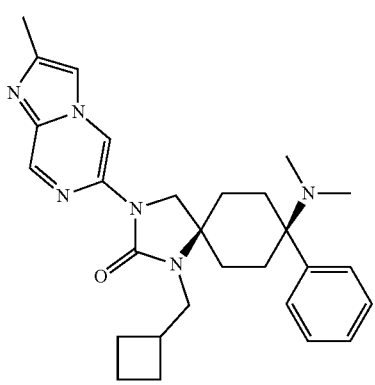
SC_3092
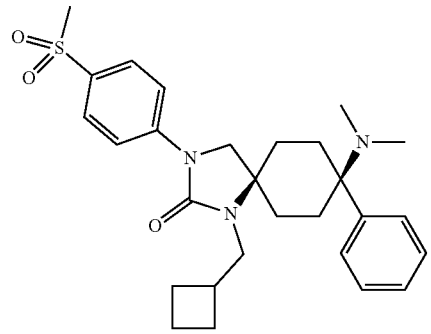
SC_3093
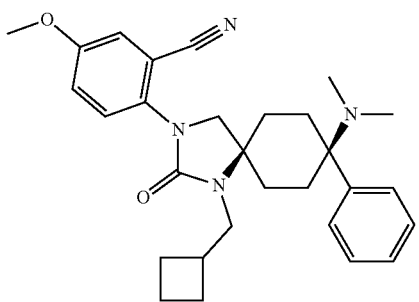
SC_3094
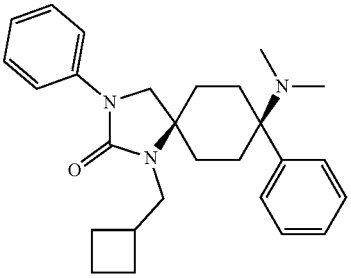
SC_3096
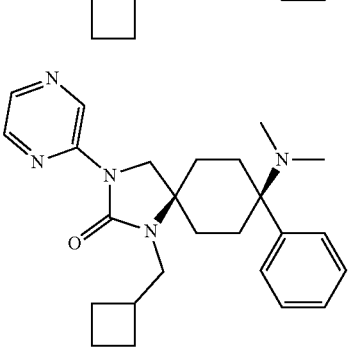
SC_3097
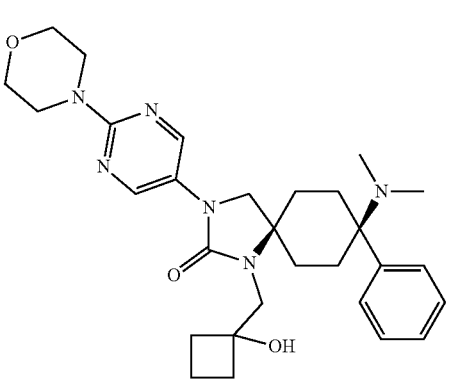

SC_3098
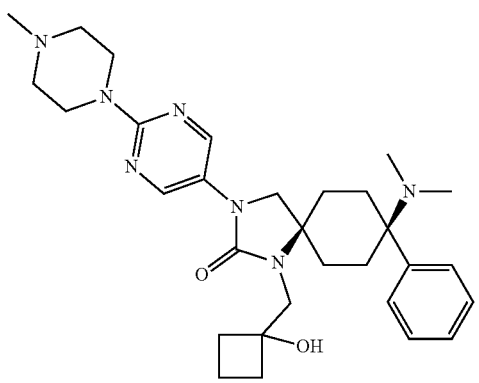
SC_3099
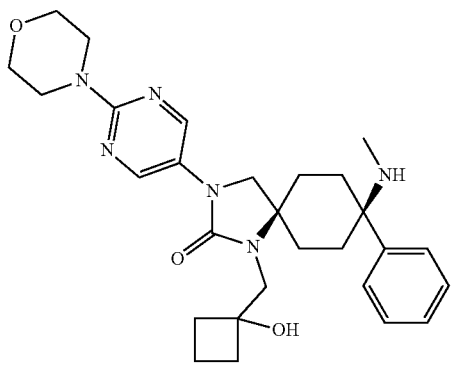
SC_3100
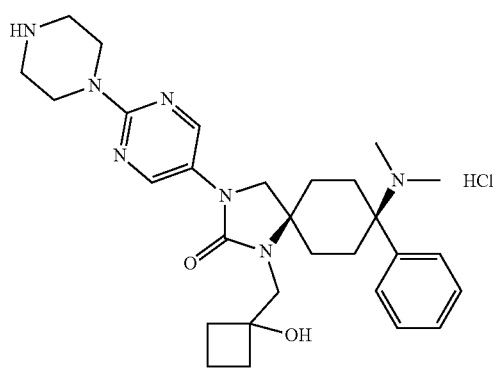
HCl
SC_3101
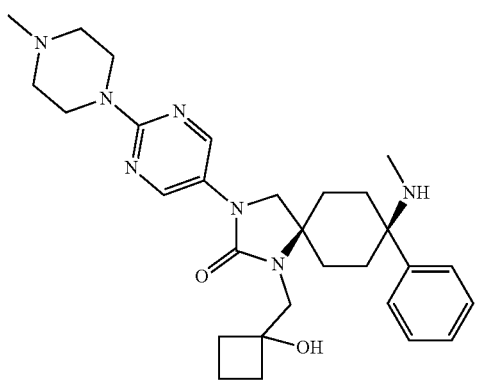
SC_3102
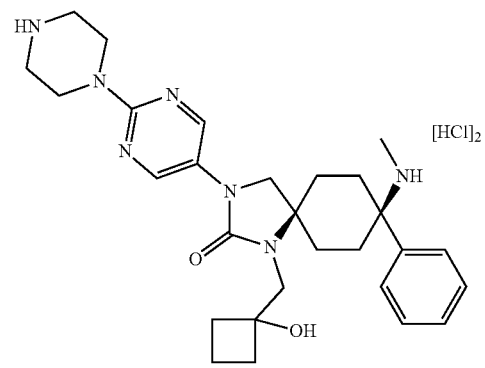
[HCl]₂
SC_3103
SC_3104
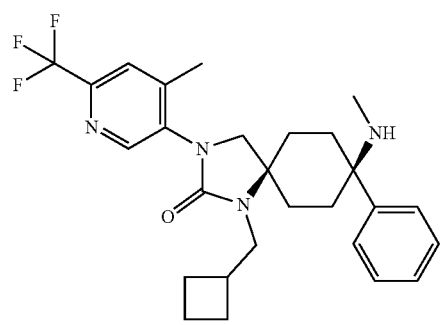
SC_3105
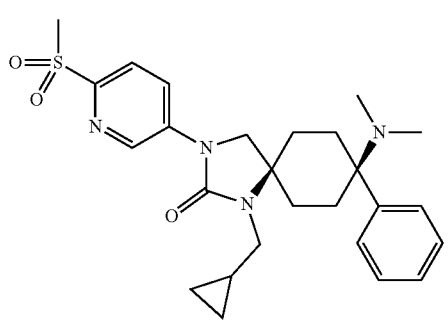

SC_3106
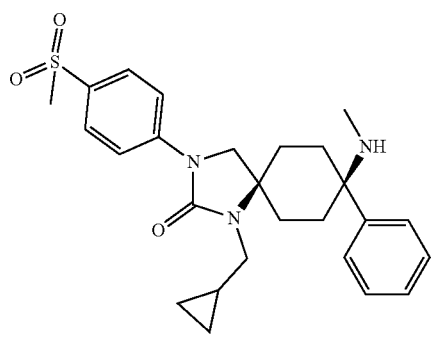
SC_3107
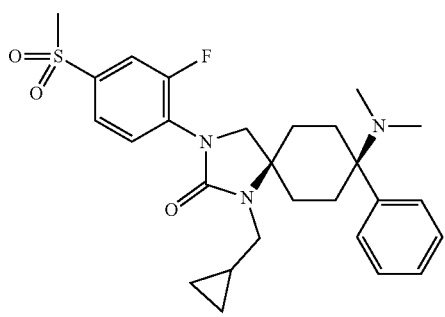
SC_3108
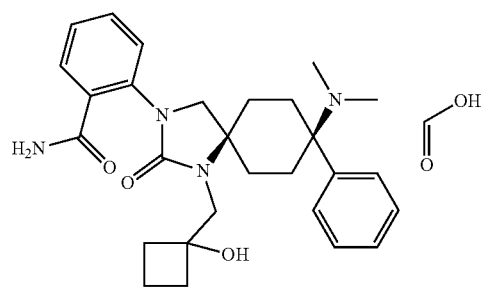
SC_3109
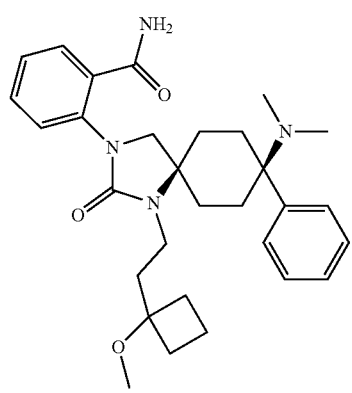
SC_3110
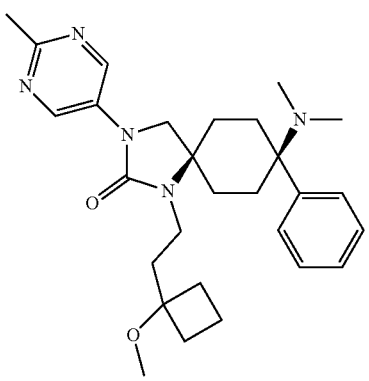
SC_3111
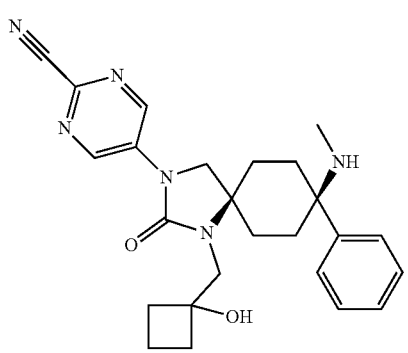
SC_3112
SC_3113
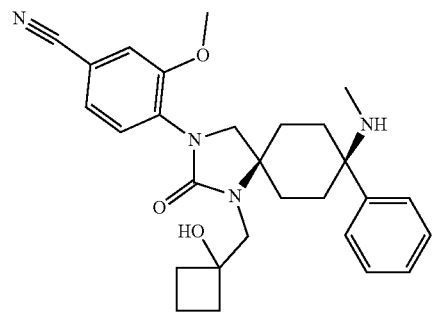

SC_3114
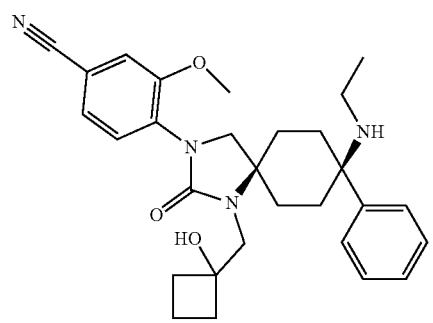
SC_3115
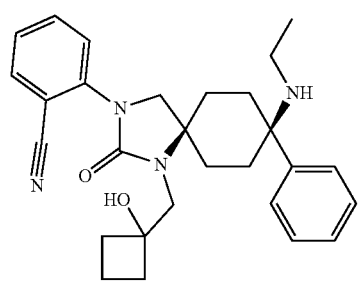
SC_3116
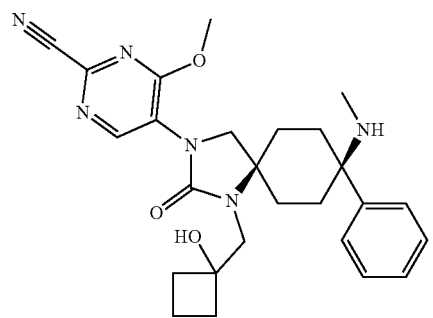
SC_3117
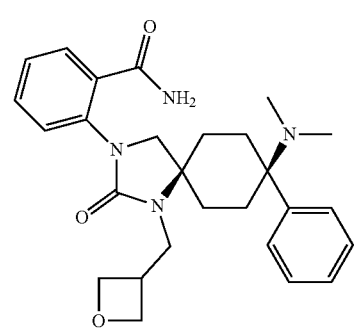
SC_3118
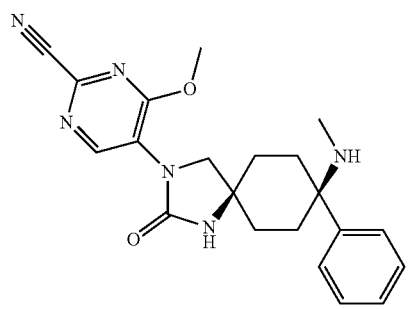
SC_3119
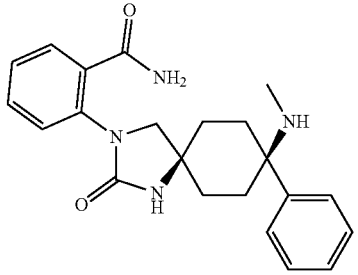
SC_3120
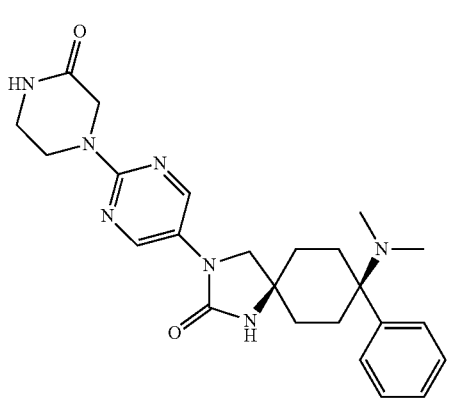
SC_3121
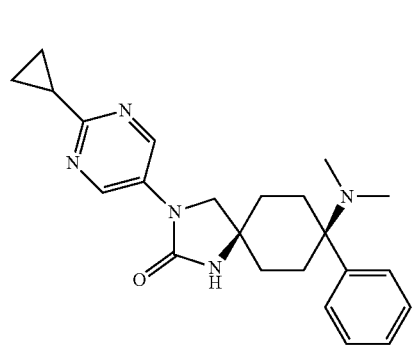
SC_3122
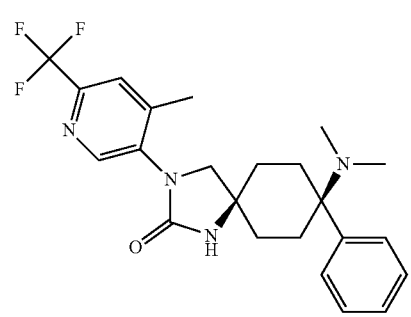
SC_3123
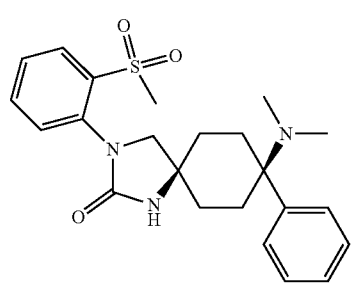

SC_3124
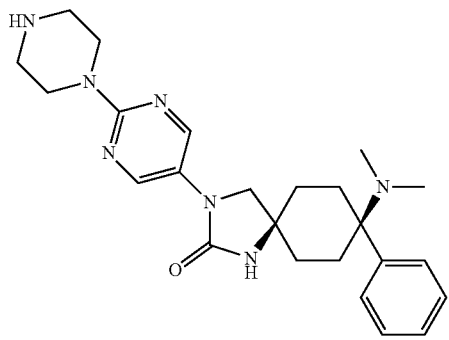
SC_3129
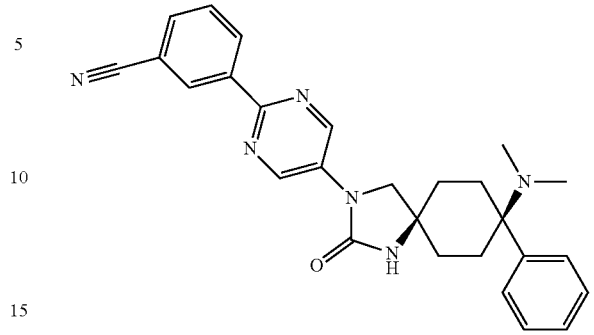
SC_3125
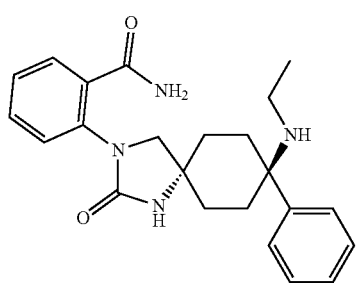
SC_3130
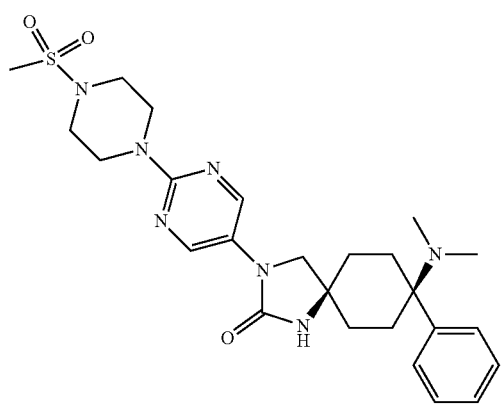
SC_3126
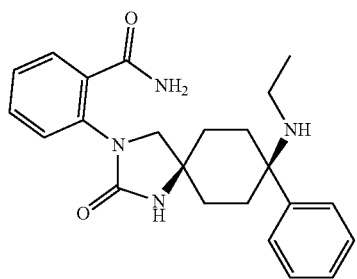
SC_3131
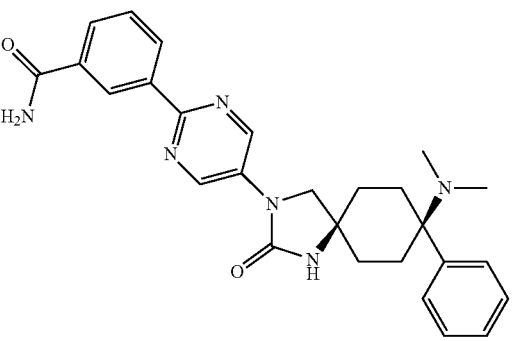
SC_3127
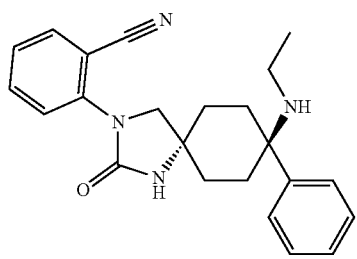
SC_3132
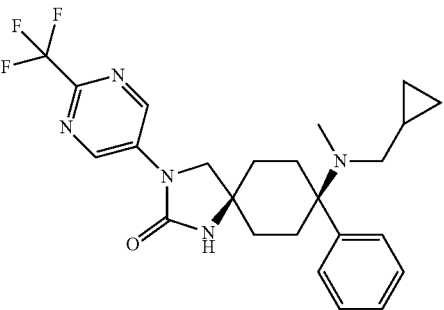
SC_3128
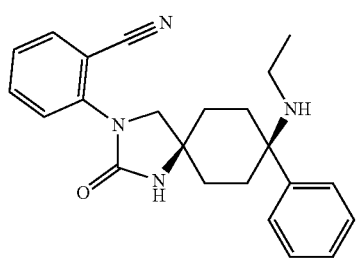

SC_3133
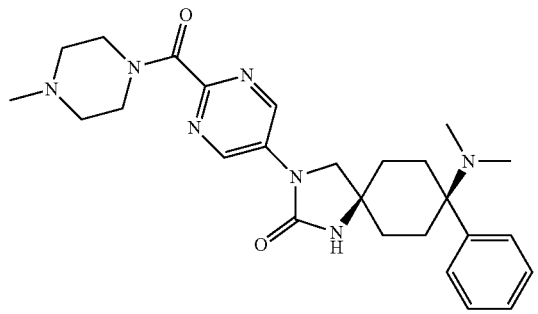
SC_3134
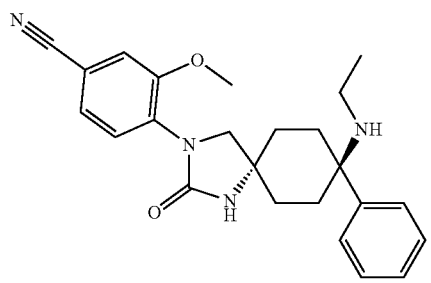
SC_3135
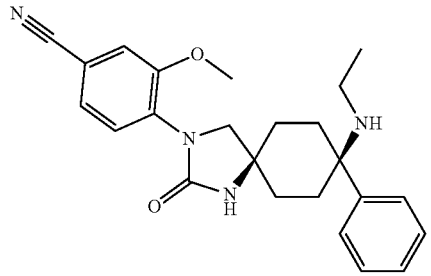
SC_3136
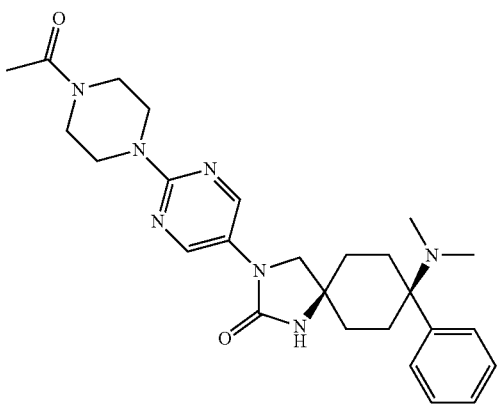
SC_3137
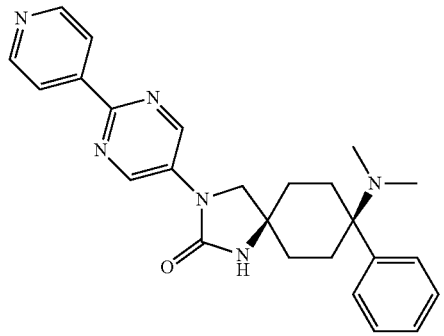
SC_3138
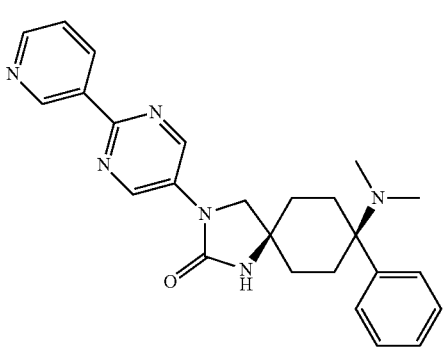
SC_3139
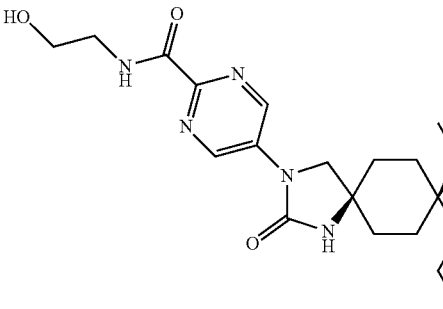
SC_3140
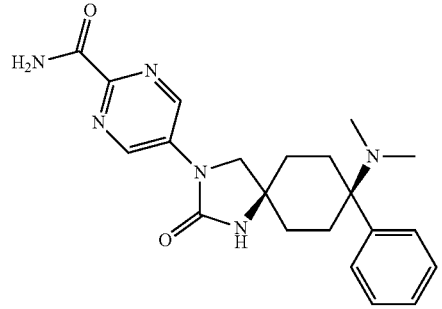

SC_3141
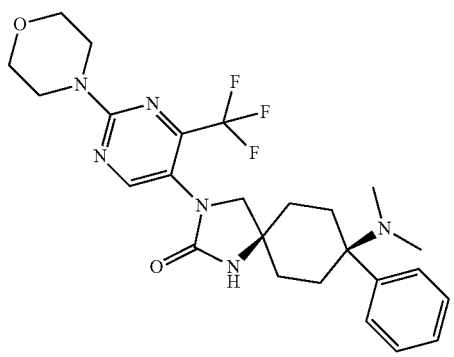
SC_3145
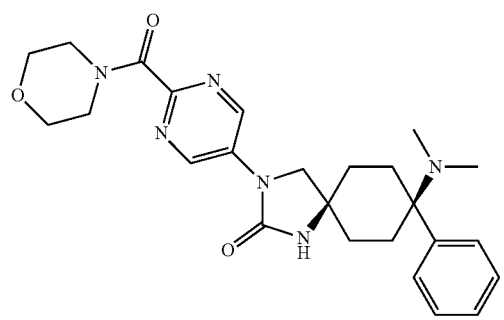
SC_3142
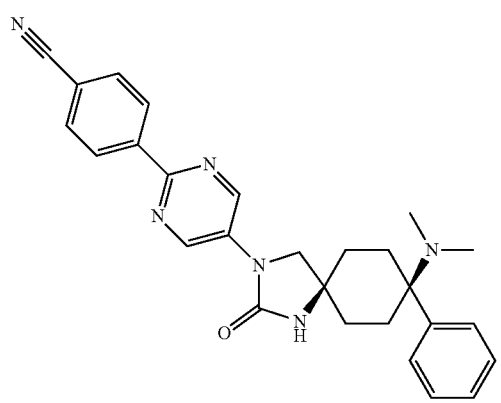
SC_3146
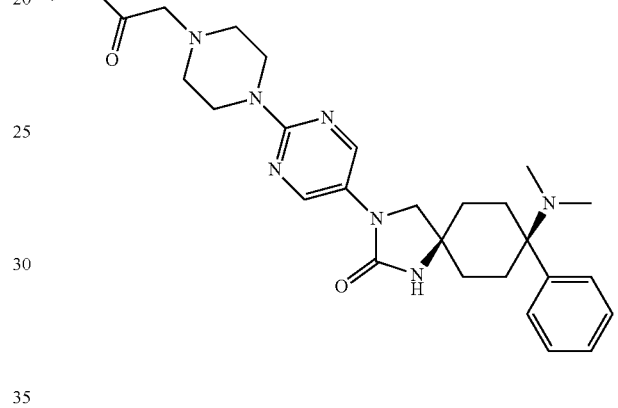
SC_3143
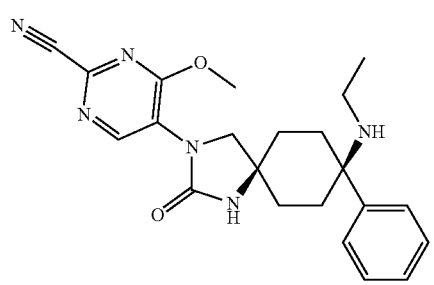
SC_3147
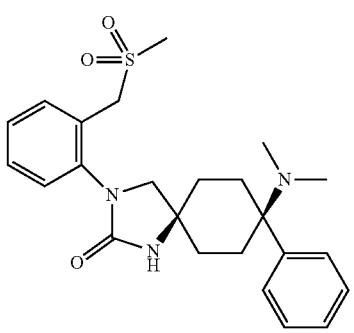
SC_3144
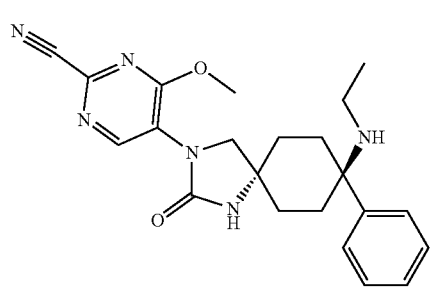
SC_3148
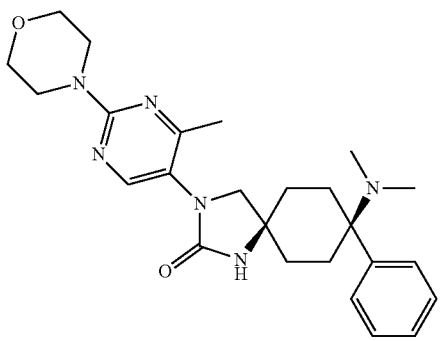

293
-continued
SC_3149
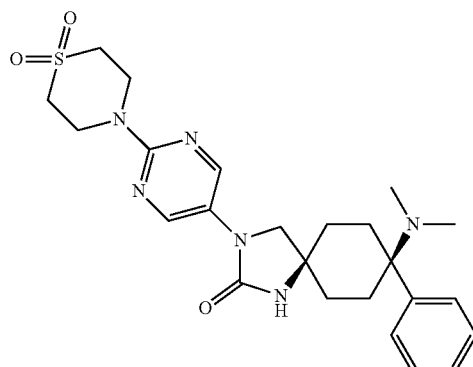
SC_3150
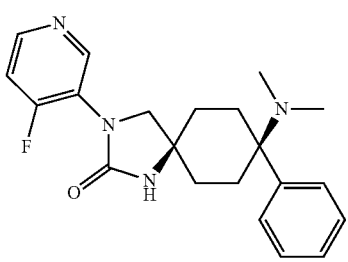
SC_3151
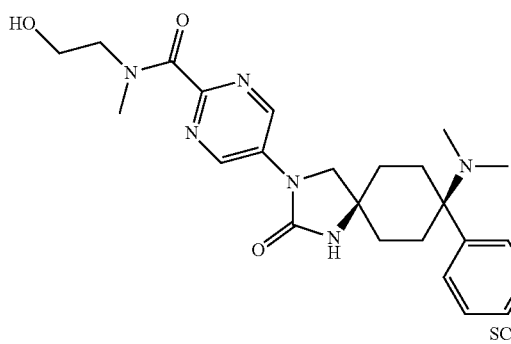
SC_3152
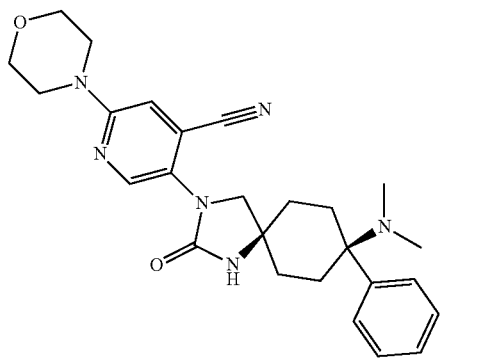
SC_3153
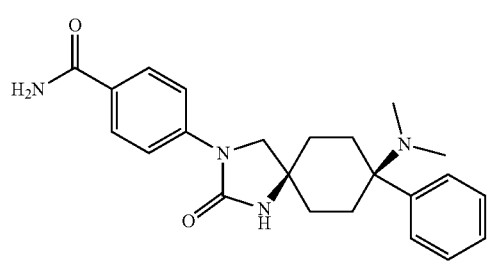
294
-continued
SC_3154
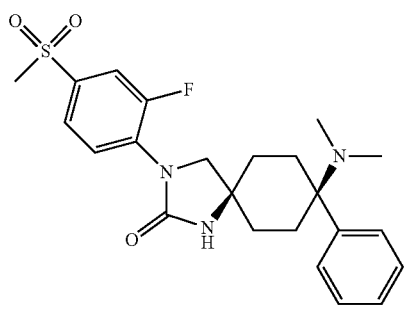
SC_3155
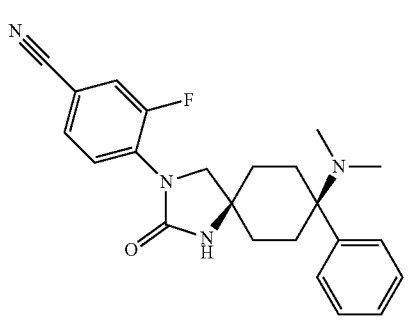
SC_3156
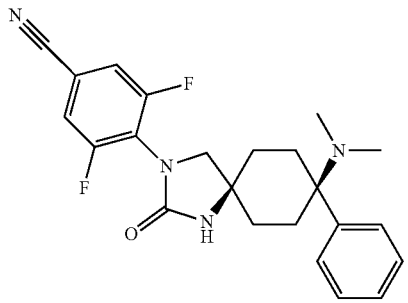
SC_3157
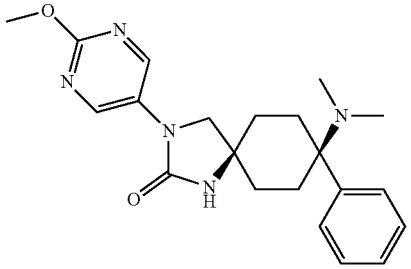
SC_3158
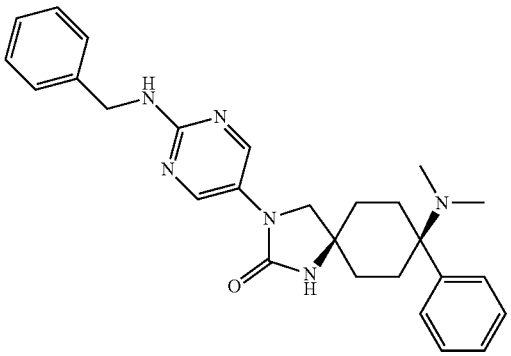

SC_3159
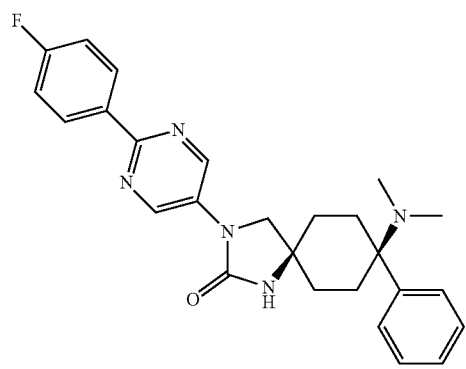
SC_3160
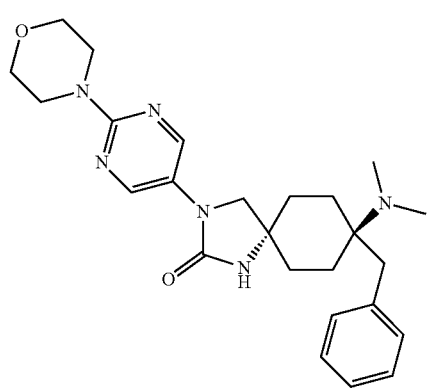
SC_3161
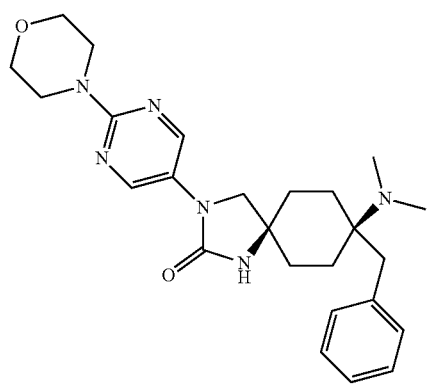
SC_3162
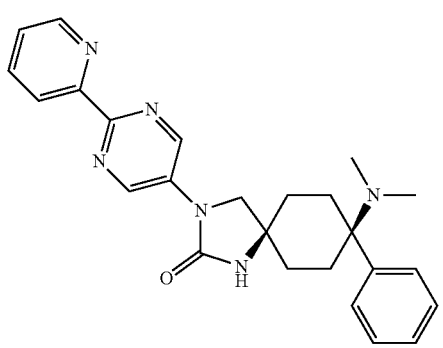
SC_3163
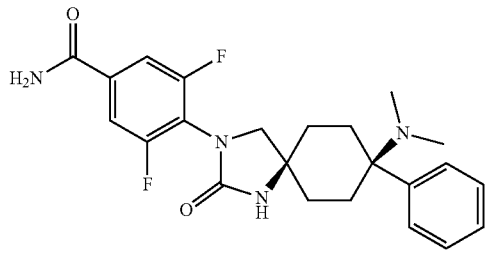
SC_3164
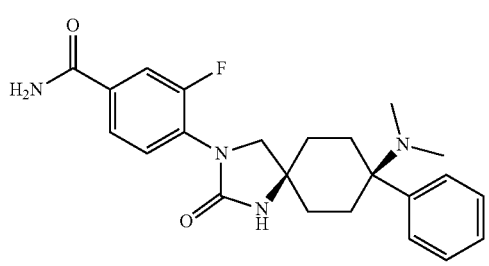
SC_3165
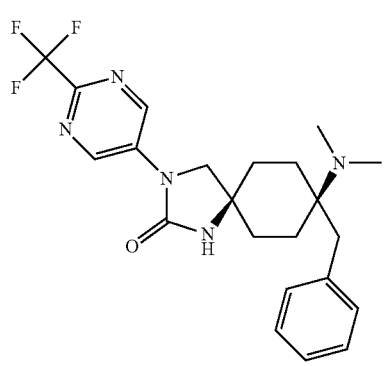
SC_3166
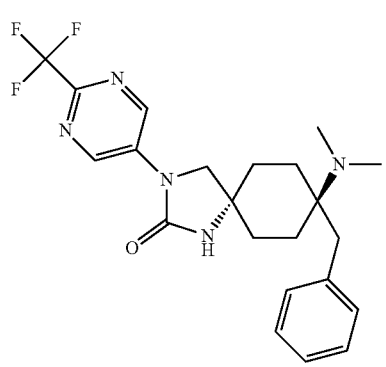
SC_3167
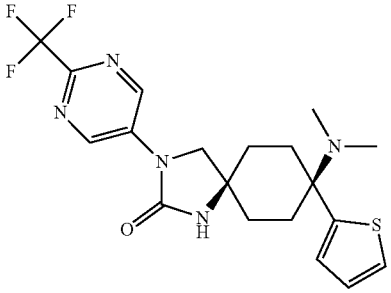

SC_3168
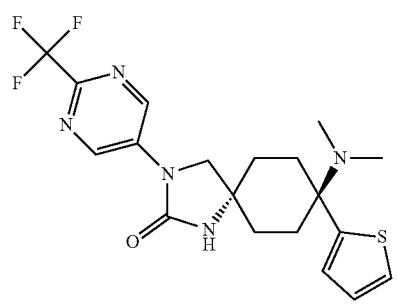
SC_3169
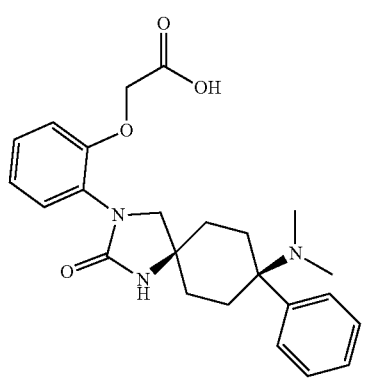
SC_3170
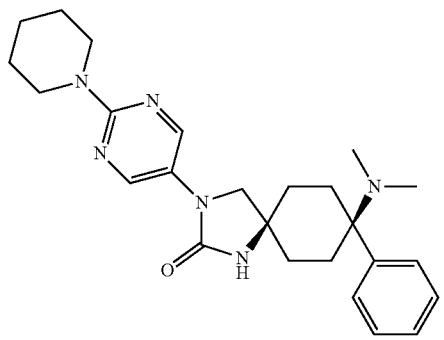
SC_3171
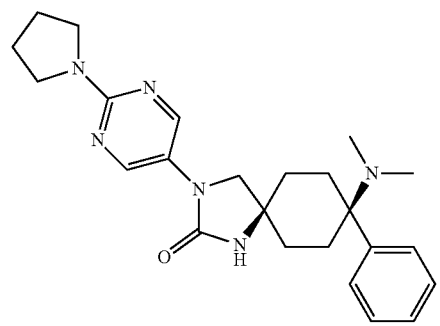
SC_3172
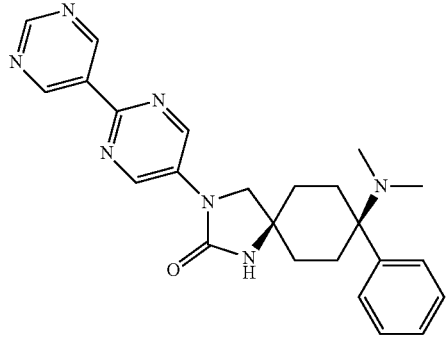
SC_3173
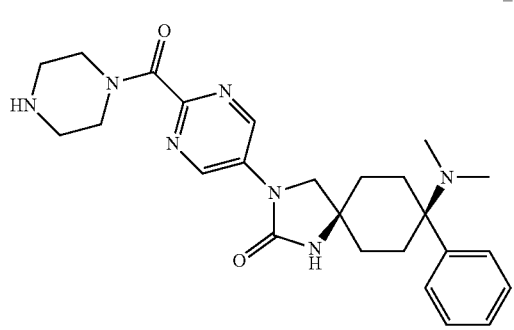
SC_3174
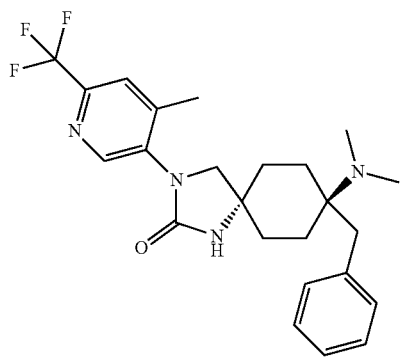
SC_3175
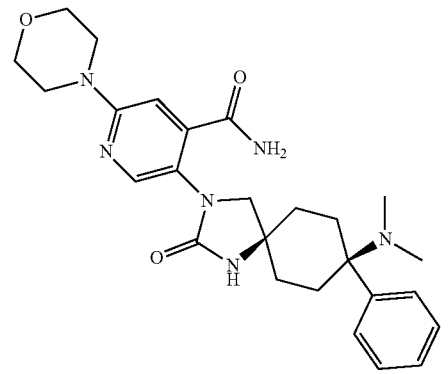

SC_3176
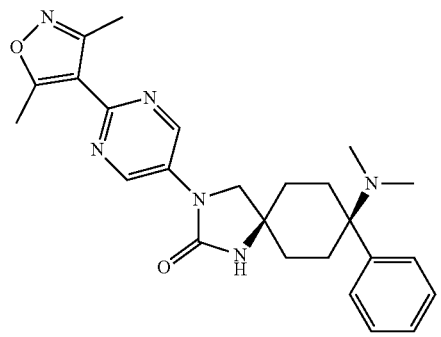
SC_3177
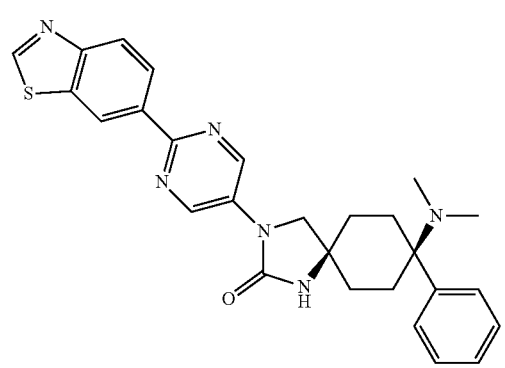
SC_3178
SC_3179
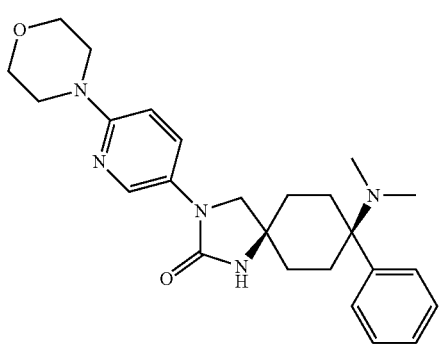
SC_3180
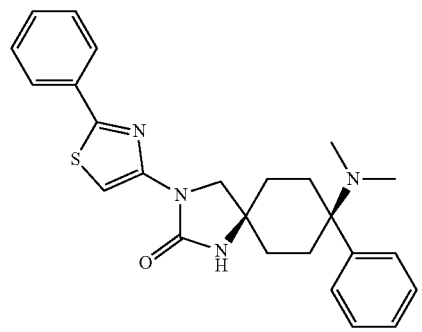
SC_3181
SC_3182
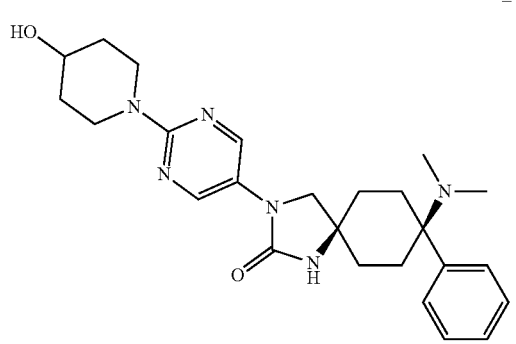
SC_3183
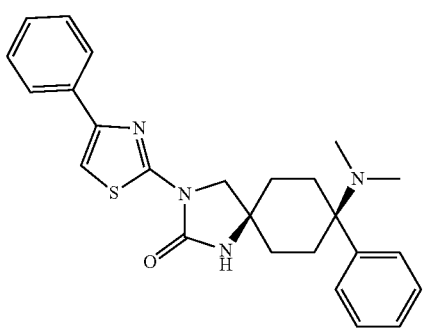

SC_3184
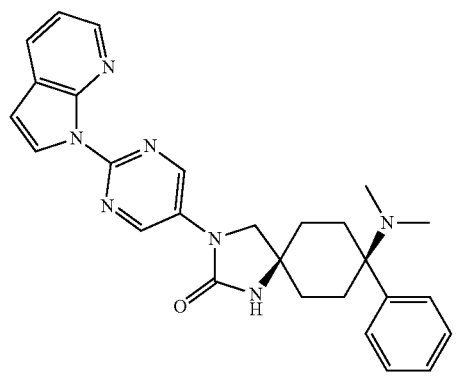
SC_3185
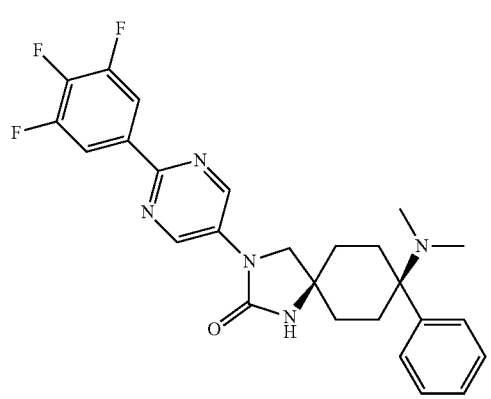
SC_3186
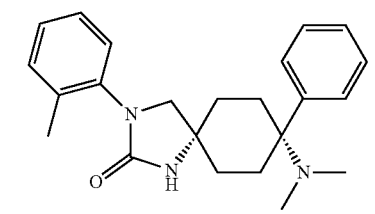
SC_3187
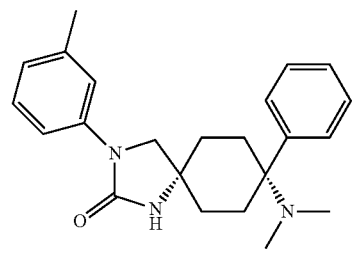
SC_3188
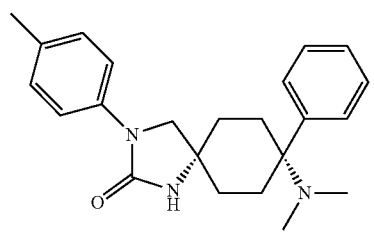
SC_3189
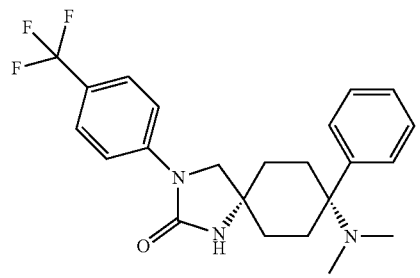
SC_3190
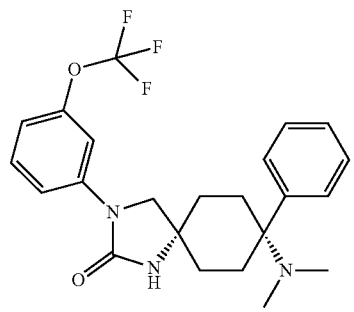
SC_3191
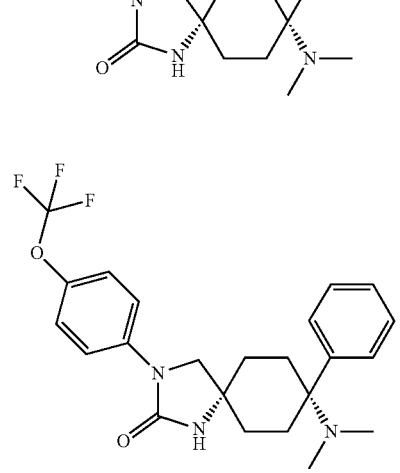
SC_3192
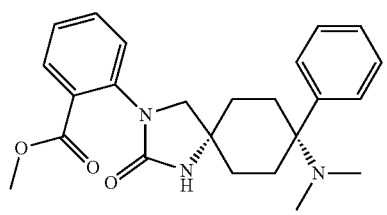
SC_3193
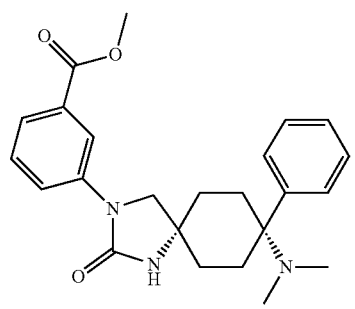

SC_3194
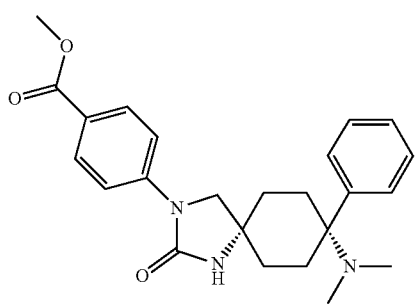
SC_3195
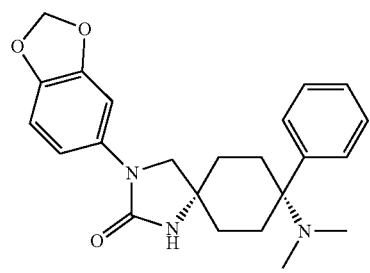
SC_3196
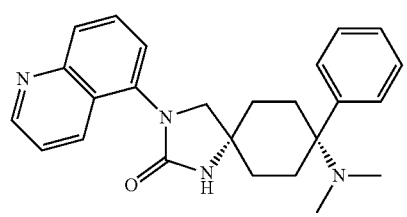
SC_3197
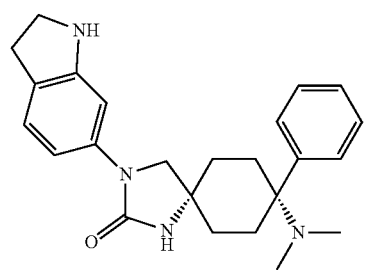
SC_3198
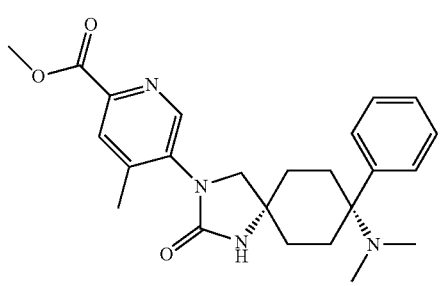
SC_3199
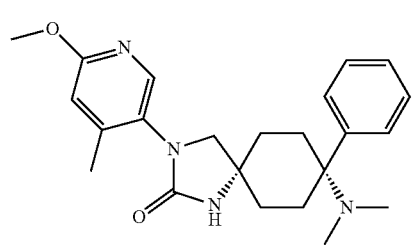
SC_3200
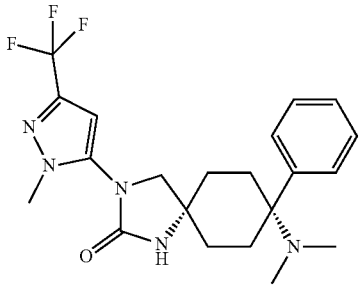
SC_3201
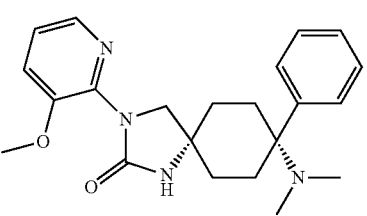
SC_3202
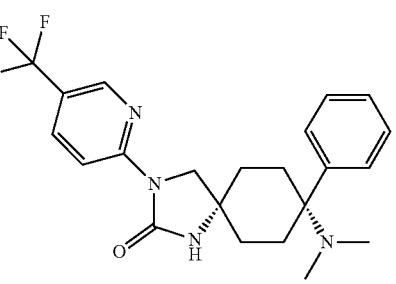
SC_3203
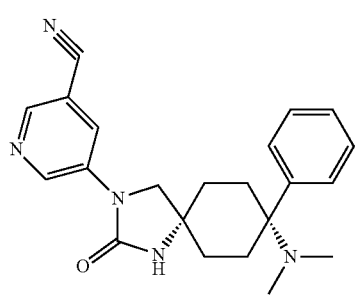
SC_3204
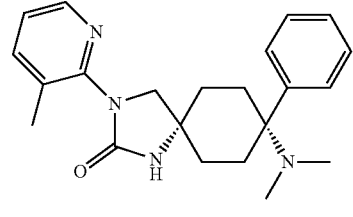
SC_3205
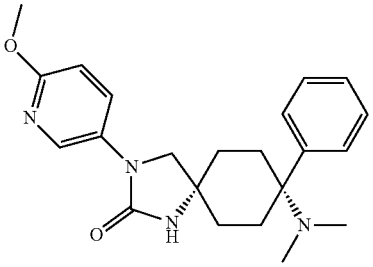

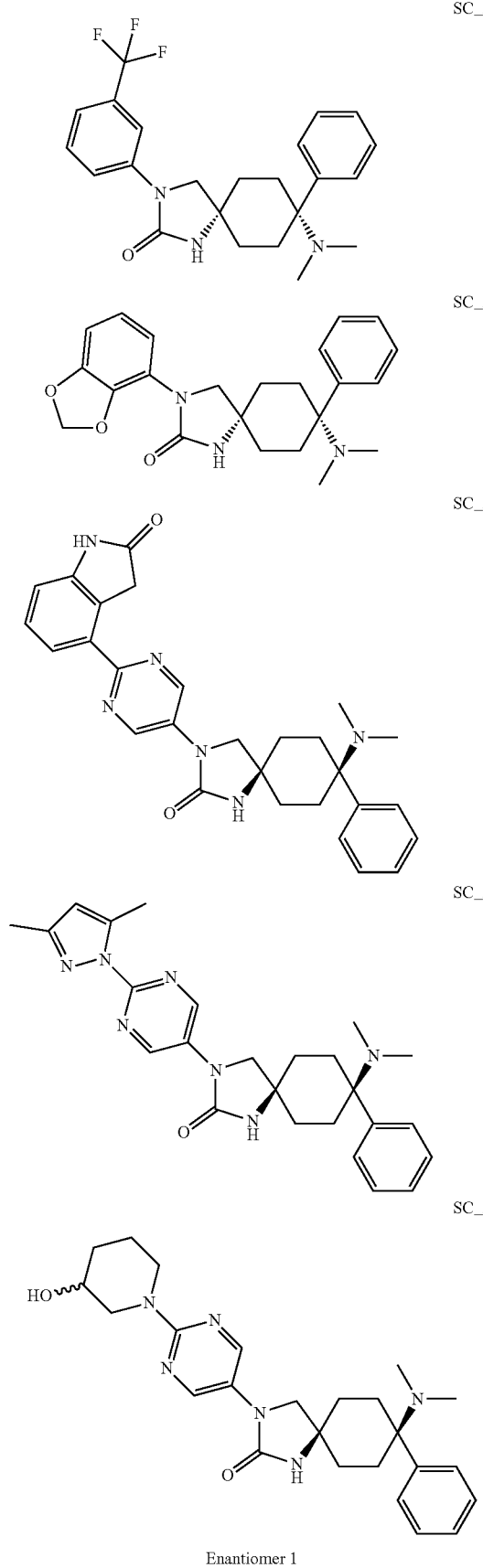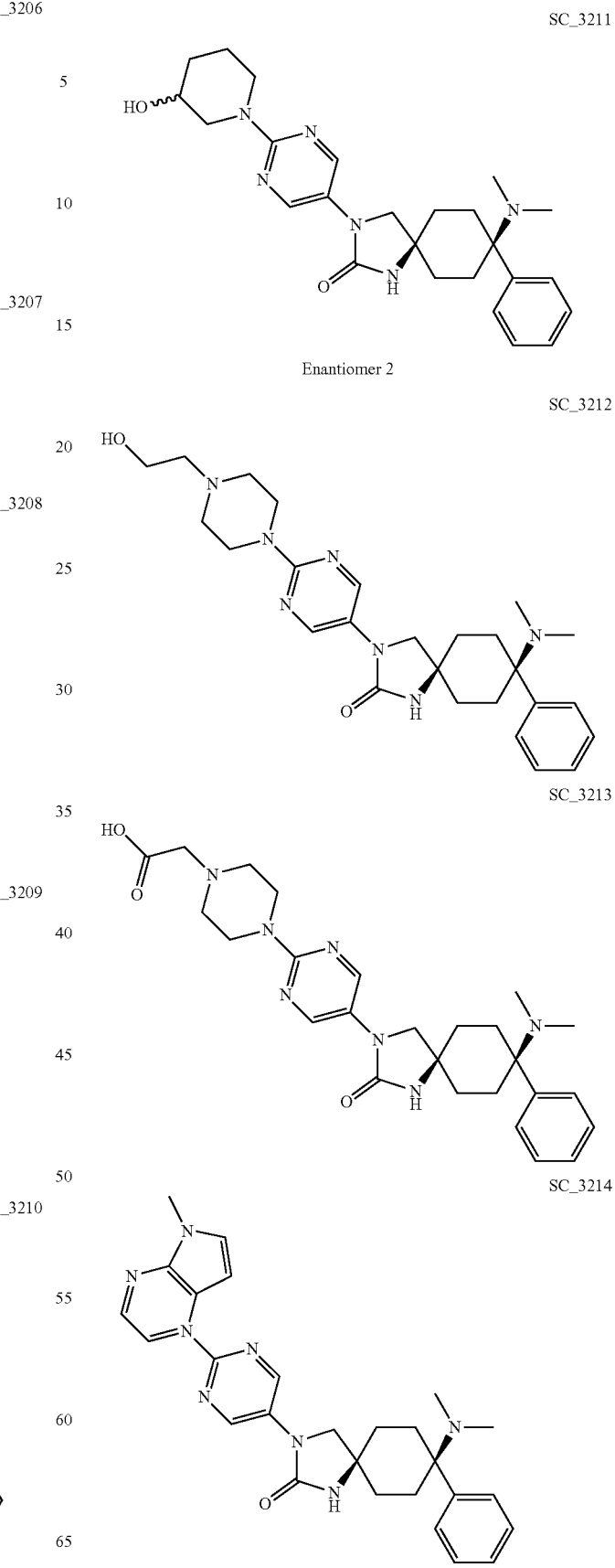

307                                        308
SC_3215                                        SC_3216
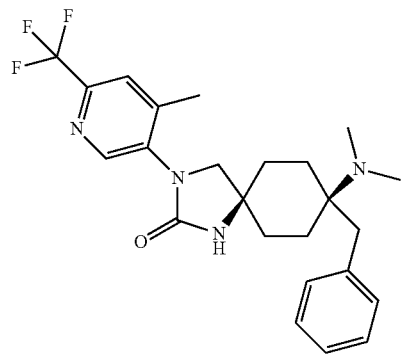 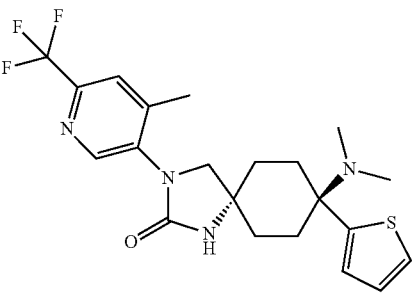
SC_3217                                        SC_3218
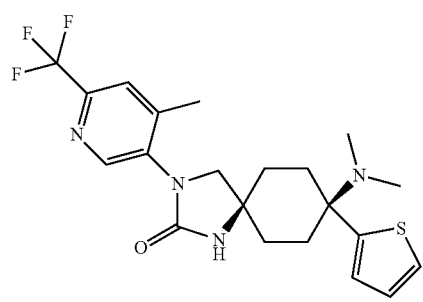 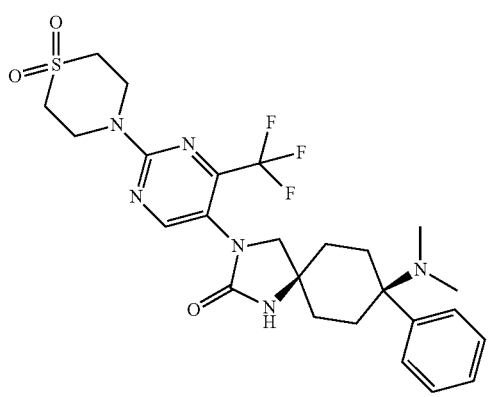
SC_3219                                        SC_3220
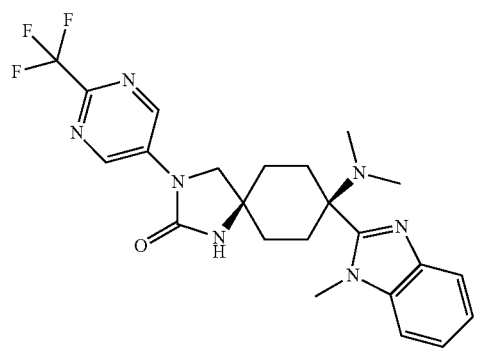 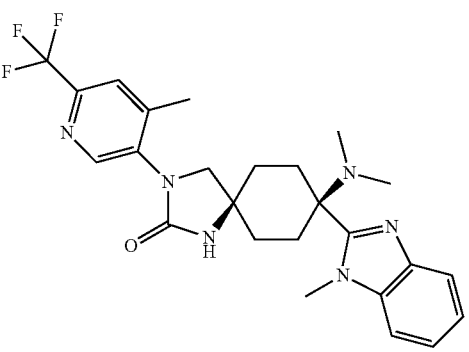
SC_3221                                        SC_3222
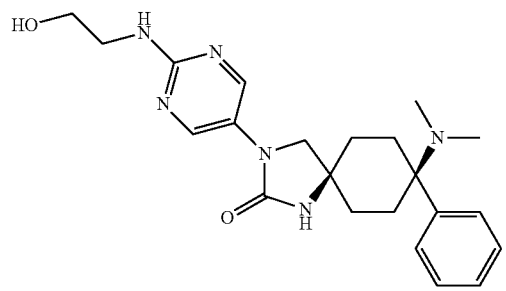 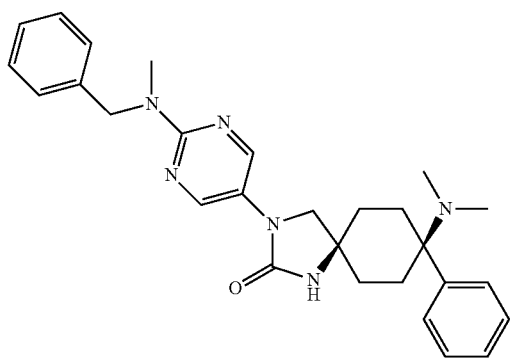

-continued
SC_3223
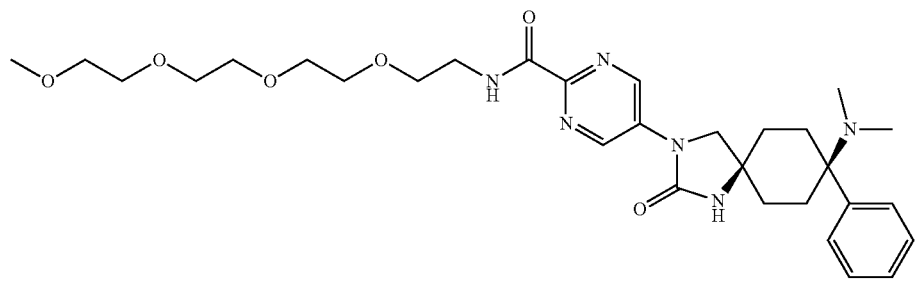
SC_3224
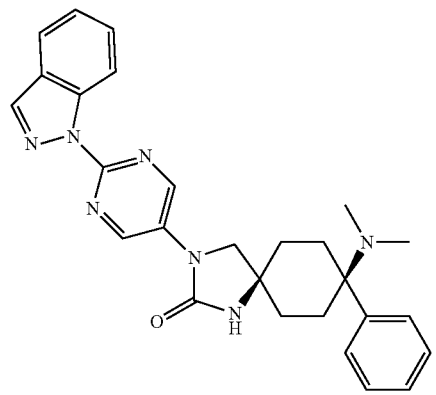
SC_3225
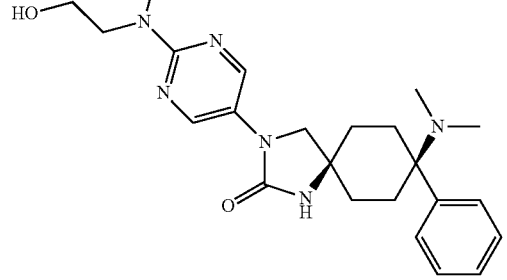
SC_3226
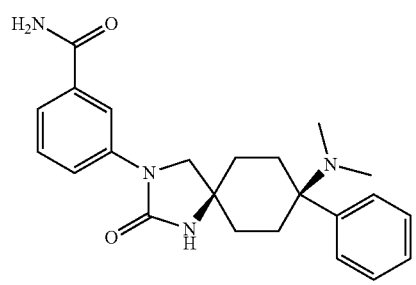
SC_3227
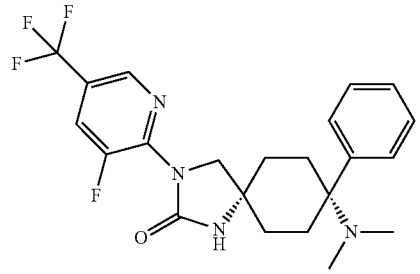
SC_3228
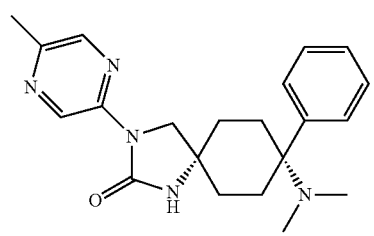
SC_3229
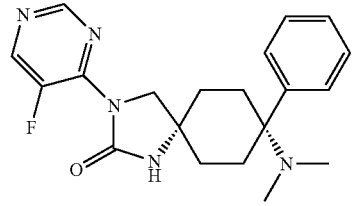
SC_3230
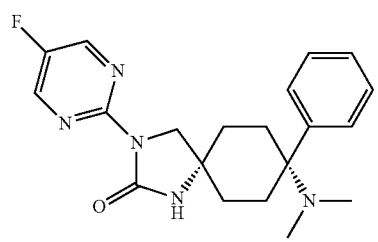
SC_3231
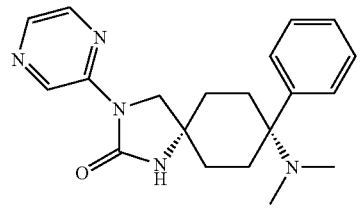

-continued
SC_3232
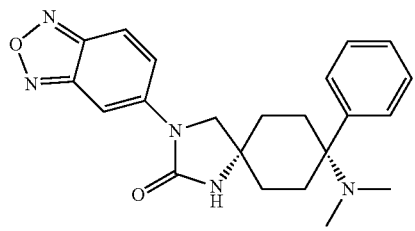
SC_3233
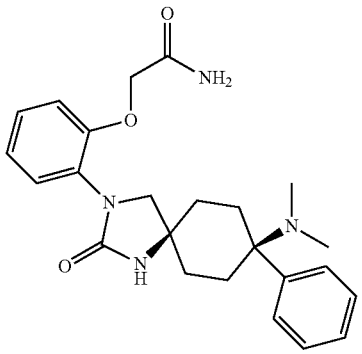
SC_3234
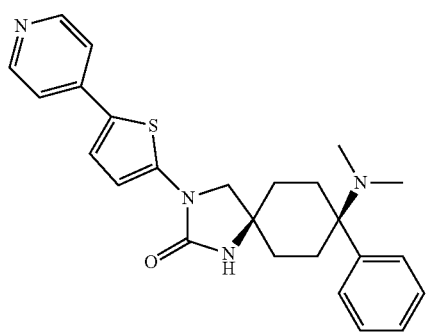
SC_3235
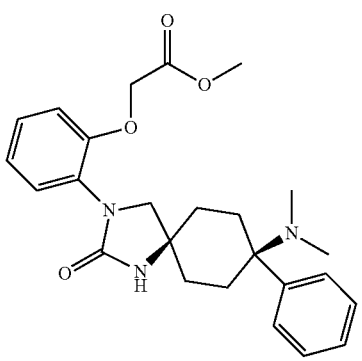
SC_3236
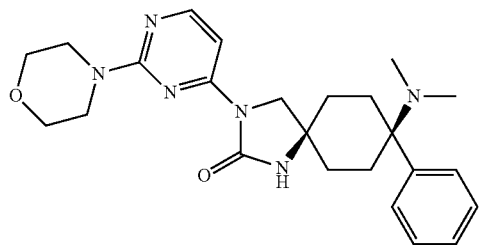
SC_3237
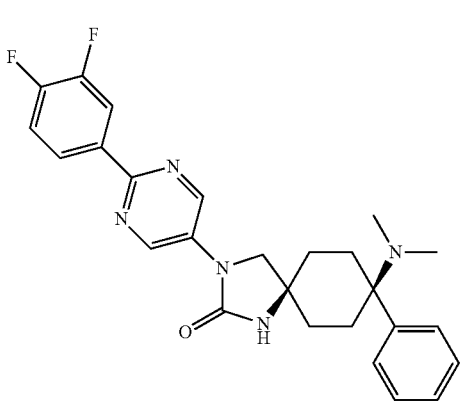
SC_3238
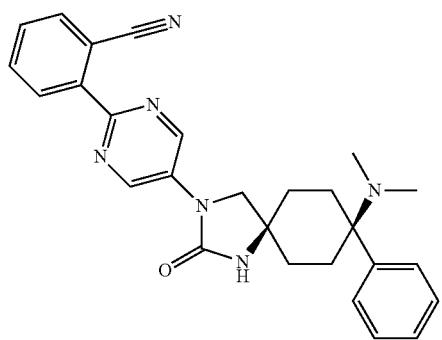
SC_3239
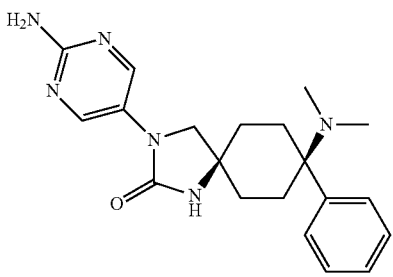

-continued
SC_3240
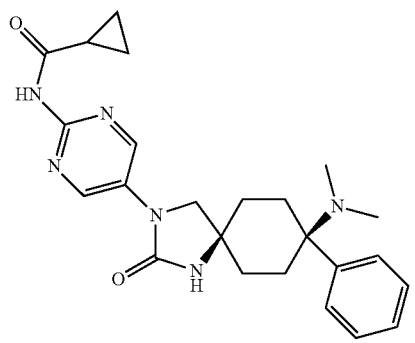
SC_3241
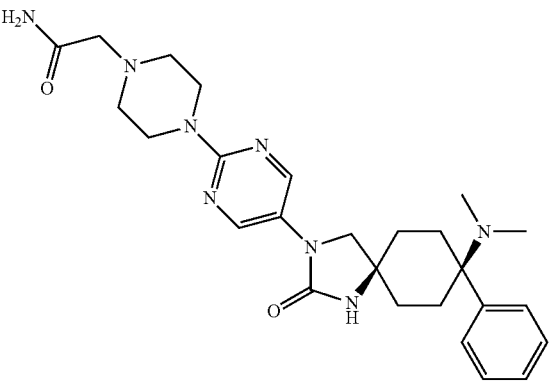
SC_3242
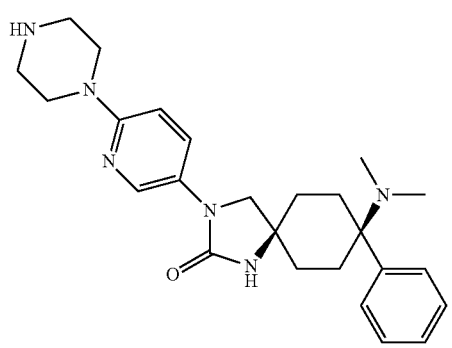
SC_3243
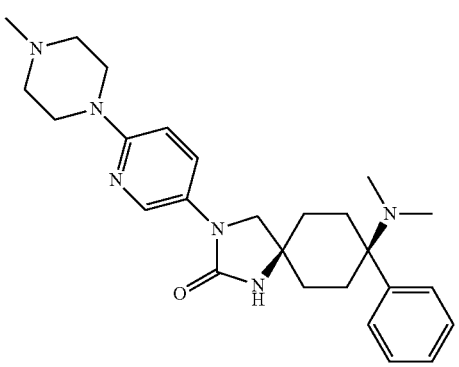
SC_3244
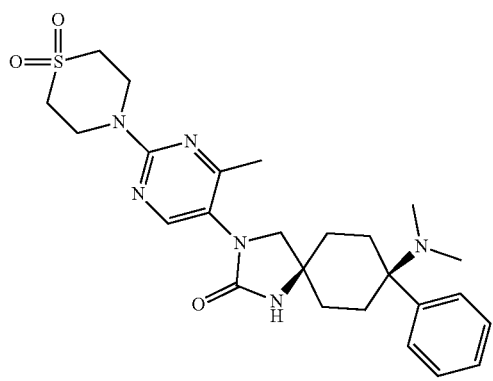
SC_3245
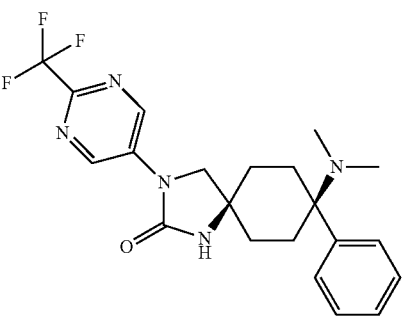
SC_3246
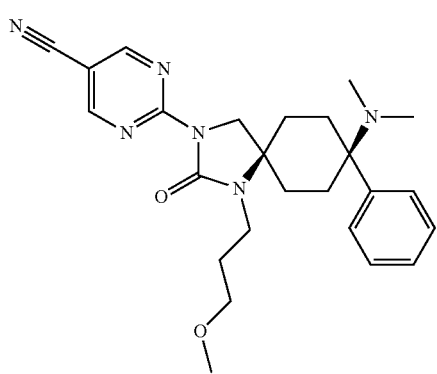
SC_3247
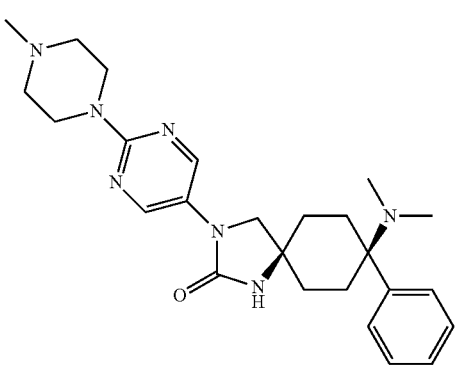

SC_3248 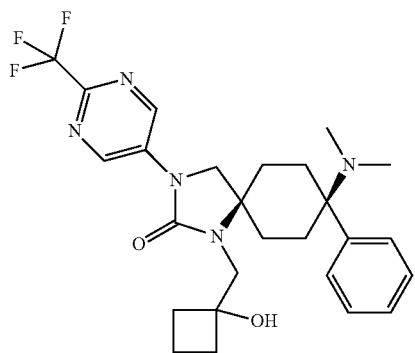 SC_3249 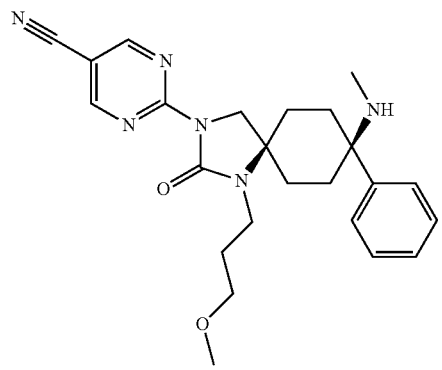
SC_3250 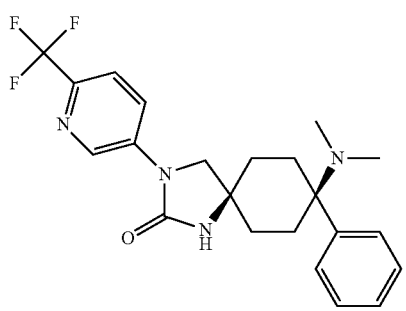 SC_3251 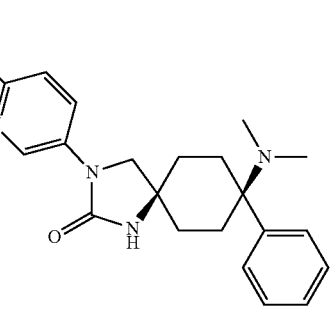
SC_3252 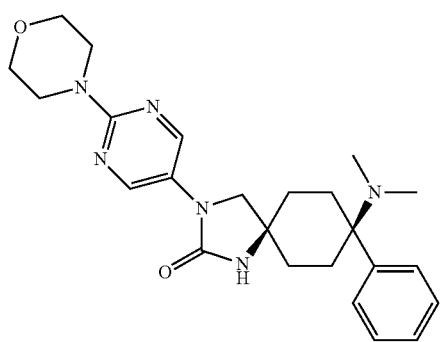 SC_3253 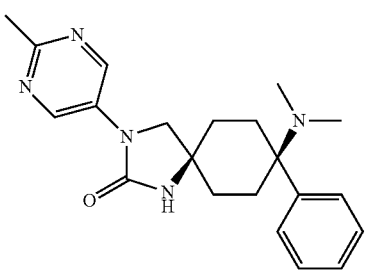
SC_3254 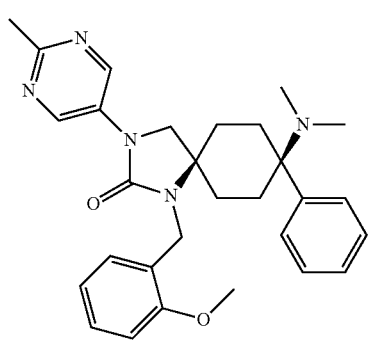 SC_3255 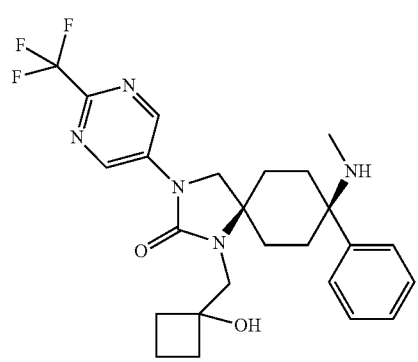

-continued
SC_3256
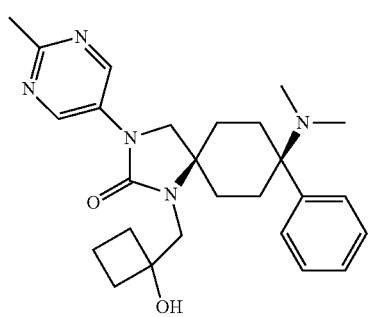
SC_3257
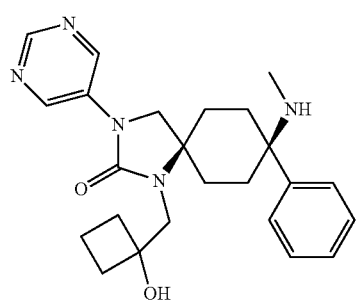
SC_3258
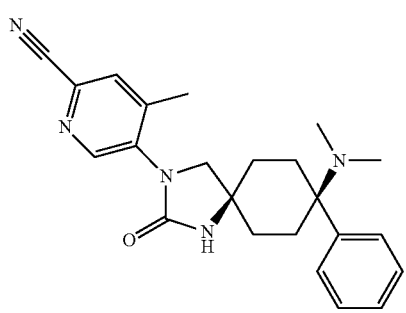
SC_3259
SC_3260
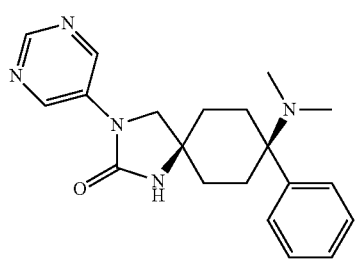
SC_3261
SC_3262
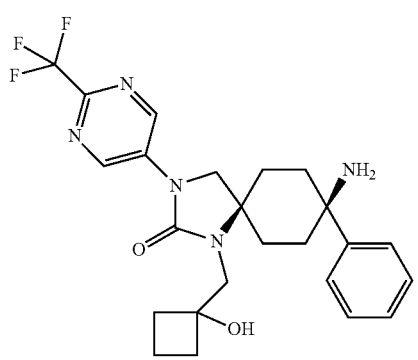
SC_3263
SC_3264
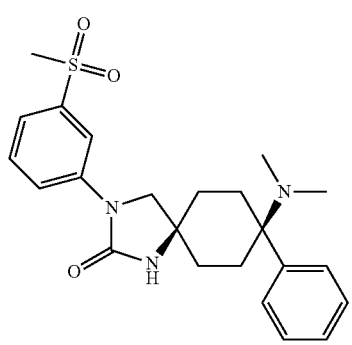
SC_3265
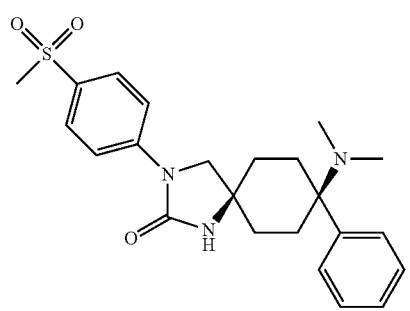

-continued
SC_3266
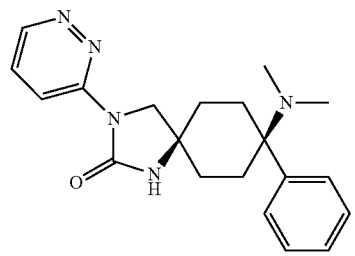
SC_3267
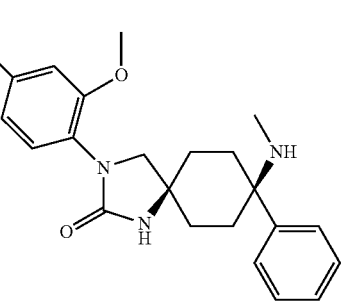
SC_3268
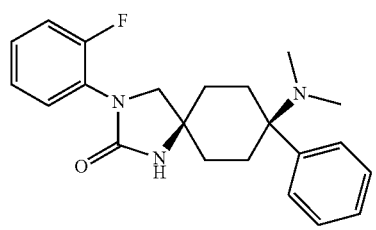
SC_3269
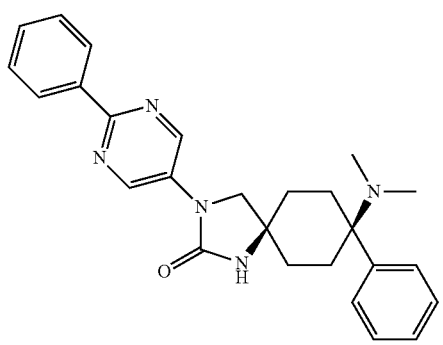
SC_3270
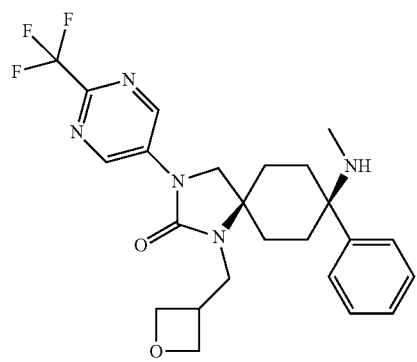
SC_3271
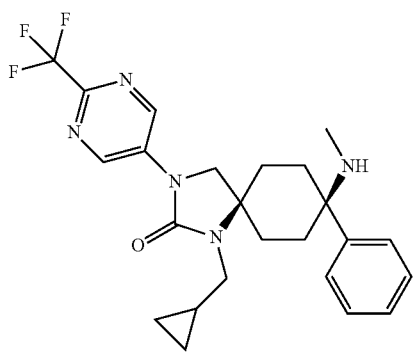
SC_3272
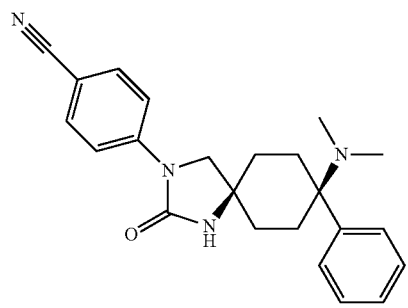
SC_3273
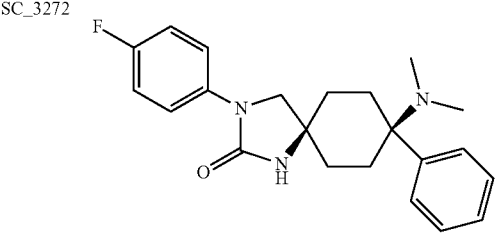

-continued
SC_3274
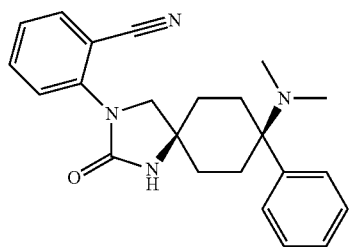
SC_3275
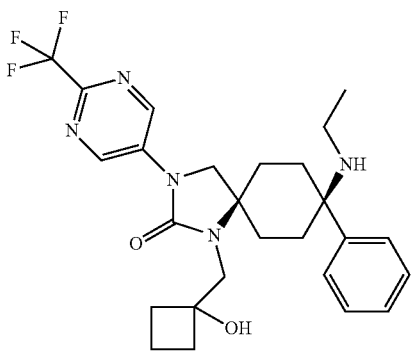
SC_3276
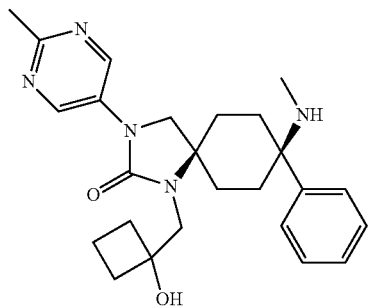
SC_3277
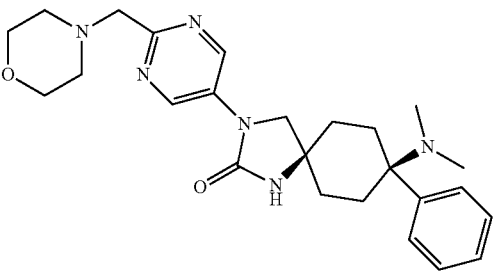
SC_3278
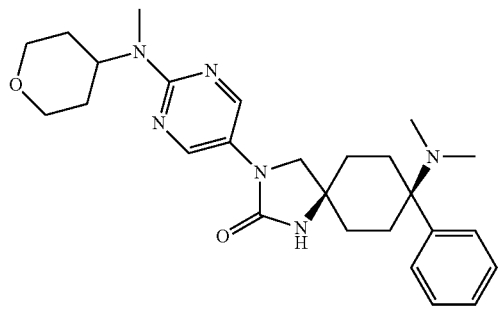
SC_3279
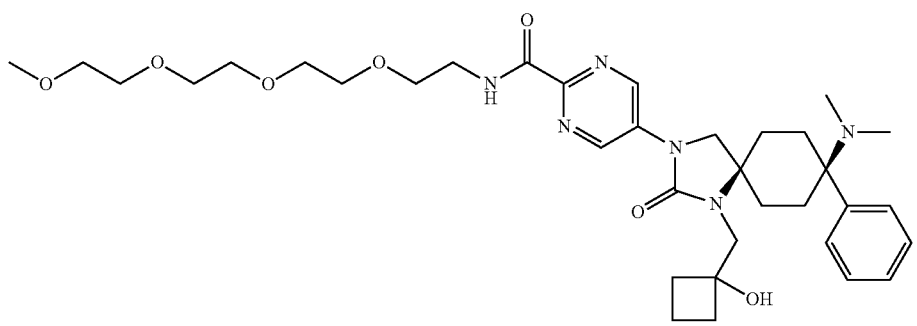
SC_3280
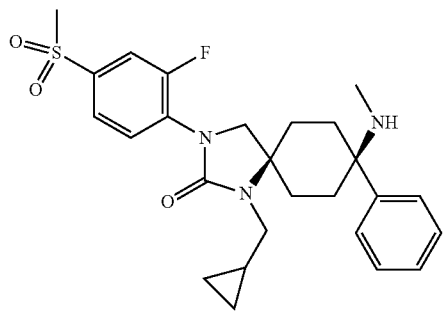
SC_3281
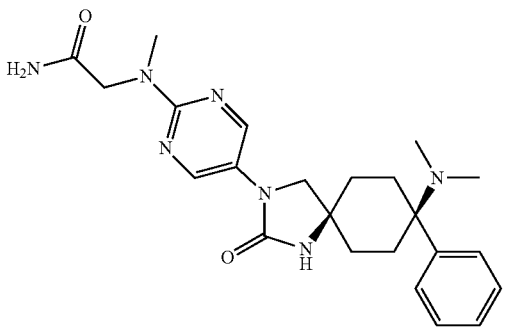

-continued
SC_3282
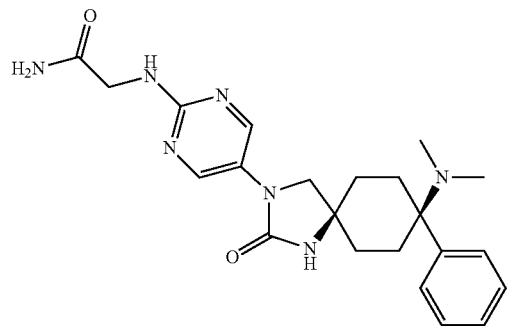
SC_3283
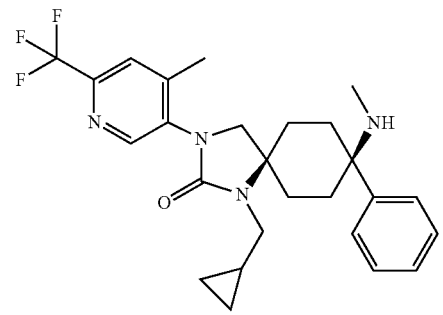
SC_3284
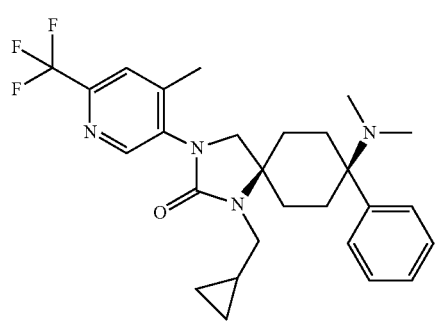
SC_3285
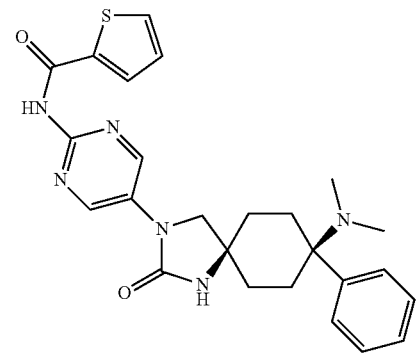
SC_3286
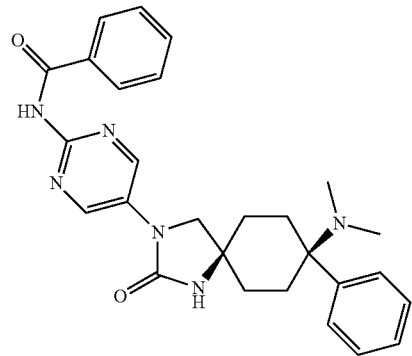
SC_3287
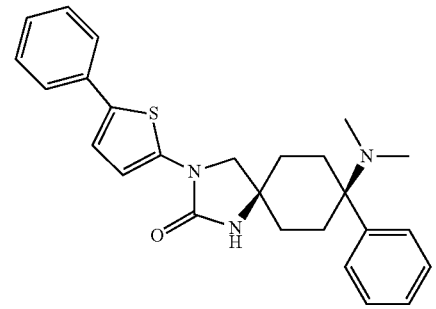
SC_3288
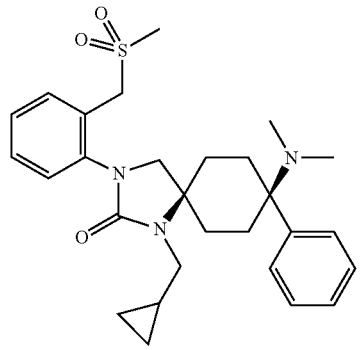
SC_3289
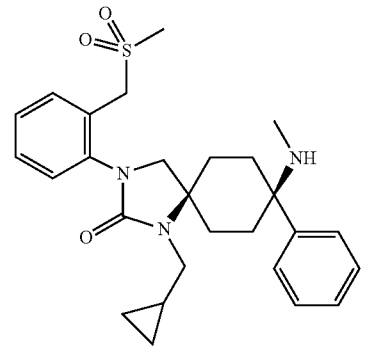

-continued
SC_3290
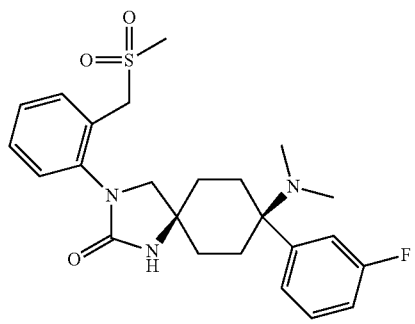
SC_3291
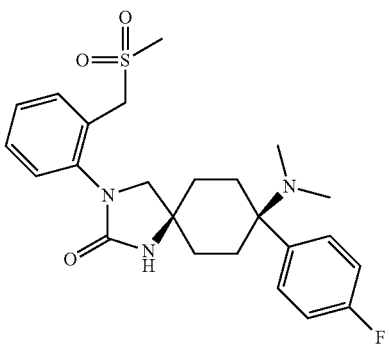
SC_3292
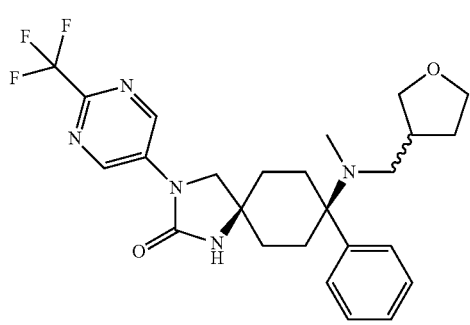
Enantiomer 1
SC_3293
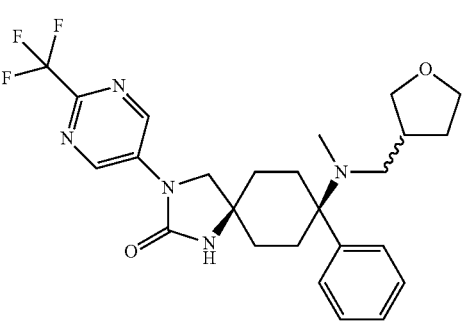
Enantiomer 2
SC_3294
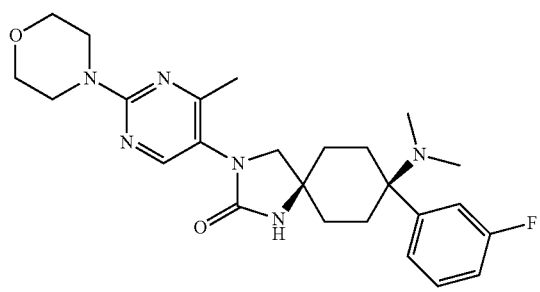
SC_3295
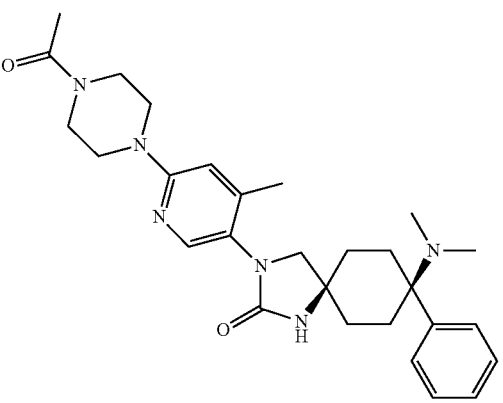
SC_3296
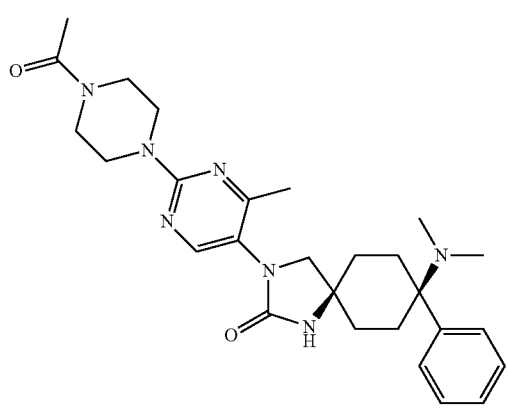
SC_3297
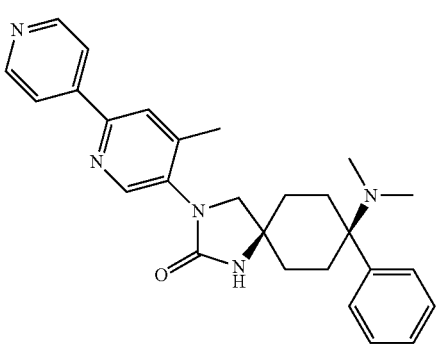

-continued
SC_3298
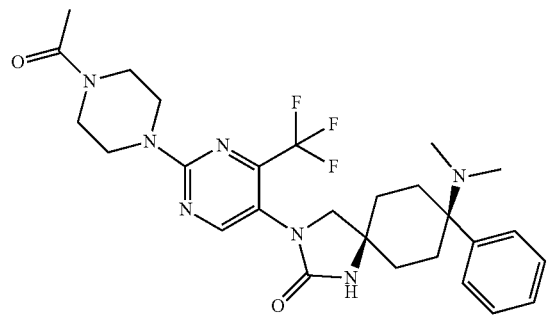
SC_3299
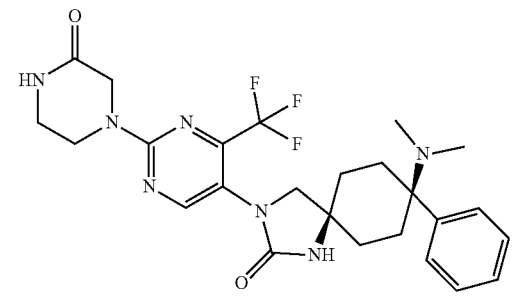
SC_3300
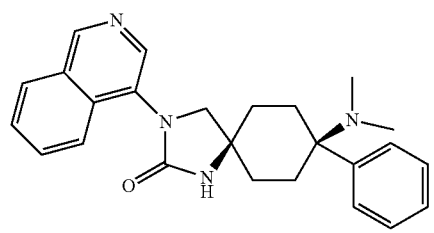
SC_3301
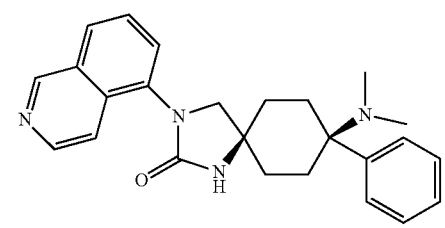
SC_3302
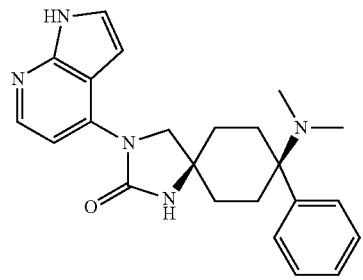
SC_3303
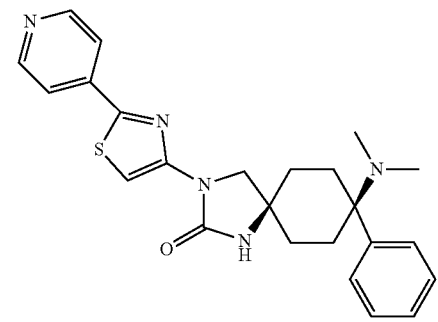
SC_3304
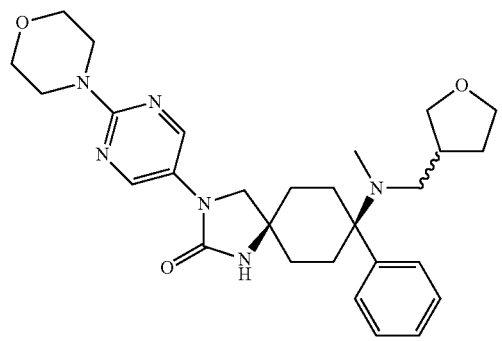
Enantiomer 1
SC_3305
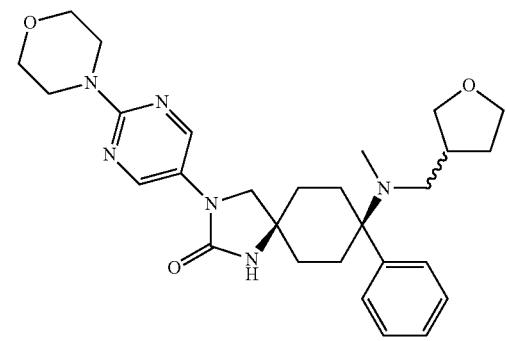
Enantiomer 2
SC_3306
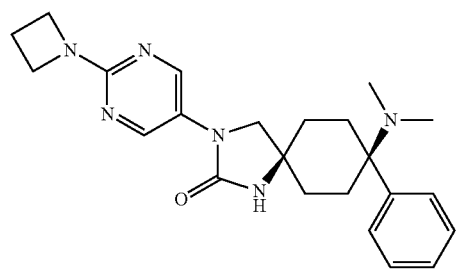
SC_3307
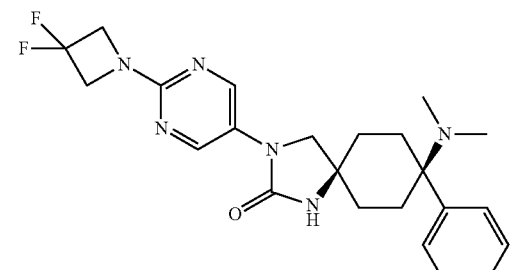

-continued
SC_3308
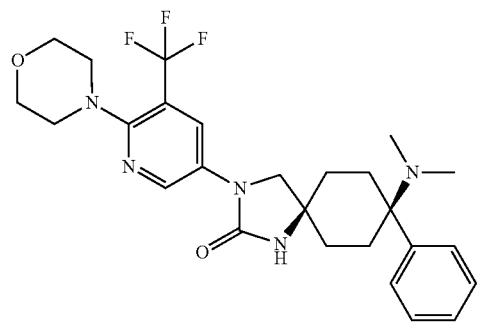
SC_3309
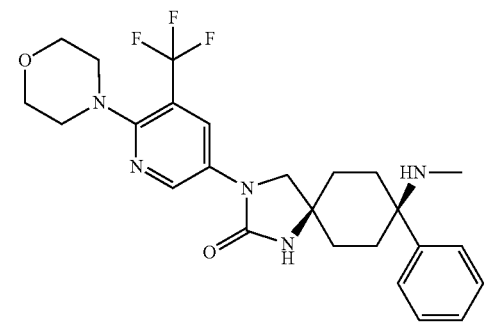
SC_3310
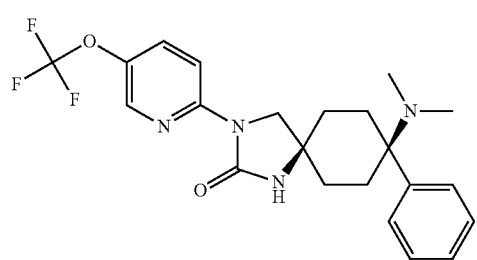
SC_3311
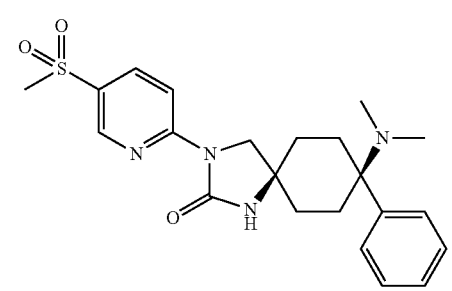
SC_3312
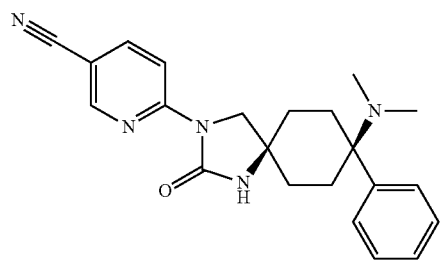
SC_3313
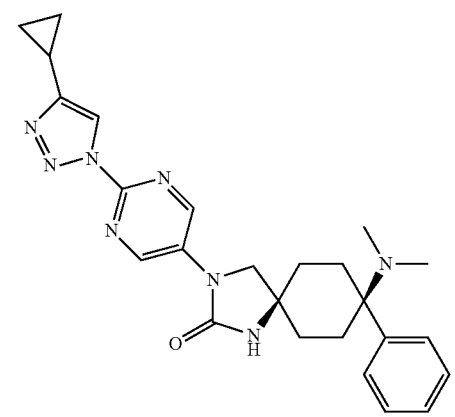
SC_3314
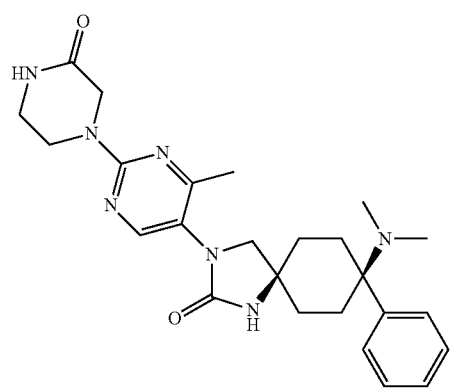
SC_3315
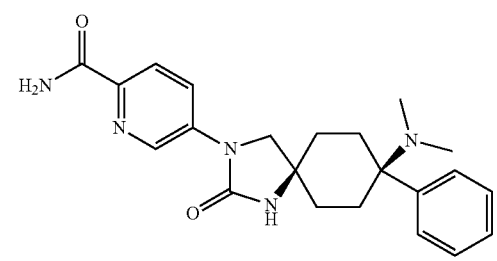

-continued
SC_3316
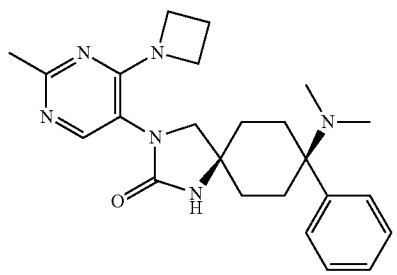
SC_3317
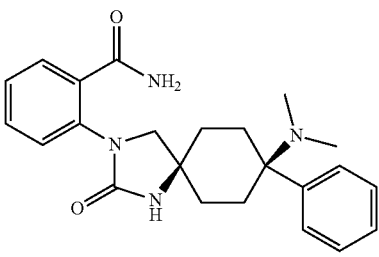
SC_3318
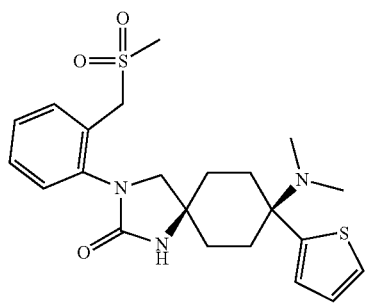
SC_3319
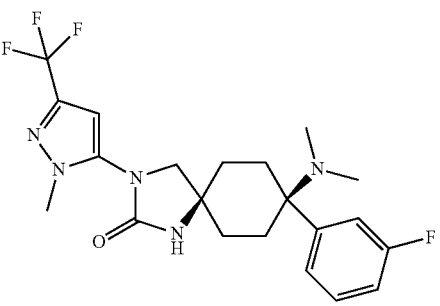
SC_3320
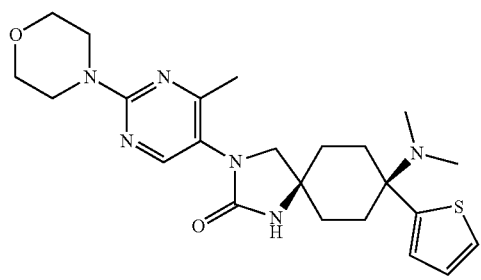
SC_3321
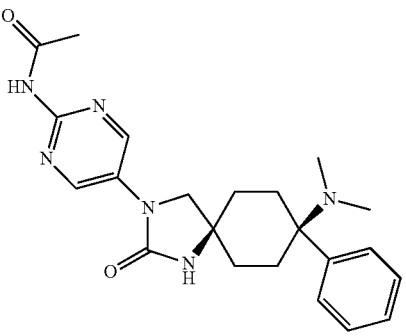
SC_3322
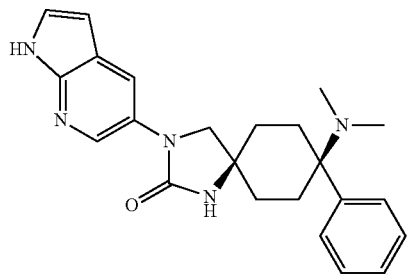
SC_3323
SC_3324
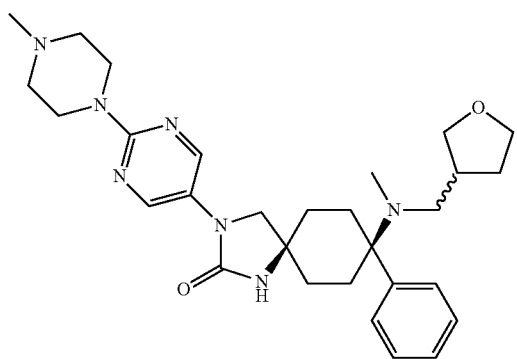
SC_3325
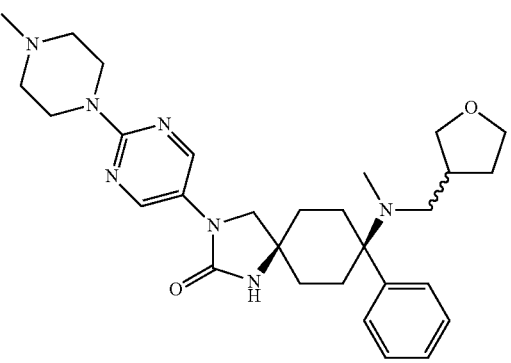
Enantiomer 1        Enantiomer 2

-continued
SC_3326
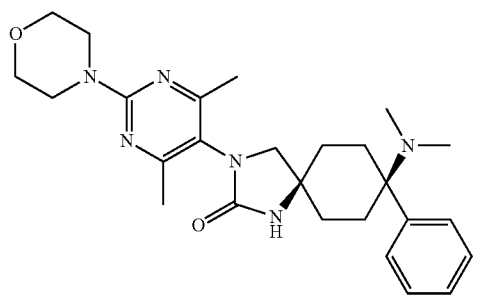
SC_3327
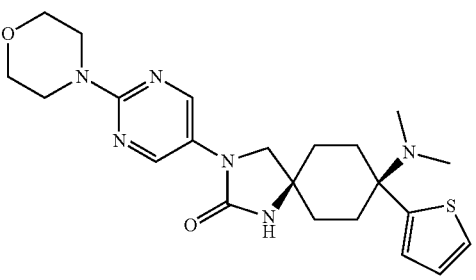
SC_3328
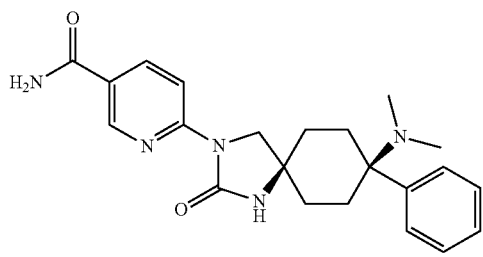
SC_3329
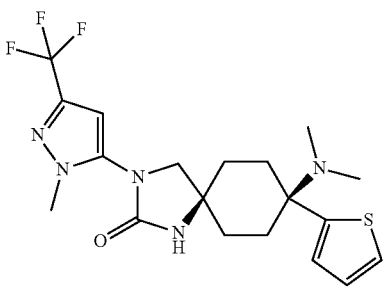
SC_3330
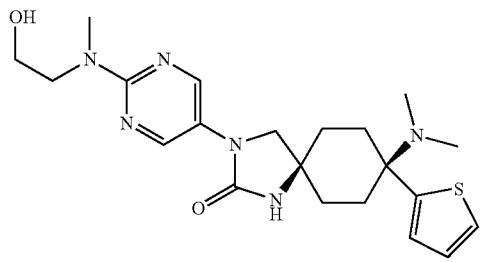
SC_3331
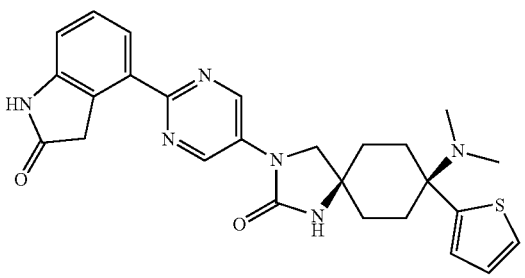
SC_3332
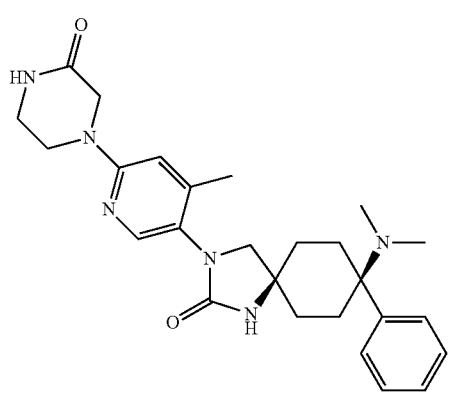
SC_3333
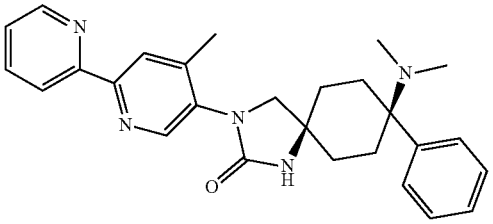
SC_3334
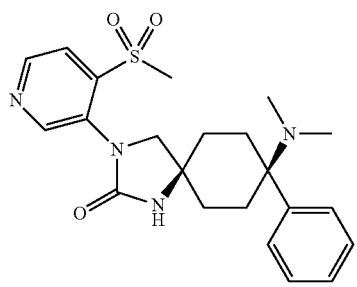
SC_3335
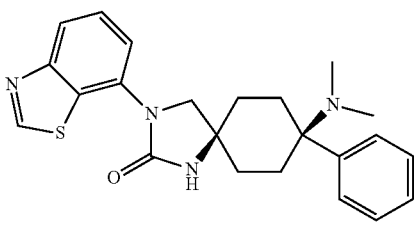

SC_3336
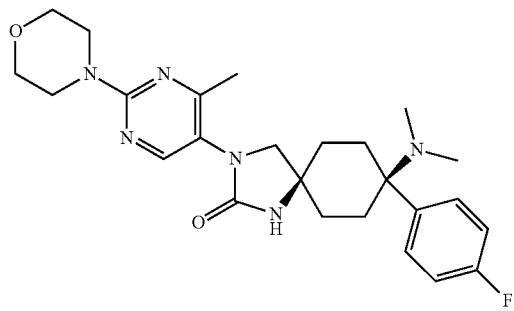
SC_3337
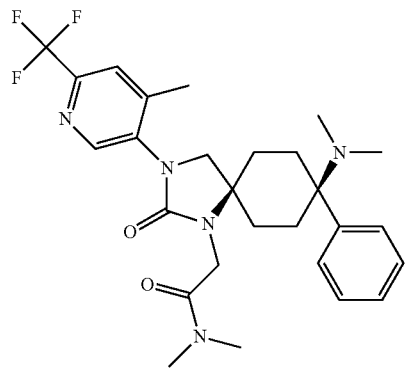
SC_3338
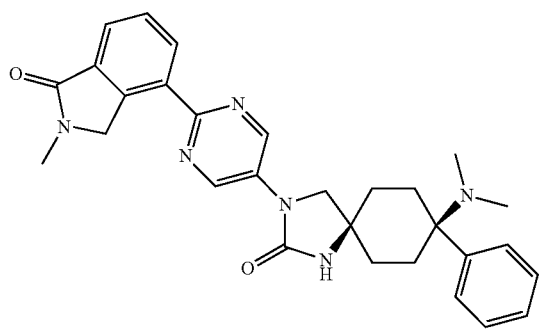
SC_3339
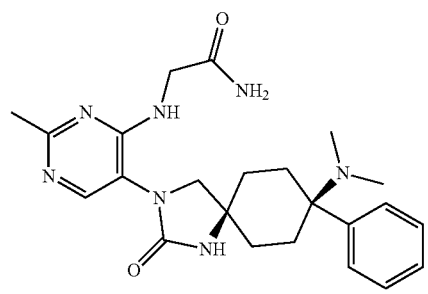
SC_3340
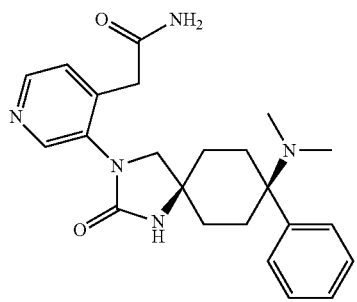
SC_3341
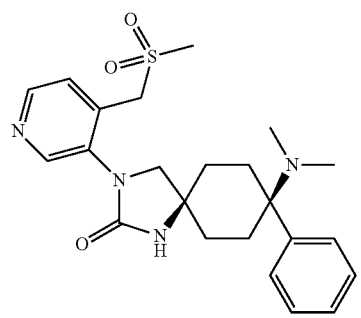
SC_3342
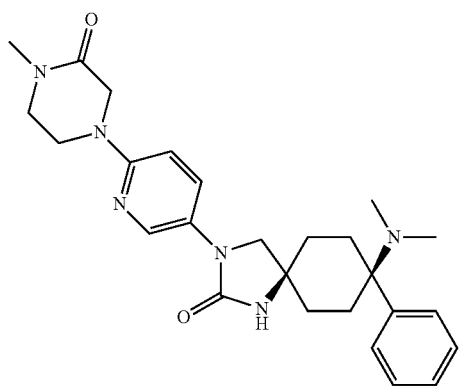
SC_3343
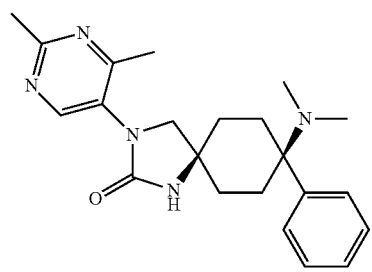

-continued
SC_3344
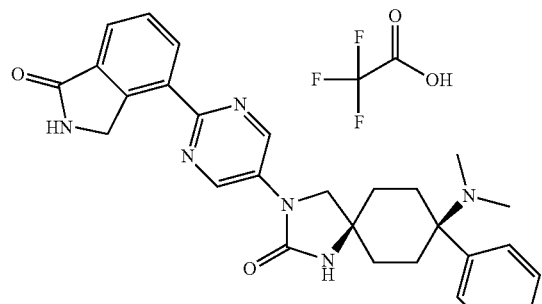
SC_3345
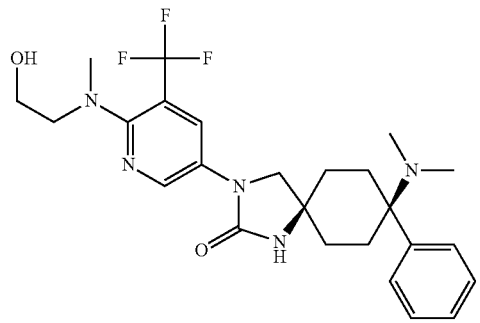
SC_3346
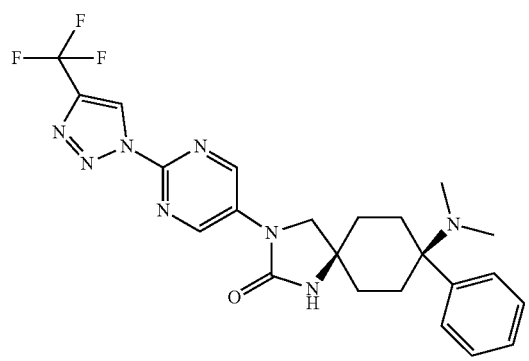
SC_3347
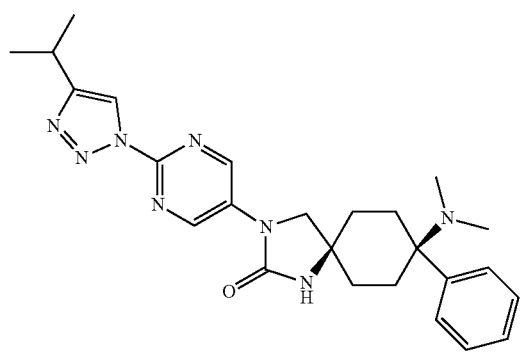
SC_3348
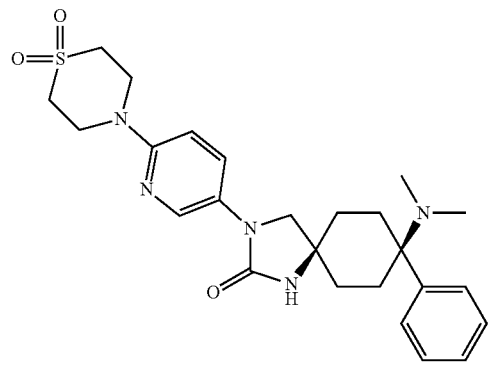
SC_3349
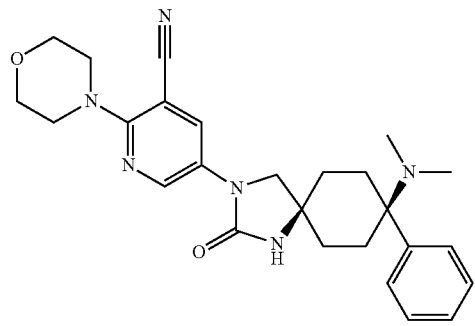
SC_3350
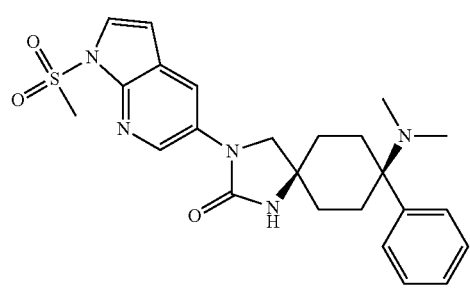
SC_3351
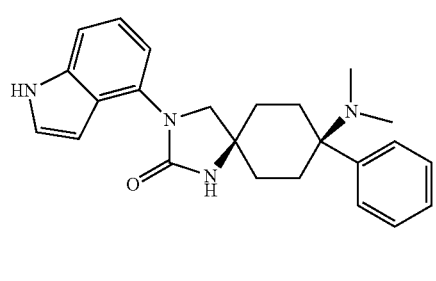
SC_3352
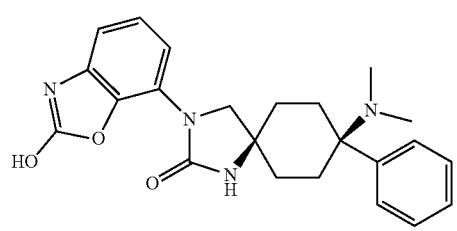
SC_3353
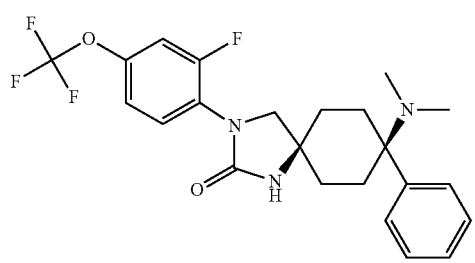

-continued
SC_3354
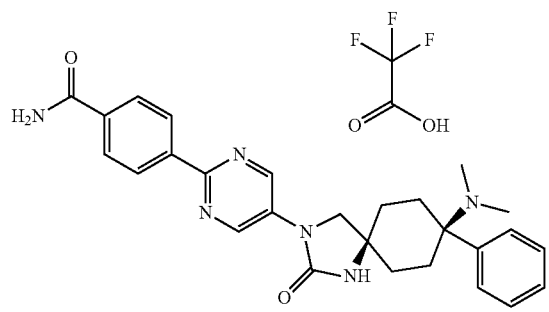
SC_3355
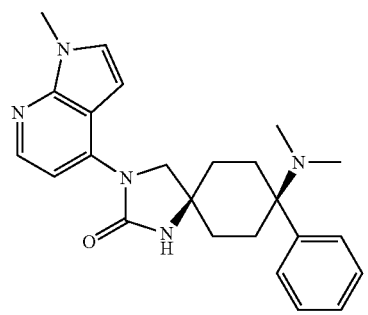
SC_3356
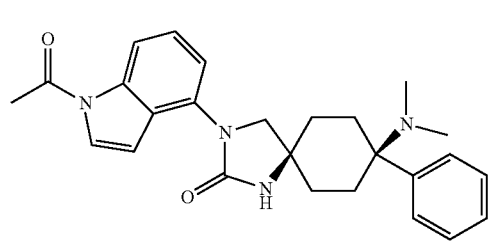
SC_3357
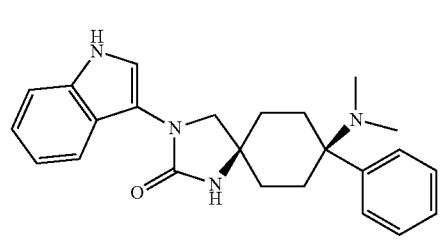
SC_3358
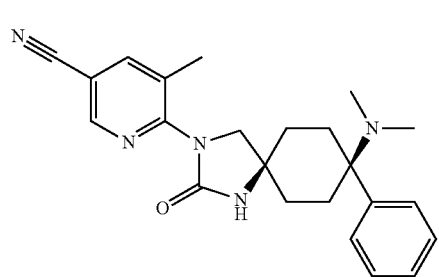
SC_3359
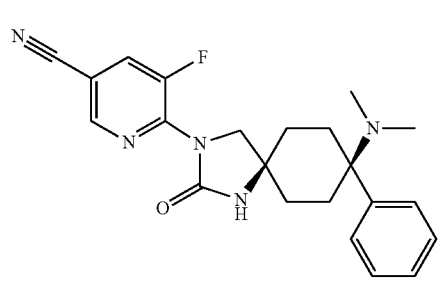
SC_3360
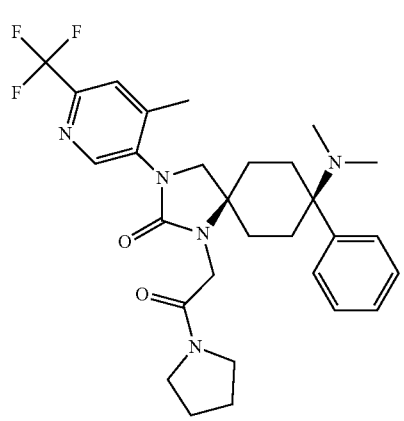
SC_3361
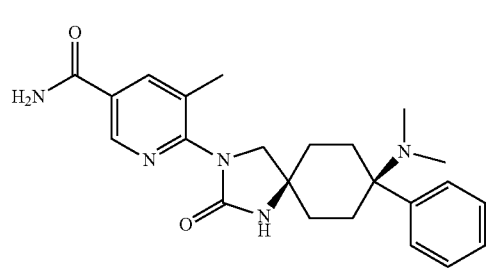
SC_3362
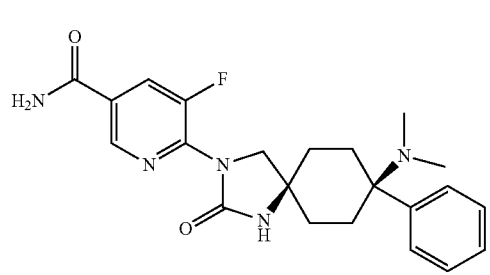
SC_3363
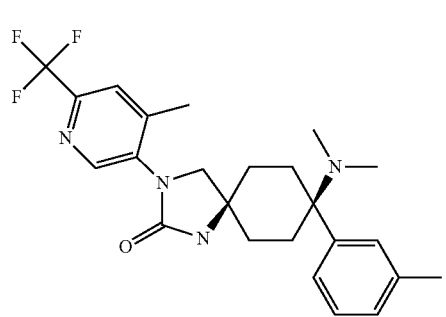

-continued
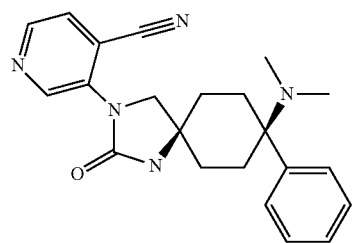
SC_3364
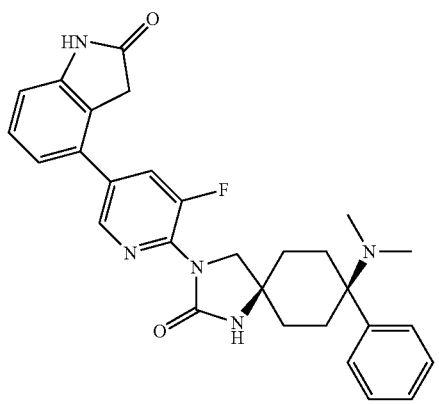
SC_3365
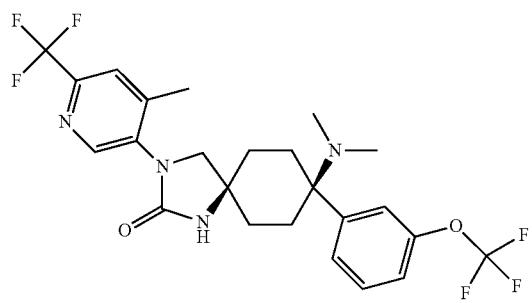
SC_3366
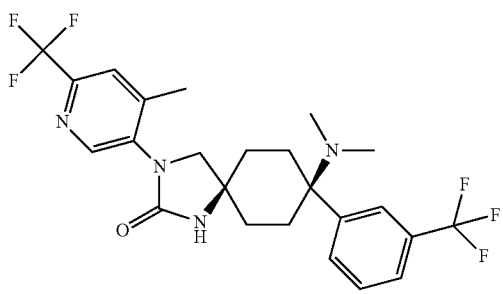
SC_3367
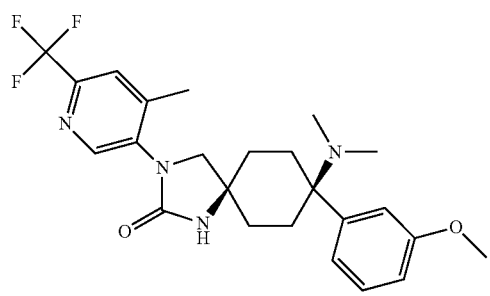
SC_3368
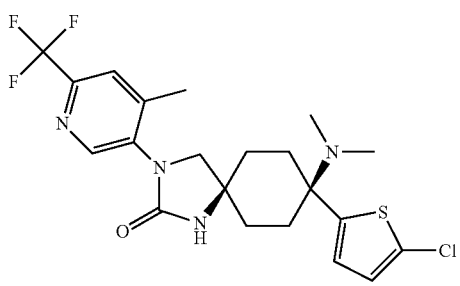
SC_3369
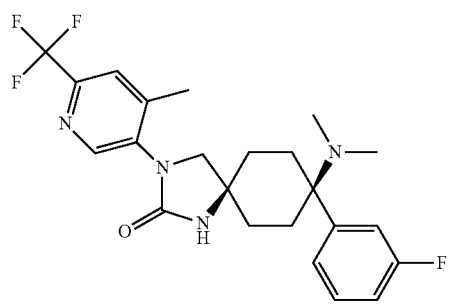
SC_3370
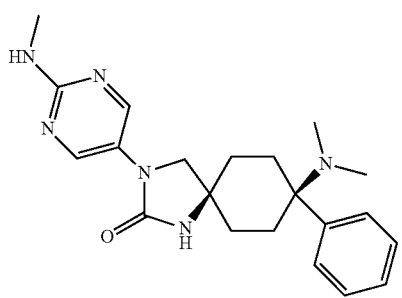
SC_3371
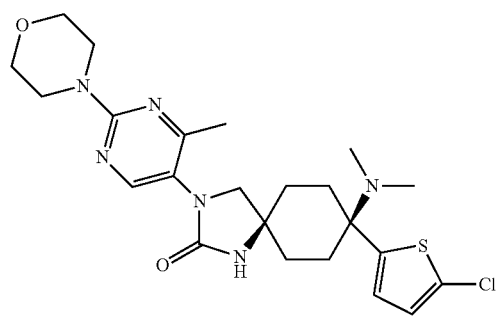
SC_3372
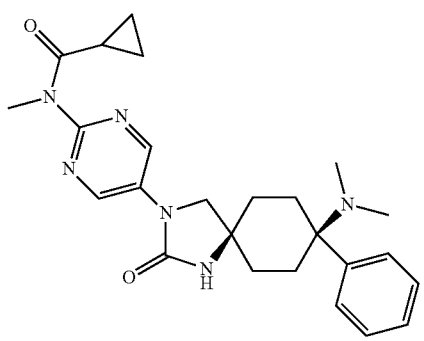
SC_3373

-continued
SC_3374
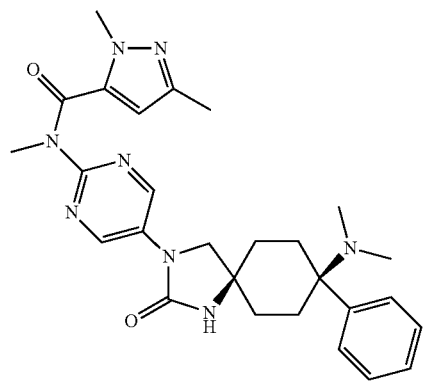
SC_3375
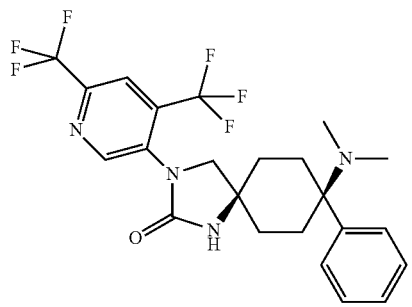
SC_3376
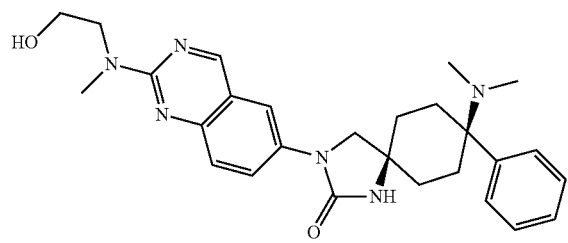
SC_3377
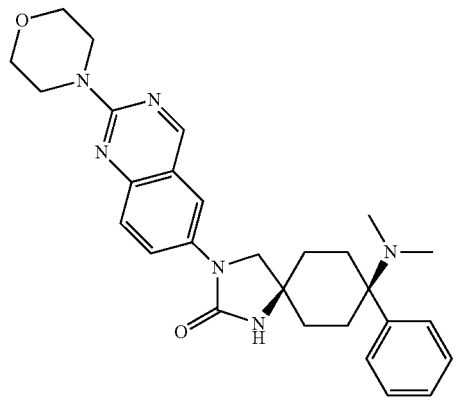
SC_3378
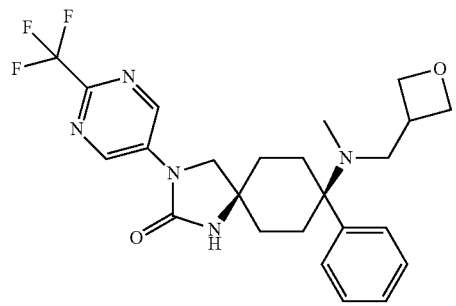
SC_3379
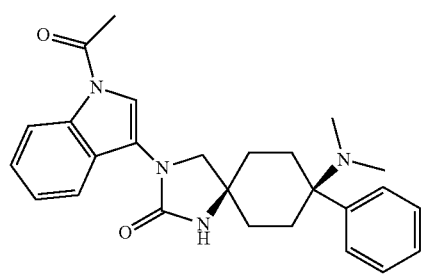
SC_3380
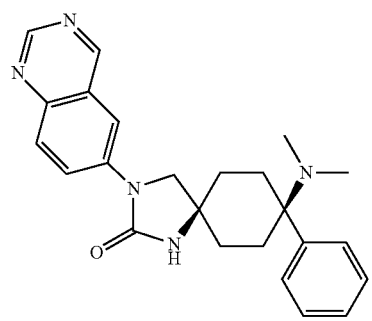
SC_3381
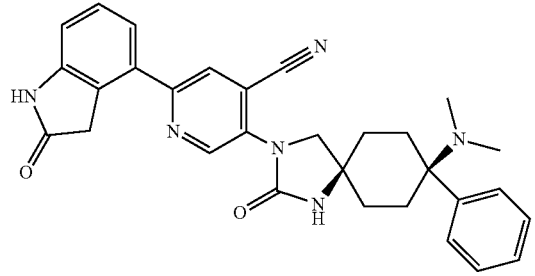

-continued
SC_3382
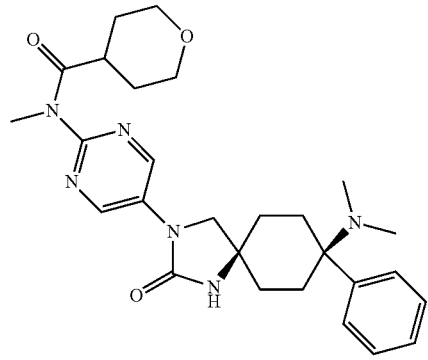
SC_3383
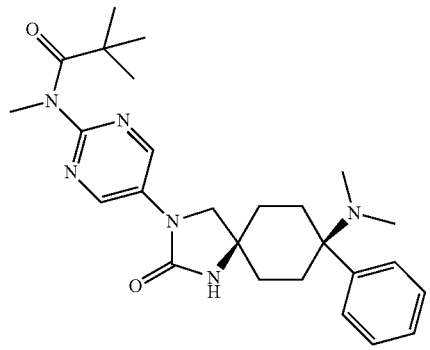
SC_3384
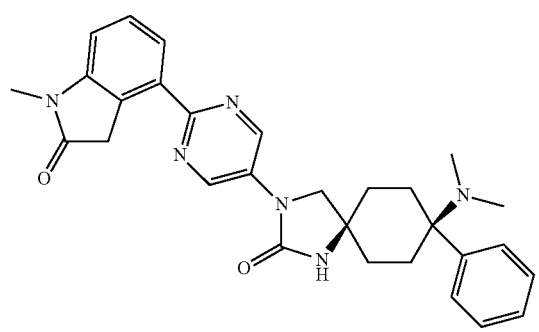
SC_3385
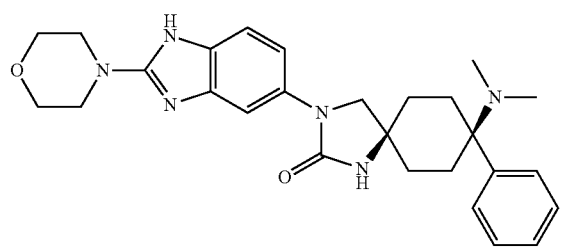
SC_3386
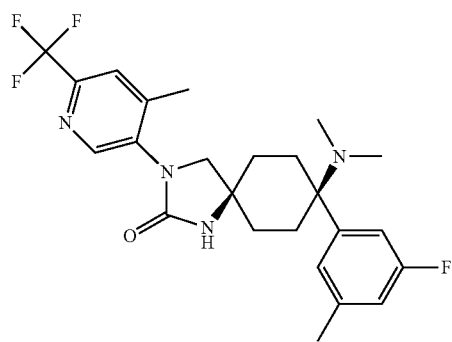
SC_3387
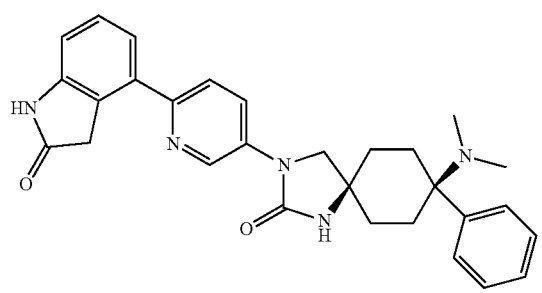
SC_3388
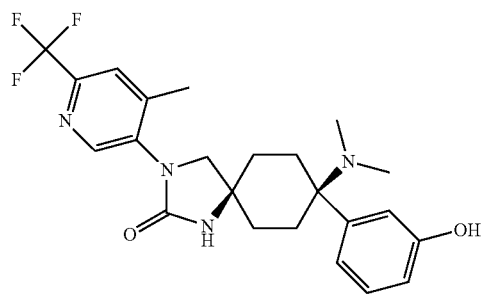
SC_3389
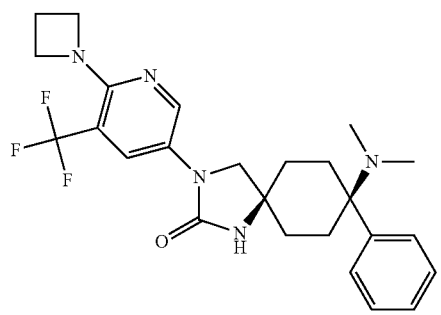

-continued
SC_3390
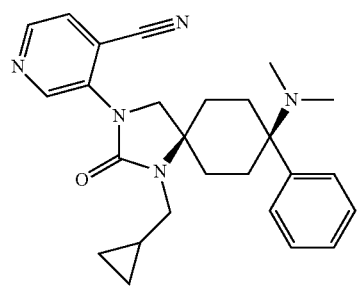
SC_3391
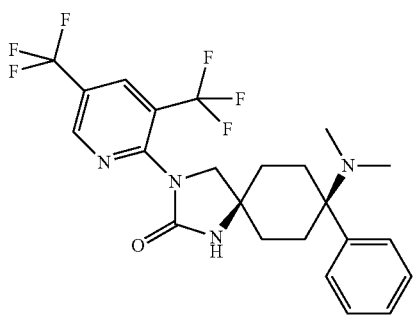
SC_3392
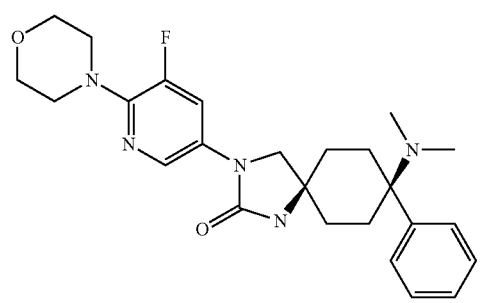
SC_3393
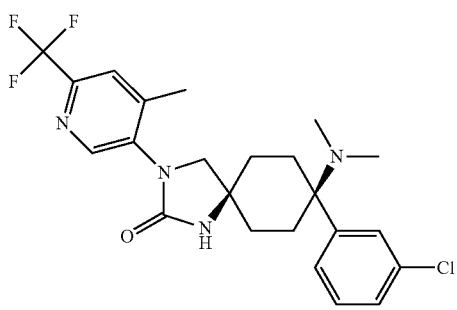
SC_3394
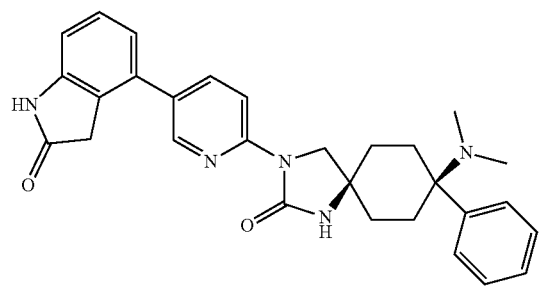
SC_3395
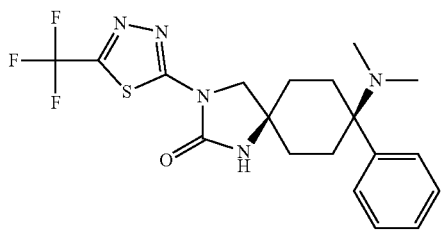
SC_3396
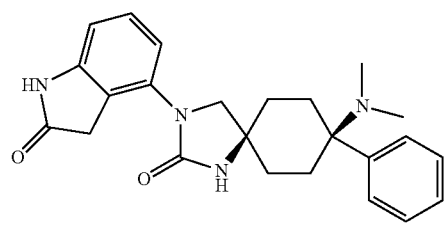
SC_3397
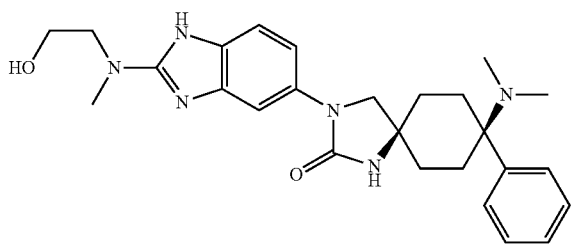
SC_3398
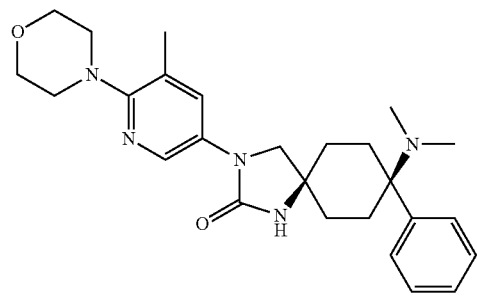
SC_3399
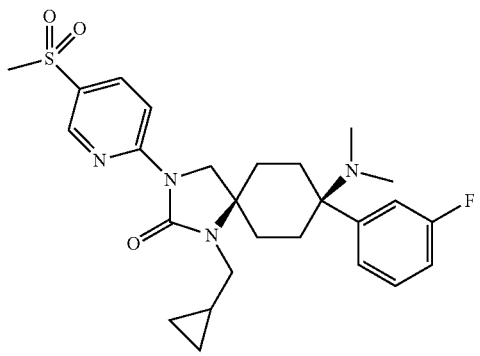

-continued
SC_3400
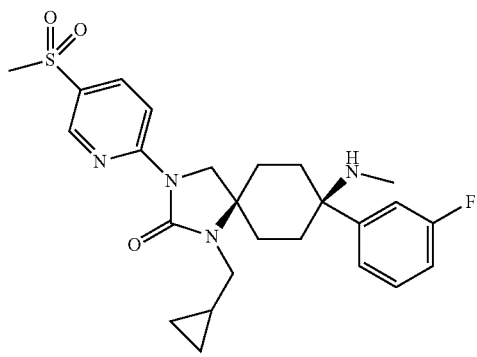
SC_3401
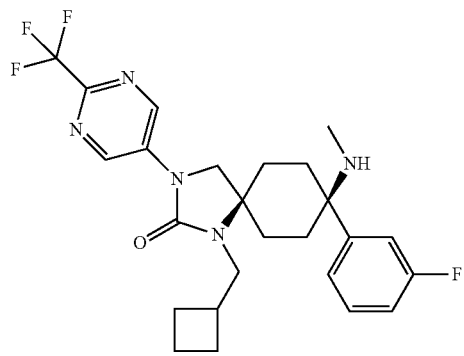
SC_3402
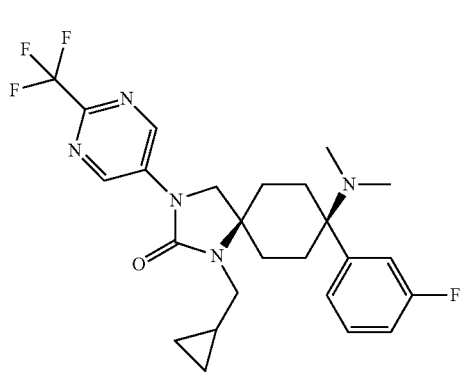
SC_3403
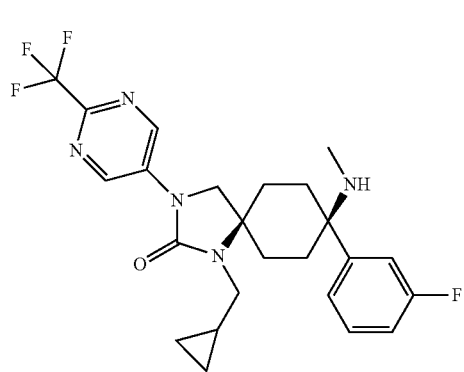
SC_3404
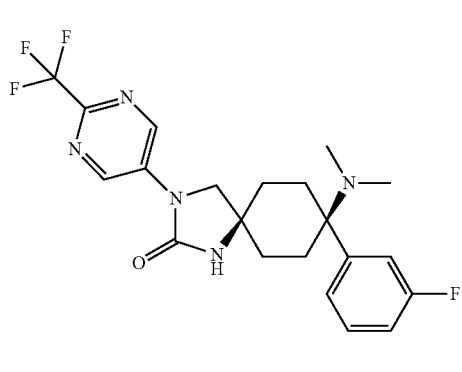
SC_3405
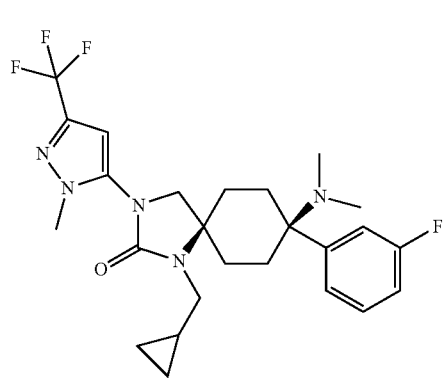
SC_3406
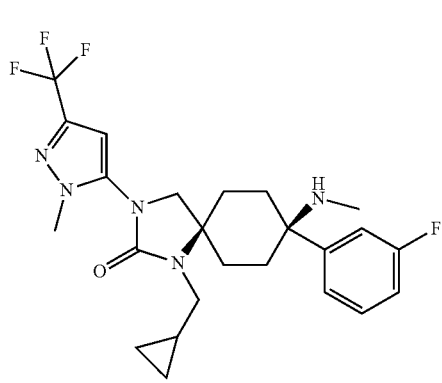
SC_3407
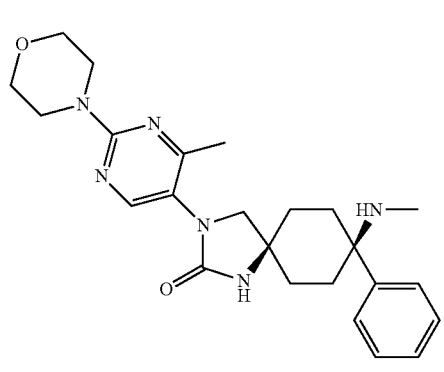

-continued
SC_3408
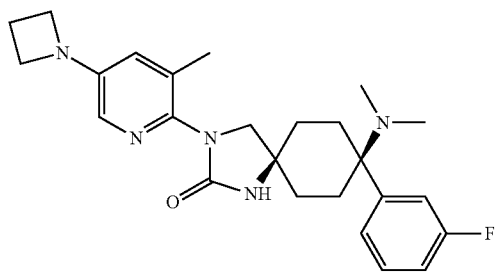
SC_3409
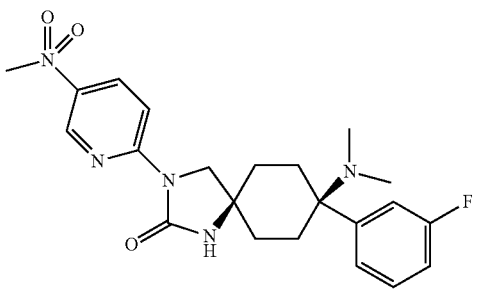
SC_3410
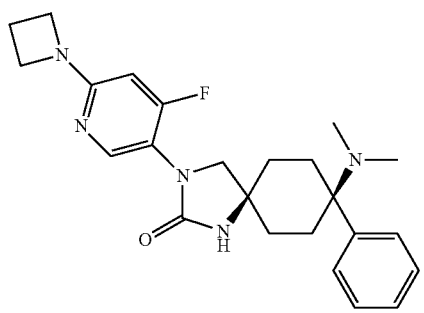
SC_3411
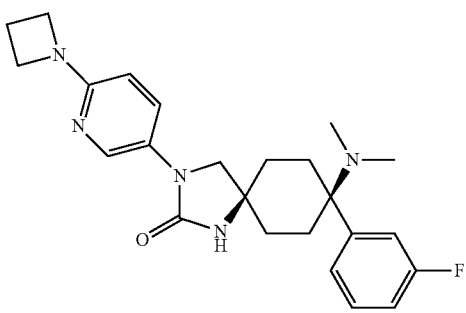
SC_3412
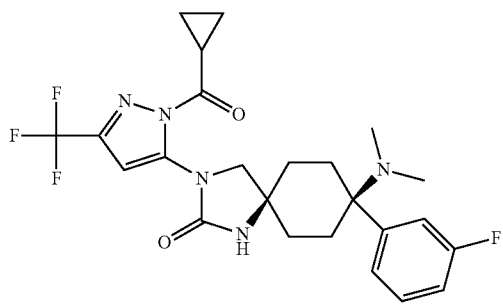
SC_3413
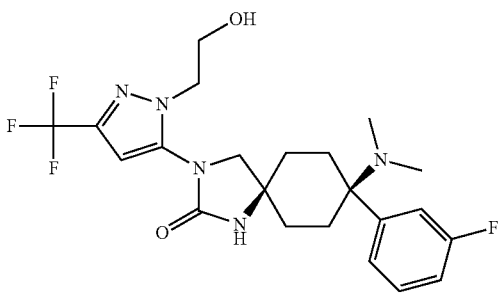
SC_3414
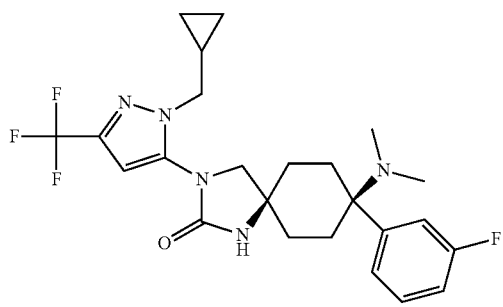
SC_3415
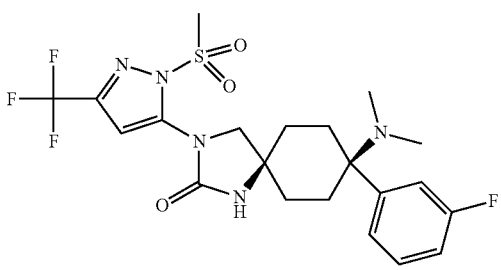
SC_3416
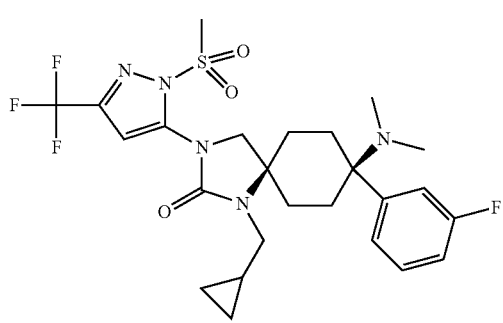
SC_3417
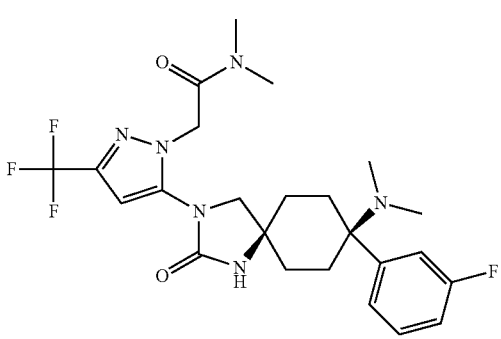

-continued
SC_3418
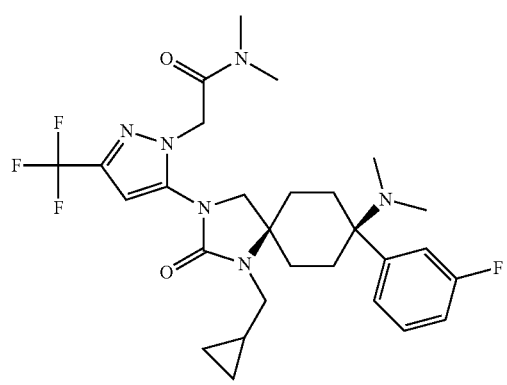
SC_3419
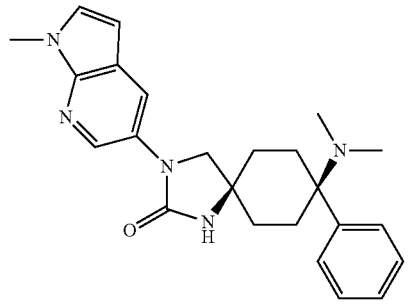
SC_3420
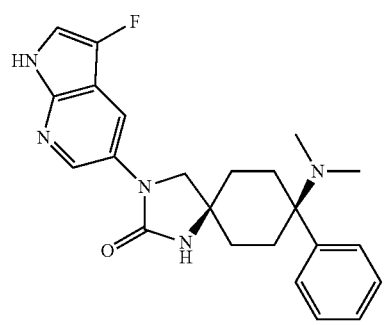
SC_3421
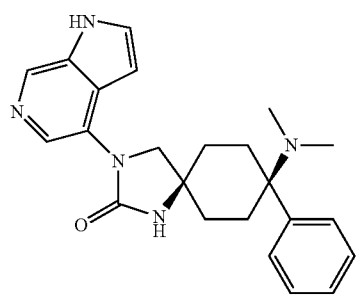
SC_3422
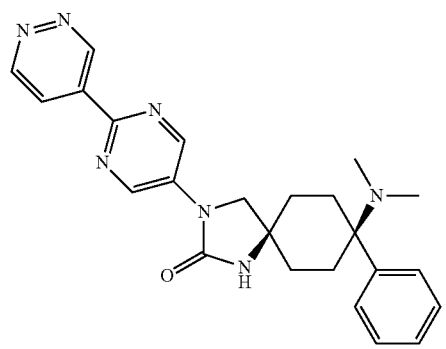
SC_3423
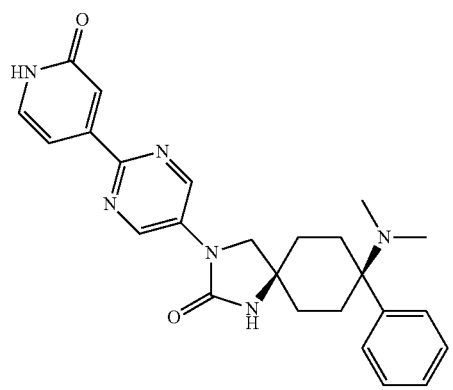
SC_3424
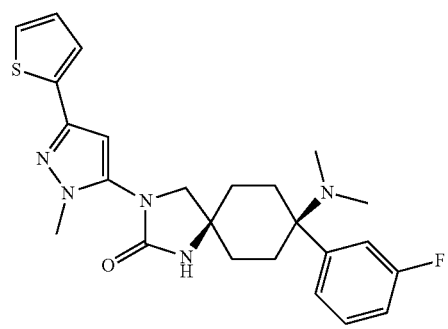
SC_3425
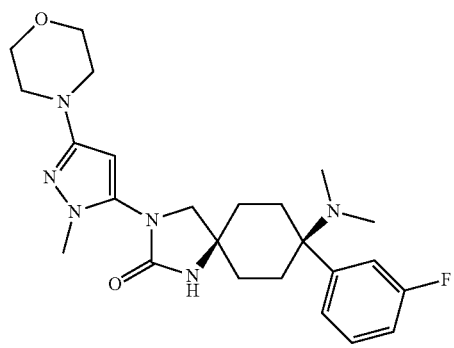

-continued
SC_3426
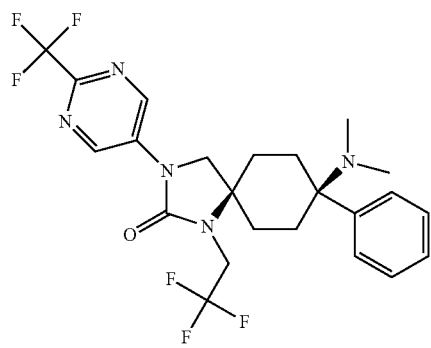
SC_3427
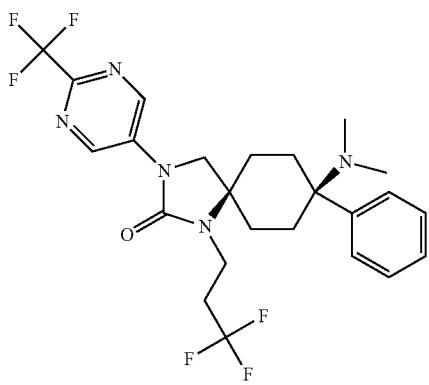
SC_3428
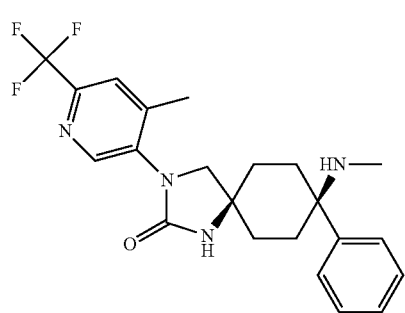
SC_3429
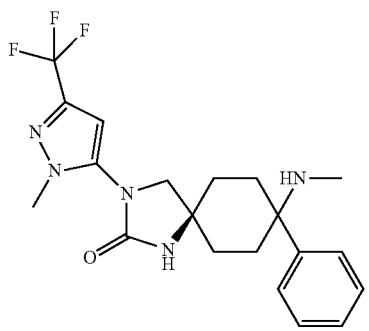
SC_3430
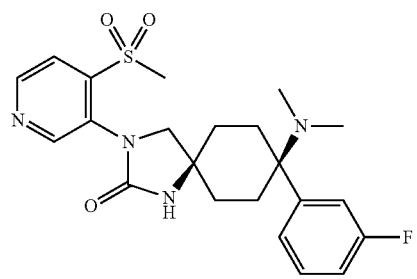
SC_3431
SC_3432
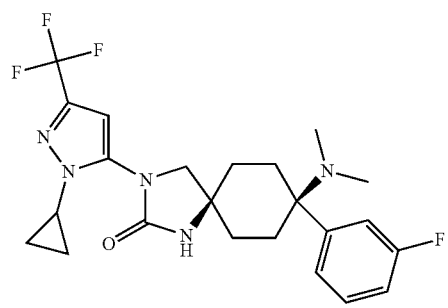
SC_3433
SC_3434
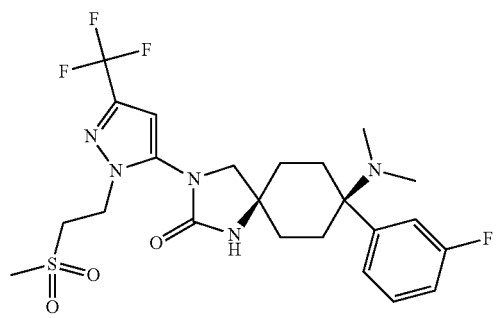
SC_3435
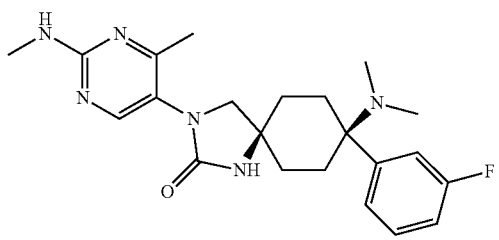

-continued

SC_3436
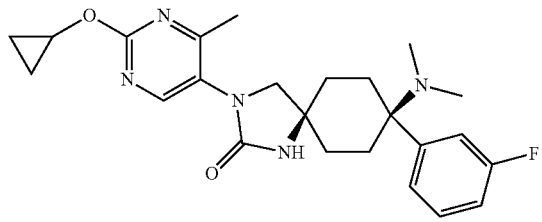

SC_3437
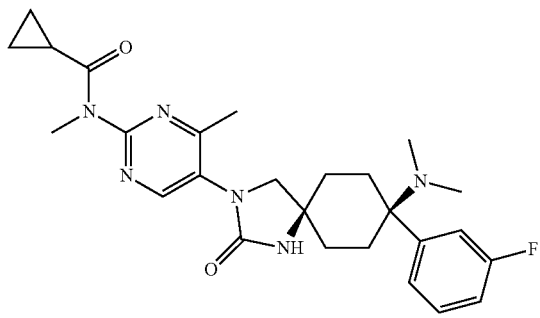

SC_3438
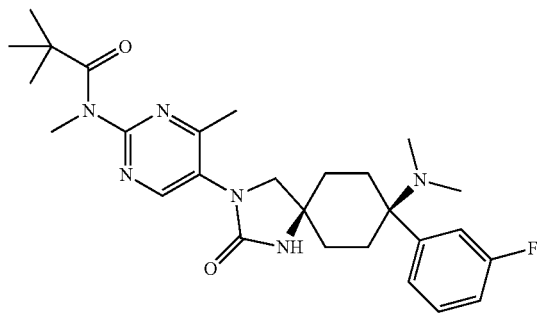

SC_3439
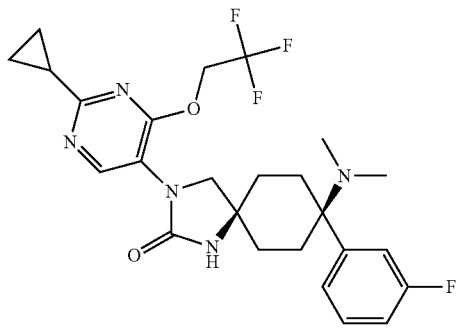

SC_3440
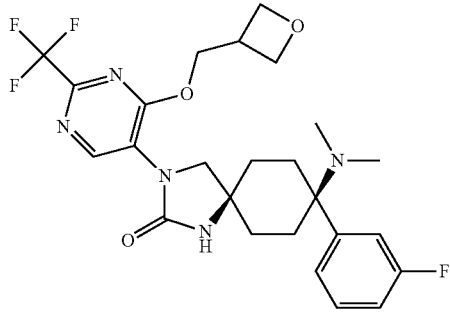

SC_3441
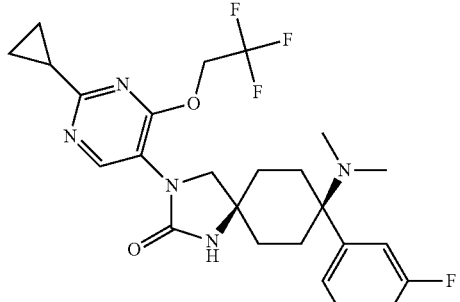

SC_3442
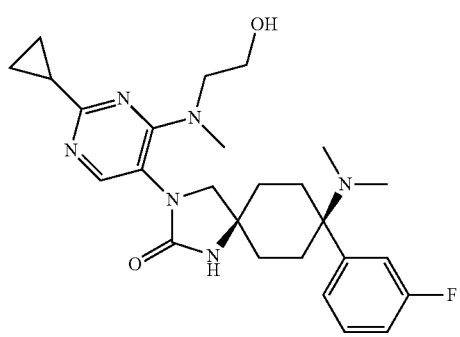

Pharmacological Investigations

Functional investigation on the human mu-opioid receptor (hMOP), human kappa-opioid receptor (hKOP), human delta-opioid receptor (hDOP), and human nociceptin/orphanin FQ peptide receptor (hNOP)

Human Mu-Opioid Peptide (hMOP) Receptor Binding Assay

The hMOP receptor binding assay was performed as homogeneous SPA-assay (scintillation proximity assay) using the assay buffer 50 mM TRIS-HCl (pH 7.4) supplemented with 0.052 mg/ml bovine serum albumin (Sigma-Aldrich Co. St. Louis. Mo.). The final assay volume (250 l/well) included 1 nM of [N-allyl-2.3-$^3$H]naloxone as ligand (PerkinElmer Life Sciences. Inc. Boston. Mass. USA). and either test compound in dilution series or 25 μM unlabelled naloxone for determination of unspecific binding. The test compound was diluted with 25% DMSO in H$_2$O to yield a final 0.5% DMSO concentration. which also served as a respective vehicle control. The assay was started by adding wheat germ agglutinin coated SPA beads (GE Healthcare UK Ltd. Buckinghamshire. UK) which had been preloaded with hMOP receptor membranes (PerkinElmer Life Sciences. Inc. Boston. Mass. USA). After incubation for 90 minutes at RT and centrifugation for 20 minutes at 500 rpm the signal rate was measured by means of a 1450 Microbeta Trilux β-counter (PerkinElmer Life Sciences/Wallac. Turku. Finland). Half-maximal inhibitory concentration (IC50) values reflecting 50% displacement of [$^3$H]naloxone-specific receptor binding were calculated by nonlinear regression analysis and Ki values were calculated by using the Cheng-Prusoff equation. (Cheng and Prusoff. 1973).

Human Kappa-Opioid Peptide (hKOP) Receptor Binding Assay

The hKOP receptor binding assay is run as homogeneous SPA-assay (scintillation proximity assay) using the assay buffer 50 mM TRIS-HCl (pH 7.4) supplemented with 0.076 mg BSA/ml. The final assay volume of 250 µl per well includes 2 nM of [$^3$H]U69,593 as ligand, and either test compound in dilution series or 100 µM unlabelled naloxone for determination of unspecific binding. The test compound is diluted with 25% DMSO in H$_2$O to yield a final 0.5% DMSO concentration which serves as respective vehicle control, as well. The assays are started by the addition of wheat germ agglutinin coated SPA beads (1 mg SPA beads/ 250 µl final assay volume per well) which has been preloaded for 15 minutes at room temperature with hKOP receptor membranes (14.8 µg/250 µl final assay volume per well). After short mixing on a mini-shaker, the microtiter plates are covered with a lid and the assay plates are incubated for 90 minutes at room temperature. After this incubation, the microtiter plates are sealed with a topseal and centrifuged for 20 minutes at 500 rpm. The signal rate is measured after a short delay of 5 minutes by means of a 1450 Microbeta Trilux β-counter (PerkinElmer Life Sciences/ Wallac, Turku, Finland). Half-maximal inhibitory concentration (IC50) values reflecting 50% displacement of [$^3$H] U69.593-specific receptor binding are calculated by nonlinear regression analysis and K$_i$ values are calculated by using the Cheng-Prusoff equation, (Cheng and Prusoff, 1973).

Human Delta-Opioid Peptide (hDOP) Receptor Binding Assay

The hDOP receptor binding assay is performed as homogeneous SPA-assay using the assay buffer 50 mM TRIS-HCl, 5 mM MgCl$_2$ (pH 7.4). The final assay volume (250 µl/well) includes 1 nM of [Tyrosyl-3,5-$^3$H]2-D-Ala-deltorphin II as ligand, and either test compound in dilution series or 10 µM unlabelled naloxone for determination of unspecific binding. The test compound is diluted with 25% DMSO in H$_2$O to yield a final 0.5% DMSO concentration which serves as respective vehicle control, as well. The assays are started by the addition of wheat germ agglutinin coated SPA beads (1 mg SPA beads/250 µl final assay volume per well) which has been preloaded for 15 minutes at room temperature with hDOP receptor membranes (15.2 µg/250 µl final assay volume per well). After short mixing on a mini-shaker, the microtiter plates are covered with a lid and the assay plates are incubated for 120 minutes at room temperature and centrifuged for 20 minutes at 500 rpm. The signal rate is measured by means of a 1450 Microbeta Trilux β-counter (PerkinElmer Life Sciences/Wallac, Turku, Finland). Half-maximal inhibitory concentration (IC50) values reflecting 50% displacement of [Tyrosyl-3,5-$^3$H]2-D-Ala-deltorphin II-specific receptor binding are calculated by nonlinear regression analysis and K$_i$ values are calculated by using the Cheng-Prusoff equation, (Cheng and Prusoff, 1973).

Human Nociceptin/Orphanin FQ Peptide (hNOP) Receptor Binding Assay

The hNOP receptor binding assay was performed as homogeneous SPA-assay (scintillation proximity assay) using the assay buffer 50 mM TRIS-HCl. 10 mM MgCl$_2$. 1 mM EDTA (pH 7.4). The final assay volume (250 µl/well) included 0.5 nM of [leucyl-$^3$H]nociceptin as ligand (PerkinElmer Life Sciences. Inc. Boston. Mass. USA). and either test compound in dilution series or 1 µM unlabelled nociceptin for determination of unspecific binding. The test compound was diluted with 25% DMSO in H$_2$O to yield a final 0.5% DMSO concentration. which also served as a respective vehicle control. The assay was started by adding wheat germ agglutinin coated SPA beads (GE Healthcare UK Ltd. Buckinghamshire. UK) which had been preloaded with hMOP receptor membranes (PerkinElmer Life Sciences. Inc. Boston. Mass. USA). After incubation for 60 minutes at RT and centrifugation for 20 minutes at 500 rpm the signal rate was measured by means of a 1450 Microbeta Trilux β-counter (PerkinElmer Life Sciences/Wallac. Turku. Finland). Half-maximal inhibitory concentration (IC50) values reflecting 50% displacement of [$^3$H]nociceptin-specific receptor binding were calculated by nonlinear regression analysis and Ki values were calculated by using the Cheng-Prusoff equation. (Cheng and Prusoff. 1973).

| Example | hNOP Ki [nM] or % inhibition at 1 µM | hMOP Ki [nM] or % inhibition at 1 µM |
| --- | --- | --- |
| SC_3001 | 0.3 | 120 |
| SC_3002 | 1.3 | 250 |
| SC_3003 | 0.4 | 350 |
| SC_3004 | 19.5 | 515 |
| SC_3005 | 0.7 | 12 |
| SC_3006 | 1.1 | 46 |
| SC_3007 | 85.8 | 705 |
| SC_3008 | 0.6 | 23 |
| SC_3009 | 1.1 | 41 |
| SC_3010 | 2.7 | 18 |
| SC_3011 | 4.4 | 4.4 |
| SC_3012 | 2.2 | 120 |
| SC_3013 | 1.4 | 39 |
| SC_3014 | 0.8 | 29.5 |
| SC_3015 | 2.6 | 32.5 |
| SC_3016 | 4.2 | 45 |
| SC_3017 | 2 | 30 |
| SC_3018 | 5.2 | 101.5 |
| SC_3019 | 10.2 | 135 |
| SC_3020 | 10.8 | 290 |
| SC_3021 | 1.8 | 14.5 |
| SC_3022 | 0.4 | 37.2 |
| SC_3023 | 7.7 | 36 |
| SC_3024 | 1 | 145 |
| SC_3025 | 236.7 | 1530 |
| SC_3026 | 4.6 | 300 |
| SC_3027 | 5 | 136 |
| SC_3028 | 0.6 | 10.4 |
| SC_3029 | 1.8 | 7.3 |
| SC_3030 | 2.2 | 59 |
| SC_3031 | 4.1 | 45.5 |
| SC_3032 | 11 | 245 |
| SC_3033 | 107 | 38%@10 µM |
| SC_3034 | 12.2 | 730 |
| SC_3035 | 6.6 | 1055 |
| SC_3036 | 1.4 | 220 |
| SC_3037 | 33.5 | 775 |
| SC_3038 | 1 | 76 |
| SC_3039 | 13 | 380 |
| SC_3040 | 4 | 335 |
| SC_3041 | 0.9 | 79.5 |
| SC_3042 | 4.1 | 136.5 |
| SC_3043 | 70 | 655 |

| Example | hNOP Ki [nM] or % inhibition at 1 μM | hMOP Ki [nM] or % inhibition at 1 μM | Example | hNOP Ki [nM] or % inhibition at 1 μM | hMOP Ki [nM] or % inhibition at 1 μM |
|---|---|---|---|---|---|
| SC_3044 | 230 | 10920 | SC_3120 | 26 | 4950 |
| SC_3045 | 55.5 | 520 | SC_3121 | 44 | 30% |
| SC_3046 | 13.9 | 63 | SC_3122 | 21 | 32% |
| SC_3047 | 10.1 | 2105 | SC_3123 | 82 | 2260 |
| SC_3048 | 1 | 38.5 | SC_3124 | 5 | 1090 |
| SC_3049 | 25 | 940 | SC_3125 | 3%@10 μM | 52%@10 μM |
| SC_3050 | 85 | 28 | SC_3126 | 0% | 0% |
| SC_3051 | 3.6 | 170 | SC_3127 | 0% | 3945 |
| SC_3052 | 160 | 355 | SC_3128 | 0% | 1% |
| SC_3053 | 73.5 | 1200 | SC_3129 | 6 | 2180 |
| SC_3054 | 16.5 | 29.5 | SC_3130 | 13 | 4530 |
| SC_3055 | 94.5 | 215 | SC_3131 | 4 | 3090 |
| SC_3056 | 9.8 | 49.5 | SC_3132 | 540 | 6% |
| SC_3057 | 955 | 245 | SC_3133 | 19 | 6515 |
| SC_3058 | 5 | 7.8 | SC_3134 | 3%@10 μM | 40%@10 μM |
| SC_3059 | 11.4 | 320 | SC_3135 | 1% | 1% |
| SC_3060 | 3 | 65 | SC_3136 | 16 | 5840 |
| SC_3061 | 4.7 | 54.5 | SC_3137 | 5 | 4235 |
| SC_3063 | 0.7 | 38 | SC_3138 | 28 | 7% |
| SC_3064 | 119 | 365 | SC_3139 | 59 | 1690 |
| SC_3065 | 6.2 | 1990 | SC_3140 | 119 | 2355 |
| SC_3066 | 2.2 | 96 | SC_3141 | 34 | 7855 |
| SC_3067 | 41.5 | 99.5 | SC_3142 | 9 | 3750 |
| SC_3068 | 5.9 | 50.5 | SC_3143 | 0% | 4% |
| SC_3069 | 2.6 | 49 | SC_3144 | 0% | 3590 |
| SC_3070 | 2.8 | 12.5 | SC_3145 | 46 | 1635 |
| SC_3071 | 8.2 | 170 | SC_3146 | 18 | 7675 |
| SC_3072 | 5.9 | 235 | SC_3147 | 27 | 3325 |
| SC_3073 | 1 | 110 | SC_3148 | 14 | 4575 |
| SC_3074 | 1.6 | 55 | SC_3149 | 18 | 6900 |
| SC_3075 | 8.1 | 260 | SC_3150 | 105 | 16% |
| SC_3076 | 0.6 | 35.3 | SC_3151 | 115 | 3490 |
| SC_3077 | 3.2 | 325 | SC_3152 | 24 | 4775 |
| SC_3078 | 0.6 | 77.5 | SC_3153 | 77 | 2220 |
| SC_3079 | 1.6 | 38.5 | SC_3154 | 17 | 3575 |
| SC_3080 | 1.6 | 90.5 | SC_3155 | 34 | 3495 |
| SC_3081 | 8 | 1320 | SC_3156 | 45 | 6375 |
| SC_3082 | 39 | 1110 | SC_3157 | 35 | 5690 |
| SC_3083 | 12 | 117.3 | SC_3158 | 19 | 2540 |
| SC_3084 | 1.8 | 22 | SC_3159 | 13 | 19% |
| SC_3085 | 1.6 | 107 | SC_3160 | 4% | 5730 |
| SC_3086 | 1.1 | 43.5 | SC_3161 | 2% | 13% |
| SC_3087 | 2.8 | 99 | SC_3162 | 5 | 1325 |
| SC_3088 | 3.1 | 770 | SC_3163 | 28 | 2095 |
| SC_3089 | 3.3 | 235 | SC_3164 | 30 | 880 |
| SC_3090 | 1.3 | 67 | SC_3165 | 4% | 17% |
| SC_3091 | 2.3 | 24 | SC_3166 | 3% | 1640 |
| SC_3092 | 2.2 | 330 | SC_3167 | 18 | 3745 |
| SC_3093 | 1.1 | 47 | SC_3168 | 11 | 5 |
| SC_3094 | 5.4 | 45.5 | SC_3169 | 635 | 3445 |
| SC_3096 | 14 | 250 | SC_3170 | 7 | 3610 |
| SC_3097 | 17 | 18 | SC_3171 | 15 | 2010 |
| SC_3098 | 2 | 6 | SC_3172 | 130 | 7% |
| SC_3099 | 13 | 19 | SC_3173 | 10 | 2525 |
| SC_3100 | 1 | 1 | SC_3174 | 3% | 1265 |
| SC_3101 | 1 | 3 | SC_3175 | — | — |
| SC_3102 | 2 | 1 | SC_3176 | 13 | 3740 |
| SC_3103 | 7 | 1 | SC_3177 | 8 | 4630 |
| SC_3104 | — | — | SC_3178 | 6 | 6700 |
| SC_3105 | 2 | 97 | SC_3179 | 15 | 3950 |
| SC_3106 | 8 | 165 | SC_3180 | 125 | 2250 |
| SC_3107 | 2 | 115 | SC_3181 | 22 | 5490 |
| SC_3108 | 5 | 26 | SC_3182 | 11 | 2990 |
| SC_3109 | 8 | 19 | SC_3183 | 165 | 1415 |
| SC_3110 | 6 | 20 | SC_3184 | 19 | 7645 |
| SC_3111 | 8 | 37 | SC_3185 | 335 | 15% |
| SC_3112 | 36 | 120 | SC_3186 | 33 | 2210 |
| SC_3113 | 24 | 26 | SC_3187 | 87 | 2240 |
| SC_3114 | 245 | 460 | SC_3188 | 25 | 1060 |
| SC_3115 | 265 | 915 | SC_3189 | 57 | 3470 |
| SC_3116 | 6 | 170 | SC_3190 | 42 | 28% |
| SC_3117 | 92 | 1380 | SC_3191 | 27 | 20% |
| SC_3118 | 80 | 5% | SC_3192 | 140 | 4270 |
| SC_3119 | 22% | 10% | SC_3193 | 100 | 2480 |

| Example | hNOP Ki [nM] or % inhibition at 1 μM | hMOP Ki [nM] or % inhibition at 1 μM |
|---|---|---|
| SC_3194 | 28 | 5120 |
| SC_3195 | 15 | 1240 |
| SC_3196 | 22 | 1595 |
| SC_3197 | 44 | 1680 |
| SC_3198 | 22 | 5885 |
| SC_3199 | 19 | 4020 |
| SC_3200 | 7 | 13% |
| SC_3201 | 115 | 3885 |
| SC_3202 | 25 | 3210 |
| SC_3203 | 68 | 1225 |
| SC_3204 | 110 | 14% |
| SC_3205 | 20 | 2465 |
| SC_3206 | 27 | 2445 |
| SC_3207 | 39 | 1505 |
| SC_3208 | 2 | 3285 |
| SC_3209 | — | — |
| SC_3210 | — | — |
| SC_3211 | — | — |
| SC_3212 | 9 | 2005 |
| SC_3213 | 52 | 18% |
| SC_3214 | 7 | 19% |
| SC_3215 | 0% | 14% |
| SC_3216 | 11 | 14 |
| SC_3217 | 23 | 2155 |
| SC_3218 | 83 | 15% |
| SC_3219 | 0% | 1% |
| SC_3220 | 10%@10 μM | 24%@10 μM |
| SC_3221 | 33 | 1935 |
| SC_3222 | 6 | 1910 |
| SC_3223 | 155 | 6150 |
| SC_3224 | 10 | 1695 |
| SC_3225 | 13 | 2520 |
| SC_3226 | — | — |
| SC_3227 | 16 | 3785 |
| SC_3228 | 67 | 3135 |
| SC_3229 | 105 | 3625 |
| SC_3230 | 145 | 2485 |
| SC_3231 | 120 | 2420 |
| SC_3232 | 15 | 3475 |
| SC_3233 | 38 | 1390 |
| SC_3234 | 4 | 1350 |
| SC_3235 | 30 | 1095 |
| SC_3236 | 285 | 18% |
| SC_3237 | 20 | 17% |
| SC_3238 | 4 | 25% |
| SC_3239 | 35 | 2410 |
| SC_3240 | 28 | 17% |
| SC_3241 | 8 | 4610 |
| SC_3242 | 5 | 675 |
| SC_3243 | 6 | 695 |
| SC_3244 | 27 | 4265 |
| SC_3245 | 67 | — |
| SC_3246 | 11 | 1025 |
| SC_3247 | 16 | 1220 |
| SC_3248 | 4 | 41 |
| SC_3249 | 740 | 855 |
| SC_3250 | 52 | — |
| SC_3251 | 185 | 4550 |
| SC_3252 | 30 | — |
| SC_3253 | 205 | — |
| SC_3254 | 22 | 240 |
| SC_3255 | 23 | 150 |
| SC_3256 | 12 | 61 |
| SC_3257 | 150 | 240 |
| SC_3258 | 58 | 7125 |
| SC_3259 | 45 | 180 |
| SC_3260 | 570 | nd |
| SC_3261 | 10 | 63 |
| SC_3262 | 540 | 3060 |
| SC_3263 | 66 | 800 |
| SC_3264 | 145 | 130 |
| SC_3265 | 38 | 2405 |
| SC_3266 | 245 | 1055 |
| SC_3267 | 460 | — |
| SC_3268 | 41 | 1625 |
| SC_3269 | 13 | 5580 |
| SC_3270 | 305 | 31 |
| SC_3271 | 34 | 245 |
| SC_3272 | 115 | 4175 |
| SC_3273 | — | — |
| SC_3274 | 63 | 1880 |
| SC_3275 | 155 | 124 |
| SC_3276 | 24 | 130 |
| SC_3277 | 37 | 13% |
| SC_3278 | 12 | 7035 |
| SC_3279 | 17 | 78 |
| SC_3280 | 6 | 300 |
| SC_3281 | 19 | 2580 |
| SC_3282 | 37 | 3510 |
| SC_3283 | 12 | 1030 |
| SC_3284 | 5 | 305 |
| SC_3285 | 15 | 20% |
| SC_3286 | 18 | 5895 |
| SC_3287 | 119 | 18% |
| SC_3288 | 15 | 115 |
| SC_3289 | 84 | 430 |
| SC_3290 | 16 | 6605 |
| SC_3291 | 350 | 15% |
| SC_3292 | 4% | 0% |
| SC_3293 | 3% | 0% |
| SC_3294 | 9 | 12% |
| SC_3295 | 28 | 2975 |
| SC_3296 | 10 | 4530 |
| SC_3297 | 8 | 4270 |
| SC_3298 | 20 | 17% |
| SC_3299 | 23 | 5705 |
| SC_3300 | 22 | 565 |
| SC_3301 | 33 | 2320 |
| SC_3302 | 31 | 1025 |
| SC_3303 | 450 | 21% |
| SC_3304 | 9% | 4% |
| SC_3305 | 10% | 0% |
| SC_3306 | 9 | 4555 |
| SC_3307 | 13 | 5345 |
| SC_3308 | 2 | 2575 |
| SC_3309 | 17 | 6910 |
| SC_3310 | 7 | 23% |
| SC_3311 | 14 | 27% |
| SC_3312 | 23 | 1830 |
| SC_3313 | 10 | 2400 |
| SC_3314 | 9 | 4090 |
| SC_3315 | 14 | 5325 |
| SC_3316 | 255 | 5430 |
| SC_3317 | 56 | 6045 |
| SC_3318 | 35 | 1235 |
| SC_3319 | 4 | 15% |
| SC_3320 | 11 | 1955 |
| SC_3321 | 13 | 5715 |
| SC_3322 | 12 | 1150 |
| SC_3323 | 27 | 5530 |
| SC_3324 | 12% | 5% |
| SC_3325 | 53%@10 μM | 20%@10 μM |
| SC_3326 | — | — |
| SC_3327 | 17 | 3360 |
| SC_3328 | 31 | 3295 |
| SC_3329 | 13 | 4285 |
| SC_3330 | 14 | 1505 |
| SC_3331 | 2 | 5265 |
| SC_3332 | 19 | 2055 |
| SC_3333 | 5 | 1580 |
| SC_3334 | 17 | 4005 |
| SC_3335 | 30 | 2305 |
| SC_3336 | 240 | 13% |
| SC_3337 | 10 | 1970 |
| SC_3338 | 36 | 7% |
| SC_3339 | 10 | 6830 |
| SC_3340 | 150 | 5750 |

-continued

| Example | hNOP Ki [nM] or % inhibition at 1 μM | hMOP Ki [nM] or % inhibition at 1 μM |
|---|---|---|
| SC_3341 | 15 | 3460 |
| SC_3342 | 21 | 3845 |
| SC_3343 | 27 | 16% |
| SC_3344 | 1 | 13% |
| SC_3345 | 4 | 1800 |
| SC_3346 | 12 | 2580 |
| SC_3347 | 15 | 4845 |
| SC_3348 | 25 | 4090 |
| SC_3349 | 8 | 3980 |
| SC_3350 | 7 | 1485 |
| SC_3351 | 20 | 2205 |
| SC_3352 | 37 | 2160 |
| SC_3353 | 53 | 15% |
| SC_3354 | 2 | 23% |
| SC_3355 | 52 | 4785 |
| SC_3356 | 9 | 4805 |
| SC_3357 | 13 | 555 |
| SC_3358 | 51 | 7020 |
| SC_3359 | 66 | 3520 |
| SC_3360 | 7 | 2870 |
| SC_3361 | 27 | 5095 |
| SC_3362 | 28 | 29% |
| SC_3363 | 33 | 8% |
| SC_3364 | 32 | 4685 |
| SC_3365 | 2 | 1655 |
| SC_3366 | 1285 | 14% |
| SC_3367 | 1220 | 8% |
| SC_3368 | 195 | 11% |
| SC_3369 | 51 | 3105 |
| SC_3370 | 4 | 14% |
| SC_3371 | 350 | 9% |
| SC_3372 | 125 | 3535 |
| SC_3373 | 19 | 18% |
| SC_3374 | 55 | 10% |
| SC_3375 | 13 | 12% |
| SC_3376 | 37 | 1720 |
| SC_3377 | 22 | 980 |
| SC_3379 | 11 | 635 |
| SC_3380 | 102 | 5415 |
| SC_3381 | 3 | 1235 |
| SC_3382 | 29 | 13% |
| SC_3383 | 10 | 17% |
| SC_3384 | 6 | 11% |
| SC_3385 | 33 | 925 |
| SC_3386 | 14 | 0% |
| SC_3387 | 2 | 1245 |
| SC_3388 | 29 | 185 |
| SC_3389 | 2 | 1970 |
| SC_3390 | 18 | 465 |
| SC_3391 | 53 | 10% |
| SC_3392 | 7 | 4490 |
| SC_3393 | 88 | 13% |
| SC_3394 | 6 | 735 |
| SC_3395 | 14 | 4990 |
| SC_3396 | 44 | 1730 |
| SC_3397 | 48 | 560 |
| SC_3398 | 9 | 5640 |
| SC_3399 | 5 | 45% |
| SC_3400 | 8 | 635 |
| SC_3401 | 1 | 455 |
| SC_3402 | 7 | 3630 |
| SC_3403 | 9 | 1440 |
| SC_3404 | 10 | 5% |
| SC_3405 | 12 | 925 |
| SC_3406 | 24 | 805 |
| SC_3407 | 77 | 13% |
| SC_3408 | 7 | 18% |
| SC_3409 | 11 | 25% |

Protocol for [$^{35}$S]GTPγS Functional NOP/MOP/KOP/DOP Assays

Cell membrane preparations of CHO-K1 cells transfected with the human MOP receptor (Art.-No. RBHOMM) or the human DOP receptor (Art.-No. RBHODM), and HEK293 cells transfected with the human NOP receptor (Art.-No. RBHORLM) or the human KOP receptor (Art.-No. 6110558) are available from PerkinElmer (Waltham, Mass.). Membranes from CHO-K1 cells transfected with the human nociceptin/orphanin FQ peptide (hNOP) receptor (Art.-No. 93-0264C2, DiscoveRx Corporation, Freemont, Calif.) are also used. [$^{35}$S]GTPγS (Art.-No. NEG030H; Lot-No. #0112, #0913, #1113 calibrated to 46.25 TBq/mmol) is available from PerkinElmer (Waltham, Mass.).

The [$^{35}$S]GTPγS assays are carried out essentially as described by Gillen et al (2000). They are run as homogeneous scintillation proximity (SPA) assays in microtiter luminescence plates, where each well contains 1.5 mg of WGA-coated SPA-beads. To test the agonistic activity of test compounds on recombinant hNOP, hMOP, hDOP, and hKOP receptor expressing cell membranes from CHO-K1 or HEK293 cells, 10 or 5 μg membrane protein per assay are incubated with 0.4 nM [$^{35}$S]GTPγS and serial concentrations of receptor-specific agonists in buffer containing 20 mM HEPES pH 7.4, 100 mM NaCl, 10 mM MgCl2, 1 mM EDTA, 1 mM dithiothreitol, 1.28 mM NaN$_3$, and 10 μM GDP for 45 min at room temperature. The microtiter plates are then centrifuged for 10 min at 830 to sediment the SPA beads. The microtiter plates are sealed and the bound radioactivity [cpm] is determined after a delay of 15 min by means of a 1450 Microbeta Trilux (PerkinElmer, Waltham, Mass.).

The unstimulated basal binding activity (UBS$_{obs}$ [cpm]) is determined from 12 unstimulated incubates and is set as 100% basal binding. For determination of the potency and the efficacy, the arithmetic mean of the observed total [$^{35}$S]GTPγS binding (TB$_{obs}$ [cpm]) of all incubates (duplicates) stimulated by the receptor-specific agonists (i.e. N/OFQ, SNC80, DAMGO, or U69,593) are transformed in percent total binding (TB$_{obs}$ [%]) relative to the basal binding activity (i.e. 100% binding). The potency (EC$_{50}$) of the respective agonist and its maximal achievable total [$^{35}$S]GTPγS binding (TB$_{calc}$ [%]) above its calculated basal binding (UBS$_{calc}$ [%]) are determined from its transformed data (TB$_{obs}$ [%]) by means of nonlinear regression analysis with XLfit for each individual concentration series. Then the difference between the calculated unstimulated [$^{35}$S]GTPγS binding (UBS$_{calc}$ [%]) and the maximal achievable total [$^{35}$S]GTPγS binding (TB$_{calc}$ [%]) by each tested agonist is determined (i.e. B1$_{calc}$ [%]). This difference (B1$_{calc}$[%]) as a measure of the maximal achievable enhancement of [$^{35}$S]GTPγS binding by a given agonist is used to calculate the relative efficacy of test compounds versus the maximal achievable enhancement by a receptor-specific full agonist, e.g. N/OFQ (B1$_{calc-N/OFQ}$ [%]) which is set as 100% relative efficacy for the hNOP receptor. Likewise, the percentage efficacies of test compounds at the hDOP, hMOP, or hKOP receptor are determined versus the calculated maximal enhancement of [$^{35}$S]GTPγS binding by the full agonists SNC80 (B1$_{calc-SNC80}$ [%]), DAMGO (B1$_{calc-DAMGO}$ [%]) and U69,593 (B1$_{calc-U69,593}$ [%]) which are set as 100% relative efficacy at each receptor, respectively.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:
1. A compound according to general formula (I)

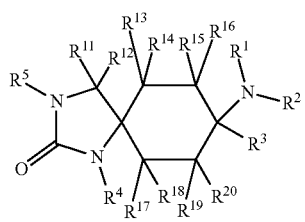

wherein
$R^1$ and $R^2$ independently of one another mean
—H;
—$C_1$-$C_6$-alkyl, linear or branched, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$;
a 3-12-membered cycloalkyl moiety, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$; wherein said 3-12-membered cycloalkyl moiety is optionally connected through —$C_1$-$C_6$-alkylene-, linear or branched, saturated or unsaturated, unsubstituted; or
a 3-12-membered heterocycloalkyl moiety, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$; wherein said 3-12-membered heterocycloalkyl moiety is optionally connected through —$C_1$-$C_6$-alkylene-, linear or branched, saturated or unsaturated, unsubstituted; or
$R^1$ and $R^2$ together with the nitrogen atom to which they are attached form a ring and mean —(CH$_2$)$_{3-6}$—; —(CH$_2$)$_2$—O—(CH$_2$)$_2$—; or —(CH$_2$)$_2$—NR$^A$—(CH$_2$)$_2$—, wherein $R^A$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;
$R^3$ means
—$C_1$-$C_6$-alkyl, linear or branched, saturated or unsaturated, unsubstituted, mono- or polysubstituted;
a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;
a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted;
a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or
a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted;
$R^4$ means
—H;
—$C_1$-$C_6$-alkyl, linear or branched, saturated or unsaturated, unsubstituted, mono- or polysubstituted; wherein said —$C_1$-$C_6$-alkyl is optionally connected through —C(=O)—, —C(=O)O—, or —S(=O)$_2$—;
a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted; or wherein said 3-12-membered cycloalkyl moiety is optionally connected through —C(=O)—, —C(=O)O—, —C(=O)O—CH$_2$—, or —S(=O)$_2$—;
a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted; or wherein said 3-12-membered heterocycloalkyl moiety is optionally connected through —C(=O)—, —C(=O)O—, —C(=O)O—CH$_2$—, or —S(=O)$_2$—;
a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or wherein said 6-14-membered aryl moiety is optionally connected through —C(=O)—, —C(=O)O—, —C(=O)O—CH$_2$—, or —S(=O)$_2$—; or
a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted; or wherein said 5-14-membered heteroaryl moiety is optionally connected through —C(=O)—, —C(=O)O—, —C(=O)O—CH$_2$—, or —S(=O)$_2$—;
$R^5$ means
a 6-14-membered aryl moiety, unsubstituted, mono- or polysubstituted; or
a 5-14-membered heteroaryl moiety, unsubstituted, mono- or polysubstituted;
$R^{11}$, $R^{12}$, $R^{13}$, $R^{14}$, $R^{15}$, $R^{16}$, $R^{17}$, $R^{18}$, $R^{19}$, and $R^{20}$ independently of one another mean —H, —F, —Cl, —Br, —I, —OH, or —$C_1$-$C_6$-alkyl, linear or branched, saturated or unsaturated, unsubstituted, mono- or polysubstituted;
wherein "mono- or polysubstituted" means that one or more hydrogen atoms are replaced by a substituent independently of one another selected from the group consisting of —F, —Cl, —Br, —I, —CN, —R$^{21}$, —C(=O)R$^{21}$, —C(=O)OR$^{21}$, —C(=O)NR$^{21}$R$^{22}$, —C(=O)NH—(CH$_2$CH$_2$—O)$_{1-30}$—CH$_3$, —O—(CH$_2$CH$_2$—O)$_{1-30}$—H, —O—(CH$_2$CH$_2$—O)$_{1-30}$—CH$_3$, =O, —OR$^{21}$, —OC(=O)R$^{21}$, —OC(=O)OR$^{21}$, —OC(=O)NR$^{21}$R$^{22}$, —NO$_2$, —NR$^{21}$R$^{22}$, —NR$^{21}$—

—(CH$_2$)$_{1-6}$—C(=O)R$^{22}$, —NR$^{21}$—(CH$_2$)$_{1-6}$—C(=O)OR$^{22}$, —NR$^{23}$—(CH$_2$)$_{1-6}$—C(=O)NR$^{21}$R$^{22}$, —NR$^{21}$C(=O)R$^{22}$, —NR$^{21}$C(=O)—OR$^{22}$, —NR$^{23}$C(=O)NR$^{21}$R$^{22}$, —NR$^{21}$S(=O)$_2$R$^{22}$, —SR$^{21}$, —S(=O)R$^{21}$, —S(=O)$_2$R$^{21}$, —S(=O)$_2$OR$^{21}$, and —S(=O)$_2$NR$^{21}$R$^{22}$;

wherein

R$^{21}$, R$^{22}$ and R$^{23}$ independently of one another mean

—H;

—C$_1$-C$_6$-alkyl, linear or branched, saturated or unsaturated, unsubstituted or substituted with one, two, three or four substituents independently of one another selected from the group consisting of —F, —Cl, —Br, —I, —CN, —OH, —NH$_2$, —C$_2$H, —C(=O)O—C$_1$-C$_6$-alkyl, —C(=O)NH$_2$, —C(=O)NHC$_1$-C$_6$-alkyl, —C(=O)N(C$_1$-C$_6$-alkyl)$_2$, —O—C$_1$-C$_6$-alkyl and —S(=O)$_2$—C$_1$-C$_6$-alkyl;

a 3-12-membered cycloalkyl moiety, saturated or unsaturated, unsubstituted, mono- or poly-substituted; wherein said 3-12-membered cycloalkyl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;

a 3-12-membered heterocycloalkyl moiety, saturated or unsaturated, unsubstituted, mono- or polysubstituted; wherein said 3-12-membered heterocycloalkyl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;

a 6-14-membered aryl moiety, unsubstituted, mono- or polysubstituted; wherein said 6-14-membered aryl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;

a 5-14-membered heteroaryl moiety, unsubstituted, mono- or polysubstituted; wherein said 5-14-membered heteroaryl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;

or R$^{21}$ and R$^{22}$ within —C(=O)NR$^{21}$R$^{22}$, —OC(=O)NR$^{21}$R$^{22}$, —NR$^{21}$R$^{22}$, —NR$^{23}$—(CH$_2$)$_{1-6}$—C(=O)NR$^{21}$R$^{22}$, —NR$^{23}$C(=O)NR$^{21}$R$^{22}$, or —S(=O)$_2$NR$^{21}$R$^{22}$ together with the nitrogen atom to which they are attached form a ring and mean —(CH$_2$)$_{3-6}$—; —(CH$_2$)$_2$—O—(CH$_2$)$_2$—; —(CH$_2$)$_2$—S(=O)$_2$—(CH$_2$)$_2$— or —(CH$_2$)$_2$—NR$^B$—(CH$_2$)$_2$—, wherein R$^B$ means —H, —C$_1$-C$_6$-alkyl, —C(=O)—C$_1$-C$_6$-alkyl, or —S(=O)$_2$—C$_1$-C$_6$-alkyl, wherein said C$_1$-C$_6$-alkyl is linear or branched, saturated or unsaturated, unsubstituted or substituted with one, two, three or four substituents independently of one another selected from the group consisting of —F, —Cl, —Br, —I, —OH, —CO$_2$H, —C(=O)O—C$_1$-C$_6$-alkyl and —C(=O)NH$_2$; and wherein said ring is unsubstituted or substituted with one, two, three or four substituents independently of one another selected from the group consisting of —F, —Cl, —Br, —I, —CN, =O, —OH, —NH$_2$, —C$_1$-C$_6$-alkyl and —O—C$_1$-C$_6$-alkyl;

or a physiologically acceptable salt thereof.

2. The compound according to claim 1, wherein R$^{11}$, R$^{12}$, R$^{13}$, R$^{14}$, R$^{15}$, R$^{16}$, R$^{17}$, R$^{18}$, R$^{19}$, and R$^{20}$ independently of one another mean —H, —F, —OH, or —C$_1$-C$_6$-alkyl.

3. The compound according to claim 1, wherein R$^1$ means —H; and R$^2$ means —C$_1$-C$_6$-alkyl, linear or branched, saturated or unsaturated, unsubstituted, mono- or polysubstituted.

4. The compound according to claim 1, wherein R$^1$ means —CH$_3$; and R$^2$ means —C$_1$-C$_6$-alkyl, linear or branched, saturated or unsaturated, unsubstituted, mono- or polysubstituted.

5. The compound according to claim 1, wherein R$^1$ means —H or —CH$_3$; and wherein R$^2$ means —CH$_2$-cycloalkyl, —CH$_2$-cyclobutyl, —CH$_2$-cyclopentyl, —CH$_2$-oxetanyl or —CH$_2$-tetrahydrofuranyl.

6. The compound according to claim 1, wherein R$^1$ and R$^2$ together with the nitrogen atom to which they are attached form a ring and mean —(CH$_2$)$_{3-6}$—.

7. The compound according to claim 1, wherein R$^3$ means —C$_1$-C$_6$-alkyl, linear or branched, saturated or unsaturated, unsubstituted, mono- or polysubstituted.

8. The compound according to claim 1, wherein R$^3$ means a 6-14-membered aryl moiety, unsubstituted, mono- or polysubstituted.

9. The compound according to claim 1, wherein R$^3$ means a 5-14-membered heteroaryl moiety, unsubstituted, mono- or polysubstituted.

10. The compound according to claim 1, wherein R$^4$ means —H.

11. The compound according to claim 1, wherein R$^4$ means —C$_1$-C$_6$-alkyl, linear or branched, saturated or unsaturated, unsubstituted, mono- or polysubstituted.

12. The compound according to claim 1, wherein R$^4$ means a 3-12-membered cycloalkyl moiety, saturated or unsaturated, unsubstituted, mono- or polysubstituted; wherein the 3-12-membered cycloalkyl moiety is connected through —C$_1$-C$_6$-alkylene-, linear or branched, saturated or unsaturated, unsubstituted, mono- or polysubstituted.

13. The compound according to claim 1, wherein R$^4$ means a 3-12-membered heterocycloalkyl moiety, saturated or unsaturated, unsubstituted, mono- or polysubstituted; wherein said 3-12-membered heterocycloalkyl moiety is connected through —C$_1$-C$_6$-alkylene-, linear or branched, saturated or unsaturated, unsubstituted, mono- or polysubstituted.

14. The compound according to claim 1, wherein R$^4$ means a 6-14-membered aryl moiety, unsubstituted, mono- or polysubstituted; wherein said 6-14-membered aryl moiety is connected through —C$_1$-C$_6$-alkylene-, linear or branched, saturated or unsaturated, unsubstituted, mono- or polysubstituted.

15. The compound according to claim 1, wherein R$^4$ means a 5-14-membered heteroaryl moiety, unsubstituted, mono- or polysubstituted; wherein said 5-14-membered heteroaryl moiety is connected through —C$_1$-C$_6$-alkylene-, linear or branched, saturated or unsaturated, unsubstituted, mono- or polysubstituted.

16. The compound according to claim 1, wherein R$^5$ means -phenyl, unsubstituted, mono- or polysubstituted.

17. The compound according to claim 1, wherein $R^5$ means a monocyclic 5-6-membered heteroaryl moiety, unsubstituted, mono- or polysubstituted.

18. The compound according to claim 1, wherein $R^5$ means a bicyclic 9-10-membered heteroaryl moiety, unsubstituted, mono- or polysubstituted.

19. The compound according to claim 17, wherein $R^5$ means -1,2-benzodioxole, -pyrazinyl, -pyridazinyl, -pyridinyl, -pyrimidinyl, -thienyl, -imidazolyl, -benzimidazolyl, -thiazolyl, -1,3,4-thiadiazolyl, -benzothiazolyl, -oxazolyl, -benzoxazolyl, -pyrazolyl, -quinolinyl, -isoquinolinyl, -quinazolinyl, -indolyl, -indolinyl, -benzo[c][1,2,5]oxadiazolyl, -imidazo[1,2-a]pyrazinyl, or -1H-pyrrolo[2,3-b]pyridinyl, in each case unsubstituted, mono- or polysubstituted.

20. The compound according to claim 1, which has a structure according to any of general formulas (II-A) to (VIII-C):

(II-A)
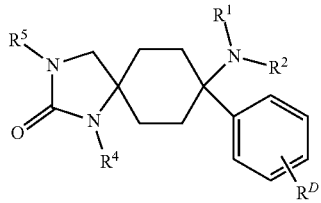

(II-B)
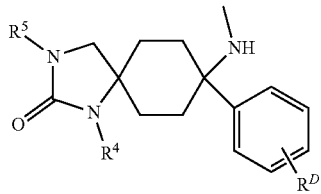

(II-C)
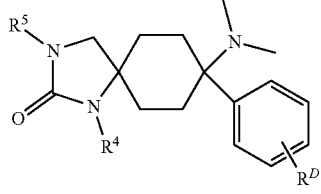

(III-A)
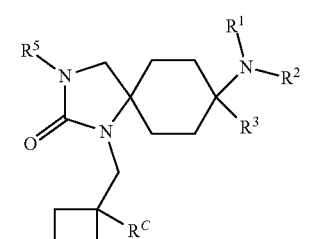

(III-B)
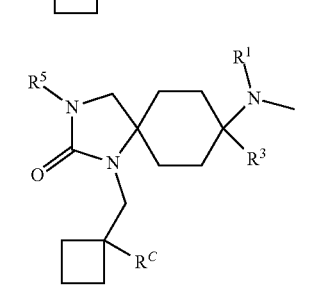

-continued (III-C)
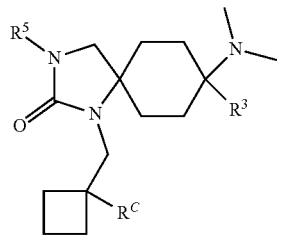

(IV-A)
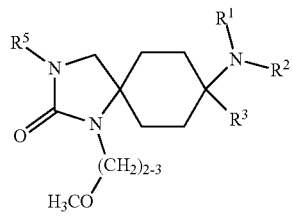

(IV-B)
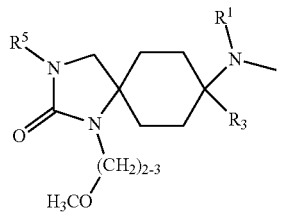

(IV-C)
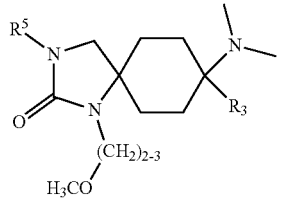

(V-A)
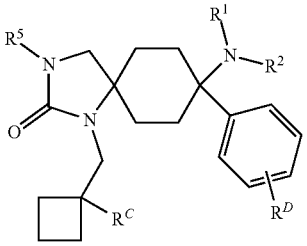

(V-B)
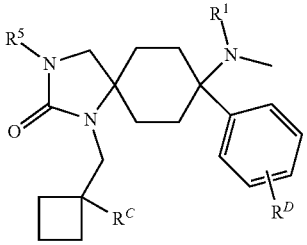

-continued
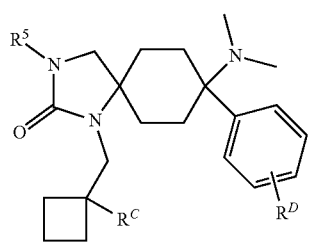 (V-C)
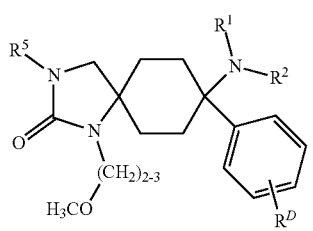 (VI-A)
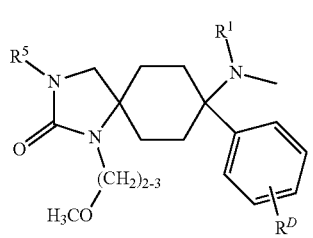 (VI-B)
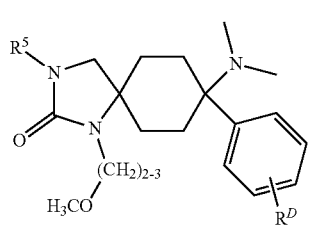 (VI-C)
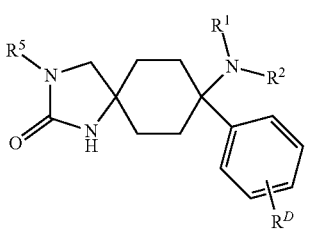 (VII-A)
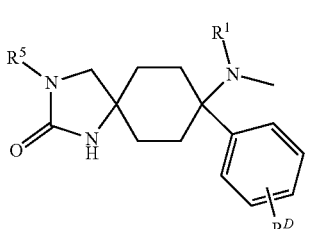 (VII-B)
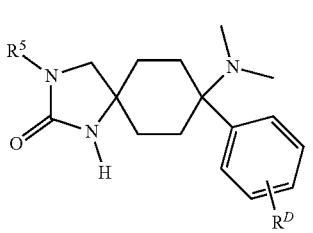 (VII-C)
-continued
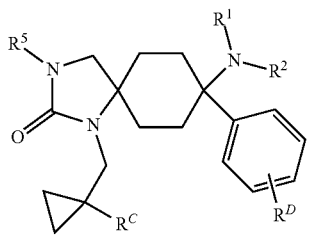 (VIII-A)
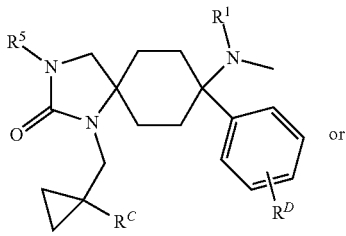 (VIII-B) or
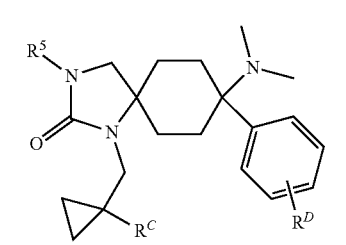 (VIII-C)
wherein in each case
$R^1$, $R^2$, $R^3$, $R^4$, and R are defined as in claim 1,
$R^C$ means —H, —OH, —F, —CN or —$C_1$-$C_4$-alkyl;
$R^D$ means —H or —F;
or a physiologically acceptable salt thereof.
21. The compound according to claim 1, wherein $R^5$ is selected from the group consisting of:
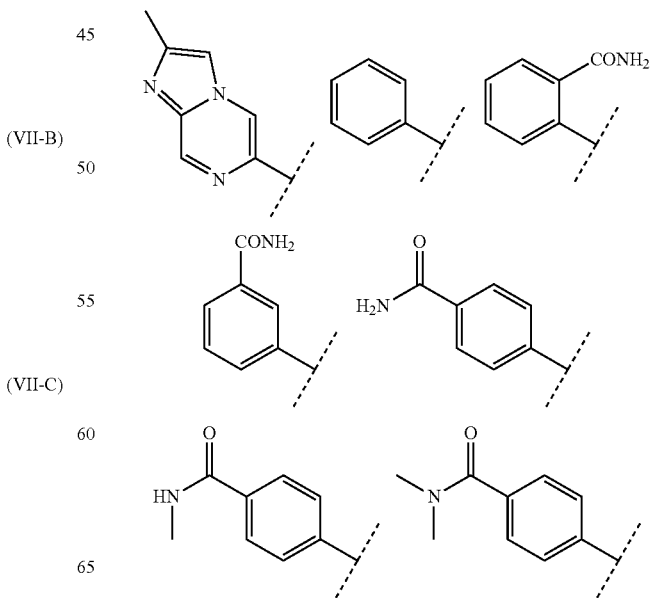

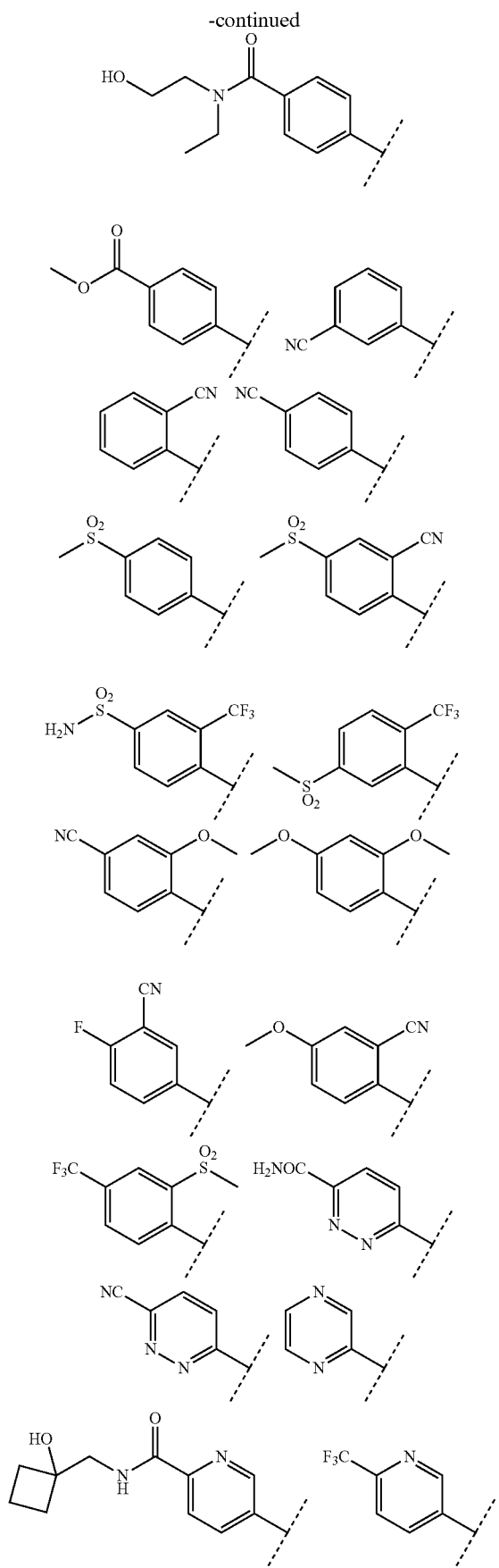
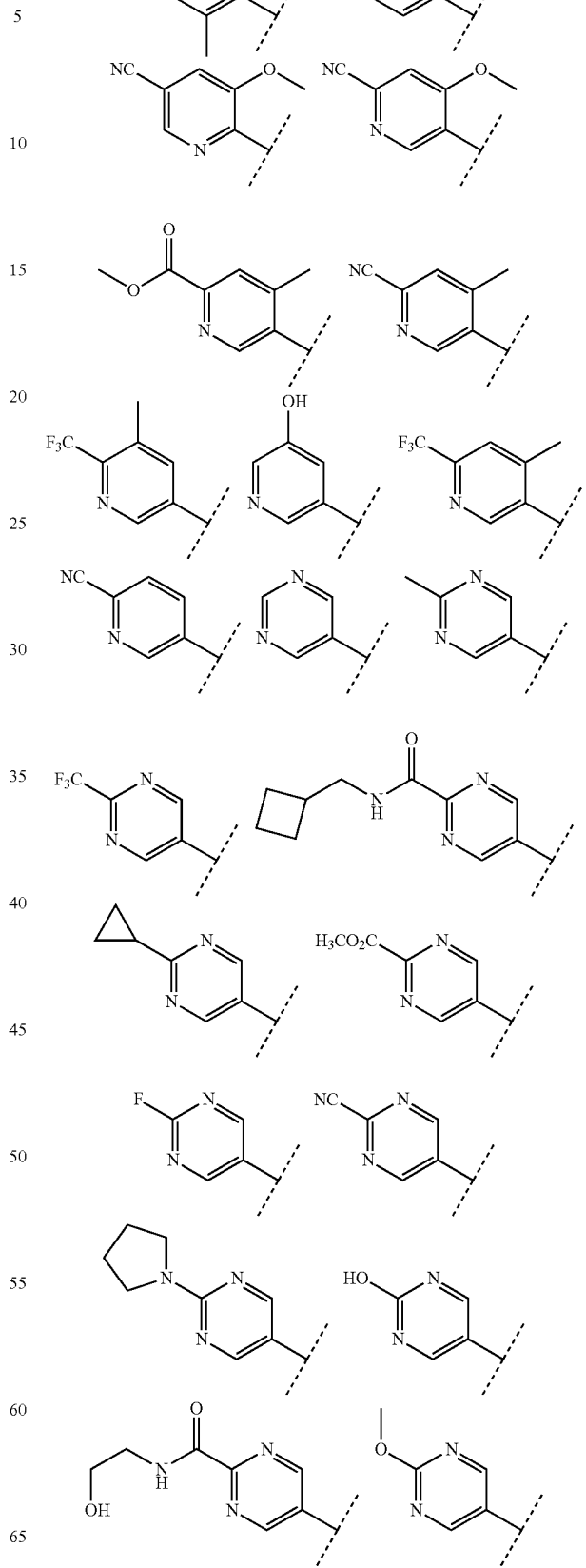

377
-continued
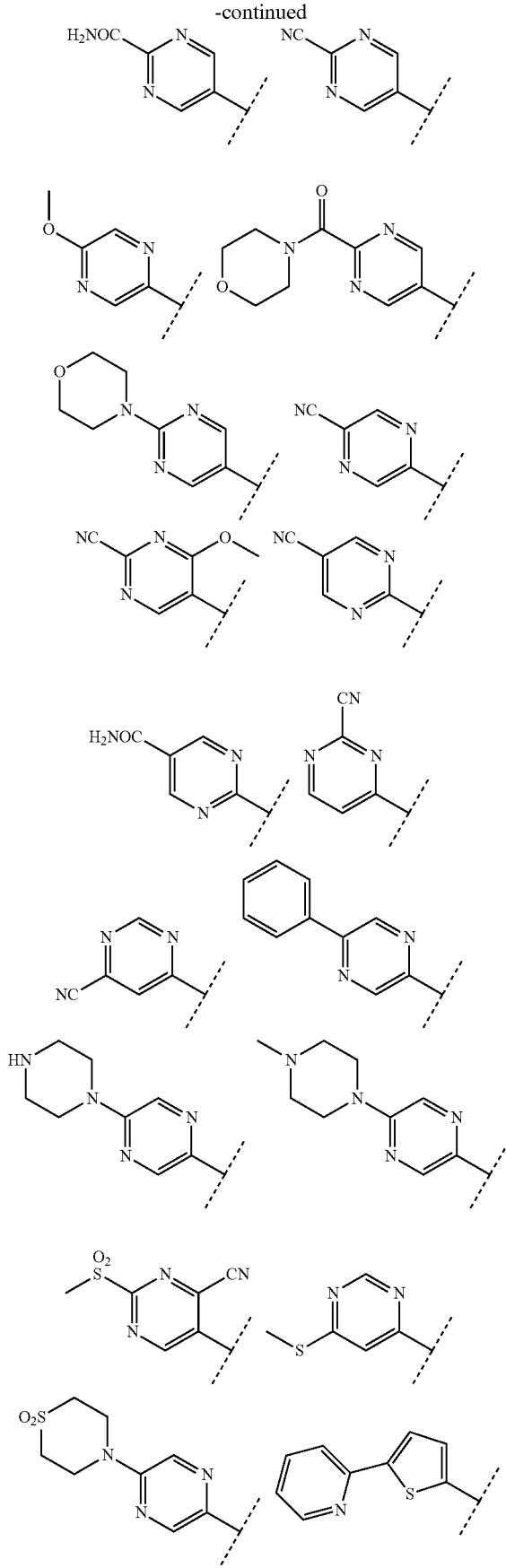
378
-continued
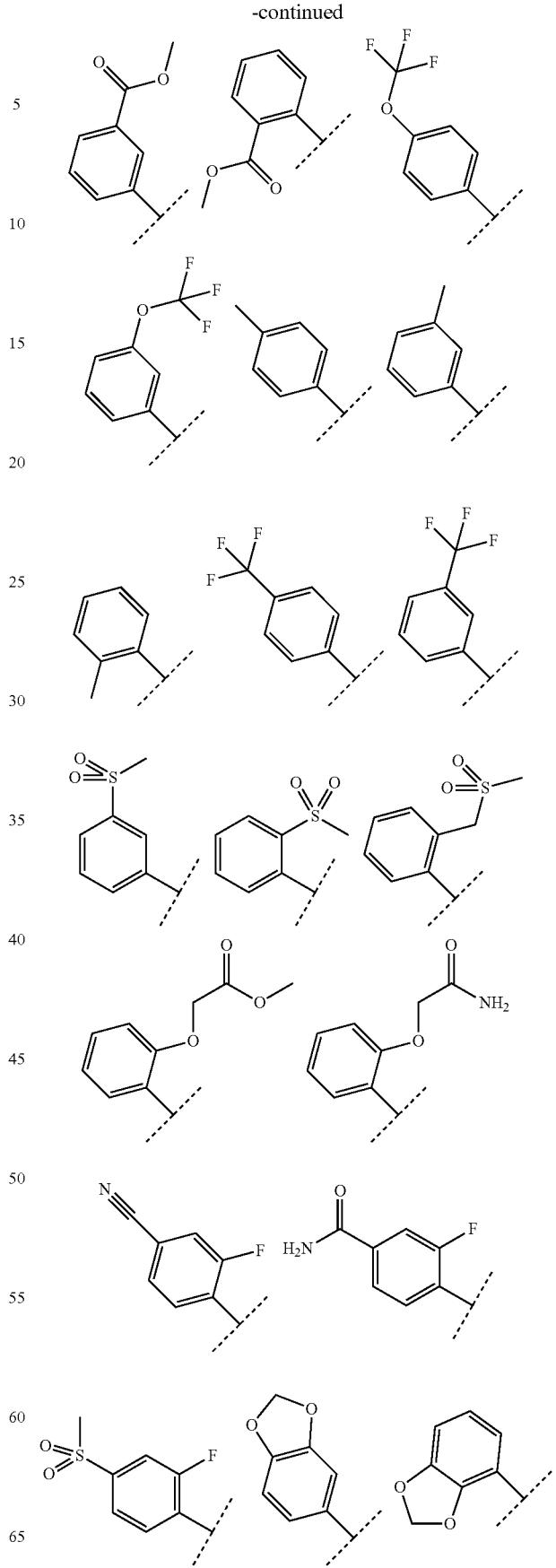

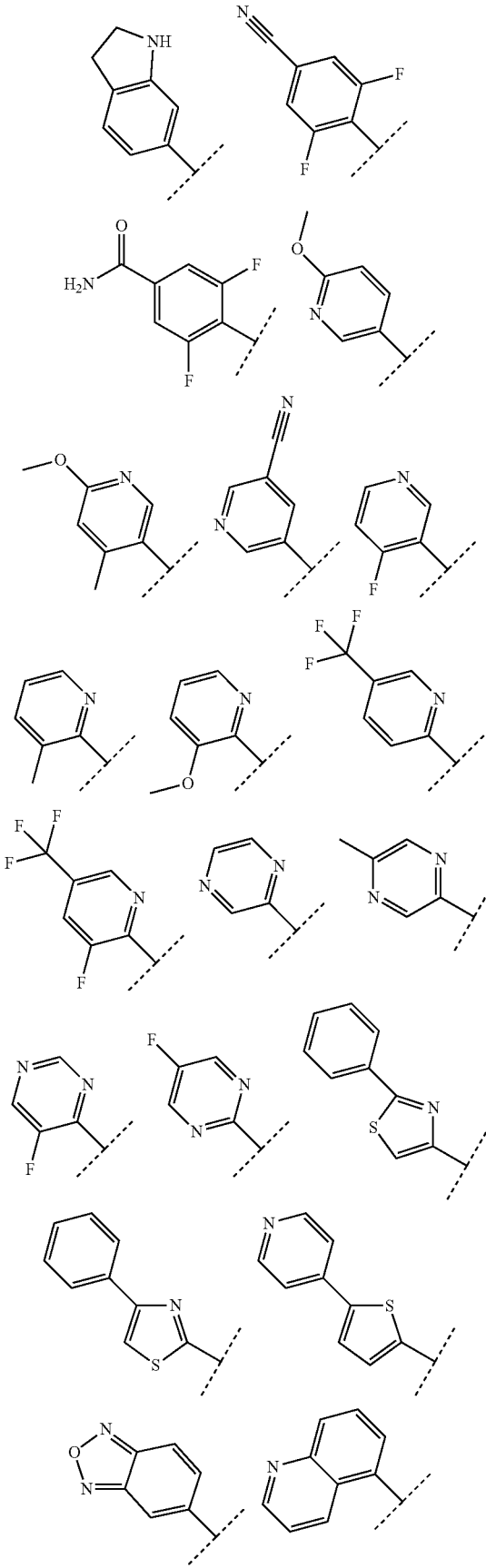
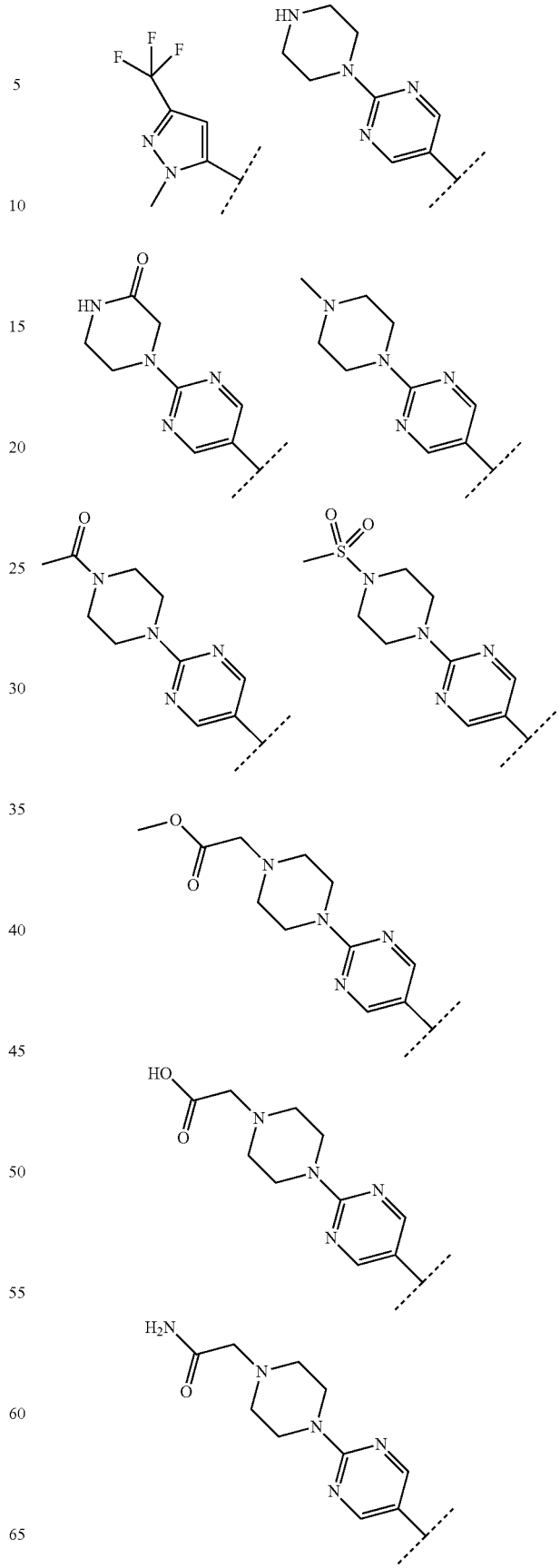

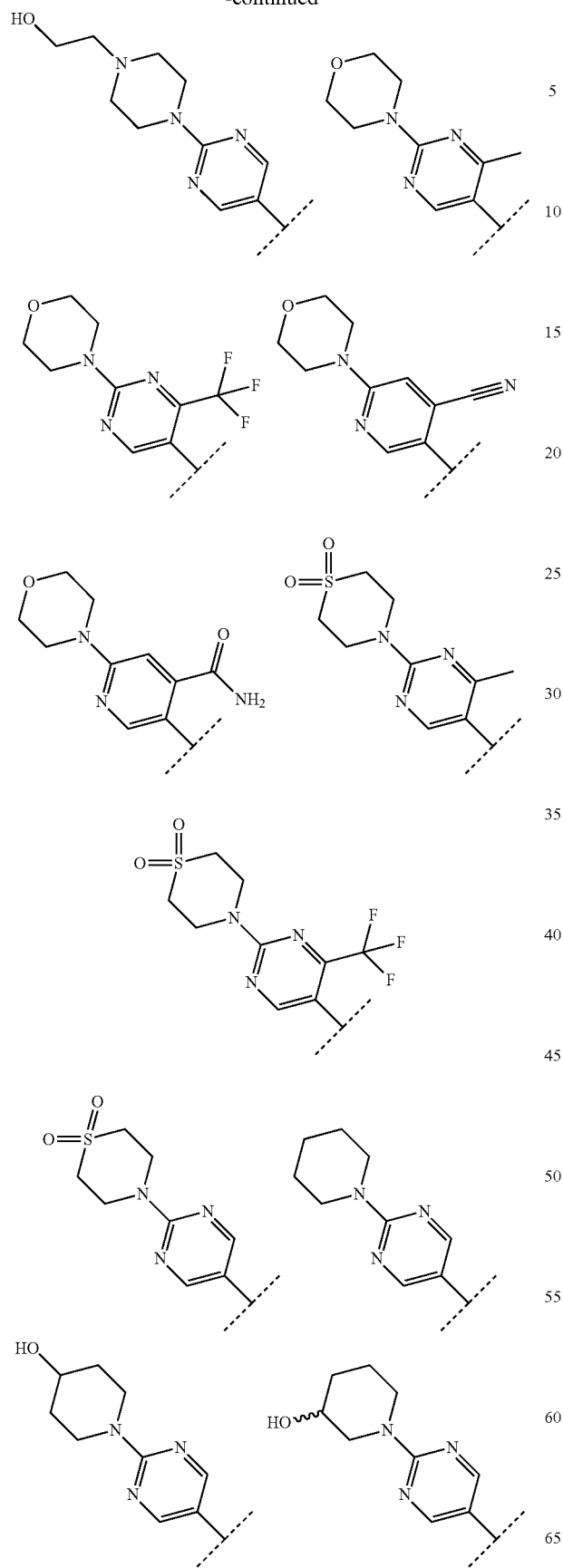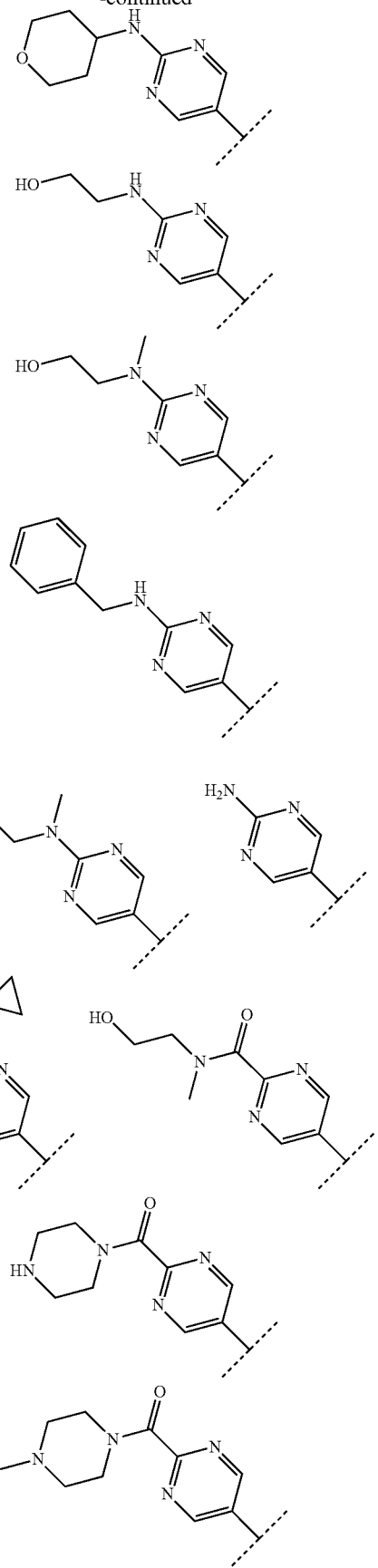

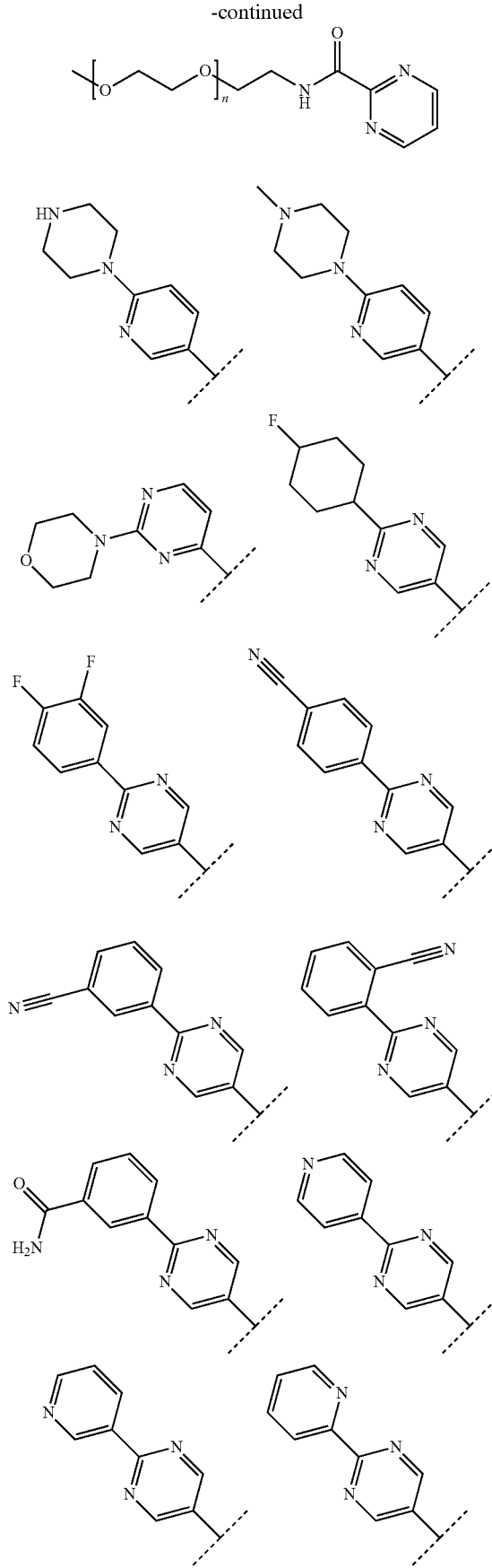
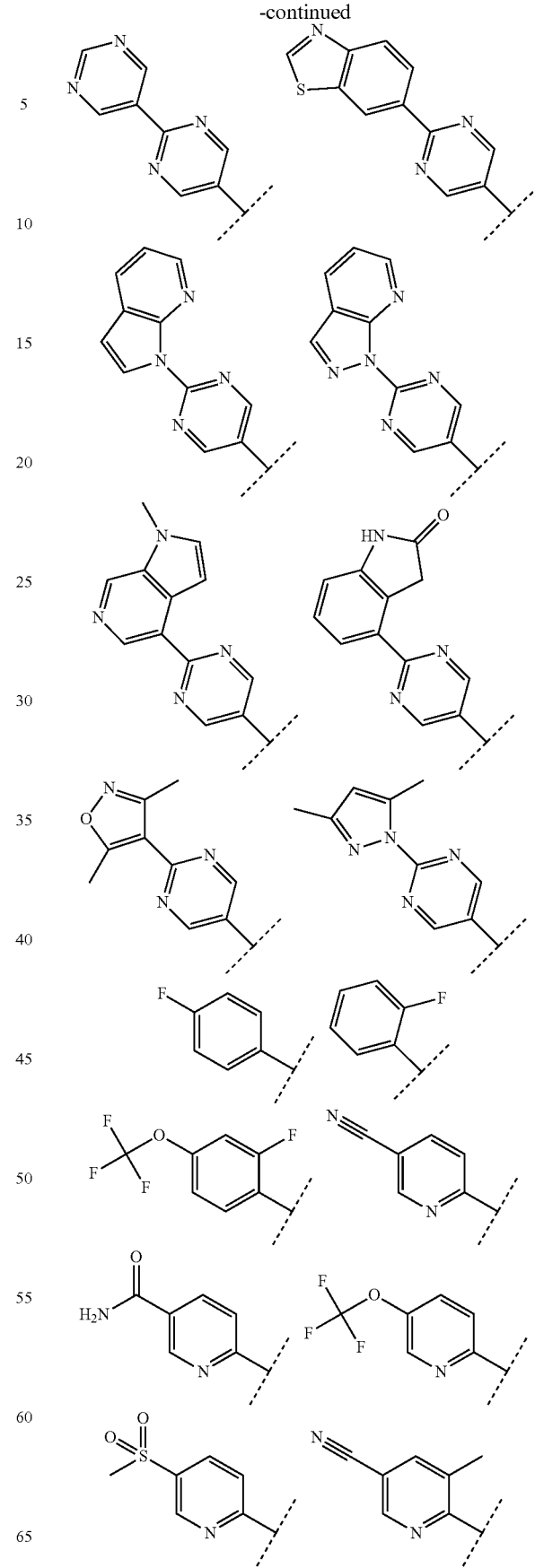

-continued
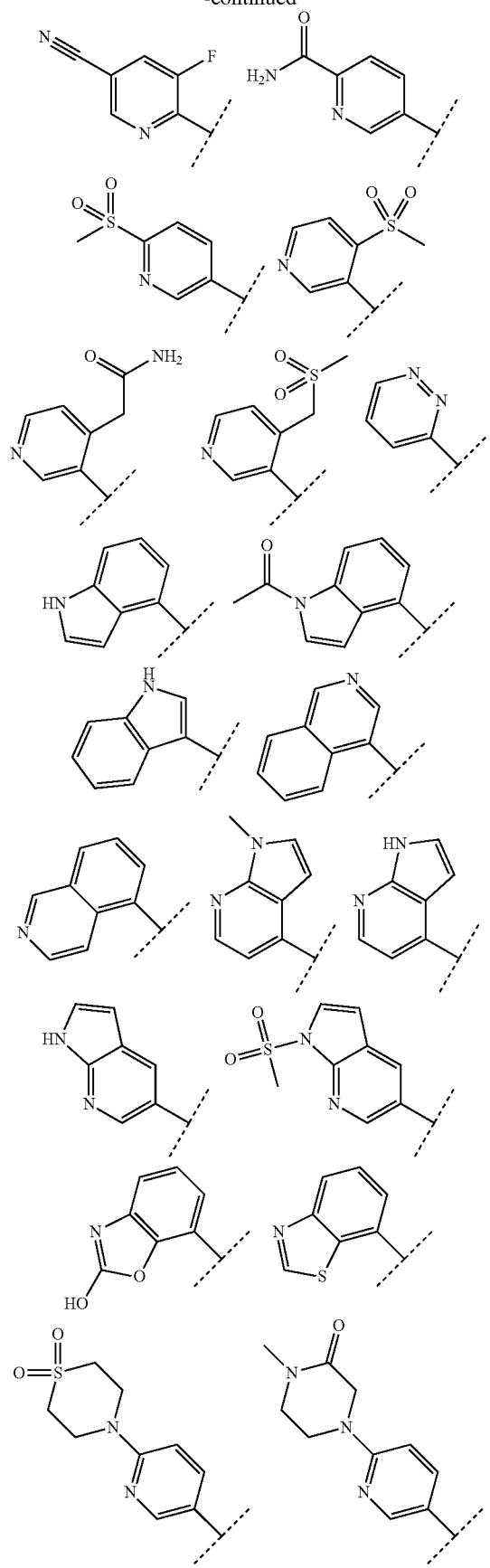
-continued
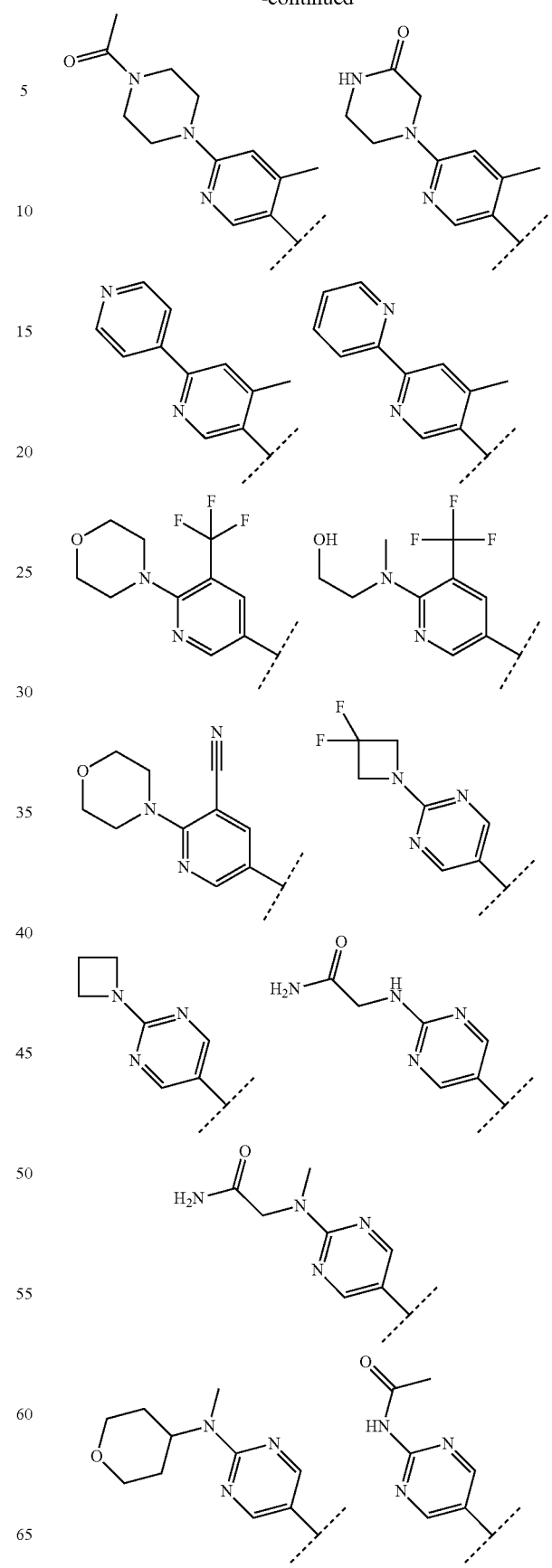

387
-continued
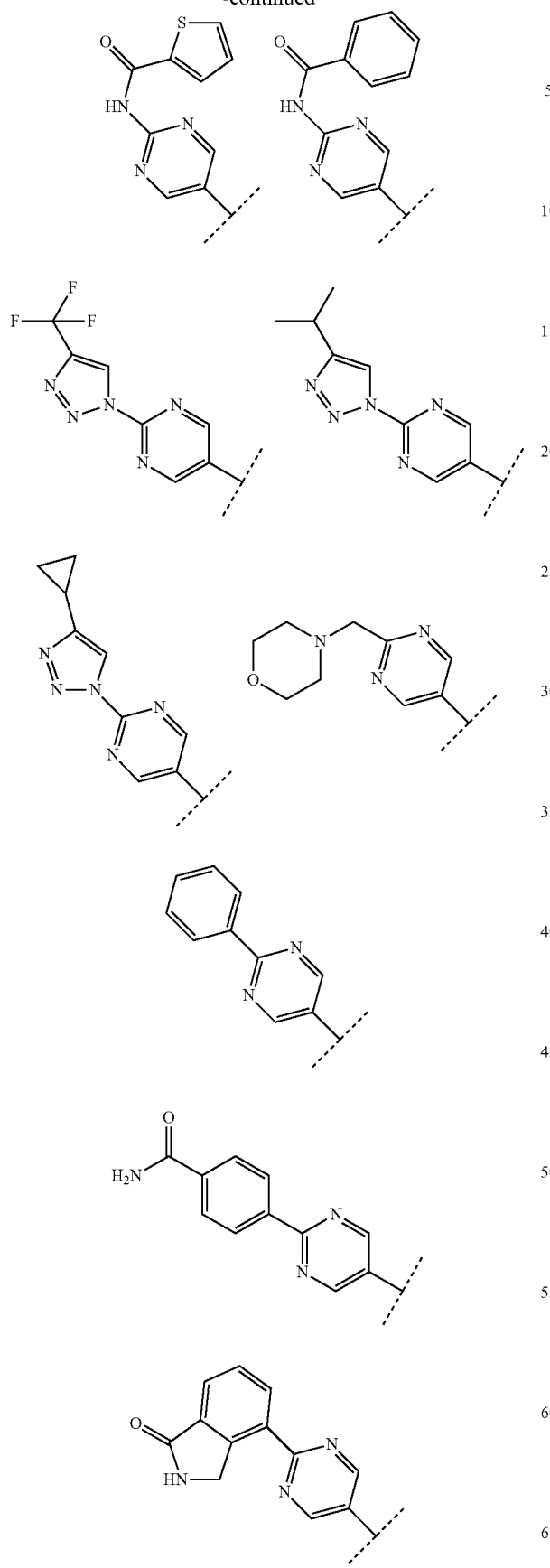
388
-continued
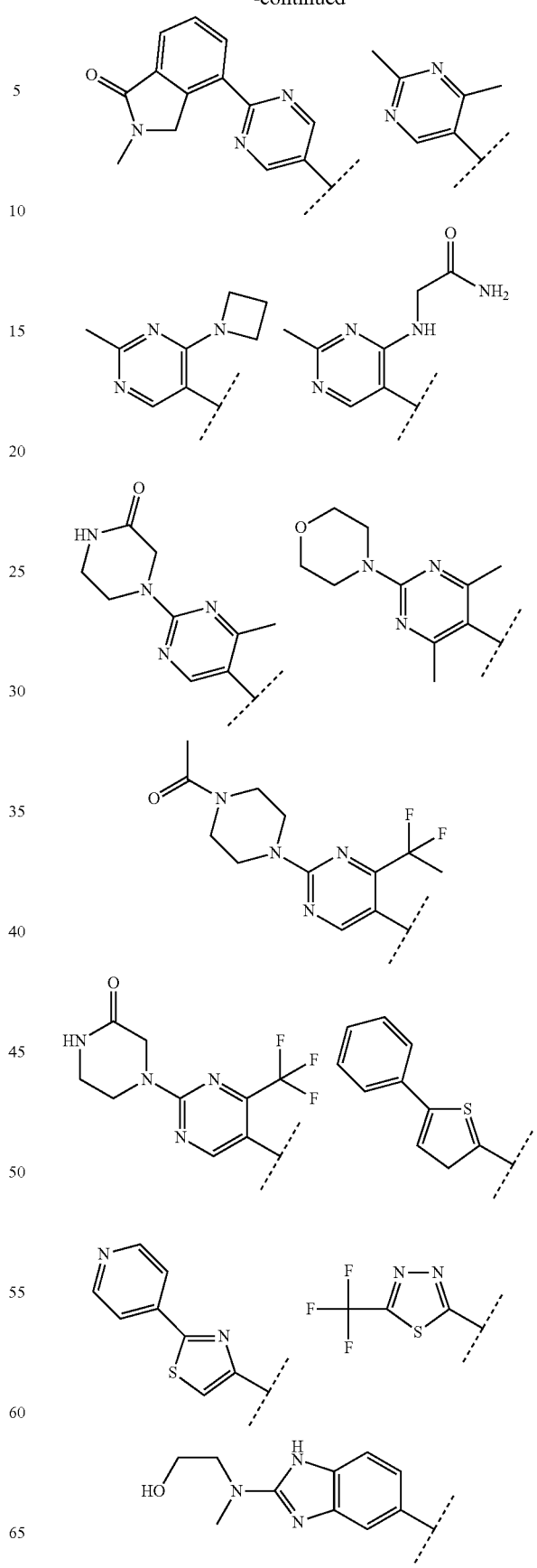

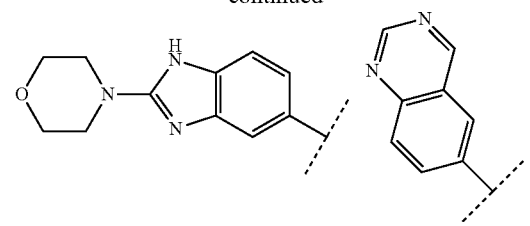
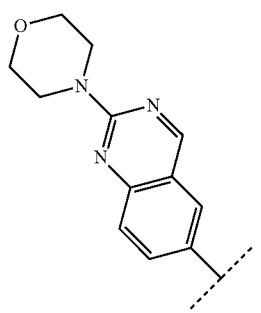
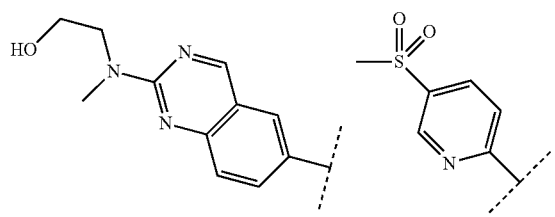
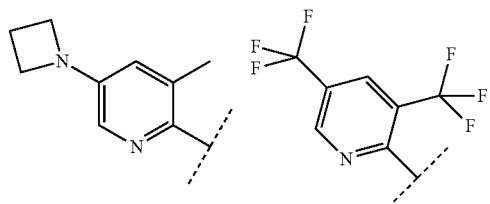
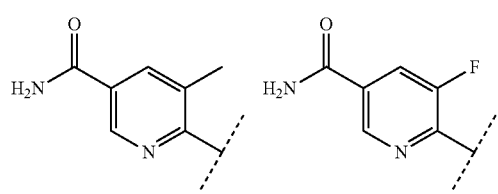
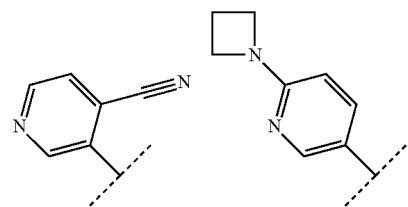
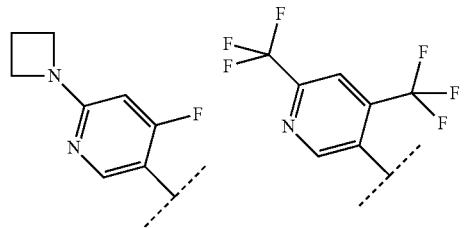
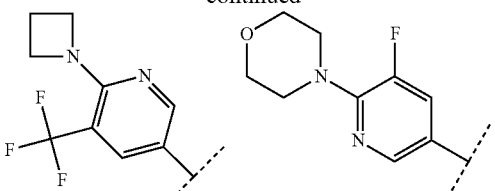
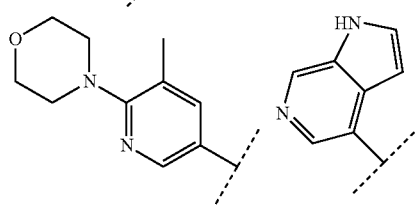
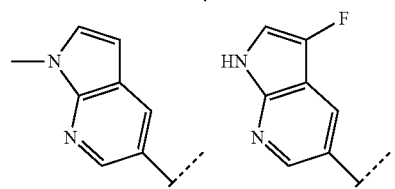
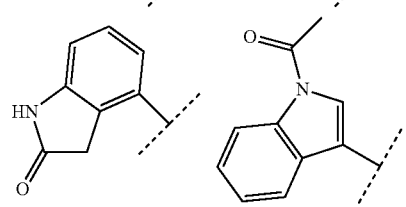
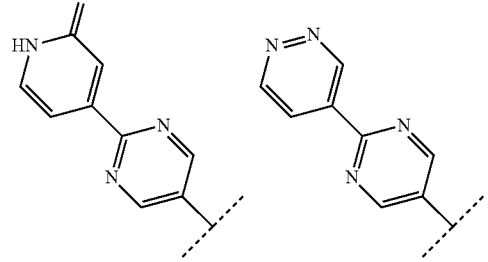
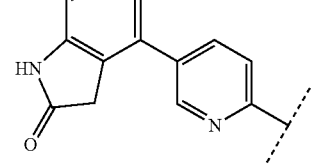
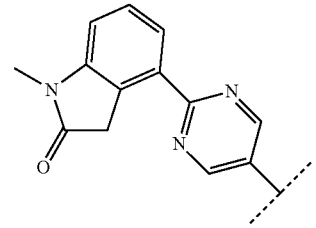
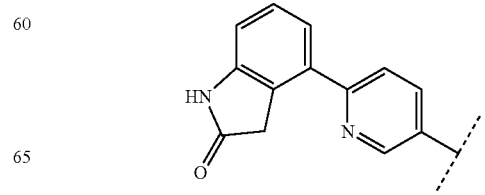

391
-continued
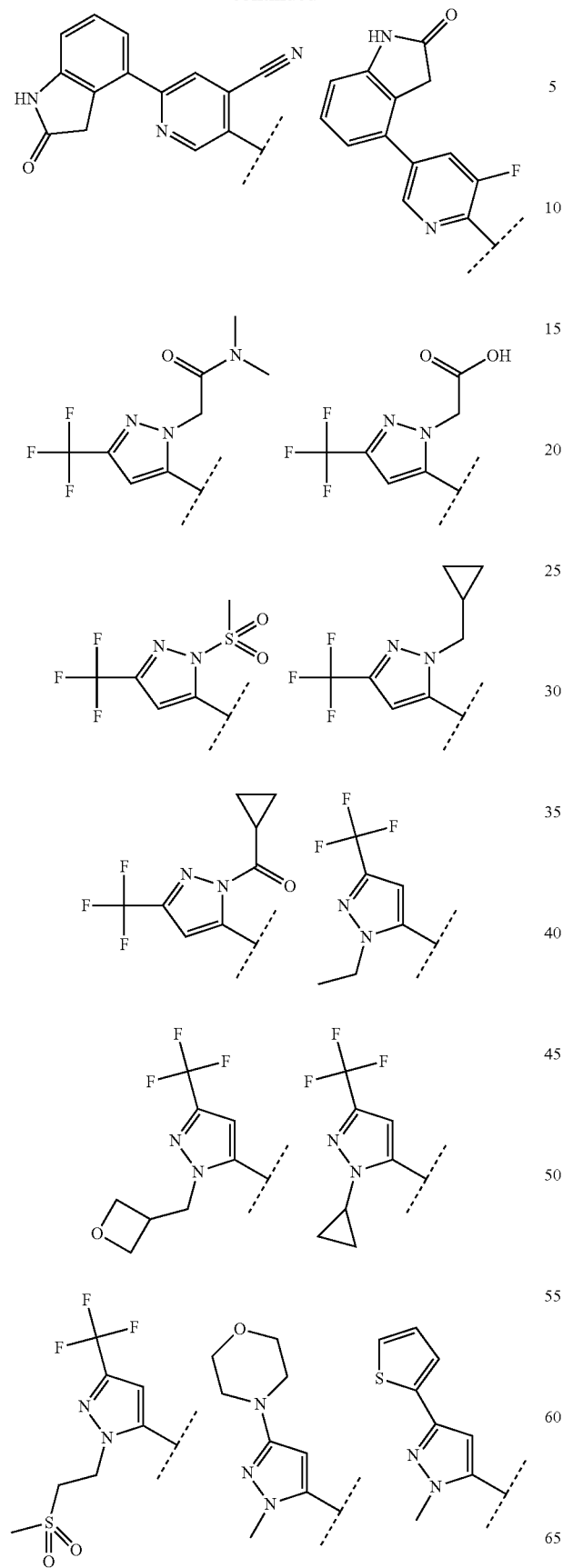
392
-continued
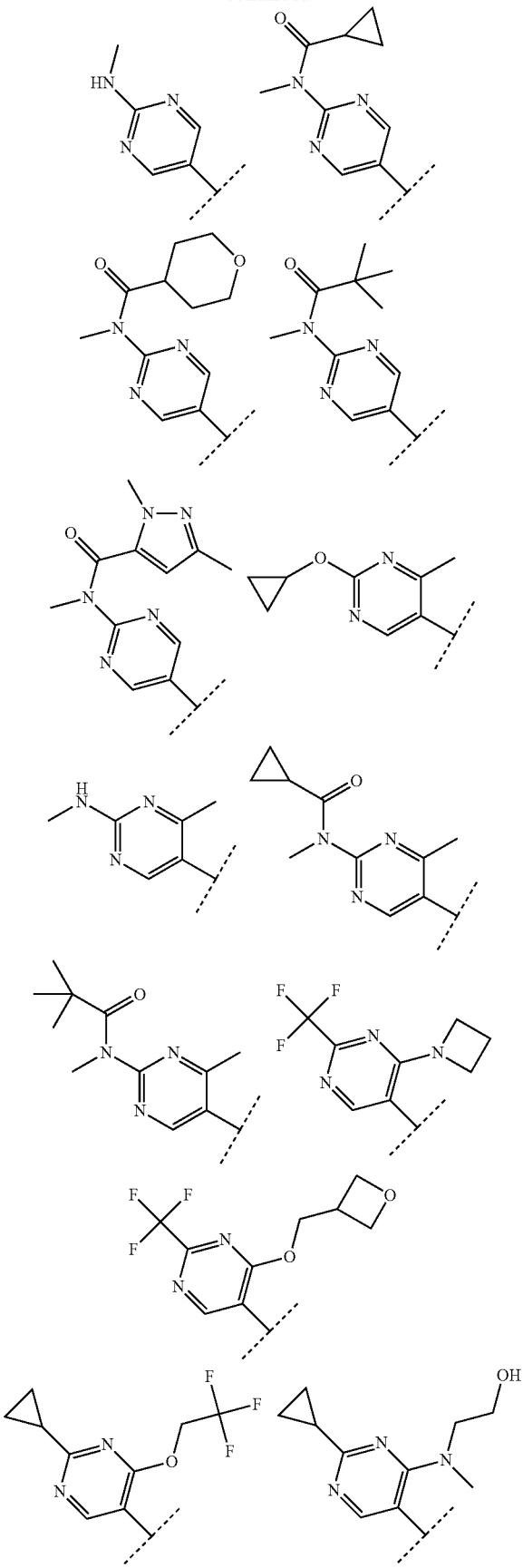

393
-continued
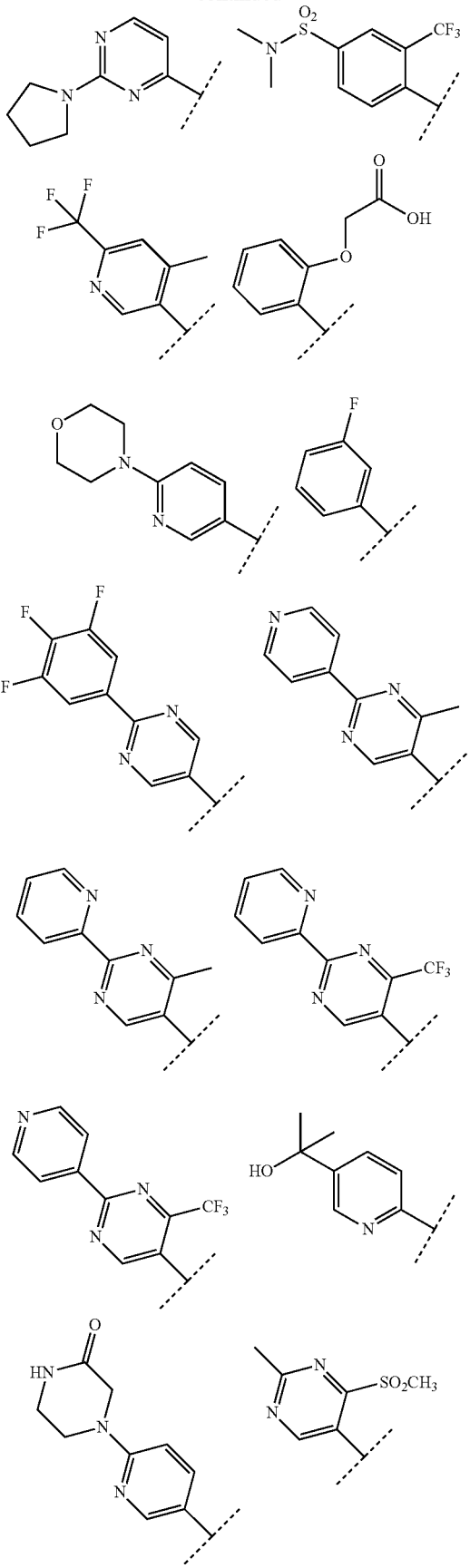
394
-continued
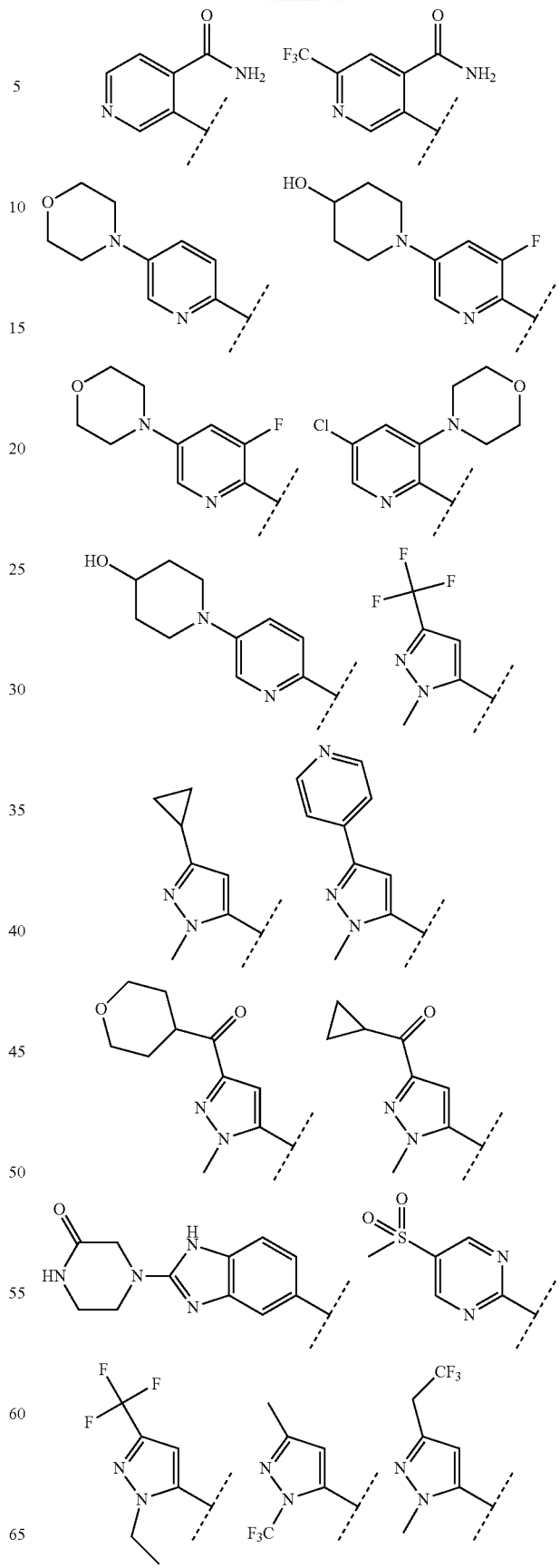

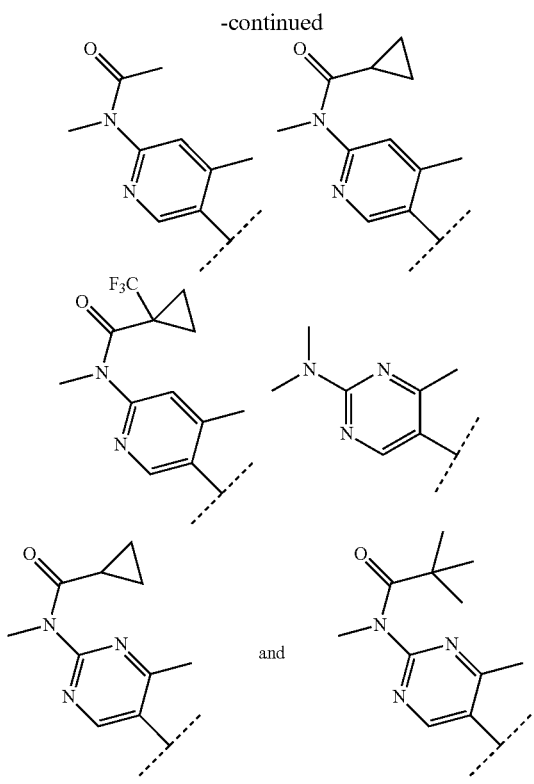

wherein n is 2.

22. The compound according to claim 1, wherein
R¹ means —H or —CH₃;
R² means —C₁-C₆-alkyl, linear or branched, saturated, unsubstituted; cyclopropyl connected through —CH₂—; or tetrahydropyranyl connected through —CH₂—;
R³ means -phenyl, benzyl, -thienyl or -pyridinyl, in each case unsubstituted or substituted with one, two, three or four substituents independently of one another selected from the group consisting of —F, —Cl, —CN, —CH₃, —CH₂CH₃, —CH₂F, —CHF₂, —CF₃, —OCF3, —OH, —OCH₃, —C(=O)NH₂, C(=O)NHCH₃, —C(=O)N(CH₃)₂, —NH₂, —NHCH₃, —N(CH₃)₂, —NHC(=O)CH₃, —CH₂OH, SOCH₃ and SO₂CH₃; or
R⁴ means
—H;
—C₁-C₆-alkyl, linear or branched, saturated, unsubstituted or substituted with one, two, three or four substituents independently of one another selected from the group consisting of —F, —Cl, —Br, —I, —CN, —OH, —O—C₁-C₄-alkyl, —C(=O)NH—C₁-C₆-alkyl, —C(=O)N(C₁-C₆-alkyl)₂ or —C(=O)NRR' wherein R and R' together with the nitrogen atom to which they are attached form a ring and mean —(CH₂)₃₋₅—;
3-6-membered cycloalkyl, unsubstituted or substituted with one, two, three or four substituents independently of one another selected from the group consisting of —F, —Cl, —Br, —I, —CN, —OH, and —O—C₁-C₄-alkyl, wherein said 3-6-membered cycloalkyl is connected through —C₁-C₆-alkylene;
3-6-membered heterocycloalkyl, unsubstituted or substituted with one, two, three or four substituents independently of one another selected from the group consisting of —F, —Cl, —Br, —I, —CN, —OH, and —O—C₁-C₄-alkyl, wherein said 3-6-membered heterocycloalkyl is connected through —C₁-C₆-alkylene;
-phenyl, unsubstituted or monosubstituted with —OCH₃; wherein said -phenyl is connected through —C₁-C₆-alkylene-; or
-pyridyl, unsubstituted, mono- or polysubstituted; wherein said -pyridyl is connected through —C₁-C₆-alkylene-;
R⁵ means
-phenyl, -1,2-benzodioxole, -pyrazinyl, -pyridazinyl, -pyridinyl, -pyrimidinyl, -thienyl, -imidazolyl, -benzimidazolyl, -thiazolyl, -1,3,4-thiadiazolyl, -benzothiazolyl, -oxazolyl, -benzoxazolyl, -pyrazolyl, -quinolinyl, -isoquinolinyl, -quinazolinyl, -indolyl, -indolinyl, -benzo[c][1,2,5]oxadiazolyl, -imidazo[1,2-a]pyrazinyl, or -1H-pyrrolo[2,3-b]pyridinyl, in each case unsubstituted or substituted with one, two, three or four substituents independently of one another selected from the group consisting of
—F; —Cl; —Br; —I;
—CN; —C₁-C₄-alkyl; —C₁-C₄-alkyl-OH; —CF₃; —C₁-C₄-alkyl-CF₃; —C₁-C₄-alkyl-C(=O)NH₂; —C₁-C₄-alkyl-C(=O)NHC₁-C₆-alkyl; —C₁-C₄-alkyl-C(=O)N(C₁-C₆-alkyl)₂; —C₁-C₄-alkyl-S(=O)₂—C₁-C₄-alkyl;
—C(=O)—C₁-C₄-alkyl; —C(=O)OH; —C(=O)O—C₁-C₄-alkyl; —C(=O)NH₂; —C(=O)NHC₁-C₄-alkyl; —C(=O)N(C₁-C₄-alkyl)₂; —C(=O)NH(C₁-C₄-alkyl-OH); —C(=O)N(C₁-C₄-alkyl)(C₁-C₄-alkyl-OH); —C(=O)NH—(CH₂CH₂O)₁₋₃₀—CH₃;
—NH₂; —NHC₁-C₄-alkyl; —N(C₁-C₄-alkyl)₂; —NHC₁-C₄-alkyl-OH; —NCH₃C₁-C₄-alkyl-OH; —NH—C₁-C₄-alkyl-C(=O)NH₂; —NCH₃—C₁-C₄-alkyl-C(=O)NH₂; —NHC(=O)—C₁-C₄-alkyl; —NCH₃C(=O)—C₁-C₄-alkyl;
—OH; —O—C₁-C₄-alkyl; —OCF₃; —O—C₁-C₄-alkyl-CO₂H; —O—C₁-C₄-alkyl-C(=O)O—C₁-C₄-alkyl; —O—C₁-C₄-alkyl-CONH₂;
—S—C₁-C₄-alkyl; —S(=O)C₁-C₄-alkyl; —S(=O)₂C₁-C₄-alkyl; and —S(=O)₂N(C₁-C₄-alkyl)₂;
-3-12-membered cycloalkyl, saturated or unsaturated, unsubstituted, mono- or polysubstituted; wherein said 3-12-membered cycloalkyl is optionally connected through —CH₂—, —O—, —NH—, —NCH₃—, —NH—(CH₂)₁₋₃—, —NCH₃(CH₂)₁₋₃—, —(C=O)—, —NHC(=O)—, —NCH₃C(=O)—, —C(=O)NH—(CH₂)₁₋₃—, —C(=O)NCH₃—(CH₂)₁₋₃—;
-3-12-membered heterocycloalkyl, saturated or unsaturated, unsubstituted, mono- or polysubstituted; wherein said 3-12-membered heterocycloalkyl is optionally connected through —CH₂—, —O—, —NH—, —NCH₃—, —NH—(CH₂)₁₋₃—, —NCH₃(CH₂)₁₋₃—, —(C=O)—, —NHC(=O)—, —NCH₃C(=O)—, —C(=O)NH—(CH₂)₁₋₃—, —C(=O)NCH₃—(CH₂)₁₋₃—;
-6-14-membered aryl, unsubstituted, mono- or polysubstituted; wherein said 6-14-membered aryl is optionally connected through —CH₂—, —O—, —NH—, —NCH₃—, —NH—(CH₂)₁₋₃—, —NCH₃(CH₂)₁₋₃—, —(C=O)—, —NHC(=O)—, —NCH₃C(=O)—, —C(=O)NH—(CH₂)₁₋₃—, —C(=O)NCH₃—(CH₂)₁₋₃—; or
-5-14-membered heteroaryl, unsubstituted, mono- or polysubstituted; wherein said 5-14-membered heteroaryl is optionally connected through —CH$_2$—, —O—, —NH—, —NCH$_3$—, —N—(CH$_2$)$_{1-3}$—, —NCH$_3$(CH$_2$)$_{1-3}$—, —(C═O)—, —NHC(═O)—, —NCH$_3$C(═O)—, —C(═O)NH—(CH$_2$)$_{1-3}$—, —C(═O)NCH$_3$—(CH$_2$)$_{1-3}$—;
and
R$^{11}$, R$^{12}$, R$^{13}$, R$^{14}$, R$^{15}$, R$^{16}$, R$^{17}$, R$^{18}$, R$^{19}$, and R$^{20}$ mean —H.

23. The compound according to claim 1, which has a structure according to general formula (I')

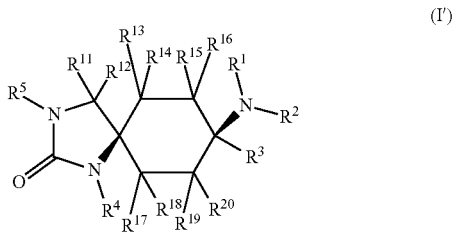

(I')

wherein R$^1$ to R$^5$, R$^{11}$ to R$^{20}$ are defined as in claim 1, or a physiologically acceptable salt thereof.

24. The compound according to claim 1, which has a structure according to general formula (IX) or (X)

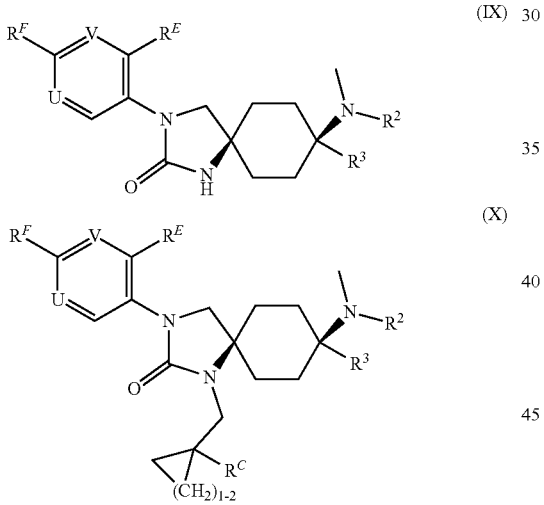

wherein
R$^2$ means —H or —CH$_3$;
R$^3$ means -phenyl or -3-fluorophenyl;
R$^C$ means —H or —OH;
R$^E$ means —H, —CH$_3$, —F, —CF$_3$, -cyclopropyl, -aziridinyl, —OH; —O—C$_1$-C$_4$-alkyl; —OCF$_3$; —O—C$_1$-C$_4$-alkyl-CO$_2$H; —O—C$_1$-C$_4$-alkyl-C(═O)O—C$_1$-C$_4$-alkyl; or —O—C$_1$-C$_4$-alkyl-CONH$_2$;
R$^F$ means
—CF$_3$, -cyclopropyl, —S(═O)$_2$CH$_3$, —NH$_2$; —NHC$_1$-C$_4$-alkyl; —N(C$_1$-C$_4$-alkyl)$_2$; —NHC$_1$-C$_4$-alkyl-OH; —NCH$_3$C$_1$-C$_4$-alkyl-OH; —NH—C$_1$-C$_4$-alkyl-C(═O)NH$_2$; —NCH$_3$—C$_1$-C$_4$-alkyl-C(═O)NH$_2$; —NHC(═O)—C$_1$-C$_4$-alkyl; —NCH$_3$C(═O)—C$_1$-C$_4$-alkyl;
-6-14-membered aryl, unsubstituted, mono- or polysubstituted; or
-5-14-membered heteroaryl, unsubstituted, mono- or polysubstituted;
U means ═CH— or ═N—; and
V means ═CH— or ═N—;
or a physiologically acceptable salt thereof.

25. The compound according to claim 1, which has a structure according to general formula (XI)

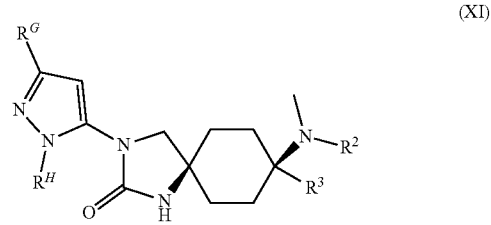

(XI)

wherein
R$^2$ means —H or —CH$_3$;
R$^3$ means -phenyl or -3-fluorophenyl;
R$^H$ means
—CN; —C$_1$-C$_4$-alkyl; —CF$_3$; —C$_1$-C$_4$-alkyl-C(═O)NH$_2$; —C$_1$-C$_4$-alkyl-S(═O)$_2$—C$_1$-C$_4$-alkyl; —C(═O)—C$_1$-C$_4$-alkyl; —C(═O)OH; —C(═O)O—C$_1$-C$_4$-alkyl; —C(═O)NH$_2$; —C(═O)NHC$_1$-C$_4$-alkyl; —C(═O)N(C$_1$-C$_4$-alkyl)$_2$; —C(═O)NH(C$_1$-C$_4$-alkyl-OH); —C(═O)N(C$_1$-C$_4$-alkyl)(C$_1$-C$_4$-alkyl-OH); —C(═O)NH—(CH$_2$CH$_2$O)$_{1-30}$—CH$_3$;
-3-12-membered cycloalkyl, saturated or unsaturated, unsubstituted, mono- or polysubstituted; wherein said 3-12-membered cycloalkyl is optionally connected through —CH$_2$—, —NH—, —NCH$_3$—, —NH—(CH$_2$)$_{1-3}$—, —NCH$_3$(CH$_2$)$_{1-3}$—, —(C═O)—, —NHC(═O)—, —NCH$_3$C(═O)—, —C(═O)NH—(CH$_2$)$_{1-3}$—, —C(═O)NCH$_3$—(CH$_2$)$_{1-3}$—; or
-3-12-membered heterocycloalkyl, saturated or unsaturated, unsubstituted, mono- or polysubstituted; 6-14-membered aryl, unsubstituted, mono- or polysubstituted; wherein said 3-12-membered heterocycloalkyl is optionally connected through —CH$_2$—, —NH—, —NCH$_3$—, —NH—(CH$_2$)$_{1-3}$—, —NCH$_3$(CH$_2$)$_{1-3}$—, —(C═O)—, —NHC(═O)—, —NCH$_3$C(═O)—, —C(═O)NH—(CH$_2$)$_{1-3}$—, —C(═O)NCH$_3$—(CH$_2$)$_{1-3}$—;
R$^G$ means
—CF$_3$, —S(═O)$_2$CH$_3$;
—NH$_2$; —NHC$_1$-C$_4$-alkyl; —N(C$_1$-C$_4$-alkyl)$_2$; —NHC$_1$-C$_4$-alkyl-OH; —NCH$_3$C$_1$-C$_4$-alkyl-OH; —NH—C$_1$-C$_4$-alkyl-C(═O)NH$_2$; —NCH$_3$—C$_1$-C$_4$-alkyl-C(═O)NH$_2$; —NHC(═O)—C$_1$-C$_4$-alkyl; —NCH$_3$C(═O)—C$_1$-C$_4$-alkyl;
-3-12-membered cycloalkyl, saturated or unsaturated, unsubstituted, mono- or polysubstituted; wherein said 3-12-membered cycloalkyl is optionally connected through —CH$_2$—, —NH—, —NCH$_3$—, —NH—(CH$_2$)$_{1-3}$—, —NCH$_3$(CH$_2$)$_{1-3}$—, —(C═O)—, —NHC(═O)—, —NCH$_3$C(═O)—, —C(═O)NH—(CH$_2$)$_{1-3}$—, —C(═O)NCH$_3$—(CH$_2$)$_{1-3}$—; or
-3-12-membered heterocycloalkyl, saturated or unsaturated, unsubstituted, mono- or polysubstituted; 6-14-membered aryl, unsubstituted, mono- or polysubstituted; wherein said 3-12-membered heterocycloalkyl is optionally connected through —CH$_2$—, —NH—, —NCH$_3$—, —N—(CH$_2$)$_{1-3}$—, —NCH$_3$(CH$_2$)$_{1-3}$—,

—(C=O)—, —NHC(=O)—, —NCH₃C(=O)—, —C(=O)NH—(CH₂)₁₋₃—, —C(=O)NCH₃—(CH₂)₁₋₃—;

or a physiologically acceptable salt thereof.

26. The compound according to claim 1, which is selected from the group consisting of cis-5-[1-(Cyclobutyl-methyl)-8-dimethylamino-2-oxo-8-phenyl-1,3-diazaspiro[4.5]decan-3-yl]-pyrimidine-2-carbonitrile;
cis-5-[1-(Cyclobutyl-methyl)-8-dimethylamino-2-oxo-8-phenyl-1,3-diazaspiro[4.5]decan-3-yl]-pyrazine-2-carbonitrile;
cis-5-[1-(Cyclobutyl-methyl)-8-dimethylamino-2-oxo-8-phenyl-1,3-diazaspiro[4.5]decan-3-yl]-4-methoxy-pyrimidine-2-carbonitrile;
cis-5-[8-Dimethylamino-1-(2-methoxy-ethyl)-2-oxo-8-phenyl-1,3-diazaspiro[4.5]decan-3-yl]-pyrimidine-2-carbonitrile;
cis-5-[1-(Cyclobutyl-methyl)-8-dimethylamino-2-oxo-8-phenyl-1,3-diazaspiro[4.5]decan-3-yl]-pyrimidine-2-carboxylic acid amide;
cis-5-[1-(Cyclobutyl-methyl)-8-dimethylamino-2-oxo-8-phenyl-1,3-diazaspiro[4.5]decan-3-yl]-2-methylsulfonyl-pyrimidine-4-carbonitrile;
cis-5-[1-(2-Methoxy-ethyl)-8-methylamino-2-oxo-8-phenyl-1,3-diazaspiro[4.5]decan-3-yl]-pyrimidine-2-carbonitrile;
cis-2-[1-(Cyclobutyl-methyl)-8-dimethylamino-2-oxo-8-phenyl-1,3-diazaspiro[4.5]decan-3-yl]-5-methylsulfonyl-benzonitrile;
cis-2-[1-(Cyclobutyl-methyl)-8-dimethylamino-2-oxo-8-phenyl-1,3-diazaspiro[4.5]decan-3-yl]-benzamide;
cis-3-[1-(Cyclobutyl-methyl)-8-dimethylamino-2-oxo-8-phenyl-1,3-diazaspiro[4.5]decan-3-yl]-benzamide;
cis-5-[8-Dimethylamino-1-[(1-hydroxy-cyclobutyl)-methyl]-2-oxo-8-phenyl-1,3-diazaspiro[4.5]decan-3-yl]-pyrimidine-2-carboxylic acid amide;
cis-5-[1-(Cyclobutyl-methyl)-8-methylamino-2-oxo-8-phenyl-1,3-diazaspiro[4.5]decan-3-yl]-4-methoxy-pyrimidine-2-carbonitrile;
cis-5-[8-Dimethylamino-1-[(1-hydroxy-cyclobutyl)-methyl]-2-oxo-8-phenyl-1,3-diazaspiro[4.5]decan-3-yl]-pyrimidine-2-carbonitrile;
cis-2-[1-(Cyclobutyl-methyl)-8-dimethylamino-2-oxo-8-phenyl-1,3-diazaspiro[4.5]decan-3-yl]-pyrimidine-5-carbonitrile;
cis-8-Dimethylamino-1-[(1-hydroxy-cyclobutyl)-methyl]-3-(2-methoxy-pyrimidin-5-yl)-8-phenyl-1,3-diazaspiro[4.5]decan-2-one;
cis-2-[1-(Cyclobutyl-methyl)-8-dimethylamino-2-oxo-8-phenyl-1,3-diazaspiro[4.5]decan-3-yl]-pyrimidine-5-carboxylic acid amide;
cis-4-[1-(Cyclobutyl-methyl)-8-dimethylamino-2-oxo-8-phenyl-1,3-diazaspiro[4.5]decan-3-yl]-N-methyl-benzamide;
cis-5-(8-Dimethylamino-2-oxo-8-phenyl-1-propyl-1,3-diazaspiro[4.5]decan-3-yl)-pyrimidine-2-carbonitrile;
cis-5-[8-Dimethylamino-1-(3-methoxy-propyl)-2-oxo-8-phenyl-1,3-diazaspiro[4.5]decan-3-yl]-pyrimidine-2-carbonitrile;
cis-5-[1-(Cyclopropyl-methyl)-8-dimethylamino-2-oxo-8-phenyl-1,3-diazaspiro[4.5]decan-3-yl]-pyrimidine-2-carbonitrile;
cis-4-[1-(Cyclobutyl-methyl)-8-dimethylamino-2-oxo-8-phenyl-1,3-diazaspiro[4.5]decan-3-yl]-benzamide;
cis-1-(Cyclobutyl-methyl)-8-dimethylamino-8-phenyl-3-[2-(trifluoromethyl)-pyrimidin-5-yl]-1,3-diazaspiro[4.5]decan-2-one;
cis-8-Dimethylamino-1-[(1-hydroxy-cyclobutyl)-methyl]-3-(2-hydroxy-pyrimidin-5-yl)-8-phenyl-1,3-diazaspiro[4.5]decan-2-one;
cis-5-[8-Dimethylamino-1-(2-methyl-propyl)-2-oxo-8-phenyl-1,3-diazaspiro[4.5]decan-3-yl]-pyrimidine-2-carbonitrile;
cis-5-[8-Dimethylamino-1-(2-hydroxy-ethyl)-2-oxo-8-phenyl-1,3-diazaspiro[4.5]decan-3-yl]-pyrimidine-2-carbonitrile;
cis-5-[1-(Cyclobutyl-methyl)-8-methylamino-2-oxo-8-phenyl-1,3-diazaspiro[4.5]decan-3-yl]-4-methyl-pyridine-2-carbonitrile;
cis-1-(Cyclobutyl-methyl)-3-(5-methoxy-pyrazin-2-yl)-8-methylamino-8-phenyl-1,3-diazaspiro[4.5]decan-2-one;
cis-4-[1-(Cyclobutyl-methyl)-8-dimethylamino-2-oxo-8-phenyl-1,3-diazaspiro[4.5]decan-3-yl]-N,N-dimethyl-benzamide;
cis-4-[1-(Cyclobutyl-methyl)-8-dimethylamino-2-oxo-8-phenyl-1,3-diazaspiro[4.5]decan-3-yl]-N-ethyl-N-(2-hydroxy-ethyl)-benzamide;
cis-2-[1-(Cyclobutyl-methyl)-8-methylamino-2-oxo-8-phenyl-1,3-diazaspiro[4.5]decan-3-yl]-5-methylsulfonyl-benzonitrile;
cis-1-(Cyclobutyl-methyl)-8-methylamino-3-[2-methylsulfonyl-4-(trifluoromethyl)-phenyl]-8-phenyl-1,3-diazaspiro[4.5]decan-2-one;
cis-4-[1-(Cyclobutyl-methyl)-8-methylamino-2-oxo-8-phenyl-1,3-diazaspiro[4.5]decan-3-yl]-N,N-dimethyl-3-(trifluoromethyl)-benzenesulfonic acid amide;
cis-4-[1-(Cyclobutyl-methyl)-8-(ethyl-methyl-amino)-2-oxo-8-phenyl-1,3-diazaspiro[4.5]decan-3-yl]-benzonitrile;
cis-1-(Cyclobutyl-methyl)-8-(ethyl-methyl-amino)-8-phenyl-3-[2-(trifluoromethyl)-pyrimidin-5-yl]-1,3-diazaspiro[4.5]decan-2-one;
cis-5-[1-(Cyclobutyl-methyl)-8-(ethyl-methyl-amino)-2-oxo-8-phenyl-1,3-diazaspiro[4.5]decan-3-yl]-pyrimidine-2-carbonitrile;
cis-5-[8-Dimethylamino-1-[(1-methyl-cyclobutyl)-methyl]-2-oxo-8-phenyl-1,3-diazaspiro[4.5]decan-3-yl]-pyrimidine-2-carbonitrile;
cis-2-[3-(2-Cyano-pyrimidin-5-yl)-8-dimethylamino-2-oxo-8-phenyl-1,3-diazaspiro[4.5]decan-1-yl]-N,N-dimethyl-acetamide;
cis-1-(Cyclobutyl-methyl)-8-methylamino-8-phenyl-3-[2-(trifluoromethyl)-pyrimidin-5-yl]-1,3-diazaspiro[4.5]decan-2-one;
cis-5-[8-Dimethylamino-8-(3-fluorophenyl)-1-(4-methoxy-butyl)-2-oxo-1,3-diazaspiro[4.5]decan-3-yl]-pyrimidine-2-carbonitrile;
cis-5-[8-Dimethylamino-1-(3-methoxy-propyl)-2-oxo-8-phenyl-1,3-diazaspiro[4.5]decan-3-yl]-4-methoxy-pyrimidine-2-carbonitrile;
cis-5-[1-[(1-Cyano-cyclobutyl)-methyl]-8-dimethylamino-2-oxo-8-phenyl-1,3-diazaspiro[4.5]decan-3-yl]-pyrimidine-2-carbonitrile;
cis-N-(Cyclobutyl-methyl)-5-[1-(cyclobutyl-methyl)-8-dimethylamino-8-(3-fluorophenyl)-2-oxo-1,3-diazaspiro[4.5]decan-3-yl]-pyrimidine-2-carboxylic acid amide;
cis-5-[1-(3-Methoxy-propyl)-8-methylamino-2-oxo-8-phenyl-1,3-diazaspiro[4.5]decan-3-yl]-pyrimidine-2-carbonitrile;

cis-5-[8-Dimethylamino-8-(3-fluorophenyl)-1-methyl-2-oxo-1,3-diazaspiro[4.5]decan-3-yl]-pyrimidine-2-carbonitrile;
cis-4-Methoxy-5-[1-(3-methoxy-propyl)-8-methylamino-2-oxo-8-phenyl-1,3-diazaspiro[4.5]decan-3-yl]-pyrimidine-2-carbonitrile;
cis-4-[8-Dimethylamino-1-(2-methoxy-ethyl)-2-oxo-8-phenyl-1,3-diazaspiro[4.5]decan-3-yl]-pyrimidine-2-carbonitrile;
cis-5-[8-Dimethylamino-1-(2-methoxy-ethyl)-2-oxo-8-phenyl-1,3-diazaspiro[4.5]decan-3-yl]-4-methoxy-pyrimidine-2-carbonitrile;
cis-4-[1-(Cyclobutyl-methyl)-8-dimethylamino-2-oxo-8-phenyl-1,3-diazaspiro[4.5]decan-3-yl]-pyrimidine-2-carbonitrile;
cis-1-(Cyclobutyl-methyl)-8-dimethylamino-3-(6-methylsulfanyl-pyrimidin-4-yl)-8-phenyl-1,3-diazaspiro[4.5]decan-2-one;
cis-2-[3-(2-Cyano-pyrimidin-4-yl)-8-dimethylamino-2-oxo-8-phenyl-1,3-diazaspiro[4.5]decan-1-yl]-N,N-dimethyl-acetamide;
cis-6-[1-(Cyclobutyl-methyl)-8-dimethylamino-2-oxo-8-phenyl-1,3-diazaspiro[4.5]decan-3-yl]-pyrimidine-4-carbonitrile;
cis-2-(8-Dimethylamino-2-oxo-3,8-diphenyl-1,3-diazaspiro[4.5]decan-1-yl)-N,N-dimethyl-acetamide;
cis-1-(Cyclobutyl-methyl)-8-dimethylamino-3,8-diphenyl-1,3-diazaspiro[4.5]decan-2-one;
cis-2-[8-Dimethylamino-1-(2-methoxy-ethyl)-2-oxo-8-phenyl-1,3-diazaspiro[4.5]decan-3-yl]-pyrimidine-5-carbonitrile;
cis-8-Dimethylamino-1-(2-methoxy-ethyl)-3,8-diphenyl-1,3-diazaspiro[4.5]decan-2-one;
cis-5-[8-Dimethylamino-1-(2-methoxy-ethyl)-2-oxo-8-phenyl-1,3-diazaspiro[4.5]decan-3-yl]-4-methyl-pyridine-2-carbonitrile;
cis-N,N-Dimethyl-2-(8-methylamino-2-oxo-3,8-diphenyl-1,3-diazaspiro[4.5]decan-1-yl)-acetamide;
cis-5-[1-[(1-Cyano-cyclobutyl)-methyl]-8-methylamino-2-oxo-8-phenyl-1,3-diazaspiro[4.5]decan-3-yl]-pyrimidine-2-carbonitrile;
cis-5-[1-[(1-Cyano-cyclobutyl)-methyl]-8-(ethyl-methyl-amino)-2-oxo-8-phenyl-1,3-diazaspiro[4.5]decan-3-yl]-pyrimidine-2-carbonitrile;
CIS-4-[8-Dimethylamino-1-[(1-hydroxy-cyclobutyl)-methyl]-2-oxo-8-phenyl-1,3-diazaspiro[4.5]decan-3-yl]-benzonitrile;
cis-3-[8-Dimethylamino-1-[(1-hydroxy-cyclobutyl)-methyl]-2-oxo-8-phenyl-1,3-diazaspiro[4.5]decan-3-yl]-benzonitrile;
cis-5-[1-[(1-Cyano-cyclobutyl)-methyl]-8-dimethylamino-2-oxo-8-phenyl-1,3-diazaspiro[4.5]decan-3-yl]-pyridine-2-carbonitrile;
cis-2-[3-(2-Cyano-pyrimidin-5-yl)-8-dimethylamino-2-oxo-8-phenyl-1,3-diazaspiro[4.5]decan-1-yl]-N-propyl-acetamide;
cis-5-[1-(Cyclobutyl-methyl)-8-(ethyl-methyl-amino)-2-oxo-8-phenyl-1,3-diazaspiro[4.5]decan-3-yl]-4-methoxy-pyrimidine-2-carbonitrile;
cis-4-[1-(Cyclobutyl-methyl)-8-methylamino-2-oxo-8-phenyl-1,3-diazaspiro[4.5]decan-3-yl]-3-methoxy-benzonitrile;
cis-5-[8-Dimethylamino-1-(3-methoxy-propyl)-2-oxo-8-phenyl-1,3-diazaspiro[4.5]decan-3-yl]-6-methoxy-pyridine-2-carbonitrile;
cis-4-[8-Dimethylamino-1-[(1-hydroxy-cyclobutyl)-methyl]-2-oxo-8-phenyl-1,3-diazaspiro[4.5]decan-3-yl]-benzamide;
cis-5-[8-Dimethylamino-1-[(1-hydroxy-cyclobutyl)-methyl]-2-oxo-8-phenyl-1,3-diazaspiro[4.5]decan-3-yl]-pyridine-2-carbonitrile;
cis-5-[8-Dimethylamino-1-[(1-hydroxy-cyclobutyl)-methyl]-2-oxo-8-phenyl-1,3-diazaspiro[4.5]decan-3-yl]-N-[(1-hydroxy-cyclobutyl)-methyl]-pyridine-2-carboxylic acid amide;
cis-2-[8-Dimethylamino-1-[(1-hydroxy-cyclobutyl)-methyl]-2-oxo-8-phenyl-1,3-diazaspiro[4.5]decan-3-yl]-benzonitrile;
cis-3-[1-(Cyclobutyl-methyl)-8-dimethylamino-2-oxo-8-phenyl-1,3-diazaspiro[4.5]decan-3-yl]-benzonitrile;
cis-1-(Cyclobutyl-methyl)-8-dimethylamino-8-phenyl-3-[2-(trifluoromethyl)-pyrimidin-5-yl]-1,3-diazaspiro[4.5]decan-2-one;
cis-5-[1-(Cyclobutyl-methyl)-8-dimethylamino-2-oxo-8-phenyl-1,3-diazaspiro[4.5]decan-3-yl]-4-methyl-pyridine-2-carboxylic acid methyl ester;
cis-1-(Cyclobutyl-methyl)-8-dimethylamino-3-(5-methoxy-pyrazin-2-yl)-8-phenyl-1,3-diazaspiro[4.5]decan-2-one;
cis-1-(Cyclobutyl-methyl)-8-dimethylamino-3-(2-methoxy-pyrimidin-5-yl)-8-phenyl-1,3-diazaspiro[4.5]decan-2-one;
cis-4-[1-(Cyclobutyl-methyl)-8-dimethylamino-2-oxo-8-phenyl-1,3-diazaspiro[4.5]decan-3-yl]-benzonitrile;
cis-5-[1-(Cyclobutyl-methyl)-8-dimethylamino-2-oxo-8-phenyl-1,3-diazaspiro[4.5]decan-3-yl]-4-methyl-pyridine-2-carbonitrile;
cis-1-(Cyclobutyl-methyl)-8-dimethylamino-3-(5-fluoro-pyrimidin-2-yl)-8-phenyl-1,3-diazaspiro[4.5]decan-2-one;
cis-4-[1-(Cyclobutyl-methyl)-8-dimethylamino-2-oxo-8-phenyl-1,3-diazaspiro[4.5]decan-3-yl]-3-methoxy-benzonitrile;
cis-4-[1-(Cyclobutyl-methyl)-8-dimethylamino-2-oxo-8-phenyl-1,3-diazaspiro[4.5]decan-3-yl]-benzoic acid methyl ester;
cis-1-(Cyclobutyl-methyl)-8-dimethylamino-8-phenyl-3-(2-pyrrolidin-1-yl-pyrimidin-4-yl)-1,3-diazaspiro[4.5]decan-2-one;
cis-1-(Cyclobutyl-methyl)-8-dimethylamino-8-phenyl-3-(5-pyridin-2-yl-thiophen-2-yl)-1,3-diazaspiro[4.5]decan-2-one;
cis-1-(Cyclobutyl-methyl)-8-dimethylamino-3-[2-methylsulfonyl-4-(trifluoromethyl)-phenyl]-8-phenyl-1,3-diazaspiro[4.5]decan-2-one;
cis-1-(Cyclobutyl-methyl)-8-dimethylamino-8-phenyl-3-[6-(trifluoromethyl)-pyridin-3-yl]-1,3-diazaspiro[4.5]decan-2-one;
cis-1-(Cyclobutyl-methyl)-3-(2,4-dimethoxy-phenyl)-8-dimethylamino-8-phenyl-1,3-diazaspiro[4.5]decan-2-one;
cis-2-[1-(Cyclobutyl-methyl)-8-dimethylamino-2-oxo-8-phenyl-1,3-diazaspiro[4.5]decan-3-yl]-4-methylsulfonyl-benzonitrile;
cis-5-[1-(Cyclobutyl-methyl)-8-dimethylamino-2-oxo-8-phenyl-1,3-diazaspiro[4.5]decan-3-yl]-2-fluoro-benzonitrile;
cis-4-[1-(Cyclobutyl-methyl)-8-dimethylamino-2-oxo-8-phenyl-1,3-diazaspiro[4.5]decan-3-yl]-N,N-dimethyl-3-(trifluoromethyl)-benzenesulfonic acid amide;
cis-2-[1-(Cyclobutyl-methyl)-8-dimethylamino-2-oxo-8-phenyl-1,3-diazaspiro[4.5]decan-3-yl]-benzonitrile;

cis-1-(Cyclobutyl-methyl)-8-dimethylamino-3-(2-methyl-imidazo[1,2-a]pyrazin-6-yl)-8-phenyl-1,3-diazaspiro[4.5]decan-2-one;

cis-1-(Cyclobutyl-methyl)-8-dimethylamino-3-(4-methylsulfonyl-phenyl)-8-phenyl-1,3-diazaspiro[4.5]decan-2-one;

cis-2-[1-(Cyclobutyl-methyl)-8-dimethylamino-2-oxo-8-phenyl-1,3-diazaspiro[4.5]decan-3-yl]-5-methoxy-benzonitrile;

cis-1-(Cyclobutyl-methyl)-8-dimethylamino-3,8-diphenyl-1,3-diazaspiro[4.5]decan-2-one;

cis-1-(Cyclobutyl-methyl)-8-dimethylamino-8-phenyl-3-pyrazin-2-yl-1,3-diazaspiro[4.5]decan-2-one;

cis-8-Dimethylamino-1-[(1-hydroxy-cyclobutyl)-methyl]-3-(2-morpholin-4-yl-pyrimidin-5-yl)-8-phenyl-1,3-diazaspiro[4.5]decan-2-one;

cis-8-Dimethylamino-1-[(1-hydroxy-cyclobutyl)-methyl]-3-[2-(4-methyl-piperazin-1-yl)-pyrimidin-5-yl]-8-phenyl-1,3-diazaspiro[4.5]decan-2-one;

cis-1-[(1-Hydroxy-cyclobutyl)-methyl]-8-methylamino-3-(2-morpholin-4-yl-pyrimidin-5-yl)-8-phenyl-1,3-diazaspiro[4.5]decan-2-one;

cis-8-Dimethylamino-1-[(1-hydroxy-cyclobutyl)-methyl]-8-phenyl-3-(2-piperazin-1-yl-pyrimidin-5-yl)-1,3-diazaspiro[4.5]decan-2-one hydrochloride;

cis-1-[(1-Hydroxy-cyclobutyl)-methyl]-8-methylamino-3-[2-(4-methyl-piperazin-1-yl)-pyrimidin-5-yl]-8-phenyl-1,3-diazaspiro[4.5]decan-2-one;

cis-1-[(1-Hydroxy-cyclobutyl)-methyl]-8-methylamino-8-phenyl-3-(2-piperazin-1-yl-pyrimidin-5-yl)-1,3-diazaspiro[4.5]decan-2-one dihydrochloride;

cis-1-(Cyclobutyl-methyl)-8-dimethylamino-3-[4-methyl-6-(trifluoromethyl)-pyridin-3-yl]-8-phenyl-1,3-diazaspiro[4.5]decan-2-one;

cis-1-(Cyclobutyl-methyl)-8-methylamino-3-[4-methyl-6-(trifluoromethyl)-pyridin-3-yl]-8-phenyl-1,3-diazaspiro[4.5]decan-2-one;

cis-1-(Cyclopropyl-methyl)-8-dimethylamino-3-(4-methylsulfonyl-phenyl)-8-phenyl-1,3-diazaspiro[4.5]decan-2-one;

cis-1-(Cyclopropyl-methyl)-8-methylamino-3-(4-methylsulfonyl-phenyl)-8-phenyl-1,3-diazaspiro[4.5]decan-2-one;

cis-1-(Cyclopropyl-methyl)-8-dimethylamino-3-(2-fluoro-4-methylsulfonyl-phenyl)-8-phenyl-1,3-diazaspiro[4.5]decan-2-one;

cis-2-[8-Dimethylamino-1-[(1-hydroxy-cyclobutyl)-methyl]-2-oxo-8-phenyl-1,3-diazaspiro[4.5]decan-3-yl]-benzamide, formic acid salt;

cis-2-[8-Dimethylamino-1-[2-(1-methoxy-cyclobutyl)-ethyl]-2-oxo-8-phenyl-1,3-diazaspiro[4.5]decan-3-yl]-benzamide;

cis-8-Dimethylamino-1-[2-(1-methoxy-cyclobutyl)-ethyl]-3-(2-methyl-pyrimidin-5-yl)-8-phenyl-1,3-diazaspiro[4.5]decan-2-one;

cis-5-[1-[(1-Hydroxy-cyclobutyl)-methyl]-8-methyl-amino-2-oxo-8-phenyl-1,3-diazaspiro[4.5]decan-3-yl]-pyrimidine-2-carbonitrile;

cis-2-[1-[(1-Hydroxy-cyclobutyl)-methyl]-8-methyl-amino-2-oxo-8-phenyl-1,3-diazaspiro[4.5]decan-3-yl]-benzonitrile;

cis-4-[1-[(1-Hydroxy-cyclobutyl)-methyl]-8-methyl-amino-2-oxo-8-phenyl-1,3-diazaspiro[4.5]decan-3-yl]-3-methoxy-benzonitrile;

cis-4-[8-Ethylamino-1-[(1-hydroxy-cyclobutyl)-methyl]-2-oxo-8-phenyl-1,3-diazaspiro[4.5]decan-3-yl]-3-methoxy-benzonitrile;

cis-2-[8-Ethylamino-1-[(1-hydroxy-cyclobutyl)-methyl]-2-oxo-8-phenyl-1,3-diazaspiro[4.5]decan-3-yl]-benzonitrile;

cis-5-[1-[(1-Hydroxy-cyclobutyl)-methyl]-8-methyl-amino-2-oxo-8-phenyl-1,3-diazaspiro[4.5]decan-3-yl]-4-methoxy-pyrimidine-2-carbonitrile;

cis-2-[8-Dimethylamino-1-(oxetan-3-yl-methyl)-2-oxo-8-phenyl-1,3-diazaspiro[4.5]decan-3-yl]-benzamide;

cis-4-Methoxy-5-(8-methylamino-2-oxo-8-phenyl-1,3-diazaspiro[4.5]decan-3-yl)-pyrimidine-2-carbonitrile;

cis-2-(8-Methylamino-2-oxo-8-phenyl-1,3-diazaspiro[4.5]decan-3-yl)-benzamide;

cis-8-Dimethylamino-3-[2-(3-oxo-piperazin-1-yl)-pyrimidin-5-yl]-8-phenyl-1,3-diazaspiro[4.5]decan-2-one;

cis-3-(2-Cyclopropyl-pyrimidin-5-yl)-8-dimethylamino-8-phenyl-1,3-diazaspiro[4.5]decan-2-one cis-8-Dimethylamino-3-[4-methyl-6-(trifluoromethyl)-pyridin-3-yl]-8-phenyl-1,3-diazaspiro[4.5]decan-2-one;

cis-8-Dimethylamino-3-(2-methylsulfonyl-phenyl)-8-phenyl-1,3-diazaspiro[4.5]decan-2-one;

cis-8-Dimethylamino-8-phenyl-3-(2-piperazin-1-yl-pyrimidin-5-yl)-1,3-diazaspiro[4.5]decan-2-one;

trans-2-(8-Ethylamino-2-oxo-8-phenyl-1,3-diazaspiro[4.5]decan-3-yl)-benzamide;

cis-2-(8-Ethylamino-2-oxo-8-phenyl-1,3-diazaspiro[4.5]decan-3-yl)-benzamide;

cis-2-(8-Ethylamino-2-oxo-8-phenyl-1,3-diazaspiro[4.5]decan-3-yl)-benzonitrile;

cis-2-(8-Ethylamino-2-oxo-8-phenyl-1,3-diazaspiro[4.5]decan-3-yl)-benzonitrile;

cis-3-[5-(8-Dimethylamino-2-oxo-8-phenyl-1,3-diazaspiro[4.5]decan-3-yl)-pyrimidin-2-yl]-benzonitrile;

cis-8-Dimethylamino-3-[2-(4-methylsulfonyl-piperazin-1-yl)-pyrimidin-5-yl]-8-phenyl-1,3-diazaspiro[4.5]decan-2-one;

cis-3-[5-(8-Dimethylamino-2-oxo-8-phenyl-1,3-diazaspiro[4.5]decan-3-yl)-pyrimidin-2-yl]-benzamide cis-8-[(Cyclopropyl-methyl)-methyl-amino]-8-phenyl-3-[2-(trifluoromethyl)-pyrimidin-5-yl]-1,3-diazaspiro[4.5]decan-2-one;

cis-8-Dimethylamino-3-[2-(4-methyl-piperazine-1-carbonyl)-pyrimidin-5-yl]-8-phenyl-1,3-diazaspiro[4.5]decan-2-one;

trans-4-(8-Ethylamino-2-oxo-8-phenyl-1,3-diazaspiro[4.5]decan-3-yl)-3-methoxy-benzonitrile;

cis-4-(8-Ethylamino-2-oxo-8-phenyl-1,3-diazaspiro[4.5]decan-3-yl)-3-methoxy-benzonitrile;

cis-3-[2-(4-Acetyl-piperazin-1-yl)-pyrimidin-5-yl]-8-dimethylamino-8-phenyl-1,3-diazaspiro[4.5]decan-2-one;

cis-8-Dimethylamino-8-phenyl-3-(2-pyridin-4-yl-pyrimidin-5-yl)-1,3-diazaspiro[4.5]decan-2-one;

cis-8-Dimethylamino-8-phenyl-3-(2-pyridin-3-yl-pyrimidin-5-yl)-1,3-diazaspiro[4.5]decan-2-one;

cis-5-(8-Dimethylamino-2-oxo-8-phenyl-1,3-diazaspiro[4.5]decan-3-yl)-N-(2-hydroxy-ethyl)-pyrimidine-2-carboxylic acid amide;

cis-5-(8-Dimethylamino-2-oxo-8-phenyl-1,3-diazaspiro[4.5]decan-3-yl)-pyrimidine-2-carboxylic acid amide;

cis-8-Dimethylamino-3-[2-morpholin-4-yl-4-(trifluoromethyl)-pyrimidin-5-yl]-8-phenyl-1,3-diazaspiro[4.5]decan-2-one;

cis-4-[5-(8-Dimethylamino-2-oxo-8-phenyl-1,3-diazaspiro[4.5]decan-3-yl)-pyrimidin-2-yl]-benzonitrile;

cis-5-(8-Ethylamino-2-oxo-8-phenyl-1,3-diazaspiro[4.5]decan-3-yl)-4-methoxy-pyrimidine-2-carbonitrile;
trans-5-(8-Ethylamino-2-oxo-8-phenyl-1,3-diazaspiro[4.5]decan-3-yl)-4-methoxy-pyrimidine-2-carbonitrile;
cis-8-Dimethylamino-3-[2-(morpholine-4-carbonyl)-pyrimidin-5-yl]-8-phenyl-1,3-diazaspiro[4.5]decan-2-one;
cis-2-[4-[5-(8-Dimethylamino-2-oxo-8-phenyl-1,3-diazaspiro[4.5]decan-3-yl)-pyrimidin-2-yl]-piperazin-1-yl]-acetic acid methyl ester;
cis-8-Dimethylamino-3-[2-(methylsulfonyl-methyl)-phenyl]-8-phenyl-1,3-diazaspiro[4.5]decan-2-one;
cis-8-Dimethylamino-3-(4-methyl-2-morpholin-4-yl-pyrimidin-5-yl)-8-phenyl-1,3-diazaspiro[4.5]decan-2-one;
cis-8-Dimethylamino-3-[2-(1,1-dioxo-[1,4]thiazinan-4-yl)-pyrimidin-5-yl]-8-phenyl-1,3-diazaspiro[4.5]decan-2-one;
cis-8-Dimethylamino-3-(4-fluoro-pyridin-3-yl)-8-phenyl-1,3-diazaspiro[4.5]decan-2-one;
cis-5-(8-Dimethylamino-2-oxo-8-phenyl-1,3-diazaspiro[4.5]decan-3-yl)-N-(2-hydroxy-ethyl)-N-methyl-pyrimidine-2-carboxylic acid amide;
cis-5-(8-Dimethylamino-2-oxo-8-phenyl-1,3-diazaspiro[4.5]decan-3-yl)-2-morpholin-4-yl-isonicotinonitrile;
cis-4-(8-Dimethylamino-2-oxo-8-phenyl-1,3-diazaspiro[4.5]decan-3-yl)-benzamide;
cis-8-Dimethylamino-3-(2-fluoro-4-methylsulfonyl-phenyl)-8-phenyl-1,3-diazaspiro[4.5]decan-2-one;
cis-4-(8-Dimethylamino-2-oxo-8-phenyl-1,3-diazaspiro[4.5]decan-3-yl)-3-fluoro-benzonitrile;
cis-4-(8-Dimethylamino-2-oxo-8-phenyl-1,3-diazaspiro[4.5]decan-3-yl)-3,5-difluoro-benzonitrile;
cis-8-Dimethylamino-3-(2-methoxy-pyrimidin-5-yl)-8-phenyl-1,3-diazaspiro[4.5]decan-2-one;
cis-3-[2-(Benzylamino)-pyrimidin-5-yl]-8-dimethylamino-8-phenyl-1,3-diazaspiro[4.5]decan-2-one;
cis-8-Dimethylamino-3-[2-(4-fluorophenyl)-pyrimidin-5-yl]-8-phenyl-1,3-diazaspiro[4.5]decan-2-one;
trans-8-Benzyl-8-dimethylamino-3-(2-morpholin-4-yl-pyrimidin-5-yl)-1,3-diazaspiro[4.5]decan-2-one;
cis-8-Benzyl-8-dimethylamino-3-(2-morpholin-4-yl-pyrimidin-5-yl)-1,3-diazaspiro[4.5]decan-2-one;
cis-8-Dimethylamino-8-phenyl-3-(2-pyridin-2-yl-pyrimidin-5-yl)-1,3-diazaspiro[4.5]decan-2-one;
cis-4-(8-Dimethylamino-2-oxo-8-phenyl-1,3-diazaspiro[4.5]decan-3-yl)-3,5-difluoro-benzamide;
cis-4-(8-Dimethylamino-2-oxo-8-phenyl-1,3-diazaspiro[4.5]decan-3-yl)-3-fluoro-benzamide;
cis-8-Benzyl-8-dimethylamino-3-[2-(trifluoromethyl)-pyrimidin-5-yl]-1,3-diazaspiro[4.5]decan-2-one;
trans-8-Benzyl-8-dimethylamino-3-[2-(trifluoromethyl)-pyrimidin-5-yl]-1,3-diazaspiro[4.5]decan-2-one;
cis-8-Dimethylamino-8-thiophen-2-yl-3-[2-(trifluoromethyl)-pyrimidin-5-yl]-1,3-diazaspiro[4.5]decan-2-one;
trans-8-Dimethylamino-8-thiophen-2-yl-3-[2-(trifluoromethyl)-pyrimidin-5-yl]-1,3-diazaspiro[4.5]decan-2-one;
cis-2-[2-(8-Dimethylamino-2-oxo-8-phenyl-1,3-diazaspiro[4.5]decan-3-yl)-phenoxy]-acetic acid;
cis-8-Dimethylamino-8-phenyl-3-(2-piperidin-1-yl-pyrimidin-5-yl)-1,3-diazaspiro[4.5]decan-2-one;
cis-8-Dimethylamino-8-phenyl-3-(2-pyrrolidin-1-yl-pyrimidin-5-yl)-1,3-diazaspiro[4.5]decan-2-one;
cis-8-Dimethylamino-8-phenyl-3-(2-pyrimidin-5-yl-pyrimidin-5-yl)-1,3-diazaspiro[4.5]decan-2-one;
cis-8-Dimethylamino-8-phenyl-3-[2-(piperazine-1-carbonyl)-pyrimidin-5-yl]-1,3-diazaspiro[4.5]decan-2-one;
trans-8-Benzyl-8-dimethylamino-3-[4-methyl-6-(trifluoromethyl)-pyridin-3-yl]-1,3-diazaspiro[4.5]decan-2-one;
cis-5-(8-Dimethylamino-2-oxo-8-phenyl-1,3-diazaspiro[4.5]decan-3-yl)-2-morpholin-4-yl-pyridine-4-carboxylic acid amide;
cis-8-Dimethylamino-3-[2-(3,5-dimethyl-isoxazol-4-yl)-pyrimidin-5-yl]-8-phenyl-1,3-diazaspiro[4.5]decan-2-one;
cis-3-[2-(Benzothiazol-6-yl)-pyrimidin-5-yl]-8-dimethylamino-8-phenyl-1,3-diazaspiro[4.5]decan-2-one;
cis-8-Dimethylamino-3-[2-fluoro-4-(trifluoromethyl)-phenyl]-8-phenyl-1,3-diazaspiro[4.5]decan-2-one;
cis-8-Dimethylamino-3-(6-morpholin-4-yl-pyridin-3-yl)-8-phenyl-1,3-diazaspiro[4.5]decan-2-one;
cis-8-Dimethylamino-8-phenyl-3-(2-phenyl-thiazol-4-yl)-1,3-diazaspiro[4.5]decan-2-one;
cis-8-Dimethylamino-8-phenyl-3-[2-(tetrahydro-pyran-4-ylamino)-pyrimidin-5-yl]-1,3-diazaspiro[4.5]decan-2-one;
cis-8-Dimethylamino-3-[2-(4-hydroxy-piperidin-1-yl)-pyrimidin-5-yl]-8-phenyl-1,3-diazaspiro[4.5]decan-2-one;
cis-8-Dimethylamino-8-phenyl-3-(4-phenyl-thiazol-2-yl)-1,3-diazaspiro[4.5]decan-2-one;
cis-8-Dimethylamino-8-phenyl-3-[2-(1H-pyrrolo[2,3-b]pyridin-1-yl)-pyrimidin-5-yl]-1,3-diazaspiro[4.5]decan-2-one;
cis-8-Dimethylamino-8-phenyl-3-[2-(3,4,5-trifluoro-phenyl)-pyrimidin-5-yl]-1,3-diazaspiro[4.5]decan-2-one;
cis-8-Dimethylamino-3-o-tolyl-8-phenyl-1,3-diazaspiro[4.5]decan-2-one;
cis-8-Dimethylamino-3-m-tolyl-8-phenyl-1,3-diazaspiro[4.5]decan-2-one;
cis-8-Dimethylamino-8-phenyl-3-p-tolyl-1,3-diazaspiro[4.5]decan-2-one;
cis-8-Dimethylamino-8-phenyl-3-[4-(trifluoromethyl)-phenyl]-1,3-diazaspiro[4.5]decan-2-one;
cis-8-Dimethylamino-8-phenyl-3-[3-(trifluoromethyloxy)-phenyl]-1,3-diazaspiro[4.5]decan-2-one;
cis-8-Dimethylamino-8-phenyl-3-[4-(trifluoromethyloxy)-phenyl]-1,3-diazaspiro[4.5]decan-2-one;
cis-2-(8-Dimethylamino-2-oxo-8-phenyl-1,3-diazaspiro[4.5]decan-3-yl)-benzoic acid methyl ester;
cis-3-(8-Dimethylamino-2-oxo-8-phenyl-1,3-diazaspiro[4.5]decan-3-yl)-benzoic acid methyl ester;
cis-4-(8-Dimethylamino-2-oxo-8-phenyl-1,3-diazaspiro[4.5]decan-3-yl)-benzoic acid methyl ester;
cis-3-(1,3-Benzodioxol-5-yl)-8-dimethylamino-8-phenyl-1,3-diazaspiro[4.5]decan-2-one;
cis-8-Dimethylamino-8-phenyl-3-quinolin-5-yl-1,3-diazaspiro[4.5]decan-2-one;
cis-3-(2,3-Dihydro-1H-indol-6-yl)-8-dimethylamino-8-phenyl-1,3-diazaspiro[4.5]decan-2-one;
cis-5-(8-Dimethylamino-2-oxo-8-phenyl-1,3-diazaspiro[4.5]decan-3-yl)-4-methyl-pyridine-2-carboxylic acid methyl ester;
cis-8-Dimethylamino-3-(6-methoxy-4-methyl-pyridin-3-yl)-8-phenyl-1,3-diazaspiro[4.5]decan-2-one;
cis-8-Dimethylamino-3-[2-methyl-5-(trifluoromethyl)-2H-pyrazol-3-yl]-8-phenyl-1,3-diazaspiro[4.5]decan-2-one;
cis-8-Dimethylamino-3-(3-methoxy-pyridin-2-yl)-8-phenyl-1,3-diazaspiro[4.5]decan-2-one;

cis-8-Dimethylamino-8-phenyl-3-[5-(trifluoromethyl)-pyridin-2-yl]-1,3-diazaspiro[4.5]decan-2-one;
cis-5-(8-Dimethylamino-2-oxo-8-phenyl-1,3-diazaspiro[4.5]decan-3-yl)-nicotinonitrile;
cis-8-Dimethylamino-3-(3-methyl-pyridin-2-yl)-8-phenyl-1,3-diazaspiro[4.5]decan-2-one;
cis-8-Dimethylamino-3-(6-methoxy-pyridin-3-yl)-8-phenyl-1,3-diazaspiro[4.5]decan-2-one;
cis-8-Dimethylamino-8-phenyl-3-[3-(trifluoromethyl)phenyl]-1,3-diazaspiro[4.5]decan-2-one;
cis-3-(1,3-Benzodioxol-4-yl)-8-dimethylamino-8-phenyl-1,3-diazaspiro[4.5]decan-2-one;
cis-8-Dimethylamino-3-[2-(2-oxo-1,3-dihydro-indol-4-yl)-pyrimidin-5-yl]-8-phenyl-1,3-diazaspiro[4.5]decan-2-one;
cis-8-Dimethylamino-3-[2-(3,5-dimethyl-1H-pyrazol-1-yl)-pyrimidin-5-yl]-8-phenyl-1,3-diazaspiro[4.5]decan-2-one;
cis-8-Dimethylamino-3-[2-(3-hydroxy-piperidin-1-yl)-pyrimidin-5-yl]-8-phenyl-1,3-diazaspiro[4.5]decan-2-one;
cis-8-Dimethylamino-3-[2-(3-hydroxy-piperidin-1-yl)-pyrimidin-5-yl]-8-phenyl-1,3-diazaspiro[4.5]decan-2-one;
cis-8-Dimethylamino-3-[2-[4-(2-hydroxy-ethyl)-piperazin-1-yl]-pyrimidin-5-yl]-8-phenyl-1,3-diazaspiro[4.5]decan-2-one;
cis-2-[4-[5-(8-Dimethylamino-2-oxo-8-phenyl-1,3-diazaspiro[4.5]decan-3-yl)-pyrimidin-2-yl]-piperazin-1-yl]-acetic acid;
cis-8-Dimethylamino-3-[2-(1-methyl-1H-pyrrolo[2,3-b]pyridin-4-yl)-pyrimidin-5-yl]-8-phenyl-1,3-diazaspiro[4.5]decan-2-one;
cis-8-Benzyl-8-dimethylamino-3-[4-methyl-6-(trifluoromethyl)-pyridin-3-yl]-1,3-diazaspiro[4.5]decan-2-one;
trans-8-Dimethylamino-3-[4-methyl-6-(trifluoromethyl)-pyridin-3-yl]-8-thiophen-2-yl-1,3-diazaspiro[4.5]decan-2-one;
cis-8-Dimethylamino-3-[4-methyl-6-(trifluoromethyl)-pyridin-3-yl]-8-thiophen-2-yl-1,3-diazaspiro[4.5]decan-2-one;
cis-8-Dimethylamino-3-[2-(1,1-dioxo-[1,4]thiazinan-4-yl)-4-(trifluoromethyl)-pyrimidin-5-yl]-8-phenyl-1,3-diazaspiro[4.5]decan-2-one;
cis-8-Dimethylamino-8-(1-methyl-1H-benzoimidazol-2-yl)-3-[2-(trifluoromethyl)-pyrimidin-5-yl]-1,3-diazaspiro[4.5]decan-2-one;
cis-8-Dimethylamino-8-(1-methyl-1H-benzoimidazol-2-yl)-3-[4-methyl-6-(trifluoromethyl)-pyridin-3-yl]-1,3-diazaspiro[4.5]decan-2-one;
cis-8-Dimethylamino-3-[2-(2-hydroxy-ethylamino)-pyrimidin-5-yl]-8-phenyl-1,3-diazaspiro[4.5]decan-2-one;
cis-3-[2-(Benzyl-methyl-amino)-pyrimidin-5-yl]-8-dimethylamino-8-phenyl-1,3-diazaspiro[4.5]decan-2-one;
cis-5-(8-Dimethylamino-2-oxo-8-phenyl-1,3-diazaspiro[4.5]decan-3-yl)-N-[2-[2-[2-(2-methoxy-ethoxy)-ethoxy]-ethoxy]-ethyl]-pyrimidine-2-carboxylic acid amide;
cis-8-Dimethylamino-3-[2-(1H-indazol-1-yl)-pyrimidin-5-yl]-8-phenyl-1,3-diazaspiro[4.5]decan-2-one;
cis-8-Dimethylamino-3-[2-[(2-hydroxy-ethyl)-methyl-amino]-pyrimidin-5-yl]-8-phenyl-1,3-diazaspiro[4.5]decan-2-one;
cis-3-(8-Dimethylamino-2-oxo-8-phenyl-1,3-diazaspiro[4.5]decan-3-yl)-benzamide;
cis-8-Dimethylamino-3-[3-fluoro-5-(trifluoromethyl)-pyridin-2-yl]-8-phenyl-1,3-diazaspiro[4.5]decan-2-one;
cis-8-Dimethylamino-3-(5-methyl-pyrazin-2-yl)-8-phenyl-1,3-diazaspiro[4.5]decan-2-one;
cis-8-Dimethylamino-3-(5-fluoro-pyrimidin-4-yl)-8-phenyl-1,3-diazaspiro[4.5]decan-2-one;
cis-8-Dimethylamino-3-(5-fluoro-pyrimidin-2-yl)-8-phenyl-1,3-diazaspiro[4.5]decan-2-one;
cis-8-Dimethylamino-8-phenyl-3-pyrazin-2-yl-1,3-diazaspiro[4.5]decan-2-one;
cis-3-([2,1,3]Benzoxadiazol-5-yl)-8-dimethylamino-8-phenyl-1,3-diazaspiro[4.5]decan-2-one;
cis-2-[2-(8-Dimethylamino-2-oxo-8-phenyl-1,3-diazaspiro[4.5]decan-3-yl)-phenoxy]-acetamide;
cis-8-Dimethylamino-8-phenyl-3-(5-pyridin-4-yl-thiophen-2-yl)-1,3-diazaspiro[4.5]decan-2-one;
cis-2-[2-(8-Dimethylamino-2-oxo-8-phenyl-1,3-diazaspiro[4.5]decan-3-yl)-phenoxy]-acetic acid methyl ester;
cis-8-Dimethylamino-3-(2-morpholin-4-yl-pyrimidin-4-yl)-8-phenyl-1,3-diazaspiro[4.5]decan-2-one;
cis-3-[2-(3,4-Difluoro-phenyl)-pyrimidin-5-yl]-8-dimethylamino-8-phenyl-1,3-diazaspiro[4.5]decan-2-one;
cis-2-[5-(8-Dimethylamino-2-oxo-8-phenyl-1,3-diazaspiro[4.5]decan-3-yl)-pyrimidin-2-yl]-benzonitrile;
cis-3-(2-Amino-pyrimidin-5-yl)-8-dimethylamino-8-phenyl-1,3-diazaspiro[4.5]decan-2-one;
cis-N-[5-(8-Dimethylamino-2-oxo-8-phenyl-1,3-diazaspiro[4.5]decan-3-yl)-pyrimidin-2-yl]-cyclopropanecarboxylic acid amide;
cis-2-[4-[5-(8-Dimethylamino-2-oxo-8-phenyl-1,3-diazaspiro[4.5]decan-3-yl)-pyrimidin-2-yl]-piperazin-1-yl]-acetamide;
cis-8-Dimethylamino-8-phenyl-3-(6-piperazin-1-yl-pyridin-3-yl)-1,3-diazaspiro[4.5]decan-2-one;
cis-8-Dimethylamino-3-[6-(4-methyl-piperazin-1-yl)-pyridin-3-yl]-8-phenyl-1,3-diazaspiro[4.5]decan-2-one;
cis-8-Dimethylamino-3-[2-(1,1-dioxo-[1,4]thiazinan-4-yl)-4-methyl-pyrimidin-5-yl]-8-phenyl-1,3-diazaspiro[4.5]decan-2-one;
cis-8-Dimethylamino-8-phenyl-3-[2-(trifluoromethyl)-pyrimidin-5-yl]-1,3-diazaspiro[4.5]decan-2-one;
cis-2-[8-Dimethylamino-1-(3-methoxy-propyl)-2-oxo-8-phenyl-1,3-diazaspiro[4.5]decan-3-yl]-pyrimidine-5-carbonitrile;
cis-8-Dimethylamino-3-[2-(4-methyl-piperazin-1-yl)-pyrimidin-5-yl]-8-phenyl-1,3-diazaspiro[4.5]decan-2-one;
cis-8-Dimethylamino-1-[(1-hydroxy-cyclobutyl)-methyl]-8-phenyl-3-[2-(trifluoromethyl)-pyrimidin-5-yl]-1,3-diazaspiro[4.5]decan-2-one;
cis-2-[1-(3-Methoxy-propyl)-8-methylamino-2-oxo-8-phenyl-1,3-diazaspiro[4.5]decan-3-yl]-pyrimidine-5-carbonitrile;
cis-8-Dimethylamino-8-phenyl-3-[6-(trifluoromethyl)-pyridin-3-yl]-1,3-diazaspiro[4.5]decan-2-one;
cis-5-(8-Dimethylamino-2-oxo-8-phenyl-1,3-diazaspiro[4.5]decan-3-yl)-pyridine-2-carbonitrile;
cis-8-Dimethylamino-3-(2-morpholin-4-yl-pyrimidin-5-yl)-8-phenyl-1,3-diazaspiro[4.5]decan-2-one;
cis-8-Dimethylamino-3-(2-methyl-pyrimidin-5-yl)-8-phenyl-1,3-diazaspiro[4.5]decan-2-one;
cis-8-Dimethylamino-1-[(2-methoxyphenyl)-methyl]-3-(2-methyl-pyrimidin-5-yl)-8-phenyl-1,3-diazaspiro[4.5]decan-2-one;

cis-1-[(1-Hydroxy-cyclobutyl)-methyl]-8-methylamino-8-phenyl-3-[2-(trifluoromethyl)-pyrimidin-5-yl]-1,3-diazaspiro[4.5]decan-2-one;
cis-8-Dimethylamino-1-[(1-hydroxy-cyclobutyl)-methyl]-3-(2-methyl-pyrimidin-5-yl)-8-phenyl-1,3-diazaspiro[4.5]decan-2-one;
cis-1-[(1-Hydroxy-cyclobutyl)-methyl]-8-methylamino-8-phenyl-3-pyrimidin-5-yl-1,3-diazaspiro[4.5]decan-2-one;
cis-5-(8-Dimethylamino-2-oxo-8-phenyl-1,3-diazaspiro[4.5]decan-3-yl)-4-methyl-pyridine-2-carbonitrile;
cis-8-Dimethylamino-3-(2-methyl-pyrimidin-5-yl)-8-phenyl-1-(pyridin-2-yl-methyl)-1,3-diazaspiro[4.5]decan-2-one;
cis-8-Dimethylamino-8-phenyl-3-pyrimidin-5-yl-1,3-diazaspiro[4.5]decan-2-one;
cis-8-Dimethylamino-1-[(1-hydroxy-cyclobutyl)-methyl]-8-phenyl-3-pyrimidin-5-yl-1,3-diazaspiro[4.5]decan-2-one;
cis-8-Amino-1-[(1-hydroxy-cyclobutyl)-methyl]-8-phenyl-3-[2-(trifluoromethyl)-pyrimidin-5-yl]-1,3-diazaspiro[4.5]decan-2-one;
cis-8-Dimethylamino-3-(3-fluorophenyl)-8-phenyl-1,3-diazaspiro[4.5]decan-2-one;
cis-8-Dimethylamino-3-(3-methylsulfonyl-phenyl)-8-phenyl-1,3-diazaspiro[4.5]decan-2-one;
cis-8-Dimethylamino-3-(4-methylsulfonyl-phenyl)-8-phenyl-1,3-diazaspiro[4.5]decan-2-one;
cis-8-Dimethylamino-8-phenyl-3-pyridazin-3-yl-1,3-diazaspiro[4.5]decan-2-one;
cis-3-Methoxy-4-(8-methylamino-2-oxo-8-phenyl-1,3-diazaspiro[4.5]decan-3-yl)-benzonitrile;
cis-8-Dimethylamino-3-(2-fluorophenyl)-8-phenyl-1,3-diazaspiro[4.5]decan-2-one;
cis-8-Dimethylamino-8-phenyl-3-(2-phenyl-pyrimidin-5-yl)-1,3-diazaspiro[4.5]decan-2-one;
cis-8-Methylamino-1-(oxetan-3-yl-methyl)-8-phenyl-3-[2-(trifluoromethyl)-pyrimidin-5-yl]-1,3-diazaspiro[4.5]decan-2-one;
cis-1-(Cyclopropyl-methyl)-8-methylamino-8-phenyl-3-[2-(trifluoromethyl)-pyrimidin-5-yl]-1,3-diazaspiro[4.5]decan-2-one;
cis-4-(8-Dimethylamino-2-oxo-8-phenyl-1,3-diazaspiro[4.5]decan-3-yl)-benzonitrile;
cis-8-Dimethylamino-3-(4-fluorophenyl)-8-phenyl-1,3-diazaspiro[4.5]decan-2-one;
cis-2-(8-Dimethylamino-2-oxo-8-phenyl-1,3-diazaspiro[4.5]decan-3-yl)-benzonitrile;
cis-8-Ethylamino-1-[(1-hydroxy-cyclobutyl)-methyl]-8-phenyl-3-[2-(trifluoromethyl)-pyrimidin-5-yl]-1,3-diazaspiro[4.5]decan-2-one;
cis-1-[(1-Hydroxy-cyclobutyl)-methyl]-8-methylamino-3-(2-methyl-pyrimidin-5-yl)-8-phenyl-1,3-diazaspiro[4.5]decan-2-one;
cis-8-Dimethylamino-3-[2-(morpholin-4-yl-methyl)-pyrimidin-5-yl]-8-phenyl-1,3-diazaspiro[4.5]decan-2-one;
cis-8-Dimethylamino-3-[2-(methyl-tetrahydro-pyran-4-yl-amino)-pyrimidin-5-yl]-8-phenyl-1,3-diazaspiro[4.5]decan-2-one;
cis-5-[8-Dimethylamino-1-[(1-hydroxy-cyclobutyl)-methyl]-2-oxo-8-phenyl-1,3-diazaspiro[4.5]decan-3-yl]-N-[2-[2-[2-(2-methoxy-ethoxy)-ethoxy]-ethoxy]-ethyl]-pyrimidine-2-carboxylic acid amide;
cis-1-(Cyclopropyl-methyl)-3-(2-fluoro-4-methylsulfonyl-phenyl)-8-methylamino-8-phenyl-1,3-diazaspiro[4.5]decan-2-one;
cis-2-[[5-(8-Dimethylamino-2-oxo-8-phenyl-1,3-diazaspiro[4.5]decan-3-yl)-pyrimidin-2-yl]-methyl-amino]-acetamide;
cis-2-[[5-(8-Dimethylamino-2-oxo-8-phenyl-1,3-diazaspiro[4.5]decan-3-yl)-pyrimidin-2-yl]amino]-acetamide;
cis-1-(Cyclopropyl-methyl)-8-methylamino-3-[4-methyl-6-(trifluoromethyl)-pyridin-3-yl]-8-phenyl-1,3-diazaspiro[4.5]decan-2-one;
cis-1-(Cyclopropyl-methyl)-8-dimethylamino-3-[4-methyl-6-(trifluoromethyl)-pyridin-3-yl]-8-phenyl-1,3-diazaspiro[4.5]decan-2-one;
cis-N-[5-(8-Dimethylamino-2-oxo-8-phenyl-1,3-diazaspiro[4.5]decan-3-yl)-pyrimidin-2-yl]-thiophene-2-carboxylic acid amide;
cis-N-[5-(8-Dimethylamino-2-oxo-8-phenyl-1,3-diazaspiro[4.5]decan-3-yl)-pyrimidin-2-yl]-benzamide;
cis-8-Dimethylamino-8-phenyl-3-(5-phenyl-thiophen-2-yl)-1,3-diazaspiro[4.5]decan-2-one;
cis-1-(Cyclopropyl-methyl)-8-dimethylamino-3-[2-(methylsulfonyl-methyl)-phenyl]-8-phenyl-1,3-diazaspiro[4.5]decan-2-one;
cis-1-(Cyclopropyl-methyl)-8-methylamino-3-[2-(methylsulfonyl-methyl)-phenyl]-8-phenyl-1,3-diazaspiro[4.5]decan-2-one;
cis-8-Dimethylamino-8-(3-fluorophenyl)-3-[2-(methylsulfonyl-methyl)-phenyl]-1,3-diazaspiro[4.5]decan-2-one;
cis-8-Dimethylamino-8-(4-fluorophenyl)-3-[2-(methylsulfonyl-methyl)-phenyl]-1,3-diazaspiro[4.5]decan-2-one;
cis-8-[Methyl-(tetrahydro-furan-3-yl-methyl)-amino]-8-phenyl-3-[2-(trifluoromethyl)-pyrimidin-5-yl]-1,3-diazaspiro[4.5]decan-2-one (enantiomer 1);
cis-8-[Methyl-(tetrahydro-furan-3-yl-methyl)-amino]-8-phenyl-3-[2-(trifluoromethyl)-pyrimidin-5-yl]-1,3-diazaspiro[4.5]decan-2-one (enantiomer 2);
cis-8-Dimethylamino-8-(3-fluorophenyl)-3-(4-methyl-2-morpholin-4-yl-pyrimidin-5-yl)-1,3-diazaspiro[4.5]decan-2-one;
cis-3-[6-(4-Acetyl-piperazin-1-yl)-4-methyl-pyridin-3-yl]-8-dimethylamino-8-phenyl-1,3-diazaspiro[4.5]decan-2-one;
cis-3-[2-(4-Acetyl-piperazin-1-yl)-4-methyl-pyrimidin-5-yl]-8-dimethylamino-8-phenyl-1,3-diazaspiro[4.5]decan-2-one;
cis-8-Dimethylamino-3-(4-methyl-6-pyridin-4-yl-pyridin-3-yl)-8-phenyl-1,3-diazaspiro[4.5]decan-2-one;
cis-3-[2-(4-Acetyl-piperazin-1-yl)-4-(trifluoromethyl)-pyrimidin-5-yl]-8-dimethylamino-8-phenyl-1,3-diazaspiro[4.5]decan-2-one;
cis-8-Dimethylamino-3-[2-(3-oxo-piperazin-1-yl)-4-(trifluoromethyl)-pyrimidin-5-yl]-8-phenyl-1,3-diazaspiro[4.5]decan-2-one;
cis-8-Dimethylamino-3-isoquinolin-4-yl-8-phenyl-1,3-diazaspiro[4.5]decan-2-one;
cis-8-Dimethylamino-3-isoquinolin-5-yl-8-phenyl-1,3-diazaspiro[4.5]decan-2-one;
cis-8-Dimethylamino-8-phenyl-3-(1H-pyrrolo[2,3-b]pyridin-4-yl)-1,3-diazaspiro[4.5]decan-2-one;
cis-8-Dimethylamino-8-phenyl-3-(2-pyridin-4-yl-thiazol-4-yl)-1,3-diazaspiro[4.5]decan-2-one;
cis-8-[Methyl-(tetrahydro-furan-3-yl-methyl)-amino]-3-(2-morpholin-4-yl-pyrimidin-5-yl)-8-phenyl-1,3-diazaspiro[4.5]decan-2-one (enantiomer 1);

cis-8-[Methyl-(tetrahydro-furan-3-yl-methyl)-amino]-3-(2-morpholin-4-yl-pyrimidin-5-yl)-8-phenyl-1,3-diazaspiro[4.5]decan-2-one (enantiomer 2);

cis-3-[2-(Azetidin-1-yl)-pyrimidin-5-yl]-8-dimethylamino-8-phenyl-1,3-diazaspiro[4.5]decan-2-one;

cis-3-[2-(3,3-Difluoro-azetidin-1-yl)-pyrimidin-5-yl]-8-dimethylamino-8-phenyl-1,3-diazaspiro[4.5]decan-2-one;

cis-8-Dimethylamino-3-[6-morpholin-4-yl-5-(trifluoromethyl)-pyridin-3-yl]-8-phenyl-1,3-diazaspiro[4.5]decan-2-one;

cis-8-Methylamino-3-[6-morpholin-4-yl-5-(trifluoromethyl)-pyridin-3-yl]-8-phenyl-1,3-diazaspiro[4.5]decan-2-one;

cis-8-Dimethylamino-8-phenyl-3-[5-(trifluoromethyloxy)-pyridin-2-yl]-1,3-diazaspiro[4.5]decan-2-one;

cis-8-Dimethylamino-3-(5-methylsulfonyl-pyridin-2-yl)-8-phenyl-1,3-diazaspiro[4.5]decan-2-one;

cis-6-(8-Dimethylamino-2-oxo-8-phenyl-1,3-diazaspiro[4.5]decan-3-yl)-nicotinonitrile;

cis-3-[2-(4-Cyclopropyl-1H-[1,2,3]triazol-1-yl)-pyrimidin-5-yl]-8-dimethylamino-8-phenyl-1,3-diazaspiro[4.5]decan-2-one;

cis-8-Dimethylamino-3-[4-methyl-2-(3-oxo-piperazin-1-yl)-pyrimidin-5-yl]-8-phenyl-1,3-diazaspiro[4.5]decan-2-one;

cis-5-(8-Dimethylamino-2-oxo-8-phenyl-1,3-diazaspiro[4.5]decan-3-yl)-pyridine-2-carboxylic acid amide;

cis-3-[4-(Azetidin-1-yl)-2-methyl-pyrimidin-5-yl]-8-dimethylamino-8-phenyl-1,3-diazaspiro[4.5]decan-2-one;

cis-2-(8-Dimethylamino-2-oxo-8-phenyl-1,3-diazaspiro[4.5]decan-3-yl)-benzamide;

cis-8-Dimethylamino-3-[2-(methylsulfonyl-methyl)-phenyl]-8-thiophen-2-yl-1,3-diazaspiro[4.5]decan-2-one;

cis-8-Dimethylamino-8-(3-fluorophenyl)-3-[2-methyl-5-(trifluoromethyl)-2H-pyrazol-3-yl]-1,3-diazaspiro[4.5]decan-2-one;

cis-8-Dimethylamino-3-(4-methyl-2-morpholin-4-yl-pyrimidin-5-yl)-8-thiophen-2-yl-1,3-diazaspiro[4.5]decan-2-one;

cis-8-Dimethylamino-3-(6-methylsulfonyl-pyridin-3-yl)-8-phenyl-1,3-diazaspiro[4.5]decan-2-one;

cis-8-Dimethylamino-8-phenyl-3-(1H-pyrrolo[2,3-b]pyridin-5-yl)-1,3-diazaspiro[4.5]decan-2-one;

cis-N-[5-(8-Dimethylamino-2-oxo-8-phenyl-1,3-diazaspiro[4.5]decan-3-yl)-pyrimidin-2-yl]-acetamide;

cis-3-[2-(4-Methyl-piperazin-1-yl)-pyrimidin-5-yl]-8-[methyl-(tetrahydro-furan-3-yl-methyl)-amino]-8-phenyl-1,3-diazaspiro[4.5]decan-2-one (enantiomer 1);

cis-3-[2-(4-Methyl-piperazin-1-yl)-pyrimidin-5-yl]-8-[methyl-(tetrahydro-furan-3-yl-methyl)-amino]-8-phenyl-1,3-diazaspiro[4.5]decan-2-one (enantiomer 2);

cis-8-Dimethylamino-3-(4,6-dimethyl-2-morpholin-4-yl-pyrimidin-5-yl)-8-phenyl-1,3-diazaspiro[4.5]decan-2-one;

cis-8-Dimethylamino-3-(2-morpholin-4-yl-pyrimidin-5-yl)-8-thiophen-2-yl-1,3-diazaspiro[4.5]decan-2-one;

cis-6-(8-Dimethylamino-2-oxo-8-phenyl-1,3-diazaspiro[4.5]decan-3-yl)-pyridine-3-carboxylic acid amide;

cis-8-Dimethylamino-3-[2-methyl-5-(trifluoromethyl)-2H-pyrazol-3-yl]-8-thiophen-2-yl-1,3-diazaspiro[4.5]decan-2-one;

cis-8-Dimethylamino-3-[2-[(2-hydroxy-ethyl)-methyl-amino]-pyrimidin-5-yl]-8-thiophen-2-yl-1,3-diazaspiro[4.5]decan-2-one;

cis-8-Dimethylamino-3-[2-(2-oxo-1,3-dihydro-indol-4-yl)-pyrimidin-5-yl]-8-thiophen-2-yl-1,3-diazaspiro[4.5]decan-2-one;

cis-8-Dimethylamino-3-[4-methyl-6-(3-oxo-piperazin-1-yl)-pyridin-3-yl]-8-phenyl-1,3-diazaspiro[4.5]decan-2-one;

cis-8-Dimethylamino-3-(4-methyl-6-pyridin-2-yl-pyridin-3-yl)-8-phenyl-1,3-diazaspiro[4.5]decan-2-one;

cis-8-Dimethylamino-3-(4-methylsulfonyl-pyridin-3-yl)-8-phenyl-1,3-diazaspiro[4.5]decan-2-one;

cis-3-(Benzothiazol-7-yl)-8-dimethylamino-8-phenyl-1,3-diazaspiro[4.5]decan-2-one;

cis-8-Dimethylamino-8-(4-fluorophenyl)-3-(4-methyl-2-morpholin-4-yl-pyrimidin-5-yl)-1,3-diazaspiro[4.5]decan-2-one;

cis-2-[8-Dimethylamino-3-[4-methyl-6-(trifluoromethyl)-pyridin-3-yl]-2-oxo-8-phenyl-1,3-diazaspiro[4.5]decan-1-yl]-N,N-dimethyl-acetamide;

cis-8-Dimethylamino-3-[2-(2-methyl-1-oxo-2,3-dihydro-isoindol-4-yl)-pyrimidin-5-yl]-8-phenyl-1,3-diazaspiro[4.5]decan-2-one;

cis-2-[[5-(8-Dimethylamino-2-oxo-8-phenyl-1,3-diazaspiro[4.5]decan-3-yl)-2-methyl-pyrimidin-4-yl]amino]-acetamide;

cis-2-[3-(8-Dimethylamino-2-oxo-8-phenyl-1,3-diazaspiro[4.5]decan-3-yl)-pyridin-4-yl]-acetamide;

cis-8-Dimethylamino-3-[4-(methylsulfonyl-methyl)-pyridin-3-yl]-8-phenyl-1,3-diazaspiro[4.5]decan-2-one;

cis-8-Dimethylamino-3-[6-(4-methyl-3-oxo-piperazin-1-yl)-pyridin-3-yl]-8-phenyl-1,3-diazaspiro[4.5]decan-2-one;

cis-8-Dimethylamino-3-(2,4-dimethyl-pyrimidin-5-yl)-8-phenyl-1,3-diazaspiro[4.5]decan-2-one;

cis-8-Dimethylamino-3-[2-(1-oxo-2,3-dihydro-isoindol-4-yl)-pyrimidin-5-yl]-8-phenyl-1,3-diazaspiro[4.5]decan-2-one, 2,2,2-trifluoro-acetic acid salt;

cis-8-Dimethylamino-3-[6-[(2-hydroxy-ethyl)-methyl-amino]-5-(trifluoromethyl)-pyridin-3-yl]-8-phenyl-1,3-diazaspiro[4.5]decan-2-one;

cis-8-Dimethylamino-8-phenyl-3-[2-[4-(trifluoromethyl)-1H-[1,2,3]triazol-1-yl]-pyrimidin-5-yl]-1,3-diazaspiro[4.5]decan-2-one;

cis-8-Dimethylamino-3-[2-(4-isopropyl-1H-[1,2,3]triazol-1-yl)-pyrimidin-5-yl]-8-phenyl-1,3-diazaspiro[4.5]decan-2-one;

cis-8-Dimethylamino-3-[6-(1,1-dioxo-[1,4]thiazinan-4-yl)-pyridin-3-yl]-8-phenyl-1,3-diazaspiro[4.5]decan-2-one;

cis-5-(8-Dimethylamino-2-oxo-8-phenyl-1,3-diazaspiro[4.5]decan-3-yl)-2-morpholin-4-yl-nicotinonitrile;

cis-8-Dimethylamino-3-(1-methylsulfonyl-1H-pyrrolo[2,3-b]pyridin-5-yl)-8-phenyl-1,3-diazaspiro[4.5]decan-2-one;

cis-8-Dimethylamino-3-(1H-indol-4-yl)-8-phenyl-1,3-diazaspiro[4.5]decan-2-one;

cis-8-Dimethylamino-3-(2-hydroxy-benzooxazol-7-yl)-8-phenyl-1,3-diazaspiro[4.5]decan-2-one;

cis-8-Dimethylamino-3-[2-fluoro-4-(trifluoromethyloxy)-phenyl]-8-phenyl-1,3-diazaspiro[4.5]decan-2-one;

cis-4-[5-(8-Dimethylamino-2-oxo-8-phenyl-1,3-diazaspiro[4.5]decan-3-yl)-pyrimidin-2-yl]-benzamide, 2,2,2-trifluoro-acetic acid salt;

cis-8-Dimethylamino-3-(1-methyl-1H-pyrrolo[2,3-b]pyridin-4-yl)-8-phenyl-1,3-diazaspiro[4.5]decan-2-one;

cis-3-(1-Acetyl-1H-indol-4-yl)-8-dimethylamino-8-phenyl-1,3-diazaspiro[4.5]decan-2-one;
cis-8-Dimethylamino-3-(1H-indol-3-yl)-8-phenyl-1,3-diazaspiro[4.5]decan-2-one;
cis-6-(8-Dimethylamino-2-oxo-8-phenyl-1,3-diazaspiro[4.5]decan-3-yl)-5-methyl-nicotinonitrile;
cis-6-(8-Dimethylamino-2-oxo-8-phenyl-1,3-diazaspiro[4.5]decan-3-yl)-5-fluoro-nicotinonitrile;
cis-8-Dimethylamino-3-[4-methyl-6-(trifluoromethyl)-pyridin-3-yl]-1-(2-oxo-2-pyrrolidin-1-yl-ethyl)-8-phenyl-1,3-diazaspiro[4.5]decan-2-one;
cis-6-(8-Dimethylamino-2-oxo-8-phenyl-1,3-diazaspiro[4.5]decan-3-yl)-5-methyl-pyridine-3-carboxylic acid amide;
cis-6-(8-Dimethylamino-2-oxo-8-phenyl-1,3-diazaspiro[4.5]decan-3-yl)-5-fluoro-pyridine-3-carboxylic acid amide;
cis-8-Dimethylamino-3-[4-methyl-6-(trifluoromethyl)-pyridin-3-yl]-8-m-tolyl-1,3-diazaspiro[4.5]decan-2-one;
cis-3-(8-Dimethylamino-2-oxo-8-phenyl-1,3-diazaspiro[4.5]decan-3-yl)-isonicotinonitrile;
cis-8-Dimethylamino-3-[3-fluoro-5-(2-oxo-1,3-dihydro-indol-4-yl)-pyridin-2-yl]-8-phenyl-1,3-diazaspiro[4.5]decan-2-one;
cis-8-Dimethylamino-3-[4-methyl-6-(trifluoromethyl)-pyridin-3-yl]-8-[3-(trifluoromethyloxy)-phenyl]-1,3-diazaspiro[4.5]decan-2-one;
cis-8-Dimethylamino-3-[4-methyl-6-(trifluoromethyl)-pyridin-3-yl]-8-[3-(trifluoromethyl)phenyl]-1,3-diazaspiro[4.5]decan-2-one;
cis-8-Dimethylamino-8-(3-methoxyphenyl)-3-[4-methyl-6-(trifluoromethyl)-pyridin-3-yl]-1,3-diazaspiro[4.5]decan-2-one;
cis-8-(5-Chloro-thiophen-2-yl)-8-dimethylamino-3-[4-methyl-6-(trifluoromethyl)-pyridin-3-yl]-1,3-diazaspiro[4.5]decan-2-one;
cis-8-Dimethylamino-8-(3-fluorophenyl)-3-[4-methyl-6-(trifluoromethyl)-pyridin-3-yl]-1,3-diazaspiro[4.5]decan-2-one;
cis-8-Dimethylamino-3-(2-methylamino-pyrimidin-5-yl)-8-phenyl-1,3-diazaspiro[4.5]decan-2-one;
cis-8-(5-Chloro-thiophen-2-yl)-8-dimethylamino-3-(4-methyl-2-morpholin-4-yl-pyrimidin-5-yl)-1,3-diazaspiro[4.5]decan-2-one;
cis-N-[5-(8-Dimethylamino-2-oxo-8-phenyl-1,3-diazaspiro[4.5]decan-3-yl)-pyrimidin-2-yl]-N-methyl-cyclopropanecarboxylic acid amide;
cis-N-[5-(8-Dimethylamino-2-oxo-8-phenyl-1,3-diazaspiro[4.5]decan-3-yl)-pyrimidin-2-yl]-N,2,5-trimethyl-2H-pyrazole-3-carboxylic acid amide;
cis-3-[4,6-Bis(trifluoromethyl)-pyridin-3-yl]-8-dimethylamino-8-phenyl-1,3-diazaspiro[4.5]decan-2-one;
cis-8-Dimethylamino-3-[2-[(2-hydroxy-ethyl)-methylamino]-quinazolin-6-yl]-8-phenyl-1,3-diazaspiro[4.5]decan-2-one;
cis-8-Dimethylamino-3-(2-morpholin-4-yl-quinazolin-6-yl)-8-phenyl-1,3-diazaspiro[4.5]decan-2-one;
cis-8-[Methyl-(oxetan-3-yl-methyl)-amino]-8-phenyl-3-[2-(trifluoromethyl)-pyrimidin-5-yl]-1,3-diazaspiro[4.5]decan-2-one;
cis-3-(1-Acetyl-1H-indol-3-yl)-8-dimethylamino-8-phenyl-1,3-diazaspiro[4.5]decan-2-one;
cis-8-Dimethylamino-8-phenyl-3-quinazolin-6-yl-1,3-diazaspiro[4.5]decan-2-one;
cis-5-(8-Dimethylamino-2-oxo-8-phenyl-1,3-diazaspiro[4.5]decan-3-yl)-2-(2-oxo-1,3-dihydro-indol-4-yl)-isonicotinonitrile;
cis-N-[5-(8-Dimethylamino-2-oxo-8-phenyl-1,3-diazaspiro[4.5]decan-3-yl)-pyrimidin-2-yl]-N-methyl-tetrahydro-pyran-4-carboxylic acid amide;
cis-N-[5-(8-Dimethylamino-2-oxo-8-phenyl-1,3-diazaspiro[4.5]decan-3-yl)-pyrimidin-2-yl]-N,2,2-trimethyl-propionamide;
cis-8-Dimethylamino-3-[2-(1-methyl-2-oxo-1,3-dihydro-indol-4-yl)-pyrimidin-5-yl]-8-phenyl-1,3-diazaspiro[4.5]decan-2-one;
cis-8-Dimethylamino-3-(2-morpholin-4-yl-1H-benzoimidazol-5-yl)-8-phenyl-1,3-diazaspiro[4.5]decan-2-one;
cis-8-Dimethylamino-8-(3-fluoro-5-methyl-phenyl)-3-[4-methyl-6-(trifluoromethyl)-pyridin-3-yl]-1,3-diazaspiro[4.5]decan-2-one;
cis-8-Dimethylamino-3-[6-(2-oxo-1,3-dihydro-indol-4-yl)-pyridin-3-yl]-8-phenyl-1,3-diazaspiro[4.5]decan-2-one;
cis-8-Dimethylamino-8-(3-hydroxyphenyl)-3-[4-methyl-6-(trifluoromethyl)-pyridin-3-yl]-1,3-diazaspiro[4.5]decan-2-one;
cis-3-[6-(Azetidin-1-yl)-5-(trifluoromethyl)-pyridin-3-yl]-8-dimethylamino-8-phenyl-1,3-diazaspiro[4.5]decan-2-one;
cis-3-[1-(Cyclopropyl-methyl)-8-dimethylamino-2-oxo-8-phenyl-1,3-diazaspiro[4.5]decan-3-yl]-isonicotinonitrile;
cis-3-[3,5-Bis(trifluoromethyl)-pyridin-2-yl]-8-dimethylamino-8-phenyl-1,3-diazaspiro[4.5]decan-2-one
cis-8-Dimethylamino-3-(5-fluoro-6-morpholin-4-yl-pyridin-3-yl)-8-phenyl-1,3-diazaspiro[4.5]decan-2-one;
cis-8-(3-Chlorophenyl)-8-dimethylamino-3-[4-methyl-6-(trifluoromethyl)-pyridin-3-yl]-1,3-diazaspiro[4.5]decan-2-one;
cis-8-Dimethylamino-3-[5-(2-oxo-1,3-dihydro-indol-4-yl)-pyridin-2-yl]-8-phenyl-1,3-diazaspiro[4.5]decan-2-one;
cis-8-Dimethylamino-8-phenyl-3-[5-(trifluoromethyl)-[1,3,4]thiadiazol-2-yl]-1,3-diazaspiro[4.5]decan-2-one;
cis-8-Dimethylamino-3-(2-oxo-1,3-dihydro-indol-4-yl)-8-phenyl-1,3-diazaspiro[4.5]decan-2-one;
cis-8-Dimethylamino-3-[2-[(2-hydroxy-ethyl)-methylamino]-1H-benzoimidazol-5-yl]-8-phenyl-1,3-diazaspiro[4.5]decan-2-one;
cis-8-Dimethylamino-3-(5-methyl-6-morpholin-4-yl-pyridin-3-yl)-8-phenyl-1,3-diazaspiro[4.5]decan-2-one;
cis-1-(Cyclopropyl-methyl)-8-dimethylamino-8-(3-fluorophenyl)-3-(5-methylsulfonyl-pyridin-2-yl)-1,3-diazaspiro[4.5]decan-2-one;
cis-1-(Cyclopropyl-methyl)-8-(3-fluorophenyl)-8-methylamino-3-(5-methylsulfonyl-pyridin-2-yl)-1,3-diazaspiro[4.5]decan-2-one;
cis-1-(Cyclobutyl-methyl)-8-(3-fluorophenyl)-8-methylamino-3-[2-(trifluoromethyl)-pyrimidin-5-yl]-1,3-diazaspiro[4.5]decan-2-one;
cis-1-(Cyclopropyl-methyl)-8-dimethylamino-8-(3-fluorophenyl)-3-[2-(trifluoromethyl)-pyrimidin-5-yl]-1,3-diazaspiro[4.5]decan-2-one;
cis-1-(Cyclopropyl-methyl)-8-(3-fluorophenyl)-8-methylamino-3-[2-(trifluoromethyl)-pyrimidin-5-yl]-1,3-diazaspiro[4.5]decan-2-one;
cis-8-Dimethylamino-8-(3-fluorophenyl)-3-[2-(trifluoromethyl)-pyrimidin-5-yl]-1,3-diazaspiro[4.5]decan-2-one;

cis-1-(Cyclopropyl-methyl)-8-dimethylamino-8-(3-fluorophenyl)-3-[2-methyl-5-(trifluoromethyl)-2H-pyrazol-3-yl]-1,3-diazaspiro[4.5]decan-2-one cis-1-(Cyclopropyl-methyl)-8-(3-fluorophenyl)-8-methylamino-3-[2-methyl-5-(trifluoromethyl)-2H-pyrazol-3-yl]-1,3-diazaspiro[4.5]decan-2-one;

cis-8-Methylamino-3-(4-methyl-2-morpholin-4-yl-pyrimidin-5-yl)-8-phenyl-1,3-diazaspiro[4.5]decan-2-one;

cis-3-[5-(Azetidin-1-yl)-3-methyl-pyridin-2-yl]-8-dimethylamino-8-(3-fluorophenyl)-1,3-diazaspiro[4.5]decan-2-one;

cis-8-Dimethylamino-8-(3-fluorophenyl)-3-(5-methylsulfonyl-pyridin-2-yl)-1,3-diazaspiro[4.5]decan-2-one;

cis-3-(6-(azetidin-1-yl)-4-fluoropyridin-3-yl)-8-(dimethylamino)-8-phenyl-1,3-diazaspiro[4.5]decan-2-one;

cis-3-(6-(azetidin-1-yl)pyridin-3-yl)-8-(dimethylamino)-8-(3-fluorophenyl)-1,3-diazaspiro[4.5]decan-2-one;

cis-3-(1-(cyclopropanecarbonyl)-3-(trifluoromethyl)-1H-pyrazol-5-yl)-8-(dimethylamino)-8-(3-fluorophenyl)-1,3-diazaspiro[4.5]decan-2-one;

cis-8-(dimethylamino)-8-(3-fluorophenyl)-3-(1-(2-hydroxyethyl)-3-(trifluoromethyl)-1H-pyrazol-5-yl)-1,3-diazaspiro[4.5]decan-2-one;

cis-3-(1-(cyclopropylmethyl)-3-(trifluoromethyl)-1H-pyrazol-5-yl)-8-(dimethylamino)-8-(3-fluorophenyl)-1,3-diazaspiro[4.5]decan-2-one;

cis-8-(dimethylamino)-8-(3-fluorophenyl)-3-(1-(methylsulfonyl)-3-(trifluoromethyl)-1H-pyrazol-5-yl)-1,3-diazaspiro[4.5]decan-2-one;

cis-1-(cyclopropylmethyl)-8-(dimethylamino)-8-(3-fluorophenyl)-3-(1-(methylsulfonyl)-3-(trifluoromethyl)-1H-pyrazol-5-yl)-1,3-diazaspiro[4.5]decan-2-one;

cis-2-(5-(8-(dimethylamino)-8-(3-fluorophenyl)-2-oxo-1,3-diazaspiro[4.5]decan-3-yl)-3-(trifluoromethyl)-1H-pyrazol-1-yl)-N,N-dimethylacetamide;

cis-2-(5-(1-(cyclopropylmethyl)-8-(dimethylamino)-8-(3-fluorophenyl)-2-oxo-1,3-diazaspiro[4.5]decan-3-yl)-3-(trifluoromethyl)-1H-pyrazol-1-yl)-N,N-dimethylacetamide;

cis-8-(dimethylamino)-3-(1-methyl-1H-pyrrolo[2,3-b]pyridin-5-yl)-8-phenyl-1,3-diazaspiro[4.5]decan-2-one;

cis-8-(dimethylamino)-3-(3-fluoro-1H-pyrrolo[2,3-b]pyridin-5-yl)-8-phenyl-1,3-diazaspiro[4.5]decan-2-one;

cis-8-(dimethylamino)-8-phenyl-3-(1H-pyrrolo[2,3-c]pyridin-4-yl)-1,3-diazaspiro[4.5]decan-2-one;

cis-8-(dimethylamino)-8-phenyl-3-(2-(pyridazin-4-yl)pyrimidin-5-yl)-1,3-diazaspiro[4.5]decan-2-one;

cis-8-(dimethylamino)-3-(2-(2-oxo-1,2-dihydropyridin-4-yl)pyrimidin-5-yl)-8-phenyl-1,3-diazaspiro[4.5]decan-2-one;

cis-8-(dimethylamino)-8-(3-fluorophenyl)-3-(1-methyl-3-(thiophen-2-yl)-1H-pyrazol-5-yl)-1,3-diazaspiro[4.5]decan-2-one;

cis-8-(dimethylamino)-8-(3-fluorophenyl)-3-(1-methyl-3-morpholino-1H-pyrazol-5-yl)-1,3-diazaspiro[4.5]decan-2-one;

cis-8-(dimethylamino)-8-phenyl-1-(2,2,2-trifluoroethyl)-3-(2-(trifluoromethyl)pyrimidin-5-yl)-1,3-diazaspiro[4.5]decan-2-one;

cis-8-(dimethylamino)-8-phenyl-3-(2-(trifluoromethyl)pyrimidin-5-yl)-1-(3,3,3-trifluoropropyl)-1,3-diazaspiro[4.5]decan-2-one;

cis-3-(4-methyl-6-(trifluoromethyl)pyridin-3-yl)-8-(methylamino)-8-phenyl-1,3-diazaspiro[4.5]decan-2-one;

cis-3-(1-methyl-3-(trifluoromethyl)-1H-pyrazol-5-yl)-8-(methylamino)-8-phenyl-1,3-diazaspiro[4.5]decan-2-one;

cis-8-(dimethylamino)-8-(3-fluorophenyl)-3-(4-(methylsulfonyl)pyridin-3-yl)-1,3-diazaspiro[4.5]decan-2-one;

cis-8-(dimethylamino)-3-(1-ethyl-3-(trifluoromethyl)-1H-pyrazol-5-yl)-8-(3-fluorophenyl)-1,3-diazaspiro[4.5]decan-2-one;

cis-3-(1-cyclopropyl-3-(trifluoromethyl)-1H-pyrazol-5-yl)-8-(dimethylamino)-8-(3-fluorophenyl)-1,3-diazaspiro[4.5]decan-2-one;

cis-8-(dimethylamino)-8-(3-fluorophenyl)-3-(1-(oxetan-3-ylmethyl)-3-(trifluoromethyl)-1H-pyrazol-5-yl)-1,3-diazaspiro[4.5]decan-2-one;

cis-8-(dimethylamino)-8-(3-fluorophenyl)-3-(1-(2-(methylsulfonyl)ethyl)-3-(trifluoromethyl)-1H-pyrazol-5-yl)-1,3-diazaspiro[4.5]decan-2-one;

cis-8-(dimethylamino)-8-(3-fluorophenyl)-3-(4-methyl-2-(methylamino)pyrimidin-5-yl)-1,3-diazaspiro[4.5]decan-2-one;

cis-3-(2-cyclopropoxy-4-methylpyrimidin-5-yl)-8-(dimethylamino)-8-(3-fluorophenyl)-1,3-diazaspiro[4.5]decan-2-one;

cis-N-(5-(8-(dimethylamino)-8-(3-fluorophenyl)-2-oxo-1,3-diazaspiro[4.5]decan-3-yl)-4-methylpyrimidin-2-yl)-N-methylcyclopropanecarboxamide;

cis-N-(5-(8-(dimethylamino)-8-(3-fluorophenyl)-2-oxo-1,3-diazaspiro[4.5]decan-3-yl)-4-methylpyrimidin-2-yl)-N-methylpivalamide;

cis-3-(4-(azetidin-1-yl)-2-(trifluoromethyl)pyrimidin-5-yl)-8-(dimethylamino)-8-(3-fluorophenyl)-1,3-diazaspiro[4.5]decan-2-one;

cis-8-(dimethylamino)-8-(3-fluorophenyl)-3-(4-(oxetan-3-ylmethoxy)-2-(trifluoromethyl)pyrimidin-5-yl)-1,3-diazaspiro[4.5]decan-2-one;

cis-3-(2-cyclopropyl-4-(2,2,2-trifluoroethoxy)pyrimidin-5-yl)-8-(dimethylamino)-8-(3-fluorophenyl)-1,3-diazaspiro[4.5]decan-2-one;

cis-3-(2-cyclopropyl-4-((2-hydroxyethyl)(methyl)amino)pyrimidin-5-yl)-8-(dimethylamino)-8-(3-fluorophenyl)-1,3-diazaspiro[4.5]decan-2-one and the physiologically acceptable salts thereof.

27. A medicament comprising a compound according to claim 1.

28. A method of treating pain, said method comprising administering to a patient in need thereof an effective amount therefor of at least one compound according to claim 1.

29. A method of treating a disorder selected from the group consisting of neurodegenerative disorders, neuroinflammatory disorders, neuropsychiatric disorders, and substance abuse/dependence, said method comprising administering to a patient in need thereof an effective amount therefor of at least one compound according to claim 1.

* * * * *